US008293979B2

(12) United States Patent
Nakajima et al.

(10) Patent No.: US 8,293,979 B2
(45) Date of Patent: *Oct. 23, 2012

(54) WEED CONTROLLER METABOLISM PROTEINS, GENES, THEREOF AND USE OF THE SAME

(75) Inventors: Hiroki Nakajima, Nishinomiya (JP); Fujio Mukumoto, Takarazuka (JP); Masanao Takaishi, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 29 days.

This patent is subject to a terminal disclaimer.

(21) Appl. No.: 12/779,305

(22) Filed: May 13, 2010

(65) Prior Publication Data

US 2010/0313300 A1    Dec. 9, 2010

Related U.S. Application Data

(62) Division of application No. 10/492,928, filed as application No. PCT/JP02/10789 on Oct. 17, 2002, now Pat. No. 7,745,699.

(30) Foreign Application Priority Data

Oct. 19, 2001 (JP) ................................ 2001-321307
Jun. 7, 2002 (JP) ................................ 2002-167239

(51) Int. Cl.
*C12N 15/52* (2006.01)
*C12N 15/82* (2006.01)

(52) U.S. Cl. ...... 800/300; 435/6.1; 435/320.1; 435/419; 435/468; 536/23.2; 800/288

(58) Field of Classification Search ........................ None
See application file for complete search history.

(56) References Cited

U.S. PATENT DOCUMENTS

| | | | |
|---|---|---|---|
| 4,859,229 A | 8/1989 | Wenger et al. | |
| 5,179,013 A | 1/1993 | Matsuoka et al. | |
| 5,212,296 A | 5/1993 | Dean et al. | |
| 5,349,127 A | 9/1994 | Dean et al. | |
| 5,466,590 A | 11/1995 | Sariaslani et al. | |
| 6,121,512 A | 9/2000 | Siminszky et al. | |
| 6,613,961 B1 | 9/2003 | Ohkawa et al. | |
| 7,521,596 B2 * | 4/2009 | Matsushima et al. | 800/288 |
| 7,563,950 B2 * | 7/2009 | Matsushima et al. | 800/300 |
| 7,745,699 B2 * | 6/2010 | Nakajima et al. | 800/300 |

FOREIGN PATENT DOCUMENTS

| | | |
|---|---|---|
| DE | 19820131 A1 | 11/1999 |
| DE | 19827777 A1 | 12/1999 |
| JP | 63-41466 A | 2/1988 |
| JP | 9252778 A | 9/1997 |
| JP | 2002/155061 A | 5/2002 |
| WO | WO 91/03561 A1 | 3/1991 |
| WO | WO 93/12236 A1 | 6/1993 |
| WO | WO 93/14073 A1 | 7/1993 |
| WO | WO 97/05116 A1 | 2/1997 |
| WO | WO 98/20144 A2 | 5/1998 |
| WO | WO 98/41093 A1 | 9/1998 |
| WO | WO 00/00585 A2 | 1/2000 |
| WO | WO 00/02866 A1 | 1/2000 |
| WO | WO 00/08168 A1 | 2/2000 |

OTHER PUBLICATIONS

Bentley et al Mar. 2001, Genbank Accession Q9EWS4.*
"Cytochrome enzyme P450SU2", Acc. No. AAR1135 Jun. 5, 1991.
"Cytochrome P450-SOY (EC 1.14.-.–)", Acc. No. P26911 Aug. 1, 1992.
"Cytochrome P450-SU2 (EC 1.14.-.–) (P450-CVB1) (CYP105B1)", Acc. No. P18327 Nov. 1, 1990.
"Ferredoxin (Tylodoxin)", Acc.No. Q9ZHQ2 May 1, 1999.
"Ferredoxin 1 (Fd-1)", Acc. No. P18324 Nov. 1, 1990.
"Ferredoxin 2 (Fd-2)", Acc. No. P18325 Nov. 1, 1990.
"Ferredoxin fas2", Acc.No. P46374 Nov. 1, 1995.
"Ferredoxin soy", Acc.No. P26901 Aug. 1, 1992.
"Ferredoxine", Acc.No. Q9EWC3 Mar. 1, 2001.
"Iron sulphur protein FeS-A", Acc.No. AAR11904 Jun. 5, 1991.
"Iron sulphur protein FeS-B", Acc.No. AAR11803 Jun. 5, 1991.
"NikF protein", Acc.No. Q9X9P7 Nov. 1, 1999.
"NysM", Acc.No. Q9L4W9 Oct. 1, 2000.
"PimF protein", Acc.No. Q9EW93 Mar. 1, 2001.
"Putative cytochrome P450 105D4", Acc.No. O84597 Nov. 1, 1998.
"Putative cytochrome P450", Acc.No. Q9EWS4 Mar. 1, 2001.
"Putative ferredoxin", Acc.No. Q9EWS5 Mar. 1, 2001.
"Putative ferredoxin", Acc.No. O85696 Nov. 1, 1998.
"Putative ferredoxin", Acc.No. Q9EWQ1 Mar. 1, 2001.
"S. fradiae tylosin biosynthetic pathway ferrodoxin protein", Acc. No. AAY83789 Jun. 21, 2000.
"S. tendae nicomycin nikF protein", Acc.No. AAY51064 Mar. 17, 2000.
"Sequence 10 from patent US 5466590", Acc.No. I15434 Apr. 8, 1996.
"Sequence 11 from patent US 5466590", Acc.No. AAA94375 Apr. 3, 1996.
"Sequence 12 from patent US 5466590", Acc.No. AAA94376 Apr. 3, 1996.
"Sequence encoding P450SU1 and FeS-B", Acc.No. AAQ11126 Jun. 5, 1991.
"Sequence soyC and soyC genes encoding cytochrome P450soy and ferredoxin-soy", Acc.No. AAQ45569 Dec. 4, 1993.
"Streptomyces griseus pab gene fragment", Acc.No. M93058 Nov. 12, 1992. "Streptomyces griseus partial ORF1, canA gene, canC gene, canF gene, canT gene, canRA gene and canRB gene", Acc.No. AJ300302 Jan. 14, 2001.
"Streptomyces lividans amplifiable element AUD4: putative transcriptional regulator, putative ferredoxin, putative cytochrome P450 oxidoreductase and putative oxidoreductase genes, complete cds; and unknown genes", Acc.No. AF072709 Jul. 8, 1998.
"Streptomyces natalensis pimaricin biosynthetic gene cluster", Acc. No. AJ278573 Jan. 6, 2001.
"Streptomyces tendea nikkomycin nikE 3', nik and nikG 5' DNA", Acc.No. AAZ24486 Feb. 18, 2000.
Aparicio, et al, "A complex multienzyme system encoding by five polyketide synthase genes is involved in the biosynthesis of the 26-membered polyene macrolide pimaricin in *Streptomyces natalensis*", *Chemistry and Biology*, vol. 7, No. 11, 2000, pp. 895-905.
Brautaset, et al. "Biosynthesis of the polyene antifungal antibiotic nystatin in *Streptomyces noursei* ATCC 11455: analysis of the gene cluster and deduction of the biosynthetic pathway", *Chemistry and Biology*, vol. 7, No. 6, 2000, pp. 395-403.
Bruntner, et al., "Molecular characterization of co-transcribed genes from *Streptomyces tendae* Tu901 involved in the biosynthesis of the peptidyl moiety of the peptidyl nucleoside antibiotic nikkomycin", *Mol. Gen Genet*, vol. 262, 1999, pp. 102-114.

(Continued)

Primary Examiner — David H Kruse
(74) Attorney, Agent, or Firm — Foley & Lardner LLP

(57) ABSTRACT

DNA encoding a herbicide metabolizing protein such DNA may, for example, be employed to produce herbicidally resistant plants.

20 Claims, 36 Drawing Sheets

OTHER PUBLICATIONS

C.A. Omer et al., "Genes for two herbicide-inducible cytochromes P-450 from Streptomyces griseolus.", *J. Bacteriol.*, 1990, vol. 172, No. 6, pp. 3335-3345.

Campelo, et al., "The candicidin gene cluster from Streptomyces griseus IMRU 3570", *Microbiology*, vol. 148, 2002, pp. 51-59.

The European Search Report received in the related case EP 02770234, dated Aug. 30, 2005.

Crespi, et al., "The fas Operon of *Rhodococcus* fascians Encodes New Genes Required for Efficient Fasciation of Host Plants", *Journal of Bacteriology*, vol. 176, No. 9, pp. 2492-2501.

Criado, et al., "The *pab* gene of *Streptomyces griseus*, encoding *p*-aminobenzoic acid synthase, is located between genes possibly involved in candicidin biosynthesis", *Gene, Elsevier*, vol. 126, No. 1, 1993, pp. 135-139.

D.P. O'Keefe et al., "Ferredoxins from two sulfonylurea herbicide monooxygenase systems in Streptomyces griseolus", *Biochemistry*, 1991, vol. 30, No. 2, pp. 447-455.

Esther Schmid et al., "AUD4, a new amplifiable element from Streptomyces lividans.", *Microbiology*, 1999, vol. 145, pp. 3331-3341.

Fouces, et al., "The tylosin biosynthetic cluster form *Streptomyces fradiae*: genetic organization of the left region", *Microbiology*, vol. 145, 1999, pp. 855-868.

Gene Bank accession No. AAK81833, Jul. 30, 2001.

GeneBank Accession No. AF071149 ("Streptomyces sclerotialus cytochrome P450 hydroxylase gene, partial cds"). (1 pg.), Jun. 1998.

Hyun, et al., "An efficient approach for cloning P450 hydroxylase genes from actinomycetes", *J. Microbiol. Biotechnol.*, 1998, vol. 8, No. 3, pp. 295-299.

Lamb, et al., "Engineering of heterologous cytochrome P450 in *acinetobacter* sp.: application for pollutant degradation", *Biochemical and Biophysical Research Communications*, 2000, vol. 276, pp. 797-802.

M.K. Trower et al., "Cloning, nucleotide sequence determination and expression of the genes encoding cytochrome P-450soy (soyC) and ferredoxinsoy (soyB) from Streptomyces griseus.", *Mol. Microbiol.*, 1992, vol. 6, No. 15, pp. 2125-2134.

O'keefe, et al. "Ferredoxins from Two Sulfonylurea Herbicide Monooxygenase Systems in *Streptomyces griseolus*", *Biochemistry, American Chemical Society*, vol. 30, No. 2, 1991, pp. 447-455.

Ohkawa, et al., "The use of cytochrome P450 genes to introduce herbicide tolerance in crops: a review", *Pestic Sci*, vol. 55, 1999, pp. 867-874.

Omer, et al, "Genes for Two Herbicide-Inducible Cytochromes P-450 from *Streptomyces griseolus*", Journal of Bacteriology, 1990, pp. 3335-3345.

Omura, et al., "Genome sequence of an industrial microorganism *Streptomyces avermitilis*: Deducing the ability of producing secondary metabolites", *PNAS*, vol. 98, No. 21, pp. 12215-12220.

S. Omura et al., "Genome sequence of an industrial microorganism Streptomyces avermitilis: deducing the ability of producing secondary metabolites", *Proc. Natl. Acad. Sci. USA*, Oct. 10, 2001, vol. 98, No. 21, pp. 12215-12220.

S.D. Bentley et al., "Complete genome sequence of the model actinomycete Streptomyces coelicolor A3 (2).", *Nature*, May 9, 2002, vol. 417, pp. 141-147.

S.E. Holmes et al., "A repeat expansion in the gene encoding junctophilin-3 is associated with Huntington disease-like 2.", *Nature Genetics*, Dec. 2001, vol. 29, No. 4, pp. 377-378.

Shiota, et al., "Expression of human cytochromes P450 1A1 and P450 1A2 as fused enzymes with yeast NADPH-cytochrome P450 oxidoreductase in transgenic tobacco plants", *Biosci. Biotechnol. Biochem*, 2000, vol. 64, No. 10, pp. 2025-2033.

Thies, et al., "Xenobiotic biotrasformation in unicellular green algae", *Plant Physiol.*, 1996, vol. 112, pp. 361-370.

Trower, et al., "Cloning, nucleotide sequence determination and expression of the genes encoding cytochrome P-450 (soyC) and ferredoxin (soyB) from Streptomyces griseus", *Molecular Microbiology*, vol. 6, No. 15, 1992, pp. 2125-2134.

Werck-Reichhart, et al., "Cytochromes P450 for engineering herbicide tolerance", *Trends in Patent Science.*, vol. 5, No. 3, 2000, pp. 116-123.

* cited by examiner

GCGGCCGCG
CGCCGGCGCTTAA

Fig. 15
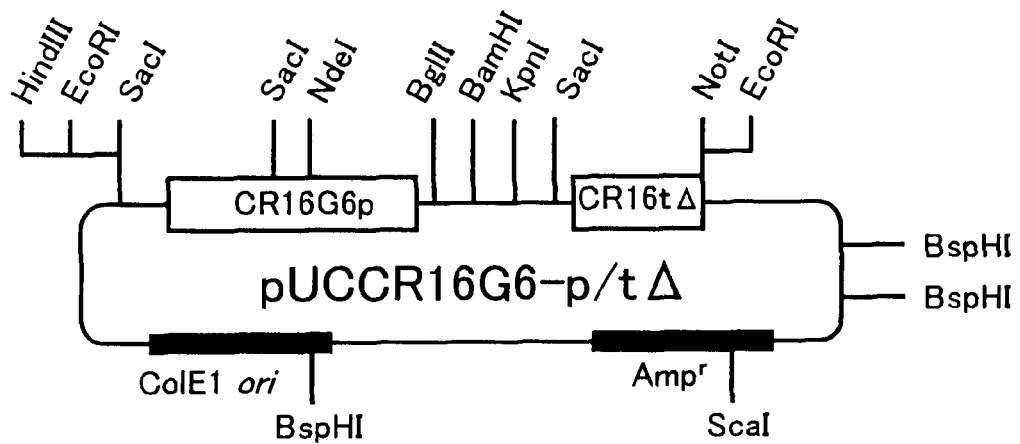
Fig. 16
AGCTTGCGGCCGC
　　　ACGCCGGCGAT
Fig. 17
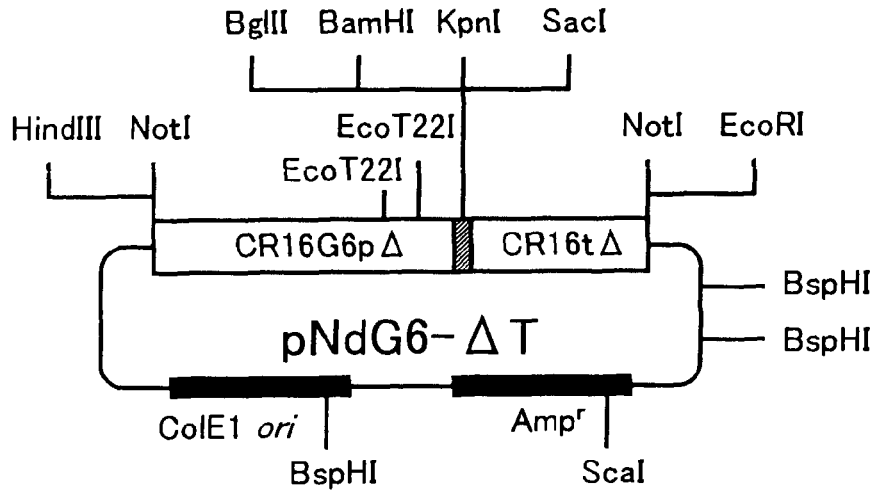

AGCTTGCGGGCCGGCGAATTC
ACGCCGGGCCGCTTAAGTCGA

AGCTATTTTTTAATAAAATCAGGAGGAAAAAAACATATGAGCAAGCTTGGCTGTTTTGGCGGATGAGAGAAGA
TAAAAAATTATTTTAGTCCTCCTTTTTTGTATACTCGTTCGAACCGACAAAACCGCCTACTCTCTTCT

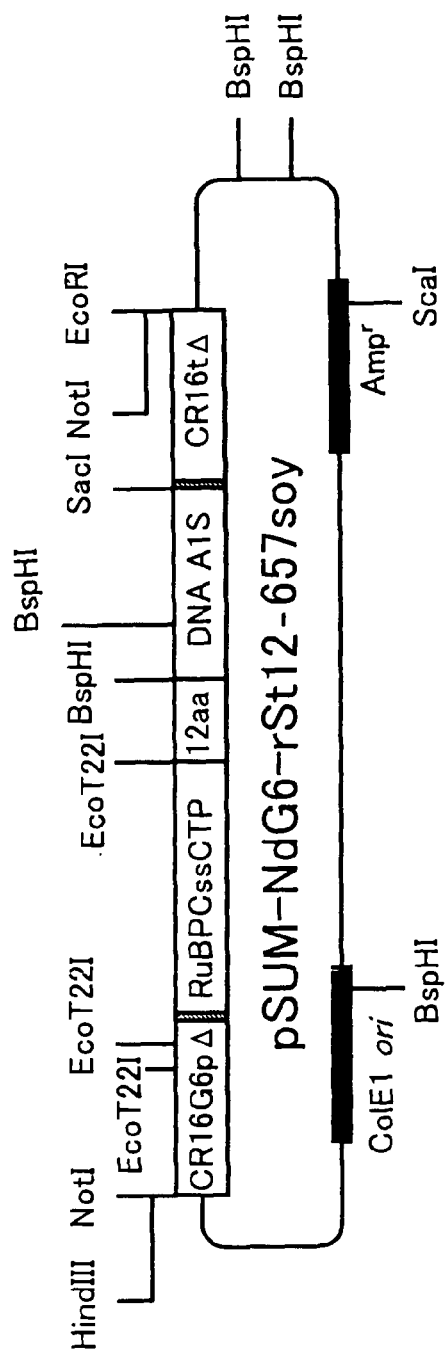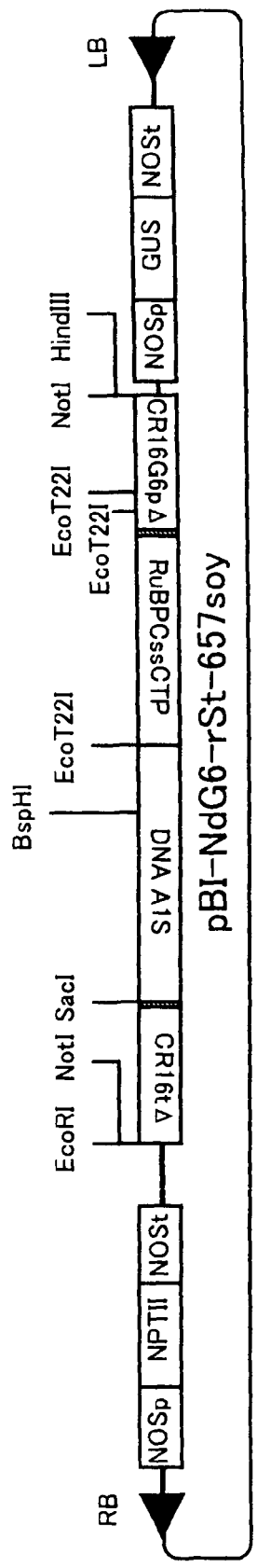
Fig. 51
Fig. 52

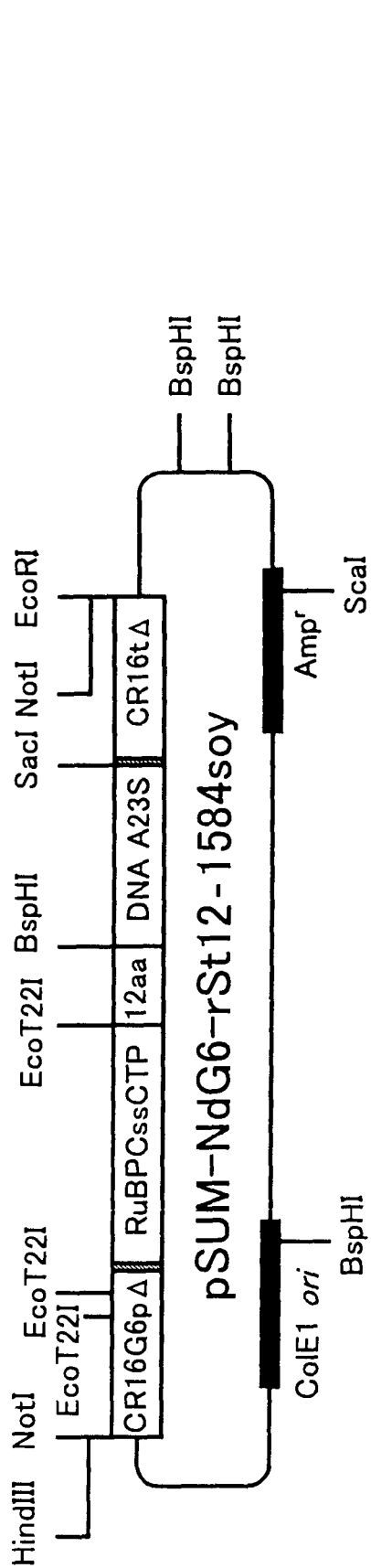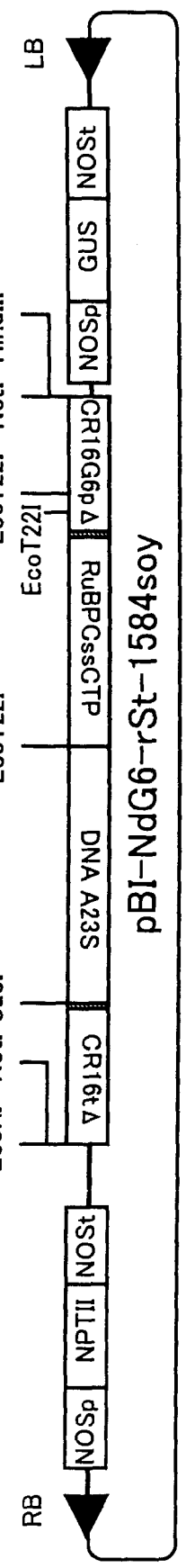
Fig. 57
Fig. 58

TGCAGGTGTGGCCACCAATTGGCAAGAAGAAATGCA
ACGTACGTCCACACCGGTGGTTAACCGTTCTTCTTT

SEQUENCE LISTING

<160> NUMBER OF SEQ ID NOS: 403

<210> SEQ ID NO 1
<211> LENGTH: 408
<212> TYPE: PRT
<213> ORGANISM: Streptmyces phaeochromogenes IFO 12898

<400> SEQUENCE: 1

Met Thr Asp Met Thr Asp Thr Ala Asp Val Lys Pro Leu Ser Ala Pro
 1               5                  10                  15

Val Ala Phe Pro Gln Asp Arg Thr Cys Pro Phe Gln Pro Pro Thr Gly
            20                  25                  30

Tyr Asp Pro Leu Arg Glu Ala Arg Pro Leu Ala Arg Val Thr Leu Tyr
            35                  40                  45

Asp Gly Arg Ala Ile Trp Leu Val Thr Gly Arg Asp Leu Ala Arg Ser
     50                  55                  60

Leu Leu Ala Asp Ser Arg Leu Ser Ser Asp Arg Leu Arg Pro Gly Phe
 65                  70                  75                  80

Pro Ala Thr Ser Pro Arg Ile Val Ala Phe Arg Asp Arg Arg Ala Ala
                 85                  90                  95

Leu Leu Asn Val Asp Asp Pro Glu His His Thr Gln Arg Arg Met Leu
                100                 105                 110

Val Pro Ser Phe Thr Leu Lys Arg Ala Ala Leu Arg Pro Ala Ile
                115                 120                 125

Gln Arg Ile Val Asp Glu Cys Ile Asp Ala Met Leu Ala Lys Gly Pro
    130                 135                 140

Pro Ala Glu Leu Val Asn Ala Phe Ala Leu Pro Val Pro Ser Met Val
145                 150                 155                 160

Ile Cys Glu Leu Leu Gly Val Pro Tyr Ala Asp His Glu Phe Phe Glu
                165                 170                 175

Glu Gln Ser Arg Arg Leu Leu Arg Gly Arg Asp Val Asp Glu Val Arg
                180                 185                 190

Asp Ala Arg Asp Gln Leu Asp Cys Tyr Leu Gly Ala Leu Ile Asp Arg
            195                 200                 205

Lys Ser Glu Ser Ser Val Gly Asp Gly Val Leu Asp Ala Leu Val His
210                 215                 220

Glu Gln Leu Arg Glu Gly Ala Val Asp Arg Gln Glu Ala Ile Ser Leu
225                 230                 235                 240

Ala Thr Ile Leu Leu Val Ala Gly His Glu Thr Thr Ala Asn Met Ile
                245                 250                 255

Ser Leu Gly Thr Tyr Thr Leu Leu Gln His Pro Glu Arg Leu Ala Glu
                260                 265                 270

Leu Arg Asp Asp Pro Ser Leu Trp Pro Ala Val Asp Glu Leu Met
            275                 280                 285

Arg Met Leu Ser Ile Ala Asp Gly Leu Met Arg Gln Ala Thr Glu Asp
    290                 295                 300

Ile Glu Val Ala Gly Thr Thr Ile Arg Ala Gly Glu Gly Val Val Phe
305                 310                 315                 320

Ala Thr Ser Val Ile Asn Arg Asp Gly Glu Val Tyr Ala Glu Pro Asp
                325                 330                 335

Ala Leu Asp Trp His Arg Pro Thr Arg His His Val Ala Phe Gly Phe
                340                 345                 350

Gly Ile His Gln Cys Leu Gly Gln Asn Leu Ala Arg Ala Glu Met Glu
            355                 360                 365

Ile Ala Leu Arg Ser Leu Phe Glu Arg Val Pro Gly Leu Arg Leu Asp
    370                 375                 380

Ile Ala Pro Asp Ala Val Arg Phe Lys Pro Gly Asp Thr Ile Gln Gly
385                 390                 395                 400

Met Leu Asp Leu Pro Val Ala Trp
                405

<210> SEQ ID NO 2
<211> LENGTH: 401
<212> TYPE: PRT
<213> ORGANISM: Saccharopolyspora taberi JCM 9383t

<400> SEQUENCE: 2

```
Met Pro Ala Ser Ser Glu Ala Leu Thr Tyr Pro Ile Pro Arg Thr Cys
  1               5                  10                  15

Pro Tyr Ser Pro Pro Asp Ser Tyr Ala Glu Leu Arg Arg Glu Gln Pro
             20                  25                  30

Val Arg Arg Val Pro Thr Leu Ala Gly Gly Ser Val Trp Leu Val Ser
         35                  40                  45

Arg His Glu Asp Val Arg Ala Val Leu Ser Asp Pro Arg Met Ser Ser
     50                  55                  60

Asp Arg Arg Lys Pro Gly Phe Pro Arg Leu Val Pro Gly Gln Ser Asp
 65                  70                  75                  80

Leu Ile Phe Ser Ser Lys Pro Ser Met Ile Gly Met Asp Gly Arg Glu
                 85                  90                  95

His Ser Ala Ala Arg Arg Ala Val Leu Gly Glu Phe Thr Val Arg Arg
            100                 105                 110

Ile Asn Ala Leu Arg Pro Arg Val Gln Glu Ile Val Asp Glu Ala Ile
            115                 120                 125

Asp Ala Met Leu Ala Ala Gly Gly Pro Val Asp Leu Val Arg Met Leu
130                 135                 140

Ser Leu Pro Val Pro Ser Leu Val Ile Cys Glu Leu Leu Gly Val Pro
145                 150                 155                 160

Tyr Ala Asp His Glu Phe Phe Gln Gln Arg Ser Gly Arg Ile Ile Ser
                165                 170                 175

Arg Ala Thr Pro Gly Ala Glu Arg Glu Glu Ala Phe Phe Glu Leu Arg
            180                 185                 190

Ala Tyr Leu Ser Asp Leu Val Ala Asp Lys Val Arg Ala Pro Gly Asp
            195                 200                 205

Asp Leu Leu Gly Arg Gln Val Ala Lys Gln Arg Ala Glu Gly Glu Val
            210                 215                 220

Asp Gln Glu Ala Leu Val Ser Leu Ala Phe Leu Leu Val Ala Gly
225                 230                 235                 240

His Glu Thr Thr Ala Asn Met Ile Ser Leu Gly Ser Leu Ala Leu Leu
                245                 250                 255

Asp Asp Ser Ala Arg Trp Ala Glu Ile Ala Ala Asp Pro Ala Lys Thr
            260                 265                 270

Pro Gly Ala Val Glu Glu Met Leu Arg Phe Phe Ser Ile Val Asp Asn
            275                 280                 285

Ala Thr Ala Arg Thr Ala Thr Glu Asp Val Glu Ile Gly Gly Val Val
            290                 295                 300

Ile Gly Glu Gly Asp Gly Val Ile Ala Met Gly Tyr Ser Ala Asn His
305                 310                 315                 320

Asp Pro Glu Val Phe Asp Arg Pro Gly Asp Leu Asp Phe Ser Arg Ala
            325                 330                 335

Ala Arg Gln His Val Ala Phe Gly Phe Gly Ala His Gln Cys Leu Gly
            340                 345                 350

Gln Asn Leu Ala Arg Val Glu Leu Gln Ile Val Phe Asp Thr Leu Val
            355                 360                 365

Arg Arg Ile Pro Asp Leu Arg Leu Ala Val Gly Phe Asp Asp Ile Arg
            370                 375                 380

Phe Lys Glu Glu Ser Ala Ile Tyr Gly Ile His Glu Leu Met Val Thr
385                 390                 395                 400

Trp
```

<210> SEQ ID NO 3

<211> LENGTH: 395
<212> TYPE: PRT
<213> ORGANISM: Streptmyces testaceus ATCC 21469

<400> SEQUENCE: 3

```
Met Thr Glu Ala Ile Ala Tyr Phe Gln Asp Arg Thr Cys Pro Tyr His
 1               5                  10                  15

Pro Pro Ala Gly Tyr Gln Pro Leu Arg Asp Ala Gly Pro Leu Ala His
            20                  25                  30

Val Thr Leu Tyr Asp Gly Arg Lys Val Trp Ala Val Thr Gly His Thr
        35                  40                  45

Glu Ala Arg Ala Leu Leu Ser Asp Pro Arg Leu Ser Ser Asp Arg Gln
 50                  55                  60

Asn Pro Ala Phe Pro Ala Pro Phe Ala Arg Phe Ala Ala Leu Arg Gln
 65                  70                  75                  80

Val Arg Ser Pro Leu Ile Gly Val Asp Pro Glu His Asn Thr Gln
                85                  90                  95

Arg Arg Met Leu Ile Pro Ser Phe Ser Val Lys Arg Thr Ala Ala Leu
            100                 105                 110

Arg Pro Gln Ile Gln Gln Ile Val Asp Gly Leu Leu Asp Arg Met Leu
        115                 120                 125

Ala Gln Gly Pro Pro Ala Glu Leu Val Ser Ala Phe Ala Leu Pro Val
130                 135                 140

Pro Ser Met Val Ile Cys Ser Leu Leu Gly Val Pro Tyr Ser Asp His
145                 150                 155                 160

Glu Phe Phe Glu Glu Ala Ser Arg Arg Leu Leu Arg Ser Arg Thr Ala
                165                 170                 175

Glu Glu Ala Glu Glu Ala Arg Leu Arg Leu Glu Asp Tyr Phe Asp Glu
            180                 185                 190

Leu Ile Ala His Lys Glu Lys Thr Pro Arg Glu Gly Leu Leu Asp Glu
        195                 200                 205

Leu Val His Asp Glu Leu Arg Thr Gly Ala Leu Glu Arg Glu Asp Leu
    210                 215                 220

Val Arg Leu Ala Met Ile Leu Leu Val Ala Gly His Glu Thr Thr Ala
225                 230                 235                 240

Asn Met Ile Ser Leu Gly Thr Phe Thr Leu Leu Glu His Pro Gly Gln
                245                 250                 255

Leu Ala Arg Leu Lys Ala Glu Glu Gly Leu Leu Pro Ala Ala Val Glu
            260                 265                 270

Glu Leu Leu Arg Phe Leu Ser Ile Ala Asp Gly Leu Leu Arg Val Ala
        275                 280                 285

Met Ala Asp Ile Glu Ile Gly Gly Gln Val Ile Arg Ala Asp Asp Gly
    290                 295                 300

Val Leu Phe Pro Thr Ser Leu Ile Asn Arg Asp Asp Gly Ala Tyr Pro
305                 310                 315                 320

Thr Pro Asp Glu Leu Asp Val Gly Arg Ser Ala Arg His His Val Ala
                325                 330                 335

Phe Gly Phe Gly Ile His Gln Cys Leu Gly Gln Asn Leu Ala Arg Ala
            340                 345                 350

Glu Met Glu Ile Ala Leu Arg Ser Leu Phe Asp Arg Ile Pro Asp Leu
        355                 360                 365

Arg Leu Ala Val Pro Ala Ala Glu Ile Pro Phe Lys Pro Gly Asp Thr
    370                 375                 380

Leu Gln Gly Met Ile Glu Leu Pro Leu Ala Trp
385                 390                 395
```

<210> SEQ ID NO 4
<211> LENGTH: 410
<212> TYPE: PRT
<213> ORGANISM: Streptmyces carbophilus SANK 62585

<400> SEQUENCE: 4

```
Met Thr Glu Met Thr Glu Lys Ala Thr Thr Phe Leu Thr Ser Gln Glu
 1               5                  10                  15

Ala Pro Ala Phe Pro Ala Asp Arg Thr Cys Pro Tyr Gln Leu Pro Thr
             20                  25                  30

Ala Tyr Ser Arg Leu Arg Asp Glu Pro Asp Ala Leu Arg Pro Val Thr
         35                  40                  45

Leu Tyr Asp Gly Arg Arg Ala Trp Val Val Thr Lys His Glu Ala Ala
     50                  55                  60

Arg Arg Leu Leu Ala Asp Pro Arg Leu Ser Ser Asp Arg Leu His Ala
 65                  70                  75                  80

Asp Phe Pro Ala Thr Ser Pro Arg Phe Lys Ala Phe Arg Gln Gly Ser
                 85                  90                  95

Pro Ala Phe Ile Gly Met Asp Pro Pro Glu His Gly Thr Arg Arg Arg
            100                 105                 110

Met Thr Ile Ser Glu Phe Thr Val Lys Arg Ile Lys Gly Met Arg Pro
        115                 120                 125

Asp Val Glu Arg Ile Val His Gly Phe Ile Asp Asp Met Leu Ala Ala
130                 135                 140

Gly Pro Thr Ala Asp Leu Val Ser Gln Phe Ala Leu Pro Val Pro Ser
145                 150                 155                 160

Met Val Ile Cys His Met Leu Gly Val Pro Tyr Ala Asp His Glu Phe
                165                 170                 175

Phe Gln Asp Ala Ser Lys Arg Leu Val Gln Ala Val Asp Ala Asp Ser
            180                 185                 190

Ala Val Ala Ala Arg Asp Asp Phe Glu Arg Tyr Leu Asp Gly Leu Ile
        195                 200                 205

Thr Lys Leu Glu Ser Glu Pro Gly Thr Gly Leu Leu Gly Lys Leu Val
    210                 215                 220

Thr His Gln Leu Ala Asp Gly Glu Ile Asp Arg Ala Glu Leu Ile Ser
225                 230                 235                 240

Thr Ala Leu Leu Leu Leu Val Ala Gly His Glu Thr Thr Ala Ser Met
                245                 250                 255

Thr Ser Leu Ser Val Ile Thr Leu Leu Glu His Pro Asp Gln His Ala
            260                 265                 270

Ala Leu Arg Ala Asp Pro Ser Leu Val Pro Gly Ala Val Glu Glu Leu
        275                 280                 285

Leu Arg Val Leu Ala Ile Ala Asp Ile Ala Gly Gly Arg Ile Ala Thr
    290                 295                 300

Ala Asp Ile Glu Ile Asp Gly Gln Leu Ile Arg Ala Gly Glu Gly Val
305                 310                 315                 320

Ile Val Thr Asn Ser Ile Ala Asn Arg Asp Ser Ser Val Phe Glu Asn
                325                 330                 335

Pro Asp Arg Leu Asp Val His Arg Ser Ala Arg His His Leu Ser Phe
            340                 345                 350

Gly Tyr Gly Val His Gln Cys Leu Gly Gln Asn Leu Ala Arg Leu Glu
        355                 360                 365

Leu Glu Val Ile Leu Thr Val Leu Phe Asp Arg Ile Pro Thr Leu Arg
    370                 375                 380
```

```
Leu Ala Val Pro Val Glu Gln Leu Thr Leu Arg Pro Gly Thr Thr Ile
385                 390                 395                 400

Gln Gly Val Asn Glu Leu Pro Val Thr Trp
            405                 410

<210> SEQ ID NO 5
<211> LENGTH: 406
<212> TYPE: PRT
<213> ORGANISM: Streptmyces griseolus ATCC 11796

<400> SEQUENCE: 5

Met Thr Asp Thr Ala Thr Thr Pro Gln Thr Thr Asp Ala Pro Ala Phe
1               5                   10                  15

Pro Ser Asn Arg Ser Cys Pro Tyr Gln Leu Pro Asp Gly Tyr Ala Gln
            20                  25                  30

Leu Arg Asp Thr Pro Gly Pro Leu His Arg Val Thr Leu Tyr Asp Gly
        35                  40                  45

Arg Gln Ala Trp Val Val Thr Lys His Glu Ala Ala Arg Lys Leu Leu
    50                  55                  60

Gly Asp Pro Arg Leu Ser Ser Asn Arg Thr Asp Asn Phe Pro Ala
65                  70                  75                  80

Thr Ser Pro Arg Phe Glu Ala Val Arg Glu Ser Pro Gln Ala Phe Ile
                85                  90                  95

Gly Leu Asp Pro Pro Glu His Gly Thr Arg Arg Met Thr Ile Ser
            100                 105                 110

Glu Phe Thr Val Lys Arg Ile Lys Gly Met Arg Pro Val Glu Glu
        115                 120                 125

Val Val His Gly Phe Leu Asp Glu Met Leu Ala Ala Gly Pro Thr Ala
130                 135                 140

Asp Leu Val Ser Gln Phe Ala Leu Pro Val Pro Ser Met Val Ile Cys
145                 150                 155                 160

Arg Leu Leu Gly Val Pro Tyr Ala Asp His Glu Phe Phe Gln Asp Ala
                165                 170                 175

Ser Lys Arg Leu Val Gln Ser Thr Asp Ala Gln Ser Ala Leu Thr Ala
            180                 185                 190

Arg Asn Asp Leu Ala Gly Tyr Leu Asp Gly Leu Ile Thr Gln Phe Gln
        195                 200                 205

Thr Glu Pro Gly Ala Gly Leu Val Gly Ala Leu Val Ala Asp Gln Leu
    210                 215                 220

Ala Asn Gly Glu Ile Asp Arg Glu Glu Leu Ile Ser Thr Ala Met Leu
225                 230                 235                 240

Leu Leu Ile Ala Gly His Glu Thr Thr Ala Ser Met Thr Ser Leu Ser
                245                 250                 255

Val Ile Thr Leu Leu Asp His Pro Glu Gln Tyr Ala Ala Leu Arg Ala
            260                 265                 270

Asp Arg Ser Leu Val Pro Gly Ala Val Glu Glu Leu Leu Arg Tyr Leu
        275                 280                 285

Ala Ile Ala Asp Ile Ala Gly Gly Arg Val Ala Thr Ala Asp Ile Glu
    290                 295                 300

Val Glu Gly Gln Leu Ile Arg Ala Gly Glu Gly Val Ile Val Val Asn
305                 310                 315                 320

Ser Ile Ala Asn Arg Asp Gly Thr Val Tyr Glu Asp Pro Asp Ala Leu
                325                 330                 335

Asp Ile His Arg Ser Ala Arg His His Leu Ala Phe Gly Phe Gly Val
            340                 345                 350
```

```
His Gln Cys Leu Gly Gln Asn Leu Ala Arg Leu Glu Leu Glu Val Ile
            355                 360                 365

Leu Asn Ala Leu Met Asp Arg Val Pro Thr Leu Arg Leu Ala Val Pro
    370                 375                 380

Val Glu Gln Leu Val Leu Arg Pro Gly Thr Thr Ile Gln Gly Val Asn
385                 390                 395                 400

Glu Leu Pro Val Thr Trp
                405

<210> SEQ ID NO 6
<211> LENGTH: 1227
<212> TYPE: DNA
<213> ORGANISM: Streptmyces phaeochromogenes IFO 12898
<220> FEATURE:
<221> NAME/KEY: CDS
<222> LOCATION: (1)..(1227)

<400> SEQUENCE: 6 atg aca gac atg acg gat acg gca gac gtg aag ccg ctc tcg gca ccc     48
Met Thr Asp Met Thr Asp Thr Ala Asp Val Lys Pro Leu Ser Ala Pro
  1               5                  10                  15 gtc gcc ttc ccc cag gac cgc acc tgc ccc ttc cag ccc ccg acg ggc     96
Val Ala Phe Pro Gln Asp Arg Thr Cys Pro Phe Gln Pro Pro Thr Gly
             20                  25                  30 tac gac ccc ctg cgt gag gcc cgg ccg ctc gcc cgc gtg acc ctc tac    144
Tyr Asp Pro Leu Arg Glu Ala Arg Pro Leu Ala Arg Val Thr Leu Tyr
         35                  40                  45 gac ggc cgg gcc atc tgg ctg gtc acc ggc cgt gac ctg gcc cgc agc    192
Asp Gly Arg Ala Ile Trp Leu Val Thr Gly Arg Asp Leu Ala Arg Ser
     50                  55                  60 ctg ctc gcc gat tcc cgc ctg tcg tcc gac cgc ctg cgc ccc ggc ttc    240
Leu Leu Ala Asp Ser Arg Leu Ser Ser Asp Arg Leu Arg Pro Gly Phe
 65                  70                  75                  80 ccg gcc acc tcg ccg cgc atc gtg gcg ttc cgc gac cgc ggc gcc gcc    288
Pro Ala Thr Ser Pro Arg Ile Val Ala Phe Arg Asp Arg Gly Ala Ala
                 85                  90                  95 ctg ctg aac gtc gac gac ccc gag cac cac acc cag cgg cgg atg ctg    336
Leu Leu Asn Val Asp Asp Pro Glu His His Thr Gln Arg Arg Met Leu
            100                 105                 110 gtc ccg agc ttc acc ctc aag cgc gcc gcc gcg ttg cgg ccg gcc atc    384
Val Pro Ser Phe Thr Leu Lys Arg Ala Ala Ala Leu Arg Pro Ala Ile
        115                 120                 125 cag cgg atc gtc gac gaa tgc atc gac gcg atg ctc gcg aag ggc ccg    432
Gln Arg Ile Val Asp Glu Cys Ile Asp Ala Met Leu Ala Lys Gly Pro
    130                 135                 140 ccc gcc gag ttg gtg aac gcc ttc gcg ctc ccc gtt ccc tcg atg gtg    480
Pro Ala Glu Leu Val Asn Ala Phe Ala Leu Pro Val Pro Ser Met Val
145                 150                 155                 160 atc tgc gaa ctg ctc ggt gtc ccg tac gcc gat cac gag ttc ttc gag    528
Ile Cys Glu Leu Leu Gly Val Pro Tyr Ala Asp His Glu Phe Phe Glu
                165                 170                 175 gag cag tcc cgt cgg ctg ctg cgc ggc cgg gac gtg gac gag gtg cgg    576
Glu Gln Ser Arg Arg Leu Leu Arg Gly Arg Asp Val Asp Glu Val Arg
            180                 185                 190 gac gcg cgg gac cag ctc gac tgc tac ctc ggg gcg ctg atc gac cgc    624
Asp Ala Arg Asp Gln Leu Asp Cys Tyr Leu Gly Ala Leu Ile Asp Arg
        195                 200                 205 aag tcc gag tcg tcc gtc ggt gac ggt gtc ctc gac gcc ctg gtc cac    672
Lys Ser Glu Ser Ser Val Gly Asp Gly Val Leu Asp Ala Leu Val His
    210                 215                 220
```

| | | |
|---|---|---|
| gag cag ttg cgc gag ggc gcg gtg gac cgg cag gag gcc atc tcg ctg<br>Glu Gln Leu Arg Glu Gly Ala Val Asp Arg Gln Glu Ala Ile Ser Leu<br>225 230 235 240 | | 720 |
| gcc acg atc ctg ctg gtc gcc ggc cac gag acc acc gcc aac atg atc<br>Ala Thr Ile Leu Leu Val Ala Gly His Glu Thr Thr Ala Asn Met Ile<br>245 250 255 | | 768 |
| tcg ctg ggc act tac acc ctg ctc caa cac ccc gag cga ctg gcg gag<br>Ser Leu Gly Thr Tyr Thr Leu Leu Gln His Pro Glu Arg Leu Ala Glu<br>260 265 270 | | 816 |
| ttg cgg gac gac ccg tcg ctg tgg ccc gcc gcc gtc gac gag ttg atg<br>Leu Arg Asp Asp Pro Ser Leu Trp Pro Ala Ala Val Asp Glu Leu Met<br>275 280 285 | | 864 |
| cgg atg ctg tcc atc gcg gac ggg ctg atg cgg cag gcc acg gag gac<br>Arg Met Leu Ser Ile Ala Asp Gly Leu Met Arg Gln Ala Thr Glu Asp<br>290 295 300 | | 912 |
| atc gag gtg gcc ggg acg acg atc cgc gcc ggt gag ggc gtg gtc ttc<br>Ile Glu Val Ala Gly Thr Thr Ile Arg Ala Gly Glu Gly Val Val Phe<br>305 310 315 320 | | 960 |
| gcg acc tcg gtc atc aac cgc gac ggg gag gtc tac gcc gaa ccc gac<br>Ala Thr Ser Val Ile Asn Arg Asp Gly Glu Val Tyr Ala Glu Pro Asp<br>325 330 335 | | 1008 |
| gcc ctc gac tgg cac cgg ccc acc cgc cat cac gtg gcg ttc ggc ttc<br>Ala Leu Asp Trp His Arg Pro Thr Arg His His Val Ala Phe Gly Phe<br>340 345 350 | | 1056 |
| ggc atc cac cag tgt ctc ggc cag aac ctg gcc cgt gcc gag atg gag<br>Gly Ile His Gln Cys Leu Gly Gln Asn Leu Ala Arg Ala Glu Met Glu<br>355 360 365 | | 1104 |
| atc gcc ctg cgt tcc ctg ttc gag cgg gtg ccc ggg ctg cgc ctc gac<br>Ile Ala Leu Arg Ser Leu Phe Glu Arg Val Pro Gly Leu Arg Leu Asp<br>370 375 380 | | 1152 |
| att gcg ccg gac gcg gtc cgc ttc aaa ccg ggc gac acg atc cag gga<br>Ile Ala Pro Asp Ala Val Arg Phe Lys Pro Gly Asp Thr Ile Gln Gly<br>385 390 395 400 | | 1200 |
| atg ctg gat ctg ccc gtg gcc tgg tag<br>Met Leu Asp Leu Pro Val Ala Trp<br>405 | | 1227 |

```
<210> SEQ ID NO 7
<211> LENGTH: 1206
<212> TYPE: DNA
<213> ORGANISM: Saccharopolyspora taberi JCM 9383t
<220> FEATURE:
<221> NAME/KEY: CDS
<222> LOCATION: (1)..(1206)

<400> SEQUENCE: 7
```

| | | |
|---|---|---|
| atg ccg gca tct tct gaa gct ctg acc tat ccg atc ccc cgg acc tgt<br>Met Pro Ala Ser Ser Glu Ala Leu Thr Tyr Pro Ile Pro Arg Thr Cys<br>1 5 10 15 | | 48 |
| ccg tac tcg ccg ccc gac tcc tac gcc gaa ctc cgg cgc gag cag ccg<br>Pro Tyr Ser Pro Pro Asp Ser Tyr Ala Glu Leu Arg Arg Glu Gln Pro<br>20 25 30 | | 96 |
| gtc cgc cgg gtg ccg acg ctg gcg gga ggc agc gtg tgg ctg gtg tcg<br>Val Arg Arg Val Pro Thr Leu Ala Gly Gly Ser Val Trp Leu Val Ser<br>35 40 45 | | 144 |
| cgg cac gag gac gtg cgc gcg gtc ctc agc gac ccg cgg atg agc tcc<br>Arg His Glu Asp Val Arg Ala Val Leu Ser Asp Pro Arg Met Ser Ser<br>50 55 60 | | 192 |
| gac cgc cgc aag ccc ggg ttc ccg cgg ctc gtg ccg ggg cag agc gac<br>Asp Arg Arg Lys Pro Gly Phe Pro Arg Leu Val Pro Gly Gln Ser Asp<br>65 70 75 80 | | 240 |
| ctg atc ttc agc tcc aag ccg tcg atg atc ggc atg gac ggg cgc gag | | 288 |

```
                Leu Ile Phe Ser Ser Lys Pro Ser Met Ile Gly Met Asp Gly Arg Glu
                                85                  90                  95 cac tcg gcg gcc cgg cgg gcg gtt ctc ggt gag ttc acc gtc cgg cgg         336
His Ser Ala Ala Arg Arg Ala Val Leu Gly Glu Phe Thr Val Arg Arg
                100                 105                 110 atc aac gcg ctg cgc ccg cgc gtg cag gag atc gtc gac gag gcc atc         384
Ile Asn Ala Leu Arg Pro Arg Val Gln Glu Ile Val Asp Glu Ala Ile
            115                 120                 125 gac gcg atg ctg gcc gcg ggc ggg ccg gtc gac ctg gtg cgg atg ctc         432
Asp Ala Met Leu Ala Ala Gly Gly Pro Val Asp Leu Val Arg Met Leu
    130                 135                 140 tcg ctt ccg gtg ccg tcg ctg gtg atc tgc gag ctg ctc ggc gtt ccc         480
Ser Leu Pro Val Pro Ser Leu Val Ile Cys Glu Leu Leu Gly Val Pro
145                 150                 155                 160 tac gcc gac cac gag ttc ttc cag cag cgc agc ggc cgc atc atc agc         528
Tyr Ala Asp His Glu Phe Phe Gln Gln Arg Ser Gly Arg Ile Ile Ser
                165                 170                 175 cgg gcg acg ccg ggg gcc gag cgg gag gag gcg ttc ttc gaa ctc cgc         576
Arg Ala Thr Pro Gly Ala Glu Arg Glu Glu Ala Phe Phe Glu Leu Arg
                180                 185                 190 gcc tac ctg tcg gat ctg gtc gcg gac aag gtc cgc gca ccg ggc gac         624
Ala Tyr Leu Ser Asp Leu Val Ala Asp Lys Val Arg Ala Pro Gly Asp
            195                 200                 205 gac ctg ctc ggc agg cag gtg gcc aag cag cgg gcc gag ggc gag gtc         672
Asp Leu Leu Gly Arg Gln Val Ala Lys Gln Arg Ala Glu Gly Glu Val
    210                 215                 220 gac cag gag gcg ctg gtc agc ctc gcg ttc ctg ctg ctg gtc gcc ggg         720
Asp Gln Glu Ala Leu Val Ser Leu Ala Phe Leu Leu Leu Val Ala Gly
225                 230                 235                 240 cac gag acc acc gcg aac atg atc tcg ctt ggt agc ctg gcg ctg ctg         768
His Glu Thr Thr Ala Asn Met Ile Ser Leu Gly Ser Leu Ala Leu Leu
                245                 250                 255 gac gat tcc gcc cgg tgg gcg gag atc gcc gcg gat ccg gcg aag acg         816
Asp Asp Ser Ala Arg Trp Ala Glu Ile Ala Ala Asp Pro Ala Lys Thr
                260                 265                 270 ccc ggc gcg gtg gag gag atg ctg cgg ttc ttc tcg atc gtc gac aac         864
Pro Gly Ala Val Glu Glu Met Leu Arg Phe Phe Ser Ile Val Asp Asn
            275                 280                 285 gcg acc gcg cgc acc gcg acc gag gac gtg gag atc ggc ggc gtg gtc         912
Ala Thr Ala Arg Thr Ala Thr Glu Asp Val Glu Ile Gly Gly Val Val
    290                 295                 300 atc ggg gag ggc gac ggg gtg atc gcg atg ggc tat tcg gcc aac cac         960
Ile Gly Glu Gly Asp Gly Val Ile Ala Met Gly Tyr Ser Ala Asn His
305                 310                 315                 320 gac ccc gag gtc ttc gac cgc ccc ggg gac ctc gac ttc tcc cgg gcc         1008
Asp Pro Glu Val Phe Asp Arg Pro Gly Asp Leu Asp Phe Ser Arg Ala
                325                 330                 335 gcc cgc cag cac gtc gcc ttc ggc ttc ggc gcg cac cag tgc ctg ggc         1056
Ala Arg Gln His Val Ala Phe Gly Phe Gly Ala His Gln Cys Leu Gly
                340                 345                 350 cag aac ctc gcg cgg gtg gag ttg cag atc gtc ttc gac acg ctg gtg         1104
Gln Asn Leu Ala Arg Val Glu Leu Gln Ile Val Phe Asp Thr Leu Val
            355                 360                 365 cgg cgg atc ccg gac ctg cgg ctg gcg gtc ggc ttc gac gac atc cgg         1152
Arg Arg Ile Pro Asp Leu Arg Leu Ala Val Gly Phe Asp Asp Ile Arg
    370                 375                 380 ttc aag gag gag tcg gcg atc tac gga atc cac gaa ctg atg gtc act         1200
Phe Lys Glu Glu Ser Ala Ile Tyr Gly Ile His Glu Leu Met Val Thr
385                 390                 395                 400 tgg tga                                                                 1206
```

Trp

```
<210> SEQ ID NO 8
<211> LENGTH: 1188
<212> TYPE: DNA
<213> ORGANISM: Streptmyces testaceus ATCC 21469
<220> FEATURE:
<221> NAME/KEY: CDS
<222> LOCATION: (1)..(1188)

<400> SEQUENCE: 8
```

| | | | | | | | | | | | | | | | | |
|---|---|---|---|---|---|---|---|---|---|---|---|---|---|---|---|---|
| atg | acc | gaa | gcc | atc | gcg | tat | ttc | cag | gac | cgc | acc | tgc | ccc | tac | cac | 48 |
| Met | Thr | Glu | Ala | Ile | Ala | Tyr | Phe | Gln | Asp | Arg | Thr | Cys | Pro | Tyr | His | |
| 1 | | | | 5 | | | | | 10 | | | | | 15 | | |
| ccg | ccg | gcc | ggc | tat | cag | ccg | ctg | cgt | gac | gca | ggc | ccg | ctg | gcc | cat | 96 |
| Pro | Pro | Ala | Gly | Tyr | Gln | Pro | Leu | Arg | Asp | Ala | Gly | Pro | Leu | Ala | His | |
| | | | 20 | | | | | 25 | | | | | 30 | | | |
| gtc | acc | ctc | tac | gac | ggc | cgc | aag | gtg | tgg | gcg | gtg | acc | ggc | cac | acc | 144 |
| Val | Thr | Leu | Tyr | Asp | Gly | Arg | Lys | Val | Trp | Ala | Val | Thr | Gly | His | Thr | |
| | 35 | | | | | 40 | | | | | 45 | | | | | |
| gag | gcg | cgg | gcg | ctg | ctg | agc | gac | ccg | cgg | ctg | tcc | tcc | gac | cgg | cag | 192 |
| Glu | Ala | Arg | Ala | Leu | Leu | Ser | Asp | Pro | Arg | Leu | Ser | Ser | Asp | Arg | Gln | |
| 50 | | | | | 55 | | | | | 60 | | | | | | |
| aac | ccg | gcc | ttc | ccg | gcg | ccg | ttc | gcc | cgc | ttc | gcg | gcg | ctg | cgc | cag | 240 |
| Asn | Pro | Ala | Phe | Pro | Ala | Pro | Phe | Ala | Arg | Phe | Ala | Ala | Leu | Arg | Gln | |
| 65 | | | | | 70 | | | | | 75 | | | | | 80 | |
| gtc | agg | tcg | ccg | ctg | atc | ggc | gtg | gac | gac | ccc | gag | cac | aac | acc | cag | 288 |
| Val | Arg | Ser | Pro | Leu | Ile | Gly | Val | Asp | Asp | Pro | Glu | His | Asn | Thr | Gln | |
| | | | | 85 | | | | | 90 | | | | | 95 | | |
| cgc | cgg | atg | ctg | atc | ccc | agc | ttc | agc | gtc | aag | cgg | acc | gcg | gcg | ctg | 336 |
| Arg | Arg | Met | Leu | Ile | Pro | Ser | Phe | Ser | Val | Lys | Arg | Thr | Ala | Ala | Leu | |
| | | | 100 | | | | | 105 | | | | | 110 | | | |
| cgg | ccg | cag | atc | cag | cag | atc | gtc | gac | ggg | ctg | ctg | gac | cgg | atg | ctg | 384 |
| Arg | Pro | Gln | Ile | Gln | Gln | Ile | Val | Asp | Gly | Leu | Leu | Asp | Arg | Met | Leu | |
| | 115 | | | | | 120 | | | | | 125 | | | | | |
| gcg | cag | ggg | ccg | ccc | gcc | gag | ctg | gtc | tcc | gcg | ttc | gcg | ctg | ccg | gtg | 432 |
| Ala | Gln | Gly | Pro | Pro | Ala | Glu | Leu | Val | Ser | Ala | Phe | Ala | Leu | Pro | Val | |
| 130 | | | | | 135 | | | | | 140 | | | | | | |
| ccc | tcg | atg | gtg | atc | tgc | tcg | ctg | ctc | ggc | gtc | ccc | tac | tcc | gac | cac | 480 |
| Pro | Ser | Met | Val | Ile | Cys | Ser | Leu | Leu | Gly | Val | Pro | Tyr | Ser | Asp | His | |
| 145 | | | | | 150 | | | | | 155 | | | | | 160 | |
| gag | ttc | ttc | gag | gag | gcc | tcc | cgc | cgg | ctc | ctg | cgc | agc | cgg | acg | gcc | 528 |
| Glu | Phe | Phe | Glu | Glu | Ala | Ser | Arg | Arg | Leu | Leu | Arg | Ser | Arg | Thr | Ala | |
| | | | | 165 | | | | | 170 | | | | | 175 | | |
| gag | gag | gcg | gag | gag | gcc | cgc | ctc | cgg | ctg | gag | gac | tac | ttc | gac | gag | 576 |
| Glu | Glu | Ala | Glu | Glu | Ala | Arg | Leu | Arg | Leu | Glu | Asp | Tyr | Phe | Asp | Glu | |
| | | | 180 | | | | | 185 | | | | | 190 | | | |
| ctg | atc | gcc | cac | aag | gag | aag | acc | ccg | cgc | gag | ggc | ctg | ctc | gac | gag | 624 |
| Leu | Ile | Ala | His | Lys | Glu | Lys | Thr | Pro | Arg | Glu | Gly | Leu | Leu | Asp | Glu | |
| | 195 | | | | | 200 | | | | | 205 | | | | | |
| ctg | gtc | cac | gac | gag | ctg | cgc | acc | ggc | gcc | ctg | gag | cgc | gag | gat | ctg | 672 |
| Leu | Val | His | Asp | Glu | Leu | Arg | Thr | Gly | Ala | Leu | Glu | Arg | Glu | Asp | Leu | |
| 210 | | | | | 215 | | | | | 220 | | | | | | |
| gtc | cgg | ctc | gcg | atg | atc | ctg | ctg | gtg | gcc | ggc | cac | gag | acc | acc | gcc | 720 |
| Val | Arg | Leu | Ala | Met | Ile | Leu | Leu | Val | Ala | Gly | His | Glu | Thr | Thr | Ala | |
| 225 | | | | | 230 | | | | | 235 | | | | | 240 | |
| aac | atg | atc | tcg | ctc | ggc | acc | ttc | acc | ctg | ctg | gag | cac | ccc | gga | cag | 768 |
| Asn | Met | Ile | Ser | Leu | Gly | Thr | Phe | Thr | Leu | Leu | Glu | His | Pro | Gly | Gln | |
| | | | | 245 | | | | | 250 | | | | | 255 | | |
| ctg | gcc | cgg | ctg | aag | gcc | gag | gag | ggg | ctg | ctg | ccg | gcc | gcc | gtc | gag | 816 |
| Leu | Ala | Arg | Leu | Lys | Ala | Glu | Glu | Gly | Leu | Leu | Pro | Ala | Ala | Val | Glu | |
| | | | 260 | | | | | 265 | | | | | 270 | | | |

```
gag ctg ttg cgg ttc ctg tcc atc gcg gac ggc ctg ctg cgg gtg gcc      864
Glu Leu Leu Arg Phe Leu Ser Ile Ala Asp Gly Leu Leu Arg Val Ala
            275                 280                 285 atg gcg gac atc gag atc ggc ggg cag gtc atc cgt gcc gac gac ggc      912
Met Ala Asp Ile Glu Ile Gly Gly Gln Val Ile Arg Ala Asp Asp Gly
        290                 295                 300 gtg ctg ttc ccc acc tcg ctg atc aac cgg gac gac ggc gcc tat ccg      960
Val Leu Phe Pro Thr Ser Leu Ile Asn Arg Asp Asp Gly Ala Tyr Pro
305                 310                 315                 320 aca ccg gac gag ctg gac gtc ggc cgg tcc gcc cgc cat cac gtg gcg     1008
Thr Pro Asp Glu Leu Asp Val Gly Arg Ser Ala Arg His His Val Ala
                325                 330                 335 ttc ggg ttc ggc atc cac cag tgc ctg ggg cag aac ctc gcc cgg gcg     1056
Phe Gly Phe Gly Ile His Gln Cys Leu Gly Gln Asn Leu Ala Arg Ala
            340                 345                 350 gag atg gag atc gcg ctg cgc tcg ctg ttc gac cgg atc ccg gat ctg     1104
Glu Met Glu Ile Ala Leu Arg Ser Leu Phe Asp Arg Ile Pro Asp Leu
        355                 360                 365 cga ctc gcc gtg ccg gct gcc gag atc ccc ttc aag ccg ggg gac act     1152
Arg Leu Ala Val Pro Ala Ala Glu Ile Pro Phe Lys Pro Gly Asp Thr
370                 375                 380 ctg caa gga atg atc gaa ctg ccg ctg gcc tgg tag                     1188
Leu Gln Gly Met Ile Glu Leu Pro Leu Ala Trp
385                 390                 395

<210> SEQ ID NO 9
<211> LENGTH: 1439
<212> TYPE: DNA
<213> ORGANISM: Streptmyces phaeochromogenes IFO 12898
<220> FEATURE:
<221> NAME/KEY: CDS
<222> LOCATION: (1)..(1227)
<220> FEATURE:
<221> NAME/KEY: CDS
<222> LOCATION: (1239)..(1439)

<400> SEQUENCE: 9 atg aca gac atg acg gat acg gca gac gtg aag ccg ctc tcg gca ccc       48
Met Thr Asp Met Thr Asp Thr Ala Asp Val Lys Pro Leu Ser Ala Pro
1               5                  10                  15 gtc gcc ttc ccc cag gac cgc acc tgc ccc ttc cag ccc ccg acg ggc       96
Val Ala Phe Pro Gln Asp Arg Thr Cys Pro Phe Gln Pro Pro Thr Gly
            20                  25                  30 tac gac ccc ctg cgt gag gcc cgg ccg ctc gcc cgc gtg acc ctc tac      144
Tyr Asp Pro Leu Arg Glu Ala Arg Pro Leu Ala Arg Val Thr Leu Tyr
        35                  40                  45 gac ggc cgg gcc atc tgg ctg gtc acc ggc cgt gac ctg gcc cgc agc      192
Asp Gly Arg Ala Ile Trp Leu Val Thr Gly Arg Asp Leu Ala Arg Ser
    50                  55                  60 ctg ctc gcc gat tcc cgc ctg tcg tcc gac cgc ctg cgc ccc ggc ttc      240
Leu Leu Ala Asp Ser Arg Leu Ser Ser Asp Arg Leu Arg Pro Gly Phe
65                  70                  75                  80 ccg gcc acc tcg ccg cgc atc gtg gcg ttc cgc gac cgc cgg gcc gcc      288
Pro Ala Thr Ser Pro Arg Ile Val Ala Phe Arg Asp Arg Arg Ala Ala
                85                  90                  95 ctg ctg aac gtc gac gac ccc gag cac cac acc cag cgg cgg atg ctg      336
Leu Leu Asn Val Asp Asp Pro Glu His His Thr Gln Arg Arg Met Leu
            100                 105                 110 gtc ccg agc ttc acc ctc aag cgc gcc gcc gcg ttg cgg ccg gcc atc      384
Val Pro Ser Phe Thr Leu Lys Arg Ala Ala Ala Leu Arg Pro Ala Ile
        115                 120                 125 cag cgg atc gtc gac gaa tgc atc gac gcg atg ctc gcg aag ggc ccg      432
```

```
      Gln Arg Ile Val Asp Glu Cys Ile Asp Ala Met Leu Ala Lys Gly Pro
              130                 135                 140 ccc gcc gag ttg gtg aac gcc ttc gcg ctc ccc gtt ccc tcg atg gtg        480
Pro Ala Glu Leu Val Asn Ala Phe Ala Leu Pro Val Pro Ser Met Val
145                 150                 155                 160 atc tgc gaa ctg ctc ggt gtc ccg tac gcc gat cac gag ttc ttc gag        528
Ile Cys Glu Leu Leu Gly Val Pro Tyr Ala Asp His Glu Phe Phe Glu
                165                 170                 175 gag cag tcc cgt cgg ctg ctg cgc ggc cgg gac gtg gac gag gtg cgg        576
Glu Gln Ser Arg Arg Leu Leu Arg Gly Arg Asp Val Asp Glu Val Arg
            180                 185                 190 gac gcg cgg gac cag ctc gac tgc tac ctc ggg gcg ctg atc gac cgc        624
Asp Ala Arg Asp Gln Leu Asp Cys Tyr Leu Gly Ala Leu Ile Asp Arg
        195                 200                 205 aag tcc gag tcg tcc gtc ggt gac ggt gtc ctc gac gcc ctg gtc cac        672
Lys Ser Glu Ser Ser Val Gly Asp Gly Val Leu Asp Ala Leu Val His
210                 215                 220 gag cag ttg cgc gag ggc gcg gtg gac cgg cag gag gcc atc tcg ctg        720
Glu Gln Leu Arg Glu Gly Ala Val Asp Arg Gln Glu Ala Ile Ser Leu
225                 230                 235                 240 gcc acg atc ctg ctg gtc gcc ggc cac gag acc acc gcc aac atg atc        768
Ala Thr Ile Leu Leu Val Ala Gly His Glu Thr Thr Ala Asn Met Ile
                245                 250                 255 tcg ctg ggc act tac acc ctg ctc caa cac ccc gag cga ctg gcg gag        816
Ser Leu Gly Thr Tyr Thr Leu Leu Gln His Pro Glu Arg Leu Ala Glu
            260                 265                 270 ttg cgg gac gac ccg tcg ctg tgg ccc gcc gcc gtc gac gag ttg atg        864
Leu Arg Asp Asp Pro Ser Leu Trp Pro Ala Ala Val Asp Glu Leu Met
        275                 280                 285 cgg atg ctg tcc atc gcg gac ggg ctg atg cgg cag gcc acg gag gac        912
Arg Met Leu Ser Ile Ala Asp Gly Leu Met Arg Gln Ala Thr Glu Asp
290                 295                 300 atc gag gtg gcc ggg acg acg atc cgc gcc ggt gag ggc gtg gtc ttc        960
Ile Glu Val Ala Gly Thr Thr Ile Arg Ala Gly Glu Gly Val Val Phe
305                 310                 315                 320 gcg acc tcg gtc atc aac cgc gac ggg gag gtc tac gcc gaa ccc gac       1008
Ala Thr Ser Val Ile Asn Arg Asp Gly Glu Val Tyr Ala Glu Pro Asp
                325                 330                 335 gcc ctc gac tgg cac cgg ccc acc cgc cat cac gtg gcg ttc ggc ttc       1056
Ala Leu Asp Trp His Arg Pro Thr Arg His His Val Ala Phe Gly Phe
            340                 345                 350 ggc atc cac cag tgt ctc ggc cag aac ctg gcc cgt gcc gag atg gag       1104
Gly Ile His Gln Cys Leu Gly Gln Asn Leu Ala Arg Ala Glu Met Glu
        355                 360                 365 atc gcc ctg cgt tcc ctg ttc gag cgg gtg ccc ggg ctg cgc ctc gac       1152
Ile Ala Leu Arg Ser Leu Phe Glu Arg Val Pro Gly Leu Arg Leu Asp
370                 375                 380 att gcg ccg gac gcg gtc cgc ttc aaa ccg ggc gac acg atc cag gga       1200
Ile Ala Pro Asp Ala Val Arg Phe Lys Pro Gly Asp Thr Ile Gln Gly
385                 390                 395                 400 atg ctg gat ctg ccc gtg gcc tgg tag ggggtccact c atg cac atc gac      1250
Met Leu Asp Leu Pro Val Ala Trp                 Met His Ile Asp
                405                                     410 atc gac acg gac gtg tgc atc ggc gcc ggc cag tgc gcg ctg tcc gcc       1298
Ile Asp Thr Asp Val Cys Ile Gly Ala Gly Gln Cys Ala Leu Ser Ala
            415                 420                 425 ccg gcc gtc ttc acg cag gac gac gac ggc ttc agc acc ctc ctg ccc       1346
Pro Ala Val Phe Thr Gln Asp Asp Asp Gly Phe Ser Thr Leu Leu Pro
        430                 435                 440 gga cag gag gac agc ggc gac ccg atg gtc cgg gag gcg gcc cga gcc       1394
```

```
Gly Gln Glu Asp Ser Gly Asp Pro Met Val Arg Glu Ala Ala Arg Ala
445                 450                 455                 460 tgc ccg gtc ggt gcc atc aag gtc tcg gaa acc gcg cga ccg tga         1439
Cys Pro Val Gly Ala Ile Lys Val Ser Glu Thr Ala Arg Pro
                465                 470

<210> SEQ ID NO 10
<211> LENGTH: 1415
<212> TYPE: DNA
<213> ORGANISM: Saccharopolyspora taberi JCM 9383t
<220> FEATURE:
<221> NAME/KEY: CDS
<222> LOCATION: (1)..(1206)
<220> FEATURE:
<221> NAME/KEY: CDS
<222> LOCATION: (1218)..(1415)

<400> SEQUENCE: 10 atg ccg gca tct tct gaa gct ctg acc tat ccg atc ccc cgg acc tgt         48
Met Pro Ala Ser Ser Glu Ala Leu Thr Tyr Pro Ile Pro Arg Thr Cys
1               5                   10                  15 ccg tac tcg ccg ccc gac tcc tac gcc gaa ctc cgg cgc gag cag ccg         96
Pro Tyr Ser Pro Pro Asp Ser Tyr Ala Glu Leu Arg Arg Glu Gln Pro
                20                  25                  30 gtc cgc cgg gtg ccg acg ctg gcg gga ggc agc gtg tgg ctg gtg tcg        144
Val Arg Arg Val Pro Thr Leu Ala Gly Gly Ser Val Trp Leu Val Ser
            35                  40                  45 cgg cac gag gac gtg cgc gcg gtc ctc agc gac ccg cgg atg agc tcc        192
Arg His Glu Asp Val Arg Ala Val Leu Ser Asp Pro Arg Met Ser Ser
        50                  55                  60 gac cgc cgc aag ccc ggg ttc ccg cgg ctc gtg ccg ggg cag agc gac        240
Asp Arg Arg Lys Pro Gly Phe Pro Arg Leu Val Pro Gly Gln Ser Asp
65                  70                  75                  80 ctg atc ttc agc tcc aag ccg tcg atg atc ggc atg gac ggg cgc gag        288
Leu Ile Phe Ser Ser Lys Pro Ser Met Ile Gly Met Asp Gly Arg Glu
                85                  90                  95 cac tcg gcg gcc cgg cgg gcg gtt ctc ggt gag ttc acc gtc cgg cgg        336
His Ser Ala Ala Arg Arg Ala Val Leu Gly Glu Phe Thr Val Arg Arg
            100                 105                 110 atc aac gcg ctg cgc ccg cgc gtg cag gag atc gtc gac gag gcc atc        384
Ile Asn Ala Leu Arg Pro Arg Val Gln Glu Ile Val Asp Glu Ala Ile
        115                 120                 125 gac gcg atg ctg gcc gcg ggg ggg ccg gtc gac ctg gtg cgg atg ctc        432
Asp Ala Met Leu Ala Ala Gly Gly Pro Val Asp Leu Val Arg Met Leu
    130                 135                 140 tcg ctt ccg gtg ccg tcg ctg gtg atc tgc gag ctg ctc ggc gtt ccc        480
Ser Leu Pro Val Pro Ser Leu Val Ile Cys Glu Leu Leu Gly Val Pro
145                 150                 155                 160 tac gcc gac cac gag ttc ttc cag cag cgc agc ggc cgc atc atc agc        528
Tyr Ala Asp His Glu Phe Phe Gln Gln Arg Ser Gly Arg Ile Ile Ser
                165                 170                 175 cgg gcg acg ccg ggg gcc gag cgg gag gag gcg ttc ttc gaa ctc cgc        576
Arg Ala Thr Pro Gly Ala Glu Arg Glu Glu Ala Phe Phe Glu Leu Arg
            180                 185                 190 gcc tac ctg tcg gat ctg gtc gcg gac aag gtc cgc gca ccg ggc gac        624
Ala Tyr Leu Ser Asp Leu Val Ala Asp Lys Val Arg Ala Pro Gly Asp
        195                 200                 205 gac ctg ctc ggc agg cag gtg gcc aag cag cgg gcc gag ggc gag gtc        672
Asp Leu Leu Gly Arg Gln Val Ala Lys Gln Arg Ala Glu Gly Glu Val
    210                 215                 220 gac cag gag gcg ctg gtc agc ctc gcg ttc ctg ctg ctg gtc gcc ggg        720
Asp Gln Glu Ala Leu Val Ser Leu Ala Phe Leu Leu Leu Val Ala Gly
225                 230                 235                 240
```

```
cac gag acc acc gcg aac atg atc tcg ctt ggt agc ctg gcg ctg ctg        768
His Glu Thr Thr Ala Asn Met Ile Ser Leu Gly Ser Leu Ala Leu Leu
                245                 250                 255 gac gat tcc gcc cgg tgg gcg gag atc gcc gcg gat ccg gcg aag acg        816
Asp Asp Ser Ala Arg Trp Ala Glu Ile Ala Ala Asp Pro Ala Lys Thr
            260                 265                 270 ccc ggc gcg gtg gag gag atg ctg cgg ttc ttc tcg atc gtc gac aac        864
Pro Gly Ala Val Glu Glu Met Leu Arg Phe Phe Ser Ile Val Asp Asn
        275                 280                 285 gcg acc gcg cgc acc gcg acc gag gac gtg gag atc ggc ggc gtg gtc        912
Ala Thr Ala Arg Thr Ala Thr Glu Asp Val Glu Ile Gly Gly Val Val
    290                 295                 300 atc ggg gag ggc gac ggg gtg atc gcg atg ggc tat tcg gcc aac cac        960
Ile Gly Glu Gly Asp Gly Val Ile Ala Met Gly Tyr Ser Ala Asn His
305                 310                 315                 320 gac ccc gag gtc ttc gac cgc ccc ggg gac ctc gac ttc tcc cgg gcc       1008
Asp Pro Glu Val Phe Asp Arg Pro Gly Asp Leu Asp Phe Ser Arg Ala
                325                 330                 335 gcc cgc cag cac gtc gcc ttc ggc ttc ggc gcg cac cag tgc ctg ggc       1056
Ala Arg Gln His Val Ala Phe Gly Phe Gly Ala His Gln Cys Leu Gly
            340                 345                 350 cag aac ctc gcg cgg gtg gag ttg cag atc gtc ttc gac acg ctg gtg       1104
Gln Asn Leu Ala Arg Val Glu Leu Gln Ile Val Phe Asp Thr Leu Val
        355                 360                 365 cgg cgg atc ccg gac ctg cgg ctg gcg gtc ggc ttc gac gac atc cgg       1152
Arg Arg Ile Pro Asp Leu Arg Leu Ala Val Gly Phe Asp Asp Ile Arg
    370                 375                 380 ttc aag gag gag tcg gcg atc tac gga atc cac gaa ctg atg gtc act       1200
Phe Lys Glu Glu Ser Ala Ile Tyr Gly Ile His Glu Leu Met Val Thr
385                 390                 395                 400 tgg tga ggagagtcgg g atg agg atc cag gcg gac gtg gag cgc tgc gtc      1250
Trp             Met Arg Ile Gln Ala Asp Val Glu Arg Cys Val
                                405                 410 gga gcg ggt cag tgc gtg ctc gcc gcg gac gcg ctg ttc gac cag cgc       1298
Gly Ala Gly Gln Cys Val Leu Ala Ala Asp Ala Leu Phe Asp Gln Arg
            415                 420                 425 gac gac gac ggc acc gtg gtg gtg ctc gcg acc gag gtc ggc gac ggg       1346
Asp Asp Asp Gly Thr Val Val Val Leu Ala Thr Glu Val Gly Asp Gly
        430                 435                 440 gac gcc gac gcg gtc cgg gac gcg gtg acg ctc tgc ccg tcg ggc gtg       1394
Asp Ala Asp Ala Val Arg Asp Ala Val Thr Leu Cys Pro Ser Gly Val
445                 450                 455                 460 ttg tcg ctc gtg gag gac tga                                           1415
Leu Ser Leu Val Glu Asp
                465

<210> SEQ ID NO 11
<211> LENGTH: 1418
<212> TYPE: DNA
<213> ORGANISM: Streptmyces testaceus ATCC 21469
<220> FEATURE:
<221> NAME/KEY: CDS
<222> LOCATION: (1)..(1188)
<220> FEATURE:
<221> NAME/KEY: CDS
<222> LOCATION: (1224)..(1418)

<400> SEQUENCE: 11 atg acc gaa gcc atc gcg tat ttc cag gac cgc acc tgc ccc tac cac         48
Met Thr Glu Ala Ile Ala Tyr Phe Gln Asp Arg Thr Cys Pro Tyr His
1               5                   10                  15 ccg ccg gcc ggc tat cag ccg ctg cgt gac gca ggc ccg ctg gcc cat         96
```

```
                Pro Pro Ala Gly Tyr Gln Pro Leu Arg Asp Ala Gly Pro Leu Ala His
                            20                  25                  30 gtc acc ctc tac gac ggc cgc aag gtg tgg gcg gtg acc ggc cac acc        144
Val Thr Leu Tyr Asp Gly Arg Lys Val Trp Ala Val Thr Gly His Thr
         35                  40                  45 gag gcg cgg gcg ctg ctg agc gac ccg cgg ctg tcc tcc gac cgg cag        192
Glu Ala Arg Ala Leu Leu Ser Asp Pro Arg Leu Ser Ser Asp Arg Gln
 50                  55                  60 aac ccg gcc ttc ccg gcg ccg ttc gcc cgc ttc gcg gcg ctg cgc cag        240
Asn Pro Ala Phe Pro Ala Pro Phe Ala Arg Phe Ala Ala Leu Arg Gln
 65                  70                  75                  80 gtc agg tcg ccg ctg atc ggc gtg gac gac ccc gag cac aac acc cag        288
Val Arg Ser Pro Leu Ile Gly Val Asp Asp Pro Glu His Asn Thr Gln
                 85                  90                  95 cgc cgg atg ctg atc ccc agc ttc agc gtc aag cgg acc gcg gcg ctg        336
Arg Arg Met Leu Ile Pro Ser Phe Ser Val Lys Arg Thr Ala Ala Leu
                100                 105                 110 cgg ccg cag atc cag cag atc gtc gac ggg ctg ctg gac cgg atg ctg        384
Arg Pro Gln Ile Gln Gln Ile Val Asp Gly Leu Leu Asp Arg Met Leu
            115                 120                 125 gcg cag ggg ccg ccc gcc gag ctg gtc tcc gcg ttc gcg ctg ccg gtg        432
Ala Gln Gly Pro Pro Ala Glu Leu Val Ser Ala Phe Ala Leu Pro Val
        130                 135                 140 ccc tcg atg gtg atc tgc tcg ctg ctc ggc gtc ccc tac tcc gac cac        480
Pro Ser Met Val Ile Cys Ser Leu Leu Gly Val Pro Tyr Ser Asp His
145                 150                 155                 160 gag ttc ttc gag gag gcc tcc cgc cgg ctc ctg cgc agc cgg acg gcc        528
Glu Phe Phe Glu Glu Ala Ser Arg Arg Leu Leu Arg Ser Arg Thr Ala
                165                 170                 175 gag gag gcg gag gag gcc cgc ctc cgg ctg gag gac tac ttc gac gag        576
Glu Glu Ala Glu Glu Ala Arg Leu Arg Leu Glu Asp Tyr Phe Asp Glu
            180                 185                 190 ctg atc gcc cac aag gag aag acc ccg cgc gag ggc ctg ctc gac gag        624
Leu Ile Ala His Lys Glu Lys Thr Pro Arg Glu Gly Leu Leu Asp Glu
        195                 200                 205 ctg gtc cac gac gag ctg cgc acc ggc gcc ctg gag cgc gag gat ctg        672
Leu Val His Asp Glu Leu Arg Thr Gly Ala Leu Glu Arg Glu Asp Leu
    210                 215                 220 gtc cgg ctc gcg atg atc ctg ctg gtg gcc ggc cac gag acc acc gcc        720
Val Arg Leu Ala Met Ile Leu Leu Val Ala Gly His Glu Thr Thr Ala
225                 230                 235                 240 aac atg atc tcg ctc ggc acc ttc acc ctg ctg gag cac ccc gga cag        768
Asn Met Ile Ser Leu Gly Thr Phe Thr Leu Leu Glu His Pro Gly Gln
                245                 250                 255 ctg gcc cgg ctg aag gcc gag gag ggg ctg ctg ccg gcc gcc gtc gag        816
Leu Ala Arg Leu Lys Ala Glu Glu Gly Leu Leu Pro Ala Ala Val Glu
            260                 265                 270 gag ctg ttg cgg ttc ctg tcc atc gcg gac ggc ctg ctg cgg gtg gcc        864
Glu Leu Leu Arg Phe Leu Ser Ile Ala Asp Gly Leu Leu Arg Val Ala
        275                 280                 285 atg gcg gac atc gag atc ggc ggg cag gtc atc cgt gcc gac gac ggc        912
Met Ala Asp Ile Glu Ile Gly Gly Gln Val Ile Arg Ala Asp Asp Gly
    290                 295                 300 gtg ctg ttc ccc acc tcg ctg atc aac cgg gac gac ggc gcc tat ccg        960
Val Leu Phe Pro Thr Ser Leu Ile Asn Arg Asp Asp Gly Ala Tyr Pro
305                 310                 315                 320 aca ccg gac gag ctg gac gtc ggc cgg tcc gcc cgc cat cac gtg gcg       1008
Thr Pro Asp Glu Leu Asp Val Gly Arg Ser Ala Arg His His Val Ala
                325                 330                 335 ttc ggg ttc ggc atc cac cag tgc ctg ggg cag aac ctc gcc cgg gcg       1056
Phe Gly Phe Gly Ile His Gln Cys Leu Gly Gln Asn Leu Ala Arg Ala
```

```
                Phe Gly Phe Gly Ile His Gln Cys Leu Gly Gln Asn Leu Ala Arg Ala
                            340                 345                 350 gag atg gag atc gcg ctg cgc tcg ctg ttc gac cgg atc ccg gat ctg              1104
Glu Met Glu Ile Ala Leu Arg Ser Leu Phe Asp Arg Ile Pro Asp Leu
            355                 360                 365 cga ctc gcc gtg ccg gct gcc gag atc ccc ttc aag ccg ggg gac act              1152
Arg Leu Ala Val Pro Ala Ala Glu Ile Pro Phe Lys Pro Gly Asp Thr
        370                 375                 380 ctg caa gga atg atc gaa ctg ccg ctg gcc tgg tag ccgcggtgca                   1198
Leu Gln Gly Met Ile Glu Leu Pro Leu Ala Trp
385                 390                 395 cccggccgaa cgaaggggtt ttgga atg cgg atc acc atc gac acc gac gtc             1250
                             Met Arg Ile Thr Ile Asp Thr Asp Val
                                                     400 tgc atc ggc gcc ggc cag tgc gcg ctg acc gcg ccc ggg gtg ttc acc              1298
Cys Ile Gly Ala Gly Gln Cys Ala Leu Thr Ala Pro Gly Val Phe Thr
405                 410                 415                 420 cag gac gac gac ggc ttc agc gag ctg ctg ccc ggc cgc gag gac ggc              1346
Gln Asp Asp Asp Gly Phe Ser Glu Leu Leu Pro Gly Arg Glu Asp Gly
                425                 430                 435 gcg ggc gac ccg atg ctg cgg gag gcc gtg cgt gcc tgc ccc gtg cag              1394
Ala Gly Asp Pro Met Leu Arg Glu Ala Val Arg Ala Cys Pro Val Gln
            440                 445                 450 gcc atc acc gtc gcg gac gac tga                                              1418
Ala Ile Thr Val Ala Asp Asp
        455

<210> SEQ ID NO 12
<211> LENGTH: 66
<212> TYPE: PRT
<213> ORGANISM: Streptmyces phaeochromogenes IFO 12898

<400> SEQUENCE: 12

Met His Ile Asp Ile Asp Thr Asp Val Cys Ile Gly Ala Gly Gln Cys
1               5                   10                  15

Ala Leu Ser Ala Pro Ala Val Phe Thr Gln Asp Asp Asp Gly Phe Ser
            20                  25                  30

Thr Leu Leu Pro Gly Gln Glu Asp Ser Gly Asp Pro Met Val Arg Glu
        35                  40                  45

Ala Ala Arg Ala Cys Pro Val Gly Ala Ile Lys Val Ser Glu Thr Ala
    50                  55                  60

Arg Pro
65

<210> SEQ ID NO 13
<211> LENGTH: 65
<212> TYPE: PRT
<213> ORGANISM: Saccharopolyspora taberi JCM 9383t

<400> SEQUENCE: 13

Met Arg Ile Gln Ala Asp Val Glu Arg Cys Val Gly Ala Gly Gln Cys
1               5                   10                  15

Val Leu Ala Ala Asp Ala Leu Phe Asp Gln Arg Asp Asp Gly Thr
            20                  25                  30

Val Val Val Leu Ala Thr Glu Val Gly Asp Gly Asp Ala Asp Ala Val
        35                  40                  45

Arg Asp Ala Val Thr Leu Cys Pro Ser Gly Ala Leu Ser Leu Val Glu
    50                  55                  60

Asp
65
```

<210> SEQ ID NO 14
<211> LENGTH: 64
<212> TYPE: PRT
<213> ORGANISM: Streptmyces testaceus ATCC 21469

<400> SEQUENCE: 14

```
Met Arg Ile Thr Ile Asp Thr Asp Val Cys Ile Gly Ala Gly Gln Cys
 1               5                  10                  15

Ala Leu Thr Ala Pro Gly Val Phe Thr Gln Asp Asp Asp Gly Phe Ser
            20                  25                  30

Glu Leu Leu Pro Gly Arg Glu Asp Gly Ala Gly Asp Pro Met Leu Arg
        35                  40                  45

Glu Ala Val Arg Ala Cys Pro Val Gln Ala Ile Thr Val Ala Asp Asp
    50                  55                  60
```

<210> SEQ ID NO 15
<211> LENGTH: 201
<212> TYPE: DNA
<213> ORGANISM: Streptmyces phaeochromogenes IFO 12898
<220> FEATURE:
<221> NAME/KEY: CDS
<222> LOCATION: (1)..(201)

<400> SEQUENCE: 15

```
atg cac atc gac atc gac acg gac gtg tgc atc ggc gcc ggc cag tgc      48
Met His Ile Asp Ile Asp Thr Asp Val Cys Ile Gly Ala Gly Gln Cys
 1               5                  10                  15 gcg ctg tcc gcc ccg gcc gtc ttc acg cag gac gac gac ggc ttc agc      96
Ala Leu Ser Ala Pro Ala Val Phe Thr Gln Asp Asp Asp Gly Phe Ser
            20                  25                  30 acc ctc ctg ccc gga cag gag gac agc ggc gac ccg atg gtc cgg gag     144
Thr Leu Leu Pro Gly Gln Glu Asp Ser Gly Asp Pro Met Val Arg Glu
        35                  40                  45 gcg gcc cga gcc tgc ccg gtc ggt gcc atc aag gtc tcg gaa acc gcg     192
Ala Ala Arg Ala Cys Pro Val Gly Ala Ile Lys Val Ser Glu Thr Ala
    50                  55                  60 cga ccg tga                                                          201
Arg Pro
 65
```

<210> SEQ ID NO 16
<211> LENGTH: 198
<212> TYPE: DNA
<213> ORGANISM: Saccharopolyspora taberi JCM 9383t
<220> FEATURE:
<221> NAME/KEY: CDS
<222> LOCATION: (1)..(198)

<400> SEQUENCE: 16

```
atg agg atc cag gcg gac gtg gag cgc tgc gtc gga gcg ggt cag tgc      48
Met Arg Ile Gln Ala Asp Val Glu Arg Cys Val Gly Ala Gly Gln Cys
 1               5                  10                  15 gtg ctc gcc gcg gac gcg ctg ttc gac cag cgc gac gac gac ggc acc      96
Val Leu Ala Ala Asp Ala Leu Phe Asp Gln Arg Asp Asp Asp Gly Thr
            20                  25                  30 gtg gtg gtg ctc gcg acc gag gtc ggc gac ggg gac gcc gac gcg gtc     144
Val Val Val Leu Ala Thr Glu Val Gly Asp Gly Asp Ala Asp Ala Val
        35                  40                  45 cgg gac gcg gtg acg ctc tgc ccg tcg ggc gcg ttg tcg ctc gtg gag     192
Arg Asp Ala Val Thr Leu Cys Pro Ser Gly Ala Leu Ser Leu Val Glu
    50                  55                  60 gac tga                                                              198
```

Asp
65

<210> SEQ ID NO 17
<211> LENGTH: 195
<212> TYPE: DNA
<213> ORGANISM: Streptmyces testaceus ATCC 21469
<220> FEATURE:
<221> NAME/KEY: CDS
<222> LOCATION: (1)..(195)

<400> SEQUENCE: 17

```
atg cgg atc acc atc gac acc gac gtc tgc atc ggc gcc ggc cag tgc      48
Met Arg Ile Thr Ile Asp Thr Asp Val Cys Ile Gly Ala Gly Gln Cys
1               5                   10                  15 gcg ctg acc gcg ccc ggg gtg ttc acc cag gac gac gac ggc ttc agc      96
Ala Leu Thr Ala Pro Gly Val Phe Thr Gln Asp Asp Asp Gly Phe Ser
            20                  25                  30 gag ctg ctg ccc ggc cgc gag gac ggc gcg ggc gac ccg atg ctg cgg     144
Glu Leu Leu Pro Gly Arg Glu Asp Gly Ala Gly Asp Pro Met Leu Arg
        35                  40                  45 gag gcc gtg cgt gcc tgc ccc gtg cag gcc atc acc gtc gcg gac gac     192
Glu Ala Val Arg Ala Cys Pro Val Gln Ala Ile Thr Val Ala Asp Asp
    50                  55                  60 tga                                                                  195
```

<210> SEQ ID NO 18
<211> LENGTH: 23
<212> TYPE: PRT
<213> ORGANISM: Streptmyces phaeochromogenes IFO 12898

<400> SEQUENCE: 18

Thr Asp Met Thr Asp Thr Ala Asp Val Lys Pro Leu Ser Ala Pro Val
1               5                   10                  15

Ala Phe Pro Gln Asp Arg Thr
            20

<210> SEQ ID NO 19
<211> LENGTH: 7
<212> TYPE: PRT
<213> ORGANISM: Streptmyces phaeochromogenes IFO 12898

<400> SEQUENCE: 19

Val Thr Leu Tyr Asp Gly Arg
1               5

<210> SEQ ID NO 20
<211> LENGTH: 19
<212> TYPE: PRT
<213> ORGANISM: Saccharopolyspora taberi JCM 9383T

<400> SEQUENCE: 20

Pro Ala Ser Ser Glu Ala Leu Thr Tyr Pro Ile Pro Arg Thr Cys Pro
1               5                   10                  15

Tyr Ser Pro

<210> SEQ ID NO 21
<211> LENGTH: 8
<212> TYPE: PRT
<213> ORGANISM: Saccharopolyspora taberi JCM 9383T

<400> SEQUENCE: 21

Gly Ala Val Glu Glu Met Leu Arg
1               5

<210> SEQ ID NO 22
<211> LENGTH: 19
<212> TYPE: PRT
<213> ORGANISM: Streptomyces griseolus ATCC11796

<400> SEQUENCE: 22

Thr Asp Thr Ala Thr Thr Pro Gln Thr Thr Asp Ala Pro Ala Phe Pro
 1               5                  10                  15

Ser Asn Arg

<210> SEQ ID NO 23
<211> LENGTH: 15
<212> TYPE: PRT
<213> ORGANISM: Streptomyces griseolus ATCC11796

<400> SEQUENCE: 23

Arg Ser Cys Pro Tyr Gln Leu Pro Asp Gly Tyr Ala Gln Leu Arg
 1               5                  10                  15

<210> SEQ ID NO 24
<211> LENGTH: 15
<212> TYPE: PRT
<213> ORGANISM: Streptomyces griseolus ATCC11796

<400> SEQUENCE: 24

Asp Thr Pro Gly Pro Leu His Arg Val Thr Leu Tyr Asp Gly Arg
 1               5                  10                  15

<210> SEQ ID NO 25
<211> LENGTH: 7
<212> TYPE: PRT
<213> ORGANISM: Streptomyces griseolus ATCC11796

<400> SEQUENCE: 25

Gln Ala Trp Val Val Thr Lys
 1               5

<210> SEQ ID NO 26
<211> LENGTH: 11
<212> TYPE: PRT
<213> ORGANISM: Streptomyces griseolus ATCC11796

<400> SEQUENCE: 26

Thr Asp Asp Asn Phe Pro Ala Thr Ser Pro Arg
 1               5                  10

<210> SEQ ID NO 27
<211> LENGTH: 17
<212> TYPE: PRT
<213> ORGANISM: Streptomyces griseolus ATCC11796

<400> SEQUENCE: 27

Glu Ser Pro Gln Ala Phe Ile Gly Leu Asp Pro Pro Glu His Gly Thr
 1               5                  10                  15

Arg

<210> SEQ ID NO 28
<211> LENGTH: 9
<212> TYPE: PRT
<213> ORGANISM: Streptomyces griseolus ATCC11796

<400> SEQUENCE: 28

Met Thr Ile Ser Glu Phe Thr Val Lys

<210> SEQ ID NO 29
<211> LENGTH: 14
<212> TYPE: PRT
<213> ORGANISM: Streptomyces griseolus ATCC11796

<400> SEQUENCE: 29

Leu Val Gln Ser Thr Asp Ala Gln Ser Ala Leu Thr Ala Arg
1               5                   10

<210> SEQ ID NO 30
<211> LENGTH: 12
<212> TYPE: PRT
<213> ORGANISM: Streptomyces griseolus ATCC11796

<400> SEQUENCE: 30

Ser Leu Val Pro Gly Ala Val Glu Glu Leu Leu Arg
1               5                   10

<210> SEQ ID NO 31
<211> LENGTH: 11
<212> TYPE: PRT
<213> ORGANISM: Streptomyces griseolus ATCC11796

<400> SEQUENCE: 31

Tyr Leu Ala Ile Ala Asp Ile Ala Gly Gly Arg
1               5                   10

<210> SEQ ID NO 32
<211> LENGTH: 14
<212> TYPE: PRT
<213> ORGANISM: Streptomyces griseolus ATCC11796

<400> SEQUENCE: 32

Ala Gly Glu Gly Val Ile Val Val Asn Ser Ile Ala Asn Arg
1               5                   10

<210> SEQ ID NO 33
<211> LENGTH: 15
<212> TYPE: PRT
<213> ORGANISM: Streptomyces griseolus ATCC11796

<400> SEQUENCE: 33

Asp Gly Thr Val Tyr Glu Asp Pro Asp Ala Leu Asp Ile His Arg
1               5                   10                  15

<210> SEQ ID NO 34
<211> LENGTH: 13
<212> TYPE: PRT
<213> ORGANISM: Streptomyces griseolus ATCC11796

<400> SEQUENCE: 34

Leu Glu Leu Glu Val Ile Leu Asn Ala Leu Met Asp Arg
1               5                   10

<210> SEQ ID NO 35
<211> LENGTH: 32
<212> TYPE: DNA
<213> ORGANISM: Artificial Sequence
<220> FEATURE:
<223> OTHER INFORMATION: Designed oligonucleotide primer for PCR
<220> FEATURE:
<221> NAME/KEY: modified_base
<222> LOCATION: (27)
<223> OTHER INFORMATION: a, t, c or g

```
<400> SEQUENCE: 35
acsgayatga csgayacsgc sgaygtnaag cc                              32

<210> SEQ ID NO 36
<211> LENGTH: 21
<212> TYPE: DNA
<213> ORGANISM: Artificial Sequence
<220> FEATURE:
<223> OTHER INFORMATION: Designed oligonucleotide primer for PCR

<400> SEQUENCE: 36
vcgsccgtcg tagagcgtca c                                         21

<210> SEQ ID NO 37
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 37
atatgaccga taccgcggat gtgaagccgc tct                            33

<210> SEQ ID NO 38
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 38
aacaatttca cacaggaaac agctatgacc                                30

<210> SEQ ID NO 39
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 39
ctggaagggg caggtgcggt cctgggggaa                                30

<210> SEQ ID NO 40
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 40
cagtcacgac gttgtaaaac gacggccagt                                30

<210> SEQ ID NO 41
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 41
cttcccccag gaccgcacct gccccttcca                                30

<210> SEQ ID NO 42
<211> LENGTH: 33
<212> TYPE: DNA
```

```
<213> ORGANISM: Artificial Sequence
<220> FEATURE:
<223> OTHER INFORMATION: Designed oligonucleotide primer for PCR

<400> SEQUENCE: 42
tgcggtcctg ggggaaggcg acgggtgccg aga                                    33

<210> SEQ ID NO 43
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 43
acgaatgcat cgacgcgatg ct                                                22

<210> SEQ ID NO 44
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 44
agttggtgaa cgccttcgcg ct                                                22

<210> SEQ ID NO 45
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 45
cctcgatggt gatctgcgaa ct                                                22

<210> SEQ ID NO 46
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 46
acttacaccc tgctccaaca                                                   20

<210> SEQ ID NO 47
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 47
acgagttgat gcggatgctg tccat                                             25

<210> SEQ ID NO 48
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 48
tctccgagcg cgaataccgt ga                                                22
```

```
<210> SEQ ID NO 49
<211> LENGTH: 23
<212> TYPE: DNA
<213> ORGANISM: Artificial Sequence
<220> FEATURE:
<223> OTHER INFORMATION: Designed oligonucleotide primer for PCR

<400> SEQUENCE: 49
ttcgacctgg acgcgctcgt cat                                              23

<210> SEQ ID NO 50
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 50
tttccgagac cttgatggca ccga                                             24

<210> SEQ ID NO 51
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 51
ctcatatgac agacatgacg gatacggca                                        29

<210> SEQ ID NO 52
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 52
gaagcttcta ccaggccacg ggcagatcca                                       30

<210> SEQ ID NO 53
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 53
aaagctttca cggtcgcgcg gtttccga                                         28

<210> SEQ ID NO 54
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 54
gaggcsctsa cstatccgat                                                  20

<210> SEQ ID NO 55
<211> LENGTH: 18
<212> TYPE: DNA
<213> ORGANISM: Artificial Sequence
<220> FEATURE:
<223> OTHER INFORMATION: Designed oligonucleotide primer for PCR
```

```
<400> SEQUENCE: 55
catctcctcc accgcgcc                                                    18

<210> SEQ ID NO 56
<211> LENGTH: 22
<212> TYPE: DNA
<213> ORGANISM: Artificial Sequence
<220> FEATURE:
<223> OTHER INFORMATION: Designed oligonucleotide primer for PCR

<400> SEQUENCE: 56
gtgccgcgac accagccaca cg                                               22

<210> SEQ ID NO 57
<211> LENGTH: 17
<212> TYPE: DNA
<213> ORGANISM: Artificial Sequence
<220> FEATURE:
<223> OTHER INFORMATION: Designed oligonucleotide primer for PCR

<400> SEQUENCE: 57
caggaaacag ctatgac                                                     17

<210> SEQ ID NO 58
<211> LENGTH: 23
<212> TYPE: DNA
<213> ORGANISM: Artificial Sequence
<220> FEATURE:
<223> OTHER INFORMATION: Designed oligonucleotide primer for PCR

<400> SEQUENCE: 58
tcgacctggt gcggatgctc tcg                                              23

<210> SEQ ID NO 59
<211> LENGTH: 17
<212> TYPE: DNA
<213> ORGANISM: Artificial Sequence
<220> FEATURE:
<223> OTHER INFORMATION: Designed oligonucleotide primer for PCR

<400> SEQUENCE: 59
gttttcccag tcacgac                                                     17

<210> SEQ ID NO 60
<211> LENGTH: 23
<212> TYPE: DNA
<213> ORGANISM: Artificial Sequence
<220> FEATURE:
<223> OTHER INFORMATION: Designed oligonucleotide primer for PCR

<400> SEQUENCE: 60
catgatctcg cttggtagcc tgg                                              23

<210> SEQ ID NO 61
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 61
cccatatgcc ggcatcttct gaagctctg                                        29

<210> SEQ ID NO 62
<211> LENGTH: 32
<212> TYPE: DNA
```

<213> ORGANISM: Artificial Sequence
<220> FEATURE:
<223> OTHER INFORMATION: Designed oligonucleotide primer for PCR

<400> SEQUENCE: 62
gaagctttca ccaagtgacc atcagttcgt gg                                32

<210> SEQ ID NO 63
<211> LENGTH: 31
<212> TYPE: DNA
<213> ORGANISM: Artificial Sequence
<220> FEATURE:
<223> OTHER INFORMATION: Designed oligonucleotide primer for PCR

<400> SEQUENCE: 63
ctaagctttc agtcctccac gagcgacaac a                                 31

<210> SEQ ID NO 64
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 64
agtgcctggg ccagaacctc                                              20

<210> SEQ ID NO 65
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 65
cgggaggaac tcgtgaccga agccatcgcg                                   30

<210> SEQ ID NO 66
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 66
gagggcgccg gctcagtcgt ccgcgacggt gat                               33

<210> SEQ ID NO 67
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 67
caggaaacag ctatgaccat gattacgcca                                   30

<210> SEQ ID NO 68
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 68
tgtaaaacga cggccagtga attgtaatac                                   30

-continued

<210> SEQ ID NO 69
<211> LENGTH: 1418
<212> TYPE: DNA
<213> ORGANISM: Streptmyces testaceus ATCC 21469
<220> FEATURE:
<221> NAME/KEY: CDS
<222> LOCATION: (1)..(1188)
<220> FEATURE:
<221> NAME/KEY: CDS
<222> LOCATION: (1224)..(1418)

<400> SEQUENCE: 69

```
gtg acc gaa gcc atc gcg tat ttc cag gac cgc acc tgc ccc tac cac      48
Val Thr Glu Ala Ile Ala Tyr Phe Gln Asp Arg Thr Cys Pro Tyr His
 1               5                  10                  15 ccg ccg gcc ggc tat cag ccg ctg cgt gac gca ggc ccg ctg gcc cat      96
Pro Pro Ala Gly Tyr Gln Pro Leu Arg Asp Ala Gly Pro Leu Ala His
             20                  25                  30 gtc acc ctc tac gac ggc cgc aag gtg tgg gcg gtg acc ggc cac acc     144
Val Thr Leu Tyr Asp Gly Arg Lys Val Trp Ala Val Thr Gly His Thr
         35                  40                  45 gag gcg cgg gcg ctg ctg agc gac ccg cgg ctg tcc tcc gac cgg cag     192
Glu Ala Arg Ala Leu Leu Ser Asp Pro Arg Leu Ser Ser Asp Arg Gln
     50                  55                  60 aac ccg gcc ttc ccg gcg ccg ttc gcc cgc ttc gcg gcg ctg cgc cag     240
Asn Pro Ala Phe Pro Ala Pro Phe Ala Arg Phe Ala Ala Leu Arg Gln
 65                  70                  75                  80 gtc agg tcg ccg ctg atc ggc gtg gac gac ccc gag cac aac acc cag     288
Val Arg Ser Pro Leu Ile Gly Val Asp Asp Pro Glu His Asn Thr Gln
                 85                  90                  95 cgc cgg atg ctg atc ccc agc ttc agc gtc aag cgg acc gcg gcg ctg     336
Arg Arg Met Leu Ile Pro Ser Phe Ser Val Lys Arg Thr Ala Ala Leu
            100                 105                 110 cgg ccg cag atc cag cag atc gtc gac ggg ctg ctg gac cgg atg ctg     384
Arg Pro Gln Ile Gln Gln Ile Val Asp Gly Leu Leu Asp Arg Met Leu
        115                 120                 125 gcg cag ggg ccg ccc gcc gag ctg gtc tcc gcg ttc gcg ctg ccg gtg     432
Ala Gln Gly Pro Pro Ala Glu Leu Val Ser Ala Phe Ala Leu Pro Val
    130                 135                 140 ccc tcg atg gtg atc tgc tcg ctg ctc ggc gtc ccc tac tcc gac cac     480
Pro Ser Met Val Ile Cys Ser Leu Leu Gly Val Pro Tyr Ser Asp His
145                 150                 155                 160 gag ttc ttc gag gag gcc tcc cgc cgg ctc ctg cgc agc cgg acg gcc     528
Glu Phe Phe Glu Glu Ala Ser Arg Arg Leu Leu Arg Ser Arg Thr Ala
                165                 170                 175 gag gag gcg gag gag gcc cgc ctc cgg ctg gag gac tac ttc gac gag     576
Glu Glu Ala Glu Glu Ala Arg Leu Arg Leu Glu Asp Tyr Phe Asp Glu
            180                 185                 190 ctg atc gcc cac aag gag aag acc ccg cgc gag ggc ctg ctc gac gag     624
Leu Ile Ala His Lys Glu Lys Thr Pro Arg Glu Gly Leu Leu Asp Glu
        195                 200                 205 ctg gtc cac gac gag ctg cgc acc ggc gcc ctg gag cgc gag gat ctg     672
Leu Val His Asp Glu Leu Arg Thr Gly Ala Leu Glu Arg Glu Asp Leu
    210                 215                 220 gtc cgg ctc gcg atg atc ctg ctg gtg gcc ggc cac gag acc acc gcc     720
Val Arg Leu Ala Met Ile Leu Leu Val Ala Gly His Glu Thr Thr Ala
225                 230                 235                 240 aac atg atc tcg ctc ggc acc ttc acc ctg ctg gag cac ccc gga cag     768
Asn Met Ile Ser Leu Gly Thr Phe Thr Leu Leu Glu His Pro Gly Gln
                245                 250                 255 ctg gcc cgg ctg aag gcc gag gag ggg ctg ctg ccg gcc gcc gtc gag     816
Leu Ala Arg Leu Lys Ala Glu Glu Gly Leu Leu Pro Ala Ala Val Glu
```

-continued

```
                  260                 265                 270
gag ctg ttg cgg ttc ctg tcc atc gcg gac ggc ctg ctg cgg gtg gcc        864
Glu Leu Leu Arg Phe Leu Ser Ile Ala Asp Gly Leu Leu Arg Val Ala
        275                 280                 285 atg gcg gac atc gag atc ggc ggg cag gtc atc cgt gcc gac gac ggc        912
Met Ala Asp Ile Glu Ile Gly Gly Gln Val Ile Arg Ala Asp Asp Gly
290                 295                 300 gtg ctg ttc ccc acc tcg ctg atc aac cgg gac gac ggc gcc tat ccg        960
Val Leu Phe Pro Thr Ser Leu Ile Asn Arg Asp Asp Gly Ala Tyr Pro
305                 310                 315                 320 aca ccg gac gag ctg gac gtc ggc cgg tcc gcc cgc cat cac gtg gcg       1008
Thr Pro Asp Glu Leu Asp Val Gly Arg Ser Ala Arg His His Val Ala
                325                 330                 335 ttc ggg ttc ggc atc cac cag tgc ctg ggg cag aac ctc gcc cgg gcg       1056
Phe Gly Phe Gly Ile His Gln Cys Leu Gly Gln Asn Leu Ala Arg Ala
        340                 345                 350 gag atg gag atc gcg ctg cgc tcg ctg ttc gac cgg atc ccg gat ctg       1104
Glu Met Glu Ile Ala Leu Arg Ser Leu Phe Asp Arg Ile Pro Asp Leu
355                 360                 365 cga ctc gcc gtg ccg gct gcc gag atc ccc ttc aag ccg ggg gac act       1152
Arg Leu Ala Val Pro Ala Ala Glu Ile Pro Phe Lys Pro Gly Asp Thr
370                 375                 380 ctg caa gga atg atc gaa ctg ccg ctg gcc tgg tag ccgcggtgca            1198
Leu Gln Gly Met Ile Glu Leu Pro Leu Ala Trp
385                 390                 395 cccggccgaa cgaaggggtt ttgga atg cgg atc acc atc gac acc gac gtc       1250
                           Met Arg Ile Thr Ile Asp Thr Asp Val
                                               400 tgc atc ggc gcc ggc cag tgc gcg ctg acc gcg ccc ggg gtg ttc acc       1298
Cys Ile Gly Ala Gly Gln Cys Ala Leu Thr Ala Pro Gly Val Phe Thr
405                 410                 415                 420 cag gac gac gac ggc ttc agc gag ctg ctg ccc ggc cgc gag gac ggc       1346
Gln Asp Asp Asp Gly Phe Ser Glu Leu Leu Pro Gly Arg Glu Asp Gly
                425                 430                 435 gcg ggc gac ccg atg ctg cgg gag gcc gtg cgt gcc tgc ccc gtg cag       1394
Ala Gly Asp Pro Met Leu Arg Glu Ala Val Arg Ala Cys Pro Val Gln
        440                 445                 450 gcc atc acc gtc gcg gac gac tga                                       1418
Ala Ile Thr Val Ala Asp Asp
        455

<210> SEQ ID NO 70
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 70
cgggaggaac atatgaccga agccatcgcg                                       30

<210> SEQ ID NO 71
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 71
gcaaagcttc taccaggcca gcggcagttc gat                                   33

<210> SEQ ID NO 72
```

-continued

```
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 72
gaggaagctt gctcagtcgt ccgcgacggt gat                              33

<210> SEQ ID NO 73
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 73
gtgccctcga tggtgatctg ctcgctgctc                                  30

<210> SEQ ID NO 74
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 74
tcgagggttc atatgaccga gatgacagag                                  30

<210> SEQ ID NO 75
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 75
gatgtggcag atcaccatgg acgggacggg                                  30

<210> SEQ ID NO 76
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 76
cccgtcccgt ccatggtgat ctgccacatg                                  30

<210> SEQ ID NO 77
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 77
ggcaagcttt caccaggtga ccgggagttc gtt                              33

<210> SEQ ID NO 78
<211> LENGTH: 1233
<212> TYPE: DNA
<213> ORGANISM: Streptmyces carbophilus SANK 62585
<220> FEATURE:
<221> NAME/KEY: CDS
<222> LOCATION: (1)..(1233)

<400> SEQUENCE: 78
```

```
atg acc gag atg aca gag aaa gcc acc aca ttc ctc acg tcg cag gag        48
Met Thr Glu Met Thr Glu Lys Ala Thr Thr Phe Leu Thr Ser Gln Glu
 1               5                  10                  15 gca ccg gcc ttc ccg gcg gac cgc aca tgt ccc tac caa cta ccc acg        96
Ala Pro Ala Phe Pro Ala Asp Arg Thr Cys Pro Tyr Gln Leu Pro Thr
             20                  25                  30 gcc tac agt cgg ttg agg gac gag ccg gat gcg ctg cgc ccg gtg acg       144
Ala Tyr Ser Arg Leu Arg Asp Glu Pro Asp Ala Leu Arg Pro Val Thr
         35                  40                  45 ctc tac gac ggc cgc cgc gcc tgg gtg gtg acc aag cac gag gcg gcg       192
Leu Tyr Asp Gly Arg Arg Ala Trp Val Val Thr Lys His Glu Ala Ala
     50                  55                  60 cgg cgg tta ctc gcg gac ccc cgg ctg tcc tcc gac cgc ctg cac gcc       240
Arg Arg Leu Leu Ala Asp Pro Arg Leu Ser Ser Asp Arg Leu His Ala
 65                  70                  75                  80 gac ttc ccc gcc acc tcg cca cgc ttc aag gcg ttc cgg cag ggc agc       288
Asp Phe Pro Ala Thr Ser Pro Arg Phe Lys Ala Phe Arg Gln Gly Ser
                 85                  90                  95 ccc gcg ttc atc ggg atg gat ccc ccc gag cac ggg acg cgt cgc cgc       336
Pro Ala Phe Ile Gly Met Asp Pro Pro Glu His Gly Thr Arg Arg Arg
             100                 105                 110 atg acg atc agc gag ttc acc gtg aag cgc atc aag ggc atg cgc ccg       384
Met Thr Ile Ser Glu Phe Thr Val Lys Arg Ile Lys Gly Met Arg Pro
         115                 120                 125 gac gtc gaa cgc atc gtg cac ggc ttc atc gac gac atg ctc gcc gcg       432
Asp Val Glu Arg Ile Val His Gly Phe Ile Asp Asp Met Leu Ala Ala
130                 135                 140 gga ccc acc gcc gat ctg gtc agc cag ttc gcc ctg ccc gtc ccg tcc       480
Gly Pro Thr Ala Asp Leu Val Ser Gln Phe Ala Leu Pro Val Pro Ser
145                 150                 155                 160 atg gtg atc tgc cac atg ctc ggc gtc ccc tac gcc gac cac gag ttc       528
Met Val Ile Cys His Met Leu Gly Val Pro Tyr Ala Asp His Glu Phe
                 165                 170                 175 ttc cag gac gcg agc aag cgc ctg gtg cag gcg gtg gac gcc gac agt       576
Phe Gln Asp Ala Ser Lys Arg Leu Val Gln Ala Val Asp Ala Asp Ser
             180                 185                 190 gcc gtc gcc gcc cgg gac gac ttc gag cgc tac ctg gac ggg ctg atc       624
Ala Val Ala Ala Arg Asp Asp Phe Glu Arg Tyr Leu Asp Gly Leu Ile
         195                 200                 205 acc aag ctg gag tcc gaa ccc ggg acc ggg ctc ctc ggc aaa ctg gtc       672
Thr Lys Leu Glu Ser Glu Pro Gly Thr Gly Leu Leu Gly Lys Leu Val
     210                 215                 220 acc cac cag ctg gcg gac ggc gag atc gac cgc gcg gag ctg atc tcc       720
Thr His Gln Leu Ala Asp Gly Glu Ile Asp Arg Ala Glu Leu Ile Ser
225                 230                 235                 240 acc gcc ctg ctg ctg ctc gtc gcc ggt cat gag acc acg gcc tcg atg       768
Thr Ala Leu Leu Leu Leu Val Ala Gly His Glu Thr Thr Ala Ser Met
                 245                 250                 255 acc tcg ctc agc gtc atc acc ctg ctc gaa cac ccc gac cag cac gcc       816
Thr Ser Leu Ser Val Ile Thr Leu Leu Glu His Pro Asp Gln His Ala
             260                 265                 270 gcc ctg cgc gcc gac ccg tcc ctc gtg ccc gga gcg gtc gag gaa ctg       864
Ala Leu Arg Ala Asp Pro Ser Leu Val Pro Gly Ala Val Glu Glu Leu
         275                 280                 285 ctg cgc gtc ctg gcc atc gcg gac atc gcg ggc ggc cgc atc gcc acc       912
Leu Arg Val Leu Ala Ile Ala Asp Ile Ala Gly Gly Arg Ile Ala Thr
     290                 295                 300 gcc gac atc gag atc gac gga cag ctc atc cgg gcc ggt gaa gga gtg       960
Ala Asp Ile Glu Ile Asp Gly Gln Leu Ile Arg Ala Gly Glu Gly Val
305                 310                 315                 320
```

```
atc gtc acc aac tcc atc gcc aac cgc gac agt tcg gtg ttc gag aac    1008
Ile Val Thr Asn Ser Ile Ala Asn Arg Asp Ser Ser Val Phe Glu Asn
            325                 330                 335 ccg gac cgc ctc gat gtg cac cgc tcg gca cgc cac cac ctc tcc ttc    1056
Pro Asp Arg Leu Asp Val His Arg Ser Ala Arg His His Leu Ser Phe
        340                 345                 350 ggg tac ggg gtg cac cag tgc ctg ggc cag aac ctg gcc cgc ctc gaa    1104
Gly Tyr Gly Val His Gln Cys Leu Gly Gln Asn Leu Ala Arg Leu Glu
    355                 360                 365 ctc gaa gtc atc ctc acc gtg ttg ttc gac cgc att ccg acc ctg cgc    1152
Leu Glu Val Ile Leu Thr Val Leu Phe Asp Arg Ile Pro Thr Leu Arg
370                 375                 380 ctg gcc gtc ccc gtg gag cag ctg acg ctg cgt ccg ggc acg acg atc    1200
Leu Ala Val Pro Val Glu Gln Leu Thr Leu Arg Pro Gly Thr Thr Ile
385                 390                 395                 400 cag ggc gtc aac gaa ctc ccg gtc acc tgg tga                        1233
Gln Gly Val Asn Glu Leu Pro Val Thr Trp
                405                 410

<210> SEQ ID NO 79
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 79
gccatatgac cgataccgcc acgacgcc                                     28

<210> SEQ ID NO 80
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 80
gcaagctttc accaggtgac cgggagttc                                    29

<210> SEQ ID NO 81
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 81
gcaagcttct attccgtgtc ctcgacga                                     28

<210> SEQ ID NO 82
<211> LENGTH: 20
<212> TYPE: DNA
<213> ORGANISM: Artificial Sequence
<220> FEATURE:
<223> OTHER INFORMATION: Designed oligonucleotide primer for PCR

<400> SEQUENCE: 82
cacggcttcc tcgacgagat                                              20

<210> SEQ ID NO 83
<211> LENGTH: 20
<212> TYPE: DNA
<213> ORGANISM: Artificial Sequence
<220> FEATURE:
<223> OTHER INFORMATION: Designed oligonucleotide primer for PCR
```

<400> SEQUENCE: 83
gtggaggaac tgctccgcta                                              20

<210> SEQ ID NO 84
<211> LENGTH: 1221
<212> TYPE: DNA
<213> ORGANISM: Streptmyces griseolus ATCC 11796
<220> FEATURE:
<221> NAME/KEY: CDS
<222> LOCATION: (1)..(1221)

<400> SEQUENCE: 84

| | | |
|---|---|---|
| atg acc gat acc gcc acg acg ccc cag acc acg gac gca ccc gcc ttc<br>Met Thr Asp Thr Ala Thr Thr Pro Gln Thr Thr Asp Ala Pro Ala Phe<br>1               5                  10                  15 | 48 | |
| ccg agc aac cgg agc tgt ccc tac cag tta ccg gac ggc tac gcc cag<br>Pro Ser Asn Arg Ser Cys Pro Tyr Gln Leu Pro Asp Gly Tyr Ala Gln<br>            20                  25                  30 | 96 | |
| ctc cgg gac acc ccc ggc ccc ctg cac cgg gtg acg ctc tac gac ggc<br>Leu Arg Asp Thr Pro Gly Pro Leu His Arg Val Thr Leu Tyr Asp Gly<br>        35                  40                  45 | 144 | |
| cgt cag gcg tgg gtg gtg acc aag cac gag gcc gcg cgc aaa ctg ctc<br>Arg Gln Ala Trp Val Val Thr Lys His Glu Ala Ala Arg Lys Leu Leu<br>    50                  55                  60 | 192 | |
| ggc gac ccc cgg ctg tcc tcc aac cgg acg gac gac aac ttc ccc gcc<br>Gly Asp Pro Arg Leu Ser Ser Asn Arg Thr Asp Asp Asn Phe Pro Ala<br>65                  70                  75                  80 | 240 | |
| acg tca ccg cgc ttc gag gcc gtc cgg gag agc ccg cag gcg ttc atc<br>Thr Ser Pro Arg Phe Glu Ala Val Arg Glu Ser Pro Gln Ala Phe Ile<br>                85                  90                  95 | 288 | |
| ggc ctg gac ccg ccc gag cac ggc acc cgg cgg cgg atg acg atc agc<br>Gly Leu Asp Pro Pro Glu His Gly Thr Arg Arg Arg Met Thr Ile Ser<br>            100                 105                 110 | 336 | |
| gag ttc acc gtc aag cgg atc aag ggc atg cgc ccc gag gtc gag gag<br>Glu Phe Thr Val Lys Arg Ile Lys Gly Met Arg Pro Glu Val Glu Glu<br>        115                 120                 125 | 384 | |
| gtg gtg cac ggc ttc ctc gac gag atg ctg gcc gcc ggc ccg acc gcc<br>Val Val His Gly Phe Leu Asp Glu Met Leu Ala Ala Gly Pro Thr Ala<br>    130                 135                 140 | 432 | |
| gac ctg gtc agt cag ttc gcg ctg ccg gtg ccc tcc atg gtg atc tgc<br>Asp Leu Val Ser Gln Phe Ala Leu Pro Val Pro Ser Met Val Ile Cys<br>145                 150                 155                 160 | 480 | |
| cga ctc ctc ggc gtg ccc tac gcc gac cac gag ttc ttc cag gac gcg<br>Arg Leu Leu Gly Val Pro Tyr Ala Asp His Glu Phe Phe Gln Asp Ala<br>                165                 170                 175 | 528 | |
| agc aag cgg ctg gtg cag tcc acg gac gcg cag agc gcg ctc acc gcg<br>Ser Lys Arg Leu Val Gln Ser Thr Asp Ala Gln Ser Ala Leu Thr Ala<br>            180                 185                 190 | 576 | |
| cgg aac gac ctc gcg ggt tac ctg gac ggc ctc atc acc cag ttc cag<br>Arg Asn Asp Leu Ala Gly Tyr Leu Asp Gly Leu Ile Thr Gln Phe Gln<br>        195                 200                 205 | 624 | |
| acc gaa ccg ggc gcg ggc ctg gtg ggc gct ctg gtc gcc gac cag ctg<br>Thr Glu Pro Gly Ala Gly Leu Val Gly Ala Leu Val Ala Asp Gln Leu<br>    210                 215                 220 | 672 | |
| gcc aac ggc gag atc gac cgt gag gaa ctg atc tcc acc gcg atg ctg<br>Ala Asn Gly Glu Ile Asp Arg Glu Glu Leu Ile Ser Thr Ala Met Leu<br>225                 230                 235                 240 | 720 | |
| ctc ctc atc gcc ggc cac gag acc acg gcc tcg atg acc tcc ctc agc<br>Leu Leu Ile Ala Gly His Glu Thr Thr Ala Ser Met Thr Ser Leu Ser<br>                245                 250                 255 | 768 | |

-continued

```
gtg atc acc ctg ctg gac cac ccc gag cag tac gcc gcc ctg cgc gcc      816
Val Ile Thr Leu Leu Asp His Pro Glu Gln Tyr Ala Ala Leu Arg Ala
        260                 265                 270 gac cgc agc ctc gtg ccc ggc gcg gtg gag gaa ctg ctc cgc tac ctc      864
Asp Arg Ser Leu Val Pro Gly Ala Val Glu Glu Leu Leu Arg Tyr Leu
    275                 280                 285 gcc atc gcc gac atc gcg ggc ggc cgc gtc gcc acg gcg gac atc gag      912
Ala Ile Ala Asp Ile Ala Gly Gly Arg Val Ala Thr Ala Asp Ile Glu
290                 295                 300 gtc gag ggg cag ctc atc cgg gcc ggc gag ggc gtg atc gtc gtc aac      960
Val Glu Gly Gln Leu Ile Arg Ala Gly Glu Gly Val Ile Val Val Asn
305                 310                 315                 320 tcg ata gcc aac cgg gac ggc acg gtg tac gag gac ccg gac gcc ctc     1008
Ser Ile Ala Asn Arg Asp Gly Thr Val Tyr Glu Asp Pro Asp Ala Leu
                325                 330                 335 gac atc cac cgc tcc gcg cgc cac cac ctc gcc ttc ggc ttc ggc gtg     1056
Asp Ile His Arg Ser Ala Arg His His Leu Ala Phe Gly Phe Gly Val
            340                 345                 350 cac cag tgc ctg ggc cag aac ctc gcc cgg ctg gag ctg gag gtc atc     1104
His Gln Cys Leu Gly Gln Asn Leu Ala Arg Leu Glu Leu Glu Val Ile
        355                 360                 365 ctc aac gcc ctc atg gac cgc gtc ccg acg ctg cga ctg gcc gtc ccc     1152
Leu Asn Ala Leu Met Asp Arg Val Pro Thr Leu Arg Leu Ala Val Pro
    370                 375                 380 gtc gag cag ttg gtg ctg cgg ccg ggt acg acg atc cag ggc gtc aac     1200
Val Glu Gln Leu Val Leu Arg Pro Gly Thr Thr Ile Gln Gly Val Asn
385                 390                 395                 400 gaa ctc ccg gtc acc tgg tga                                          1221
Glu Leu Pro Val Thr Trp
                405

<210> SEQ ID NO 85
<211> LENGTH: 1451
<212> TYPE: DNA
<213> ORGANISM: Streptmyces griseolus ATCC 11796
<220> FEATURE:
<221> NAME/KEY: CDS
<222> LOCATION: (1)..(1221)
<220> FEATURE:
<221> NAME/KEY: CDS
<222> LOCATION: (1242)..(1451)

<400> SEQUENCE: 85 atg acc gat acc gcc acg acg ccc cag acc acg gac gca ccc gcc ttc       48
Met Thr Asp Thr Ala Thr Thr Pro Gln Thr Thr Asp Ala Pro Ala Phe
  1               5                  10                  15 ccg agc aac cgg agc tgt ccc tac cag tta ccg gac ggc tac gcc cag       96
Pro Ser Asn Arg Ser Cys Pro Tyr Gln Leu Pro Asp Gly Tyr Ala Gln
                 20                  25                  30 ctc cgg gac acc ccc ggc ccc ctg cac cgg gtg acg ctc tac gac ggc      144
Leu Arg Asp Thr Pro Gly Pro Leu His Arg Val Thr Leu Tyr Asp Gly
             35                  40                  45 cgt cag gcg tgg gtg gtg acc aag cac gag gcc gcg cgc aaa ctg ctc      192
Arg Gln Ala Trp Val Val Thr Lys His Glu Ala Ala Arg Lys Leu Leu
         50                  55                  60 ggc gac ccc cgg ctg tcc tcc aac cgg acg gac gac aac ttc ccc gcc      240
Gly Asp Pro Arg Leu Ser Ser Asn Arg Thr Asp Asp Asn Phe Pro Ala
 65                  70                  75                  80 acg tca ccg cgc ttc gag gcc gtc cgg gag agc ccg cag gcg ttc atc      288
Thr Ser Pro Arg Phe Glu Ala Val Arg Glu Ser Pro Gln Ala Phe Ile
                 85                  90                  95 ggc ctg gac ccg ccc gag cac ggc acc cgg cgg cgg atg acg atc agc      336
Gly Leu Asp Pro Pro Glu His Gly Thr Arg Arg Arg Met Thr Ile Ser
```

```
            100                 105                 110
gag ttc acc gtc aag cgg atc aag ggc atg cgc ccc gag gtc gag gag    384
Glu Phe Thr Val Lys Arg Ile Lys Gly Met Arg Pro Glu Val Glu Glu
        115                 120                 125 gtg gtg cac ggc ttc ctc gac gag atg ctg gcc gcc ggc ccg acc gcc    432
Val Val His Gly Phe Leu Asp Glu Met Leu Ala Ala Gly Pro Thr Ala
    130                 135                 140 gac ctg gtc agt cag ttc gcg ctg ccg gtg ccc tcc atg gtg atc tgc    480
Asp Leu Val Ser Gln Phe Ala Leu Pro Val Pro Ser Met Val Ile Cys
145                 150                 155                 160 cga ctc ctc ggc gtg ccc tac gcc gac cac gag ttc ttc cag gac gcg    528
Arg Leu Leu Gly Val Pro Tyr Ala Asp His Glu Phe Phe Gln Asp Ala
            165                 170                 175 agc aag cgg ctg gtg cag tcc acg gac gcg cag agc gcg ctc acc gcg    576
Ser Lys Arg Leu Val Gln Ser Thr Asp Ala Gln Ser Ala Leu Thr Ala
        180                 185                 190 cgg aac gac ctc gcg ggt tac ctg gac ggc ctc atc acc cag ttc cag    624
Arg Asn Asp Leu Ala Gly Tyr Leu Asp Gly Leu Ile Thr Gln Phe Gln
    195                 200                 205 acc gaa ccg ggc gcg ggc ctg gtg ggc gct ctg gtc gcc gac cag ctg    672
Thr Glu Pro Gly Ala Gly Leu Val Gly Ala Leu Val Ala Asp Gln Leu
210                 215                 220 gcc aac ggc gag atc gac cgt gag gaa ctg atc tcc acc gcg atg ctg    720
Ala Asn Gly Glu Ile Asp Arg Glu Glu Leu Ile Ser Thr Ala Met Leu
225                 230                 235                 240 ctc ctc atc gcc ggc cac gag acc acg gcc tcg atg acc tcc ctc agc    768
Leu Leu Ile Ala Gly His Glu Thr Thr Ala Ser Met Thr Ser Leu Ser
            245                 250                 255 gtg atc acc ctg ctg gac cac ccc gag cag tac gcc gcc ctg cgc gcc    816
Val Ile Thr Leu Leu Asp His Pro Glu Gln Tyr Ala Ala Leu Arg Ala
        260                 265                 270 gac cgc agc ctc gtg ccc ggc gcg gtg gag gaa ctg ctc cgc tac ctc    864
Asp Arg Ser Leu Val Pro Gly Ala Val Glu Glu Leu Leu Arg Tyr Leu
    275                 280                 285 gcc atc gcc gac atc gcg ggc ggc cgc gtc gcc acg gcg gac atc gag    912
Ala Ile Ala Asp Ile Ala Gly Gly Arg Val Ala Thr Ala Asp Ile Glu
290                 295                 300 gtc gag ggg cag ctc atc cgg gcc ggc gag ggc gtg atc gtc gtc aac    960
Val Glu Gly Gln Leu Ile Arg Ala Gly Glu Gly Val Ile Val Val Asn
305                 310                 315                 320 tcg ata gcc aac cgg gac ggc acg gtg tac gag gac ccg gac gcc ctc   1008
Ser Ile Ala Asn Arg Asp Gly Thr Val Tyr Glu Asp Pro Asp Ala Leu
            325                 330                 335 gac atc cac cgc tcc gcg cgc cac cac ctc gcc ttc ggc ttc ggc gtg   1056
Asp Ile His Arg Ser Ala Arg His His Leu Ala Phe Gly Phe Gly Val
        340                 345                 350 cac cag tgc ctg ggc cag aac ctc gcc cgg ctg gag ctg gag gtc atc   1104
His Gln Cys Leu Gly Gln Asn Leu Ala Arg Leu Glu Leu Glu Val Ile
    355                 360                 365 ctc aac gcc ctc atg gac cgc gtc ccg acg ctg cga ctg gcc gtc ccc   1152
Leu Asn Ala Leu Met Asp Arg Val Pro Thr Leu Arg Leu Ala Val Pro
370                 375                 380 gtc gag cag ttg gtg ctg cgg ccg ggt acg acg atc cag ggc gtc aac   1200
Val Glu Gln Leu Val Leu Arg Pro Gly Thr Thr Ile Gln Gly Val Asn
385                 390                 395                 400 gaa ctc ccg gtc acc tgg tga cgggggagag gggcaaggac atg acc atg cgg   1253
Glu Leu Pro Val Thr Trp                         Met Thr Met Arg
            405                                             410 gtg agt gcg gat cgg acg gtc tgc gtc ggt gcc ggg ctg tgt gcg ctg   1301
Val Ser Ala Asp Arg Thr Val Cys Val Gly Ala Gly Leu Cys Ala Leu
```

| | | | | | | | | | | | | | | | | |
|---|---|---|---|---|---|---|---|---|---|---|---|---|---|---|---|---|
| | | | 415 | | | | 420 | | | | | 425 | | | | |
| acg | gcg | ccg | ggc | gtc | ctc | gac | cag | gac | gac | gac | ggg | atc | gtc | acg | gtg | 1349 |
| Thr | Ala | Pro | Gly | Val | Leu | Asp | Gln | Asp | Asp | Asp | Gly | Ile | Val | Thr | Val | |
| | | | 430 | | | | | 435 | | | | | 440 | | | |
| ctg | acg | gcc | gaa | ccc | gcc | gcc | gac | gac | gac | cgg | cgc | acc | gcg | cgc | gag | 1397 |
| Leu | Thr | Ala | Glu | Pro | Ala | Ala | Asp | Asp | Asp | Arg | Arg | Thr | Ala | Arg | Glu | |
| | | | | 445 | | | | | 450 | | | | | 455 | | |
| gcc | ggc | cat | ctc | tgt | ccg | tcc | ggt | gcg | gtc | cgc | gtc | gtc | gag | gac | acg | 1445 |
| Ala | Gly | His | Leu | Cys | Pro | Ser | Gly | Ala | Val | Arg | Val | Val | Glu | Asp | Thr | |
| | | 460 | | | | | 465 | | | | | 470 | | | | |
| gaa | tag | | | | | | | | | | | | | | | 1451 |
| Glu | | | | | | | | | | | | | | | | |
| 475 | | | | | | | | | | | | | | | | |

<210> SEQ ID NO 86
<211> LENGTH: 37
<212> TYPE: DNA
<213> ORGANISM: Artificial Sequence
<220> FEATURE:
<223> OTHER INFORMATION: Designed oligonucleotide primer for PCR

<400> SEQUENCE: 86
gaaagcttag aggatccaaa tggcttcctc aatgatc           37

<210> SEQ ID NO 87
<211> LENGTH: 38
<212> TYPE: DNA
<213> ORGANISM: Artificial Sequence
<220> FEATURE:
<223> OTHER INFORMATION: Designed oligonucleotide primer for PCR

<400> SEQUENCE: 87
cgaggtaccg caagtaggaa agagtcatga acttcttc           38

<210> SEQ ID NO 88
<211> LENGTH: 248
<212> TYPE: DNA
<213> ORGANISM: Glycine max (L.) Merrill
<220> FEATURE:
<221> NAME/KEY: CDS
<222> LOCATION: (20)..(220)

<400> SEQUENCE: 88

| | | | | | | | | | | | |
|---|---|---|---|---|---|---|---|---|---|---|---|
| gaaagcttag aggatccaa | atg | gct | tcc | tca | atg | atc | tcc | tcc | cca | gct | gtt | 52 |
| | Met | Ala | Ser | Ser | Met | Ile | Ser | Ser | Pro | Ala | Val | |
| | 1 | | | | 5 | | | | | 10 | | |
| acc | acc | gtc | aac | cgt | gcc | ggt | gcc | ggc | atg | gtt | gct | cca | ttc | acc | ggc | 100 |
| Thr | Thr | Val | Asn | Arg | Ala | Gly | Ala | Gly | Met | Val | Ala | Pro | Phe | Thr | Gly | |
| | | | 15 | | | | | 20 | | | | | 25 | | | |
| ctc | aaa | tcc | atg | gct | ggc | ttc | ccc | acg | agg | aag | acc | aac | aat | gac | att | 148 |
| Leu | Lys | Ser | Met | Ala | Gly | Phe | Pro | Thr | Arg | Lys | Thr | Asn | Asn | Asp | Ile | |
| | 30 | | | | | 35 | | | | | 40 | | | | | |
| acc | tcc | att | gct | agc | aac | ggt | gga | aga | gta | caa | tgc | atg | cag | gtg | tgg | 196 |
| Thr | Ser | Ile | Ala | Ser | Asn | Gly | Gly | Arg | Val | Gln | Cys | Met | Gln | Val | Trp | |
| | 45 | | | | | 50 | | | | | 55 | | | | | |
| cca | cca | att | ggc | aag | aag | aag | ttc | atgactcttt cctacttgcg gtacctcg | | | | | | | | 248 |
| Pro | Pro | Ile | Gly | Lys | Lys | Lys | Phe | | | | | | | | | |
| 60 | | | | | 65 | | | | | | | | | | | |

<210> SEQ ID NO 89
<211> LENGTH: 9
<212> TYPE: DNA
<213> ORGANISM: Artificial Sequence
<220> FEATURE:
<223> OTHER INFORMATION: Designed oligonucleotide linker for

```
                construction of expression vector

<400> SEQUENCE: 89 gcggccgcg                                                                  9

<210> SEQ ID NO 90
<211> LENGTH: 13
<212> TYPE: DNA
<213> ORGANISM: Artificial Sequence
<220> FEATURE:
<223> OTHER INFORMATION: Designed oligonucleotide linker for
      construction of expression vector

<400> SEQUENCE: 90
aattcgcggc cgc                                                            13

<210> SEQ ID NO 91
<211> LENGTH: 13
<212> TYPE: DNA
<213> ORGANISM: Artificial Sequence
<220> FEATURE:
<223> OTHER INFORMATION: Designed oligonucleotide linker for
      construction of expression vector

<400> SEQUENCE: 91
agcttgcggc cgc                                                            13

<210> SEQ ID NO 92
<211> LENGTH: 11
<212> TYPE: DNA
<213> ORGANISM: Artificial Sequence
<220> FEATURE:
<223> OTHER INFORMATION: Designed oligonucleotide linker for
      construction of expression vector

<400> SEQUENCE: 92
tagcggccgc a                                                              11

<210> SEQ ID NO 93
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 93
tcatgcatga cagacatgac ggatacggca                                          30

<210> SEQ ID NO 94
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 94
ggagctccta ccaggccacg ggcagatcca                                          30

<210> SEQ ID NO 95
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 95
ggagctctca cggtcgcgcg gtttccgag a                                         30
```

-continued

<210> SEQ ID NO 96
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 96
tctttcatga cagacatgac ggatacggca                                    30

<210> SEQ ID NO 97
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 97
ggagctctca cggtcgcgcg gtttccgag a                                   30

<210> SEQ ID NO 98
<211> LENGTH: 19
<212> TYPE: DNA
<213> ORGANISM: Artificial Sequence
<220> FEATURE:
<223> OTHER INFORMATION: Designed oligonucleotide linker for
      construction of expression vector

<400> SEQUENCE: 98
agcttgcggc cgcgaattc                                                19

<210> SEQ ID NO 99
<211> LENGTH: 19
<212> TYPE: DNA
<213> ORGANISM: Artificial Sequence
<220> FEATURE:
<223> OTHER INFORMATION: Designed oligonucleotide linker for
      construction of expression vector

<400> SEQUENCE: 99
agctgaattc gcggccgca                                                19

<210> SEQ ID NO 100
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 100
ccaagcttgc atgccggcat cttctgaagc tctga                              35

<210> SEQ ID NO 101
<211> LENGTH: 35
<212> TYPE: DNA
<213> ORGANISM: Artificial Sequence
<220> FEATURE:
<223> OTHER INFORMATION: Designed oligonucleotide primer for PCR

<400> SEQUENCE: 101
gaagcttggt acctcaccaa gtgaccatca gttcg                              35

<210> SEQ ID NO 102
<211> LENGTH: 29
<212> TYPE: DNA
<213> ORGANISM: Artificial Sequence

```
<220> FEATURE:
<223> OTHER INFORMATION: Designed oligonucleotide primer for PCR

<400> SEQUENCE: 102
aatgcatgac cgaagccatc gcgtatttc                                    29

<210> SEQ ID NO 103
<211> LENGTH: 24
<212> TYPE: DNA
<213> ORGANISM: Artificial Sequence
<220> FEATURE:
<223> OTHER INFORMATION: Designed oligonucleotide primer for PCR

<400> SEQUENCE: 103
ggggtaccgc ggctaccagg ccag                                         24

<210> SEQ ID NO 104
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 104
aactcatgac cgaagccatc gcgtatttc                                    29

<210> SEQ ID NO 105
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 105
ggtccacata tgcacatcga catcgacacg                                   30

<210> SEQ ID NO 106
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 106
agagtccata tgaggatcca ggcggacgtg                                   30

<210> SEQ ID NO 107
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 107
ggttttcata tgcggatcac catcgacacc                                   30

<210> SEQ ID NO 108
<211> LENGTH: 411
<212> TYPE: PRT
<213> ORGANISM: Streptomyces achromogenes IFO 12735

<400> SEQUENCE: 108

Met Thr Gln Ser Ala Asp Ala Val Pro Glu Ala Glu Ala Pro Pro Val
 1               5                  10                  15

Gln Phe Pro Leu Arg Arg Thr Cys Pro Phe Ala Glu Pro Pro Glu Tyr
             20                  25                  30
```

```
Ala Gly Leu Arg Ala Asp Thr Pro Val Ala Arg Ala Ala Leu Lys Val
         35                  40                  45

Asn Gly Lys Pro Ala Trp Leu Val Thr Arg His Glu His Val Arg Gln
 50                  55                  60

Val Leu Gly Asp Ser Arg Val Ser Ser Asn Leu Lys Leu Pro Gly Tyr
 65                  70                  75                  80

Pro His Gln Phe His Ile Pro Glu Glu Leu Leu Ala Gln Val Arg Leu
                 85                  90                  95

Met Met Leu Asn Met Asp Pro Pro Glu His Thr Ala His Arg Arg Met
            100                 105                 110

Leu Ile Pro Glu Phe Thr Ala Arg Arg Val Arg Glu Leu Arg Pro Arg
        115                 120                 125

Ile Gln Gln Ile Val Asp Glu His Val Asp Ala Met Leu Ala Ala Gly
    130                 135                 140

Gly Pro Val Asp Leu Val Thr Ala Leu Ala Leu Pro Val Pro Ser Leu
145                 150                 155                 160

Val Ile Cys Glu Leu Leu Gly Val Pro Tyr Glu Asp His Ala Arg Phe
                165                 170                 175

Glu Glu Trp Ser Ala Ala Leu Met Asn His Asp Leu Ser Pro Gln Glu
            180                 185                 190

Tyr Gly Ala Ala Val Gln Ala Leu Asp Thr Tyr Leu Asp Gln Leu Val
        195                 200                 205

Thr Leu Lys Glu Asn Glu Pro Gly Asp Asp Leu Ile Ser Arg Phe Leu
    210                 215                 220

Glu Lys Asn Arg Thr Glu Arg Val Ala Asp His Thr Asp Val Val Thr
225                 230                 235                 240

Met Ala Arg Leu Met Leu Val Gly Gly His Glu Thr Thr Ala Asn Met
                245                 250                 255

Ile Ala Leu Gly Val Leu Ala Leu Leu Arg His Pro Glu Gln Met Ala
            260                 265                 270

Glu Leu Arg Ala Asp Pro Ala Leu Leu Pro Asn Ala Val Glu Glu Leu
        275                 280                 285

Leu Arg Val Phe Ser Ile Ser Asp Ser Gly Thr Ala Arg Val Ala Val
    290                 295                 300

Ala Asp Ile Glu Val Gly Asp Val Thr Ile Arg Ala Gly Glu Gly Ile
305                 310                 315                 320

Leu Ala Leu Asn Asn Ala Ala Asp His Asp Glu Ser Val Phe Pro Asp
                325                 330                 335

Pro Asp Thr Leu Asp Ile His Arg Lys Glu Ala Arg Ser His Leu Ala
            340                 345                 350

Phe Gly Tyr Gly Val His Gln Cys Ile Gly Ala Asn Leu Ala Arg Ala
        355                 360                 365

Glu Leu Glu Ala Val Tyr Gly Thr Leu Leu Arg Val Pro Gly Leu
    370                 375                 380

Arg Leu Ala Ala Glu Pro Glu Asp Leu Arg Phe Lys Asp Asp Ala Met
385                 390                 395                 400

Val Tyr Gly Val Tyr Glu Leu Pro Val Thr Trp
                405                 410

<210> SEQ ID NO 109
<211> LENGTH: 1236
<212> TYPE: DNA
<213> ORGANISM: Streptomyces achromogenes IFO 12735
<220> FEATURE:
<221> NAME/KEY: CDS
```

<222> LOCATION: (1)..(1236)

<400> SEQUENCE: 109

| | | |
|---|---|---|
| atg acc cag tcc gcc gac gcc gta ccc gag gcg gaa gca ccg ccg gtg<br>Met Thr Gln Ser Ala Asp Ala Val Pro Glu Ala Glu Ala Pro Pro Val<br>1                 5                      10                  15 | 48 |
| cag ttc ccc ctg cgg cgc acc tgt ccg ttc gcc gag ccg ccc gag tac<br>Gln Phe Pro Leu Arg Arg Thr Cys Pro Phe Ala Glu Pro Pro Glu Tyr<br>                 20                   25                    30 | 96 |
| gcc ggg ctg cgc gcc gac aca ccc gtc gcc cgc gcc gcc ctg aaa gtg<br>Ala Gly Leu Arg Ala Asp Thr Pro Val Ala Arg Ala Ala Leu Lys Val<br>35                      40                    45 | 144 |
| aac ggc aag ccg gcc tgg ctg gtc acc cgg cac gag cac gtc cgg cag<br>Asn Gly Lys Pro Ala Trp Leu Val Thr Arg His Glu His Val Arg Gln<br>  50                    55                    60 | 192 |
| gtg ctg ggc gac agc cgg gtc agc tcc aac ctc aaa ctg ccg ggc tat<br>Val Leu Gly Asp Ser Arg Val Ser Ser Asn Leu Lys Leu Pro Gly Tyr<br>65                      70                   75                  80 | 240 |
| ccc cac cag ttc cac atc ccc gag gaa ctg ctg gcg cag gtc cgg ctg<br>Pro His Gln Phe His Ile Pro Glu Glu Leu Leu Ala Gln Val Arg Leu<br>                 85                    90                    95 | 288 |
| atg atg ctg aac atg gac ccg ccg gaa cac acc gcc cac cgg cgc atg<br>Met Met Leu Asn Met Asp Pro Pro Glu His Thr Ala His Arg Arg Met<br>                100                  105                110 | 336 |
| ctg ata ccg gag ttc acg gcc cgc cgg gtg cgg gag ttg cgc ccg cgg<br>Leu Ile Pro Glu Phe Thr Ala Arg Arg Val Arg Glu Leu Arg Pro Arg<br>115                    120                  125 | 384 |
| atc cag cag atc gtg gac gag cac gtg gac gcg atg ctg gcc gcg ggc<br>Ile Gln Gln Ile Val Asp Glu His Val Asp Ala Met Leu Ala Ala Gly<br>130                    135                  140 | 432 |
| ggc ccg gtg gac ctg gtc acc gcc ctc gcg ctg ccg gtg ccc tcg ctg<br>Gly Pro Val Asp Leu Val Thr Ala Leu Ala Leu Pro Val Pro Ser Leu<br>145                    150                  155                160 | 480 |
| gtg atc tgc gaa ctg ctc ggc gtg ccc tac gag gac cac gcg cgg ttc<br>Val Ile Cys Glu Leu Leu Gly Val Pro Tyr Glu Asp His Ala Arg Phe<br>                165                  170                175 | 528 |
| gag gag tgg tcg gcg gcg ctg atg aac cac gat ctg agc ccg cag gag<br>Glu Glu Trp Ser Ala Ala Leu Met Asn His Asp Leu Ser Pro Gln Glu<br>            180                  185                190 | 576 |
| tac ggg gcg gcc gtg cag gcc ctg gac acg tac ctc gac cag ctc gtc<br>Tyr Gly Ala Ala Val Gln Ala Leu Asp Thr Tyr Leu Asp Gln Leu Val<br>          195                  200                  205 | 624 |
| acc ctg aag gag aac gag ccg ggc gac gac ctc atc agc cgc ttc ctg<br>Thr Leu Lys Glu Asn Glu Pro Gly Asp Asp Leu Ile Ser Arg Phe Leu<br>210                    215                  220 | 672 |
| gag aag aac cgc acc gag cgg gtc gcc gac cac acc gat gtg gtg acg<br>Glu Lys Asn Arg Thr Glu Arg Val Ala Asp His Thr Asp Val Val Thr<br>225                    230                  235                240 | 720 |
| atg gcc cgg ctg atg ctg gtc ggc ggc cac gag acc acc gcc aac atg<br>Met Ala Arg Leu Met Leu Val Gly Gly His Glu Thr Thr Ala Asn Met<br>                245                  250                255 | 768 |
| atc gcc ctc ggg gtg ctg gcc ctg ctg cgg cac ccg gag cag atg gcc<br>Ile Ala Leu Gly Val Leu Ala Leu Leu Arg His Pro Glu Gln Met Ala<br>            260                  265                270 | 816 |
| gag ttg cgg gcc gat ccg gcc ctg ctg ccg aac gcc gtg gag gag ttg<br>Glu Leu Arg Ala Asp Pro Ala Leu Leu Pro Asn Ala Val Glu Glu Leu<br>          275                  280                  285 | 864 |
| ctg cgc gtc ttc tcc atc tcc gac tcc ggc acc gcc cgg gtc gcg gtg<br>Leu Arg Val Phe Ser Ile Ser Asp Ser Gly Thr Ala Arg Val Ala Val<br>290                    295                  300 | 912 |

```
gcg gac atc gag gtc ggt gac gtc acc atc cgc gcg ggt gag ggc atc        960
Ala Asp Ile Glu Val Gly Asp Val Thr Ile Arg Ala Gly Glu Gly Ile
305                 310                 315                 320 ctc gcc ctg aac aac gcg gcc gac cac gac gag tcg gtc ttc ccg gac       1008
Leu Ala Leu Asn Asn Ala Ala Asp His Asp Glu Ser Val Phe Pro Asp
                325                 330                 335 ccg gac acc ctc gac atc cac cgc aag gag gcc cgc tcc cac ctg gcc       1056
Pro Asp Thr Leu Asp Ile His Arg Lys Glu Ala Arg Ser His Leu Ala
            340                 345                 350 ttc ggc tac ggc gtc cac cag tgc atc ggc gcc aac ctc gcc cgg gcg       1104
Phe Gly Tyr Gly Val His Gln Cys Ile Gly Ala Asn Leu Ala Arg Ala
        355                 360                 365 gag ctg gag gcg gtc tac ggc acg ctg ctg cgc cgc gtc ccc ggc ctg       1152
Glu Leu Glu Ala Val Tyr Gly Thr Leu Leu Arg Arg Val Pro Gly Leu
    370                 375                 380 cgg ctg gcc gcc gag ccg gag gac ctg cgg ttc aag gac gac gcc atg       1200
Arg Leu Ala Ala Glu Pro Glu Asp Leu Arg Phe Lys Asp Asp Ala Met
385                 390                 395                 400 gtc tac ggc gtc tac gaa ctc ccc gtc acc tgg tga                       1236
Val Tyr Gly Val Tyr Glu Leu Pro Val Thr Trp
                405                 410

<210> SEQ ID NO 110
<211> LENGTH: 1454
<212> TYPE: DNA
<213> ORGANISM: Streptomyces achromogenes IFO 12735
<220> FEATURE:
<221> NAME/KEY: CDS
<222> LOCATION: (1)..(1236)
<220> FEATURE:
<221> NAME/KEY: CDS
<222> LOCATION: (1263)..(1454)

<400> SEQUENCE: 110 atg acc cag tcc gcc gac gcc gta ccc gag gcg gaa gca ccg ccg gtg         48
Met Thr Gln Ser Ala Asp Ala Val Pro Glu Ala Glu Ala Pro Pro Val
1               5                   10                  15 cag ttc ccc ctg cgg cgc acc tgt ccg ttc gcc gag ccg ccc gag tac         96
Gln Phe Pro Leu Arg Arg Thr Cys Pro Phe Ala Glu Pro Pro Glu Tyr
                20                  25                  30 gcc ggg ctg cgc gcc gac aca ccc gtc gcc cgc gcc gcc ctg aaa gtg        144
Ala Gly Leu Arg Ala Asp Thr Pro Val Ala Arg Ala Ala Leu Lys Val
            35                  40                  45 aac ggc aag ccg gcc tgg ctg gtc acc cgg cac gag cac gtc cgg cag        192
Asn Gly Lys Pro Ala Trp Leu Val Thr Arg His Glu His Val Arg Gln
        50                  55                  60 gtg ctg ggc gac agc cgg gtc agc tcc aac ctc aaa ctg ccg ggc tat        240
Val Leu Gly Asp Ser Arg Val Ser Ser Asn Leu Lys Leu Pro Gly Tyr
65                  70                  75                  80 ccc cac cag ttc cac atc ccc gag gaa ctg ctg gcg cag gtc cgg ctg        288
Pro His Gln Phe His Ile Pro Glu Glu Leu Leu Ala Gln Val Arg Leu
                85                  90                  95 atg atg ctg aac atg gac ccg ccg gaa cac acc gcc cac cgg cgc atg        336
Met Met Leu Asn Met Asp Pro Pro Glu His Thr Ala His Arg Arg Met
                100                 105                 110 ctg ata ccg gag ttc acg gcc cgc cgg gtg cgg gag ttg cgc ccg cgg        384
Leu Ile Pro Glu Phe Thr Ala Arg Arg Val Arg Glu Leu Arg Pro Arg
            115                 120                 125 atc cag cag atc gtg gac gag cac gtg gac gcg atg ctg gcc gcg ggc        432
Ile Gln Gln Ile Val Asp Glu His Val Asp Ala Met Leu Ala Ala Gly
        130                 135                 140 ggc ccg gtg gac ctg gtc acc gcc ctc gcg ctg ccg gtg ccc tcg ctg        480
Gly Pro Val Asp Leu Val Thr Ala Leu Ala Leu Pro Val Pro Ser Leu
```

```
                 145                 150                 155                 160
gtg atc tgc gaa ctg ctc ggc gtg ccc tac gag gac cac gcg cgg ttc        528
Val Ile Cys Glu Leu Leu Gly Val Pro Tyr Glu Asp His Ala Arg Phe
                165                 170                 175 gag gag tgg tcg gcg gcg ctg atg aac cac gat ctg agc ccg cag gag        576
Glu Glu Trp Ser Ala Ala Leu Met Asn His Asp Leu Ser Pro Gln Glu
            180                 185                 190 tac ggg gcg gcc gtg cag gcc ctg gac acg tac ctc gac cag ctc gtc        624
Tyr Gly Ala Ala Val Gln Ala Leu Asp Thr Tyr Leu Asp Gln Leu Val
        195                 200                 205 acc ctg aag gag aac gag ccg ggc gac gac ctc atc agc cgc ttc ctg        672
Thr Leu Lys Glu Asn Glu Pro Gly Asp Asp Leu Ile Ser Arg Phe Leu
    210                 215                 220 gag aag aac cgc acc gag cgg gtc gcc gac cac acc gat gtg gtg acg        720
Glu Lys Asn Arg Thr Glu Arg Val Ala Asp His Thr Asp Val Val Thr
225                 230                 235                 240 atg gcc cgg ctg atg ctg gtc ggc ggc cac gag acc acc gcg aac atg        768
Met Ala Arg Leu Met Leu Val Gly Gly His Glu Thr Thr Ala Asn Met
                245                 250                 255 atc gcc ctc ggg gtg ctg gcc ctg ctg cgg cac ccg gag cag atg gcc        816
Ile Ala Leu Gly Val Leu Ala Leu Leu Arg His Pro Glu Gln Met Ala
            260                 265                 270 gag ttg cgg gcc gat ccg gcc ctg ctg ccg aac gcc gtg gag gag ttg        864
Glu Leu Arg Ala Asp Pro Ala Leu Leu Pro Asn Ala Val Glu Glu Leu
        275                 280                 285 ctg cgc gtc ttc tcc atc tcc gac tcc ggc acc gcc cgg gtc gcg gtg        912
Leu Arg Val Phe Ser Ile Ser Asp Ser Gly Thr Ala Arg Val Ala Val
    290                 295                 300 gcg gac atc gag gtc ggt gac gtc acc atc cgc gcg ggt gag ggc atc        960
Ala Asp Ile Glu Val Gly Asp Val Thr Ile Arg Ala Gly Glu Gly Ile
305                 310                 315                 320 ctc gcc ctg aac aac gcg gcc gac cac gac gag tcg gtc ttc ccg gac       1008
Leu Ala Leu Asn Asn Ala Ala Asp His Asp Glu Ser Val Phe Pro Asp
                325                 330                 335 ccg gac acc ctc gac atc cac cgc aag gag gcc cgc tcc cac ctg gcc       1056
Pro Asp Thr Leu Asp Ile His Arg Lys Glu Ala Arg Ser His Leu Ala
            340                 345                 350 ttc ggc tac ggc gtc cac cag tgc atc ggc gcc aac ctc gcc cgg gcg       1104
Phe Gly Tyr Gly Val His Gln Cys Ile Gly Ala Asn Leu Ala Arg Ala
        355                 360                 365 gag ctg gag gcg gtc tac ggc acg ctg ctg cgc cgc gtc ccc ggc ctg       1152
Glu Leu Glu Ala Val Tyr Gly Thr Leu Leu Arg Arg Val Pro Gly Leu
    370                 375                 380 cgg ctg gcc gcc gag ccg gag gac ctg cgg ttc aag gac gac gcc atg       1200
Arg Leu Ala Ala Glu Pro Glu Asp Leu Arg Phe Lys Asp Asp Ala Met
385                 390                 395                 400 gtc tac ggc gtc tac gaa ctc ccc gtc acc tgg tga cggccgacgc            1246
Val Tyr Gly Val Tyr Glu Leu Pro Val Thr Trp
                405                 410 gaacggactg cccctg atg cgt gtc tcc gcc gaa cgc gac cgg tgc gtg ggc     1298
                  Met Arg Val Ser Ala Glu Arg Asp Arg Cys Val Gly
                                415                 420 tcc ggc cag tgc gcg ctg ctg agc ccc gag gtg ttc gac cag gac gcc       1346
Ser Gly Gln Cys Ala Leu Leu Ser Pro Glu Val Phe Asp Gln Asp Ala
    425                 430                 435 gac ggc ctg gtc acc ctg ctg agc gag gag ccg gcc gag gag ctg cgc       1394
Asp Gly Leu Val Thr Leu Leu Ser Glu Glu Pro Ala Glu Glu Leu Arg
440                 445                 450                 455 gag cag gtc gct cag gcc gcg gac ctg tgc ccg tcc cgc tcg atc cgc       1442
Glu Gln Val Ala Gln Ala Ala Asp Leu Cys Pro Ser Arg Ser Ile Arg
```

```
                        460             465             470
gtg cac gac tga                                                          1454
Val His Asp <210> SEQ ID NO 111
<211> LENGTH: 63
<212> TYPE: PRT
<213> ORGANISM: Streptomyces achromogenes IFO 12735

<400> SEQUENCE: 111

Met Arg Val Ser Ala Glu Arg Asp Arg Cys Val Gly Ser Gly Gln Cys
  1               5                  10                  15

Ala Leu Leu Ser Pro Glu Val Phe Asp Gln Asp Ala Asp Gly Leu Val
             20                  25                  30

Thr Leu Leu Ser Glu Glu Pro Ala Glu Glu Leu Arg Glu Gln Val Ala
         35                  40                  45

Gln Ala Ala Asp Leu Cys Pro Ser Arg Ser Ile Arg Val His Asp
     50                  55                  60

<210> SEQ ID NO 112
<211> LENGTH: 192
<212> TYPE: DNA
<213> ORGANISM: Streptomyces achromogenes IFO 12735
<220> FEATURE:
<221> NAME/KEY: CDS
<222> LOCATION: (1)..(192)

<400> SEQUENCE: 112 atg cgt gtc tcc gcc gaa cgc gac cgg tgc gtg ggc tcc ggc cag tgc         48
Met Arg Val Ser Ala Glu Arg Asp Arg Cys Val Gly Ser Gly Gln Cys
  1               5                  10                  15 gcg ctg ctg agc ccc gag gtg ttc gac cag gac gcc gac ggc ctg gtc         96
Ala Leu Leu Ser Pro Glu Val Phe Asp Gln Asp Ala Asp Gly Leu Val
             20                  25                  30 acc ctg ctg agc gag gag ccg gcc gag gag ctg cgc gag cag gtc gct        144
Thr Leu Leu Ser Glu Glu Pro Ala Glu Glu Leu Arg Glu Gln Val Ala
         35                  40                  45 cag gcc gcg gac ctg tgc ccg tcc cgc tcg atc cgc gtg cac gac tga        192
Gln Ala Ala Asp Leu Cys Pro Ser Arg Ser Ile Arg Val His Asp
     50                  55                  60

<210> SEQ ID NO 113
<211> LENGTH: 20
<212> TYPE: PRT
<213> ORGANISM: Streptomyces achromogenes IFO 12735

<400> SEQUENCE: 113

Met Thr Gln Ser Ala Asp Ala Val Pro Glu Ala Glu Ala Pro Pro Val
  1               5                  10                  15

Gln Phe Pro Leu
             20

<210> SEQ ID NO 114
<211> LENGTH: 23
<212> TYPE: DNA
<213> ORGANISM: Artificial Sequence
<220> FEATURE:
<223> OTHER INFORMATION: Designed oligonucleotide primer for PCR

<400> SEQUENCE: 114
gacgcsgtsc csgaggcsga agc                                                23

<210> SEQ ID NO 115
```

```
<211> LENGTH: 23
<212> TYPE: DNA
<213> ORGANISM: Artificial Sequence
<220> FEATURE:
<223> OTHER INFORMATION: Designed oligonucleotide primer for PCR

<400> SEQUENCE: 115
gaggcsccsc csgtscagtt ccc                                        23

<210> SEQ ID NO 116
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 116
tcggcgaacg dacaggtgcg ccgca                                      25

<210> SEQ ID NO 117
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 117
ccctcgctgg tgatctgcga actgctc                                    27

<210> SEQ ID NO 118
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 118
agctcgtcac cctgaaggag aacgagc                                    27

<210> SEQ ID NO 119
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 119
accatatgac ccagtccgcc gacgccgt                                   28

<210> SEQ ID NO 120
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 120
gtaagctttc accaggtgac ggggagtt                                   28

<210> SEQ ID NO 121
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 121
```

```
cgaagctttc agtcgtgcac gcggatcg                                              28

<210> SEQ ID NO 122
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 122
ttcctggaga agaaccgcac cgagcgg                                               27

<210> SEQ ID NO 123
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 123
cacccggagc agatggccga gttgcg                                                26

<210> SEQ ID NO 124
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 124
tgmtcggcvt sgacgacccc gagcac                                                26

<210> SEQ ID NO 125
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 125
cgctgccsgt gccstcsatg gtgatctg                                              28

<210> SEQ ID NO 126
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 126
cgctgccggt gccgtcsctg gtgatctg                                              28

<210> SEQ ID NO 127
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 127
ggcgtsccct acgccgacca cgagttcttc                                            30

<210> SEQ ID NO 128
<211> LENGTH: 30
<212> TYPE: DNA
<213> ORGANISM: Artificial Sequence
<220> FEATURE:
```

```
<223> OTHER INFORMATION: Designed oligonucleotide primer for PCR

<400> SEQUENCE: 128
ggcgtsccct acgaggacca cgssttcttc                                   30

<210> SEQ ID NO 129
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 129
aggcactggt gsacsccgaa sccgaagg                                     28

<210> SEQ ID NO 130
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 130
cttcccccag gaccgcacct gccccttcca                                   30

<210> SEQ ID NO 131
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 131
ggatcgtggc cagcgagatg gcctcctgcc                                   30

<210> SEQ ID NO 132
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 132
tttccaggac cgcacctgcc cctaccaccc                                   30

<210> SEQ ID NO 133
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 133
ggatcatcgc gagccggacc agatcctcgc                                   30

<210> SEQ ID NO 134
<211> LENGTH: 72
<212> TYPE: DNA
<213> ORGANISM: Artificial Sequence
<220> FEATURE:
<223> OTHER INFORMATION: Designed oligonucleotide linker for
      construction of expression vector

<400> SEQUENCE: 134
agctattttt taataaaatc aggaggaaaa aacatatgag caagcttggc tgttttggcg    60
gatgagagaa ga                                                      72
```

<210> SEQ ID NO 135
<211> LENGTH: 68
<212> TYPE: DNA
<213> ORGANISM: Artificial Sequence
<220> FEATURE:
<223> OTHER INFORMATION: Designed oligonucleotide linker for
      construction of expression vector

<400> SEQUENCE: 135
tcttctctca tccgccaaaa cagccaagct tgctcatatg ttttttcctc ctgattttat    60
taaaaaat                                                             68

<210> SEQ ID NO 136
<211> LENGTH: 402
<212> TYPE: PRT
<213> ORGANISM: Streptmyces thermocoerulescens IFO 14273t

<400> SEQUENCE: 136

Met Thr Asp Met Thr Glu Thr Pro Thr Val Ala Phe Pro Gln Ser Arg
 1               5                  10                  15

Thr Cys Pro Tyr His Pro Pro Ala Ala Tyr Ala Pro Leu Arg Asp Thr
            20                  25                  30

Arg Pro Leu Ala Arg Ala Arg Leu Tyr Asp Gly Arg Leu Val Trp Thr
        35                  40                  45

Val Thr Gly His Gly Leu Ala Arg Thr Leu Leu Ala Asp Pro Arg Leu
    50                  55                  60

Ser Thr Asp Pro Thr Arg Pro Glu Phe Pro Ala Thr Thr Glu Arg Ile
65                  70                  75                  80

Ala Arg Ile Arg Arg Arg Thr Ala Leu Leu Gly Val Asp Pro
            85                  90                  95

Glu His Arg Val Gln Arg Arg Met Met Val Pro Ser Phe Thr Leu Gln
            100                 105                 110

Arg Ala Thr Ala Leu Arg Pro Arg Ile Gln Arg Val Val Asp Glu Arg
        115                 120                 125

Leu Asp Ala Met Ile Ala Gly Gly Pro Pro Ala Asp Leu Val Thr Ala
    130                 135                 140

Phe Ala Leu Pro Val Pro Ser Met Val Ile Cys Ala Leu Leu Gly Val
145                 150                 155                 160

Pro Tyr Glu Asp His Asp Phe Phe Glu Glu Gln Ser Arg Arg Leu Leu
            165                 170                 175

Arg Gly Pro Thr Ala Glu Asp Ser Met Asp Ala Arg Ala Arg Met Glu
        180                 185                 190

Ala Tyr Phe Asp Glu Leu Ile Asp Arg Lys Gln Arg Gln Asp Ala Pro
    195                 200                 205

Gly Asp Gly Val Leu Asp Glu Leu Val His Gln Arg Leu Ala Ala Gly
210                 215                 220

Glu Leu Asp Arg Glu Gly Leu Ile Ala Met Ala Ile Ile Leu Leu Val
225                 230                 235                 240

Ala Gly His Glu Thr Thr Ala Asn Met Ile Ser Leu Gly Thr Phe Thr
            245                 250                 255

Leu Leu Gly His Pro Glu Arg Leu Ala Glu Leu Arg Ala Asp Pro Asp
        260                 265                 270

Leu Val Pro Ala Ala Val Glu Glu Leu Leu Arg Met Leu Ser Ile Ala
    275                 280                 285

Asp Gly Leu Leu Arg Val Ala Val Glu Asp Ile Glu Val Ala Gly Glu
290                 295                 300

```
Thr Ile Arg Ala Gly Asp Gly Val Ile Phe Ser Thr Ser Val Ile Asn
305                 310                 315                 320

Arg Asp Glu Ala Val Tyr Pro Glu Pro Asp Thr Leu Asp Leu His Arg
            325                 330                 335

Pro Ala Arg His His Val Ala Phe Gly Phe Gly Ile His Gln Cys Leu
            340                 345                 350

Gly Gln Asn Leu Ala Arg Ala Glu Met Glu Ile Ala Leu Arg Thr Leu
        355                 360                 365

Phe Gly Arg Leu Pro Gly Leu Arg Leu Ala Val Pro Pro Glu Glu Ile
    370                 375                 380

Pro Phe Lys Pro Gly Asp Thr Ile Gln Gly Met Leu Glu Leu Pro Val
385                 390                 395                 400

Thr Trp

<210> SEQ ID NO 137
<211> LENGTH: 409
<212> TYPE: PRT
<213> ORGANISM: Streptmyces glomerochromogenes IFO 13673T

<400> SEQUENCE: 137

Met Thr Glu Leu Thr Asp Ile Thr Gly Pro Ala Gly Gln Ala Gln Pro
1               5                   10                  15

Val Ala Phe Pro Gln Asp Arg Thr Cys Pro Tyr His Pro Pro Thr Gly
            20                  25                  30

Tyr Asp Pro Leu Arg Asp Gly Arg Pro Leu Ser Arg Val Thr Leu Tyr
        35                  40                  45

Asp Gly Arg Glu Val Trp Leu Val Thr Ala Gln Ala Thr Ala Arg Ala
    50                  55                  60

Leu Leu Ala Asp Pro Arg Leu Ser Thr Asp Arg Arg Asp Gly Phe
65                  70                  75                  80

Pro Val Pro Ser Pro Arg Phe Glu Ala Gly Arg Asp Arg Lys Leu Ala
            85                  90                  95

Leu Leu Gly Leu Asp Asp Pro Glu His His Gln Gln Arg Arg Met Leu
        100                 105                 110

Ile Pro Ser Phe Thr Val Lys Arg Ala Thr Ala Leu Arg Pro Trp Ile
    115                 120                 125

Gln Arg Ile Val Asp Glu Leu Leu Asp Asp Met Ile Ala Arg Gly Pro
130                 135                 140

Val Ala Asp Leu Val Ser Ala Phe Ala Leu Pro Val Pro Ser Met Val
            150                 155                 160
145

Ile Cys Glu Leu Leu Gly Val Pro Tyr Ala Asp His Glu Phe Phe Glu
            165                 170                 175

Glu Gln Ser Arg Arg Leu Leu Arg Gly Pro Gly Ala Asp Thr Leu
        180                 185                 190

Asp Ala Arg Asp Arg Leu Glu Ala Tyr Leu Gly Glu Leu Ile Asp Ala
    195                 200                 205

Lys Ala Lys Glu Ala Glu Pro Gly Asp Gly Val Leu Asp Asp Leu Val
210                 215                 220

His Asn Arg Leu Arg Ala Gly Glu Leu Asp Arg Thr Asp Leu Val Ser
225                 230                 235                 240

Leu Ala Leu Ile Leu Leu Val Ala Gly His Glu Thr Thr Ala Asn Met
            245                 250                 255

Ile Ser Leu Gly Thr Tyr Thr Leu Leu Gln His Pro Gly Arg Leu Ala
        260                 265                 270
```

```
Glu Leu Arg Ala Asp Pro Thr Val Leu Pro Ala Val Val Glu Glu Leu
    275                 280                 285

Leu Arg Met Leu Ser Ile Ala Glu Gly Leu Gln Arg Leu Ala Leu Glu
    290                 295                 300

Asp Ile Glu Ile Asp Gly Thr Thr Ile Arg Ala Gly Asp Gly Val Leu
305                 310                 315                 320

Phe Ser Thr Ser Val Ile Asn Arg Asp Thr Ala Val Tyr Asp Asp Pro
                325                 330                 335

Asp Asp Leu Asp Phe His Arg Ala Asp Arg His His Val Ala Phe Gly
                340                 345                 350

Phe Gly Ile His Gln Cys Leu Gly Gln Asn Leu Ala Arg Ala Glu Leu
                355                 360                 365

Glu Ile Ala Leu Gly Ser Leu Phe Thr Arg Leu Pro Gly Leu Arg Leu
    370                 375                 380

Ala Ala Pro Ala Glu Glu Ile Pro Phe Lys Pro Gly Asp Thr Ile Gln
385                 390                 395                 400

Gly Met Leu Glu Leu Pro Val Thr Trp
                405

<210> SEQ ID NO 138
<211> LENGTH: 409
<212> TYPE: PRT
<213> ORGANISM: Streptmyces olivochromogenes IFO 12444

<400> SEQUENCE: 138

Met Thr Glu Leu Thr Asp Ile Thr Gly Pro Ala Gly Gln Ala Glu Pro
1               5                   10                  15

Val Ala Phe Pro Gln Asp Arg Thr Cys Pro Tyr His Pro Pro Thr Gly
                20                  25                  30

Tyr Asp Pro Leu Arg Asp Gly Arg Pro Leu Ser Arg Val Thr Leu Tyr
            35                  40                  45

Asp Gly Arg Glu Val Trp Leu Val Thr Ala Gln Ala Thr Ala Arg Ala
        50                  55                  60

Leu Leu Ala Asp Pro Arg Leu Ser Thr Asp Arg Arg Asp Gly Phe
65                  70                  75                  80

Pro Val Pro Ser Pro Arg Phe Glu Ala Gly Arg Asp Arg Lys Leu Ala
                85                  90                  95

Leu Leu Gly Leu Asp Asp Pro Glu His Gln Gln Arg Arg Met Leu
                100                 105                 110

Ile Pro Ser Phe Thr Val Lys Arg Ala Thr Ala Leu Arg Pro Trp Ile
            115                 120                 125

Gln Arg Ile Val Asp Glu Leu Leu Asp Asp Met Ile Ala Arg Gly Pro
        130                 135                 140

Val Ala Asp Leu Val Ser Ala Phe Ala Leu Pro Val Pro Ser Met Val
145                 150                 155                 160

Ile Cys Glu Leu Leu Gly Val Pro Tyr Ala Asp His Glu Phe Phe Glu
                165                 170                 175

Glu Gln Ser Arg Arg Leu Leu Arg Gly Pro Gly Gly Ala Asp Thr Leu
            180                 185                 190

Asp Ala Arg Asp Arg Leu Glu Ala Tyr Leu Gly Glu Leu Ile Asp Ala
        195                 200                 205

Lys Ala Lys Glu Ala Glu Pro Gly Asp Gly Ile Leu Asp Asp Leu Val
    210                 215                 220

His Asn Arg Leu Arg Ala Gly Glu Leu Asp Arg Thr Asp Leu Val Ser
225                 230                 235                 240
```

-continued

```
Leu Ala Leu Ile Leu Leu Val Ala Gly His Glu Thr Thr Ala Asn Met
                245                 250                 255

Ile Ser Leu Gly Thr Tyr Thr Leu Leu Gln His Pro Glu Arg Leu Ala
            260                 265                 270

Glu Leu Arg Ala Asp Pro Thr Val Leu Pro Ala Val Val Glu Glu Leu
        275                 280                 285

Leu Arg Met Leu Ser Ile Ala Glu Gly Leu Gln Arg Val Ala Leu Glu
    290                 295                 300

Asp Ile Glu Ile Asp Gly Thr Thr Ile Arg Ala Gly Asp Gly Val Leu
305                 310                 315                 320

Phe Ser Thr Ser Val Ile Asn Arg Asp Thr Ala Val Tyr Asp Asp Pro
                325                 330                 335

Asp Gly Leu Asp Phe His Arg Ala Asp Arg His His Val Ala Phe Gly
            340                 345                 350

Phe Gly Ile His Gln Cys Leu Gly Gln Asn Leu Ala Arg Ala Glu Leu
        355                 360                 365

Glu Ile Ala Leu Gly Ser Leu Phe Thr Arg Leu Pro Gly Leu Arg Leu
    370                 375                 380

Ala Ala Pro Ala Glu Glu Ile Pro Phe Lys Pro Gly Asp Thr Ile Gln
385                 390                 395                 400

Gly Met Leu Glu Leu Pro Val Thr Trp
                405

<210> SEQ ID NO 139
<211> LENGTH: 1230
<212> TYPE: DNA
<213> ORGANISM: Streptmyces nogalater IFO 13445
<220> FEATURE:
<221> NAME/KEY: CDS
<222> LOCATION: (1)..(1230)

<400> SEQUENCE: 139 atg acg gaa ctg acg gac acc acc ggc ccg gcc gac gcg gcc gaa ccc      48
Met Thr Glu Leu Thr Asp Thr Thr Gly Pro Ala Asp Ala Ala Glu Pro
  1               5                  10                  15 gtc gca ttc ccc cag gac cgc acc tgc ccc tac cac ccc ccg acc ggc      96
Val Ala Phe Pro Gln Asp Arg Thr Cys Pro Tyr His Pro Pro Thr Gly
                 20                  25                  30 tac gac ccg ctg cgc gac ggg cgg ccc ctg tcc cgg gtc acc ctc tac     144
Tyr Asp Pro Leu Arg Asp Gly Arg Pro Leu Ser Arg Val Thr Leu Tyr
             35                  40                  45 gac ggc cgt gag gtc tgg ctg gtc acc gcg cag gcc acc gcc cgc acc     192
Asp Gly Arg Glu Val Trp Leu Val Thr Ala Gln Ala Thr Ala Arg Thr
         50                  55                  60 ctg ctc gcc gac ccc cgg ctg tcc acc gac cgc cgc cgc gac ggc ttc     240
Leu Leu Ala Asp Pro Arg Leu Ser Thr Asp Arg Arg Arg Asp Gly Phe
 65                  70                  75                  80 ccc gtg ccc acc ccc cgc ttc gag ggc gga cgc gac cgc aag ctg gcc     288
Pro Val Pro Thr Pro Arg Phe Glu Gly Gly Arg Asp Arg Lys Leu Ala
                 85                  90                  95 ctg ctc gga ctg gac gac ccc gag cac cag cag cag cgc cgg atg ctg     336
Leu Leu Gly Leu Asp Asp Pro Glu His Gln Gln Gln Arg Arg Met Leu
            100                 105                 110 atc ccg tcg ttc acc gtg aaa cgc gcc acc gcg cta cgc ccc tgg atc     384
Ile Pro Ser Phe Thr Val Lys Arg Ala Thr Ala Leu Arg Pro Trp Ile
        115                 120                 125 cag cgg atc gtc gac gga ctg ctg gac gcc atg atc acc cgg ggg ccg     432
Gln Arg Ile Val Asp Gly Leu Leu Asp Ala Met Ile Thr Arg Gly Pro
    130                 135                 140
```

| | | | | | | | | | | | | | | | | |
|---|---|---|---|---|---|---|---|---|---|---|---|---|---|---|---|---|
| gtc | gcc | gac | ctc | gtg | tcc | gcc | ttc | gcg | ctg | ccc | gtg | ccg | tcc | atg | gtc | 480 |
| Val | Ala | Asp | Leu | Val | Ser | Ala | Phe | Ala | Leu | Pro | Val | Pro | Ser | Met | Val | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| atc | tgc | gaa | ctg | ctc | ggc | gtg | ccc | tac | gcc | gac | cac | gag | ttc | ttc | gag | 528 |
| Ile | Cys | Glu | Leu | Leu | Gly | Val | Pro | Tyr | Ala | Asp | His | Glu | Phe | Phe | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| gag | cag | tcc | cgc | cga | ctg | ctg | agc | gcc | tcg | acc | agc | gcc | gac | acc | ctg | 576 |
| Glu | Gln | Ser | Arg | Arg | Leu | Leu | Ser | Ala | Ser | Thr | Ser | Ala | Asp | Thr | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| gac | gcc | cgg | gac | cgg | ctg | gag | acg | tac | ctc | ggc | gac | ctg | atc | gac | gcc | 624 |
| Asp | Ala | Arg | Asp | Arg | Leu | Glu | Thr | Tyr | Leu | Gly | Asp | Leu | Ile | Asp | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| aag | gcc | aag | gag | gcc | gag | ccc | ggc | gac | ggc | atc | ctg | gac | gag | ctc | gtc | 672 |
| Lys | Ala | Lys | Glu | Ala | Glu | Pro | Gly | Asp | Gly | Ile | Leu | Asp | Glu | Leu | Val | |
| 210 | | | | | 215 | | | | | 220 | | | | | | |

| | | | | | | | | | | | | | | | | |
|---|---|---|---|---|---|---|---|---|---|---|---|---|---|---|---|---|
| cac | aac | cgg | ctc | cgc | aag | ggc | gag | ctg | gac | cgg | acc | gac | ctg | gtg | tcg | 720 |
| His | Asn | Arg | Leu | Arg | Lys | Gly | Glu | Leu | Asp | Arg | Thr | Asp | Leu | Val | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctc | gcc | gtc | atc | ctg | ctg | gtc | gcc | ggg | cac | gag | acg | acc | gcc | aac | atg | 768 |
| Leu | Ala | Val | Ile | Leu | Leu | Val | Ala | Gly | His | Glu | Thr | Thr | Ala | Asn | Met | |
| | | | | 245 | | | | | 250 | | | | | 255 | | |

| | | | | | | | | | | | | | | | | |
|---|---|---|---|---|---|---|---|---|---|---|---|---|---|---|---|---|
| atc | tcc | ctg | ggc | acc | tac | acg | ctg | ctc | cag | cac | ccc | gag | cgc | ctg | gcc | 816 |
| Ile | Ser | Leu | Gly | Thr | Tyr | Thr | Leu | Leu | Gln | His | Pro | Glu | Arg | Leu | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| gag | ctg | cgc | gcc | gac | ccc | gcg | ctg | ctc | ccc | gcc | gtc | gtc | gag | gaa | ctg | 864 |
| Glu | Leu | Arg | Ala | Asp | Pro | Ala | Leu | Leu | Pro | Ala | Val | Val | Glu | Glu | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| ctg | cgg | atg | ctg | tcc | atc | gcc | gag | ggg | ctg | caa | cgg | gtg | gcg | ctg | gag | 912 |
| Leu | Arg | Met | Leu | Ser | Ile | Ala | Glu | Gly | Leu | Gln | Arg | Val | Ala | Leu | Glu | |
| | | 290 | | | | | 295 | | | | | 300 | | | | |

| | | | | | | | | | | | | | | | | |
|---|---|---|---|---|---|---|---|---|---|---|---|---|---|---|---|---|
| gac | atc | gag | atc | gac | ggc | acc | acc | atc | cgg | gcc | ggc | gac | ggc | gtc | ctc | 960 |
| Asp | Ile | Glu | Ile | Asp | Gly | Thr | Thr | Ile | Arg | Ala | Gly | Asp | Gly | Val | Leu | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| ttc | tcc | acc | tcg | gtc | atc | aac | cgg | gac | acg | gcc | gtc | tac | gac | gac | ccg | 1008 |
| Phe | Ser | Thr | Ser | Val | Ile | Asn | Arg | Asp | Thr | Ala | Val | Tyr | Asp | Asp | Pro | |
| | | | | 325 | | | | | 330 | | | | | 335 | | |

| | | | | | | | | | | | | | | | | |
|---|---|---|---|---|---|---|---|---|---|---|---|---|---|---|---|---|
| gac | gac | ctg | gac | ttc | cac | cgc | gcc | gac | cgg | cac | cac | gtg | gcg | ttc | ggc | 1056 |
| Asp | Asp | Leu | Asp | Phe | His | Arg | Ala | Asp | Arg | His | His | Val | Ala | Phe | Gly | |
| | | | 340 | | | | | 345 | | | | | 350 | | | |

| | | | | | | | | | | | | | | | | |
|---|---|---|---|---|---|---|---|---|---|---|---|---|---|---|---|---|
| ttc | ggc | atc | cac | cag | tgc | ctg | ggc | cag | aac | ctg | gcc | cgc | gcg | gaa | ctg | 1104 |
| Phe | Gly | Ile | His | Gln | Cys | Leu | Gly | Gln | Asn | Leu | Ala | Arg | Ala | Glu | Leu | |
| | | | 355 | | | | | 360 | | | | | 365 | | | |

| | | | | | | | | | | | | | | | | |
|---|---|---|---|---|---|---|---|---|---|---|---|---|---|---|---|---|
| gag | atc | gct | ctc | ggc | agc | ctg | ttc | acc | cgc | ttg | ccc | ggg | ctc | cgt | ctg | 1152 |
| Glu | Ile | Ala | Leu | Gly | Ser | Leu | Phe | Thr | Arg | Leu | Pro | Gly | Leu | Arg | Leu | |
| | | | 370 | | | | | 375 | | | | | 380 | | | |

| | | | | | | | | | | | | | | | | |
|---|---|---|---|---|---|---|---|---|---|---|---|---|---|---|---|---|
| gcc | gta | ccg | gcg | aag | gac | att | ccc | ttc | aaa | ccg | ggc | gac | acg | atc | cag | 1200 |
| Ala | Val | Pro | Ala | Lys | Asp | Ile | Pro | Phe | Lys | Pro | Gly | Asp | Thr | Ile | Gln | |
| 385 | | | | | 390 | | | | | 395 | | | | | 400 | |

| | | | | | | | | |
|---|---|---|---|---|---|---|---|---|
| ggg | atg | ctg | gaa | ctc | ccc | gtg | acc | tgg taa | 1230 |
| Gly | Met | Leu | Glu | Leu | Pro | Val | Thr | Trp | |
| | | | | 405 | | | | | |

<210> SEQ ID NO 140
<211> LENGTH: 1278
<212> TYPE: DNA
<213> ORGANISM: Streptmyces tsusimaensis IFO 13782T
<220> FEATURE:
<221> NAME/KEY: CDS
<222> LOCATION: (1)..(1278)

<400> SEQUENCE: 140

| | | | | | | | | | | | | | | | | |
|---|---|---|---|---|---|---|---|---|---|---|---|---|---|---|---|---|
| atg | acg | gaa | tcc | acg | aca | gat | ccg | acg | acc | cgc | cag | gcc | ctc | ggc | tcc | 48 |

-continued

```
Met Thr Glu Ser Thr Thr Asp Pro Thr Thr Arg Gln Ala Leu Gly Ser
 1               5                  10                  15 acc acc ccc gcc gct gcc acc gcg acc gcc atc gac ccg acc ctc gcg      96
Thr Thr Pro Ala Ala Ala Thr Ala Thr Ala Ile Asp Pro Thr Leu Ala
                 20                  25                  30 aca ccc ttc ccg cag gac cgg ggg tgc ccg tac cac ccg ccc gcc ggg     144
Thr Pro Phe Pro Gln Asp Arg Gly Cys Pro Tyr His Pro Pro Ala Gly
             35                  40                  45 tac gcg ccg ctg cgt gag ggc cga ccc ctc agc agg gtc gcc ctc ttc     192
Tyr Ala Pro Leu Arg Glu Gly Arg Pro Leu Ser Arg Val Ala Leu Phe
         50                  55                  60 gac ggg cgc ccg gtc tgg gcg gtc acc gga cac gcc ctg gcc cgc cgg     240
Asp Gly Arg Pro Val Trp Ala Val Thr Gly His Ala Leu Ala Arg Arg
 65                  70                  75                  80 ttg ctg gcc gat cca cgg ctc tcc acc gac cgt acc cac ccg gac ttc     288
Leu Leu Ala Asp Pro Arg Leu Ser Thr Asp Arg Thr His Pro Asp Phe
                 85                  90                  95 ccc gcc ccg gcc ccg cgc ttc gcc aac gcg aac cgg cgc cgc gtg gcc     336
Pro Ala Pro Ala Pro Arg Phe Ala Asn Ala Asn Arg Arg Arg Val Ala
            100                 105                 110 ctg ctc ggc gtc gac gac ccc gag cac aac acc cag cgc aga atg ctc     384
Leu Leu Gly Val Asp Asp Pro Glu His Asn Thr Gln Arg Arg Met Leu
        115                 120                 125 atc ccg gcc ttc tcc gtg aag cgg atc aac gct ctc cgc ccc cgc atc     432
Ile Pro Ala Phe Ser Val Lys Arg Ile Asn Ala Leu Arg Pro Arg Ile
    130                 135                 140 cag gag acc gtg gac cgg ttg ctc gac gcg atg gag cgc cag ggg cca     480
Gln Glu Thr Val Asp Arg Leu Leu Asp Ala Met Glu Arg Gln Gly Pro
145                 150                 155                 160 ccg gcc gag ctg gtg agc gcg ttc gcc ctg ccg gtg ccg tcg atg gtg     528
Pro Ala Glu Leu Val Ser Ala Phe Ala Leu Pro Val Pro Ser Met Val
                165                 170                 175 atc tgc tcc ctg ctc gga gtg ccg tac gcc gac cac gag ttc ttc gag     576
Ile Cys Ser Leu Leu Gly Val Pro Tyr Ala Asp His Glu Phe Phe Glu
            180                 185                 190 gag cgc tcg cgg cgg ctc ctg cgc ggc ccc ggc gcg gcc gac gtg gac     624
Glu Arg Ser Arg Arg Leu Leu Arg Gly Pro Gly Ala Ala Asp Val Asp
        195                 200                 205 agg gcc ctc gac gaa ctc gag gag tac ctc ggc gcg ctg atc gac cgc     672
Arg Ala Leu Asp Glu Leu Glu Glu Tyr Leu Gly Ala Leu Ile Asp Arg
    210                 215                 220 aag cgt acg gaa ccg ggc gac ggc ctc ctc gac gag ctg atc cac cgc     720
Lys Arg Thr Glu Pro Gly Asp Gly Leu Leu Asp Glu Leu Ile His Arg
225                 230                 235                 240 gac cac ccc ggc gga ccg gtc gac cgc gag gag ctg gtc tcg ttc gcc     768
Asp His Pro Gly Gly Pro Val Asp Arg Glu Glu Leu Val Ser Phe Ala
                245                 250                 255 gtg atc ctg ctc atc gcg ggg cac gag acg acg gcg aac atg atc tcg     816
Val Ile Leu Leu Ile Ala Gly His Glu Thr Thr Ala Asn Met Ile Ser
            260                 265                 270 ctc ggc acc ttc acc ctg ctg cgc cac ccc gaa cag ctc gcg gcg ctg     864
Leu Gly Thr Phe Thr Leu Leu Arg His Pro Glu Gln Leu Ala Ala Leu
        275                 280                 285 cgg gcc ggc ggg acg acc acc gcc gtg gcg gtc gag gaa ctg ttg cgg     912
Arg Ala Gly Gly Thr Thr Thr Ala Val Ala Val Glu Glu Leu Leu Arg
    290                 295                 300 ttc ctc tcc atc gcc gac ggc ctg cag cgg ctg gcg acc gag gac atc     960
Phe Leu Ser Ile Ala Asp Gly Leu Gln Arg Leu Ala Thr Glu Asp Ile
305                 310                 315                 320 gag gtg ccg gac gcc ggg gtg acg atc cgc aag ggc gaa ggt gtg gtc    1008
```

-continued

```
Glu Val Pro Asp Ala Gly Val Thr Ile Arg Lys Gly Glu Gly Val Val
            325                 330                 335 ttc tcg acc tcg ctc atc aac cgc gac gac ggc gtg ttc ccg cag ccc      1056
Phe Ser Thr Ser Leu Ile Asn Arg Asp Asp Gly Val Phe Pro Gln Pro
            340                 345                 350 gaa acg ctc gac tgg gac cgc ccg gcc cgt cac cat ctc gcc ttc ggc      1104
Glu Thr Leu Asp Trp Asp Arg Pro Ala Arg His His Leu Ala Phe Gly
            355                 360                 365 ttc ggc gta cac cag tgc ctg ggg cag aac ctg gcc cgc gcg gaa ctc      1152
Phe Gly Val His Gln Cys Leu Gly Gln Asn Leu Ala Arg Ala Glu Leu
    370                 375                 380 gac atc gcg atg cgc acg ctc ttc gag cgg ctg ccg ggc ctc cgg ctc      1200
Asp Ile Ala Met Arg Thr Leu Phe Glu Arg Leu Pro Gly Leu Arg Leu
385                 390                 395                 400 gcc gta ccc gcg cag gag atc ccc cat aaa ccg ggg gac acg atc cag      1248
Ala Val Pro Ala Gln Glu Ile Pro His Lys Pro Gly Asp Thr Ile Gln
            405                 410                 415 ggc atg ctc gaa ctg ccc gtg gcc tgg tga                              1278
Gly Met Leu Glu Leu Pro Val Ala Trp
            420                 425

<210> SEQ ID NO 141
<211> LENGTH: 1209
<212> TYPE: DNA
<213> ORGANISM: Streptmyces thermocoerulescens IFO 14273t
<220> FEATURE:
<221> NAME/KEY: CDS
<222> LOCATION: (1)..(1209)

<400> SEQUENCE: 141 atg acg gac atg acg gaa acc ccc acc gtc gcc ttt ccc cag agc cgg        48
Met Thr Asp Met Thr Glu Thr Pro Thr Val Ala Phe Pro Gln Ser Arg
  1               5                  10                  15 acc tgt ccg tac cac ccg ccc gcc gcc tac gcc ccg ctg cgc gac acc       96
Thr Cys Pro Tyr His Pro Pro Ala Ala Tyr Ala Pro Leu Arg Asp Thr
                20                  25                  30 cgc ccg ctg gcc cgc gcc cgt ctc tac gac ggc cgc ctc gtc tgg acg      144
Arg Pro Leu Ala Arg Ala Arg Leu Tyr Asp Gly Arg Leu Val Trp Thr
            35                  40                  45 gtc acc ggt cac ggc ctc gcc cgc acc ctg ctc gcc gac ccc cgc ctg      192
Val Thr Gly His Gly Leu Ala Arg Thr Leu Leu Ala Asp Pro Arg Leu
        50                  55                  60 tcc acc gac ccc acc cgg ccg gag ttc ccc gcc acc acg gaa cgc atc      240
Ser Thr Asp Pro Thr Arg Pro Glu Phe Pro Ala Thr Thr Glu Arg Ile
 65                  70                  75                  80 gcc cgg atc cgg cgc cgg acc gcc ctg ctg ggc gtc gac gac ccc          288
Ala Arg Ile Arg Arg Arg Thr Ala Leu Leu Gly Val Asp Asp Pro
                 85                  90                  95 gaa cac cgc gtc cag cgg cgc atg atg gtc ccc agc ttc acc ctc cag      336
Glu His Arg Val Gln Arg Arg Met Met Val Pro Ser Phe Thr Leu Gln
                100                 105                 110 cgc gcc acc gcg ctg cgc ccc cgg atc cag cgg gtc gtc gac gaa cgc      384
Arg Ala Thr Ala Leu Arg Pro Arg Ile Gln Arg Val Val Asp Glu Arg
            115                 120                 125 ctc gac gcg atg atc gcc ggc ggc ccg ccc gcc gat ctc gtc acc gcg      432
Leu Asp Ala Met Ile Ala Gly Gly Pro Pro Ala Asp Leu Val Thr Ala
130                 135                 140 ttc gcg ctg ccg gtg ccg tcc atg gtg atc tgc gcc ctg ctc ggc gtg      480
Phe Ala Leu Pro Val Pro Ser Met Val Ile Cys Ala Leu Leu Gly Val
145                 150                 155                 160 ccc tac gag gac cac gac ttc ttc gag gag cag tca cgc cgg ctg ctg      528
Pro Tyr Glu Asp His Asp Phe Phe Glu Glu Gln Ser Arg Arg Leu Leu
```

```
                         165                 170                 175
cgc ggc ccg acg gcc gag gac tcc atg gac gcc cgc gcc cga atg gag      576
Arg Gly Pro Thr Ala Glu Asp Ser Met Asp Ala Arg Ala Arg Met Glu
            180                 185                 190 gcc tac ttc gac gag ctg atc gac cgc aag cag cgg cag gac gcg ccc      624
Ala Tyr Phe Asp Glu Leu Ile Asp Arg Lys Gln Arg Gln Asp Ala Pro
                195                 200                 205 ggt gac ggc gtc ctg gac gaa ctc gtc cac cag cgg ctg gcc gcg ggc      672
Gly Asp Gly Val Leu Asp Glu Leu Val His Gln Arg Leu Ala Ala Gly
    210                 215                 220 gag ctg gac cgc gag ggg ctc atc gcc atg gcg atc atc ctg ctc gtc      720
Glu Leu Asp Arg Glu Gly Leu Ile Ala Met Ala Ile Ile Leu Leu Val
225                 230                 235                 240 gcc ggt cac gag acg acc gcc aac atg atc tcg ctc ggc acc ttc acg      768
Ala Gly His Glu Thr Thr Ala Asn Met Ile Ser Leu Gly Thr Phe Thr
                245                 250                 255 ctg ctc ggg cac ccc gag cgg ctg gcc gag ctg cgc gcc gac ccg gac      816
Leu Leu Gly His Pro Glu Arg Leu Ala Glu Leu Arg Ala Asp Pro Asp
            260                 265                 270 ctg gtg ccc gcg gcc gtc gag gag ctg ctg cgc atg ctg tcc atc gcg      864
Leu Val Pro Ala Ala Val Glu Glu Leu Leu Arg Met Leu Ser Ile Ala
        275                 280                 285 gac ggc ctg ctg cgc gtc gcc gtc gag gac atc gag gtg gcc ggg gag      912
Asp Gly Leu Leu Arg Val Ala Val Glu Asp Ile Glu Val Ala Gly Glu
    290                 295                 300 acg atc cgc gcg ggc gac ggc gtc atc ttc tcg acg tcg gtc atc aac      960
Thr Ile Arg Ala Gly Asp Gly Val Ile Phe Ser Thr Ser Val Ile Asn
305                 310                 315                 320 cgg gac gag gcc gtc tac ccc gaa ccc gac acc ctg gac ctg cac cgc     1008
Arg Asp Glu Ala Val Tyr Pro Glu Pro Asp Thr Leu Asp Leu His Arg
                325                 330                 335 ccg gcc cgg cac cac gtc gcc ttc ggg ttc ggc atc cac cag tgc ctc     1056
Pro Ala Arg His His Val Ala Phe Gly Phe Gly Ile His Gln Cys Leu
            340                 345                 350 ggg cag aac ctg gcc cgc gcc gag atg gag atc gcc ctg cgc acc ctg     1104
Gly Gln Asn Leu Ala Arg Ala Glu Met Glu Ile Ala Leu Arg Thr Leu
        355                 360                 365 ttc ggc cgc ctg ccc gga ctg cgt ctg gcg gtc ccc ccg gag gaa atc     1152
Phe Gly Arg Leu Pro Gly Leu Arg Leu Ala Val Pro Pro Glu Glu Ile
    370                 375                 380 ccg ttc aaa ccc ggc gac acg atc cag ggg atg ctg gaa ctc ccc gtg     1200
Pro Phe Lys Pro Gly Asp Thr Ile Gln Gly Met Leu Glu Leu Pro Val
385                 390                 395                 400 acc tgg taa                                                          1209
Thr Trp <210> SEQ ID NO 142
<211> LENGTH: 1230
<212> TYPE: DNA
<213> ORGANISM: Streptmyces glomerochromogenes IFO 13673T
<220> FEATURE:
<221> NAME/KEY: CDS
<222> LOCATION: (1)..(1230)

<400> SEQUENCE: 142 atg acg gaa ctg acg gac atc acc ggc ccg gct ggc cag gcc caa ccc       48
Met Thr Glu Leu Thr Asp Ile Thr Gly Pro Ala Gly Gln Ala Gln Pro
1               5                   10                  15 gtc gca ttc ccc cag gac cgc acc tgt ccc tac cac ccc ccc acc gga       96
Val Ala Phe Pro Gln Asp Arg Thr Cys Pro Tyr His Pro Pro Thr Gly
            20                  25                  30
```

-continued

| | | |
|---|---|---|
| tac gac ccg ctg cgc gac ggg cga ccc ctg tcc cgc gtc acc ctc tac<br>Tyr Asp Pro Leu Arg Asp Gly Arg Pro Leu Ser Arg Val Thr Leu Tyr<br>35                    40                      45 | 144 | |
| gac ggc cgc gag gtc tgg ctg gtc acc gcc cag gcc acc gcc cgc gcc<br>Asp Gly Arg Glu Val Trp Leu Val Thr Ala Gln Ala Thr Ala Arg Ala<br>50                    55                      60 | 192 | |
| ctg ctc gcc gac ccc cgg ctg tcc acc gac cgc cgc gac ggc ttt<br>Leu Leu Ala Asp Pro Arg Leu Ser Thr Asp Arg Arg Arg Asp Gly Phe<br>65                    70                      75                      80 | 240 | |
| ccc gtg ccc agc ccc cgc ttc gag gcc ggc cgc gac cgc aaa ctg gcc<br>Pro Val Pro Ser Pro Arg Phe Glu Ala Gly Arg Asp Arg Lys Leu Ala<br>85                    90                      95 | 288 | |
| ctg ctc ggg ctg gac gac ccc gag cac cac cag cag cgc cgg atg ctg<br>Leu Leu Gly Leu Asp Asp Pro Glu His His Gln Gln Arg Arg Met Leu<br>                  100                    105                    110 | 336 | |
| atc ccg tcg ttc acc gtc aaa cgc gcc acc gcg cta cgc ccc tgg atc<br>Ile Pro Ser Phe Thr Val Lys Arg Ala Thr Ala Leu Arg Pro Trp Ile<br>                  115                    120                    125 | 384 | |
| cag cgg atc gtc gac gaa ctg ctg gac gac atg atc gcc cgg ggg ccg<br>Gln Arg Ile Val Asp Glu Leu Leu Asp Asp Met Ile Ala Arg Gly Pro<br>130                      135                    140 | 432 | |
| gtc gcc gac ctc gtg tcc gcg ttc gcg ctg ccc gtg ccg tcc atg gtc<br>Val Ala Asp Leu Val Ser Ala Phe Ala Leu Pro Val Pro Ser Met Val<br>145                      150                    155                    160 | 480 | |
| atc tgc gaa ctg ctc ggc gtg ccc tac gcc gac cac gag ttc ttc gag<br>Ile Cys Glu Leu Leu Gly Val Pro Tyr Ala Asp His Glu Phe Phe Glu<br>                  165                    170                    175 | 528 | |
| gaa cag tcc cgc cgg ctg ctg cgc ggc ccg ggc gcc gac acc ctg<br>Glu Gln Ser Arg Arg Leu Leu Arg Gly Pro Gly Ala Asp Thr Leu<br>180                      185                    190 | 576 | |
| gac gcc cgg gac cgg ctg gag gcg tac ctc ggc gag ctg atc gac gcc<br>Asp Ala Arg Asp Arg Leu Glu Ala Tyr Leu Gly Glu Leu Ile Asp Ala<br>                  195                    200                    205 | 624 | |
| aag gcc aag gag gcc gag ccc ggc gac ggc gtt ctg gac gac ctg gtc<br>Lys Ala Lys Glu Ala Glu Pro Gly Asp Gly Val Leu Asp Asp Leu Val<br>210                      215                    220 | 672 | |
| cac aac cgg ctc cgc gcg ggc gag ctg gac cgg acc gac ctg gtg tcg<br>His Asn Arg Leu Arg Ala Gly Glu Leu Asp Arg Thr Asp Leu Val Ser<br>225                      230                    235                    240 | 720 | |
| ctc gcc ctc atc ctg ctg gtc gcc ggg cac gag acg acc gcc aac atg<br>Leu Ala Leu Ile Leu Leu Val Ala Gly His Glu Thr Thr Ala Asn Met<br>                  245                    250                    255 | 768 | |
| atc tcc ctg ggc acc tac acc ctg ctc cag cac ccc gaa cgg ctg gcc<br>Ile Ser Leu Gly Thr Tyr Thr Leu Leu Gln His Pro Glu Arg Leu Ala<br>                    260                    265                    270 | 816 | |
| gag ctg cgt gcc gac ccc acg gtg ctg ccc gcc gtc gtc gag gaa ctg<br>Glu Leu Arg Ala Asp Pro Thr Val Leu Pro Ala Val Val Glu Glu Leu<br>                  275                    280                    285 | 864 | |
| ctg cgg atg ctg tcc atc gcc gag ggg ctg caa cgg ctg gcg ctg gag<br>Leu Arg Met Leu Ser Ile Ala Glu Gly Leu Gln Arg Leu Ala Leu Glu<br>290                      295                    300 | 912 | |
| gac atc gag atc gac ggc acc acc atc cgg gcc ggt gac ggc gtc ctc<br>Asp Ile Glu Ile Asp Gly Thr Thr Ile Arg Ala Gly Asp Gly Val Leu<br>305                      310                    315                    320 | 960 | |
| ttc tcc acc tcg gtc atc aac cgg gac acg gcc gtc tac gac gac ccc<br>Phe Ser Thr Ser Val Ile Asn Arg Asp Thr Ala Val Tyr Asp Asp Pro<br>                  325                    330                    335 | 1008 | |
| gac gac ctg gac ttc cac cgc gcc gac cgg cac cac gtg gcg ttc ggc<br>Asp Asp Leu Asp Phe His Arg Ala Asp Arg His His Val Ala Phe Gly<br>                  340                    345                    350 | 1056 | |

```
ttc ggc atc cac cag tgc ctg ggc cag aac ctg gcc cgc gcg gaa ctg      1104
Phe Gly Ile His Gln Cys Leu Gly Gln Asn Leu Ala Arg Ala Glu Leu
            355                 360                 365 gag atc gcc ctc ggc agc ctc ttc acc cgg ctg ccc ggg ctg cgt ctt      1152
Glu Ile Ala Leu Gly Ser Leu Phe Thr Arg Leu Pro Gly Leu Arg Leu
    370                 375                 380 gcc gcc ccg gcc gag gag atc ccc ttc aaa ccg ggc gac acg atc cag      1200
Ala Ala Pro Ala Glu Glu Ile Pro Phe Lys Pro Gly Asp Thr Ile Gln
385                 390                 395                 400 ggg atg ctg gaa ctc ccc gtg acc tgg taa                              1230
Gly Met Leu Glu Leu Pro Val Thr Trp
                405

<210> SEQ ID NO 143
<211> LENGTH: 1230
<212> TYPE: DNA
<213> ORGANISM: Streptmyces olivochromogenes IFO 12444
<220> FEATURE:
<221> NAME/KEY: CDS
<222> LOCATION: (1)..(1230)

<400> SEQUENCE: 143 atg acg gaa ctg acg gac atc acc ggc ccg gct ggc cag gcc gaa ccc      48
Met Thr Glu Leu Thr Asp Ile Thr Gly Pro Ala Gly Gln Ala Glu Pro
1               5                   10                  15 gtc gca ttc ccc cag gac cgc acc tgt ccc tac cac ccc ccc acc gga      96
Val Ala Phe Pro Gln Asp Arg Thr Cys Pro Tyr His Pro Pro Thr Gly
                20                  25                  30 tac gac ccg ctg cgc gac ggg cga ccc ctg tcc cgc gtc acc ctc tac      144
Tyr Asp Pro Leu Arg Asp Gly Arg Pro Leu Ser Arg Val Thr Leu Tyr
            35                  40                  45 gac ggc cgc gag gtc tgg ctg gtc acc gcc cag gcc acc gcc cgc gcc      192
Asp Gly Arg Glu Val Trp Leu Val Thr Ala Gln Ala Thr Ala Arg Ala
        50                  55                  60 ctg ctc gcc gac ccc cgg ctg tcc acc gac cgc cgc cgc gac ggt ttt      240
Leu Leu Ala Asp Pro Arg Leu Ser Thr Asp Arg Arg Arg Asp Gly Phe
65                  70                  75                  80 ccc gtg ccc agc ccc cgc ttc gag gcc ggc cgc gac cgc aaa ctg gcc      288
Pro Val Pro Ser Pro Arg Phe Glu Ala Gly Arg Asp Arg Lys Leu Ala
                85                  90                  95 ctg ctc ggg ctg gac gac ccc gag cac cac cag cag cgc cgg atg ctg      336
Leu Leu Gly Leu Asp Asp Pro Glu His His Gln Gln Arg Arg Met Leu
            100                 105                 110 atc ccg tcg ttc acc gtc aaa cgc gcc acc gcg cta cgc ccc tgg atc      384
Ile Pro Ser Phe Thr Val Lys Arg Ala Thr Ala Leu Arg Pro Trp Ile
        115                 120                 125 cag cgg atc gtc gac gaa ctg ctg gac gac atg atc gcc cgg ggg ccg      432
Gln Arg Ile Val Asp Glu Leu Leu Asp Asp Met Ile Ala Arg Gly Pro
    130                 135                 140 gtc gcc gac ctc gtg tcc gcg ttc gcg ctg ccc gtg ccg tcc atg gtc      480
Val Ala Asp Leu Val Ser Ala Phe Ala Leu Pro Val Pro Ser Met Val
145                 150                 155                 160 atc tgc gaa ctg ctc ggc gtg ccc tac gcc gac cac gag ttc ttc gag      528
Ile Cys Glu Leu Leu Gly Val Pro Tyr Ala Asp His Glu Phe Phe Glu
                165                 170                 175 gaa cag tcc cgc cgg ctg ctg cgc ggc ccg ggc ggc gcc gac aca ctg      576
Glu Gln Ser Arg Arg Leu Leu Arg Gly Pro Gly Gly Ala Asp Thr Leu
            180                 185                 190 gac gcc cgg gac cgg ctg gag gcg tac ctc ggc gag ctg atc gac gcc      624
Asp Ala Arg Asp Arg Leu Glu Ala Tyr Leu Gly Glu Leu Ile Asp Ala
        195                 200                 205 aag gcc aag gag gcc gag ccc ggc gac ggc att ctg gac gat ctg gtc      672

```
                                                                                  -continued Lys Ala Lys Glu Ala Glu Pro Gly Asp Gly Ile Leu Asp Asp Leu Val
    210             215                 220 cac aac cgg ctc cgc gcg ggc gag ctg gac cgg acc gac ctg gtg tcg        720
His Asn Arg Leu Arg Ala Gly Glu Leu Asp Arg Thr Asp Leu Val Ser
225                 230                 235                 240 ctc gcc ctc atc ctg ctg gtc gcc ggg cac gag aca acc gcc aac atg        768
Leu Ala Leu Ile Leu Leu Val Ala Gly His Glu Thr Thr Ala Asn Met
                245                 250                 255 atc tcc ctg ggc acc tac acc ctc cag cac ccc gaa cgg ctg gcc            816
Ile Ser Leu Gly Thr Tyr Thr Leu Gln His Pro Glu Arg Leu Ala
            260                 265                 270 gag ctg cgt gcc gac ccc acg gtg ctg ccc gcc gtc gtc gag gaa ctg        864
Glu Leu Arg Ala Asp Pro Thr Val Leu Pro Ala Val Val Glu Glu Leu
        275                 280                 285 ctg cgg atg ctg tcc atc gcc gag ggg ctg caa cgg gtg gcg ctg gag        912
Leu Arg Met Leu Ser Ile Ala Glu Gly Leu Gln Arg Val Ala Leu Glu
    290                 295                 300 gac atc gag atc gac ggc acc acc atc cgg gcc ggt gac ggc gtc ctc        960
Asp Ile Glu Ile Asp Gly Thr Thr Ile Arg Ala Gly Asp Gly Val Leu
305                 310                 315                 320 ttc tcc acc tcg gtc atc aac cgg gac acg gcc gtc tac gac gac ccc       1008
Phe Ser Thr Ser Val Ile Asn Arg Asp Thr Ala Val Tyr Asp Asp Pro
                325                 330                 335 gac ggc ctg gac ttc cac cgc gcc gac cgg cac cac gtg gcg ttc ggc       1056
Asp Gly Leu Asp Phe His Arg Ala Asp Arg His His Val Ala Phe Gly
            340                 345                 350 ttc ggc atc cac cag tgc ctg ggc cag aac ctg gcc cgc gcg gaa ctg       1104
Phe Gly Ile His Gln Cys Leu Gly Gln Asn Leu Ala Arg Ala Glu Leu
        355                 360                 365 gag atc gcc ctc ggc agc ctc ttc acc cgg ctg ccc gga ctg cgt ctt       1152
Glu Ile Ala Leu Gly Ser Leu Phe Thr Arg Leu Pro Gly Leu Arg Leu
    370                 375                 380 gcc gcc ccg gcc gag gag atc ccc ttc aaa ccg ggc gac acg atc cag       1200
Ala Ala Pro Ala Glu Glu Ile Pro Phe Lys Pro Gly Asp Thr Ile Gln
385                 390                 395                 400 ggg atg ctg gaa ctc ccc gtg acc tgg taa                                1230
Gly Met Leu Glu Leu Pro Val Thr Trp
                405

<210> SEQ ID NO 144
<211> LENGTH: 1449
<212> TYPE: DNA
<213> ORGANISM: Streptmyces nogalater IFO 13445
<220> FEATURE:
<221> NAME/KEY: CDS
<222> LOCATION: (1)..(1230)
<220> FEATURE:
<221> NAME/KEY: CDS
<222> LOCATION: (1243)..(1449)

<400> SEQUENCE: 144 atg acg gaa ctg acg gac acc acc ggc ccg gcc gac gcg gcc gaa ccc         48
Met Thr Glu Leu Thr Asp Thr Thr Gly Pro Ala Asp Ala Ala Glu Pro
  1               5                  10                  15 gtc gca ttc ccc cag gac cgc acc tgc ccc tac cac ccc ccg acc ggc         96
Val Ala Phe Pro Gln Asp Arg Thr Cys Pro Tyr His Pro Pro Thr Gly
                 20                  25                  30 tac gac ccg ctg cgc gac ggg cgg ccc ctg tcc cgg gtc acc ctc tac        144
Tyr Asp Pro Leu Arg Asp Gly Arg Pro Leu Ser Arg Val Thr Leu Tyr
             35                  40                  45 gac ggc cgt gag gtc tgg ctg gtc acc gcg cag gcc acc gcc cgc acc        192
Asp Gly Arg Glu Val Trp Leu Val Thr Ala Gln Ala Thr Ala Arg Thr
         50                  55                  60
```

-continued

| | |
|---|---|
| ctg ctc gcc gac ccc cgg ctg tcc acc gac cgc cgc gac ggc ttc<br>Leu Leu Ala Asp Pro Arg Leu Ser Thr Asp Arg Arg Asp Gly Phe<br>65                   70                   75                   80 | 240 |
| ccc gtg ccc acc ccc cgc ttc gag ggc gga cgc gac cgc aag ctg gcc<br>Pro Val Pro Thr Pro Arg Phe Glu Gly Gly Arg Asp Arg Lys Leu Ala<br>                   85                   90                   95 | 288 |
| ctg ctc gga ctg gac gac ccc gag cac cag cag cag cgc cgg atg ctg<br>Leu Leu Gly Leu Asp Asp Pro Glu His Gln Gln Gln Arg Arg Met Leu<br>          100                   105                   110 | 336 |
| atc ccg tcg ttc acc gtg aaa cgc gcc acc gcg cta cgc ccc tgg atc<br>Ile Pro Ser Phe Thr Val Lys Arg Ala Thr Ala Leu Arg Pro Trp Ile<br>         115                   120                   125 | 384 |
| cag cgg atc gtc gac gga ctg ctg gac gcc atg atc acc cgg ggg ccg<br>Gln Arg Ile Val Asp Gly Leu Leu Asp Ala Met Ile Thr Arg Gly Pro<br>130                   135                   140 | 432 |
| gtc gcc gac ctc gtg tcc gcc ttc gcg ctg ccc gtg ccg tcc atg gtc<br>Val Ala Asp Leu Val Ser Ala Phe Ala Leu Pro Val Pro Ser Met Val<br>145                   150                   155                   160 | 480 |
| atc tgc gaa ctg ctc ggc gtg ccc tac gcc gac cac gag ttc ttc gag<br>Ile Cys Glu Leu Leu Gly Val Pro Tyr Ala Asp His Glu Phe Phe Glu<br>                   165                   170                   175 | 528 |
| gag cag tcc cgc cga ctg ctg agc gcc tcg acc agc gcc gac acc ctg<br>Glu Gln Ser Arg Arg Leu Leu Ser Ala Ser Thr Ser Ala Asp Thr Leu<br>         180                   185                   190 | 576 |
| gac gcc cgg gac cgg ctg gag acg tac ctc ggc gac ctg atc gac gcc<br>Asp Ala Arg Asp Arg Leu Glu Thr Tyr Leu Gly Asp Leu Ile Asp Ala<br>         195                   200                   205 | 624 |
| aag gcc aag gag gcc gag ccc ggc gac ggc atc ctg gac gag ctc gtc<br>Lys Ala Lys Glu Ala Glu Pro Gly Asp Gly Ile Leu Asp Glu Leu Val<br>210                   215                   220 | 672 |
| cac aac cgg ctc cgc aag ggc gag ctg gac cgg acc gac ctg gtg tcg<br>His Asn Arg Leu Arg Lys Gly Glu Leu Asp Arg Thr Asp Leu Val Ser<br>225                   230                   235                   240 | 720 |
| ctc gcc gtc atc ctg ctg gtc gcc ggg cac gag acg acc gcc aac atg<br>Leu Ala Val Ile Leu Leu Val Ala Gly His Glu Thr Thr Ala Asn Met<br>         245                   250                   255 | 768 |
| atc tcc ctg ggc acc tac acg ctg ctc cag cac ccc gag cgc ctg gcc<br>Ile Ser Leu Gly Thr Tyr Thr Leu Leu Gln His Pro Glu Arg Leu Ala<br>          260                   265                   270 | 816 |
| gag ctg cgc gcc gac ccc gcg ctg ctc ccc gcc gtc gtc gag gaa ctg<br>Glu Leu Arg Ala Asp Pro Ala Leu Leu Pro Ala Val Val Glu Glu Leu<br>         275                   280                   285 | 864 |
| ctg cgg atg ctg tcc atc gcc gag ggg ctg caa cgg gtg gcg ctg gag<br>Leu Arg Met Leu Ser Ile Ala Glu Gly Leu Gln Arg Val Ala Leu Glu<br>         290                   295                   300 | 912 |
| gac atc gag atc gac ggc acc acc atc cgg gcc ggc gac ggc gtc ctc<br>Asp Ile Glu Ile Asp Gly Thr Thr Ile Arg Ala Gly Asp Gly Val Leu<br>305                   310                   315                   320 | 960 |
| ttc tcc acc tcg gtc atc aac cgg gac acg gcc gtc tac gac gac ccg<br>Phe Ser Thr Ser Val Ile Asn Arg Asp Thr Ala Val Tyr Asp Asp Pro<br>         325                   330                   335 | 1008 |
| gac gac ctg gac ttc cac cgc gcc gac cgg cac cac gtg gcg ttc ggc<br>Asp Asp Leu Asp Phe His Arg Ala Asp Arg His His Val Ala Phe Gly<br>          340                   345                   350 | 1056 |
| ttc ggc atc cac cag tgc ctg ggc cag aac ctg gcc cgc gcg gaa ctg<br>Phe Gly Ile His Gln Cys Leu Gly Gln Asn Leu Ala Arg Ala Glu Leu<br>         355                   360                   365 | 1104 |
| gag atc gct ctc ggc agc ctg ttc acc cgc ttg ccc ggg ctc cgt ctg<br>Glu Ile Ala Leu Gly Ser Leu Phe Thr Arg Leu Pro Gly Leu Arg Leu<br>         370                   375                   380 | 1152 |

-continued

```
gcc gta ccg gcg aag gac att ccc ttc aaa ccg ggc gac acg atc cag      1200
Ala Val Pro Ala Lys Asp Ile Pro Phe Lys Pro Gly Asp Thr Ile Gln
385                 390                 395                 400 ggg atg ctg gaa ctc ccc gtg acc tgg taa gaggcttcgt tc atg cac atc    1251
Gly Met Leu Glu Leu Pro Val Thr Trp                    Met His Ile
            405                 410 gac atc gat atc gac cag gac gtc tgc atc ggc gcc ggg cag tgc gcg      1299
Asp Ile Asp Ile Asp Gln Asp Val Cys Ile Gly Ala Gly Gln Cys Ala
        415                 420                 425 ctg gcg gca ccg ggc gtc ttc acc cag gac gac gac ggc tac agc acc      1347
Leu Ala Ala Pro Gly Val Phe Thr Gln Asp Asp Asp Gly Tyr Ser Thr
430                 435                 440 ctg ctg ccc ggc cag gag aac ggc gtg acc gac ccg atg gtc cgg gag      1395
Leu Leu Pro Gly Gln Glu Asn Gly Val Thr Asp Pro Met Val Arg Glu
445                 450                 455                 460 gcc gcc cgc gcc tgc ccg gtc agc gcg atc acc gtg cgg gag cgc acc      1443
Ala Ala Arg Ala Cys Pro Val Ser Ala Ile Thr Val Arg Glu Arg Thr
                465                 470                 475 gcc tga                                                               1449
Ala
```

<210> SEQ ID NO 145
<211> LENGTH: 1480
<212> TYPE: DNA
<213> ORGANISM: Streptmyces tsusimaensis IFO 13782T
<220> FEATURE:
<221> NAME/KEY: CDS
<222> LOCATION: (1)..(1278)
<220> FEATURE:
<221> NAME/KEY: CDS
<222> LOCATION: (1284)..(1478)

<400> SEQUENCE: 145

```
atg acg gaa tcc acg aca gat ccg acg acc cgc cag gcc ctc ggc tcc      48
Met Thr Glu Ser Thr Thr Asp Pro Thr Thr Arg Gln Ala Leu Gly Ser
1               5                   10                  15 acc acc ccc gcc gct gcc acc gcg acc gcc atc gac ccg acc ctc gcg      96
Thr Thr Pro Ala Ala Ala Thr Ala Thr Ala Ile Asp Pro Thr Leu Ala
                20                  25                  30 aca ccc ttc ccg cag gac cgg ggg tgc ccg tac cac ccg ccc gcc ggg      144
Thr Pro Phe Pro Gln Asp Arg Gly Cys Pro Tyr His Pro Pro Ala Gly
            35                  40                  45 tac gcg ccg ctg cgt gag ggc cga ccg ctc agc agg gtc gcc ctc ttc      192
Tyr Ala Pro Leu Arg Glu Gly Arg Pro Leu Ser Arg Val Ala Leu Phe
        50                  55                  60 gac ggg cgc ccg gtc tgg gcg gtc acc gga cac gcc ctg gcc cgc cgg      240
Asp Gly Arg Pro Val Trp Ala Val Thr Gly His Ala Leu Ala Arg Arg
65                  70                  75                  80 ttg ctg gcc gat cca cgg ctc tcc acc gac cgt acc cac ccg gac ttc      288
Leu Leu Ala Asp Pro Arg Leu Ser Thr Asp Arg Thr His Pro Asp Phe
                85                  90                  95 ccc gcc ccg gcc ccg cgc ttc gcc aac gcg aac cgg cgc cgc gtg gcc      336
Pro Ala Pro Ala Pro Arg Phe Ala Asn Ala Asn Arg Arg Arg Val Ala
                100                 105                 110 ctg ctc ggc gtc gac gac ccc gag cac aac acc cag cgc aga atg ctc      384
Leu Leu Gly Val Asp Asp Pro Glu His Asn Thr Gln Arg Arg Met Leu
            115                 120                 125 atc ccg gcc ttc tcc gtg aag cgg atc aac gct ctc cgc ccc cgc atc      432
Ile Pro Ala Phe Ser Val Lys Arg Ile Asn Ala Leu Arg Pro Arg Ile
        130                 135                 140 cag gag acc gtg gac cgg ttg ctc gac gcg atg gag cgc cag ggg cca      480
Gln Glu Thr Val Asp Arg Leu Leu Asp Ala Met Glu Arg Gln Gly Pro
```

-continued

```
                145                 150                 155                 160
ccg gcc gag ctg gtg agc gcg ttc gcc ctg ccg gtg ccg tcg atg gtg         528
Pro Ala Glu Leu Val Ser Ala Phe Ala Leu Pro Val Pro Ser Met Val
                    165                 170                 175
atc tgc tcc ctg ctc gga gtg ccg tac gcc gac cac gag ttc ttc gag         576
Ile Cys Ser Leu Leu Gly Val Pro Tyr Ala Asp His Glu Phe Phe Glu
                    180                 185                 190
gag cgc tcg cgg cgg ctc ctg cgc ggc ccc ggc gcg gcc gac gtg gac         624
Glu Arg Ser Arg Arg Leu Leu Arg Gly Pro Gly Ala Ala Asp Val Asp
                    195                 200                 205
agg gcc ctc gac gaa ctc gag gag tac ctc ggc gcg ctg atc gac cgc         672
Arg Ala Leu Asp Glu Leu Glu Glu Tyr Leu Gly Ala Leu Ile Asp Arg
                    210                 215                 220
aag cgt acg gaa ccg ggc gac ggc ctc ctc gac gag ctg atc cac cgc         720
Lys Arg Thr Glu Pro Gly Asp Gly Leu Leu Asp Glu Leu Ile His Arg
225                 230                 235                 240
gac cac ccc ggc gga ccg gtc gac cgc gag gag ctg gtc tcg ttc gcc         768
Asp His Pro Gly Gly Pro Val Asp Arg Glu Glu Leu Val Ser Phe Ala
                    245                 250                 255
gtg atc ctg ctc atc gcg ggg cac gag acg acg gcg aac atg atc tcg         816
Val Ile Leu Leu Ile Ala Gly His Glu Thr Thr Ala Asn Met Ile Ser
                    260                 265                 270
ctc ggc acc ttc acc ctg ctg cgc cac ccc gaa cag ctc gcg gcg ctg         864
Leu Gly Thr Phe Thr Leu Leu Arg His Pro Glu Gln Leu Ala Ala Leu
                    275                 280                 285
cgg gcc ggc ggg acg acc acg gcc gtg gcg gtc gag gaa ctg ttg cgg         912
Arg Ala Gly Gly Thr Thr Thr Ala Val Ala Val Glu Glu Leu Leu Arg
                    290                 295                 300
ttc ctc tcc atc gcc gac ggc ctg cag cgg ctg gcg acc gag gac atc         960
Phe Leu Ser Ile Ala Asp Gly Leu Gln Arg Leu Ala Thr Glu Asp Ile
305                 310                 315                 320
gag gtg ccg gac gcc ggg gtg acg atc cgc aag ggc gaa ggt gtg gtc        1008
Glu Val Pro Asp Ala Gly Val Thr Ile Arg Lys Gly Glu Gly Val Val
                    325                 330                 335
ttc tcg acc tcg ctc atc aac cgc gac gac ggc gtg ttc ccg cag ccc        1056
Phe Ser Thr Ser Leu Ile Asn Arg Asp Asp Gly Val Phe Pro Gln Pro
                    340                 345                 350
gaa acg ctc gac tgg gac cgc ccg gcc cgt cac cat ctc gcc ttc ggc        1104
Glu Thr Leu Asp Trp Asp Arg Pro Ala Arg His His Leu Ala Phe Gly
                    355                 360                 365
ttc ggc gta cac cag tgc ctg ggg cag aac ctg gcc cgc gcg gaa ctc        1152
Phe Gly Val His Gln Cys Leu Gly Gln Asn Leu Ala Arg Ala Glu Leu
                    370                 375                 380
gac atc gcg atg cgc acg ctc ttc gag cgg ctg ccg ggc ctc cgg ctc        1200
Asp Ile Ala Met Arg Thr Leu Phe Glu Arg Leu Pro Gly Leu Arg Leu
385                 390                 395                 400
gcc gta ccc gcg cag gag atc ccc cat aaa ccg ggg gac acg atc cag        1248
Ala Val Pro Ala Gln Glu Ile Pro His Lys Pro Gly Asp Thr Ile Gln
                    405                 410                 415
ggc atg ctc gaa ctg ccc gtg gcc tgg tga gcggc atg ggc gtc cag gtc      1298
Gly Met Leu Glu Leu Pro Val Ala Trp           Met Gly Val Gln Val
                    420                 425                         430
gac agg gaa cgc tgc gtg ggg gcg ggc atg tgc gcg ctg acc gcg ccg        1346
Asp Arg Glu Arg Cys Val Gly Ala Gly Met Cys Ala Leu Thr Ala Pro
                    435                 440                 445
gac gtg ttc acg cag gac gac gac ggc ctc agc gag gtg ctc ccg ggc        1394
Asp Val Phe Thr Gln Asp Asp Asp Gly Leu Ser Glu Val Leu Pro Gly
                    450                 455                 460
cgc gcg gag acc gct gga gga cat ccc ttg gtg ggg gag gct gta cgg        1442
Arg Ala Glu Thr Ala Gly Gly His Pro Leu Val Gly Glu Ala Val Arg
```

```
                465                 470                 475
gcc tgc ccg gtg ggg gcg gtg gcc ctg tcc gcc gac tg                    1480
Ala Cys Pro Val Gly Ala Val Ala Leu Ser Ala Asp
    480                 485                 490

<210> SEQ ID NO 146
<211> LENGTH: 1473
<212> TYPE: DNA
<213> ORGANISM: Streptomyces thermocoerulescens IFO 14273t
<220> FEATURE:
<221> NAME/KEY: CDS
<222> LOCATION: (1)..(1209)
<220> FEATURE:
<221> NAME/KEY: CDS
<222> LOCATION: (1222)..(1473)

<400> SEQUENCE: 146 atg acg gac atg acg gaa acc ccc acc gtc gcc ttt ccc cag agc cgg    48
Met Thr Asp Met Thr Glu Thr Pro Thr Val Ala Phe Pro Gln Ser Arg
  1               5                  10                  15 acc tgt ccg tac cac ccg ccc gcc gcc tac gcc ccg ctg cgc gac acc    96
Thr Cys Pro Tyr His Pro Pro Ala Ala Tyr Ala Pro Leu Arg Asp Thr
                 20                  25                  30 cgc ccg ctg gcc cgc gcc cgt ctc tac gac ggc cgc ctc gtc tgg acg   144
Arg Pro Leu Ala Arg Ala Arg Leu Tyr Asp Gly Arg Leu Val Trp Thr
             35                  40                  45 gtc acc ggt cac ggc ctc gcc cgc acc ctc ctc gcc gac ccc cgc ctg   192
Val Thr Gly His Gly Leu Ala Arg Thr Leu Leu Ala Asp Pro Arg Leu
         50                  55                  60 tcc acc gac ccc acc cgg ccg gag ttc ccc gcc acc acg gaa cgc atc   240
Ser Thr Asp Pro Thr Arg Pro Glu Phe Pro Ala Thr Thr Glu Arg Ile
 65                  70                  75                  80 gcc cgg atc cgg cgc cgg acc gcc ctg ctg ggc gtc gac gac ccc       288
Ala Arg Ile Arg Arg Arg Thr Ala Leu Leu Gly Val Asp Asp Pro
                 85                  90                  95 gaa cac cgc gtc cag cgg cgc atg atg gtc ccc agc ttc acc ctc cag   336
Glu His Arg Val Gln Arg Arg Met Met Val Pro Ser Phe Thr Leu Gln
                100                 105                 110 cgc gcc acc gcg ctg cgc ccc cgg atc cag cgg gtc gtc gac gaa cgc   384
Arg Ala Thr Ala Leu Arg Pro Arg Ile Gln Arg Val Val Asp Glu Arg
            115                 120                 125 ctc gac gcg atg atc gcc ggc ggc ccg ccc gcc gat ctc gtc acc gcg   432
Leu Asp Ala Met Ile Ala Gly Gly Pro Pro Ala Asp Leu Val Thr Ala
        130                 135                 140 ttc gcg ctg ccg gtg ccg tcc atg gtg atc tgc gcc ctg ctc ggc gtg   480
Phe Ala Leu Pro Val Pro Ser Met Val Ile Cys Ala Leu Leu Gly Val
145                 150                 155                 160 ccc tac gag gac cac gac ttc ttc gag gag cag tca cgc cgg ctg ctg   528
Pro Tyr Glu Asp His Asp Phe Phe Glu Glu Gln Ser Arg Arg Leu Leu
                165                 170                 175 cgc ggc ccg acg gcc gag gac tcc atg gac gcc cgc gcc cga atg gag   576
Arg Gly Pro Thr Ala Glu Asp Ser Met Asp Ala Arg Ala Arg Met Glu
            180                 185                 190 gcc tac ttc gac gag ctg atc gac cgc aag cag cgg cag gac gcg ccc   624
Ala Tyr Phe Asp Glu Leu Ile Asp Arg Lys Gln Arg Gln Asp Ala Pro
        195                 200                 205 ggt gac ggc gtc ctg gac gaa ctc gtc cac cag cgg ctg gcc gcg ggc   672
Gly Asp Gly Val Leu Asp Glu Leu Val His Gln Arg Leu Ala Ala Gly
    210                 215                 220 gag ctg gac cgc gag ggg ctc atc gcc atg gcg atc atc ctg ctc gtc   720
Glu Leu Asp Arg Glu Gly Leu Ile Ala Met Ala Ile Ile Leu Leu Val
225                 230                 235                 240
```

```
gcc ggt cac gag acg acc gcc aac atg atc tcg ctc ggc acc ttc acg    768
Ala Gly His Glu Thr Thr Ala Asn Met Ile Ser Leu Gly Thr Phe Thr
            245                 250                 255 ctg ctc ggg cac ccc gag cgg ctg gcc gag ctg cgc gcc gac ccg gac    816
Leu Leu Gly His Pro Glu Arg Leu Ala Glu Leu Arg Ala Asp Pro Asp
        260                 265                 270 ctg gtg ccc gcg gcc gtc gag gag ctg ctg cgc atg ctg tcc atc gcg    864
Leu Val Pro Ala Ala Val Glu Glu Leu Leu Arg Met Leu Ser Ile Ala
    275                 280                 285 gac ggc ctg ctg cgc gtc gcc gtc gag gac atc gag gtg gcc ggg gag    912
Asp Gly Leu Leu Arg Val Ala Val Glu Asp Ile Glu Val Ala Gly Glu
290                 295                 300 acg atc cgc gcg ggc gac ggc gtc atc ttc tcg acg tcg gtc atc aac    960
Thr Ile Arg Ala Gly Asp Gly Val Ile Phe Ser Thr Ser Val Ile Asn
305                 310                 315                 320 cgg gac gag gcc gtc tac ccc gaa ccc gac acc ctg gac ctg cac cgc    1008
Arg Asp Glu Ala Val Tyr Pro Glu Pro Asp Thr Leu Asp Leu His Arg
                325                 330                 335 ccg gcc cgg cac cac gtc gcc ttc ggg ttc ggc atc cac cag tgc ctc    1056
Pro Ala Arg His His Val Ala Phe Gly Phe Gly Ile His Gln Cys Leu
            340                 345                 350 ggg cag aac ctg gcc cgc gcc gag atg gag atc gcc ctg cgc acc ctg    1104
Gly Gln Asn Leu Ala Arg Ala Glu Met Glu Ile Ala Leu Arg Thr Leu
        355                 360                 365 ttc ggc cgc ctg ccc gga ctg cgt ctg gcg gtc ccc ccg gag gaa atc    1152
Phe Gly Arg Leu Pro Gly Leu Arg Leu Ala Val Pro Pro Glu Glu Ile
    370                 375                 380 ccg ttc aaa ccc ggc gac acg atc cag ggg atg ctg gaa ctc ccc gtg    1200
Pro Phe Lys Pro Gly Asp Thr Ile Gln Gly Met Leu Glu Leu Pro Val
385                 390                 395                 400 acc tgg taa gaggctccgg tc atg cac aac gaa acg cat gag aca cac gag    1251
Thr Trp           Met His Asn Glu Thr His Glu Thr His Glu
                                    405                 410 acc acc gcg gcg gcc tcc ggg acc cgt atc gac atc gac cac gac ctc    1299
Thr Thr Ala Ala Ala Ser Gly Thr Arg Ile Asp Ile Asp His Asp Leu
            415                 420                 425 tgc gtc ggc gcc ggg cag tgc gcc ctg gtc gcc ccg tcc gtc ttc acc    1347
Cys Val Gly Ala Gly Gln Cys Ala Leu Val Ala Pro Ser Val Phe Thr
        430                 435                 440 cag gac gac gac ggc ttc agc gag ctg atc ccc ggc cgc gag gac ggt    1395
Gln Asp Asp Asp Gly Phe Ser Glu Leu Ile Pro Gly Arg Glu Asp Gly
445                 450                 455                 460 gcc ggc gac ccg atg gtc cgg gag gcc gtc cgc gcc tgc ccc gtc agc    1443
Ala Gly Asp Pro Met Val Arg Glu Ala Val Arg Ala Cys Pro Val Ser
                465                 470                 475 gcc atc acc gtg acg gag gcc gcc gtc tga                            1473
Ala Ile Thr Val Thr Glu Ala Ala Val
            480                 485

<210> SEQ ID NO 147
<211> LENGTH: 1449
<212> TYPE: DNA
<213> ORGANISM: Streptmyces glomerochromogenes IFO 13673T
<220> FEATURE:
<221> NAME/KEY: CDS
<222> LOCATION: (1)..(1230)
<220> FEATURE:
<221> NAME/KEY: CDS
<222> LOCATION: (1243)..(1449)

<400> SEQUENCE: 147 atg acg gaa ctg acg gac atc acc ggc ccg gct ggc cag gcc caa ccc    48
Met Thr Glu Leu Thr Asp Ile Thr Gly Pro Ala Gly Gln Ala Gln Pro
```

-continued

```
           1               5              10              15
gtc gca ttc ccc cag gac cgc acc tgt ccc tac cac ccc ccc acc gga    96
Val Ala Phe Pro Gln Asp Arg Thr Cys Pro Tyr His Pro Pro Thr Gly
                20              25              30 tac gac ccg ctg cgc gac ggg cga ccc ctg tcc cgc gtc acc ctc tac   144
Tyr Asp Pro Leu Arg Asp Gly Arg Pro Leu Ser Arg Val Thr Leu Tyr
            35              40              45 gac ggc cgc gag gtc tgg ctg gtc acc gcc cag gcc acc gcc cgc gcc   192
Asp Gly Arg Glu Val Trp Leu Val Thr Ala Gln Ala Thr Ala Arg Ala
        50              55              60 ctg ctc gcc gac ccc cgg ctg tcc acc gac cgc cgc cgc gac ggc ttt   240
Leu Leu Ala Asp Pro Arg Leu Ser Thr Asp Arg Arg Arg Asp Gly Phe
 65              70              75              80 ccc gtg ccc agc ccc cgc ttc gag gcc ggc cgc gac cgc aaa ctg gcc   288
Pro Val Pro Ser Pro Arg Phe Glu Ala Gly Arg Asp Arg Lys Leu Ala
                85              90              95 ctc ctc ggg ctg gac gac ccc gag cac cac cag cag cgc cgg atg ctg   336
Leu Leu Gly Leu Asp Asp Pro Glu His His Gln Gln Arg Arg Met Leu
            100             105             110 atc ccg tcg ttc acc gtc aaa cgc gcc acc gcg cta cgc ccc tgg atc   384
Ile Pro Ser Phe Thr Val Lys Arg Ala Thr Ala Leu Arg Pro Trp Ile
        115             120             125 cag cgg atc gtc gac gaa ctg ctg gac gac atg atc gcc cgg ggg ccg   432
Gln Arg Ile Val Asp Glu Leu Leu Asp Asp Met Ile Ala Arg Gly Pro
    130             135             140 gtc gcc gac ctc gtg tcc gcg ttc gcg ctg ccc gtg ccg tcc atg gtc   480
Val Ala Asp Leu Val Ser Ala Phe Ala Leu Pro Val Pro Ser Met Val
145             150             155             160 atc tgc gaa ctg ctc ggc gtg ccc tac gcc gac cac gag ttc ttc gag   528
Ile Cys Glu Leu Leu Gly Val Pro Tyr Ala Asp His Glu Phe Phe Glu
                165             170             175 gaa cag tcc cgc cgg ctg ctg cgc ggc ccg ggc ggc gcc gac acc ctg   576
Glu Gln Ser Arg Arg Leu Leu Arg Gly Pro Gly Gly Ala Asp Thr Leu
            180             185             190 gac gcc cgg gac cgg ctg gag gcg tac ctc ggc gag ctg atc gac gcc   624
Asp Ala Arg Asp Arg Leu Glu Ala Tyr Leu Gly Glu Leu Ile Asp Ala
        195             200             205 aag gcc aag gag gcc gag ccc ggc gac ggc gtt ctg gac gac ctg gtc   672
Lys Ala Lys Glu Ala Glu Pro Gly Asp Gly Val Leu Asp Asp Leu Val
    210             215             220 cac aac cgg ctc cgc gcg ggc gag ctg gac cgg acc gac ctg gtg tcg   720
His Asn Arg Leu Arg Ala Gly Glu Leu Asp Arg Thr Asp Leu Val Ser
225             230             235             240 ctc gcc ctc atc ctg ctg gtc gcc ggg cac gag acg acc gcc aac atg   768
Leu Ala Leu Ile Leu Leu Val Ala Gly His Glu Thr Thr Ala Asn Met
                245             250             255 atc tcc ctg ggc acc tac acc ctg ctc cag cac ccc gaa cgg ctg gcc   816
Ile Ser Leu Gly Thr Tyr Thr Leu Leu Gln His Pro Glu Arg Leu Ala
            260             265             270 gag ctg cgt gcc gac ccc acg gtg ctg ccc gcc gtc gtc gag gaa ctg   864
Glu Leu Arg Ala Asp Pro Thr Val Leu Pro Ala Val Val Glu Glu Leu
        275             280             285 ctg cgg atg ctg tcc atc gcc gag ggg ctg caa cgg ctg gcg ctg gag   912
Leu Arg Met Leu Ser Ile Ala Glu Gly Leu Gln Arg Leu Ala Leu Glu
    290             295             300 gac atc gag atc gac ggc acc acc atc cgg gcc ggt gac ggc gtc ctc   960
Asp Ile Glu Ile Asp Gly Thr Thr Ile Arg Ala Gly Asp Gly Val Leu
305             310             315             320 ttc tcc acc tcg gtc atc aac cgg gac acg gcc gtc tac gac gac ccc  1008
Phe Ser Thr Ser Val Ile Asn Arg Asp Thr Ala Val Tyr Asp Asp Pro
```

```
                         325                 330                 335
gac gac ctg gac ttc cac cgc gcc gac cgg cac cac gtg gcg ttc ggc      1056
Asp Asp Leu Asp Phe His Arg Ala Asp Arg His His Val Ala Phe Gly
            340                 345                 350 ttc ggc atc cac cag tgc ctg ggc cag aac ctg gcc cgc gcg gaa ctg      1104
Phe Gly Ile His Gln Cys Leu Gly Gln Asn Leu Ala Arg Ala Glu Leu
        355                 360                 365 gag atc gcc ctc ggc agc ctc ttc acc cgg ctg ccc ggg ctg cgt ctt      1152
Glu Ile Ala Leu Gly Ser Leu Phe Thr Arg Leu Pro Gly Leu Arg Leu
    370                 375                 380 gcc gcc ccg gcc gag gag atc ccc ttc aaa ccg ggc gac acg atc cag      1200
Ala Ala Pro Ala Glu Glu Ile Pro Phe Lys Pro Gly Asp Thr Ile Gln
385                 390                 395                 400 ggg atg ctg gaa ctc ccc gtg acc tgg taa gaggcttcgc tc atg cac atg    1251
Gly Met Leu Glu Leu Pro Val Thr Trp                Met His Met
                405                 410 gac atc gac atc gac cag gac gtc tgt atc ggc gcc ggg cag tgc gcg      1299
Asp Ile Asp Ile Asp Gln Asp Val Cys Ile Gly Ala Gly Gln Cys Ala
            415                 420                 425 ctg gcg gca ccg ggc gtc ttc acc cag gac gac gac ggc tac agc acc      1347
Leu Ala Ala Pro Gly Val Phe Thr Gln Asp Asp Asp Gly Tyr Ser Thr
        430                 435                 440 ctg ctg ccc ggc cag gag aac ggc gtc acc gac ccg atg gtc cgg gag      1395
Leu Leu Pro Gly Gln Glu Asn Gly Val Thr Asp Pro Met Val Arg Glu
445                 450                 455                 460 gcc gcc cgc gcc tgc ccg gtc agc gcc atc acc gta cgg gag cgc acc      1443
Ala Ala Arg Ala Cys Pro Val Ser Ala Ile Thr Val Arg Glu Arg Thr
            465                 470                 475 gcc tga                                                              1449
Ala

<210> SEQ ID NO 148
<211> LENGTH: 1449
<212> TYPE: DNA
<213> ORGANISM: Streptmyces olivochromogenes IFO 12444
<220> FEATURE:
<221> NAME/KEY: CDS
<222> LOCATION: (1)..(1230)
<220> FEATURE:
<221> NAME/KEY: CDS
<222> LOCATION: (1243)..(1449)

<400> SEQUENCE: 148 atg acg gaa ctg acg gac atc acc ggc ccg gct ggc cag gcc gaa ccc       48
Met Thr Glu Leu Thr Asp Ile Thr Gly Pro Ala Gly Gln Ala Glu Pro
 1               5                  10                  15 gtc gca ttc ccc cag gac cgc acc tgt ccc tac cac ccc ccc acc gga       96
Val Ala Phe Pro Gln Asp Arg Thr Cys Pro Tyr His Pro Pro Thr Gly
            20                  25                  30 tac gac ccg ctg cgc gac ggg cga ccc ctg tcc cgc gtc acc ctc tac      144
Tyr Asp Pro Leu Arg Asp Gly Arg Pro Leu Ser Arg Val Thr Leu Tyr
        35                  40                  45 gac ggc cgc gag gtc tgg ctg gtc acc gcc cag gcc acc gcc cgc gcc      192
Asp Gly Arg Glu Val Trp Leu Val Thr Ala Gln Ala Thr Ala Arg Ala
    50                  55                  60 ctg ctc gcc gac ccc cgg ctg tcc acc gac cgc cgc cgc gac ggt ttt      240
Leu Leu Ala Asp Pro Arg Leu Ser Thr Asp Arg Arg Arg Asp Gly Phe
65                  70                  75                  80 ccc gtg ccc agc ccc cgc ttc gag gcc ggc cgc gac cgc aaa ctg gcc      288
Pro Val Pro Ser Pro Arg Phe Glu Ala Gly Arg Asp Arg Lys Leu Ala
                85                  90                  95 ctg ctc ggg ctg gac gac ccc gag cac cac cag cag cgc cgg atg ctg      336
```

-continued

```
                Leu Leu Gly Leu Asp Asp Pro Glu His His Gln Gln Arg Arg Met Leu
                            100                 105                 110 atc ccg tcg ttc acc gtc aaa cgc gcc acc gcg cta cgc ccc tgg atc        384
Ile Pro Ser Phe Thr Val Lys Arg Ala Thr Ala Leu Arg Pro Trp Ile
            115                 120                 125 cag cgg atc gtc gac gaa ctg ctg gac gac atg atc gcc cgg ggg ccg        432
Gln Arg Ile Val Asp Glu Leu Leu Asp Asp Met Ile Ala Arg Gly Pro
        130                 135                 140 gtc gcc gac ctc gtg tcc gcg ttc gcg ctg ccc gtg ccg tcc atg gtc        480
Val Ala Asp Leu Val Ser Ala Phe Ala Leu Pro Val Pro Ser Met Val
145                 150                 155                 160 atc tgc gaa ctg ctc ggc gtg ccc tac gcc gac cac gag ttc ttc gag        528
Ile Cys Glu Leu Leu Gly Val Pro Tyr Ala Asp His Glu Phe Phe Glu
                165                 170                 175 gaa cag tcc cgc cgg ctg ctg cgc ggc ccg ggc ggc gcc gac aca ctg        576
Glu Gln Ser Arg Arg Leu Leu Arg Gly Pro Gly Gly Ala Asp Thr Leu
            180                 185                 190 gac gcc cgg gac cgg ctg gag gcg tac ctc ggc gag ctg atc gac gcc        624
Asp Ala Arg Asp Arg Leu Glu Ala Tyr Leu Gly Glu Leu Ile Asp Ala
        195                 200                 205 aag gcc aag gag gcc gag ccc ggc gac ggc att ctg gac gat ctg gtc        672
Lys Ala Lys Glu Ala Glu Pro Gly Asp Gly Ile Leu Asp Asp Leu Val
    210                 215                 220 cac aac cgg ctc cgc gcg ggc gag ctg gac cgg acc gac ctg gtg tcg        720
His Asn Arg Leu Arg Ala Gly Glu Leu Asp Arg Thr Asp Leu Val Ser
225                 230                 235                 240 ctc gcc ctc atc ctg ctg gtc gcc ggg cac gag aca acc gcc aac atg        768
Leu Ala Leu Ile Leu Leu Val Ala Gly His Glu Thr Thr Ala Asn Met
                245                 250                 255 atc tcc ctg ggc acc tac acc ctg ctc cag cac ccc gaa cgg ctg gcc        816
Ile Ser Leu Gly Thr Tyr Thr Leu Leu Gln His Pro Glu Arg Leu Ala
            260                 265                 270 gag ctg cgt gcc gac ccc acg gtg ctg ccc gcc gtc gtc gag gaa ctg        864
Glu Leu Arg Ala Asp Pro Thr Val Leu Pro Ala Val Val Glu Glu Leu
        275                 280                 285 ctg cgg atg ctg tcc atc gcc gag ggg ctg caa cgg gtg gcg ctg gag        912
Leu Arg Met Leu Ser Ile Ala Glu Gly Leu Gln Arg Val Ala Leu Glu
    290                 295                 300 gac atc gag atc gac ggc acc acc atc cgg gcc ggt gac ggc gtc ctc        960
Asp Ile Glu Ile Asp Gly Thr Thr Ile Arg Ala Gly Asp Gly Val Leu
305                 310                 315                 320 ttc tcc acc tcg gtc atc aac cgg gac acg gcc gtc tac gac gac ccc       1008
Phe Ser Thr Ser Val Ile Asn Arg Asp Thr Ala Val Tyr Asp Asp Pro
                325                 330                 335 gac ggc ctg gac ttc cac cgc gcc gac cgg cac cac gtg gcg ttc ggc       1056
Asp Gly Leu Asp Phe His Arg Ala Asp Arg His His Val Ala Phe Gly
            340                 345                 350 ttc ggc atc cac cag tgc ctg ggc cag aac ctg gcc cgc gcg gaa ctg       1104
Phe Gly Ile His Gln Cys Leu Gly Gln Asn Leu Ala Arg Ala Glu Leu
        355                 360                 365 gag atc gcc ctc ggc agc ctc ttc acc cgg ctg ccc gga ctg cgt ctt       1152
Glu Ile Ala Leu Gly Ser Leu Phe Thr Arg Leu Pro Gly Leu Arg Leu
    370                 375                 380 gcc gcc ccg gcc gag gag atc ccc ttc aaa ccg ggc gac acg atc cag       1200
Ala Ala Pro Ala Glu Glu Ile Pro Phe Lys Pro Gly Asp Thr Ile Gln
385                 390                 395                 400 ggg atg ctg gaa ctc ccc gtg acc tgg taa gaggcttcgc tc atg cac atg     1251
Gly Met Leu Glu Leu Pro Val Thr Trp              Met His Met
                405                                  410 gac atc gac atc gac cag gac atc tgt atc ggc gcc ggg cag tgc gcg       1299
```

```
            Asp Ile Asp Ile Asp Gln Asp Ile Cys Ile Gly Ala Gly Gln Cys Ala
                415                 420                 425 ctg gcg gca ccg ggc gtc ttc acc cag gac gac gac ggc tac agc acc        1347
Leu Ala Ala Pro Gly Val Phe Thr Gln Asp Asp Asp Gly Tyr Ser Thr
    430                 435                 440 ctg ctg ccc ggc cag gag aac ggc gtc acc gac ccg atg gtc cgg gag        1395
Leu Leu Pro Gly Gln Glu Asn Gly Val Thr Asp Pro Met Val Arg Glu
445                 450                 455                 460 gcc gcc cgc gcc tgc ccg gtc agc gcc atc acc gta cgg gag cgc acc        1443
Ala Ala Arg Ala Cys Pro Val Ser Ala Ile Thr Val Arg Glu Arg Thr
                465                 470                 475 gcc tga                                                                1449
Ala

<210> SEQ ID NO 149
<211> LENGTH: 68
<212> TYPE: PRT
<213> ORGANISM: Streptmyces nogalater IFO 13445

<400> SEQUENCE: 149

Met His Ile Asp Ile Asp Ile Asp Gln Asp Val Cys Ile Gly Ala Gly
  1               5                  10                  15

Gln Cys Ala Leu Ala Ala Pro Gly Val Phe Thr Gln Asp Asp Asp Gly
                 20                  25                  30

Tyr Ser Thr Leu Leu Pro Gly Gln Glu Asn Gly Val Thr Asp Pro Met
             35                  40                  45

Val Arg Glu Ala Ala Arg Ala Cys Pro Val Ser Ala Ile Thr Val Arg
         50                  55                  60

Glu Arg Thr Ala
 65

<210> SEQ ID NO 150
<211> LENGTH: 65
<212> TYPE: PRT
<213> ORGANISM: Streptmyces tsusimaensis IFO 13782T

<400> SEQUENCE: 150

Met Gly Val Gln Val Asp Arg Glu Arg Cys Val Gly Ala Gly Met Cys
  1               5                  10                  15

Ala Leu Thr Ala Pro Asp Val Phe Thr Gln Asp Asp Asp Gly Leu Ser
                 20                  25                  30

Glu Val Leu Pro Gly Arg Ala Glu Thr Ala Gly Gly His Pro Leu Val
             35                  40                  45

Gly Glu Ala Val Arg Ala Cys Pro Val Gly Ala Val Ala Leu Ser Ala
         50                  55                  60

Asp
 65

<210> SEQ ID NO 151
<211> LENGTH: 83
<212> TYPE: PRT
<213> ORGANISM: Streptmyces thermocoerulescens IFO 14273t

<400> SEQUENCE: 151

Met His Asn Glu Thr His Glu Thr His Glu Thr Thr Ala Ala Ala Ser
  1               5                  10                  15

Gly Thr Arg Ile Asp Ile Asp His Asp Leu Cys Val Gly Ala Gly Gln
                 20                  25                  30

Cys Ala Leu Val Ala Pro Ser Val Phe Thr Gln Asp Asp Asp Gly Phe
             35                  40                  45
```

```
Ser Glu Leu Ile Pro Gly Arg Glu Asp Gly Ala Gly Asp Pro Met Val
         50                  55                  60

Arg Glu Ala Val Arg Ala Cys Pro Val Ser Ala Ile Thr Val Thr Glu
 65                  70                  75                  80

Ala Ala Val
```

<210> SEQ ID NO 152
<211> LENGTH: 68
<212> TYPE: PRT
<213> ORGANISM: Streptmyces glomerochromogenes IFO 13673T

<400> SEQUENCE: 152

```
Met His Met Asp Ile Asp Ile Asp Gln Asp Val Cys Ile Gly Ala Gly
  1               5                  10                  15

Gln Cys Ala Leu Ala Ala Pro Gly Val Phe Thr Gln Asp Asp Asp Gly
                 20                  25                  30

Tyr Ser Thr Leu Leu Pro Gly Gln Glu Asn Gly Val Thr Asp Pro Met
             35                  40                  45

Val Arg Glu Ala Ala Arg Ala Cys Pro Val Ser Ala Ile Thr Val Arg
 50                  55                  60

Glu Arg Thr Ala
 65
```

<210> SEQ ID NO 153
<211> LENGTH: 68
<212> TYPE: PRT
<213> ORGANISM: Streptmyces olivochromogenes IFO 12444

<400> SEQUENCE: 153

```
Met His Met Asp Ile Asp Ile Asp Gln Asp Ile Cys Ile Gly Ala Gly
  1               5                  10                  15

Gln Cys Ala Leu Ala Ala Pro Gly Val Phe Thr Gln Asp Asp Asp Gly
                 20                  25                  30

Tyr Ser Thr Leu Leu Pro Gly Gln Glu Asn Gly Val Thr Asp Pro Met
             35                  40                  45

Val Arg Glu Ala Ala Arg Ala Cys Pro Val Ser Ala Ile Thr Val Arg
 50                  55                  60

Glu Arg Thr Ala
 65
```

<210> SEQ ID NO 154
<211> LENGTH: 207
<212> TYPE: DNA
<213> ORGANISM: Streptmyces nogalater IFO 13445
<220> FEATURE:
<221> NAME/KEY: CDS
<222> LOCATION: (1)..(207)

<400> SEQUENCE: 154

```
atg cac atc gac atc gat atc gac cag gac gtc tgc atc ggc gcc ggg      48
Met His Ile Asp Ile Asp Ile Asp Gln Asp Val Cys Ile Gly Ala Gly
  1               5                  10                  15 cag tgc gcg ctg gcg gca ccg ggc gtc ttc acc cag gac gac gac ggc      96
Gln Cys Ala Leu Ala Ala Pro Gly Val Phe Thr Gln Asp Asp Asp Gly
                 20                  25                  30 tac agc acc ctg ctg ccc ggc cag gag aac ggc gtg acc gac ccg atg     144
Tyr Ser Thr Leu Leu Pro Gly Gln Glu Asn Gly Val Thr Asp Pro Met
             35                  40                  45 gtc cgg gag gcc gcc cgc gcc tgc ccg gtc agc gcg atc acc gtg cgg     192
Val Arg Glu Ala Ala Arg Ala Cys Pro Val Ser Ala Ile Thr Val Arg
 50                  55                  60
```

```
                50                   55                   60
gag cgc acc gcc tga                                                              207
Glu Arg Thr Ala
 65

<210> SEQ ID NO 155
<211> LENGTH: 198
<212> TYPE: DNA
<213> ORGANISM: Streptmyces tsusimaensis IFO 13782T
<220> FEATURE:
<221> NAME/KEY: CDS
<222> LOCATION: (1)..(198)

<400> SEQUENCE: 155 atg ggc gtc cag gtc gac agg gaa cgc tgc gtg ggg gcg ggc atg tgc     48
Met Gly Val Gln Val Asp Arg Glu Arg Cys Val Gly Ala Gly Met Cys
  1               5                  10                  15 gcg ctg acc gcg ccg gac gtg ttc acg cag gac gac gac ggc ctc agc     96
Ala Leu Thr Ala Pro Asp Val Phe Thr Gln Asp Asp Asp Gly Leu Ser
             20                  25                  30 gag gtg ctc ccg ggc cgc gcg gag acc gct gga gga cat ccc ttg gtg    144
Glu Val Leu Pro Gly Arg Ala Glu Thr Ala Gly Gly His Pro Leu Val
         35                  40                  45 ggg gag gct gta cgg gcc tgc ccg gtg ggg gcg gtg gcc ctg tcc gcc    192
Gly Glu Ala Val Arg Ala Cys Pro Val Gly Ala Val Ala Leu Ser Ala
     50                  55                  60 gac tga                                                            198
Asp
 65

<210> SEQ ID NO 156
<211> LENGTH: 252
<212> TYPE: DNA
<213> ORGANISM: Streptmyces thermocoerulescens IFO 14273t
<220> FEATURE:
<221> NAME/KEY: CDS
<222> LOCATION: (1)..(252)

<400> SEQUENCE: 156 atg cac aac gaa acg cat gag aca cac gag acc acc gcg gcg gcc tcc     48
Met His Asn Glu Thr His Glu Thr His Glu Thr Thr Ala Ala Ala Ser
  1               5                  10                  15 ggg acc cgt atc gac atc gac cac gac ctc tgc gtc ggc gcc ggg cag     96
Gly Thr Arg Ile Asp Ile Asp His Asp Leu Cys Val Gly Ala Gly Gln
             20                  25                  30 tgc gcc ctg gtc gcc ccg tcc gtc ttc acc cag gac gac gac ggc ttc    144
Cys Ala Leu Val Ala Pro Ser Val Phe Thr Gln Asp Asp Asp Gly Phe
         35                  40                  45 agc gag ctg atc ccc ggc cgc gag gac ggt gcc ggc gac ccg atg gtc    192
Ser Glu Leu Ile Pro Gly Arg Glu Asp Gly Ala Gly Asp Pro Met Val
     50                  55                  60 cgg gag gcc gtc cgc gcc tgc ccc gtc agc gcc atc acc gtg acg gag    240
Arg Glu Ala Val Arg Ala Cys Pro Val Ser Ala Ile Thr Val Thr Glu
 65                  70                  75                  80 gcc gcc gtc tga                                                    252
Ala Ala Val <210> SEQ ID NO 157
<211> LENGTH: 207
<212> TYPE: DNA
<213> ORGANISM: Streptmyces glomerochromogenes IFO 13673T
<220> FEATURE:
<221> NAME/KEY: CDS
<222> LOCATION: (1)..(207)
```

-continued

```
<400> SEQUENCE: 157 atg cac atg gac atc gac atc gac cag gac gtc tgt atc ggc gcc ggg      48
Met His Met Asp Ile Asp Ile Asp Gln Asp Val Cys Ile Gly Ala Gly
 1               5                  10                  15 cag tgc gcg ctg gcg gca ccg ggc gtc ttc acc cag gac gac gac ggc      96
Gln Cys Ala Leu Ala Ala Pro Gly Val Phe Thr Gln Asp Asp Asp Gly
             20                  25                  30 tac agc acc ctg ctg ccc ggc cag gag aac ggc gtc acc gac ccg atg     144
Tyr Ser Thr Leu Leu Pro Gly Gln Glu Asn Gly Val Thr Asp Pro Met
         35                  40                  45 gtc cgg gag gcc gcc cgc gcc tgc ccg gtc agc gcc atc acc gta cgg     192
Val Arg Glu Ala Ala Arg Ala Cys Pro Val Ser Ala Ile Thr Val Arg
     50                  55                  60 gag cgc acc gcc tga                                                  207
Glu Arg Thr Ala
 65

<210> SEQ ID NO 158
<211> LENGTH: 207
<212> TYPE: DNA
<213> ORGANISM: Streptmyces olivochromogenes IFO 12444
<220> FEATURE:
<221> NAME/KEY: CDS
<222> LOCATION: (1)..(207)

<400> SEQUENCE: 158 atg cac atg gac atc gac atc gac cag gac atc tgt atc ggc gcc ggg      48
Met His Met Asp Ile Asp Ile Asp Gln Asp Ile Cys Ile Gly Ala Gly
 1               5                  10                  15 cag tgc gcg ctg gcg gca ccg ggc gtc ttc acc cag gac gac gac ggc      96
Gln Cys Ala Leu Ala Ala Pro Gly Val Phe Thr Gln Asp Asp Asp Gly
             20                  25                  30 tac agc acc ctg ctg ccc ggc cag gag aac ggc gtc acc gac ccg atg     144
Tyr Ser Thr Leu Leu Pro Gly Gln Glu Asn Gly Val Thr Asp Pro Met
         35                  40                  45 gtc cgg gag gcc gcc cgc gcc tgc ccg gtc agc gcc atc acc gta cgg     192
Val Arg Glu Ala Ala Arg Ala Cys Pro Val Ser Ala Ile Thr Val Arg
     50                  55                  60 gag cgc acc gcc tga                                                  207
Glu Arg Thr Ala
 65

<210> SEQ ID NO 159
<211> LENGTH: 409
<212> TYPE: PRT
<213> ORGANISM: Streptmyces nogalater IFO 13445

<400> SEQUENCE: 159

Met Thr Glu Leu Thr Asp Thr Thr Gly Pro Ala Asp Ala Ala Glu Pro
 1               5                  10                  15

Val Ala Phe Pro Gln Asp Arg Thr Cys Pro Tyr His Pro Thr Gly
             20                  25                  30

Tyr Asp Pro Leu Arg Asp Gly Arg Pro Leu Ser Arg Val Thr Leu Tyr
         35                  40                  45

Asp Gly Arg Glu Val Trp Leu Val Thr Ala Gln Ala Thr Ala Arg Thr
     50                  55                  60

Leu Leu Ala Asp Pro Arg Leu Ser Thr Asp Arg Arg Asp Gly Phe
 65                  70                  75                  80

Pro Val Pro Thr Pro Arg Phe Glu Gly Gly Arg Asp Arg Lys Leu Ala
                 85                  90                  95

Leu Leu Gly Leu Asp Asp Pro Glu His Gln Gln Gln Arg Arg Met Leu
```

```
                100                 105                 110
Ile Pro Ser Phe Thr Val Lys Arg Ala Thr Ala Leu Arg Pro Trp Ile
            115                 120                 125

Gln Arg Ile Val Asp Gly Leu Leu Asp Ala Met Ile Thr Arg Gly Pro
        130                 135                 140

Val Ala Asp Leu Val Ser Ala Phe Ala Leu Pro Val Pro Ser Met Val
145                 150                 155                 160

Ile Cys Glu Leu Leu Gly Val Pro Tyr Ala Asp His Glu Phe Phe Glu
                165                 170                 175

Glu Gln Ser Arg Arg Leu Leu Ser Ala Ser Thr Ser Ala Asp Thr Leu
            180                 185                 190

Asp Ala Arg Asp Arg Leu Glu Thr Tyr Leu Gly Asp Leu Ile Asp Ala
        195                 200                 205

Lys Ala Lys Glu Ala Glu Pro Gly Asp Gly Ile Leu Asp Glu Leu Val
    210                 215                 220

His Asn Arg Leu Arg Lys Gly Glu Leu Asp Arg Thr Asp Leu Val Ser
225                 230                 235                 240

Leu Ala Val Ile Leu Leu Val Ala Gly His Glu Thr Thr Ala Asn Met
                245                 250                 255

Ile Ser Leu Gly Thr Tyr Thr Leu Leu Gln His Pro Glu Arg Leu Ala
            260                 265                 270

Glu Leu Arg Ala Asp Pro Ala Leu Pro Ala Val Val Glu Glu Leu
        275                 280                 285

Leu Arg Met Leu Ser Ile Ala Glu Gly Leu Gln Arg Val Ala Leu Glu
    290                 295                 300

Asp Ile Glu Ile Asp Gly Thr Thr Ile Arg Ala Gly Asp Gly Val Leu
305                 310                 315                 320

Phe Ser Thr Ser Val Ile Asn Arg Asp Thr Ala Val Tyr Asp Asp Pro
                325                 330                 335

Asp Asp Leu Asp Phe His Arg Ala Asp Arg His Val Ala Phe Gly
            340                 345                 350

Phe Gly Ile His Gln Cys Leu Gly Gln Asn Leu Ala Arg Ala Glu Leu
        355                 360                 365

Glu Ile Ala Leu Gly Ser Leu Phe Thr Arg Leu Pro Gly Leu Arg Leu
    370                 375                 380

Ala Val Pro Ala Lys Asp Ile Pro Phe Lys Pro Gly Asp Thr Ile Gln
385                 390                 395                 400

Gly Met Leu Glu Leu Pro Val Thr Trp
                405

<210> SEQ ID NO 160
<211> LENGTH: 425
<212> TYPE: PRT
<213> ORGANISM: Streptmyces tsusimaensis IFO 13782T

<400> SEQUENCE: 160

Met Thr Glu Ser Thr Thr Asp Pro Thr Thr Arg Gln Ala Leu Gly Ser
1               5                   10                  15

Thr Thr Pro Ala Ala Ala Thr Ala Thr Ala Ile Asp Pro Thr Leu Ala
            20                  25                  30

Thr Pro Phe Pro Gln Asp Arg Gly Cys Pro Tyr His Pro Pro Ala Gly
        35                  40                  45

Tyr Ala Pro Leu Arg Glu Gly Arg Pro Leu Ser Arg Val Ala Leu Phe
    50                  55                  60

Asp Gly Arg Pro Val Trp Ala Val Thr Gly His Ala Leu Ala Arg Arg
```

```
            65                  70                  75                  80
Leu Leu Ala Asp Pro Arg Leu Ser Thr Asp Arg Thr His Pro Asp Phe
                85                  90                  95
Pro Ala Pro Ala Pro Arg Phe Ala Asn Ala Asn Arg Arg Val Ala
            100                 105                 110
Leu Leu Gly Val Asp Asp Pro Glu His Asn Thr Gln Arg Arg Met Leu
        115                 120                 125
Ile Pro Ala Phe Ser Val Lys Arg Ile Asn Ala Leu Arg Pro Arg Ile
    130                 135                 140
Gln Glu Thr Val Asp Arg Leu Leu Asp Ala Met Glu Arg Gln Gly Pro
145                 150                 155                 160
Pro Ala Glu Leu Val Ser Ala Phe Ala Leu Pro Val Pro Ser Met Val
                165                 170                 175
Ile Cys Ser Leu Leu Gly Val Pro Tyr Ala Asp His Glu Phe Phe Glu
                180                 185                 190
Glu Arg Ser Arg Arg Leu Leu Arg Gly Pro Gly Ala Ala Asp Val Asp
            195                 200                 205
Arg Ala Leu Asp Glu Leu Glu Glu Tyr Leu Gly Ala Leu Ile Asp Arg
210                 215                 220
Lys Arg Thr Glu Pro Gly Asp Gly Leu Leu Asp Glu Leu Ile His Arg
225                 230                 235                 240
Asp His Pro Gly Gly Pro Val Asp Arg Glu Glu Leu Val Ser Phe Ala
                245                 250                 255
Val Ile Leu Leu Ile Ala Gly His Glu Thr Thr Ala Asn Met Ile Ser
            260                 265                 270
Leu Gly Thr Phe Thr Leu Leu Arg His Pro Glu Gln Leu Ala Ala Leu
        275                 280                 285
Arg Ala Gly Gly Thr Thr Thr Ala Val Ala Val Glu Glu Leu Leu Arg
    290                 295                 300
Phe Leu Ser Ile Ala Asp Gly Leu Gln Arg Leu Ala Thr Glu Asp Ile
305                 310                 315                 320
Glu Val Pro Asp Ala Gly Val Thr Ile Arg Lys Gly Glu Gly Val Val
                325                 330                 335
Phe Ser Thr Ser Leu Ile Asn Arg Asp Asp Gly Val Phe Pro Gln Pro
            340                 345                 350
Glu Thr Leu Asp Trp Asp Arg Pro Ala Arg His His Leu Ala Phe Gly
        355                 360                 365
Phe Gly Val His Gln Cys Leu Gly Gln Asn Leu Ala Arg Ala Glu Leu
    370                 375                 380
Asp Ile Ala Met Arg Thr Leu Phe Glu Arg Leu Pro Gly Leu Arg Leu
385                 390                 395                 400
Ala Val Pro Ala Gln Glu Ile Pro His Lys Pro Gly Asp Thr Ile Gln
                405                 410                 415
Gly Met Leu Glu Leu Pro Val Ala Trp
            420                 425

<210> SEQ ID NO 161
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 161
agcagttcgc agatgaccat ggacggca                                          28
```

```
<210> SEQ ID NO 162
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 162
tttcacggtg aacgacggga tcagcat                                            27

<210> SEQ ID NO 163
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 163
acgagacgac cgccaacatg atctccct                                           28

<210> SEQ ID NO 164
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 164
tcctcttctc cacctcggtc atcaacc                                            27

<210> SEQ ID NO 165
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 165
ttcatatgac ggaactgacg gacacca                                            27

<210> SEQ ID NO 166
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 166
cgaagctttc aggcggtgcg ctcccgca                                           28

<210> SEQ ID NO 167
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 167
agcaaccggt ccacggtctc ctggatg                                            27

<210> SEQ ID NO 168
<211> LENGTH: 28
<212> TYPE: DNA
<213> ORGANISM: Artificial Sequence
<220> FEATURE:
<223> OTHER INFORMATION: Designed oligonucleotide primer for PCR
```

```
<400> SEQUENCE: 168
gagagcgttg atccgcttca cggagaag                                    28

<210> SEQ ID NO 169
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 169
caagggcgaa ggtgtggtct tctcgac                                     27

<210> SEQ ID NO 170
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 170
ctcatcaacc gcgacgacgg cgtgttc                                     27

<210> SEQ ID NO 171
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 171
accatatgac ggaatccacg acagatc                                     27

<210> SEQ ID NO 172
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 172
cgaagctttc agtcggcgga cagggccac                                   29

<210> SEQ ID NO 173
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 173
ctcctcgaag aagtcgtggt cctcgta                                     27

<210> SEQ ID NO 174
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 174
atcatcgcgt cgaggcgttc gtcgacga                                    28

<210> SEQ ID NO 175
<211> LENGTH: 27
<212> TYPE: DNA
```

```
<213> ORGANISM: Artificial Sequence
<220> FEATURE:
<223> OTHER INFORMATION: Designed oligonucleotide primer for PCR

<400> SEQUENCE: 175
ccaacatgat ctcgctcggc accttca                                          27

<210> SEQ ID NO 176
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 176
cgtcatcttc tcgacgtcgg tcatcaa                                          27

<210> SEQ ID NO 177
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 177
ctcatatgac ggacatgacg gaaaccccca                                       30

<210> SEQ ID NO 178
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 178
cgaagctttc agacggcggc ctccgtca                                         28

<210> SEQ ID NO 179
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 179
cagttcgtcg acgatccgct ggatcca                                          27

<210> SEQ ID NO 180
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 180
tttgacggtg aacgacggga tcagcat                                          27

<210> SEQ ID NO 181
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 181
gacatcgaga tcgacggcac caccatc                                          27
```

<210> SEQ ID NO 182
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 182
gtcctcttct ccacctcggt catcaac                                          27

<210> SEQ ID NO 183
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 183
cgaggtcttc atatgacgga actgacggac atc                                   33

<210> SEQ ID NO 184
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 184
ccgccgaagc tttcaggcgg tgcgctcccg tac                                   33

<210> SEQ ID NO 185
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 185
cgaggtcata tgacggaact gacggacatc                                       30

<210> SEQ ID NO 186
<211> LENGTH: 27
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 186
atgctgatcc cgtcgttcac cgtgaaa                                          27

<210> SEQ ID NO 187
<211> LENGTH: 28
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 187
cttctccgtg aagcggatca acgctctc                                         28

<210> SEQ ID NO 188
<211> LENGTH: 28
<212> TYPE: DNA
<213> ORGANISM: Artificial Sequence
<220> FEATURE:

-continued

<223> OTHER INFORMATION: Designed oligonucleotide primer for DNA
      sequencing

<400> SEQUENCE: 188
tcgtcgacga acgcctcgac gcgatgat                                         28

<210> SEQ ID NO 189
<211> LENGTH: 27
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 189
atggtcatct gcgaactgct cggcgtg                                          27

<210> SEQ ID NO 190
<211> LENGTH: 78
<212> TYPE: DNA
<213> ORGANISM: Artificial Sequence
<220> FEATURE:
<223> OTHER INFORMATION: Designed oligonucleotide primer for PCR

<400> SEQUENCE: 190
cgggatccca tatgacagat atgacagata ctgcagacgt taaaccacta tctgcaccag      60
ttgcatttcc tcaagata                                                    78

<210> SEQ ID NO 191
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 191
agttgcattt cctcaagata gaacctgtcc attccagcct cctactgggt atgatccact      60
tcgtgaagct                                                             70

<210> SEQ ID NO 192
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 192
atgatccact tcgtgaagct aggcctcttg ctagagttac actttacgat ggaagggcta      60
tctggcttgt                                                             70

<210> SEQ ID NO 193
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 193
gttgatgacc ctgaacatca cactcaaagg cggatgttag ttcctagctt tacactcaag      60
cgcgctgctg                                                             70

<210> SEQ ID NO 194
<211> LENGTH: 70
<212> TYPE: DNA

```
<213> ORGANISM: Artificial Sequence
<220> FEATURE:
<223> OTHER INFORMATION: Designed oligonucleotide primer for PCR

<400> SEQUENCE: 194
tacactcaag cgcgctgctg cgttgaggcc agccattcag aggattgtcg atgagtgcat    60
agatgctatg                                                          70

<210> SEQ ID NO 195
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 195
atgagtgcat agatgctatg ttagctaagg gaccacctgc agagttggtt aacgccttcg    60
cacttcccgt                                                          70

<210> SEQ ID NO 196
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 196
tgctacttag gagcactgat tgaccgcaag tccgaatcat ccgttggtga tggtgtcctc    60
gacgccttgg                                                          70

<210> SEQ ID NO 197
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 197
tggtgtcctc gacgccttgg ttcacgagca attgagagaa ggagctgtgg ataggcagga    60
ggctatcagc                                                          70

<210> SEQ ID NO 198
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 198
ataggcagga ggctatcagc ttggccacga ttctgttggt cgctggtcat gaaaccactg    60
ctaatatgat                                                          70

<210> SEQ ID NO 199
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 199
caagccacag aggacatcga ggtggcaggt actactatta gagccggtga aggcgtggtc    60
tttgcgacct                                                          70
```

-continued

<210> SEQ ID NO 200
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 200
aggcgtggtc tttgcgacct ctgtaatcaa cagagatggg gaggtttacg cagaacccga    60
cgccctcgat                                                           70

<210> SEQ ID NO 201
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 201
cagaacccga cgccctcgat tggcataggc ccaccagaca tcacgtggca ttcggctttg    60
gcattcatca                                                           70

<210> SEQ ID NO 202
<211> LENGTH: 79
<212> TYPE: DNA
<213> ORGANISM: Artificial Sequence
<220> FEATURE:
<223> OTHER INFORMATION: Designed oligonucleotide primer for PCR

<400> SEQUENCE: 202
accagatgct gtccgcttta aaccaggtga cacgattcag ggaatgctgg atcttcccgt    60
ggcctggtag aagcttggg                                                 79

<210> SEQ ID NO 203
<211> LENGTH: 80
<212> TYPE: DNA
<213> ORGANISM: Artificial Sequence
<220> FEATURE:
<223> OTHER INFORMATION: Designed oligonucleotide primer for PCR

<400> SEQUENCE: 203
gatggagata gcacttcgta gtttgttcga gagagtgcct gggttgagac tcgacattgc    60
accagatgct gtccgcttta                                                80

<210> SEQ ID NO 204
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 204
ttcggctttg gcattcatca atgtctcgga cagaatctag cacgtgccga gatggagata    60
gcacttcgta                                                           70

<210> SEQ ID NO 205
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 205

-continued

```
ctgttgatga gttgatgagg atgctttcta tagcggacgg gctgatgaga caagccacag    60
aggacatcga                                                           70

<210> SEQ ID NO 206
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 206
ccccgagcga ctggcggaat tgagggatga cccgagtttg tggcctgctg ctgttgatga    60
gttgatgagg                                                           70

<210> SEQ ID NO 207
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 207
gaaaccactg ctaatatgat ctcattgggc acttatacat tactccaaca ccccgagcga    60
ctggcggaat                                                           70

<210> SEQ ID NO 208
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 208
tacgcggacg ggatgtggac gaggtgcgtg atgcaaggga ccagctcgat tgctacttag    60
gagcactgat                                                           70

<210> SEQ ID NO 209
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 209
tgtaccgtat gccgatcatg aattctttga ggaacaaagt cgtaggcttc tacgcggacg    60
ggatgtggac                                                           70

<210> SEQ ID NO 210
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 210
aacgccttcg cacttcccgt tccatcaatg gtgatatgtg aactgctcgg tgtaccgtat    60
gccgatcatg                                                           70

<210> SEQ ID NO 211
<211> LENGTH: 70
<212> TYPE: DNA
<213> ORGANISM: Artificial Sequence
<220> FEATURE:
```

-continued

<223> OTHER INFORMATION: Designed oligonucleotide primer for PCR

<400> SEQUENCE: 211

```
cctctccacg cattgtagca ttcagagacc gcagggctgc ccttcttaat gttgatgacc    60
ctgaacatca                                                          70
```

<210> SEQ ID NO 212
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 212

```
cgcagattca cgactatcgt ccgatagact tcgacctggc tttccagcta cctctccacg    60
cattgtagca                                                          70
```

<210> SEQ ID NO 213
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 213

```
ggaagggcta tctggcttgt taccggacgt gaccttgcta gaagcctgct cgcagattca    60
cgactatcgt                                                          70
```

<210> SEQ ID NO 214
<211> LENGTH: 1227
<212> TYPE: DNA
<213> ORGANISM: Artificial Sequence
<220> FEATURE:
<221> NAME/KEY: CDS
<222> LOCATION: (1)..(1227)
<223> OTHER INFORMATION: Designed polynucleotide encoding amino acid
      sequence of SEQ ID No.1

<400> SEQUENCE: 214

```
atg aca gat atg aca gat act gca gac gtt aaa cca cta tct gca cca     48
Met Thr Asp Met Thr Asp Thr Ala Asp Val Lys Pro Leu Ser Ala Pro
 1               5                  10                  15 gtt gca ttt cct caa gat aga acc tgt cca ttc cag cct cct act ggg     96
Val Ala Phe Pro Gln Asp Arg Thr Cys Pro Phe Gln Pro Pro Thr Gly
                20                  25                  30 tat gat cca ctt cgt gaa gct agg cct ctt gct aga gtt aca ctt tac    144
Tyr Asp Pro Leu Arg Glu Ala Arg Pro Leu Ala Arg Val Thr Leu Tyr
             35                  40                  45 gat gga agg gct atc tgg ctt gtt acc gga cgt gac ctt gct aga agc    192
Asp Gly Arg Ala Ile Trp Leu Val Thr Gly Arg Asp Leu Ala Arg Ser
         50                  55                  60 ctg ctc gca gat tca cga cta tcg tcc gat aga ctt cga cct ggc ttt    240
Leu Leu Ala Asp Ser Arg Leu Ser Ser Asp Arg Leu Arg Pro Gly Phe
     65                  70                  75                  80 cca gct acc tct cca cgc att gta gca ttc aga gac cgc agg gct gcc    288
Pro Ala Thr Ser Pro Arg Ile Val Ala Phe Arg Asp Arg Arg Ala Ala
                 85                  90                  95 ctt ctt aat gtt gat gac cct gaa cat cac act caa agg cgg atg tta    336
Leu Leu Asn Val Asp Asp Pro Glu His His Thr Gln Arg Arg Met Leu
            100                 105                 110 gtt cct agc ttt aca ctc aag cgc gct gct gcg ttg agg cca gcc att    384
Val Pro Ser Phe Thr Leu Lys Arg Ala Ala Ala Leu Arg Pro Ala Ile
        115                 120                 125
```

| | | | | | | | | | | | | | | | | |
|---|---|---|---|---|---|---|---|---|---|---|---|---|---|---|---|---|
| cag | agg | att | gtc | gat | gag | tgc | ata | gat | gct | atg | tta | gct | aag | gga | cca | 432 |
| Gln | Arg | Ile | Val | Asp | Glu | Cys | Ile | Asp | Ala | Met | Leu | Ala | Lys | Gly | Pro | |
| | 130 | | | | 135 | | | | | 140 | | | | | | |
| cct | gca | gag | ttg | gtt | aac | gcc | ttc | gca | ctt | ccc | gtt | cca | tca | atg | gtg | 480 |
| Pro | Ala | Glu | Leu | Val | Asn | Ala | Phe | Ala | Leu | Pro | Val | Pro | Ser | Met | Val | |
| 145 | | | | | 150 | | | | | 155 | | | | | 160 | |
| ata | tgt | gaa | ctg | ctc | ggt | gta | ccg | tat | gcc | gat | cat | gaa | ttc | ttt | gag | 528 |
| Ile | Cys | Glu | Leu | Leu | Gly | Val | Pro | Tyr | Ala | Asp | His | Glu | Phe | Phe | Glu | |
| | | | | 165 | | | | | 170 | | | | | 175 | | |
| gaa | caa | agt | cgt | agg | ctt | cta | cgc | gga | cgg | gat | gtg | gac | gag | gtg | cgt | 576 |
| Glu | Gln | Ser | Arg | Arg | Leu | Leu | Arg | Gly | Arg | Asp | Val | Asp | Glu | Val | Arg | |
| | | | 180 | | | | | 185 | | | | | 190 | | | |
| gat | gca | agg | gac | cag | ctc | gat | tgc | tac | tta | gga | gca | ctg | att | gac | cgc | 624 |
| Asp | Ala | Arg | Asp | Gln | Leu | Asp | Cys | Tyr | Leu | Gly | Ala | Leu | Ile | Asp | Arg | |
| | | 195 | | | | | 200 | | | | | 205 | | | | |
| aag | tcc | gaa | tca | tcc | gtt | ggt | gat | ggt | gtc | ctc | gac | gcc | ttg | gtt | cac | 672 |
| Lys | Ser | Glu | Ser | Ser | Val | Gly | Asp | Gly | Val | Leu | Asp | Ala | Leu | Val | His | |
| | 210 | | | | | 215 | | | | | 220 | | | | | |
| gag | caa | ttg | aga | gaa | gga | gct | gtg | gat | agg | cag | gag | gct | atc | agc | ttg | 720 |
| Glu | Gln | Leu | Arg | Glu | Gly | Ala | Val | Asp | Arg | Gln | Glu | Ala | Ile | Ser | Leu | |
| 225 | | | | | 230 | | | | | 235 | | | | | 240 | |
| gcc | acg | att | ctg | ttg | gtc | gct | ggt | cat | gaa | acc | act | gct | aat | atg | atc | 768 |
| Ala | Thr | Ile | Leu | Leu | Val | Ala | Gly | His | Glu | Thr | Thr | Ala | Asn | Met | Ile | |
| | | | | 245 | | | | | 250 | | | | | 255 | | |
| tca | ttg | ggc | act | tat | aca | tta | ctc | caa | cac | ccc | gag | cga | ctg | gcg | gaa | 816 |
| Ser | Leu | Gly | Thr | Tyr | Thr | Leu | Leu | Gln | His | Pro | Glu | Arg | Leu | Ala | Glu | |
| | | | 260 | | | | | 265 | | | | | 270 | | | |
| ttg | agg | gat | gac | ccg | agt | ttg | tgg | cct | gct | gct | gtt | gat | gag | ttg | atg | 864 |
| Leu | Arg | Asp | Asp | Pro | Ser | Leu | Trp | Pro | Ala | Ala | Val | Asp | Glu | Leu | Met | |
| | | 275 | | | | | 280 | | | | | 285 | | | | |
| agg | atg | ctt | tct | ata | gcg | gac | ggg | ctg | atg | aga | caa | gcc | aca | gag | gac | 912 |
| Arg | Met | Leu | Ser | Ile | Ala | Asp | Gly | Leu | Met | Arg | Gln | Ala | Thr | Glu | Asp | |
| | 290 | | | | | 295 | | | | | 300 | | | | | |
| atc | gag | gtg | gca | ggt | act | act | att | aga | gcc | ggt | gaa | ggc | gtg | gtc | ttt | 960 |
| Ile | Glu | Val | Ala | Gly | Thr | Thr | Ile | Arg | Ala | Gly | Glu | Gly | Val | Val | Phe | |
| 305 | | | | | 310 | | | | | 315 | | | | | 320 | |
| gcg | acc | tct | gta | atc | aac | aga | gat | ggg | gag | gtt | tac | gca | gaa | ccc | gac | 1008 |
| Ala | Thr | Ser | Val | Ile | Asn | Arg | Asp | Gly | Glu | Val | Tyr | Ala | Glu | Pro | Asp | |
| | | | | 325 | | | | | 330 | | | | | 335 | | |
| gcc | ctc | gat | tgg | cat | agg | ccc | acc | aga | cat | cac | gtg | gca | ttc | ggc | ttt | 1056 |
| Ala | Leu | Asp | Trp | His | Arg | Pro | Thr | Arg | His | His | Val | Ala | Phe | Gly | Phe | |
| | | | | 340 | | | | | 345 | | | | | 350 | | |
| ggc | att | cat | caa | tgt | ctc | gga | cag | aat | cta | gca | cgt | gcc | gag | atg | gag | 1104 |
| Gly | Ile | His | Gln | Cys | Leu | Gly | Gln | Asn | Leu | Ala | Arg | Ala | Glu | Met | Glu | |
| | | 355 | | | | | 360 | | | | | 365 | | | | |
| ata | gca | ctt | cgt | agt | ttg | ttc | gag | aga | gtg | cct | ggg | ttg | aga | ctc | gac | 1152 |
| Ile | Ala | Leu | Arg | Ser | Leu | Phe | Glu | Arg | Val | Pro | Gly | Leu | Arg | Leu | Asp | |
| | 370 | | | | | 375 | | | | | 380 | | | | | |
| att | gca | cca | gat | gct | gtc | cgc | ttt | aaa | cca | ggt | gac | acg | att | cag | gga | 1200 |
| Ile | Ala | Pro | Asp | Ala | Val | Arg | Phe | Lys | Pro | Gly | Asp | Thr | Ile | Gln | Gly | |
| 385 | | | | | 390 | | | | | 395 | | | | | 400 | |
| atg | ctg | gat | ctt | ccc | gtg | gcc | tgg | tag | | | | | | | | 1227 |
| Met | Leu | Asp | Leu | Pro | Val | Ala | Trp | | | | | | | | | |
| | | | | 405 | | | | | | | | | | | | |

<210> SEQ ID NO 215
<211> LENGTH: 416
<212> TYPE: PRT
<213> ORGANISM: Streptomyces ornatus IFO 13069t

<400> SEQUENCE: 215

```
Met Thr Glu Ser Thr Thr Glu Pro Ala Arg Gln Asp Pro Ala Pro Thr
  1               5                  10                  15
Ala Pro Pro Thr Gln Pro Thr Ser Thr Thr Pro Phe Pro Gln Asn Arg
             20                  25                  30
Asp Cys Pro Tyr His Pro Pro Thr Gly Tyr Gln Pro Leu Arg Ala Asp
             35                  40                  45
Arg Pro Leu Ser Arg Val Thr Leu Phe Asp Gly Arg Pro Val Trp Ala
         50                  55                  60
Val Thr Gly His Ala Leu Ala Arg Arg Leu Leu Ala Asp Pro Arg Leu
 65                  70                  75                  80
Ser Thr Asp Arg Thr His Pro Asp Phe Pro Val Pro Ala Glu Arg Phe
                 85                  90                  95
Ala Asn Val Glu Arg Arg Val Ala Leu Leu Gly Val Asp Asp Pro
                100                 105                 110
Glu His Asn Ala Gln Arg Arg Met Leu Ile Pro Ser Phe Ser Val Lys
             115                 120                 125
Arg Ile Ala Ala Leu Arg Pro Arg Ile Gln Glu Thr Val Asp Gly Leu
         130                 135                 140
Leu Asp Ala Met Glu Arg Gln Gly Pro Pro Ser Glu Leu Val Ala Asp
145                 150                 155                 160
Phe Ala Leu Pro Val Pro Ser Met Val Ile Cys Ala Leu Leu Gly Val
                165                 170                 175
Pro Tyr Ala Asp His Glu Phe Phe Glu Gly Cys Ser Arg Arg Leu Leu
             180                 185                 190
Gln Gly Pro Gly Ala Ala Asp Val Asn Glu Ala Arg Ile Glu Leu Glu
         195                 200                 205
Gly Tyr Leu Gly Ala Leu Ile Asp Arg Lys Arg Val Glu Pro Gly Glu
     210                 215                 220
Gly Leu Leu Asp Glu Leu Ile His Arg Asp His Pro Gly Gly Pro Val
225                 230                 235                 240
Asp Arg Glu Asp Leu Val Ser Phe Ala Val Ile Leu Leu Val Ala Gly
                245                 250                 255
His Glu Thr Thr Ala Asn Met Ile Ser Leu Gly Thr Phe Thr Leu Leu
             260                 265                 270
Asn His Pro Glu Gln Leu Glu Ala Leu Arg Ser Gly Ser Thr Thr Thr
         275                 280                 285
Ala Ala Val Val Glu Glu Leu Leu Arg Phe Leu Ser Ile Ala Glu Gly
     290                 295                 300
Leu Gln Arg Leu Ala Thr Glu Asp Ile Glu Val Ala Gly Thr Thr Ile
305                 310                 315                 320
Arg Glu Gly Glu Gly Val Phe Phe Ser Thr Ser Leu Ile Asn Arg Asp
                325                 330                 335
Thr Glu Val Tyr Glu Asn Pro Glu Thr Leu Asp Trp Asp Arg Pro Ser
             340                 345                 350
Arg His His Leu Ala Phe Gly Phe Gly Val His Gln Cys Leu Gly Gln
         355                 360                 365
Asn Leu Ala Arg Thr Glu Leu Asp Ile Ala Leu Arg Thr Leu Phe Glu
     370                 375                 380
Arg Leu Pro Gly Leu Arg Leu Ala Val Pro Ala His Glu Ile Arg His
385                 390                 395                 400
Lys Pro Gly Asp Thr Ile Gln Gly Leu Leu His Leu Pro Val Ala Trp
                405                 410                 415
```

<210> SEQ ID NO 216
<211> LENGTH: 416
<212> TYPE: PRT
<213> ORGANISM: Streptomyces griseus ATCC 10137

<400> SEQUENCE: 216

```
Met Thr Glu Ser Thr Thr Glu Pro Ala Arg Gln Asp Pro Ala Pro Thr
 1               5                  10                  15

Ala Pro Pro Thr Gln Pro Thr Ser Thr Thr Pro Phe Pro Gln Asn Arg
            20                  25                  30

Asp Cys Pro Tyr His Pro Pro Thr Gly Tyr Gln Pro Leu Arg Ala Asp
        35                  40                  45

Arg Pro Leu Ser Arg Val Thr Leu Phe Asp Gly Arg Pro Val Trp Ala
    50                  55                  60

Val Thr Gly His Ala Leu Ala Arg Arg Leu Leu Ala Asp Pro Arg Leu
 65                  70                  75                  80

Ser Thr Asp Arg Thr His Pro Asp Phe Pro Val Pro Ala Glu Arg Phe
                85                  90                  95

Ala Asn Val Glu Arg Arg Val Ala Leu Leu Gly Val Asp Asp Pro
            100                 105                 110

Glu His Asn Ala Gln Arg Arg Met Leu Ile Pro Ser Phe Ser Val Lys
        115                 120                 125

Arg Ile Ala Ala Leu Arg Pro Arg Ile Gln Glu Thr Val Asp Gly Leu
    130                 135                 140

Leu Asp Ala Met Glu Arg Gln Gly Pro Pro Ser Glu Leu Val Ala Asp
145                 150                 155                 160

Phe Ala Leu Pro Val Pro Ser Met Val Ile Cys Ala Leu Leu Gly Val
                165                 170                 175

Pro Tyr Ala Asp His Glu Phe Phe Glu Gly Cys Ser Arg Arg Leu Leu
            180                 185                 190

Gln Gly Pro Gly Ala Ala Asp Val Asn Glu Ala Arg Ile Glu Leu Glu
        195                 200                 205

Gly Tyr Leu Gly Ala Leu Ile Asp Arg Lys Arg Val Glu Pro Gly Glu
    210                 215                 220

Gly Leu Leu Asp Glu Leu Ile His Arg Asp His Pro Gly Gly Pro Val
225                 230                 235                 240

Asp Arg Glu Asp Leu Val Ser Phe Ala Val Ile Leu Leu Val Ala Gly
                245                 250                 255

His Glu Thr Thr Ala Asn Met Ile Ser Leu Gly Thr Phe Thr Leu Leu
            260                 265                 270

Asn His Pro Glu Gln Leu Glu Ala Leu Arg Ser Gly Arg Thr Thr Thr
        275                 280                 285

Ala Ala Val Val Glu Glu Leu Leu Arg Phe Leu Ser Ile Ala Glu Gly
    290                 295                 300

Leu Gln Arg Leu Ala Thr Glu Asp Ile Glu Val Ala Gly Thr Thr Ile
305                 310                 315                 320

Arg Glu Gly Glu Gly Val Phe Phe Ser Thr Ser Leu Ile Asn Arg Asp
                325                 330                 335

Thr Glu Val Tyr Glu Asn Pro Glu Thr Leu Asp Trp Asp Arg Pro Ser
            340                 345                 350

Arg His His Leu Ala Phe Gly Phe Gly Val His Gln Cys Leu Gly Gln
        355                 360                 365

Asn Leu Ala Arg Thr Glu Leu Asp Ile Ala Leu Arg Thr Leu Phe Glu
    370                 375                 380

Arg Leu Pro Gly Leu Arg Leu Ala Val Pro Ala His Glu Ile Arg His
```

```
            385                 390                 395                 400
Lys Pro Gly Asp Thr Ile Gln Gly Leu Leu His Leu Pro Val Ala Trp
                405                 410                 415

<210> SEQ ID NO 217
<211> LENGTH: 409
<212> TYPE: PRT
<213> ORGANISM: Streptomyces achromogenes IFO 12735

<400> SEQUENCE: 217

Met Thr Glu Leu Thr Asp Ile Thr Gly Pro Ala Ala Glu Ala Glu Pro
  1               5                  10                  15

Val Ala Phe Pro Gln Asp Arg Thr Cys Pro Tyr His Pro Pro Thr Gly
                 20                  25                  30

Tyr Asp Pro Leu Arg Asp Gly Arg Pro Leu Ser Arg Val Thr Leu Tyr
             35                  40                  45

Asp Gly Arg Glu Ala Trp Leu Val Thr Gly Gln Ala Thr Ala Arg Ala
 50                  55                  60

Leu Leu Ala Asp Pro Arg Leu Ser Thr Asp Arg Arg Asp Gly Phe
 65                  70                  75                  80

Pro Val Pro Thr Pro Arg Phe Glu Ala Gly Arg Asp Arg Lys Val Ala
                 85                  90                  95

Leu Leu Gly Val Asp Asp Pro Glu His His Gln Gln Arg Arg Met Leu
                100                 105                 110

Ile Pro Ser Phe Thr Leu Lys Arg Ala Thr Ala Leu Arg Pro Trp Ile
            115                 120                 125

Gln Arg Ile Val Asp Glu Leu Leu Asp Ala Met Ile Glu Arg Gly Pro
130                 135                 140

Gly Ala Glu Leu Val Ser Ala Phe Ala Leu Pro Val Pro Ser Met Val
145                 150                 155                 160

Ile Cys Gly Leu Leu Gly Val Pro Tyr Ala Asp His Glu Phe Phe Glu
                165                 170                 175

Glu Gln Ser Arg Arg Leu Leu Arg Gly Pro Thr Ser Ala Asp Thr Leu
            180                 185                 190

Asp Ala Arg Asp Arg Leu Glu Arg Phe Leu Gly Asp Leu Ile Asp Ala
        195                 200                 205

Lys Ala Lys Glu Ala Glu Pro Gly Asp Gly Ile Leu Asp Asp Leu Val
210                 215                 220

His His Arg Leu Arg Glu Gly Glu Leu Asp Arg Gly Asp Leu Val Ser
225                 230                 235                 240

Leu Ala Val Ile Leu Leu Val Ala Gly His Glu Thr Thr Ala Asn Met
                245                 250                 255

Ile Ser Leu Gly Thr Tyr Thr Leu Leu Gln His Pro Asp Arg Leu Ala
            260                 265                 270

Glu Leu Arg Ala Asp Pro Ala Leu Leu Pro Ala Val Val Glu Glu Leu
        275                 280                 285

Met Arg Met Leu Ser Ile Ala Glu Gly Leu Gly Arg Val Ala Leu Glu
290                 295                 300

Asp Val Glu Ile Ala Gly Thr Thr Ile Arg Ala Gly Asp Gly Val Leu
305                 310                 315                 320

Phe Ser Thr Ser Val Ile Asn Arg Asp Thr Ala Val Tyr Asp Asp Pro
                325                 330                 335

Asp Ala Leu Asp Phe His Arg Ala Asp Arg His His Val Ala Phe Gly
            340                 345                 350

Phe Gly Ile His Gln Cys Leu Gly Gln Asn Leu Ala Arg Ala Glu Leu
```

```
              355                 360                 365
Glu Ile Ala Leu Gly Ser Leu Phe Thr Arg Leu Pro Gly Leu Arg Leu
370                 375                 380

Ala Ala Pro Ala Glu Glu Ile Pro Phe Lys Pro Gly Asp Thr Ile Gln
385                 390                 395                 400

Gly Met Leu Glu Leu Pro Val Thr Trp
                405

<210> SEQ ID NO 218
<211> LENGTH: 416
<212> TYPE: PRT
<213> ORGANISM: Streptomyces griseus IFO 13849T

<400> SEQUENCE: 218

Met Thr Glu Ser Thr Thr Glu Pro Ala Arg Gln Asp Ala Ala Leu Thr
  1               5                  10                  15

Gly Ala Thr Thr Glu Pro Thr Ser Ala Pro Pro Phe Pro Gln Asp Arg
                 20                  25                  30

Glu Cys Pro Tyr His Pro Pro Thr Gly Tyr Glu Pro Leu Arg Ala Asp
             35                  40                  45

Arg Pro Leu Ser Arg Val Thr Leu Tyr Asp Gly Arg Pro Val Trp Ala
 50                  55                  60

Val Thr Gly His Ala Leu Ala Arg Arg Leu Leu Ala Asp Pro Arg Leu
 65                  70                  75                  80

Ser Thr Asp Arg Thr His Pro Ala Phe Pro Val Pro Ala Glu Arg Phe
                 85                  90                  95

Ala Gln Thr Arg Gln Arg Val Ala Leu Leu Gly Val Asp Asp Pro
            100                 105                 110

Glu His Asn Thr Gln Arg Arg Met Leu Ile Pro Ser Phe Ser Val Lys
            115                 120                 125

Arg Ile Ala Ala Leu Arg Pro Arg Ile Gln Glu Thr Val Asp Arg Leu
130                 135                 140

Leu Asp Ala Met Glu Arg Gln Gly Pro Pro Ser Glu Leu Val Ala Asp
145                 150                 155                 160

Phe Ala Leu Pro Val Pro Ser Met Val Ile Cys Ala Leu Leu Gly Val
                165                 170                 175

Pro Tyr Ala Asp His Ala Leu Phe Glu Gly Cys Ser Arg Arg Leu Leu
            180                 185                 190

Arg Gly Pro Gly Ala Asp Asp Val Asp Ala Ala Arg Val Glu Leu Glu
        195                 200                 205

Glu Tyr Leu Gly Ala Leu Ile Asp Arg Lys Arg Ala Asp Pro Gly Glu
210                 215                 220

Gly Leu Leu Asp Glu Leu Ile His Arg Asp Arg Pro Asp Gly Pro Val
225                 230                 235                 240

Ser Arg Glu Asp Leu Val Ser Phe Ala Leu Ile Leu Leu Val Ala Gly
                245                 250                 255

His Glu Thr Thr Ala Asn Met Ile Ser Leu Gly Thr Phe Thr Leu Leu
            260                 265                 270

Arg His Pro Gly Gln Leu Ala Ala Leu Arg Ser Gly Glu Thr Thr Thr
        275                 280                 285

Ala Val Val Glu Glu Leu Leu Arg Phe Leu Ser Ile Ala Glu Gly
        290                 295                 300

Leu Gln Arg Leu Ala Ile Glu Asp Ile Glu Val Asp Gly Thr Thr Ile
305                 310                 315                 320

Arg Glu Gly Glu Gly Val Phe Phe Ser Thr Ser Leu Val Asn Arg Asp
```

```
                       325                 330                 335
Ala Asp Val Phe Ala Asp Pro Glu Thr Leu Asp Trp Glu Arg Ser Ala
                340                 345                 350

Arg His His Leu Ala Phe Gly Phe Gly Val His Gln Cys Leu Gly Gln
            355                 360                 365

Asn Leu Ala Arg Ala Glu Leu Asp Ile Ala Leu Arg Thr Leu Phe Glu
        370                 375                 380

Arg Leu Pro Ala Leu Arg Leu Ala Val Pro Ala Asp Glu Val Arg His
385                 390                 395                 400

Lys Pro Gly Asp Thr Ile Gln Gly Leu Leu Glu Leu Pro Val Ala Trp
                405                 410                 415

<210> SEQ ID NO 219
<211> LENGTH: 405
<212> TYPE: PRT
<213> ORGANISM: Streptomyces lanatus IFO 12787T

<400> SEQUENCE: 219

Met Thr Asp Met Thr Asp Met Thr Arg Pro Pro Thr Val Ala Phe Pro
 1               5                  10                  15

Gln Asn Arg Thr Cys Pro Tyr His Pro Pro Thr Ala Tyr Asp Pro Leu
            20                  25                  30

Arg Asp Thr Arg Pro Leu Ala Arg Ile Thr Leu Tyr Asp Gly Arg Pro
        35                  40                  45

Val Trp Leu Val Thr Gly His Ala Leu Ala Arg Thr Leu Leu Ala Asp
    50                  55                  60

Pro Arg Leu Ser Ser Asp Arg Gly Arg Pro Gly Phe Pro Ala Pro Asn
65                  70                  75                  80

Glu Arg Phe Ala Ala Val Arg Asp Arg Lys Ser Ala Leu Leu Gly Val
                85                  90                  95

Asp Asp Pro Glu His Arg Val Gln Arg Arg Met Met Val Pro Ser Phe
            100                 105                 110

Thr Leu Arg Arg Ala Ala Glu Leu Arg Pro Gln Ile Gln Arg Ile Val
        115                 120                 125

Asp Glu Arg Leu Asp Ala Met Ile Asp Gln Gly Ala Pro Ala Glu Leu
    130                 135                 140

Val Asn Ala Phe Ala Leu Pro Val Pro Ser Met Val Ile Cys Ala Leu
145                 150                 155                 160

Leu Gly Val Pro Tyr Ala Asp His Asp Phe Phe Glu Gly Glu Ser Arg
                165                 170                 175

Arg Leu Leu Arg Gly Ala Thr Ala Ala Glu Ala Met Asp Ala Arg Asp
            180                 185                 190

Arg Leu Glu Asn Tyr Phe Ile Glu Leu Ile Asp Arg Lys Gln Lys Asp
        195                 200                 205

Pro Glu Pro Gly Asp Gly Val Leu Asp Glu Leu Val His Arg Gln Leu
    210                 215                 220

Arg Asp Gly Asp Leu Asp Arg Glu Glu Val Val Ala Leu Ser Thr Ile
225                 230                 235                 240

Leu Leu Val Ala Gly His Glu Thr Thr Ala Asn Met Ile Ser Leu Gly
                245                 250                 255

Thr Phe Thr Leu Leu Gln His Pro Glu Gln Leu Ala Glu Leu Arg Ala
            260                 265                 270

Asp Ala Gly Leu Leu Pro Ala Ala Val Glu Glu Leu Met Arg Met Leu
        275                 280                 285

Ser Ile Ala Asp Gly Leu Leu Arg Val Ala Ser Glu Asp Ile Glu Ala
```

```
                290                 295                 300
Gly Gly Glu Thr Ile Arg Ala Gly Asp Gly Val Val Phe Ser Thr Ser
305                 310                 315                 320

Val Ile Asn Arg Asp Glu Ser Val Tyr Pro Asp Pro Asp Ala Ile Asp
                325                 330                 335

Trp His Arg Pro Thr Arg His His Ile Ala Phe Gly Phe Gly Ile His
                340                 345                 350

Gln Cys Leu Gly Gln Asn Leu Ala Arg Ala Glu Met Glu Ile Ala Leu
                355                 360                 365

Arg Thr Leu Phe Glu Arg Leu Pro Thr Leu Arg Leu Ala Val Pro Ala
            370                 375                 380

Gly Glu Ile Pro Phe Lys Pro Gly Asp Thr Ile Gln Gly Met Leu Glu
385                 390                 395                 400

Leu Pro Val Thr Trp
                405

<210> SEQ ID NO 220
<211> LENGTH: 414
<212> TYPE: PRT
<213> ORGANISM: Streptomyces misawanensis IFO 13855T

<400> SEQUENCE: 220

Met Lys Glu Leu Thr Asp Leu Thr Glu Pro Ile Ser Pro Ala Gly Gln
1               5                   10                  15

Ala Asp Pro Val Ala Trp Pro Gln Asp Arg Thr Cys Pro Tyr His Pro
                20                  25                  30

Pro Thr Gly Tyr Asp Pro Leu Arg Asp Gly Thr Pro Leu Ser Arg Val
            35                  40                  45

Thr Leu Tyr Asp Gly Arg Thr Val Trp Ala Val Thr Gly His Gly Thr
        50                  55                  60

Ala Arg Ala Leu Leu Ser Asp Pro Arg Leu Ser Ser Asp Arg Arg
65                  70                  75                  80

Asp Asp Phe Pro Met Pro Asn Ala Arg Phe Ala Ala Ala Arg Glu Arg
                85                  90                  95

Arg Gln Leu Ala Leu Leu Gly Leu Asp Asp Pro Glu His Gln Ile Gln
            100                 105                 110

Arg Arg Met Leu Ile Pro Asp Phe Thr Leu Lys Arg Ala Thr Val Met
        115                 120                 125

Arg Pro Ala Ile Gln Arg Ile Val Asp Asp Leu Leu Asp Arg Met Ile
    130                 135                 140

Ala Ala Gly Pro Pro Ala Asp Leu Val Ser Ser Phe Ala Leu Pro Val
145                 150                 155                 160

Pro Ser Met Val Ile Cys Asp Leu Leu Gly Val Pro Tyr Ala Asp His
                165                 170                 175

Glu Phe Phe Glu Ala Gln Ser Arg Arg Leu Leu Arg Gly Pro Ala Pro
            180                 185                 190

Ala Asp Ser Leu Asp Ala Arg Asp Gln Leu Glu Ala Tyr Leu Gly Asp
        195                 200                 205

Leu Ala Asp Arg Lys Ser Arg Asp Ala Val Pro Gly Asp Gly Val Leu
    210                 215                 220

Asp Asp Leu Val His Gln Arg Leu Arg Asp Gly Ala Leu Asp Arg Ala
225                 230                 235                 240

Glu Val Val Ala Leu Ala Leu Ile Leu Leu Val Ala Gly His Glu Thr
                245                 250                 255

Thr Ala Asn Met Ile Ser Leu Gly Thr Phe Thr Leu Leu Gln Gln Pro
```

```
                    260                 265                 270
Glu Arg Leu Ala Glu Leu Arg Ala Asp Pro Ala Leu Val Pro Ala Ala
            275                 280                 285

Val Glu Glu Leu Met Arg Met Leu Ser Ile Ala Asp Gly Leu Leu Arg
        290                 295                 300

Val Ala Leu Glu Asp Ile Glu Thr Asp Gly Thr Thr Ile Arg Lys
305                 310                 315                 320

Gly Glu Gly Val Leu Phe Ala Thr Ser Val Ile Asn Arg Asp Glu Ser
                325                 330                 335

Val Tyr Asp Asp Pro Asp Ala Leu Asp Trp His Arg Pro Ala Arg His
            340                 345                 350

His Val Ala Phe Gly Phe Gly Ile His Gln Cys Leu Gly Gln Asn Leu
            355                 360                 365

Ala Arg Thr Glu Leu Glu Ile Ala Leu Arg Thr Leu Trp Glu Arg Leu
            370                 375                 380

Pro Asp Leu Arg Leu Ala Ala Pro Pro Glu Glu Ile Pro Phe Lys Pro
385                 390                 395                 400

Gly Asp Thr Ile Gln Gly Met Leu Glu Leu Pro Val Thr Trp
                405                 410

<210> SEQ ID NO 221
<211> LENGTH: 409
<212> TYPE: PRT
<213> ORGANISM: Streptomyces pallidus IFO 13434T

<400> SEQUENCE: 221

Met Ala Asp Thr Leu Ala Gly Ala Thr Pro Asp Ala Ala Ala Thr Val
  1               5                  10                  15

Pro Ala Tyr Pro Met Ala Arg Ala Ala Gly Cys Pro Phe Asp Pro Pro
            20                  25                  30

Pro Asp Leu Thr Ala Arg Gln Asp Glu Gly Arg Leu Val Arg Val Arg
        35                  40                  45

Leu Trp Asp Gly Ser Thr Pro Trp Leu Val Thr Arg Tyr Glu Asp Gln
    50                  55                  60

Arg Ala Leu Leu Leu Asp Pro Arg Val Ser Ala Asp Ile Thr Arg Pro
65                  70                  75                  80

Gly Tyr Pro Leu Gln Ala Ala Gly Ala Gly Glu Asn Asn Ala Ser Phe
                85                  90                  95

Ile Leu Met Asp Asp Pro Glu His Ala Arg Leu Arg Arg Met Val Thr
            100                 105                 110

Ala Pro Phe Ala Ile Lys Arg Val Glu Ala Met Arg Pro Gly Val Gln
        115                 120                 125

Gln Leu Val Asp Asp Leu Ile Asp Gly Met Leu Ala Gly Pro Lys Pro
    130                 135                 140

Val Asp Leu Val Glu Ala Phe Ala Leu Pro Val Pro Ser Leu Val Ile
145                 150                 155                 160

Cys Arg Met Leu Gly Val Pro Tyr Glu Asp His Asp Phe Phe Gln Glu
                165                 170                 175

Asn Ser Arg Ile Leu Ile Lys Arg Asp Ala Ala Met Glu Asp Arg Met
            180                 185                 190

Ala Ala His Gly Arg Leu Ile Ala Tyr Leu Asp Glu Leu Met Gly Glu
        195                 200                 205

Lys Thr Ala Arg Pro Ala Asp Asp Leu Leu Ser Gly Leu Val Glu Arg
    210                 215                 220

Val Arg Thr Gly Glu Leu Thr Arg Arg Glu Ser Ala Arg Met Gly Val
```

```
                225                 230                 235                 240
Leu Leu Leu Ile Ala Gly His Glu Thr Thr Ala Asn Met Ile Ala Leu
                245                 250                 255

Gly Thr Leu Ala Leu Leu Glu His Pro Asp Gln Leu Ala Leu Leu Arg
                260                 265                 270

Asp Thr Asp Asp Pro Lys Leu Val Ala Gly Ala Ala Glu Glu Leu Leu
                275                 280                 285

Arg Tyr Leu Thr Ile Val His Asn Gly Arg Arg Ala Ala Leu Ala
                290                 295                 300

Asp Ile Glu Ile Gly Gly Gln Val Ile Arg Ala Gly Glu Gly Met Ile
305                 310                 315                 320

Met Pro Asn Asp Leu Ala Asn Arg Asp Pro Gly Ala Phe Thr Asp Pro
                325                 330                 335

Asp Arg Leu Asp Leu Arg Arg Asp Ala Arg Arg His Ile Ala Phe Gly
                340                 345                 350

Phe Gly Val His Gln Cys Leu Gly Gln Pro Leu Ala Arg Met Glu Leu
                355                 360                 365

Gln Val Val Tyr Gly Thr Leu Tyr Arg Arg Ile Pro Thr Leu Arg Leu
            370                 375                 380

Ala Ala Pro Val Glu Ser Leu Ser Phe Lys His Asp Gly Ser Val Tyr
385                 390                 395                 400

Gly Val Tyr Glu Leu Pro Val Thr Trp
                405

<210> SEQ ID NO 222
<211> LENGTH: 398
<212> TYPE: PRT
<213> ORGANISM: Streptomyces roseorubens IFO 13682T

<400> SEQUENCE: 222

Met Thr Asp Thr Thr Ala Pro Val Ala Phe Pro Gln Ser Arg Thr Cys
 1               5                  10                  15

Pro Tyr His Pro Pro Ala Ala Tyr Glu Pro Leu Arg Ala Glu Arg Pro
                20                  25                  30

Leu Thr Arg Ile Thr Leu Phe Asp Gly Arg Glu Ala Trp Leu Val Ser
            35                  40                  45

Gly His Ala Thr Ala Arg Ala Leu Leu Ala Asp Pro Arg Leu Ser Ser
        50                  55                  60

Asp Arg Asp Arg Pro Gly Phe Pro Thr Pro Thr Ala Arg Phe Ala Gly
65                  70                  75                  80

Ile Arg Asn Arg Arg Thr Ala Leu Leu Gly Val Asp Pro Glu His
                85                  90                  95

Arg Ala Gln Arg Arg Met Val Val Gly Asp Phe Thr Leu Lys Arg Ala
                100                 105                 110

Ala Ala Leu Arg Pro Arg Ile Gln Arg Ile Val Asp Glu Arg Leu Asp
            115                 120                 125

Ala Met Ile Ala Gln Gly Pro Pro Ala Asp Leu Val Ser Ala Phe Ala
130                 135                 140

Leu Pro Val Pro Ser Met Val Ile Cys Ala Leu Leu Gly Val Pro Tyr
145                 150                 155                 160

Ala Asp His Asp Phe Phe Glu Ala Gln Ser Arg Arg Leu Leu Arg Gly
                165                 170                 175

Pro Gly Thr Ala Asp Val Gln Asp Ala Arg Ser Arg Leu Glu Glu Tyr
            180                 185                 190

Phe Gly Glu Leu Ile Asp Arg Lys Arg Glu Asp Pro Gly Thr Gly Leu
```

-continued

```
                195                 200                 205
Leu Asp Asp Leu Val Gln Arg Gln Pro Gly Asp Gly Gly Pro Asp Arg
210                 215                 220

Glu Gly Leu Ile Ala Met Ala Leu Ile Leu Val Ala Gly His Glu
225                 230                 235                 240

Thr Thr Ala Asn Met Ile Ser Leu Gly Thr Phe Thr Leu Leu Gln His
                245                 250                 255

Pro Glu Arg Leu Ala Glu Leu Arg Ala Asp Ser Glu Val Met Pro Ala
                260                 265                 270

Ala Val Glu Glu Leu Met Arg Leu Leu Ser Ile Ala Asp Gly Leu Leu
                275                 280                 285

Arg Ile Ala Val Glu Asp Val Glu Val Ala Gly Thr Thr Ile Arg Ala
290                 295                 300

Gly Glu Gly Val Val Phe Ala Thr Ser Val Ile Asn Arg Asp Glu Thr
305                 310                 315                 320

Val Phe Ala Glu Pro Asp Thr Leu Asp Trp Ser Arg Pro Ala Arg His
                325                 330                 335

His Val Ala Phe Gly Phe Gly Ile His Gln Cys Leu Gly Gln Asn Leu
                340                 345                 350

Ala Arg Ala Glu Leu Glu Ile Ala Leu Gly Thr Leu Phe Gly Arg Leu
                355                 360                 365

Pro Thr Leu Arg Leu Ala Ala Pro Pro Asp Glu Ile Pro Phe Lys Pro
                370                 375                 380

Gly Asp Thr Ile Gln Gly Met Leu Glu Leu Pro Val Thr Trp
385                 390                 395

<210> SEQ ID NO 223
<211> LENGTH: 414
<212> TYPE: PRT
<213> ORGANISM: Streptomyces rutgersensis IFO 15875T

<400> SEQUENCE: 223

Met Thr Glu Thr Leu Ala Glu Thr Thr Thr Glu Ala Glu Glu Pro Leu
1               5                   10                  15

Pro Glu Phe Pro Met Pro Arg Ala Asn Gly Cys Pro Phe Ala Pro Pro
                20                  25                  30

Pro Thr Ala Arg Ala Leu His Thr Glu Arg Pro Val Thr Arg Val Arg
            35                  40                  45

Leu Trp Asp Gly Ser Ala Pro Trp Leu Val Thr Arg Tyr Ala Asp Gln
        50                  55                  60

Arg Ala Leu Leu Gly Asp Pro Arg Val Ser Ser Glu Ala Thr Arg Pro
65                  70                  75                  80

Gly Phe Pro His Ala Ser Ala Gly Phe Arg Glu Asn Ala Arg Arg Arg
                85                  90                  95

Arg Ser Phe Ile Thr Met Asp Asp Pro Glu His Ala Arg Ile Arg Arg
                100                 105                 110

Met Val Thr Ala Pro Phe Ala Ile Lys Arg Val Glu Ala Met Arg Pro
            115                 120                 125

Asp Ile Gln Lys Ile Thr Asp Asp Leu Ile Asp Ser Met Leu Ala Gly
    130                 135                 140

Pro Thr Pro Val Asp Leu Val Arg Ala Leu Ala Leu Pro Leu Pro Ser
145                 150                 155                 160

Leu Val Ile Cys Arg Leu Leu Gly Val Pro Tyr Glu Asp His Asp Phe
                165                 170                 175

Phe Gln Arg Asn Ser Ser Leu Leu Ile Asn Arg Asn Ser Thr Thr Glu
```

```
                    180             185             190
Glu Val Val Gly Ala Asn Glu Ala Leu Thr Asp Tyr Leu Asp Glu Leu
            195                 200                 205

Val Ser Ala Lys Leu Ala Asn Pro Ala Asp Asp Met Leu Ser Glu Leu
210                 215                 220

Ala Ala Arg Val Thr Ala Gly Glu Leu Thr Gln Arg Glu Ala Ala Asn
225                 230                 235                 240

Met Gly Val Leu Leu Ile Ala Gly His Glu Thr Thr Ala Asn Met
                245                 250                 255

Ile Ala Leu Gly Thr Val Ala Leu Leu Glu Asn Pro Asp Gln Leu Ala
                260                 265                 270

Val Leu Arg Glu Thr Asp Asp Pro Lys Ala Val Ala Lys Ala Val Glu
            275                 280                 285

Glu Leu Leu Arg Tyr Leu Thr Ile Val His Thr Gly Arg Arg Val
290                 295                 300

Ala Arg Glu Asp Ile Glu Ile Gly Gly Glu Thr Ile Arg Ala Gly Asp
305                 310                 315                 320

Gly Ile Ile Ile Tyr Thr Gly Thr Gly Asn Trp Asp Ala Glu Val Phe
                325                 330                 335

Pro Glu Pro Glu Arg Leu Asp Ile Gly Arg Asp Ala Arg His Met
            340                 345                 350

Ala Phe Gly Phe Gly Val His Gln Cys Leu Gly Gln Pro Leu Ala Arg
            355                 360                 365

Val Glu Leu Gln Val Val Tyr Gly Thr Leu Tyr Arg Arg Ile Pro Thr
370                 375                 380

Leu Arg Leu Ala Thr Gly Val Asp Gln Leu Pro Phe Lys Asp Asp Gly
385                 390                 395                 400

Leu Val Tyr Gly Val Tyr Glu Leu Pro Val Thr Trp Thr Ser
                405                 410

<210> SEQ ID NO 224
<211> LENGTH: 398
<212> TYPE: PRT
<213> ORGANISM: Streptomyces steffisburgensis IFO 13446T

<400> SEQUENCE: 224

Met Ser Asp Thr Thr Ala Pro Val Ala Phe Pro Gln Ser Arg Thr Cys
1               5                   10                  15

Pro Tyr His Pro Pro Ala Ala Tyr Glu Pro Leu Arg Ala Glu Arg Pro
            20                  25                  30

Leu Thr Arg Ile Thr Leu Phe Asp Gly Arg Glu Ala Trp Leu Val Ser
        35                  40                  45

Gly His Ala Thr Ala Arg Ala Leu Leu Ala Asp Pro Arg Leu Ser Ser
    50                  55                  60

Asp Arg Asp Arg Pro Gly Phe Pro Ala Pro Thr Ala Arg Phe Ala Gly
65                  70                  75                  80

Ile Arg Asn Arg Arg Thr Ala Leu Leu Gly Val Asp Asp Pro Glu His
                85                  90                  95

Arg Val Gln Arg Arg Met Val Ala Gly Asp Phe Thr Leu Lys Arg Ala
            100                 105                 110

Ala Gly Leu Arg Pro Arg Ile Gln Arg Ile Val Asp Arg Leu Asp
        115                 120                 125

Ala Met Ile Ala Gln Gly Pro Pro Ala Asp Leu Val Ser Ser Phe Ala
130                 135                 140

Leu Pro Val Pro Ser Met Val Ile Cys Ala Leu Leu Gly Val Pro Tyr
```

```
                145                 150                 155                 160
Ala Asp His Asp Phe Phe Glu Thr Gln Ser Arg Arg Leu Leu Arg Gly
                    165                 170                 175

Pro Gln Thr Ala Asp Val Met Asp Ala Arg Ala Arg Leu Asp Glu Tyr
                180                 185                 190

Phe Gly Glu Leu Ile Asp Arg Lys Arg Lys Glu Pro Gly Ala Gly Leu
            195                 200                 205

Leu Asp Asp Leu Val Gln Arg Gln Leu Arg Asp Gly Ala Leu Asp Arg
        210                 215                 220

Glu Gly Leu Ile Ala Leu Ala Leu Ile Leu Val Ala Gly His Glu
225                 230                 235                 240

Thr Thr Ala Asn Met Ile Ser Leu Gly Thr Phe Thr Leu Leu Gln His
                    245                 250                 255

Pro Glu Arg Leu Ala Glu Leu Arg Ala Asp Pro Arg Leu Leu Pro Ala
                260                 265                 270

Ala Val Glu Glu Leu Met Arg Met Leu Ser Ile Ala Asp Gly Leu Leu
            275                 280                 285

Arg Leu Ala Val Glu Asp Ile Glu Val Ala Gly Thr Thr Ile Arg Lys
        290                 295                 300

Gly Asp Gly Val Val Phe Leu Thr Ser Val Ile Asn Arg Asp Glu Thr
305                 310                 315                 320

Val Tyr Pro Glu Pro Asp Thr Leu Asp Trp His Arg Ser Ala Arg His
                    325                 330                 335

His Val Ala Phe Gly Phe Gly Ile His Gln Cys Leu Gly Gln Asn Leu
                340                 345                 350

Ala Arg Ala Glu Leu Glu Ile Ala Leu Trp Thr Leu Phe Asp Arg Leu
            355                 360                 365

Pro Thr Leu Arg Leu Ala Ala Pro Ala Glu Glu Ile Ala Phe Lys Pro
        370                 375                 380

Gly Asp Thr Ile Gln Gly Met Leu Glu Leu Pro Val Thr Trp
385                 390                 395

<210> SEQ ID NO 225
<211> LENGTH: 1251
<212> TYPE: DNA
<213> ORGANISM: Streptomyces ornatus IFO 13069t
<220> FEATURE:
<221> NAME/KEY: CDS
<222> LOCATION: (1)..(1251)

<400> SEQUENCE: 225 atg acg gaa tcc acg acg gaa ccg gcc cgc cag gac ccc gct ccc acc      48
Met Thr Glu Ser Thr Thr Glu Pro Ala Arg Gln Asp Pro Ala Pro Thr
1               5                   10                  15 gcc cct ccg acg caa ccg acc tcc acg aca ccc ttc ccc cag aac cgc      96
Ala Pro Pro Thr Gln Pro Thr Ser Thr Thr Pro Phe Pro Gln Asn Arg
            20                  25                  30 gac tgc ccc tac cac ccg ccc acc ggg tac caa ccg ctc cgc gcg gac     144
Asp Cys Pro Tyr His Pro Pro Thr Gly Tyr Gln Pro Leu Arg Ala Asp
        35                  40                  45 cgg ccg ctc agc cgg gtc acc ctc ttc gac ggg cgt ccg gtc tgg gcc     192
Arg Pro Leu Ser Arg Val Thr Leu Phe Asp Gly Arg Pro Val Trp Ala
    50                  55                  60 gtc acc ggc cac gcc ctg gcc cgc cgg cta ctg gcg gat ccg cgc ctg     240
Val Thr Gly His Ala Leu Ala Arg Arg Leu Leu Ala Asp Pro Arg Leu
65                  70                  75                  80 tcc acc gat cgc acc cac ccc gac ttc ccc gtt ccg gcc gag cgg ttc     288
Ser Thr Asp Arg Thr His Pro Asp Phe Pro Val Pro Ala Glu Arg Phe
```

-continued

```
                       85                       90                       95
gcg aac gtc gag cgg cgg cgc gtg gcc ctg ctc ggc gtc gac gac ccc     336
Ala Asn Val Glu Arg Arg Arg Val Ala Leu Leu Gly Val Asp Asp Pro
            100                     105                     110 gag cac aac gcc cag cgc agg atg ctc atc ccg agc ttc tcc gtg aag     384
Glu His Asn Ala Gln Arg Arg Met Leu Ile Pro Ser Phe Ser Val Lys
            115                     120                     125 cgg ata gcc gcg ctg cgc ccc cgc atc cag gag acg gtg gac gga ctg     432
Arg Ile Ala Ala Leu Arg Pro Arg Ile Gln Glu Thr Val Asp Gly Leu
    130                     135                     140 ctg gac gcg atg gag cgg cag ggc ccg ccg tcc gaa ctg gtc gcc gac     480
Leu Asp Ala Met Glu Arg Gln Gly Pro Pro Ser Glu Leu Val Ala Asp
145                     150                     155                     160 ttc gcg ctg ccg gtg ccg tcg atg gtg atc tgc gcg ctc ctc ggt gtg     528
Phe Ala Leu Pro Val Pro Ser Met Val Ile Cys Ala Leu Leu Gly Val
                165                     170                     175 ccg tac gcc gac cac gag ttc ttc gag ggc tgc tcc cgg cgg ctc ctg     576
Pro Tyr Ala Asp His Glu Phe Phe Glu Gly Cys Ser Arg Arg Leu Leu
            180                     185                     190 cag ggc ccg ggc gcg gcc gat gtg aac gag gcc cgg atc gag ctg gag     624
Gln Gly Pro Gly Ala Ala Asp Val Asn Glu Ala Arg Ile Glu Leu Glu
    195                     200                     205 ggc tat ctg ggc gcc ctg atc gac cgc aag cgg gtg gag ccg ggg gag     672
Gly Tyr Leu Gly Ala Leu Ile Asp Arg Lys Arg Val Glu Pro Gly Glu
210                     215                     220 ggg ctc ctg gac gaa ctg atc cac cgg gac cac ccc ggc gga ccc gtc     720
Gly Leu Leu Asp Glu Leu Ile His Arg Asp His Pro Gly Gly Pro Val
225                     230                     235                     240 gac cgc gag gac ctc gtc tcg ttc gcg gtg atc ctc ctc gtc gcg ggg     768
Asp Arg Glu Asp Leu Val Ser Phe Ala Val Ile Leu Leu Val Ala Gly
                245                     250                     255 cac gag acg acg gcg aac atg atc tcg ctc ggc acg ttc acg ctg ctg     816
His Glu Thr Thr Ala Asn Met Ile Ser Leu Gly Thr Phe Thr Leu Leu
            260                     265                     270 aac cac ccg gaa cag ctg gag gcg ctg cgg tcc ggg agc acg acg acg     864
Asn His Pro Glu Gln Leu Glu Ala Leu Arg Ser Gly Ser Thr Thr Thr
    275                     280                     285 gcc gcg gtg gtc gag gaa ctg ctg cgg ttc ctc tcc atc gcc gag gga     912
Ala Ala Val Val Glu Glu Leu Leu Arg Phe Leu Ser Ile Ala Glu Gly
290                     295                     300 ctg caa cgg ctg gcc acc gag gac atc gag gtg gcc ggg acg acg atc     960
Leu Gln Arg Leu Ala Thr Glu Asp Ile Glu Val Ala Gly Thr Thr Ile
305                     310                     315                     320 cgc gag gga gag ggc gtg ttc ttc tcg acc tcg ctc atc aac cgc gac    1008
Arg Glu Gly Glu Gly Val Phe Phe Ser Thr Ser Leu Ile Asn Arg Asp
                325                     330                     335 acc gag gtc tac gag aat ccg gag acg ctc gac tgg gac cgg cct tcc    1056
Thr Glu Val Tyr Glu Asn Pro Glu Thr Leu Asp Trp Asp Arg Pro Ser
            340                     345                     350 cgg cac cac ctc gcc ttc ggc ttc ggc gtc cat cag tgc ctg ggc cag    1104
Arg His His Leu Ala Phe Gly Phe Gly Val His Gln Cys Leu Gly Gln
    355                     360                     365 aat ctg gcc cgc acc gag ctc gac atc gcc ctg cgc act ctc ttc gag    1152
Asn Leu Ala Arg Thr Glu Leu Asp Ile Ala Leu Arg Thr Leu Phe Glu
370                     375                     380 cgg ctg ccg gga ctc agg ctc gcc gtg ccc gcg cac gag atc cgg cac    1200
Arg Leu Pro Gly Leu Arg Leu Ala Val Pro Ala His Glu Ile Arg His
385                     390                     395                     400 aaa ccc ggg gac acg atc cag ggc ctt ctg cac ctg ccc gtg gcc tgg    1248
Lys Pro Gly Asp Thr Ile Gln Gly Leu Leu His Leu Pro Val Ala Trp
```

```
                         405                 410                 415
tga                                                                         1251

<210> SEQ ID NO 226
<211> LENGTH: 1251
<212> TYPE: DNA
<213> ORGANISM: Streptomyces griseus ATCC 10137
<220> FEATURE:
<221> NAME/KEY: CDS
<222> LOCATION: (1)..(1251)

<400> SEQUENCE: 226 atg acg gaa tcc acg acg gaa ccg gcc cgc cag gac ccc gct ccc acc        48
Met Thr Glu Ser Thr Thr Glu Pro Ala Arg Gln Asp Pro Ala Pro Thr
1               5                   10                  15 gcc cct ccg acg caa ccg acc tcc acg aca ccc ttc ccc cag aac cgc        96
Ala Pro Pro Thr Gln Pro Thr Ser Thr Thr Pro Phe Pro Gln Asn Arg
            20                  25                  30 gac tgc ccc tac cac ccg ccc acc ggg tac caa ccg ctc cgc gcg gac       144
Asp Cys Pro Tyr His Pro Pro Thr Gly Tyr Gln Pro Leu Arg Ala Asp
        35                  40                  45 cgg ccg ctc agc cgg gtc acc ctc ttc gac ggg cgt ccg gtc tgg gcc       192
Arg Pro Leu Ser Arg Val Thr Leu Phe Asp Gly Arg Pro Val Trp Ala
    50                  55                  60 gtc acc ggc cac gcc ctg gcc cgc cgg cta ctg gcg gat ccg cgc ctg       240
Val Thr Gly His Ala Leu Ala Arg Arg Leu Leu Ala Asp Pro Arg Leu
65                  70                  75                  80 tcc acc gat cgc acc cac ccc gac ttc ccc gtt ccg gcc gag cgg ttc       288
Ser Thr Asp Arg Thr His Pro Asp Phe Pro Val Pro Ala Glu Arg Phe
                85                  90                  95 gcg aac gtc gag cgg agg cga gtg gcc ctg ctc ggc gtc gac gac ccc       336
Ala Asn Val Glu Arg Arg Arg Val Ala Leu Leu Gly Val Asp Asp Pro
            100                 105                 110 gag cac aac gcc cag cgc agg atg ctc atc ccg agc ttc tcc gtg aag       384
Glu His Asn Ala Gln Arg Arg Met Leu Ile Pro Ser Phe Ser Val Lys
        115                 120                 125 cgg ata gcc gcg ctg cgc ccc cgc atc cag gag acg gtg gac gga ctg       432
Arg Ile Ala Ala Leu Arg Pro Arg Ile Gln Glu Thr Val Asp Gly Leu
    130                 135                 140 ctg gac gcg atg gag cgg cag ggc ccg ccg tcc gaa ctg gtc gcc gac       480
Leu Asp Ala Met Glu Arg Gln Gly Pro Pro Ser Glu Leu Val Ala Asp
145                 150                 155                 160 ttc gcg ctg ccg gtg ccg tcg atg gtg atc tgc gcg ctc ctc ggt gtg       528
Phe Ala Leu Pro Val Pro Ser Met Val Ile Cys Ala Leu Leu Gly Val
                165                 170                 175 ccg tac gcc gac cac gag ttc ttc gag ggc tgc tcc cgg cgg ctc ctg       576
Pro Tyr Ala Asp His Glu Phe Phe Glu Gly Cys Ser Arg Arg Leu Leu
            180                 185                 190 cag ggc ccg ggc gcg gcc gat gtg aac gag gcc cgg atc gag ctg gag       624
Gln Gly Pro Gly Ala Ala Asp Val Asn Glu Ala Arg Ile Glu Leu Glu
        195                 200                 205 ggc tat ctg ggc gcc ctg atc gac cgc aag cgg gtg gag ccg ggg gag       672
Gly Tyr Leu Gly Ala Leu Ile Asp Arg Lys Arg Val Glu Pro Gly Glu
    210                 215                 220 ggg ctc ctg gac gaa ctg atc cac cgg gac cac ccc ggc gga ccc gtc       720
Gly Leu Leu Asp Glu Leu Ile His Arg Asp His Pro Gly Gly Pro Val
225                 230                 235                 240 gac cgc gag gac ctc gtc tcg ttc gcg gtg atc ctc ctc gtc gcg ggg       768
Asp Arg Glu Asp Leu Val Ser Phe Ala Val Ile Leu Leu Val Ala Gly
                245                 250                 255 cac gag acg acg gcg aac atg atc tcg ctc ggc acg ttc acg ctg ctg       816
```

```
                His Glu Thr Thr Ala Asn Met Ile Ser Leu Gly Thr Phe Thr Leu Leu
                                260                 265                 270 aac cac ccg gaa cag ctg gag gcg ctg cgc tcc ggg agg acg acg acg            864
Asn His Pro Glu Gln Leu Glu Ala Leu Arg Ser Gly Arg Thr Thr Thr
            275                 280                 285 gcc gcg gtc gtc gag gaa ctg ctg cgg ttc ctc tcc atc gcc gag gga            912
Ala Ala Val Val Glu Glu Leu Leu Arg Phe Leu Ser Ile Ala Glu Gly
        290                 295                 300 ctg caa cgg ctg gcc acc gag gac atc gag gtg gcc ggg acg acg atc            960
Leu Gln Arg Leu Ala Thr Glu Asp Ile Glu Val Ala Gly Thr Thr Ile
305                 310                 315                 320 cgc gag gga gag ggc gtg ttc ttc tcg acc tcg ctc atc aac cgc gac           1008
Arg Glu Gly Glu Gly Val Phe Phe Ser Thr Ser Leu Ile Asn Arg Asp
                325                 330                 335 acc gag gtc tac gag aat ccg gag acg ctc gac tgg gac cgg cct tcc           1056
Thr Glu Val Tyr Glu Asn Pro Glu Thr Leu Asp Trp Asp Arg Pro Ser
            340                 345                 350 cgg cac cac ctc gcc ttc ggc ttc ggc gtc cac cag tgc ctg ggc cag           1104
Arg His His Leu Ala Phe Gly Phe Gly Val His Gln Cys Leu Gly Gln
        355                 360                 365 aat ctg gcc cgc acc gag ctc gac atc gcc ctg cgc act ctc ttc gag           1152
Asn Leu Ala Arg Thr Glu Leu Asp Ile Ala Leu Arg Thr Leu Phe Glu
370                 375                 380 cgg ctg ccg gga ctc agg ctc gcc gtg ccc gcg cac gag atc cgg cac           1200
Arg Leu Pro Gly Leu Arg Leu Ala Val Pro Ala His Glu Ile Arg His
385                 390                 395                 400 aaa ccc ggg gac acg atc cag ggc ctt ctg cac ctg ccc gtg gcc tgg           1248
Lys Pro Gly Asp Thr Ile Gln Gly Leu Leu His Leu Pro Val Ala Trp
                405                 410                 415 tga                                                                       1251

<210> SEQ ID NO 227
<211> LENGTH: 1230
<212> TYPE: DNA
<213> ORGANISM: Streptomyces achromogenes IFO 12735
<220> FEATURE:
<221> NAME/KEY: CDS
<222> LOCATION: (1)..(1230)

<400> SEQUENCE: 227 atg acg gaa ctg acg gac atc acc ggc ccg gct gcc gag gcc gaa ccc             48
Met Thr Glu Leu Thr Asp Ile Thr Gly Pro Ala Ala Glu Ala Glu Pro
  1               5                  10                  15 gtc gcc ttc ccc cag gac cgc acc tgt ccc tac cac ccc ccc acc gga             96
Val Ala Phe Pro Gln Asp Arg Thr Cys Pro Tyr His Pro Pro Thr Gly
                 20                  25                  30 tac gac ccg ctg cgc gac ggg cga ccc ctg tcc cgc gtc acc ctc tac            144
Tyr Asp Pro Leu Arg Asp Gly Arg Pro Leu Ser Arg Val Thr Leu Tyr
             35                  40                  45 gac ggc cgc gag gcc tgg ctg gtc acc ggc cag gcc acc gcc cgc gcc            192
Asp Gly Arg Glu Ala Trp Leu Val Thr Gly Gln Ala Thr Ala Arg Ala
         50                  55                  60 ctg ctc gcc gac ccg cgg ctg tcc acc gac cgc cgc gcc gac ggc ttc            240
Leu Leu Ala Asp Pro Arg Leu Ser Thr Asp Arg Arg Ala Asp Gly Phe
 65                  70                  75                  80 ccc gtg ccc acc ccc cgc ttc gag gcc ggc cgc gac cgc aag gtg gcc            288
Pro Val Pro Thr Pro Arg Phe Glu Ala Gly Arg Asp Arg Lys Val Ala
                 85                  90                  95 ctg ctc ggg gtg gac gat ccc gag cac cac cag cag cgc cgg atg ctg            336
Leu Leu Gly Val Asp Asp Pro Glu His His Gln Gln Arg Arg Met Leu
            100                 105                 110
```

```
atc ccg tcg ttc acc ctc aaa cgc gcc acc gcg ctg cgc ccc tgg atc      384
Ile Pro Ser Phe Thr Leu Lys Arg Ala Thr Ala Leu Arg Pro Trp Ile
115                 120                 125 cag cgg atc gtg gac gaa ctg ctg gac gcg atg atc gag cgg ggg ccg      432
Gln Arg Ile Val Asp Glu Leu Leu Asp Ala Met Ile Glu Arg Gly Pro
    130                 135                 140 ggg gcc gaa ctg gtc tcc gcc ttc gcg ctg ccc gtg ccg tcc atg gtc      480
Gly Ala Glu Leu Val Ser Ala Phe Ala Leu Pro Val Pro Ser Met Val
145                 150                 155                 160 atc tgc ggc ctg ctc ggc gtg ccc tac gcc gac cac gag ttc ttc gag      528
Ile Cys Gly Leu Leu Gly Val Pro Tyr Ala Asp His Glu Phe Phe Glu
                165                 170                 175 gag cag tcc cgc cgg ctg ctc cgc ggg ccg acc agc gcc gac acc ctg      576
Glu Gln Ser Arg Arg Leu Leu Arg Gly Pro Thr Ser Ala Asp Thr Leu
            180                 185                 190 gac gcc cgg gac cgg ctg gag cgg ttc ctc ggc gac ctg atc gac gcc      624
Asp Ala Arg Asp Arg Leu Glu Arg Phe Leu Gly Asp Leu Ile Asp Ala
        195                 200                 205 aag gcc aag gag gcc gag ccc ggc gac ggc att ctg gac gac ctc gtc      672
Lys Ala Lys Glu Ala Glu Pro Gly Asp Gly Ile Leu Asp Asp Leu Val
    210                 215                 220 cac cac cgg ctc cgc gag ggc gaa ctg gac cgg ggt gac ctg gtg tcg      720
His His Arg Leu Arg Glu Gly Glu Leu Asp Arg Gly Asp Leu Val Ser
225                 230                 235                 240 ctc gcc gtg atc ctg ttg gtc gcc ggg cac gag acg acc gcc aac atg      768
Leu Ala Val Ile Leu Leu Val Ala Gly His Glu Thr Thr Ala Asn Met
                245                 250                 255 atc tcc ctg ggc acc tac acc ctg ctc cag cac ccc gac cgg ctg gcc      816
Ile Ser Leu Gly Thr Tyr Thr Leu Leu Gln His Pro Asp Arg Leu Ala
            260                 265                 270 gag ctg cgg gcc gac ccc gcg ctg ctg ccc gcc gtc gtc gag gaa ctg      864
Glu Leu Arg Ala Asp Pro Ala Leu Leu Pro Ala Val Val Glu Glu Leu
        275                 280                 285 atg cgg atg ctg tcc atc gcc gag ggc ctg caa cgg gtg gcg ctg gag      912
Met Arg Met Leu Ser Ile Ala Glu Gly Leu Gln Arg Val Ala Leu Glu
    290                 295                 300 gac gtc gag atc gcc ggc acc acc atc cgg gcc ggc gac ggc gtc ctg      960
Asp Val Glu Ile Ala Gly Thr Thr Ile Arg Ala Gly Asp Gly Val Leu
305                 310                 315                 320 ttc tcc acc tcg gtc atc aac cgg gac acg gcc gtc tac gac gac ccc     1008
Phe Ser Thr Ser Val Ile Asn Arg Asp Thr Ala Val Tyr Asp Asp Pro
                325                 330                 335 gac gcg ctg gac ttc cac cgc gcc gac cgg cac cac gtg gcg ttc ggc     1056
Asp Ala Leu Asp Phe His Arg Ala Asp Arg His His Val Ala Phe Gly
            340                 345                 350 ttc ggc atc cac cag tgc ctg ggc cag aac ctg gcg cgc gcg gag ctg     1104
Phe Gly Ile His Gln Cys Leu Gly Gln Asn Leu Ala Arg Ala Glu Leu
        355                 360                 365 gag atc gcc ctc ggc agc ctg ttc acc cgg ttg ccc ggg ctg cgg ctc     1152
Glu Ile Ala Leu Gly Ser Leu Phe Thr Arg Leu Pro Gly Leu Arg Leu
    370                 375                 380 gcc gct ccg gcc gag gag atc ccc ttc aaa ccg ggc gac acg atc cag     1200
Ala Ala Pro Ala Glu Glu Ile Pro Phe Lys Pro Gly Asp Thr Ile Gln
385                 390                 395                 400 ggg atg ctg gaa ctc ccc gtg acc tgg taa                             1230
Gly Met Leu Glu Leu Pro Val Thr Trp
                405

<210> SEQ ID NO 228
<211> LENGTH: 1251
<212> TYPE: DNA
```

<213> ORGANISM: Streptomyces griseus IFO 13849T
<220> FEATURE:
<221> NAME/KEY: CDS
<222> LOCATION: (1)..(1251)

<400> SEQUENCE: 228

| | | | | | | | | | | | | | | | | |
|---|---|---|---|---|---|---|---|---|---|---|---|---|---|---|---|---|
| atg | acg | gaa | tcc | acg | gaa | ccg | gcc | cgc | cag | gac | gcc | gcc | ctc | acc | | 48 |
| Met | Thr | Glu | Ser | Thr | Glu | Pro | Ala | Arg | Gln | Asp | Ala | Ala | Leu | Thr | | |
| 1 | | | | 5 | | | | | 10 | | | | | 15 | | |
| ggc | gcc | acc | acc | gaa | ccg | acc | tcc | gcc | cca | ccg | ttc | ccg | cag | gac | cgc | 96 |
| Gly | Ala | Thr | Thr | Glu | Pro | Thr | Ser | Ala | Pro | Pro | Phe | Pro | Gln | Asp | Arg | |
| | | | 20 | | | | | 25 | | | | | 30 | | | |
| gag | tgc | ccc | tac | cac | ccg | ccc | acc | ggg | tac | gaa | ccg | ctg | cgc | gcg | gac | 144 |
| Glu | Cys | Pro | Tyr | His | Pro | Pro | Thr | Gly | Tyr | Glu | Pro | Leu | Arg | Ala | Asp | |
| | | 35 | | | | | 40 | | | | | 45 | | | | |
| cgg | ccg | ttg | agc | cgg | gtc | acg | ctc | tac | gac | gga | cgc | ccg | gtc | tgg | gcc | 192 |
| Arg | Pro | Leu | Ser | Arg | Val | Thr | Leu | Tyr | Asp | Gly | Arg | Pro | Val | Trp | Ala | |
| | 50 | | | | | 55 | | | | | 60 | | | | | |
| gtc | acc | gga | cac | gcc | ctg | gcc | cgc | cgc | ctc | ctg | gcc | gac | ccc | cga | ctc | 240 |
| Val | Thr | Gly | His | Ala | Leu | Ala | Arg | Arg | Leu | Leu | Ala | Asp | Pro | Arg | Leu | |
| 65 | | | | | 70 | | | | | 75 | | | | | 80 | |
| tcc | acc | gac | cgc | acc | cac | ccc | gcc | ttc | ccc | gtc | ccg | gcc | gag | cgg | ttc | 288 |
| Ser | Thr | Asp | Arg | Thr | His | Pro | Ala | Phe | Pro | Val | Pro | Ala | Glu | Arg | Phe | |
| | | | | 85 | | | | | 90 | | | | | 95 | | |
| gcg | cag | acc | cgg | cag | cgg | cgc | gtg | gcc | ctg | ctc | ggc | gtc | gac | gac | ccc | 336 |
| Ala | Gln | Thr | Arg | Gln | Arg | Arg | Val | Ala | Leu | Leu | Gly | Val | Asp | Asp | Pro | |
| | | | 100 | | | | | 105 | | | | | 110 | | | |
| gag | cac | aac | acc | cag | cgc | agg | atg | ctc | atc | ccg | agc | ttc | tcc | gtg | aaa | 384 |
| Glu | His | Asn | Thr | Gln | Arg | Arg | Met | Leu | Ile | Pro | Ser | Phe | Ser | Val | Lys | |
| | | 115 | | | | | 120 | | | | | 125 | | | | |
| cgg | atc | gcc | gcg | ctg | cgc | ccc | cgt | atc | cag | gag | acg | gtg | gac | cgg | ctg | 432 |
| Arg | Ile | Ala | Ala | Leu | Arg | Pro | Arg | Ile | Gln | Glu | Thr | Val | Asp | Arg | Leu | |
| | 130 | | | | | 135 | | | | | 140 | | | | | |
| ctg | gac | gcc | atg | gag | cgg | cag | ggg | ccg | ccg | tcc | gaa | ctg | gtc | gcc | gac | 480 |
| Leu | Asp | Ala | Met | Glu | Arg | Gln | Gly | Pro | Pro | Ser | Glu | Leu | Val | Ala | Asp | |
| 145 | | | | | 150 | | | | | 155 | | | | | 160 | |
| ttc | gcg | ctg | ccg | gtg | ccg | tcc | atg | gtg | atc | tgc | gcc | ctc | ctc | ggc | gtg | 528 |
| Phe | Ala | Leu | Pro | Val | Pro | Ser | Met | Val | Ile | Cys | Ala | Leu | Leu | Gly | Val | |
| | | | | 165 | | | | | 170 | | | | | 175 | | |
| ccc | tac | gcc | gac | cac | gcg | ctc | ttc | gag | ggc | tgt | tcg | cgc | cgg | ctc | ctg | 576 |
| Pro | Tyr | Ala | Asp | His | Ala | Leu | Phe | Glu | Gly | Cys | Ser | Arg | Arg | Leu | Leu | |
| | | | 180 | | | | | 185 | | | | | 190 | | | |
| cgc | ggt | ccg | ggc | gcg | gac | gac | gtg | gac | gcg | gcc | cgc | gtc | gaa | ctg | gag | 624 |
| Arg | Gly | Pro | Gly | Ala | Asp | Asp | Val | Asp | Ala | Ala | Arg | Val | Glu | Leu | Glu | |
| | | 195 | | | | | 200 | | | | | 205 | | | | |
| gag | tac | ctc | ggc | gcg | ttg | atc | gac | cgc | aaa | cgc | gcc | gat | ccg | ggg | gag | 672 |
| Glu | Tyr | Leu | Gly | Ala | Leu | Ile | Asp | Arg | Lys | Arg | Ala | Asp | Pro | Gly | Glu | |
| | 210 | | | | | 215 | | | | | 220 | | | | | |
| ggg | ctg | ctg | gac | gag | ctg | atc | cac | cgg | gac | cgt | ccg | gac | gga | ccc | gtg | 720 |
| Gly | Leu | Leu | Asp | Glu | Leu | Ile | His | Arg | Asp | Arg | Pro | Asp | Gly | Pro | Val | |
| 225 | | | | | 230 | | | | | 235 | | | | | 240 | |
| agc | cgg | gag | gac | ctc | gtc | tcc | ttc | gcc | ctg | atc | ctg | ctc | gtc | gcc | gga | 768 |
| Ser | Arg | Glu | Asp | Leu | Val | Ser | Phe | Ala | Leu | Ile | Leu | Leu | Val | Ala | Gly | |
| | | | | 245 | | | | | 250 | | | | | 255 | | |
| cac | gag | acg | acc | gcg | aac | atg | atc | tcg | ctc | ggc | acg | ttc | acc | ctg | ctg | 816 |
| His | Glu | Thr | Thr | Ala | Asn | Met | Ile | Ser | Leu | Gly | Thr | Phe | Thr | Leu | Leu | |
| | | | 260 | | | | | 265 | | | | | 270 | | | |
| cgc | cac | ccc | ggt | caa | ctg | gcg | gcg | ctg | cgc | tcg | ggg | gag | acc | acg | acg | 864 |
| Arg | His | Pro | Gly | Gln | Leu | Ala | Ala | Leu | Arg | Ser | Gly | Glu | Thr | Thr | Thr | |
| | | 275 | | | | | 280 | | | | | 285 | | | | |
| gcc | gtc | gtg | gtc | gag | gag | ttg | ctg | cgc | ttc | ctc | tcc | atc | gcc | gag | ggg | 912 |

```
Ala Val Val Glu Glu Leu Leu Arg Phe Leu Ser Ile Ala Glu Gly
        290                 295                 300 ctg caa cgc ctc gcg atc gag gac atc gag gtg gac ggg acg acg atc    960
Leu Gln Arg Leu Ala Ile Glu Asp Ile Glu Val Asp Gly Thr Thr Ile
305                 310                 315                 320 cgc gag ggg gag ggc gtc ttc ttc tcc acc tcg ctc gtc aac cgc gac    1008
Arg Glu Gly Glu Gly Val Phe Phe Ser Thr Ser Leu Val Asn Arg Asp
                325                 330                 335 gcc gac gtg ttc gcg gac ccg gag acc ctg gac tgg gag cgg tcc gcc    1056
Ala Asp Val Phe Ala Asp Pro Glu Thr Leu Asp Trp Glu Arg Ser Ala
            340                 345                 350 cgg cac cac ctc gcg ttc ggc ttc ggc gtc cac cag tgc ctg gga cag    1104
Arg His His Leu Ala Phe Gly Phe Gly Val His Gln Cys Leu Gly Gln
        355                 360                 365 aac ctg gcc cgc gcc gaa ctc gac atc gcg ctc cgc acg ctc ttc gaa    1152
Asn Leu Ala Arg Ala Glu Leu Asp Ile Ala Leu Arg Thr Leu Phe Glu
370                 375                 380 cgg ctg ccc gcg ctc agg ctc gcc gta ccg gcg gac gag gtg agg cac    1200
Arg Leu Pro Ala Leu Arg Leu Ala Val Pro Ala Asp Glu Val Arg His
385                 390                 395                 400 aag ccc ggc gac acc atc cag ggc ctg ctc gaa ctg ccc gtg gcc tgg    1248
Lys Pro Gly Asp Thr Ile Gln Gly Leu Leu Glu Leu Pro Val Ala Trp
                405                 410                 415 tga                                                                1251

<210> SEQ ID NO 229
<211> LENGTH: 1218
<212> TYPE: DNA
<213> ORGANISM: Streptomyces lanatus IFO 12787T
<220> FEATURE:
<221> NAME/KEY: CDS
<222> LOCATION: (1)..(1218)

<400> SEQUENCE: 229 atg acg gac atg acc gat atg acg cga ccc ccc acc gtc gcc ttc ccc    48
Met Thr Asp Met Thr Asp Met Thr Arg Pro Pro Thr Val Ala Phe Pro
1               5                   10                  15 cag aac cgc acc tgc ccc tac cac cca ccc acc gcc tac gac ccg ctc    96
Gln Asn Arg Thr Cys Pro Tyr His Pro Pro Thr Ala Tyr Asp Pro Leu
                20                  25                  30 cgc gac acc cgc ccc ctg gcg cgc atc acc ctc tac gac ggc cgc ccg    144
Arg Asp Thr Arg Pro Leu Ala Arg Ile Thr Leu Tyr Asp Gly Arg Pro
            35                  40                  45 gtc tgg ctg gtc acc ggg cac gcc ctc gcc cgc acc ctg ctc gcc gac    192
Val Trp Leu Val Thr Gly His Ala Leu Ala Arg Thr Leu Leu Ala Asp
        50                  55                  60 cct cgg ctg tcc tcc gac cgc ggc cgg ccc ggc ttc ccc gcg ccc aac    240
Pro Arg Leu Ser Ser Asp Arg Gly Arg Pro Gly Phe Pro Ala Pro Asn
65                  70                  75                  80 gag cgg ttc gcg gcg gta cgc gac cgc aag tcc gcg ctc ctc ggc gtc    288
Glu Arg Phe Ala Ala Val Arg Asp Arg Lys Ser Ala Leu Leu Gly Val
                85                  90                  95 gac gac ccc gaa cac cgg gtc cag cga cgg atg atg gtc ccc agc ttc    336
Asp Asp Pro Glu His Arg Val Gln Arg Arg Met Met Val Pro Ser Phe
            100                 105                 110 act ctc cgc cga gcc gcc gaa ctg cgc ccg cag atc cag cgg atc gtg    384
Thr Leu Arg Arg Ala Ala Glu Leu Arg Pro Gln Ile Gln Arg Ile Val
        115                 120                 125 gac gaa cgg ctc gac gcg atg atc gac cag ggg gcg ccc gcc gag ctg    432
Asp Glu Arg Leu Asp Ala Met Ile Asp Gln Gly Ala Pro Ala Glu Leu
130                 135                 140
```

```
gtg aac gcc ttc gcg ctg ccc gtg ccc tcg atg gtc atc tgc gcc ctg       480
Val Asn Ala Phe Ala Leu Pro Val Pro Ser Met Val Ile Cys Ala Leu
145                 150                 155                 160 ctg ggc gtg ccc tat gcc gac cac gac ttc ttc gag ggg gag tcc cgg       528
Leu Gly Val Pro Tyr Ala Asp His Asp Phe Phe Glu Gly Glu Ser Arg
                165                 170                 175 cgc ctg ctg cgc ggt gcc acg gcg gcc gag gcc atg gac gcc cgg gac       576
Arg Leu Leu Arg Gly Ala Thr Ala Ala Glu Ala Met Asp Ala Arg Asp
            180                 185                 190 cgg ctg gag aac tac ttc atc gag ctg atc gac cgc aag cag aag gac       624
Arg Leu Glu Asn Tyr Phe Ile Glu Leu Ile Asp Arg Lys Gln Lys Asp
        195                 200                 205 ccg gag ccc ggc gac ggc gtc ctc gac gaa ctc gtc cac cgg cag ctg       672
Pro Glu Pro Gly Asp Gly Val Leu Asp Glu Leu Val His Arg Gln Leu
    210                 215                 220 cgc gac ggc gac ctc gac cgc gag gaa gtc gtc gcc ctc tcg acc atc       720
Arg Asp Gly Asp Leu Asp Arg Glu Glu Val Val Ala Leu Ser Thr Ile
225                 230                 235                 240 ctg ctg gtc gcc ggc cac gag acg acc gcc aac atg atc tcg ctg ggt       768
Leu Leu Val Ala Gly His Glu Thr Thr Ala Asn Met Ile Ser Leu Gly
                245                 250                 255 acc ttc aca ctg ctc caa cac ccg gag cag ctg gcc gag ttg cgc gcc       816
Thr Phe Thr Leu Leu Gln His Pro Glu Gln Leu Ala Glu Leu Arg Ala
            260                 265                 270 gac gcc ggg ttg ctg ccc gcg gtc gag gag ctc atg cgg atg ctg           864
Asp Ala Gly Leu Leu Pro Ala Val Glu Glu Leu Met Arg Met Leu
        275                 280                 285 tcg atc gcg gac ggg ctg ctg cgc gtc gcc tcc gag gac atc gag gcg       912
Ser Ile Ala Asp Gly Leu Leu Arg Val Ala Ser Glu Asp Ile Glu Ala
290                 295                 300 ggc ggc gag acg atc cgg gcg ggc gac ggc gtg gtc ttc tcg acc tcg       960
Gly Gly Glu Thr Ile Arg Ala Gly Asp Gly Val Val Phe Ser Thr Ser
305                 310                 315                 320 gtc atc aac cgc gac gag tcc gtc tac ccc gac ccc gat gcc atc gac      1008
Val Ile Asn Arg Asp Glu Ser Val Tyr Pro Asp Pro Asp Ala Ile Asp
                325                 330                 335 tgg cac cgc ccc acc cgc cac cac atc gcc ttc ggg ttc ggc atc cac      1056
Trp His Arg Pro Thr Arg His His Ile Ala Phe Gly Phe Gly Ile His
            340                 345                 350 cag tgc ctc ggc cag aac ctg gcc cgc gcc gag atg gag atc gcc ctg      1104
Gln Cys Leu Gly Gln Asn Leu Ala Arg Ala Glu Met Glu Ile Ala Leu
        355                 360                 365 cgc acc ctc ttc gag cgc ctg ccc acc ctg cgc ctt gcc gtc ccg gcg      1152
Arg Thr Leu Phe Glu Arg Leu Pro Thr Leu Arg Leu Ala Val Pro Ala
370                 375                 380 ggg gaa atc ccc ttc aaa ccc ggc gac acg atc cag ggg atg ctg gaa      1200
Gly Glu Ile Pro Phe Lys Pro Gly Asp Thr Ile Gln Gly Met Leu Glu
385                 390                 395                 400 ctc ccc gtg acc tgg taa                                              1218
Leu Pro Val Thr Trp
                405

<210> SEQ ID NO 230
<211> LENGTH: 1245
<212> TYPE: DNA
<213> ORGANISM: Streptomyces misawanensis IFO 13855T
<220> FEATURE:
<221> NAME/KEY: CDS
<222> LOCATION: (1)..(1245)

<400> SEQUENCE: 230 atg aaa gaa ctg acg gac ctg acg gaa ccc atc tct ccc gcc ggc cag        48
```

-continued

| | | |
|---|---|---|
| Met Lys Glu Leu Thr Asp Leu Thr Glu Pro Ile Ser Pro Ala Gly Gln<br>1               5                    10                 15 | |
| gcc gac ccc gtg gcc tgg ccg cag gac cgc acg tgc ccc tac cac ccg<br>Ala Asp Pro Val Ala Trp Pro Gln Asp Arg Thr Cys Pro Tyr His Pro<br>             20                   25                   30 | 96 |
| ccc acc ggc tac gac ccg ctc cgc gac ggc acc ccg ctg tcc cgc gtc<br>Pro Thr Gly Tyr Asp Pro Leu Arg Asp Gly Thr Pro Leu Ser Arg Val<br>             35                   40                   45 | 144 |
| acc ctc tac gac ggc cgc acc gtc tgg gcg gtc acc ggc cac ggc acg<br>Thr Leu Tyr Asp Gly Arg Thr Val Trp Ala Val Thr Gly His Gly Thr<br>     50                   55                   60 | 192 |
| gcc cgg gcg ctg ctc tcc gac ccc cgc ctc tcc agc gac cgc cgg cgc<br>Ala Arg Ala Leu Leu Ser Asp Pro Arg Leu Ser Ser Asp Arg Arg Arg<br>65                   70                   75                 80 | 240 |
| gac gac ttc ccg atg ccg aac gcc cgg ttc gcg gcg gcc cgg gag cgc<br>Asp Asp Phe Pro Met Pro Asn Ala Arg Phe Ala Ala Ala Arg Glu Arg<br>                   85                   90                   95 | 288 |
| cga cag ctc gcc ctg ctg ggc ctc gac gac ccc gag cac cag atc cag<br>Arg Gln Leu Ala Leu Leu Gly Leu Asp Asp Pro Glu His Gln Ile Gln<br>                 100                 105               110 | 336 |
| cgc cgg atg ctg atc ccg gac ttc acc ctc aag cgg gcg acc gtg atg<br>Arg Arg Met Leu Ile Pro Asp Phe Thr Leu Lys Arg Ala Thr Val Met<br>         115                 120                125 | 384 |
| cgg ccg gcc atc cag cgg atc gtc gac gat ctg ctc gac agg atg atc<br>Arg Pro Ala Ile Gln Arg Ile Val Asp Asp Leu Leu Asp Arg Met Ile<br>130                   135                 140 | 432 |
| gcc gcg ggc ccg ccc gcc gac ctg gtg agc tcc ttc gcg ctg ccc gtg<br>Ala Ala Gly Pro Pro Ala Asp Leu Val Ser Ser Phe Ala Leu Pro Val<br>145                   150                155                160 | 480 |
| ccg tcc atg gtc atc tgt gac ctg ctc ggc gtg ccc tac gcc gac cac<br>Pro Ser Met Val Ile Cys Asp Leu Leu Gly Val Pro Tyr Ala Asp His<br>                 165                 170               175 | 528 |
| gag ttc ttc gag gcg cag tcc cgg cgg ctg ctc cgc ggt ccg gcg ccc<br>Glu Phe Phe Glu Ala Gln Ser Arg Arg Leu Leu Arg Gly Pro Ala Pro<br>             180                 185               190 | 576 |
| gcc gac tcc ctg gac gcg cgc gac cag ctg gag gcc tat ctg ggc gac<br>Ala Asp Ser Leu Asp Ala Arg Asp Gln Leu Glu Ala Tyr Leu Gly Asp<br>         195                 200               205 | 624 |
| ctg gcc gac cgc aag agc cgg gac gcg gtc ccc ggc gac ggc gtc ctc<br>Leu Ala Asp Arg Lys Ser Arg Asp Ala Val Pro Gly Asp Gly Val Leu<br>210                   215                220 | 672 |
| gac gac ctc gtc cac cag cgg ctg cgg gac ggc gcc ctg gac cgc gcc<br>Asp Asp Leu Val His Gln Arg Leu Arg Asp Gly Ala Leu Asp Arg Ala<br>225                   230                235                240 | 720 |
| gag gtc gtc gcg ctg gcc ctc atc ctg ctg gtc gcc ggc cac gag acc<br>Glu Val Val Ala Leu Ala Leu Ile Leu Leu Val Ala Gly His Glu Thr<br>             245                 250               255 | 768 |
| acc gcc aac atg atc tcg ctc ggc acc ttc acc ctg ctc cag cag ccc<br>Thr Ala Asn Met Ile Ser Leu Gly Thr Phe Thr Leu Leu Gln Gln Pro<br>         260                 265                270 | 816 |
| gaa cgg ctc gcc gaa ctg cgc gcc gac ccc gcg ctg gtg ccc gcc gcc<br>Glu Arg Leu Ala Glu Leu Arg Ala Asp Pro Ala Leu Val Pro Ala Ala<br>275                   280                285 | 864 |
| gtc gag gaa ctg atg cgg atg ctg tcc atc gcc gac ggg ctg ctg cgc<br>Val Glu Glu Leu Met Arg Met Leu Ser Ile Ala Asp Gly Leu Leu Arg<br>             290                 295               300 | 912 |
| gtc gca ctg gag gac atc gag acg gac ggc ggc acc acc atc cgc aag<br>Val Ala Leu Glu Asp Ile Glu Thr Asp Gly Gly Thr Thr Ile Arg Lys<br>305                   310                315                320 | 960 |
| ggc gag ggc gtg ctc ttc gcg acc tcg gtc atc aac cgt gac gag tcc | 1008 |

```
                Gly Glu Gly Val Leu Phe Ala Thr Ser Val Ile Asn Arg Asp Glu Ser
                                325                 330                 335 gtg tac gac gac ccc gac gcc ctc gac tgg cac cgc ccg gcc cgc cac        1056
Val Tyr Asp Asp Pro Asp Ala Leu Asp Trp His Arg Pro Ala Arg His
                340                 345                 350 cac gtg gcc ttc ggc ttc ggc atc cac cag tgc ctg ggc cag aac ctg        1104
His Val Ala Phe Gly Phe Gly Ile His Gln Cys Leu Gly Gln Asn Leu
                355                 360                 365 gcc cgc acc gag ctg gag atc gcc ctg cgc acc ctg tgg gag cgg ctc        1152
Ala Arg Thr Glu Leu Glu Ile Ala Leu Arg Thr Leu Trp Glu Arg Leu
    370                 375                 380 ccg gac ctg cgg ctc gcc gca ccg ccg gag gag att ccc ttc aaa ccc        1200
Pro Asp Leu Arg Leu Ala Ala Pro Pro Glu Glu Ile Pro Phe Lys Pro
385                 390                 395                 400 ggc gac acg atc cag ggg atg ctg gaa ctc ccc gtg acc tgg taa            1245
Gly Asp Thr Ile Gln Gly Met Leu Glu Leu Pro Val Thr Trp
                405                 410

<210> SEQ ID NO 231
<211> LENGTH: 1230
<212> TYPE: DNA
<213> ORGANISM: Streptomyces pallidus IFO 13434T
<220> FEATURE:
<221> NAME/KEY: CDS
<222> LOCATION: (1)..(1230)

<400> SEQUENCE: 231 atg gcc gac acc ctc gcc ggc gcc acg ccc gac gcc gcc gcg acg gtc         48
Met Ala Asp Thr Leu Ala Gly Ala Thr Pro Asp Ala Ala Ala Thr Val
1               5                   10                  15 ccc gcg tac ccc atg gcc cgg gcc gcg ggc tgc ccc ttc gac ccg ccc         96
Pro Ala Tyr Pro Met Ala Arg Ala Ala Gly Cys Pro Phe Asp Pro Pro
                20                  25                  30 ccg gac ctc acc gcc cgg cag gac gag ggt cgg ctc gtc agg gtg cgc        144
Pro Asp Leu Thr Ala Arg Gln Asp Glu Gly Arg Leu Val Arg Val Arg
            35                  40                  45 ctc tgg gac ggc agt acg ccc tgg ctc gtg acc cgc tac gag gac cag        192
Leu Trp Asp Gly Ser Thr Pro Trp Leu Val Thr Arg Tyr Glu Asp Gln
        50                  55                  60 cgc gcc ctg ctc ctc gac ccc agg gtc agt gcc gac atc acc agg ccc        240
Arg Ala Leu Leu Leu Asp Pro Arg Val Ser Ala Asp Ile Thr Arg Pro
65                  70                  75                  80 gga tac ccc ctc cag gcc gcc ggc gcc ggc gag aac aac gcc agc ttc        288
Gly Tyr Pro Leu Gln Ala Ala Gly Ala Gly Glu Asn Asn Ala Ser Phe
                85                  90                  95 atc ctc atg gac gac ccg gag cac gca cgg ctg cgc cgc atg gtg acc        336
Ile Leu Met Asp Asp Pro Glu His Ala Arg Leu Arg Arg Met Val Thr
                100                 105                 110 gcg ccc ttc gcg atc aag cgc gtc gag gcg atg cgg ccg ggc gtg cag        384
Ala Pro Phe Ala Ile Lys Arg Val Glu Ala Met Arg Pro Gly Val Gln
            115                 120                 125 cag ctc gtg gac gac ctc atc gac ggc atg ctc gcc ggg ccc aag ccg        432
Gln Leu Val Asp Asp Leu Ile Asp Gly Met Leu Ala Gly Pro Lys Pro
        130                 135                 140 gtc gac ctg gtg gag gcg ttc gcg ctg ccg gtg ccc tcg ctg gtc atc        480
Val Asp Leu Val Glu Ala Phe Ala Leu Pro Val Pro Ser Leu Val Ile
145                 150                 155                 160 tgc cgg atg ctc gga gtg ccg tac gag gac cac gac ttc ttc cag gag        528
Cys Arg Met Leu Gly Val Pro Tyr Glu Asp His Asp Phe Phe Gln Glu
                165                 170                 175 aac agc cgg atc ctc atc aag cgg gac gcg gcc atg gag gac cgc atg        576
Asn Ser Arg Ile Leu Ile Lys Arg Asp Ala Ala Met Glu Asp Arg Met
```

```
                      180                 185                 190
gcc gcg cac ggg cgg ctg atc gcc tac ctc gac gag ctg atg ggc gag         624
Ala Ala His Gly Arg Leu Ile Ala Tyr Leu Asp Glu Leu Met Gly Glu
            195                 200                 205 aag acg gcc cgt ccg gcg gac gat ctg ctc tcc ggg ctc gtc gag cgg         672
Lys Thr Ala Arg Pro Ala Asp Asp Leu Leu Ser Gly Leu Val Glu Arg
210                 215                 220 gtc agg acg ggg gag ctg acc cgg cgc gag tcg gcc cgc atg ggc gtg         720
Val Arg Thr Gly Glu Leu Thr Arg Arg Glu Ser Ala Arg Met Gly Val
225                 230                 235                 240 ctc ctg ctc atc gcc ggg cac gag acc acc gcc aac atg atc gcg ctc         768
Leu Leu Leu Ile Ala Gly His Glu Thr Thr Ala Asn Met Ile Ala Leu
            245                 250                 255 ggc acg ctc gcc ctg ctc gaa cac ccg gac cag ctc gcc ctg ctg cgt         816
Gly Thr Leu Ala Leu Leu Glu His Pro Asp Gln Leu Ala Leu Leu Arg
            260                 265                 270 gac acc gac gac ccg aag ctg gtc gcc gga gcg gcc gag gaa ctg ctg         864
Asp Thr Asp Asp Pro Lys Leu Val Ala Gly Ala Ala Glu Glu Leu Leu
            275                 280                 285 cgc tat ctg acc atc gtg cac aac gga cgc cgc cgg gcg gcc ctc gcg         912
Arg Tyr Leu Thr Ile Val His Asn Gly Arg Arg Arg Ala Ala Leu Ala
290                 295                 300 gac atc gag atc ggc gga cag gtc atc cgg gcc ggc gag ggc atg atc         960
Asp Ile Glu Ile Gly Gly Gln Val Ile Arg Ala Gly Glu Gly Met Ile
305                 310                 315                 320 atg ccc aac gac ctc gcc aac cgg gac ccc ggc gcc ttc acc gac ccg        1008
Met Pro Asn Asp Leu Ala Asn Arg Asp Pro Gly Ala Phe Thr Asp Pro
            325                 330                 335 gac cgg ctg gac ctg cgc cgc gac gcc cgc cgg cac atc gcg ttc ggc        1056
Asp Arg Leu Asp Leu Arg Arg Asp Ala Arg Arg His Ile Ala Phe Gly
            340                 345                 350 ttc ggc gtg cac cag tgc ctg ggc cag ccg ctg gcc cgc atg gaa ctc        1104
Phe Gly Val His Gln Cys Leu Gly Gln Pro Leu Ala Arg Met Glu Leu
            355                 360                 365 cag gtc gtc tac ggc acc ctc tac cgc cgc atc ccc acg ctg cgg ctc        1152
Gln Val Val Tyr Gly Thr Leu Tyr Arg Arg Ile Pro Thr Leu Arg Leu
370                 375                 380 gcc gcc ccg gtg gag agc ctg tcg ttc aag cac gac gga tcg gtc tac        1200
Ala Ala Pro Val Glu Ser Leu Ser Phe Lys His Asp Gly Ser Val Tyr
385                 390                 395                 400 ggc gtc tac gaa ctg ccc gtc acg tgg tga                                1230
Gly Val Tyr Glu Leu Pro Val Thr Trp
            405

<210> SEQ ID NO 232
<211> LENGTH: 1197
<212> TYPE: DNA
<213> ORGANISM: Streptomyces roseorubens IFO 13682T
<220> FEATURE:
<221> NAME/KEY: CDS
<222> LOCATION: (1)..(1197)

<400> SEQUENCE: 232 atg acg gac acg acc gca ccc gtc gcc ttc ccc cag agc agg acc tgc          48
Met Thr Asp Thr Thr Ala Pro Val Ala Phe Pro Gln Ser Arg Thr Cys
1               5                  10                  15 ccc tac cac ccg ccc gcc gcc tac gag ccg ctg cgc gcc gag cgc ccc          96
Pro Tyr His Pro Pro Ala Ala Tyr Glu Pro Leu Arg Ala Glu Arg Pro
            20                  25                  30 ctg acc cgg atc acc ctc ttc gac ggc cgt gag gcc tgg ctg gtc agc         144
Leu Thr Arg Ile Thr Leu Phe Asp Gly Arg Glu Ala Trp Leu Val Ser
        35                  40                  45
```

```
ggc cac gcc acc gcc cgc gcc ctg ctc gcc gac ccc cgc ctg tcc tcc     192
Gly His Ala Thr Ala Arg Ala Leu Leu Ala Asp Pro Arg Leu Ser Ser
    50              55                  60 gac cgc gac cgc ccc ggc ttc ccc acc ccc acc gcg cgc ttc gcc ggc     240
Asp Arg Asp Arg Pro Gly Phe Pro Thr Pro Thr Ala Arg Phe Ala Gly
65              70                  75                  80 atc cgc aac cgc cgt acg gcc ctg ctc ggc gtg gac gac ccc gag cac     288
Ile Arg Asn Arg Arg Thr Ala Leu Leu Gly Val Asp Asp Pro Glu His
                85                  90                  95 cgc gcc cag cgg cgg atg gtc gtc ggg gac ttc acc ctc aaa cgg gcc     336
Arg Ala Gln Arg Arg Met Val Val Gly Asp Phe Thr Leu Lys Arg Ala
            100                 105                 110 gcc gca ctg cgg ccc cgc atc cag cgg atc gtc gac gaa cga ctc gac     384
Ala Ala Leu Arg Pro Arg Ile Gln Arg Ile Val Asp Glu Arg Leu Asp
        115                 120                 125 gcg atg atc gcc cag ggc ccg ccc gcc gac ctg gtg agc gcc ttc gcg     432
Ala Met Ile Ala Gln Gly Pro Pro Ala Asp Leu Val Ser Ala Phe Ala
    130                 135                 140 ctg ccc gtg ccc tcc atg gtg atc tgc gcc ctg ctc ggc gtc ccc tac     480
Leu Pro Val Pro Ser Met Val Ile Cys Ala Leu Leu Gly Val Pro Tyr
145                 150                 155                 160 gcc gac cac gac ttc ttc gag gct cag tcg cgg cgc ctg ctg cgc ggc     528
Ala Asp His Asp Phe Phe Glu Ala Gln Ser Arg Arg Leu Leu Arg Gly
                165                 170                 175 ccg ggg acc gcc gac gtg cag gac gcc cgg agc agg ctg gag gag tac     576
Pro Gly Thr Ala Asp Val Gln Asp Ala Arg Ser Arg Leu Glu Glu Tyr
            180                 185                 190 ttc ggc gag ctg atc gac cgc aag cgc gag gac ccc ggc acc ggc ctc     624
Phe Gly Glu Leu Ile Asp Arg Lys Arg Glu Asp Pro Gly Thr Gly Leu
        195                 200                 205 ctg gac gac ctg gtc caa cgg cag ccc ggc gac ggc gga ccc gac cgc     672
Leu Asp Asp Leu Val Gln Arg Gln Pro Gly Asp Gly Gly Pro Asp Arg
    210                 215                 220 gag ggc ctg atc gcc atg gcc ctc atc ctg ctg gtc gcc ggc cac gag     720
Glu Gly Leu Ile Ala Met Ala Leu Ile Leu Leu Val Ala Gly His Glu
225                 230                 235                 240 acg acc gcc aac atg atc tcc ctc ggc acc ttc acg ctc ctg cag cac     768
Thr Thr Ala Asn Met Ile Ser Leu Gly Thr Phe Thr Leu Leu Gln His
                245                 250                 255 ccc gag cgg ctc gcc gaa ctg cgc gcc gac tcc gag gtc atg ccg gcc     816
Pro Glu Arg Leu Ala Glu Leu Arg Ala Asp Ser Glu Val Met Pro Ala
            260                 265                 270 gcg gtc gag gaa ctg atg cgg ctg ctg tcc atc gcg gac ggc ctg ctg     864
Ala Val Glu Glu Leu Met Arg Leu Leu Ser Ile Ala Asp Gly Leu Leu
        275                 280                 285 cgc atc gcc gtc gag gac gtc gag gtg gcc ggg acg acg atc cgc gcc     912
Arg Ile Ala Val Glu Asp Val Glu Val Ala Gly Thr Thr Ile Arg Ala
    290                 295                 300 ggc gag ggc gtg gtg ttc gcg acg tcg gtc atc aac cgc gac gag acg     960
Gly Glu Gly Val Val Phe Ala Thr Ser Val Ile Asn Arg Asp Glu Thr
305                 310                 315                 320 gtc ttc gcc gag ccg gac acc ctc gac tgg agc cgc ccg gcc cgc cac    1008
Val Phe Ala Glu Pro Asp Thr Leu Asp Trp Ser Arg Pro Ala Arg His
                325                 330                 335 cac gtg gcg ttc ggc ttc ggc atc cac cag tgc ctc ggc caa aac ctc    1056
His Val Ala Phe Gly Phe Gly Ile His Gln Cys Leu Gly Gln Asn Leu
            340                 345                 350 gca cgc gcc gaa ctg gag atc gcc ctc ggc acc ctc ttc ggc cgg ctg    1104
Ala Arg Ala Glu Leu Glu Ile Ala Leu Gly Thr Leu Phe Gly Arg Leu
        355                 360                 365
```

-continued

```
ccc acg ctg cgc ctg gcc gcc ccg ccc gac gag atc ccc ttc aag ccg      1152
Pro Thr Leu Arg Leu Ala Ala Pro Pro Asp Glu Ile Pro Phe Lys Pro
370                 375                 380 ggc gac acg atc cag ggg atg ctg gaa ctc ccc gtg acc tgg taa          1197
Gly Asp Thr Ile Gln Gly Met Leu Glu Leu Pro Val Thr Trp
385                 390                 395

<210> SEQ ID NO 233
<211> LENGTH: 1245
<212> TYPE: DNA
<213> ORGANISM: Streptomyces rutgersensis IFO 15875T
<220> FEATURE:
<221> NAME/KEY: CDS
<222> LOCATION: (1)..(1245)

<400> SEQUENCE: 233 atg acc gaa acg ctg gca gag acc acg acc gag gcg gaa gag ccg ctt      48
Met Thr Glu Thr Leu Ala Glu Thr Thr Thr Glu Ala Glu Glu Pro Leu
1               5                   10                  15 ccg gag ttc ccg atg ccg cgg gcg aac ggc tgc ccc ttc gcc ccg ccc      96
Pro Glu Phe Pro Met Pro Arg Ala Asn Gly Cys Pro Phe Ala Pro Pro
                20                  25                  30 ccg acc gca cgg gcg ctg cac acc gaa cgg ccg gtc acg cgg gta cgg     144
Pro Thr Ala Arg Ala Leu His Thr Glu Arg Pro Val Thr Arg Val Arg
            35                  40                  45 ctg tgg gac ggc agc gcc ccc tgg ctg gtg acc cgg tac gcc gac cag     192
Leu Trp Asp Gly Ser Ala Pro Trp Leu Val Thr Arg Tyr Ala Asp Gln
    50                  55                  60 cgc gcc ctg ctc ggc gac ccg cgg gtc agc tcc gag gcc acc cgg ccc     240
Arg Ala Leu Leu Gly Asp Pro Arg Val Ser Ser Glu Ala Thr Arg Pro
65                  70                  75                  80 ggc ttt ccg cat gcg agc gcc ggc ttc cgc gag aat gcc agg cgg cgg     288
Gly Phe Pro His Ala Ser Ala Gly Phe Arg Glu Asn Ala Arg Arg Arg
                85                  90                  95 cgc tcc ttc atc acc atg gac gac ccc gag cac gcc cgg atc cgc cgg     336
Arg Ser Phe Ile Thr Met Asp Asp Pro Glu His Ala Arg Ile Arg Arg
                100                 105                 110 atg gtc acc gcg ccg ttc gcc atc aag cgg gtc gag gcg atg cgg ccc     384
Met Val Thr Ala Pro Phe Ala Ile Lys Arg Val Glu Ala Met Arg Pro
            115                 120                 125 gac atc cag aag atc acc gac gat ctg atc gac tcc atg ctg gcc ggg     432
Asp Ile Gln Lys Ile Thr Asp Asp Leu Ile Asp Ser Met Leu Ala Gly
    130                 135                 140 ccg acc ccg gtc gac ctg gtg cgc gcg ttg gcg ctg ccg ctg ccg tcg     480
Pro Thr Pro Val Asp Leu Val Arg Ala Leu Ala Leu Pro Leu Pro Ser
145                 150                 155                 160 ctg gtg atc tgc cgg ctg ctc gga gtg ccg tac gag gac cac gac ttc     528
Leu Val Ile Cys Arg Leu Leu Gly Val Pro Tyr Glu Asp His Asp Phe
                165                 170                 175 ttc cag cgc aac agc tcg ctc ctg atc aac cgt aac tcc acg acc gaa     576
Phe Gln Arg Asn Ser Ser Leu Leu Ile Asn Arg Asn Ser Thr Thr Glu
                180                 185                 190 gag gtg gtc ggc gcc aac gag gcg ctg acc gac tat ctg gac gag ctg     624
Glu Val Val Gly Ala Asn Glu Ala Leu Thr Asp Tyr Leu Asp Glu Leu
            195                 200                 205 gtc agc gcc aaa ctc gcc aac ccc gcc gac gac atg ctc tcc gag ctg     672
Val Ser Ala Lys Leu Ala Asn Pro Ala Asp Asp Met Leu Ser Glu Leu
    210                 215                 220 gcc gcc cgg gtc acg gcc gga gag ctg acc cag cgc gag gcc gcc aat     720
Ala Ala Arg Val Thr Ala Gly Glu Leu Thr Gln Arg Glu Ala Ala Asn
225                 230                 235                 240
```

```
atg ggc gtg ctg ctg ctg atc gcc ggc cat gag acc acc gcc aac atg        768
Met Gly Val Leu Leu Leu Ile Ala Gly His Glu Thr Thr Ala Asn Met
            245                 250                 255 atc gcc ctc ggc acc gtc gcc ctg ctg gag aac ccc gac cag ctc gcc        816
Ile Ala Leu Gly Thr Val Ala Leu Leu Glu Asn Pro Asp Gln Leu Ala
        260                 265                 270 gtc ctg cgg gag acc gac gac ccg aag gcg gtc gcc aag gcc gtc gag        864
Val Leu Arg Glu Thr Asp Asp Pro Lys Ala Val Ala Lys Ala Val Glu
    275                 280                 285 gaa ctg ctg cgc tat ctg acc atc gtg cac acc ggc cgg cgc cgg gtc        912
Glu Leu Leu Arg Tyr Leu Thr Ile Val His Thr Gly Arg Arg Arg Val
290                 295                 300 gcg cgg gag gac atc gag atc ggc ggc gag acc atc cgt gcc ggg gac        960
Ala Arg Glu Asp Ile Glu Ile Gly Gly Glu Thr Ile Arg Ala Gly Asp
305                 310                 315                 320 ggg atc atc atc tac acc ggc acc ggc aac tgg gac gcg gag gtc ttc       1008
Gly Ile Ile Ile Tyr Thr Gly Thr Gly Asn Trp Asp Ala Glu Val Phe
            325                 330                 335 ccc gag ccc gag cgg ctg gac atc ggc cgc gac gcc cgc cgc cac atg       1056
Pro Glu Pro Glu Arg Leu Asp Ile Gly Arg Asp Ala Arg Arg His Met
        340                 345                 350 gcg ttc ggt ttc ggc gtc cac cag tgc ctg ggc cag ccg ctg gcc cgg       1104
Ala Phe Gly Phe Gly Val His Gln Cys Leu Gly Gln Pro Leu Ala Arg
    355                 360                 365 gtg gag ctg cag gtg gtc tac ggc acg ctc tac cgc gtc atc ccc acg       1152
Val Glu Leu Gln Val Val Tyr Gly Thr Leu Tyr Arg Val Ile Pro Thr
370                 375                 380 ctg cgg ctg gcg acc ggg gtc gac caa cta ccg ttc aag gac gac ggt       1200
Leu Arg Leu Ala Thr Gly Val Asp Gln Leu Pro Phe Lys Asp Asp Gly
385                 390                 395                 400 ttg gtc tac ggc gtc tat gaa ctg ccc gtc acc tgg acg tct tga           1245
Leu Val Tyr Gly Val Tyr Glu Leu Pro Val Thr Trp Thr Ser
            405                 410

<210> SEQ ID NO 234
<211> LENGTH: 1197
<212> TYPE: DNA
<213> ORGANISM: Streptomyces steffisburgensis IFO 13446T
<220> FEATURE:
<221> NAME/KEY: CDS
<222> LOCATION: (1)..(1197)

<400> SEQUENCE: 234 atg tcg gac acg acc gca ccc gtg gcc ttc ccc cag agc cgg acc tgc         48
Met Ser Asp Thr Thr Ala Pro Val Ala Phe Pro Gln Ser Arg Thr Cys
1               5                   10                  15 ccc tac cac ccg ccc gcc gcc tac gag ccg ctg cgc gcc gag cgc ccc         96
Pro Tyr His Pro Pro Ala Ala Tyr Glu Pro Leu Arg Ala Glu Arg Pro
            20                  25                  30 ctg acc cgt atc acc ctc ttc gac ggc cgt gag gcc tgg ctg gtc agc        144
Leu Thr Arg Ile Thr Leu Phe Asp Gly Arg Glu Ala Trp Leu Val Ser
        35                  40                  45 ggc cac gcc acc gcc cgc gcg ctg ctc gcc gac ccg cgc ctg tcc tcc        192
Gly His Ala Thr Ala Arg Ala Leu Leu Ala Asp Pro Arg Leu Ser Ser
    50                  55                  60 gac cgc gac cgc ccc ggc ttc ccc gcc ccc acc gcg cgc ttc gcc ggg        240
Asp Arg Asp Arg Pro Gly Phe Pro Ala Pro Thr Ala Arg Phe Ala Gly
65                  70                  75                  80 atc cgc aac cgc aga acg gcc ctg ctg ggc gtc gac gac ccc gag cac        288
Ile Arg Asn Arg Arg Thr Ala Leu Leu Gly Val Asp Asp Pro Glu His
                85                  90                  95 cga gtc cag cgg cgg atg gtg gcc ggg gac ttc acc ctc aaa cgg gcc        336
```

```
Arg Val Gln Arg Arg Met Val Ala Gly Asp Phe Thr Leu Lys Arg Ala
            100                 105                 110 gcc gga ctg cga ccc cgc atc cag cgg atc gtg gac cga cga ctc gac       384
Ala Gly Leu Arg Pro Arg Ile Gln Arg Ile Val Asp Arg Arg Leu Asp
        115                 120                 125 gcg atg atc gcc cag ggc cca ccg gcc gac ctg gtg agc agc ttc gcg       432
Ala Met Ile Ala Gln Gly Pro Pro Ala Asp Leu Val Ser Ser Phe Ala
    130                 135                 140 ctg ccc gtc ccg tcc atg gtg atc tgt gcc ctc ggc gtc ccg tac           480
Leu Pro Val Pro Ser Met Val Ile Cys Ala Leu Gly Val Pro Tyr
145                 150                 155                 160 gcc gac cac gac ttc ttc gag acc cag tca cgg cgg ctg ctg cgc ggc       528
Ala Asp His Asp Phe Phe Glu Thr Gln Ser Arg Arg Leu Leu Arg Gly
                165                 170                 175 ccg cag acc gcc gac gtg atg gac gcc cgg gcc cgg ctg gac gag tac       576
Pro Gln Thr Ala Asp Val Met Asp Ala Arg Ala Arg Leu Asp Glu Tyr
            180                 185                 190 ttc ggc gaa ctg atc gac cgc aag cgg aag gaa ccc ggc gcc ggc ctg       624
Phe Gly Glu Leu Ile Asp Arg Lys Arg Lys Glu Pro Gly Ala Gly Leu
        195                 200                 205 ctg gac gac ctg gtc cag cga cag ctg cgc gac ggc gca ctc gac cgc       672
Leu Asp Asp Leu Val Gln Arg Gln Leu Arg Asp Gly Ala Leu Asp Arg
    210                 215                 220 gag ggc ctg atc gcc ctg gcg ctc atc ctg ctg gtc gcg ggc cac gag       720
Glu Gly Leu Ile Ala Leu Ala Leu Ile Leu Leu Val Ala Gly His Glu
225                 230                 235                 240 acg acc gcc aac atg atc tcg ctc ggc acc ttc acc ctg ctg cag cac       768
Thr Thr Ala Asn Met Ile Ser Leu Gly Thr Phe Thr Leu Leu Gln His
                245                 250                 255 ccc gaa cgg ctc gcc gag ctg cgc gcc gac ccg cgg ctg ctg cct gcg       816
Pro Glu Arg Leu Ala Glu Leu Arg Ala Asp Pro Arg Leu Leu Pro Ala
            260                 265                 270 gcg gtc gag gag ctg atg cgc atg ctg tcc atc gcg gac ggt ctg ctc       864
Ala Val Glu Glu Leu Met Arg Met Leu Ser Ile Ala Asp Gly Leu Leu
        275                 280                 285 cgc ctc gcc gtc gag gac ata gag gtg gcc ggg acc acg atc cgc aag       912
Arg Leu Ala Val Glu Asp Ile Glu Val Ala Gly Thr Thr Ile Arg Lys
    290                 295                 300 ggg gac ggc gtg gtg ttc ctg acg tcc gtc atc aac cgc gac gag acg       960
Gly Asp Gly Val Val Phe Leu Thr Ser Val Ile Asn Arg Asp Glu Thr
305                 310                 315                 320 gtc tac ccc gag ccg gac acc ctc gac tgg cac cgc tcg gcc cgg cat      1008
Val Tyr Pro Glu Pro Asp Thr Leu Asp Trp His Arg Ser Ala Arg His
                325                 330                 335 cac gtc gcg ttc ggc ttc ggc atc cac cag tgc ctc ggc cag aac ctc      1056
His Val Ala Phe Gly Phe Gly Ile His Gln Cys Leu Gly Gln Asn Leu
            340                 345                 350 gcg cgc gcc gag ctg gag atc gcc ctg tgg acc ctc ttc gac cgt ctg      1104
Ala Arg Ala Glu Leu Glu Ile Ala Leu Trp Thr Leu Phe Asp Arg Leu
        355                 360                 365 ccc acc ctg cgc ctg gcc gcg ccg gcc gag gag atc gcc ttc aag ccg      1152
Pro Thr Leu Arg Leu Ala Ala Pro Ala Glu Glu Ile Ala Phe Lys Pro
    370                 375                 380 ggc gac acg atc cag ggg atg ctg gaa ctc ccc gtg act tgg taa          1197
Gly Asp Thr Ile Gln Gly Met Leu Glu Leu Pro Val Thr Trp
385                 390                 395

<210> SEQ ID NO 235
<211> LENGTH: 1454
<212> TYPE: DNA
<213> ORGANISM: Streptomyces ornatus IFO 13069t
```

```
<220> FEATURE:
<221> NAME/KEY: CDS
<222> LOCATION: (1)..(1251)
<220> FEATURE:
<221> NAME/KEY: CDS
<222> LOCATION: (1257)..(1454)

<400> SEQUENCE: 235 atg acg gaa tcc acg acg gaa ccg gcc cgc cag gac ccc gct ccc acc     48
Met Thr Glu Ser Thr Thr Glu Pro Ala Arg Gln Asp Pro Ala Pro Thr
 1               5                  10                  15 gcc cct ccg acg caa ccg acc tcc acg aca ccc ttc ccc cag aac cgc     96
Ala Pro Pro Thr Gln Pro Thr Ser Thr Thr Pro Phe Pro Gln Asn Arg
             20                  25                  30 gac tgc ccc tac cac ccg ccc acc ggg tac caa ccc ctc cgc gcg gac    144
Asp Cys Pro Tyr His Pro Pro Thr Gly Tyr Gln Pro Leu Arg Ala Asp
         35                  40                  45 cgg ccg ctc agc cgg gtc acc ctc ttc gac ggg cgt ccg gtc tgg gcc    192
Arg Pro Leu Ser Arg Val Thr Leu Phe Asp Gly Arg Pro Val Trp Ala
 50                  55                  60 gtc acc ggc cac gcc ctg gcc cgc cgg cta ctg gcg gat ccg cgc ctg    240
Val Thr Gly His Ala Leu Ala Arg Arg Leu Leu Ala Asp Pro Arg Leu
 65                  70                  75                  80 tcc acc gat cgc acc cac ccc gac ttc ccc gtt ccg gcc gag cgg ttc    288
Ser Thr Asp Arg Thr His Pro Asp Phe Pro Val Pro Ala Glu Arg Phe
                 85                  90                  95 gcg aac gtc gag cgg cgg cgc gtg gcc ctg ctc ggc gtc gac gac ccc    336
Ala Asn Val Glu Arg Arg Arg Val Ala Leu Leu Gly Val Asp Asp Pro
            100                 105                 110 gag cac aac gcc cag cgc agg atg ctc atc ccg agc ttc tcc gtg aag    384
Glu His Asn Ala Gln Arg Arg Met Leu Ile Pro Ser Phe Ser Val Lys
        115                 120                 125 cgg ata gcc gcg ctg cgc ccc cgc atc cag gag acg gtg gac gga ctg    432
Arg Ile Ala Ala Leu Arg Pro Arg Ile Gln Glu Thr Val Asp Gly Leu
    130                 135                 140 ctg gac gcg atg gag cgg cag ggc ccg ccg tcc gaa ctg gtc gcc gac    480
Leu Asp Ala Met Glu Arg Gln Gly Pro Pro Ser Glu Leu Val Ala Asp
145                 150                 155                 160 ttc gcg ctg ccg gtg ccg tcg atg gtg atc tgc gcg ctc ctc ggt gtg    528
Phe Ala Leu Pro Val Pro Ser Met Val Ile Cys Ala Leu Leu Gly Val
                165                 170                 175 ccg tac gcc gac cac gag ttc ttc gag ggc tgc tcc cgg cgg ctc ctg    576
Pro Tyr Ala Asp His Glu Phe Phe Glu Gly Cys Ser Arg Arg Leu Leu
            180                 185                 190 cag ggc ccg ggc gcg gcc gat gtg aac gag gcc cgg atc gag ctg gag    624
Gln Gly Pro Gly Ala Ala Asp Val Asn Glu Ala Arg Ile Glu Leu Glu
        195                 200                 205 ggc tat ctg ggc gcc ctg atc gac cgc aag cgg gtg gag ccg ggg gag    672
Gly Tyr Leu Gly Ala Leu Ile Asp Arg Lys Arg Val Glu Pro Gly Glu
    210                 215                 220 ggg ctc ctg gac gaa ctg atc cac cgg gac cac ccc ggc gga ccc gtc    720
Gly Leu Leu Asp Glu Leu Ile His Arg Asp His Pro Gly Gly Pro Val
225                 230                 235                 240 gac cgc gag gac ctc gtc tcg ttc gcg gtg atc ctc ctc gtc gcg ggg    768
Asp Arg Glu Asp Leu Val Ser Phe Ala Val Ile Leu Leu Val Ala Gly
                245                 250                 255 cac gag acg acg gcg aac atg atc tcg ctc ggc acg ttc acg ctg ctg    816
His Glu Thr Thr Ala Asn Met Ile Ser Leu Gly Thr Phe Thr Leu Leu
            260                 265                 270 aac cac ccg gaa cag ctg gag gcg ctg cgg tcc ggg agc acg acg acg    864
Asn His Pro Glu Gln Leu Glu Ala Leu Arg Ser Gly Ser Thr Thr Thr
        275                 280                 285
```

```
gcc gcg gtg gtc gag gaa ctg ctg cgg ttc ctc tcc atc gcc gag gga      912
Ala Ala Val Val Glu Glu Leu Leu Arg Phe Leu Ser Ile Ala Glu Gly
        290                 295                 300 ctg caa cgg ctg gcc acc gag gac atc gag gtg gcc ggg acg acg atc      960
Leu Gln Arg Leu Ala Thr Glu Asp Ile Glu Val Ala Gly Thr Thr Ile
305                 310                 315                 320 cgc gag gga gag ggc gtg ttc ttc tcg acc tcg ctc atc aac cgc gac     1008
Arg Glu Gly Glu Gly Val Phe Phe Ser Thr Ser Leu Ile Asn Arg Asp
                325                 330                 335 acc gag gtc tac gag aat ccg gag acg ctc gac tgg gac cgg cct tcc     1056
Thr Glu Val Tyr Glu Asn Pro Glu Thr Leu Asp Trp Asp Arg Pro Ser
        340                 345                 350 cgg cac cac ctc gcc ttc ggc ttc ggc gtc cat cag tgc ctg ggc cag     1104
Arg His His Leu Ala Phe Gly Phe Gly Val His Gln Cys Leu Gly Gln
    355                 360                 365 aat ctg gcc cgc acc gag ctc gac atc gcc ctg cgc act ctc ttc gag     1152
Asn Leu Ala Arg Thr Glu Leu Asp Ile Ala Leu Arg Thr Leu Phe Glu
370                 375                 380 cgg ctg ccg gga ctc agg ctc gcc gtg ccc gcg cac gag atc cgg cac     1200
Arg Leu Pro Gly Leu Arg Leu Ala Val Pro Ala His Glu Ile Arg His
385                 390                 395                 400 aaa ccc ggg gac acg atc cag ggc ctt ctg cac ctg ccc gtg gcc tgg     1248
Lys Pro Gly Asp Thr Ile Gln Gly Leu Leu His Leu Pro Val Ala Trp
                405                 410                 415 tga gcggc atg ggc gtg cgg gtc gac agg gaa cgg tgc gtg ggg gcc ggc   1298
        Met Gly Val Arg Val Asp Arg Glu Arg Cys Val Gly Ala Gly
                420                 425                 430 atg tgc gcg ctg acc gcg ccc gac gtg ttc acg cag gac gac gac ggg     1346
Met Cys Ala Leu Thr Ala Pro Asp Val Phe Thr Gln Asp Asp Asp Gly
                435                 440                 445 ttc agc gag atg ctt ccc ggg agc acg gcg ggg acg ggg gac cac cca     1394
Phe Ser Glu Met Leu Pro Gly Ser Thr Ala Gly Thr Gly Asp His Pro
            450                 455                 460 cgg gtg cgg gag gcc gtt cgg gcc tgc ccg gtc ggg gcg gtg tcc ctg     1442
Arg Val Arg Glu Ala Val Arg Ala Cys Pro Val Gly Ala Val Ser Leu
            465                 470                 475 acc gac gac tga                                                      1454
Thr Asp Asp
480

<210> SEQ ID NO 236
<211> LENGTH: 1454
<212> TYPE: DNA
<213> ORGANISM: Streptomyces griseus ATCC 10137
<220> FEATURE:
<221> NAME/KEY: CDS
<222> LOCATION: (1)..(1251)
<220> FEATURE:
<221> NAME/KEY: CDS
<222> LOCATION: (1257)..(1454)

<400> SEQUENCE: 236 atg acg gaa tcc acg acg gaa ccg gcc cgc cag gac ccc gct ccc acc       48
Met Thr Glu Ser Thr Thr Glu Pro Ala Arg Gln Asp Pro Ala Pro Thr
1               5                   10                  15 gcc cct ccg acg caa ccg acc tcc acg aca ccc ttc ccc cag aac cgc       96
Ala Pro Pro Thr Gln Pro Thr Ser Thr Thr Pro Phe Pro Gln Asn Arg
            20                  25                  30 gac tgc ccc tac cac ccg ccc acc ggg tac caa ccg ctc cgc gcg gac      144
Asp Cys Pro Tyr His Pro Pro Thr Gly Tyr Gln Pro Leu Arg Ala Asp
        35                  40                  45 cgg ccg ctc agc cgg gtc acc ctc ttc gac ggg cgt ccg gtc tgg gcc      192
```

```
                    -continued

Arg Pro Leu Ser Arg Val Thr Leu Phe Asp Gly Arg Pro Val Trp Ala
    50              55                  60 gtc acc ggc cac gcc ctg gcc cgc cgg cta ctg gcg gat ccg cgc ctg    240
Val Thr Gly His Ala Leu Ala Arg Arg Leu Leu Ala Asp Pro Arg Leu
65              70                  75                  80 tcc acc gat cgc acc cac ccc gac ttc ccc gtt ccg gcc gag cgg ttc    288
Ser Thr Asp Arg Thr His Pro Asp Phe Pro Val Pro Ala Glu Arg Phe
                85                  90                  95 gcg aac gtc gag cgg agg cga gtg gcc ctg ctc ggc gtc gac gac ccc    336
Ala Asn Val Glu Arg Arg Arg Val Ala Leu Leu Gly Val Asp Asp Pro
            100                 105                 110 gag cac aac gcc cag cgc agg atg ctc atc ccg agc ttc tcc gtg aag    384
Glu His Asn Ala Gln Arg Arg Met Leu Ile Pro Ser Phe Ser Val Lys
        115                 120                 125 cgg ata gcc gcg ctg cgc ccc cgc atc cag gag acg gtg gac gga ctg    432
Arg Ile Ala Ala Leu Arg Pro Arg Ile Gln Glu Thr Val Asp Gly Leu
    130                 135                 140 ctg gac gcg atg gag cgg cag ggc ccg ccg tcc gaa ctg gtc gcc gac    480
Leu Asp Ala Met Glu Arg Gln Gly Pro Pro Ser Glu Leu Val Ala Asp
145                 150                 155                 160 ttc gcg ctg ccg gtg ccg tcg atg gtg atc tgc gcg ctc ctc ggt gtg    528
Phe Ala Leu Pro Val Pro Ser Met Val Ile Cys Ala Leu Leu Gly Val
                165                 170                 175 ccg tac gcc gac cac gag ttc ttc gag ggc tgc tcc cgg cgg ctc ctg    576
Pro Tyr Ala Asp His Glu Phe Phe Glu Gly Cys Ser Arg Arg Leu Leu
            180                 185                 190 cag ggc ccg ggc gcg gcc gat gtg aac gag gcc cgg atc gag ctg gag    624
Gln Gly Pro Gly Ala Ala Asp Val Asn Glu Ala Arg Ile Glu Leu Glu
        195                 200                 205 ggc tat ctg ggc gcc ctg atc gac cgc aag cgg gtg gag ccg ggg gag    672
Gly Tyr Leu Gly Ala Leu Ile Asp Arg Lys Arg Val Glu Pro Gly Glu
    210                 215                 220 ggg ctc ctg gac gaa ctg atc cac cgg gac cac ccc ggc gga ccc gtc    720
Gly Leu Leu Asp Glu Leu Ile His Arg Asp His Pro Gly Gly Pro Val
225                 230                 235                 240 gac cgc gag gac ctc gtc tcg ttc gcg gtg atc ctc ctc gtc gcg ggg    768
Asp Arg Glu Asp Leu Val Ser Phe Ala Val Ile Leu Leu Val Ala Gly
                245                 250                 255 cac gag acg acg gcg aac atg atc tcg ctc ggc acg ttc acg ctg ctg    816
His Glu Thr Thr Ala Asn Met Ile Ser Leu Gly Thr Phe Thr Leu Leu
            260                 265                 270 aac cac ccg gaa cag ctg gag gcg ctg cgc tcc ggg agg acg acg acg    864
Asn His Pro Glu Gln Leu Glu Ala Leu Arg Ser Gly Arg Thr Thr Thr
        275                 280                 285 gcc gcg gtg gtc gag gaa ctg ctg cgg ttc ctc tcc atc gcc gag gga    912
Ala Ala Val Val Glu Glu Leu Leu Arg Phe Leu Ser Ile Ala Glu Gly
    290                 295                 300 ctg caa cgg ctg gcc acc gag gac atc gag gtg gcc ggg acg acg atc    960
Leu Gln Arg Leu Ala Thr Glu Asp Ile Glu Val Ala Gly Thr Thr Ile
305                 310                 315                 320 cgc gag gga gag ggc gtg ttc ttc tcg acc tcg ctc atc aac cgc gac   1008
Arg Glu Gly Glu Gly Val Phe Phe Ser Thr Ser Leu Ile Asn Arg Asp
                325                 330                 335 acc gag gtc tac gag aat ccg gag acg ctc gac tgg gac cgg cct tcc   1056
Thr Glu Val Tyr Glu Asn Pro Glu Thr Leu Asp Trp Asp Arg Pro Ser
            340                 345                 350 cgg cac cac ctc gcc ttc ggc ttc ggc gtc cac cag tgc ctg ggc cag   1104
Arg His His Leu Ala Phe Gly Phe Gly Val His Gln Cys Leu Gly Gln
        355                 360                 365 aat ctg gcc cgc acc gag ctc gac atc gcc ctg cgc act ctc ttc gag   1152
```

```
Asn Leu Ala Arg Thr Glu Leu Asp Ile Ala Leu Arg Thr Leu Phe Glu
        370                 375                 380 cgg ctg ccg gga ctc agg ctc gcc gtg ccc gcg cac gag atc cgg cac      1200
Arg Leu Pro Gly Leu Arg Leu Ala Val Pro Ala His Glu Ile Arg His
385                 390                 395                 400 aaa ccc ggg gac acg atc cag ggc ctt ctg cac ctg ccc gtg gcc tgg      1248
Lys Pro Gly Asp Thr Ile Gln Gly Leu Leu His Leu Pro Val Ala Trp
                405                 410                 415 tga gcggc atg ggc gtg cgg gtc gac agg gaa cgg tgc gtg ggg gcc ggc    1298
        Met Gly Val Arg Val Asp Arg Glu Arg Cys Val Gly Ala Gly
                420                 425                 430 atg tgc gcg ctg acc gcg ccc gac gtg ttc acg cag gac gac gac ggg      1346
Met Cys Ala Leu Thr Ala Pro Asp Val Phe Thr Gln Asp Asp Asp Gly
                435                 440                 445 ttc agc gag atg ctt ccc ggg agc acg gcg ggg acg ggg gac cac cca      1394
Phe Ser Glu Met Leu Pro Gly Ser Thr Ala Gly Thr Gly Asp His Pro
                450                 455                 460 cgg gtg cgg gag gcc gtt cgg gcc tgc ccg gtc ggg gcg gtg tcc ctg      1442
Arg Val Arg Glu Ala Val Arg Ala Cys Pro Val Gly Ala Val Ser Leu
                465                 470                 475 acc gac gac tga                                                       1454
Thr Asp Asp
    480

<210> SEQ ID NO 237
<211> LENGTH: 1449
<212> TYPE: DNA
<213> ORGANISM: Streptomyces achromogenes IFO 12735
<220> FEATURE:
<221> NAME/KEY: CDS
<222> LOCATION: (1)..(1230)
<220> FEATURE:
<221> NAME/KEY: CDS
<222> LOCATION: (1243)..(1449)

<400> SEQUENCE: 237 atg acg gaa ctg acg gac atc acc ggc ccg gct gcc gag gcc gaa ccc        48
Met Thr Glu Leu Thr Asp Ile Thr Gly Pro Ala Ala Glu Ala Glu Pro
1               5                   10                  15 gtc gcc ttc ccc cag gac cgc acc tgt ccc tac cac ccc ccc acc gga        96
Val Ala Phe Pro Gln Asp Arg Thr Cys Pro Tyr His Pro Pro Thr Gly
            20                  25                  30 tac gac ccg ctg cgc gac ggg cga ccc ctg tcc cgc gtc acc ctc tac       144
Tyr Asp Pro Leu Arg Asp Gly Arg Pro Leu Ser Arg Val Thr Leu Tyr
        35                  40                  45 gac ggc cgc gag gcc tgg ctg gtc acc ggc cag gcc acc gcc cgc gcc       192
Asp Gly Arg Glu Ala Trp Leu Val Thr Gly Gln Ala Thr Ala Arg Ala
    50                  55                  60 ctc ctc gcc gac ccg cgg ctg tcc acc gac cgc cgc cgc gac ggc ttc       240
Leu Leu Ala Asp Pro Arg Leu Ser Thr Asp Arg Arg Arg Asp Gly Phe
65                  70                  75                  80 ccc gtg ccc acc ccc cgc ttc gag gcc ggc cgc gac cgc aag gtg gcc       288
Pro Val Pro Thr Pro Arg Phe Glu Ala Gly Arg Asp Arg Lys Val Ala
                85                  90                  95 ctg ctc ggg gtg gac gat ccc gag cac cac cag cag cgc cgg atg ctg       336
Leu Leu Gly Val Asp Asp Pro Glu His His Gln Gln Arg Arg Met Leu
            100                 105                 110 atc ccg tcg ttc acc ctc aaa cgc gcc acc gcg ctg cgc ccc tgg atc       384
Ile Pro Ser Phe Thr Leu Lys Arg Ala Thr Ala Leu Arg Pro Trp Ile
        115                 120                 125 cag cgg atc gtg gac gaa ctg ctg gac gcg atg atc gag cgg ggg ccg       432
Gln Arg Ile Val Asp Glu Leu Leu Asp Ala Met Ile Glu Arg Gly Pro
    130                 135                 140
```

| | | | | | | | | | | | | | | | | |
|---|---|---|---|---|---|---|---|---|---|---|---|---|---|---|---|---|
| ggg | gcc | gaa | ctg | gtc | tcc | gcc | ttc | gcg | ctg | ccc | gtg | ccg | tcc | atg | gtc | 480 |
| Gly | Ala | Glu | Leu | Val | Ser | Ala | Phe | Ala | Leu | Pro | Val | Pro | Ser | Met | Val | |
| 145 | | | | 150 | | | | | 155 | | | | | 160 | | |
| atc | tgc | ggc | ctg | ctc | ggc | gtg | ccc | tac | gcc | gac | cac | gag | ttc | ttc | gag | 528 |
| Ile | Cys | Gly | Leu | Leu | Gly | Val | Pro | Tyr | Ala | Asp | His | Glu | Phe | Phe | Glu | |
| | | | | 165 | | | | | 170 | | | | | 175 | | |
| gag | cag | tcc | cgc | cgg | ctg | ctg | cgc | ggg | ccg | acc | agc | gcc | gac | acc | ctg | 576 |
| Glu | Gln | Ser | Arg | Arg | Leu | Leu | Arg | Gly | Pro | Thr | Ser | Ala | Asp | Thr | Leu | |
| | | | 180 | | | | | 185 | | | | | 190 | | | |
| gac | gcc | cgg | gac | cgg | ctg | gag | cgg | ttc | ctc | ggc | gac | ctg | atc | gac | gcc | 624 |
| Asp | Ala | Arg | Asp | Arg | Leu | Glu | Arg | Phe | Leu | Gly | Asp | Leu | Ile | Asp | Ala | |
| | | 195 | | | | | 200 | | | | | 205 | | | | |
| aag | gcc | aag | gag | gcc | gag | ccc | ggc | gac | ggc | att | ctg | gac | gac | ctc | gtc | 672 |
| Lys | Ala | Lys | Glu | Ala | Glu | Pro | Gly | Asp | Gly | Ile | Leu | Asp | Asp | Leu | Val | |
| 210 | | | | | 215 | | | | | 220 | | | | | | |
| cac | cac | cgg | ctc | cgc | gag | ggc | gaa | ctg | gac | cgg | ggt | gac | ctg | gtg | tcg | 720 |
| His | His | Arg | Leu | Arg | Glu | Gly | Glu | Leu | Asp | Arg | Gly | Asp | Leu | Val | Ser | |
| 225 | | | | | 230 | | | | | 235 | | | | | 240 | |
| ctc | gcc | gtg | atc | ctg | ttg | gtc | gcc | ggg | cac | gag | acg | acc | gcc | aac | atg | 768 |
| Leu | Ala | Val | Ile | Leu | Leu | Val | Ala | Gly | His | Glu | Thr | Thr | Ala | Asn | Met | |
| | | | | 245 | | | | | 250 | | | | | 255 | | |
| atc | tcc | ctg | ggc | acc | tac | acc | ctg | ctc | cag | cac | ccc | gac | cgg | ctg | gcc | 816 |
| Ile | Ser | Leu | Gly | Thr | Tyr | Thr | Leu | Leu | Gln | His | Pro | Asp | Arg | Leu | Ala | |
| | | | | 260 | | | | | 265 | | | | | 270 | | |
| gag | ctg | cgg | gcc | gac | ccc | gcg | ctg | ctg | ccc | gcc | gtc | gtc | gag | gaa | ctg | 864 |
| Glu | Leu | Arg | Ala | Asp | Pro | Ala | Leu | Leu | Pro | Ala | Val | Val | Glu | Glu | Leu | |
| | | 275 | | | | | 280 | | | | | 285 | | | | |
| atg | cgg | atg | ctg | tcc | atc | gcc | gag | ggg | ctg | caa | cgg | gtg | gcg | ctg | gag | 912 |
| Met | Arg | Met | Leu | Ser | Ile | Ala | Glu | Gly | Leu | Gln | Arg | Val | Ala | Leu | Glu | |
| | 290 | | | | | 295 | | | | | 300 | | | | | |
| gac | gtc | gag | atc | gcc | ggc | acc | acc | atc | cgg | gcc | ggc | gac | ggc | gtc | ctg | 960 |
| Asp | Val | Glu | Ile | Ala | Gly | Thr | Thr | Ile | Arg | Ala | Gly | Asp | Gly | Val | Leu | |
| 305 | | | | | 310 | | | | | 315 | | | | | 320 | |
| ttc | tcc | acc | tcg | gtc | atc | aac | cgg | gac | acg | gcc | gtc | tac | gac | gac | ccc | 1008 |
| Phe | Ser | Thr | Ser | Val | Ile | Asn | Arg | Asp | Thr | Ala | Val | Tyr | Asp | Asp | Pro | |
| | | | | 325 | | | | | 330 | | | | | 335 | | |
| gac | gcg | ctg | gac | ttc | cac | cgc | gcc | gac | cgg | cac | cac | gtg | gcg | ttc | ggc | 1056 |
| Asp | Ala | Leu | Asp | Phe | His | Arg | Ala | Asp | Arg | His | His | Val | Ala | Phe | Gly | |
| | | | | 340 | | | | | 345 | | | | | 350 | | |
| ttc | ggc | atc | cac | cag | tgc | ctg | ggc | cag | aac | ctg | gcg | cgc | gcg | gag | ctg | 1104 |
| Phe | Gly | Ile | His | Gln | Cys | Leu | Gly | Gln | Asn | Leu | Ala | Arg | Ala | Glu | Leu | |
| | | 355 | | | | | 360 | | | | | 365 | | | | |
| gag | atc | gcc | ctc | ggc | agc | ctg | ttc | acc | cgg | ttg | ccc | ggg | ctg | cgg | ctc | 1152 |
| Glu | Ile | Ala | Leu | Gly | Ser | Leu | Phe | Thr | Arg | Leu | Pro | Gly | Leu | Arg | Leu | |
| | 370 | | | | | 375 | | | | | 380 | | | | | |
| gcc | gct | ccg | gcc | gag | gag | atc | ccc | ttc | aaa | ccg | ggc | gac | acg | atc | cag | 1200 |
| Ala | Ala | Pro | Ala | Glu | Glu | Ile | Pro | Phe | Lys | Pro | Gly | Asp | Thr | Ile | Gln | |
| 385 | | | | | 390 | | | | | 395 | | | | | 400 | |
| ggg | atg | ctg | gaa | ctc | ccc | gtg | acc | tgg | taa | gaggcttcgc | | tc | atg | cac | atg | 1251 |
| Gly | Met | Leu | Glu | Leu | Pro | Val | Thr | Trp | | | | | Met | His | Met | |
| | | | | 405 | | | | | 410 | | | | | | | |
| gac | atc | gac | atc | gac | cag | gac | gtc | tgt | atc | ggc | gcc | ggg | cag | tgc | gcg | 1299 |
| Asp | Ile | Asp | Ile | Asp | Gln | Asp | Val | Cys | Ile | Gly | Ala | Gly | Gln | Cys | Ala | |
| | | | 415 | | | | | 420 | | | | | 425 | | | |
| ctg | gcg | gca | ccg | ggc | gtc | ttc | acc | cag | gac | gac | gac | ggc | tac | agc | acc | 1347 |
| Leu | Ala | Ala | Pro | Gly | Val | Phe | Thr | Gln | Asp | Asp | Asp | Gly | Tyr | Ser | Thr | |
| | | 430 | | | | | 435 | | | | | 440 | | | | |
| ctg | ctg | ccc | ggc | cgg | gag | aac | ggc | gtc | acc | gac | ccg | atg | gtc | cgg | gag | 1395 |
| Leu | Leu | Pro | Gly | Arg | Glu | Asn | Gly | Val | Thr | Asp | Pro | Met | Val | Arg | Glu | |
| 445 | | | | | 450 | | | | | 455 | | | | | 460 | |

-continued

```
gcc gcc cgc gcc tgc ccg gtc agc gcc atc acc gta cga gag cgc acc      1443
Ala Ala Arg Ala Cys Pro Val Ser Ala Ile Thr Val Arg Glu Arg Thr
            465                 470                 475 gcc tga                                                              1449
Ala

<210> SEQ ID NO 238
<211> LENGTH: 1454
<212> TYPE: DNA
<213> ORGANISM: Streptomyces griseus IFO 13849T
<220> FEATURE:
<221> NAME/KEY: CDS
<222> LOCATION: (1)..(1251)
<220> FEATURE:
<221> NAME/KEY: CDS
<222> LOCATION: (1299)..(1454)

<400> SEQUENCE: 238 atg acg gaa tcc acg acg gaa ccg gcc cgc cag gac gcc gcc ctc acc       48
Met Thr Glu Ser Thr Thr Glu Pro Ala Arg Gln Asp Ala Ala Leu Thr
  1               5                  10                  15 ggc gcc acc acc gaa ccg acc tcc gcc cca ccg ttc ccg cag gac cgc       96
Gly Ala Thr Thr Glu Pro Thr Ser Ala Pro Pro Phe Pro Gln Asp Arg
                 20                  25                  30 gag tgc ccc tac cac ccg gcc acc ggg tac gaa ccg ctg cgc gcg gac      144
Glu Cys Pro Tyr His Pro Pro Thr Gly Tyr Glu Pro Leu Arg Ala Asp
             35                  40                  45 cgg ccg ttg agc cgg gtc acg ctc tac gac gga cgc ccg gtc tgg gcc      192
Arg Pro Leu Ser Arg Val Thr Leu Tyr Asp Gly Arg Pro Val Trp Ala
         50                  55                  60 gtc acc gga cac gcc ctg gcc cgc cgc ctc ctg gcc gac ccc cga ctc      240
Val Thr Gly His Ala Leu Ala Arg Arg Leu Leu Ala Asp Pro Arg Leu
 65                  70                  75                  80 tcc acc gac cgc acc cac ccc gcc ttc ccc gtc ccg gcc gag cgg ttc      288
Ser Thr Asp Arg Thr His Pro Ala Phe Pro Val Pro Ala Glu Arg Phe
                 85                  90                  95 gcg cag acc cgg cag cgg cgc gtg gcc ctg ctc ggc gtc gac gac ccc      336
Ala Gln Thr Arg Gln Arg Arg Val Ala Leu Leu Gly Val Asp Asp Pro
            100                 105                 110 gag cac aac acc cag cgc agg atg ctc atc ccg agc ttc tcc gtg aaa      384
Glu His Asn Thr Gln Arg Arg Met Leu Ile Pro Ser Phe Ser Val Lys
        115                 120                 125 cgg atc gcc gcg ctg cgc ccc cgt atc cag gag acg gtg gac cgg ctg      432
Arg Ile Ala Ala Leu Arg Pro Arg Ile Gln Glu Thr Val Asp Arg Leu
    130                 135                 140 ctg gac gcc atg gag cgg cag ggg ccg ccg tcc gaa ctg gtc gcc gac      480
Leu Asp Ala Met Glu Arg Gln Gly Pro Pro Ser Glu Leu Val Ala Asp
145                 150                 155                 160 ttc gcg ctg ccg gtg ccg tcc atg gtg atc tgc gcc ctc ctc ggc gtg      528
Phe Ala Leu Pro Val Pro Ser Met Val Ile Cys Ala Leu Leu Gly Val
                165                 170                 175 ccc tac gcc gac cac gcg ctc ttc gag ggc tgt tcg cgc cgg ctc ctg      576
Pro Tyr Ala Asp His Ala Leu Phe Glu Gly Cys Ser Arg Arg Leu Leu
            180                 185                 190 cgc ggt ccg ggc gcg gac gac gtg gac gcg gcc cgc gtc gaa ctg gag      624
Arg Gly Pro Gly Ala Asp Asp Val Asp Ala Ala Arg Val Glu Leu Glu
        195                 200                 205 gag tac ctc ggc gcg ttg atc gac cgc aaa cgc gcc gat ccg ggg gag      672
Glu Tyr Leu Gly Ala Leu Ile Asp Arg Lys Arg Ala Asp Pro Gly Glu
    210                 215                 220 ggg ctg ctg gac gag ctg atc cac cgg gac cgt ccg gac gga ccc gtg      720
Gly Leu Leu Asp Glu Leu Ile His Arg Asp Arg Pro Asp Gly Pro Val
```

|   |   |
|---|---|
| agc cgg gag gac ctc gtc tcc ttc gcc ctg atc ctg ctc gtc gcc gga<br>Ser Arg Glu Asp Leu Val Ser Phe Ala Leu Ile Leu Leu Val Ala Gly<br>245 250 255 | 768 |
| cac gag acg acc gcg aac atg atc tcg ctc ggc acg ttc acc ctg ctg<br>His Glu Thr Thr Ala Asn Met Ile Ser Leu Gly Thr Phe Thr Leu Leu<br>260 265 270 | 816 |
| cgc cac ccc ggt caa ctg gcg gcg ctg cgc tcg ggg gag acc acg acg<br>Arg His Pro Gly Gln Leu Ala Ala Leu Arg Ser Gly Glu Thr Thr Thr<br>275 280 285 | 864 |
| gcc gtc gtg gtc gag gag ttg ctg cgc ttc ctc tcc atc gcc gag ggg<br>Ala Val Val Val Glu Glu Leu Leu Arg Phe Leu Ser Ile Ala Glu Gly<br>290 295 300 | 912 |
| ctg caa cgc ctc gcg atc gag gac atc gag gtg gac ggg acg acg atc<br>Leu Gln Arg Leu Ala Ile Glu Asp Ile Glu Val Asp Gly Thr Thr Ile<br>305 310 315 320 | 960 |
| cgc gag ggg gag ggc gtc ttc ttc tcc acc tcg ctc gtc aac cgc gac<br>Arg Glu Gly Glu Gly Val Phe Phe Ser Thr Ser Leu Val Asn Arg Asp<br>325 330 335 | 1008 |
| gcc gac gtg ttc gcg gac ccg gag acc ctg gac tgg gag cgg tcc gcc<br>Ala Asp Val Phe Ala Asp Pro Glu Thr Leu Asp Trp Glu Arg Ser Ala<br>340 345 350 | 1056 |
| cgg cac cac ctc gcg ttc ggc ttc ggc gtc cac cag tgc ctg gga cag<br>Arg His His Leu Ala Phe Gly Phe Gly Val His Gln Cys Leu Gly Gln<br>355 360 365 | 1104 |
| aac ctg gcc cgc gcc gaa ctc gac atc gcg ctc cgc acg ctc ttc gaa<br>Asn Leu Ala Arg Ala Glu Leu Asp Ile Ala Leu Arg Thr Leu Phe Glu<br>370 375 380 | 1152 |
| cgg ctg ccc gcg ctc agg ctc gcc gta ccg gcg gac gag gtg agg cac<br>Arg Leu Pro Ala Leu Arg Leu Ala Val Pro Ala Asp Glu Val Arg His<br>385 390 395 400 | 1200 |
| aag ccc ggc gac acc atc cag ggc ctg ctc gaa ctg ccc gtg gcc tgg<br>Lys Pro Gly Asp Thr Ile Gln Gly Leu Leu Glu Leu Pro Val Ala Trp<br>405 410 415 | 1248 |
| tga gcggcgtgga cgtccaggta acagggaac gctgcgtggg agccggc atg tgc<br>Met Cys | 1304 |
| gcg ctg acc gcg ccg gag gtg ttc aca cag gac gac gac ggt ttc agc<br>Ala Leu Thr Ala Pro Glu Val Phe Thr Gln Asp Asp Asp Gly Phe Ser<br>420 425 430 | 1352 |
| gag gtg cgt ccc ggt ggc acg gcc gcc act gct ggc cac ccg ctg gta<br>Glu Val Arg Pro Gly Gly Thr Ala Ala Thr Ala Gly His Pro Leu Val<br>435 440 445 450 | 1400 |
| cgc gat gcc gca cgg gcc tgc ccg gtc ggg gcg gtg acc ctg acc gac<br>Arg Asp Ala Ala Arg Ala Cys Pro Val Gly Ala Val Thr Leu Thr Asp<br>455 460 465 | 1448 |
| gac tga<br>Asp | 1454 |

```
<210> SEQ ID NO 239
<211> LENGTH: 1461
<212> TYPE: DNA
<213> ORGANISM: Streptomyces lanatus IFO 12787T
<220> FEATURE:
<221> NAME/KEY: CDS
<222> LOCATION: (1)..(1218)
<220> FEATURE:
<221> NAME/KEY: CDS
<222> LOCATION: (1231)..(1461)

<400> SEQUENCE: 239
```

|   |   |
|---|---|
| atg acg gac atg acc gat atg acg cga ccc ccc acc gtc gcc ttc ccc<br>Met Thr Asp Met Thr Asp Met Thr Arg Pro Pro Thr Val Ala Phe Pro | 48 |

```
         1               5                  10                  15
cag aac cgc acc tgc ccc tac cac cca ccc acc gcc tac gac ccg ctc      96
Gln Asn Arg Thr Cys Pro Tyr His Pro Pro Thr Ala Tyr Asp Pro Leu
                 20                  25                  30 cgc gac acc cgc ccc ctg gcg cgc atc acc ctc tac gac ggc cgc ccg     144
Arg Asp Thr Arg Pro Leu Ala Arg Ile Thr Leu Tyr Asp Gly Arg Pro
             35                  40                  45 gtc tgg ctg gtc acc ggg cac gcc ctc gcc cgc acc ctg ctc gcc gac     192
Val Trp Leu Val Thr Gly His Ala Leu Ala Arg Thr Leu Leu Ala Asp
         50                  55                  60 cct cgg ctg tcc tcc gac cgc ggc cgg ccc ggc ttc ccc gcg ccc aac     240
Pro Arg Leu Ser Ser Asp Arg Gly Arg Pro Gly Phe Pro Ala Pro Asn
65                  70                  75                  80 gag cgg ttc gcg gcg gta cgc gac cgc aag tcc gcg ctg ctc ggc gtc     288
Glu Arg Phe Ala Ala Val Arg Asp Arg Lys Ser Ala Leu Leu Gly Val
                 85                  90                  95 gac gac ccc gaa cac cgg gtc cag cga cgg atg atg gtc ccc agc ttc     336
Asp Asp Pro Glu His Arg Val Gln Arg Arg Met Met Val Pro Ser Phe
            100                 105                 110 act ctc cgc cga gcc gcc gaa ctg cgc ccg cag atc cag cgg atc gtg     384
Thr Leu Arg Arg Ala Ala Glu Leu Arg Pro Gln Ile Gln Arg Ile Val
            115                 120                 125 gac gaa cgg ctc gac gcg atg atc gac cag ggg gcg ccc gcc gag ctg     432
Asp Glu Arg Leu Asp Ala Met Ile Asp Gln Gly Ala Pro Ala Glu Leu
        130                 135                 140 gtg aac gcc ttc gcg ctg ccc gtg ccc tcg atg gtc atc tgc gcc ctg     480
Val Asn Ala Phe Ala Leu Pro Val Pro Ser Met Val Ile Cys Ala Leu
145                 150                 155                 160 ctg ggc gtg ccc tat gcc gac cac gac ttc ttc gag ggg gag tcc cgg     528
Leu Gly Val Pro Tyr Ala Asp His Asp Phe Phe Glu Gly Glu Ser Arg
                165                 170                 175 cgc ctg ctg cgc ggt gcc acg gcg gcc gag gcc atg gac gcc cgg gac     576
Arg Leu Leu Arg Gly Ala Thr Ala Ala Glu Ala Met Asp Ala Arg Asp
            180                 185                 190 cgg ctg gag aac tac ttc atc gag ctg atc gac cgc aag cag aag gac     624
Arg Leu Glu Asn Tyr Phe Ile Glu Leu Ile Asp Arg Lys Gln Lys Asp
        195                 200                 205 ccg gag ccc ggc gac ggc gtc ctc gac gaa ctc gtc cac cgg cag ctg     672
Pro Glu Pro Gly Asp Gly Val Leu Asp Glu Leu Val His Arg Gln Leu
    210                 215                 220 cgc gac ggc gac ctc gac cgc gag gaa gtc gtc gcc ctc tcg acc atc     720
Arg Asp Gly Asp Leu Asp Arg Glu Glu Val Val Ala Leu Ser Thr Ile
225                 230                 235                 240 ctg ctg gtc gcc ggc cac gag acg acc gcc aac atg atc tcg ctg ggt     768
Leu Leu Val Ala Gly His Glu Thr Thr Ala Asn Met Ile Ser Leu Gly
                245                 250                 255 acc ttc aca ctg ctc caa cac ccg gag cag ctg gcc gag ttg cgc gcc     816
Thr Phe Thr Leu Leu Gln His Pro Glu Gln Leu Ala Glu Leu Arg Ala
            260                 265                 270 gac gcc ggg ttg ctg ccc gcc gcg gtc gag gag ctc atg cgg atg ctg     864
Asp Ala Gly Leu Leu Pro Ala Ala Val Glu Glu Leu Met Arg Met Leu
        275                 280                 285 tcg atc gcg gac ggg ctg ctg cgc gtc gcc tcc gag gac atc gag gcg     912
Ser Ile Ala Asp Gly Leu Leu Arg Val Ala Ser Glu Asp Ile Glu Ala
    290                 295                 300 ggc ggc gag acg atc cgg gcg ggc gac ggc gtg gtc ttc tcg acc tcg     960
Gly Gly Glu Thr Ile Arg Ala Gly Asp Gly Val Val Phe Ser Thr Ser
305                 310                 315                 320 gtc atc aac cgc gac gag tcc gtc tac ccc gac ccc gat gcc atc gac    1008
Val Ile Asn Arg Asp Glu Ser Val Tyr Pro Asp Pro Asp Ala Ile Asp
```

```
                    325                 330                 335
tgg cac cgc ccc acc cgc cac cac atc gcc ttc ggg ttc ggc atc cac      1056
Trp His Arg Pro Thr Arg His His Ile Ala Phe Gly Phe Gly Ile His
            340                 345                 350 cag tgc ctc ggc cag aac ctg gcc cgc gcc gag atg gag atc gcc ctg      1104
Gln Cys Leu Gly Gln Asn Leu Ala Arg Ala Glu Met Glu Ile Ala Leu
        355                 360                 365 cgc acc ctc ttc gag cgc ctg ccc acc ctg cgc ctt gcc gtc ccg gcg      1152
Arg Thr Leu Phe Glu Arg Leu Pro Thr Leu Arg Leu Ala Val Pro Ala
    370                 375                 380 ggg gaa atc ccc ttc aaa ccc ggc gac acg atc cag ggg atg ctg gaa      1200
Gly Glu Ile Pro Phe Lys Pro Gly Asp Thr Ile Gln Gly Met Leu Glu
385                 390                 395                 400 ctc ccc gtg acc tgg taa gaggctccgg tc atg cac aac gaa acg cac gaa   1251
Leu Pro Val Thr Trp            Met His Asn Glu Thr His Glu
            405                                      410 tca ggc cat atc cac atc gac atc gac cat gac gtc tgc gtc ggc gcc      1299
Ser Gly His Ile His Ile Asp Ile Asp His Asp Val Cys Val Gly Ala
            415                 420                 425 ggg cag tgc gcc ctc gcc gcc ccc tcc gtg ttc acc cag gac gac gac      1347
Gly Gln Cys Ala Leu Ala Ala Pro Ser Val Phe Thr Gln Asp Asp Asp
        430                 435                 440 ggc ttc agc acc ctg ctt ccc ggc cgc gag gac ggc ggc gac ccc          1395
Gly Phe Ser Thr Leu Leu Pro Gly Arg Glu Asp Gly Gly Asp Pro
445                 450                 455                 460 atg gtg cgg gag gcg gcc cgg gcg tgc ccg gtc agc gcc atc acc gtg      1443
Met Val Arg Glu Ala Ala Arg Ala Cys Pro Val Ser Ala Ile Thr Val
            465                 470                 475 tcc gaa ggg ggg agt tga                                               1461
Ser Glu Gly Gly Ser
            480

<210> SEQ ID NO 240
<211> LENGTH: 1458
<212> TYPE: DNA
<213> ORGANISM: Streptomyces misawanensis IFO 13855T
<220> FEATURE:
<221> NAME/KEY: CDS
<222> LOCATION: (1)..(1245)
<220> FEATURE:
<221> NAME/KEY: CDS
<222> LOCATION: (1258)..(1458)

<400> SEQUENCE: 240 atg aaa gaa ctg acg gac ctg acg gaa ccc atc tct ccc gcc ggc cag      48
Met Lys Glu Leu Thr Asp Leu Thr Glu Pro Ile Ser Pro Ala Gly Gln
1               5                   10                  15 gcc gac ccc gtg gcc tgg ccg cag gac cgc acg tgc ccc tac cac ccg      96
Ala Asp Pro Val Ala Trp Pro Gln Asp Arg Thr Cys Pro Tyr His Pro
            20                  25                  30 ccc acc ggc tac gac ccg ctc cgc gac ggc acc ccg ctg tcc cgc gtc      144
Pro Thr Gly Tyr Asp Pro Leu Arg Asp Gly Thr Pro Leu Ser Arg Val
        35                  40                  45 acc ctc tac gac ggc cgc acc gtc tgg gcg gtc acc ggc cac ggc acg      192
Thr Leu Tyr Asp Gly Arg Thr Val Trp Ala Val Thr Gly His Gly Thr
    50                  55                  60 gcc cgg gcg ctg ctc tcc gac ccc cgc ctc tcc agc gac cgc cgg cgc      240
Ala Arg Ala Leu Leu Ser Asp Pro Arg Leu Ser Ser Asp Arg Arg Arg
65                  70                  75                  80 gac gac ttc ccg atg ccg aac gcc cgg ttc gcg gcg gcc cgg gag cgc      288
Asp Asp Phe Pro Met Pro Asn Ala Arg Phe Ala Ala Ala Arg Glu Arg
            85                  90                  95
```

| | | |
|---|---|---|
| cga cag ctc gcc ctg ctg ggc ctc gac gac ccc gag cac cag atc cag<br>Arg Gln Leu Ala Leu Leu Gly Leu Asp Asp Pro Glu His Gln Ile Gln<br>100 105 110 | | 336 |
| cgc cgg atg ctg atc ccg gac ttc acc ctc aag cgg gcg acc gtg atg<br>Arg Arg Met Leu Ile Pro Asp Phe Thr Leu Lys Arg Ala Thr Val Met<br>115 120 125 | | 384 |
| cgg ccg gcc atc cag cgg atc gtc gac gat ctg ctc gac agg atg atc<br>Arg Pro Ala Ile Gln Arg Ile Val Asp Asp Leu Leu Asp Arg Met Ile<br>130 135 140 | | 432 |
| gcc gcg ggc ccg ccc gcc gac ctg gtg agc tcc ttc gcg ctg ccc gtg<br>Ala Ala Gly Pro Pro Ala Asp Leu Val Ser Ser Phe Ala Leu Pro Val<br>145 150 155 160 | | 480 |
| ccg tcc atg gtc atc tgt gac ctg ctc ggc gtg ccc tac gcc gac cac<br>Pro Ser Met Val Ile Cys Asp Leu Leu Gly Val Pro Tyr Ala Asp His<br>165 170 175 | | 528 |
| gag ttc ttc gag gcg cag tcc cgg cgg ctg ctg cgc ggt ccg gcg ccc<br>Glu Phe Phe Glu Ala Gln Ser Arg Arg Leu Leu Arg Gly Pro Ala Pro<br>180 185 190 | | 576 |
| gcc gac tcc ctg gac gcg cgc gac cag ctg gag gcc tat ctg ggc gac<br>Ala Asp Ser Leu Asp Ala Arg Asp Gln Leu Glu Ala Tyr Leu Gly Asp<br>195 200 205 | | 624 |
| ctg gcc gac cgc aag agc cgg gac gcg gtc ccc ggc gac ggc gtc ctc<br>Leu Ala Asp Arg Lys Ser Arg Asp Ala Val Pro Gly Asp Gly Val Leu<br>210 215 220 | | 672 |
| gac gac ctc gtc cac cag cgg ctg cgg gac ggc gcc ctg gac cgc gcc<br>Asp Asp Leu Val His Gln Arg Leu Arg Asp Gly Ala Leu Asp Arg Ala<br>225 230 235 240 | | 720 |
| gag gtc gtc gcg ctg gcc ctc atc ctg ctg gtc gcc ggc cac gag acc<br>Glu Val Val Ala Leu Ala Leu Ile Leu Leu Val Ala Gly His Glu Thr<br>245 250 255 | | 768 |
| acc gcc aac atg atc tcg ctc ggc acc ttc acc ctg ctc cag cag ccc<br>Thr Ala Asn Met Ile Ser Leu Gly Thr Phe Thr Leu Leu Gln Gln Pro<br>260 265 270 | | 816 |
| gaa cgg ctc gcc gaa ctg cgc gcc gac ccc gcg ctg gtg ccc gcc gcc<br>Glu Arg Leu Ala Glu Leu Arg Ala Asp Pro Ala Leu Val Pro Ala Ala<br>275 280 285 | | 864 |
| gtc gag gaa ctg atg cgg atg ctg tcc atc gcc gac ggg ctg ctg cgc<br>Val Glu Glu Leu Met Arg Met Leu Ser Ile Ala Asp Gly Leu Leu Arg<br>290 295 300 | | 912 |
| gtc gca ctg gag gac atc gag acg gac ggc ggc acc acc atc cgc aag<br>Val Ala Leu Glu Asp Ile Glu Thr Asp Gly Gly Thr Thr Ile Arg Lys<br>305 310 315 320 | | 960 |
| ggc gag ggc gtg ctc ttc gcg acc tcg gtc atc aac cgt gac gag tcc<br>Gly Glu Gly Val Leu Phe Ala Thr Ser Val Ile Asn Arg Asp Glu Ser<br>325 330 335 | | 1008 |
| gtg tac gac gac ccc gac gcc ctc gac tgg cac cgc ccg gcc cgc cac<br>Val Tyr Asp Asp Pro Asp Ala Leu Asp Trp His Arg Pro Ala Arg His<br>340 345 350 | | 1056 |
| cac gtg gcc ttc ggc ttc ggc atc cac cag tgc ctg ggc cag aac ctg<br>His Val Ala Phe Gly Phe Gly Ile His Gln Cys Leu Gly Gln Asn Leu<br>355 360 365 | | 1104 |
| gcc cgc acc gag ctg gag atc gcc ctg cgc acc ctg tgg gag cgg ctc<br>Ala Arg Thr Glu Leu Glu Ile Ala Leu Arg Thr Leu Trp Glu Arg Leu<br>370 375 380 | | 1152 |
| ccg gac ctg cgg ctc gcc gca ccg ccg gag gag att ccc ttc aaa ccc<br>Pro Asp Leu Arg Leu Ala Ala Pro Pro Glu Glu Ile Pro Phe Lys Pro<br>385 390 395 400 | | 1200 |
| ggc gac acg atc cag ggg atg ctg gaa ctc ccc gtg acc tgg taa<br>Gly Asp Thr Ile Gln Gly Met Leu Glu Leu Pro Val Thr Trp<br>405 410 | | 1245 |

-continued

```
gaggctcctg cc atg cac atc gag atc gac agt gac gtc tgc atc ggc gcg    1296
              Met His Ile Glu Ile Asp Ser Asp Val Cys Ile Gly Ala
              415                 420                 425 ggg cag tgt gcc ctg acc gcc ccc aac gtc ttc acc cag gac gac gac        1344
Gly Gln Cys Ala Leu Thr Ala Pro Asn Val Phe Thr Gln Asp Asp Asp
        430                 435                 440 ggt ttc agc acc ctg ctc ccc ggg atg gcg gac ggc ggc gac ccg            1392
Gly Phe Ser Thr Leu Leu Pro Gly Met Ala Asp Gly Gly Asp Pro
445                 450                 455 ctg gtc aag gag gcg gcc cgg gcc tgc ccg gtg cac gcc atc acg gtc        1440
Leu Val Lys Glu Ala Ala Arg Ala Cys Pro Val His Ala Ile Thr Val
460                 465                 470                 475 gag gaa ccg tcg ggt tag                                                 1458
Glu Glu Pro Ser Gly
                480

<210> SEQ ID NO 241
<211> LENGTH: 1448
<212> TYPE: DNA
<213> ORGANISM: Streptomyces pallidus IFO 13434T
<220> FEATURE:
<221> NAME/KEY: CDS
<222> LOCATION: (1)..(1230)
<220> FEATURE:
<221> NAME/KEY: CDS
<222> LOCATION: (1254)..(1448)

<400> SEQUENCE: 241 atg gcc gac acc ctc gcc ggc gcc acg ccc gac gcc gcc gcg acg gtc         48
Met Ala Asp Thr Leu Ala Gly Ala Thr Pro Asp Ala Ala Ala Thr Val
1               5                   10                  15 ccc gcg tac ccc atg gcc cgg gcc gcg ggc tgc ccc ttc gac ccg ccc         96
Pro Ala Tyr Pro Met Ala Arg Ala Ala Gly Cys Pro Phe Asp Pro Pro
                20                  25                  30 ccg gac ctc acc gcc cgg cag gac gag ggt cgg ctc gtc agg gtg cgc        144
Pro Asp Leu Thr Ala Arg Gln Asp Glu Gly Arg Leu Val Arg Val Arg
            35                  40                  45 ctc tgg gac ggc agt acg ccc tgg ctc gtg acc cgc tac gag gac cag        192
Leu Trp Asp Gly Ser Thr Pro Trp Leu Val Thr Arg Tyr Glu Asp Gln
        50                  55                  60 cgc gcc ctg ctc ctc gac ccc agg gtc agt gcc gac atc acc agg ccc        240
Arg Ala Leu Leu Leu Asp Pro Arg Val Ser Ala Asp Ile Thr Arg Pro
65                  70                  75                  80 gga tac ccc ctc cag gcc gcc ggc gcc ggc gag aac aac gcc agc ttc        288
Gly Tyr Pro Leu Gln Ala Ala Gly Ala Gly Glu Asn Asn Ala Ser Phe
                85                  90                  95 atc ctc atg gac gac ccg gag cac gca cgg ctg cgc cgc atg gtg acc        336
Ile Leu Met Asp Asp Pro Glu His Ala Arg Leu Arg Arg Met Val Thr
                100                 105                 110 gcg ccc ttc gcg atc aag cgc gtc gag gcg atg cgg ccg ggc gtg cag        384
Ala Pro Phe Ala Ile Lys Arg Val Glu Ala Met Arg Pro Gly Val Gln
            115                 120                 125 cag ctc gtg gac gac ctc atc gac ggc atg ctc gcc ggg ccc aag ccg        432
Gln Leu Val Asp Asp Leu Ile Asp Gly Met Leu Ala Gly Pro Lys Pro
        130                 135                 140 gtc gac ctg gtg gag gcg ttc gcg ctg ccg gtg ccc tcg ctg gtc atc        480
Val Asp Leu Val Glu Ala Phe Ala Leu Pro Val Pro Ser Leu Val Ile
145                 150                 155                 160 tgc cgg atg ctc gga gtg ccg tac gag gac cac gac ttc ttc cag gag        528
Cys Arg Met Leu Gly Val Pro Tyr Glu Asp His Asp Phe Phe Gln Glu
                165                 170                 175 aac agc cgg atc ctc atc aag cgg gac gcg gcc atg gag gac cgc atg        576
Asn Ser Arg Ile Leu Ile Lys Arg Asp Ala Ala Met Glu Asp Arg Met
```

```
                    180              185                 190
gcc gcg cac ggg cgg ctg atc gcc tac ctc gac gag ctg atg ggc gag        624
Ala Ala His Gly Arg Leu Ile Ala Tyr Leu Asp Glu Leu Met Gly Glu
        195                 200                 205 aag acg gcc cgt ccg gcg gac gat ctg ctc tcc ggg ctc gtc gag cgg        672
Lys Thr Ala Arg Pro Ala Asp Asp Leu Leu Ser Gly Leu Val Glu Arg
210                 215                 220 gtc agg acg ggg gag ctg acc cgg cgc gag tcg gcc cgc atg ggc gtg        720
Val Arg Thr Gly Glu Leu Thr Arg Arg Glu Ser Ala Arg Met Gly Val
225                 230                 235                 240 ctc ctg ctc atc gcc ggg cac gag acc acc gcc aac atg atc gcg ctc        768
Leu Leu Leu Ile Ala Gly His Glu Thr Thr Ala Asn Met Ile Ala Leu
                245                 250                 255 ggc acg ctc gcc ctg ctc gaa cac ccg gac cag ctc gcc ctg ctg cgt        816
Gly Thr Leu Ala Leu Leu Glu His Pro Asp Gln Leu Ala Leu Leu Arg
            260                 265                 270 gac acc gac gac ccg aag ctg gtc gcc gga gcg gcc gag gaa ctg ctg        864
Asp Thr Asp Asp Pro Lys Leu Val Ala Gly Ala Ala Glu Glu Leu Leu
        275                 280                 285 cgc tat ctg acc atc gtg cac aac gga cgc cgc ggc gcc ctc gcg        912
Arg Tyr Leu Thr Ile Val His Asn Gly Arg Arg Ala Ala Leu Ala
    290                 295                 300 gac atc gag atc ggc gga cag gtc atc cgg gcc ggc gag ggc atg atc        960
Asp Ile Glu Ile Gly Gly Gln Val Ile Arg Ala Gly Glu Gly Met Ile
305                 310                 315                 320 atg ccc aac gac ctc gcc aac cgg gac ccc ggc gcc ttc acc gac ccg       1008
Met Pro Asn Asp Leu Ala Asn Arg Asp Pro Gly Ala Phe Thr Asp Pro
                325                 330                 335 gac cgg ctg gac ctg cgc cgc gac gcc cgc cgg cac atc gcg ttc ggc       1056
Asp Arg Leu Asp Leu Arg Arg Asp Ala Arg Arg His Ile Ala Phe Gly
            340                 345                 350 ttc ggc gtg cac cag tgc ctg ggc cag ccg ctg gcc cgc atg gaa ctc       1104
Phe Gly Val His Gln Cys Leu Gly Gln Pro Leu Ala Arg Met Glu Leu
        355                 360                 365 cag gtc gtc tac ggc acc ctc tac cgc cgc atc ccc acg ctg cgg ctc       1152
Gln Val Val Tyr Gly Thr Leu Tyr Arg Arg Ile Pro Thr Leu Arg Leu
    370                 375                 380 gcc gcc ccg gtg gag agc ctg tcg ttc aag cac gac gga tcg gtc tac       1200
Ala Ala Pro Val Glu Ser Leu Ser Phe Lys His Asp Gly Ser Val Tyr
385                 390                 395                 400 ggc gtc tac gaa ctg ccc gtc acg tgg tga cgcgggaacc ggaggaggca acc     1253
Gly Val Tyr Glu Leu Pro Val Thr Trp
                405 atg cga gtg gaa ctg gac gag ccg aag tgc gtc gcg tcg ggg cag tgc       1301
Met Arg Val Glu Leu Asp Glu Pro Lys Cys Val Ala Ser Gly Gln Cys
410                 415                 420                 425 gtg atg gcc gcc ccc gag gtc ttc gac cag cgc gag gag gac ggc atc       1349
Val Met Ala Ala Pro Glu Val Phe Asp Gln Arg Glu Glu Asp Gly Ile
                430                 435                 440 gcc ttc gtg ctg gac gag cgg ccg gcg gcg gac gtc ctg gcg gag gtg       1397
Ala Phe Val Leu Asp Glu Arg Pro Ala Ala Asp Val Leu Ala Glu Val
            445                 450                 455 cgc gag gcc gtg gcg atc tgc ccc gcc gcc gcg atc cgg ctg gtg gag       1445
Arg Glu Ala Val Ala Ile Cys Pro Ala Ala Ala Ile Arg Leu Val Glu
        460                 465                 470 tga                                                                    1448

<210> SEQ ID NO 242
<211> LENGTH: 1411
<212> TYPE: DNA
```

```
<213> ORGANISM: Streptomyces roseorubens IFO 13682T
<220> FEATURE:
<221> NAME/KEY: CDS
<222> LOCATION: (1)..(1197)
<220> FEATURE:
<221> NAME/KEY: CDS
<222> LOCATION: (1211)..(1411)

<400> SEQUENCE: 242
```

| | | | | | | | | | | | | | | | | |
|---|---|---|---|---|---|---|---|---|---|---|---|---|---|---|---|---|
| atg | acg | gac | acg | acc | gca | ccc | gtc | gcc | ttc | ccc | cag | agc | agg | acc | tgc | 48 |
| Met | Thr | Asp | Thr | Thr | Ala | Pro | Val | Ala | Phe | Pro | Gln | Ser | Arg | Thr | Cys | |
| 1 | | | | 5 | | | | | 10 | | | | | 15 | | |
| ccc | tac | cac | ccg | ccc | gcc | gcc | tac | gag | ccg | ctg | cgc | gcc | gag | cgc | ccc | 96 |
| Pro | Tyr | His | Pro | Pro | Ala | Ala | Tyr | Glu | Pro | Leu | Arg | Ala | Glu | Arg | Pro | |
| | | | 20 | | | | | 25 | | | | | 30 | | | |
| ctg | acc | cgg | atc | acc | ctc | ttc | gac | ggc | cgt | gag | gcc | tgg | ctg | gtc | agc | 144 |
| Leu | Thr | Arg | Ile | Thr | Leu | Phe | Asp | Gly | Arg | Glu | Ala | Trp | Leu | Val | Ser | |
| | | 35 | | | | | 40 | | | | | 45 | | | | |
| ggc | cac | gcc | acc | gcc | cgc | gcc | ctg | ctc | gcc | gac | ccc | cgc | ctg | tcc | tcc | 192 |
| Gly | His | Ala | Thr | Ala | Arg | Ala | Leu | Leu | Ala | Asp | Pro | Arg | Leu | Ser | Ser | |
| | 50 | | | | | 55 | | | | | 60 | | | | | |
| gac | cgc | gac | cgc | ccc | ggc | ttc | ccc | acc | ccc | acc | gcg | cgc | ttc | gcc | ggc | 240 |
| Asp | Arg | Asp | Arg | Pro | Gly | Phe | Pro | Thr | Pro | Thr | Ala | Arg | Phe | Ala | Gly | |
| 65 | | | | | 70 | | | | | 75 | | | | | 80 | |
| atc | cgc | aac | cgc | cgt | acg | gcc | ctg | ctc | ggc | gtg | gac | gac | ccc | gag | cac | 288 |
| Ile | Arg | Asn | Arg | Arg | Thr | Ala | Leu | Leu | Gly | Val | Asp | Asp | Pro | Glu | His | |
| | | | | 85 | | | | | 90 | | | | | 95 | | |
| cgc | gcc | cag | cgg | cgg | atg | gtc | gtc | ggg | gac | ttc | acc | ctc | aaa | cgg | gcc | 336 |
| Arg | Ala | Gln | Arg | Arg | Met | Val | Val | Gly | Asp | Phe | Thr | Leu | Lys | Arg | Ala | |
| | | | 100 | | | | | 105 | | | | | 110 | | | |
| gcc | gca | ctg | cgg | ccc | cgc | atc | cag | cgg | atc | gtc | gac | gaa | cga | ctc | gac | 384 |
| Ala | Ala | Leu | Arg | Pro | Arg | Ile | Gln | Arg | Ile | Val | Asp | Glu | Arg | Leu | Asp | |
| | | 115 | | | | | 120 | | | | | 125 | | | | |
| gcg | atc | atc | gcc | cag | ggc | ccg | ccc | gcc | gac | ctg | gtg | agc | gcc | ttc | gcg | 432 |
| Ala | Met | Ile | Ala | Gln | Gly | Pro | Pro | Ala | Asp | Leu | Val | Ser | Ala | Phe | Ala | |
| | 130 | | | | | 135 | | | | | 140 | | | | | |
| ctg | ccc | gtg | ccc | tcc | atg | gtg | atc | tgc | gcc | ctg | ctc | ggc | gtc | ccc | tac | 480 |
| Leu | Pro | Val | Pro | Ser | Met | Val | Ile | Cys | Ala | Leu | Leu | Gly | Val | Pro | Tyr | |
| 145 | | | | | 150 | | | | | 155 | | | | | 160 | |
| gcc | gac | cac | gac | ttc | ttc | gag | gct | cag | tcg | cgg | cgc | ctg | ctg | cgc | ggc | 528 |
| Ala | Asp | His | Asp | Phe | Phe | Glu | Ala | Gln | Ser | Arg | Arg | Leu | Leu | Arg | Gly | |
| | | | | 165 | | | | | 170 | | | | | 175 | | |
| ccg | ggg | acc | gcc | gac | gtg | cag | gac | gcc | cgg | agc | agg | ctg | gag | gag | tac | 576 |
| Pro | Gly | Thr | Ala | Asp | Val | Gln | Asp | Ala | Arg | Ser | Arg | Leu | Glu | Glu | Tyr | |
| | | | 180 | | | | | 185 | | | | | 190 | | | |
| ttc | ggc | gag | ctg | atc | gac | cgc | aag | cgc | gag | gac | ccc | ggc | acc | ggc | ctc | 624 |
| Phe | Gly | Glu | Leu | Ile | Asp | Arg | Lys | Arg | Glu | Asp | Pro | Gly | Thr | Gly | Leu | |
| | | 195 | | | | | 200 | | | | | 205 | | | | |
| ctg | gac | gac | ctg | gtc | caa | cgg | cag | ccc | ggc | gac | ggc | gga | ccc | gac | cgc | 672 |
| Leu | Asp | Asp | Leu | Val | Gln | Arg | Gln | Pro | Gly | Asp | Gly | Gly | Pro | Asp | Arg | |
| | 210 | | | | | 215 | | | | | 220 | | | | | |
| gag | ggc | ctg | atc | gcc | atg | gcc | ctc | atc | ctg | ctg | gtc | gcc | ggc | cac | gag | 720 |
| Glu | Gly | Leu | Ile | Ala | Met | Ala | Leu | Ile | Leu | Leu | Val | Ala | Gly | His | Glu | |
| 225 | | | | | 230 | | | | | 235 | | | | | 240 | |
| acg | acc | gcc | aac | atg | atc | tcc | ctc | ggc | acc | ttc | acg | ctc | ctg | cag | cac | 768 |
| Thr | Thr | Ala | Asn | Met | Ile | Ser | Leu | Gly | Thr | Phe | Thr | Leu | Leu | Gln | His | |
| | | | | 245 | | | | | 250 | | | | | 255 | | |
| ccc | gag | cgg | ctc | gcc | gaa | ctg | cgc | gcc | gac | tcc | gag | gtc | atg | ccg | gcc | 816 |
| Pro | Glu | Arg | Leu | Ala | Glu | Leu | Arg | Ala | Asp | Ser | Glu | Val | Met | Pro | Ala | |
| | | | 260 | | | | | 265 | | | | | 270 | | | |
| gcg | gtc | gag | gaa | ctg | atg | cgg | ctg | ctg | tcc | atc | gcg | gac | ggc | ctg | ctg | 864 |
| Ala | Val | Glu | Glu | Leu | Met | Arg | Leu | Leu | Ser | Ile | Ala | Asp | Gly | Leu | Leu | |

```
                      275                  280                  285
cgc atc gcc gtc gag gac gtc gag gtg gcc ggg acg acg atc cgc gcc      912
Arg Ile Ala Val Glu Asp Val Glu Val Ala Gly Thr Thr Ile Arg Ala
    290                  295                  300 ggc gag ggc gtg gtg ttc gcg acg tcg gtc atc aac cgc gac gag acg      960
Gly Glu Gly Val Val Phe Ala Thr Ser Val Ile Asn Arg Asp Glu Thr
305                  310                  315                  320 gtc ttc gcc gag ccg gac acc ctc gac tgg agc cgc ccg gcc cgc cac     1008
Val Phe Ala Glu Pro Asp Thr Leu Asp Trp Ser Arg Pro Ala Arg His
                325                  330                  335 cac gtg gcg ttc ggc ttc ggc atc cac cag tgc ctc ggc caa aac ctc     1056
His Val Ala Phe Gly Phe Gly Ile His Gln Cys Leu Gly Gln Asn Leu
            340                  345                  350 gca cgc gcc gaa ctg gag atc gcc ctc ggc acc ctc ttc ggc cgg ctg     1104
Ala Arg Ala Glu Leu Glu Ile Ala Leu Gly Thr Leu Phe Gly Arg Leu
        355                  360                  365 ccc acg ctg cgc ctg gcc gcc ccg ccc gac gag atc ccc ttc aag ccg     1152
Pro Thr Leu Arg Leu Ala Ala Pro Pro Asp Glu Ile Pro Phe Lys Pro
    370                  375                  380 ggc gac acg atc cag ggg atg ctg gaa ctc ccc gtg acc tgg taa         1197
Gly Asp Thr Ile Gln Gly Met Leu Glu Leu Pro Val Thr Trp
385                  390                  395 gaggcttgcg ggc atg cgc atc gac atc gac aag gac gtc tgc atc ggc      1246
            Met Arg Ile Asp Ile Asp Lys Asp Val Cys Ile Gly
                400                  405                  410 gcg ggc cag tgc gcc ctg acc gcc ccg gac gtg ttc acc cag gac gac     1294
Ala Gly Gln Cys Ala Leu Thr Ala Pro Asp Val Phe Thr Gln Asp Asp
                415                  420                  425 gac ggc tac agc acc ctg ctg ccc ggc cgg gag gac ggc ggc ggc agc     1342
Asp Gly Tyr Ser Thr Leu Leu Pro Gly Arg Glu Asp Gly Gly Gly Ser
            430                  435                  440 ccg ctg ctg cgg gag gcg gcc cgg gcc tgc ccg gtg agc gcc atc acc     1390
Pro Leu Leu Arg Glu Ala Ala Arg Ala Cys Pro Val Ser Ala Ile Thr
        445                  450                  455 gtc tcg gag acc gtc ggc tga                                         1411
Val Ser Glu Thr Val Gly
    460

<210> SEQ ID NO 243
<211> LENGTH: 1466
<212> TYPE: DNA
<213> ORGANISM: Streptomyces rutgersensis IFO 15875T
<220> FEATURE:
<221> NAME/KEY: CDS
<222> LOCATION: (1)..(1245)
<220> FEATURE:
<221> NAME/KEY: CDS
<222> LOCATION: (1269)..(1466)

<400> SEQUENCE: 243 atg acc gaa acg ctg gca gag acc acg acc gag gcg gaa gag ccg ctt       48
Met Thr Glu Thr Leu Ala Glu Thr Thr Thr Glu Ala Glu Glu Pro Leu
1               5                   10                  15 ccg gag ttc ccg atg ccg cgg gcg aac ggc tgc ccc ttc gcc ccg ccc       96
Pro Glu Phe Pro Met Pro Arg Ala Asn Gly Cys Pro Phe Ala Pro Pro
            20                  25                  30 ccg acc gca cgg gcg ctg cac acc gaa cgg ccg gtc acg cgg gta cgg      144
Pro Thr Ala Arg Ala Leu His Thr Glu Arg Pro Val Thr Arg Val Arg
        35                  40                  45 ctg tgg gac ggc agc gcc ccc tgg ctg gtg acc cgg tac gcc gac cag      192
Leu Trp Asp Gly Ser Ala Pro Trp Leu Val Thr Arg Tyr Ala Asp Gln
    50                  55                  60
```

-continued

| | |
|---|---|
| cgc gcc ctg ctc ggc gac ccg cgg gtc agc tcc gag gcc acc cgg ccc<br>Arg Ala Leu Leu Gly Asp Pro Arg Val Ser Ser Glu Ala Thr Arg Pro<br>65                       70                   75                  80 | 240 |
| ggc ttt ccg cat gcg agc gcc ggc ttc cgc gag aat gcc agg cgg cgg<br>Gly Phe Pro His Ala Ser Ala Gly Phe Arg Glu Asn Ala Arg Arg Arg<br>                    85                   90                   95 | 288 |
| cgc tcc ttc atc acc atg gac gac ccc gag cac gcc cgg atc cgc cgg<br>Arg Ser Phe Ile Thr Met Asp Asp Pro Glu His Ala Arg Ile Arg Arg<br>                 100                 105               110 | 336 |
| atg gtc acc gcg ccg ttc gcc atc aag cgg gtc gag gcg atg cgg ccc<br>Met Val Thr Ala Pro Phe Ala Ile Lys Arg Val Glu Ala Met Arg Pro<br>        115                   120                 125 | 384 |
| gac atc cag aag atc acc gac gat ctg atc gac tcc atg ctg gcc ggg<br>Asp Ile Gln Lys Ile Thr Asp Asp Leu Ile Asp Ser Met Leu Ala Gly<br>130                 135                   140 | 432 |
| ccg acc ccg gtc gac ctg gtg cgc gcg ttg gcg ctg ccg ctg ccg tcg<br>Pro Thr Pro Val Asp Leu Val Arg Ala Leu Ala Leu Pro Leu Pro Ser<br>145                       150                 155                 160 | 480 |
| ctg gtg atc tgc cgg ctg ctc gga gtg ccg tac gag gac cac gac ttc<br>Leu Val Ile Cys Arg Leu Leu Gly Val Pro Tyr Glu Asp His Asp Phe<br>                 165                 170               175 | 528 |
| ttc cag cgc aac agc tcg ctc ctg atc aac cgt aac tcc acg acc gaa<br>Phe Gln Arg Asn Ser Ser Leu Leu Ile Asn Arg Asn Ser Thr Thr Glu<br>                   180                 185               190 | 576 |
| gag gtg gtc ggc gcc aac gag gcg ctg acc gac tat ctg gac gag ctg<br>Glu Val Val Gly Ala Asn Glu Ala Leu Thr Asp Tyr Leu Asp Glu Leu<br>                195                 200               205 | 624 |
| gtc agc gcc aaa ctc gcc aac ccc gcc gac gac atg ctc tcc gag ctg<br>Val Ser Ala Lys Leu Ala Asn Pro Ala Asp Asp Met Leu Ser Glu Leu<br>210                 215                   220 | 672 |
| gcc gcc cgg gtc acg gcc gga gag ctg acc cag cgc gag gcc gcc aat<br>Ala Ala Arg Val Thr Ala Gly Glu Leu Thr Gln Arg Glu Ala Ala Asn<br>225                       230                 235                 240 | 720 |
| atg ggc gtg ctg ctg ctg atc gcc ggc cat gag acc acc gcc aac atg<br>Met Gly Val Leu Leu Leu Ile Ala Gly His Glu Thr Thr Ala Asn Met<br>                 245                 250               255 | 768 |
| atc gcc ctc ggc acc gtc gcc ctg ctg gag aac ccc gac cag ctc gcc<br>Ile Ala Leu Gly Thr Val Ala Leu Leu Glu Asn Pro Asp Gln Leu Ala<br>                260                 265               270 | 816 |
| gtc ctg cgg gag acc gac gac ccg aag gcg gtc gcc aag gcc gtc gag<br>Val Leu Arg Glu Thr Asp Asp Pro Lys Ala Val Ala Lys Ala Val Glu<br>               275                 280               285 | 864 |
| gaa ctg ctg cgc tat ctg acc atc gtg cac acc ggc cgg cgc cgg gtc<br>Glu Leu Leu Arg Tyr Leu Thr Ile Val His Thr Gly Arg Arg Arg Val<br>290                 295                   300 | 912 |
| gcg cgg gag gac atc gag atc ggc ggc gag acc atc cgt gcc ggg gac<br>Ala Arg Glu Asp Ile Glu Ile Gly Gly Glu Thr Ile Arg Ala Gly Asp<br>305                       310                 315                 320 | 960 |
| ggg atc atc atc tac acc ggc acc ggc aac tgg gac gcg gag gtc ttc<br>Gly Ile Ile Ile Tyr Thr Gly Thr Gly Asn Trp Asp Ala Glu Val Phe<br>                325                 330               335 | 1008 |
| ccc gag ccc gag cgg ctg gac atc ggc cgc gac gcc cgc cgc cac atg<br>Pro Glu Pro Glu Arg Leu Asp Ile Gly Arg Asp Ala Arg Arg His Met<br>                 340                 345               350 | 1056 |
| gcg ttc ggt ttc ggc gtc cac cag tgc ctg ggc cag ccg ctg gcc cgg<br>Ala Phe Gly Phe Gly Val His Gln Cys Leu Gly Gln Pro Leu Ala Arg<br>                355                 360               365 | 1104 |
| gtg gag ctg cag gtg gtc tac ggc acg ctc tac cgc cgt atc ccc acg<br>Val Glu Leu Gln Val Val Tyr Gly Thr Leu Tyr Arg Arg Ile Pro Thr<br>370                 375                   380 | 1152 |

-continued

```
ctg cgg ctg gcg acc ggg gtc gac caa cta ccg ttc aag gac gac ggt      1200
Leu Arg Leu Ala Thr Gly Val Asp Gln Leu Pro Phe Lys Asp Asp Gly
385                 390                 395                 400 ttg gtc tac ggc gtc tat gaa ctg ccc gtc acc tgg acg tct tga          1245
Leu Val Tyr Gly Val Tyr Glu Leu Pro Val Thr Trp Thr Ser
            405                 410 gcaacggagg caagggagtc acc atg cgt gtg gaa gtc gat gtt ccc aag tgt    1298
                         Met Arg Val Glu Val Asp Val Pro Lys Cys
                         415                 420 gtg gca tcg ggt cag tgc gtg atg atc gca ccc gat gtg ttc gac cag      1346
Val Ala Ser Gly Gln Cys Val Met Ile Ala Pro Asp Val Phe Asp Gln
425                 430                 435                 440 cgg gag gag gac ggc atc gtg atc ctg ctg gac gag cag ccc gcg tcc      1394
Arg Glu Glu Asp Gly Ile Val Ile Leu Leu Asp Glu Gln Pro Ala Ser
            445                 450                 455 gaa ctc cac gcc gat gtg cgt gag tcc gcg gtg gtc tgc ccg gcg gcg      1442
Glu Leu His Ala Asp Val Arg Glu Ser Ala Val Val Cys Pro Ala Ala
460                 465                 470 gcg ata cgg gtg gtc gag aat tga                                      1466
Ala Ile Arg Val Val Glu Asn
            475

<210> SEQ ID NO 244
<211> LENGTH: 1411
<212> TYPE: DNA
<213> ORGANISM: Streptomyces steffisburgensis IFO 13446T
<220> FEATURE:
<221> NAME/KEY: CDS
<222> LOCATION: (1)..(1197)
<220> FEATURE:
<221> NAME/KEY: CDS
<222> LOCATION: (1211)..(1411)

<400> SEQUENCE: 244 atg tcg gac acg acc gca ccc gtg gcc ttc ccc cag agc cgg acc tgc      48
Met Ser Asp Thr Thr Ala Pro Val Ala Phe Pro Gln Ser Arg Thr Cys
1               5                   10                  15 ccc tac cac ccg ccc gcc gcc tac gag ccg ctg cgc gcc gag cgc ccc      96
Pro Tyr His Pro Pro Ala Ala Tyr Glu Pro Leu Arg Ala Glu Arg Pro
            20                  25                  30 ctg acc cgt atc acc ctc ttc gac ggc cgt gag gcc tgg ctg gtc agc      144
Leu Thr Arg Ile Thr Leu Phe Asp Gly Arg Glu Ala Trp Leu Val Ser
        35                  40                  45 ggc cac gcc acc gcc cgc gcg ctg ctc gcc gac ccg cgc ctg tcc tcc      192
Gly His Ala Thr Ala Arg Ala Leu Leu Ala Asp Pro Arg Leu Ser Ser
50                  55                  60 gac cgc gac cgc ccc ggc ttc ccc gcc ccc acc gcg cgc ttc gcc ggg      240
Asp Arg Asp Arg Pro Gly Phe Pro Ala Pro Thr Ala Arg Phe Ala Gly
65                  70                  75                  80 atc cgc aac cgc aga acg gcc ctg ctg ggc gtc gac gac ccc gag cac      288
Ile Arg Asn Arg Arg Thr Ala Leu Leu Gly Val Asp Asp Pro Glu His
            85                  90                  95 cga gtc cag cgg cgg atg gtg gcc ggg gac ttc acc ctc aaa cgg gcc      336
Arg Val Gln Arg Arg Met Val Ala Gly Asp Phe Thr Leu Lys Arg Ala
            100                 105                 110 gcc gga ctg cga ccc cgc atc cag cgg atc gtg gac cga cga ctc gac      384
Ala Gly Leu Arg Pro Arg Ile Gln Arg Ile Val Asp Arg Arg Leu Asp
        115                 120                 125 gcg atg atc gcc cag ggc cca ccg gcc gac ctg gtg agc agc ttc gcg      432
Ala Met Ile Ala Gln Gly Pro Pro Ala Asp Leu Val Ser Ser Phe Ala
130                 135                 140 ctg ccc gtc ccg tcc atg gtg atc tgt gcc ctg ctc ggc gtc ccg tac      480
Leu Pro Val Pro Ser Met Val Ile Cys Ala Leu Leu Gly Val Pro Tyr
```

```
                145                 150                 155                 160
gcc gac cac gac ttc ttc gag acc cag tca cgg cgg ctg ctg cgc ggc       528
Ala Asp His Asp Phe Phe Glu Thr Gln Ser Arg Arg Leu Leu Arg Gly
                    165                 170                 175 ccg cag acc gcc gac gtg atg gac gcc cgg gcc cgg ctg gac gag tac       576
Pro Gln Thr Ala Asp Val Met Asp Ala Arg Ala Arg Leu Asp Glu Tyr
            180                 185                 190 ttc ggc gaa ctg atc gac cgc aag cgg aag gaa ccc ggc gcc ggc ctg       624
Phe Gly Glu Leu Ile Asp Arg Lys Arg Lys Glu Pro Gly Ala Gly Leu
        195                 200                 205 ctg gac gac ctg gtc cag cga cag ctg cgc gac ggc gca ctc gac cgc       672
Leu Asp Asp Leu Val Gln Arg Gln Leu Arg Asp Gly Ala Leu Asp Arg
    210                 215                 220 gag ggc ctg atc gcc ctg gcg ctc atc ctg ctg gtc gcg ggc cac gag       720
Glu Gly Leu Ile Ala Leu Ala Leu Ile Leu Leu Val Ala Gly His Glu
225                 230                 235                 240 acg acc gcc aac atg atc tcg ctc ggc acc ttc acc ctg ctg cag cac       768
Thr Thr Ala Asn Met Ile Ser Leu Gly Thr Phe Thr Leu Leu Gln His
                    245                 250                 255 ccc gaa cgg ctc gcc gag ctg cgc gcc gac ccg cgg ctg ctg cct gcg       816
Pro Glu Arg Leu Ala Glu Leu Arg Ala Asp Pro Arg Leu Leu Pro Ala
            260                 265                 270 gcg gtc gag gag ctg atg cgc atg ctg tcc atc gcg gac ggt ctg ctc       864
Ala Val Glu Glu Leu Met Arg Met Leu Ser Ile Ala Asp Gly Leu Leu
        275                 280                 285 cgc ctc gcc gtc gag gac ata gag gtg gcc ggg acc acg atc cgc aag       912
Arg Leu Ala Val Glu Asp Ile Glu Val Ala Gly Thr Thr Ile Arg Lys
    290                 295                 300 ggg gac ggc gtg gtg ttc ctg acg tcc gtc atc aac cgc gac gag acg       960
Gly Asp Gly Val Val Phe Leu Thr Ser Val Ile Asn Arg Asp Glu Thr
305                 310                 315                 320 gtc tac ccc gag ccg gac acc ctc gac tgg cac cgc tcg gcc cgg cat      1008
Val Tyr Pro Glu Pro Asp Thr Leu Asp Trp His Arg Ser Ala Arg His
                    325                 330                 335 cac gtc gcg ttc ggc ttc ggc atc cac cag tgc ctc ggc cag aac ctc      1056
His Val Ala Phe Gly Phe Gly Ile His Gln Cys Leu Gly Gln Asn Leu
            340                 345                 350 gcg cgc gcc gag ctg gag atc gcc ctg tgg acc ctc ttc gac cgt ctg      1104
Ala Arg Ala Glu Leu Glu Ile Ala Leu Trp Thr Leu Phe Asp Arg Leu
        355                 360                 365 ccc acc ctg cgc ctg gcc gcg ccg gcc gag gag atc gcc ttc aag ccg      1152
Pro Thr Leu Arg Leu Ala Ala Pro Ala Glu Glu Ile Ala Phe Lys Pro
    370                 375                 380 ggc gac acg atc cag ggg atg ctg gaa ctc ccc gtg act tgg taa gaggc   1202
Gly Asp Thr Ile Gln Gly Met Leu Glu Leu Pro Val Thr Trp
385                 390                 395 ttcccccc atg cac atc gac atc gac aag gac gtc tgc atc ggc gcg ggc    1252
         Met His Ile Asp Ile Asp Lys Asp Val Cys Ile Gly Ala Gly
                    400                 405                 410 cag tgc gcc ctg acc gcc ccg gac gtg ttc acc cag gac gac gac ggc     1300
Gln Cys Ala Leu Thr Ala Pro Asp Val Phe Thr Gln Asp Asp Asp Gly
            415                 420                 425 atc agc gcc ctg ctg ccg gga cag gag gac ggc ggc agc ccg ctg         1348
Ile Ser Ala Leu Leu Pro Gly Gln Glu Asp Gly Gly Ser Pro Leu
        430                 435                 440 gtg cgg gag gcg gcc cgt gcc tgc ccg gtg agc gcc atc acc gtg tcg     1396
Val Arg Glu Ala Ala Arg Ala Cys Pro Val Ser Ala Ile Thr Val Ser
445                 450                 455                 460 gag acg gtg agc tga                                                 1411
Glu Thr Val Ser
```

<210> SEQ ID NO 245
<211> LENGTH: 65
<212> TYPE: PRT
<213> ORGANISM: Streptomyces ornatus IFO 13069t

<400> SEQUENCE: 245

Met Gly Val Arg Val Asp Arg Glu Arg Cys Val Gly Ala Gly Met Cys
1               5                   10                  15

Ala Leu Thr Ala Pro Asp Val Phe Thr Gln Asp Asp Gly Phe Ser
            20                  25                  30

Glu Met Leu Pro Gly Ser Thr Ala Gly Thr Gly Asp His Pro Arg Val
        35                  40                  45

Arg Glu Ala Val Arg Ala Cys Pro Val Gly Ala Val Ser Leu Thr Asp
    50                  55                  60

Asp
65

<210> SEQ ID NO 246
<211> LENGTH: 65
<212> TYPE: PRT
<213> ORGANISM: Streptomyces griseus ATCC 10137

<400> SEQUENCE: 246

Met Gly Val Arg Val Asp Arg Glu Arg Cys Val Gly Ala Gly Met Cys
1               5                   10                  15

Ala Leu Thr Ala Pro Asp Val Phe Thr Gln Asp Asp Gly Phe Ser
            20                  25                  30

Glu Met Leu Pro Gly Ser Thr Ala Gly Thr Gly Asp His Pro Arg Val
        35                  40                  45

Arg Glu Ala Val Arg Ala Cys Pro Val Gly Ala Val Ser Leu Thr Asp
    50                  55                  60

Asp
65

<210> SEQ ID NO 247
<211> LENGTH: 68
<212> TYPE: PRT
<213> ORGANISM: Streptomyces achromogenes IFO 12735

<400> SEQUENCE: 247

Met His Met Asp Ile Asp Ile Asp Gln Asp Val Cys Ile Gly Ala Gly
1               5                   10                  15

Gln Cys Ala Leu Ala Ala Pro Gly Val Phe Thr Gln Asp Asp Gly
            20                  25                  30

Tyr Ser Thr Leu Leu Pro Gly Arg Glu Asn Gly Val Thr Asp Pro Met
        35                  40                  45

Val Arg Glu Ala Ala Arg Ala Cys Pro Val Ser Ala Ile Thr Val Arg
    50                  55                  60

Glu Arg Thr Ala
65

<210> SEQ ID NO 248
<211> LENGTH: 51
<212> TYPE: PRT
<213> ORGANISM: Streptomyces griseus IFO 13849T

<400> SEQUENCE: 248

Met Cys Ala Leu Thr Ala Pro Glu Val Phe Thr Gln Asp Asp Gly

-continued

```
                1               5                  10                 15
Phe Ser Glu Val Arg Pro Gly Gly Thr Ala Ala Thr Ala Gly His Pro
                    20                  25                  30

Leu Val Arg Asp Ala Ala Arg Ala Cys Pro Val Gly Ala Val Thr Leu
            35                  40                  45

Thr Asp Asp
        50

<210> SEQ ID NO 249
<211> LENGTH: 76
<212> TYPE: PRT
<213> ORGANISM: Streptomyces lanatus IFO 12787T

<400> SEQUENCE: 249

Met His Asn Glu Thr His Glu Ser Gly His Ile His Ile Asp Ile Asp
  1               5                  10                  15

His Asp Val Cys Val Gly Ala Gly Gln Cys Ala Leu Ala Ala Pro Ser
                 20                  25                  30

Val Phe Thr Gln Asp Asp Gly Phe Ser Thr Leu Leu Pro Gly Arg
            35                  40                  45

Glu Asp Gly Gly Gly Asp Pro Met Val Arg Glu Ala Ala Arg Ala Cys
    50                  55                  60

Pro Val Ser Ala Ile Thr Val Ser Glu Gly Gly Ser
 65                  70                  75

<210> SEQ ID NO 250
<211> LENGTH: 66
<212> TYPE: PRT
<213> ORGANISM: Streptomyces misawanensis IFO 13855T

<400> SEQUENCE: 250

Met His Ile Glu Ile Asp Ser Asp Val Cys Ile Gly Ala Gly Gln Cys
  1               5                  10                  15

Ala Leu Thr Ala Pro Asn Val Phe Thr Gln Asp Asp Gly Phe Ser
                 20                  25                  30

Thr Leu Leu Pro Gly Met Ala Asp Gly Gly Gly Asp Pro Leu Val Lys
            35                  40                  45

Glu Ala Ala Arg Ala Cys Pro Val His Ala Ile Thr Val Glu Glu Pro
    50                  55                  60

Ser Gly
 65

<210> SEQ ID NO 251
<211> LENGTH: 64
<212> TYPE: PRT
<213> ORGANISM: Streptomyces pallidus IFO 13434T

<400> SEQUENCE: 251

Met Arg Val Glu Leu Asp Glu Pro Lys Cys Val Ala Ser Gly Gln Cys
  1               5                  10                  15

Val Met Ala Ala Pro Glu Val Phe Asp Gln Arg Glu Glu Asp Gly Ile
                 20                  25                  30

Ala Phe Val Leu Asp Glu Arg Pro Ala Ala Asp Val Leu Ala Glu Val
            35                  40                  45

Arg Glu Ala Val Ala Ile Cys Pro Ala Ala Ala Ile Arg Leu Val Glu
    50                  55                  60

<210> SEQ ID NO 252
<211> LENGTH: 66
```

```
<212> TYPE: PRT
<213> ORGANISM: Streptomyces roseorubens IFO 13682T

<400> SEQUENCE: 252

Met Arg Ile Asp Ile Asp Lys Asp Val Cys Ile Gly Ala Gly Gln Cys
1               5                   10                  15

Ala Leu Thr Ala Pro Asp Val Phe Thr Gln Asp Asp Gly Tyr Ser
            20                  25                  30

Thr Leu Leu Pro Gly Arg Glu Asp Gly Gly Ser Pro Leu Leu Arg
        35                  40                  45

Glu Ala Ala Arg Ala Cys Pro Val Ser Ala Ile Thr Val Ser Glu Thr
    50                  55                  60

Val Gly
 65

<210> SEQ ID NO 253
<211> LENGTH: 65
<212> TYPE: PRT
<213> ORGANISM: Streptomyces rutgersensis IFO 15875T

<400> SEQUENCE: 253

Met Arg Val Glu Val Asp Val Pro Lys Cys Val Ala Ser Gly Gln Cys
1               5                   10                  15

Val Met Ile Ala Pro Asp Val Phe Asp Gln Arg Glu Glu Asp Gly Ile
            20                  25                  30

Val Ile Leu Leu Asp Glu Gln Pro Ala Ser Glu Leu His Ala Asp Val
        35                  40                  45

Arg Glu Ser Ala Val Val Cys Pro Ala Ala Ala Ile Arg Val Val Glu
    50                  55                  60

Asn
 65

<210> SEQ ID NO 254
<211> LENGTH: 66
<212> TYPE: PRT
<213> ORGANISM: Streptomyces steffisburgensis IFO 13446T

<400> SEQUENCE: 254

Met His Ile Asp Ile Asp Lys Asp Val Cys Ile Gly Ala Gly Gln Cys
1               5                   10                  15

Ala Leu Thr Ala Pro Asp Val Phe Thr Gln Asp Asp Asp Gly Ile Ser
            20                  25                  30

Ala Leu Leu Pro Gly Gln Glu Asp Gly Gly Ser Pro Leu Val Arg
        35                  40                  45

Glu Ala Ala Arg Ala Cys Pro Val Ser Ala Ile Thr Val Ser Glu Thr
    50                  55                  60

Val Ser
 65

<210> SEQ ID NO 255
<211> LENGTH: 198
<212> TYPE: DNA
<213> ORGANISM: Streptomyces ornatus IFO 13069t
<220> FEATURE:
<221> NAME/KEY: CDS
<222> LOCATION: (1)..(198)

<400> SEQUENCE: 255 atg ggc gtg cgg gtc gac agg gaa cgg tgc gtg ggg gcc ggc atg tgc      48
Met Gly Val Arg Val Asp Arg Glu Arg Cys Val Gly Ala Gly Met Cys
1               5                   10                  15
```

```
gcg ctg acc gcg ccc gac gtg ttc acg cag gac gac gac ggg ttc agc      96
Ala Leu Thr Ala Pro Asp Val Phe Thr Gln Asp Asp Asp Gly Phe Ser
             20                  25                  30 gag atg ctt ccc ggg agc acg gcg ggg acg ggg gac cac cca cgg gtg     144
Glu Met Leu Pro Gly Ser Thr Ala Gly Thr Gly Asp His Pro Arg Val
         35                  40                  45 cgg gag gcc gtt cgg gcc tgc ccg gtc ggg gcg gtg tcc ctg acc gac     192
Arg Glu Ala Val Arg Ala Cys Pro Val Gly Ala Val Ser Leu Thr Asp
     50                  55                  60 gac tga                                                              198
Asp
 65

<210> SEQ ID NO 256
<211> LENGTH: 198
<212> TYPE: DNA
<213> ORGANISM: Streptomyces griseus ATCC 10137
<220> FEATURE:
<221> NAME/KEY: CDS
<222> LOCATION: (1)..(198)

<400> SEQUENCE: 256 atg ggc gtg cgg gtc gac agg gaa cgg tgc gtg ggg gcc ggc atg tgc      48
Met Gly Val Arg Val Asp Arg Glu Arg Cys Val Gly Ala Gly Met Cys
  1               5                  10                  15 gcg ctg acc gcg ccc gac gtg ttc acg cag gac gac gac ggg ttc agc      96
Ala Leu Thr Ala Pro Asp Val Phe Thr Gln Asp Asp Asp Gly Phe Ser
             20                  25                  30 gag atg ctt ccc ggg agc acg gcg ggg acg ggg gac cac cca cgg gtg     144
Glu Met Leu Pro Gly Ser Thr Ala Gly Thr Gly Asp His Pro Arg Val
         35                  40                  45 cgg gag gcc gtt cgg gcc tgc ccg gtc ggg gcg gtg tcc ctg acc gac     192
Arg Glu Ala Val Arg Ala Cys Pro Val Gly Ala Val Ser Leu Thr Asp
     50                  55                  60 gac tga                                                              198
Asp
 65

<210> SEQ ID NO 257
<211> LENGTH: 207
<212> TYPE: DNA
<213> ORGANISM: Streptomyces achromogenes IFO 12735
<220> FEATURE:
<221> NAME/KEY: CDS
<222> LOCATION: (1)..(207)

<400> SEQUENCE: 257 atg cac atg gac atc gac atc gac cag gac gtc tgt atc ggc gcc ggg      48
Met His Met Asp Ile Asp Ile Asp Gln Asp Val Cys Ile Gly Ala Gly
  1               5                  10                  15 cag tgc gcg ctg gcg gca ccg ggc gtc ttc acc cag gac gac gac ggc      96
Gln Cys Ala Leu Ala Ala Pro Gly Val Phe Thr Gln Asp Asp Asp Gly
             20                  25                  30 tac agc acc ctg ctg ccc ggc cgg gag aac ggc gtc acc gac ccg atg     144
Tyr Ser Thr Leu Leu Pro Gly Arg Glu Asn Gly Val Thr Asp Pro Met
         35                  40                  45 gtc cgg gag gcc gcc cgc gcc tgc ccg gtc agc gcc atc acc gta cga     192
Val Arg Glu Ala Ala Arg Ala Cys Pro Val Ser Ala Ile Thr Val Arg
     50                  55                  60 gag cgc acc gcc tga                                                  207
Glu Arg Thr Ala
 65
```

-continued

```
<210> SEQ ID NO 258
<211> LENGTH: 156
<212> TYPE: DNA
<213> ORGANISM: Streptomyces griseus IFO 13849T
<220> FEATURE:
<221> NAME/KEY: CDS
<222> LOCATION: (1)..(156)

<400> SEQUENCE: 258 atg tgc gcg ctg acc gcg ccg gag gtg ttc aca cag gac gac gac ggt        48
Met Cys Ala Leu Thr Ala Pro Glu Val Phe Thr Gln Asp Asp Asp Gly
 1               5                  10                  15 ttc agc gag gtg cgt ccc ggt ggc acg gcc gcc act gct ggc cac ccg        96
Phe Ser Glu Val Arg Pro Gly Gly Thr Ala Ala Thr Ala Gly His Pro
                20                  25                  30 ctg gta cgc gat gcc gca cgg gcc tgc ccg gtc ggg gcg gtg acc ctg       144
Leu Val Arg Asp Ala Ala Arg Ala Cys Pro Val Gly Ala Val Thr Leu
         35                  40                  45 acc gac gac tga                                                        156
Thr Asp Asp
     50

<210> SEQ ID NO 259
<211> LENGTH: 231
<212> TYPE: DNA
<213> ORGANISM: Streptomyces lanatus IFO 12787T
<220> FEATURE:
<221> NAME/KEY: CDS
<222> LOCATION: (1)..(231)

<400> SEQUENCE: 259 atg cac aac gaa acg cac gaa tca ggc cat atc cac atc gac atc gac        48
Met His Asn Glu Thr His Glu Ser Gly His Ile His Ile Asp Ile Asp
 1               5                  10                  15 cat gac gtc tgc gtc ggc gcc ggg cag tgc gcc ctc gcc gcc ccc tcc        96
His Asp Val Cys Val Gly Ala Gly Gln Cys Ala Leu Ala Ala Pro Ser
                20                  25                  30 gtg ttc acc cag gac gac gac ggc ttc agc acc ctg ctt ccc ggc cgc       144
Val Phe Thr Gln Asp Asp Asp Gly Phe Ser Thr Leu Leu Pro Gly Arg
         35                  40                  45 gag gac ggc ggc ggc gac ccc atg gtg cgg gag gcg gcc cgg gcg tgc       192
Glu Asp Gly Gly Gly Asp Pro Met Val Arg Glu Ala Ala Arg Ala Cys
 50                  55                  60 ccg gtc agc gcc atc acc gtg tcc gaa ggg ggg agt tga                   231
Pro Val Ser Ala Ile Thr Val Ser Glu Gly Gly Ser
 65                  70                  75

<210> SEQ ID NO 260
<211> LENGTH: 201
<212> TYPE: DNA
<213> ORGANISM: Streptomyces misawanensis IFO 13855T
<220> FEATURE:
<221> NAME/KEY: CDS
<222> LOCATION: (1)..(201)

<400> SEQUENCE: 260 atg cac atc gag atc gac agt gac gtc tgc atc ggc gcg ggg cag tgt        48
Met His Ile Glu Ile Asp Ser Asp Val Cys Ile Gly Ala Gly Gln Cys
 1               5                  10                  15 gcc ctg acc gcc ccc aac gtc ttc acc cag gac gac gac ggt ttc agc        96
Ala Leu Thr Ala Pro Asn Val Phe Thr Gln Asp Asp Asp Gly Phe Ser
                20                  25                  30 acc ctg ctc ccc ggg atg gcg gac ggc ggc gac ccg ctg gtc aag           144
Thr Leu Leu Pro Gly Met Ala Asp Gly Gly Asp Pro Leu Val Lys
         35                  40                  45
```

```
gag gcg gcc cgg gcc tgc ccg gtg cac gcc atc acg gtc gag gaa ccg      192
Glu Ala Ala Arg Ala Cys Pro Val His Ala Ile Thr Val Glu Glu Pro
 50                  55                  60 tcg ggt tag                                                           201
Ser Gly
 65

<210> SEQ ID NO 261
<211> LENGTH: 195
<212> TYPE: DNA
<213> ORGANISM: Streptomyces pallidus IFO 13434T
<220> FEATURE:
<221> NAME/KEY: CDS
<222> LOCATION: (1)..(195)

<400> SEQUENCE: 261 atg cga gtg gaa ctg gac gag ccg aag tgc gtc gcg tcg ggg cag tgc       48
Met Arg Val Glu Leu Asp Glu Pro Lys Cys Val Ala Ser Gly Gln Cys
  1               5                  10                  15 gtg atg gcc gcc ccc gag gtc ttc gac cag cgc gag gag gac ggc atc       96
Val Met Ala Ala Pro Glu Val Phe Asp Gln Arg Glu Glu Asp Gly Ile
             20                  25                  30 gcc ttc gtg ctg gac gag cgg ccg gcg gcg gac gtc ctg gcg gag gtg      144
Ala Phe Val Leu Asp Glu Arg Pro Ala Ala Asp Val Leu Ala Glu Val
         35                  40                  45 cgc gag gcc gtg gcg atc tgc ccc gcc gcc gcg atc cgg ctg gtg gag      192
Arg Glu Ala Val Ala Ile Cys Pro Ala Ala Ala Ile Arg Leu Val Glu
 50                  55                  60 tga                                                                   195

<210> SEQ ID NO 262
<211> LENGTH: 201
<212> TYPE: DNA
<213> ORGANISM: Streptomyces roseorubens IFO 13682T
<220> FEATURE:
<221> NAME/KEY: CDS
<222> LOCATION: (1)..(201)

<400> SEQUENCE: 262 atg cgc atc gac atc gac aag gac gtc tgc atc ggc gcg ggc cag tgc       48
Met Arg Ile Asp Ile Asp Lys Asp Val Cys Ile Gly Ala Gly Gln Cys
  1               5                  10                  15 gcc ctg acc gcc ccg gac gtg ttc acc cag gac gac gac ggc tac agc       96
Ala Leu Thr Ala Pro Asp Val Phe Thr Gln Asp Asp Asp Gly Tyr Ser
             20                  25                  30 acc ctg ctg ccc ggc cgg gag gac ggc ggc agc ccg ctg ctg cgg           144
Thr Leu Leu Pro Gly Arg Glu Asp Gly Gly Ser Pro Leu Leu Arg
         35                  40                  45 gag gcg gcc cgg gcc tgc ccg gtg agc gcc atc acc gtc tcg gag acc      192
Glu Ala Ala Arg Ala Cys Pro Val Ser Ala Ile Thr Val Ser Glu Thr
 50                  55                  60 gtc ggc tga                                                           201
Val Gly
 65

<210> SEQ ID NO 263
<211> LENGTH: 198
<212> TYPE: DNA
<213> ORGANISM: Streptomyces rutgersensis IFO 15875T
<220> FEATURE:
<221> NAME/KEY: CDS
<222> LOCATION: (1)..(198)

<400> SEQUENCE: 263 atg cgt gtg gaa gtc gat gtt ccc aag tgt gtg gca tcg ggt cag tgc       48
```

```
Met Arg Val Glu Val Asp Val Pro Lys Cys Val Ala Ser Gly Gln Cys
 1               5                  10                  15 gtg atg atc gca ccc gat gtg ttc gac cag cgg gag gag gac ggc atc        96
Val Met Ile Ala Pro Asp Val Phe Asp Gln Arg Glu Glu Asp Gly Ile
             20                  25                  30 gtg atc ctg ctg gac gag cag ccc gcg tcc gaa ctc cac gcc gat gtg       144
Val Ile Leu Leu Asp Glu Gln Pro Ala Ser Glu Leu His Ala Asp Val
             35                  40                  45 cgt gag tcc gcg gtg gtc tgc ccg gcg gcg gcg ata cgg gtg gtc gag       192
Arg Glu Ser Ala Val Val Cys Pro Ala Ala Ala Ile Arg Val Val Glu
 50                  55                  60 aat tga                                                                198
Asn
 65

<210> SEQ ID NO 264
<211> LENGTH: 201
<212> TYPE: DNA
<213> ORGANISM: Streptomyces steffisburgensis IFO 13446T
<220> FEATURE:
<221> NAME/KEY: CDS
<222> LOCATION: (1)..(201)

<400> SEQUENCE: 264 atg cac atc gac atc gac aag gac gtc tgc atc ggc gcg ggc cag tgc        48
Met His Ile Asp Ile Asp Lys Asp Val Cys Ile Gly Ala Gly Gln Cys
 1               5                  10                  15 gcc ctg acc gcc ccg gac gtg ttc acc cag gac gac gac ggc atc agc        96
Ala Leu Thr Ala Pro Asp Val Phe Thr Gln Asp Asp Asp Gly Ile Ser
             20                  25                  30 gcc ctg ctg ccg gga cag gag gac ggc ggc ggc agc ccg ctg gtg cgg       144
Ala Leu Leu Pro Gly Gln Glu Asp Gly Gly Gly Ser Pro Leu Val Arg
             35                  40                  45 gag gcg gcc cgt gcc tgc ccg gtg agc gcc atc acc gtg tcg gag acg       192
Glu Ala Ala Arg Ala Cys Pro Val Ser Ala Ile Thr Val Ser Glu Thr
 50                  55                  60 gtg agc tga                                                            201
Val Ser
 65

<210> SEQ ID NO 265
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 265
ctcgaagaac tcgtggtcgg cgtacgg                                           27

<210> SEQ ID NO 266
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 266
cacaccgagg agcgcgcaga tcaccat                                           27

<210> SEQ ID NO 267
<211> LENGTH: 29
<212> TYPE: DNA
<213> ORGANISM: Artificial Sequence
<220> FEATURE:
```

```
<223> OTHER INFORMATION: Designed oligonucleotide primer for PCR

<400> SEQUENCE: 267
cgtgttcttc tcgacctcgc tcatcaacc                                    29

<210> SEQ ID NO 268
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 268
ctacgagaat ccggagacgc tcgactg                                      27

<210> SEQ ID NO 269
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 269
ccaagctttc agtcgtcggt cagggacac                                    29

<210> SEQ ID NO 270
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 270
agcagtccgt ccaccgtctc ctggatg                                      27

<210> SEQ ID NO 271
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 271
ctatccgctt cacggagaag ctcgggatga                                   30

<210> SEQ ID NO 272
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 272
ggcgtgttct tctcgacctc gctcatc                                      27

<210> SEQ ID NO 273
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 273
caccgaggtc tacgagaatc cggagac                                      27

<210> SEQ ID NO 274
```

```
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 274
gccatatgac ggaatccacg acggaac                                     27

<210> SEQ ID NO 275
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 275
ccaagctttc agtcgtcggt cagggacac                                   29

<210> SEQ ID NO 276
<211> LENGTH: 23
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 276
gagcttctcc gtgaagcgga tag                                         23

<210> SEQ ID NO 277
<211> LENGTH: 30
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 277
caaagctttc accaggccac gggcaggtgc                                  30

<210> SEQ ID NO 278
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 278
ccagggagat catgttggcg gtcgtct                                     27

<210> SEQ ID NO 279
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 279
cttggcgtcg atcaggtcgc cgaggaa                                     27

<210> SEQ ID NO 280
<211> LENGTH: 27
<212> TYPE: DNA
<213> ORGANISM: Artificial Sequence
<220> FEATURE:
<223> OTHER INFORMATION: Designed oligonucleotide primer for PCR
```

```
<400> SEQUENCE: 280
accgccgaag ctttcaggcg gtgcgct                                        27

<210> SEQ ID NO 281
<211> LENGTH: 27
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 281
ggacgaactg ctggacgcga tgatcga                                        27

<210> SEQ ID NO 282
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 282
agcagccggt ccaccgtctc ctggatac                                       28

<210> SEQ ID NO 283
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 283
cgtttcacgg agaagctcgg gatgagca                                       28

<210> SEQ ID NO 284
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 284
gatcgaggac atcgaggtgg acgggac                                        27

<210> SEQ ID NO 285
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 285
tcttcttctc cacctcgctc gtcaaccg                                       28

<210> SEQ ID NO 286
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 286
atcatatgac ggaatccacg acggaacc                                       28

<210> SEQ ID NO 287
<211> LENGTH: 29
```

```
<212> TYPE: DNA
<213> ORGANISM: Artificial Sequence
<220> FEATURE:
<223> OTHER INFORMATION: Designed oligonucleotide primer for PCR

<400> SEQUENCE: 287
cgaagctttc agtcgtcggt cagggtcac                                    29

<210> SEQ ID NO 288
<211> LENGTH: 20
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 288
gtatccagga gacggtggac                                              20

<210> SEQ ID NO 289
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 289
gcggagagtg aagctgggga ccatcat                                      27

<210> SEQ ID NO 290
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 290
cgaggagctc atgcggatgc tgtcgat                                      27

<210> SEQ ID NO 291
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 291
cgtggtcttc tcgacctcgg tcatcaa                                      27

<210> SEQ ID NO 292
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 292
cgaggtccat atgacggaca tgaccgatat                                   30

<210> SEQ ID NO 293
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 293
```

| | |
|---|---|
| gatgccaagc tttcaactcc ccccttcgga | 30 |

<210> SEQ ID NO 294
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 294

| | |
|---|---|
| cgagcagatc gtcgacgatc cgctggat | 28 |

<210> SEQ ID NO 295
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 295

| | |
|---|---|
| ttgagggtga agtccgggat cagcatc | 27 |

<210> SEQ ID NO 296
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 296

| | |
|---|---|
| gaggaactga tgcggatgct gtccatc | 27 |

<210> SEQ ID NO 297
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 297

| | |
|---|---|
| catcaaccgt gacgagtccg tgtacga | 27 |

<210> SEQ ID NO 298
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 298

| | |
|---|---|
| ctcatatgaa agaactgacg gacctga | 27 |

<210> SEQ ID NO 299
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 299

| | |
|---|---|
| gcaagcttct aacccgacgg ttcctcgac | 29 |

<210> SEQ ID NO 300
<211> LENGTH: 22
<212> TYPE: DNA
<213> ORGANISM: Artificial Sequence
<220> FEATURE:

```
<223> OTHER INFORMATION: Designed oligonucleotide primer for DNA
      sequencing

<400> SEQUENCE: 300
gatgctgatc ccggacttca cc                                           22

<210> SEQ ID NO 301
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 301
cttctcgccc atcagctcgt cgaggta                                      27

<210> SEQ ID NO 302
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 302
gaggatccgg ctgttctcct ggaagaa                                      27

<210> SEQ ID NO 303
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 303
catgaggatg aagctggcgt tgttctc                                      27

<210> SEQ ID NO 304
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 304
gacatcgaga tcggcggaca ggtcatc                                      27

<210> SEQ ID NO 305
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 305
atgatcatgc ccaacgacct cgccaac                                      27

<210> SEQ ID NO 306
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 306
cgaccgagga gacatatggc cgacaccctc gcc                               33
```

-continued

<210> SEQ ID NO 307
<211> LENGTH: 33
<212> TYPE: DNA
<213> ORGANISM: Artificial Sequence
<220> FEATURE:
<223> OTHER INFORMATION: Designed oligonucleotide primer for PCR

<400> SEQUENCE: 307
aaatcgaagc tttcactcca ccagccggat cgc                33

<210> SEQ ID NO 308
<211> LENGTH: 30
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 308
ggagtgccgt acgaggacca cgacttcttc                30

<210> SEQ ID NO 309
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 309
agcctcgaag aagtcgtggt cggcgta                27

<210> SEQ ID NO 310
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 310
gagtcgttcg tcgacgatcc gctggat                27

<210> SEQ ID NO 311
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 311
ccaacatgat ctccctcggc accttca                27

<210> SEQ ID NO 312
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 312
ggtcatcaac cgcgacgaga cggtctt                27

<210> SEQ ID NO 313
<211> LENGTH: 33
<212> TYPE: DNA
<213> ORGANISM: Artificial Sequence
<220> FEATURE:
<223> OTHER INFORMATION: Designed oligonucleotide primer for PCR

```
<400> SEQUENCE: 313
gtctgcgagg tccatatgac ggacacgacc gca                          33

<210> SEQ ID NO 314
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 314
tgacaagctt tcagccgacg gtctccgaga                              30

<210> SEQ ID NO 315
<211> LENGTH: 27
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 315
cgtcgacgaa cgactcgacg cgatgat                                 27

<210> SEQ ID NO 316
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 316
cgtggagtta cggttgatca ggagcga                                 27

<210> SEQ ID NO 317
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 317
cagatcgtcg gtgatcttct ggatgtc                                 27

<210> SEQ ID NO 318
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 318
gaactgctgc gctatctgac catcgtg                                 27

<210> SEQ ID NO 319
<211> LENGTH: 28
<212> TYPE: DNA
<213> ORGANISM: Artificial Sequence
<220> FEATURE:
<223> OTHER INFORMATION: Designed oligonucleotide primer for PCR

<400> SEQUENCE: 319
atcatcgtct acaccggcac cggcaact                                28

<210> SEQ ID NO 320
<211> LENGTH: 30
```

```
<212> TYPE: DNA
<213> ORGANISM: Artificial Sequence
<220> FEATURE:
<223> OTHER INFORMATION: Designed oligonucleotide primer for PCR

<400> SEQUENCE: 320
ccgaggagac atatgaccga aacgctggca                                         30

<210> SEQ ID NO 321
<211> LENGTH: 30
<212> TYPE: DNA
<213> ORGANISM: Artificial Sequence
<220> FEATURE:
<223> OTHER INFORMATION: Designed oligonucleotide primer for PCR

<400> SEQUENCE: 321
ccaccacaag cttcttcaat tctcgaccac                                         30

<210> SEQ ID NO 322
<211> LENGTH: 27
<212> TYPE: DNA
<213> ORGANISM: Artificial Sequence
<220> FEATURE:
<223> OTHER INFORMATION: Designed oligonucleotide primer for DNA
      sequencing

<400> SEQUENCE: 322
atggtgatct gccggctgct cggagtg                                            27

<210> SEQ ID NO 323
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 323
ggtctcgaag aagtcgtggt cggcgta                                            27

<210> SEQ ID NO 324
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 324
tttgagggtg aagtccccgg ccaccat                                            27

<210> SEQ ID NO 325
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 325
cgtcatcaac cgcgacgaga cggtcta                                            27

<210> SEQ ID NO 326
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 326
```

```
gaggtccata tgtcggacac gaccgca                                           27

<210> SEQ ID NO 327
<211> LENGTH: 26
<212> TYPE: DNA
<213> ORGANISM: Artificial Sequence
<220> FEATURE:
<223> OTHER INFORMATION: Designed oligonucleotide primer for PCR

<400> SEQUENCE: 327
tacaagcttt cagctcaccg tctccg                                            26

<210> SEQ ID NO 328
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 328
atgacccagt ccgccgacgc cgtaccc                                           27

<210> SEQ ID NO 329
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 329
tcaccaggtg acggggagtt cgtagac                                           27

<210> SEQ ID NO 330
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 330
atgacggaac tgacggacat caccggc                                           27

<210> SEQ ID NO 331
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 331
ttaccaggtc acggggagtt ccagcat                                           27

<210> SEQ ID NO 332
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 332
atgacggaat ccacgacaga tccgacg                                           27

<210> SEQ ID NO 333
<211> LENGTH: 26
<212> TYPE: DNA
<213> ORGANISM: Artificial Sequence
<220> FEATURE:
```

<223> OTHER INFORMATION: Designed oligonucleotide primer for PCR

<400> SEQUENCE: 333
tcaccaggcc acgggcagtt cgagca                                              26

<210> SEQ ID NO 334
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 334
atgacggaca tgacggaaac ccccacc                                             27

<210> SEQ ID NO 335
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 335
atgacggaat ccacgacgga accggcc                                             27

<210> SEQ ID NO 336
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 336
tcaccaggcc acgggcaggt gcagaag                                             27

<210> SEQ ID NO 337
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 337
atgacggaca tgacggaaac ccccacc                                             27

<210> SEQ ID NO 338
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 338
atgaaagaac tgacggacct gacggaa                                             27

<210> SEQ ID NO 339
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 339
atgtcggaca cgaccgaccc cgtggcc                                             27

<210> SEQ ID NO 340

```
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 340
atggccgaca ccctcgccgg cgccacg                                          27

<210> SEQ ID NO 341
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 341
tcaccacgtg acgggcagtt cgtagac                                          27

<210> SEQ ID NO 342
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 342
atgaccgaaa cgctggcaga gaccacg                                          27

<210> SEQ ID NO 343
<211> LENGTH: 27
<212> TYPE: DNA
<213> ORGANISM: Artificial Sequence
<220> FEATURE:
<223> OTHER INFORMATION: Designed oligonucleotide primer for PCR

<400> SEQUENCE: 343
tcaagacgtc caggtgacgg gcagttc                                          27

<210> SEQ ID NO 344
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 344
catatgacag atactactgc acctgttgca tttcctcaga gtaggacctg tccatatcat      60
ccacctgctg                                                             70

<210> SEQ ID NO 345
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 345
tccatatcat ccacctgctg catacgaacc acttcgtgct gaacgtcctc tgactaggat      60
tactctcttt                                                             70

<210> SEQ ID NO 346
<211> LENGTH: 70
<212> TYPE: DNA
<213> ORGANISM: Artificial Sequence
<220> FEATURE:
```

-continued

<223> OTHER INFORMATION: Designed oligonucleotide primer for PCR

<400> SEQUENCE: 346
tgactaggat tactctcttt gatggacgtg aagcatggtt ggttagtggt catgccaccg    60
cacgtgctct    70

<210> SEQ ID NO 347
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 347
aggaggatgg tcgttgggga cttcactctc aaacgggcag ctgcattgag gccccgcatt    60
cagaggattg    70

<210> SEQ ID NO 348
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 348
gccccgcatt cagaggattg ttgatgaacg actcgatgcg atgattgctc aaggaccacc    60
tgcagatttg    70

<210> SEQ ID NO 349
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 349
aaggaccacc tgcagatttg gtgagcgcat ttgcattgcc agtgccttca atggtgatat    60
gcgctttgct    70

<210> SEQ ID NO 350
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 350
aagagagaag atcctggtac tggattactt gatgaccttg ttcaacggca gccaggagat    60
ggtggacccg    70

<210> SEQ ID NO 351
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 351
gccaggagat ggtggacccg atagagaagg actgatagcc atggccctca tcctgcttgt    60
agcaggccat    70

<210> SEQ ID NO 352

```
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 352
tcctgcttgt agcaggccat gagacgaccg ccaacatgat atcactaggc acctttacac    60
tcttgcaaca                                                           70

<210> SEQ ID NO 353
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 353
acaacaatcc gagctggaga aggcgtagtg ttcgcgacat cggtcatcaa tagagatgag    60
acagtctttg                                                           70

<210> SEQ ID NO 354
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 354
tagagatgag acagtctttg ctgagccgga cactctcgac tggtctagac cagccagaca    60
tcacgtagcg                                                           70

<210> SEQ ID NO 355
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 355
cagccagaca tcacgtagcg ttcggctttg ggattcacca gtgcttaggt caaaacttag    60
caagagccga                                                           70

<210> SEQ ID NO 356
<211> LENGTH: 56
<212> TYPE: DNA
<213> ORGANISM: Artificial Sequence
<220> FEATURE:
<223> OTHER INFORMATION: Designed oligonucleotide primer for PCR

<400> SEQUENCE: 356
aagcttttac caggtcacgg ggagttccaa catcccttgg atcgtgtcgc ctggct        56

<210> SEQ ID NO 357
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 357
ttggatcgtg tcgcctggct tgaagggaat ctcatctgga ggagcggcca atctaagtgt    60
gggcaaccta                                                           70
```

<210> SEQ ID NO 358
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 358
atctaagtgt gggcaaccta ccgaagaggg tgcctaaggc gatctcaagt tcggctcttg    60
ctaagttttg                                                           70

<210> SEQ ID NO 359
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 359
tctccagctc ggattgttgt cccggccact tcaacatcct caacagcaat gcgcaacaga    60
ccatctgcaa                                                           70

<210> SEQ ID NO 360
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 360
gcgcaacaga ccatctgcaa tggacagcaa cctcataagt tcctcaactg cggccggcat    60
gacctcggag                                                           70

<210> SEQ ID NO 361
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 361
cggccggcat gacctcggag tcagctcgaa gttcagctag cctctcaggg tgttgcaaga    60
gtgtaaaggt                                                           70

<210> SEQ ID NO 362
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 362
gtaccaggat cttctctctt gcggtcaata agctcaccga agtactcctc aagcctgctc    60
ctagcatcct                                                           70

<210> SEQ ID NO 363
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 363

```
aagcctgctc ctagcatcct gcacatcagc agtccctggt cctctcagaa gtctccttga      60
ttgagcttca                                                             70

<210> SEQ ID NO 364
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 364
gtctccttga ttgagcttca aagaagtcat ggtcagcata gggaacacct agcaaagcgc      60
atatcaccat                                                             70

<210> SEQ ID NO 365
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 365
tccccaacga ccatcctcct ttgggcacgg tgctcaggat cgtccacacc gagaagagct      60
gtacgtctat                                                             70

<210> SEQ ID NO 366
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 366
gagaagagct gtacgtctat tgcgtatccc agcaaatctc gcagtagggg ttgggaatcc      60
aggtctgtcg                                                             70

<210> SEQ ID NO 367
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 367
ttgggaatcc aggtctgtcg cgatcagaag acaatcttgg atctgctaga agagcacgtg      60
cggtggcatg                                                             70

<210> SEQ ID NO 368
<211> LENGTH: 1197
<212> TYPE: DNA
<213> ORGANISM: Artificial Sequence
<220> FEATURE:
<221> NAME/KEY: CDS
<222> LOCATION: (1)..(1197)
<223> OTHER INFORMATION: Designed polynucleotide encoding amino acid
      sequence of SEQ ID No.222

<400> SEQUENCE: 368 atg aca gat act act gca cct gtt gca ttt cct cag agt agg acc tgt       48
Met Thr Asp Thr Thr Ala Pro Val Ala Phe Pro Gln Ser Arg Thr Cys
 1               5                  10                  15 cca tat cat cca cct gct gca tac gaa cca ctt cgt gct gaa cgt cct       96
Pro Tyr His Pro Pro Ala Ala Tyr Glu Pro Leu Arg Ala Glu Arg Pro
             20                  25                  30
```

-continued

| | |
|---|---|
| ctg act agg att act ctc ttt gat gga cgt gaa gca tgg ttg gtt agt<br>Leu Thr Arg Ile Thr Leu Phe Asp Gly Arg Glu Ala Trp Leu Val Ser<br>        35                    40                    45 | 144 |
| ggt cat gcc acc gca cgt gct ctt cta gca gat cca aga ttg tct tct<br>Gly His Ala Thr Ala Arg Ala Leu Leu Ala Asp Pro Arg Leu Ser Ser<br>        50                    55                    60 | 192 |
| gat cgc gac aga cct gga ttc cca acc cct act gcg aga ttt gct ggg<br>Asp Arg Asp Arg Pro Gly Phe Pro Thr Pro Thr Ala Arg Phe Ala Gly<br>65                    70                    75                  80 | 240 |
| ata cgc aat aga cgt aca gct ctt ctc ggt gtg gac gat cct gag cac<br>Ile Arg Asn Arg Arg Thr Ala Leu Leu Gly Val Asp Asp Pro Glu His<br>                85                    90                    95 | 288 |
| cgt gcc caa agg agg atg gtc gtt ggg gac ttc act ctc aaa cgg gca<br>Arg Ala Gln Arg Arg Met Val Val Gly Asp Phe Thr Leu Lys Arg Ala<br>              100                  105               110 | 336 |
| gct gca ttg agg ccc cgc att cag agg att gtt gat gaa cga ctc gat<br>Ala Ala Leu Arg Pro Arg Ile Gln Arg Ile Val Asp Glu Arg Leu Asp<br>              115                  120               125 | 384 |
| gcg atg att gct caa gga cca cct gca gat ttg gtg agc gca ttt gca<br>Ala Met Ile Ala Gln Gly Pro Pro Ala Asp Leu Val Ser Ala Phe Ala<br>130                        135                  140 | 432 |
| ttg cca gtg cct tca atg gtg ata tgc gct ttg cta ggt gtt ccc tat<br>Leu Pro Val Pro Ser Met Val Ile Cys Ala Leu Leu Gly Val Pro Tyr<br>145                        150                  155               160 | 480 |
| gct gac cat gac ttc ttt gaa gct caa tca agg aga ctt ctg aga gga<br>Ala Asp His Asp Phe Phe Glu Ala Gln Ser Arg Arg Leu Leu Arg Gly<br>              165                  170               175 | 528 |
| cca ggg act gct gat gtg cag gat gct agg agc agg ctt gag gag tac<br>Pro Gly Thr Ala Asp Val Gln Asp Ala Arg Ser Arg Leu Glu Glu Tyr<br>                180                  185               190 | 576 |
| ttc ggt gag ctt att gac cgc aag aga gaa gat cct ggt act gga tta<br>Phe Gly Glu Leu Ile Asp Arg Lys Arg Glu Asp Pro Gly Thr Gly Leu<br>              195                  200               205 | 624 |
| ctt gat gac ctt gtt caa cgg cag cca gga gat ggt gga ccc gat aga<br>Leu Asp Asp Leu Val Gln Arg Gln Pro Gly Asp Gly Gly Pro Asp Arg<br>210                      215                  220 | 672 |
| gaa gga ctg ata gcc atg gcc ctc atc ctg ctt gta gca ggc cat gag<br>Glu Gly Leu Ile Ala Met Ala Leu Ile Leu Leu Val Ala Gly His Glu<br>225                      230                  235               240 | 720 |
| acg acc gcc aac atg ata tca cta ggc acc ttt aca ctc ttg caa cac<br>Thr Thr Ala Asn Met Ile Ser Leu Gly Thr Phe Thr Leu Leu Gln His<br>              245                  250               255 | 768 |
| cct gag agg cta gct gaa ctt cga gct gac tcc gag gtc atg ccg gcc<br>Pro Glu Arg Leu Ala Glu Leu Arg Ala Asp Ser Glu Val Met Pro Ala<br>                260                  265               270 | 816 |
| gca gtt gag gaa ctt atg agg ttg ctg tcc att gca gat ggt ctg ttg<br>Ala Val Glu Glu Leu Met Arg Leu Leu Ser Ile Ala Asp Gly Leu Leu<br>              275                  280               285 | 864 |
| cgc att gct gtt gag gat gtt gaa gtg gcc ggg aca aca atc cga gct<br>Arg Ile Ala Val Glu Asp Val Glu Val Ala Gly Thr Thr Ile Arg Ala<br>290                      295                  300 | 912 |
| gga gaa ggc gta gtg ttc gcg aca tcg gtc atc aat aga gat gag aca<br>Gly Glu Gly Val Val Phe Ala Thr Ser Val Ile Asn Arg Asp Glu Thr<br>305                      310                  315               320 | 960 |
| gtc ttt gct gag ccg gac act ctc gac tgg tct aga cca gcc aga cat<br>Val Phe Ala Glu Pro Asp Thr Leu Asp Trp Ser Arg Pro Ala Arg His<br>                      325                  330               335 | 1008 |
| cac gta gcg ttc ggc ttt ggg att cac cag tgc tta ggt caa aac tta<br>His Val Ala Phe Gly Phe Gly Ile His Gln Cys Leu Gly Gln Asn Leu<br>              340                  345               350 | 1056 |

-continued

```
gca aga gcc gaa ctt gag atc gcc tta ggc acc ctc ttc ggt agg ttg      1104
Ala Arg Ala Glu Leu Glu Ile Ala Leu Gly Thr Leu Phe Gly Arg Leu
        355                 360                 365 ccc aca ctt aga ttg gcc gct cct cca gat gag att ccc ttc aag cca      1152
Pro Thr Leu Arg Leu Ala Ala Pro Pro Asp Glu Ile Pro Phe Lys Pro
370                 375                 380 ggc gac acg atc caa ggg atg ttg gaa ctc ccc gtg acc tgg taa          1197
Gly Asp Thr Ile Gln Gly Met Leu Glu Leu Pro Val Thr Trp
385                 390                 395
```

<210> SEQ ID NO 369
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 369
catatgtctg atactacagc acctgttgct tttccacaat ctcgtacctg cccctatcat      60
cctcctgctg      70

<210> SEQ ID NO 370
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 370
cccctatcat cctcctgctg cctatgaacc gttacgtgct gagagaccct tgactagaat      60
cacactcttt      70

<210> SEQ ID NO 371
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 371
tgactagaat cacactcttt gatggtagag aagcctggtt ggtcagtgga catgccacag      60
ctagggcatt      70

<210> SEQ ID NO 372
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 372
cgtaggatgg ttgcagggga ctttacactc aaaagagctg caggattgag gccacgcatt      60
caacggattg      70

<210> SEQ ID NO 373
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 373
gccacgcatt caacggattg tggacaggcg actcgatgcg atgatagctc agggtccacc      60

```
tgcagacctt                                                            70

<210> SEQ ID NO 374
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 374
agggtccacc tgcagacctt gtgagcagct tcgcgttacc agttccgtcc atggtgatct      60
gtgccttgct                                                            70

<210> SEQ ID NO 375
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 375
aaacggaagg aaccaggagc tggactgctt gatgacttgg ttcaacgaca gcttagagat      60
ggagcattag                                                            70

<210> SEQ ID NO 376
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 376
gcttagagat ggagcattag acagggaagg tctgattgcc cttgcactca tcttgcttgt      60
tgctggtcac                                                            70

<210> SEQ ID NO 377
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 377
tcttgcttgt tgctggtcac gagacgacag ccaacatgat ctctcttggc accttcaccc      60
tattgcaaca                                                            70

<210> SEQ ID NO 378
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 378
accacaattc gcaaggggga tggagtggtg tttctgacta gtgtcatcaa ccgcgatgag      60
acagtctacc                                                            70

<210> SEQ ID NO 379
<211> LENGTH: 70
<212> TYPE: DNA
<213> ORGANISM: Artificial Sequence
<220> FEATURE:
<223> OTHER INFORMATION: Designed oligonucleotide primer for PCR
```

<400> SEQUENCE: 379
ccgcgatgag acagtctacc ctgaaccaga caccctcgat tggcaccgtt ctgctagaca    60
tcacgtagcg    70

<210> SEQ ID NO 380
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 380
ctgctagaca tcacgtagcg ttcggcttcg gcattcacca gtgcctcggc cagaatcttg    60
cacgcgctga    70

<210> SEQ ID NO 381
<211> LENGTH: 56
<212> TYPE: DNA
<213> ORGANISM: Artificial Sequence
<220> FEATURE:
<223> OTHER INFORMATION: Designed oligonucleotide primer for PCR

<400> SEQUENCE: 381
aagcttttac caagtcacag gaagttccaa catcccttga atcgtgtcac ctggct    56

<210> SEQ ID NO 382
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 382
ttgaatcgtg tcacctggct tgaaggcaat ctcctcggct ggagctgcta agcgtagagt    60
gggcaaacga    70

<210> SEQ ID NO 383
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 383
agcgtagagt gggcaaacga tcgaagaggg tccaaagtgc aatctcaagc tcagcgcgtg    60
caagattctg    70

<210> SEQ ID NO 384
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 384
tccccctcgc gaattgtggt cccagcaact tctatgtcct caacggcgag tctaagcaaa    60
ccatccgcta    70

<210> SEQ ID NO 385
<211> LENGTH: 70
<212> TYPE: DNA
<213> ORGANISM: Artificial Sequence

```
<220> FEATURE:
<223> OTHER INFORMATION: Designed oligonucleotide primer for PCR

<400> SEQUENCE: 385
tctaagcaaa ccatccgcta tggacagcat gcgcatcagt tcctcgactg cagcaggcaa      60
tagacgagga                                                            70

<210> SEQ ID NO 386
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 386
cagcaggcaa tagacgagga tctgctctca actcagcaag cctttcggga tgttgcaata      60
gggtgaaggt                                                            70

<210> SEQ ID NO 387
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 387
gctcctggtt ccttccgttt cctgtcaatc agttctccaa agtactcatc caaccgtgct      60
ctagcatcca                                                            70

<210> SEQ ID NO 388
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 388
caaccgtgct ctagcatcca tcacatcggc agtctgagga cctctaagta gtctccttga      60
ctgggtctca                                                            70

<210> SEQ ID NO 389
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 389
gtctccttga ctgggtctca aagaaatcgt gatcggcgta tggaactccg agcaaggcac      60
agatcaccat                                                            70

<210> SEQ ID NO 390
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 390
tcccctgcaa ccatcctacg ttgtactcga tgttcaggat cgtcaacacc cagtagtgca      60
gttctcctat                                                            70
```

```
<210> SEQ ID NO 391
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 391
cagtagtgca gttctcctat tccttatccc agcaaacctt gcagtgggag ctgggaagcc      60
aggtctgtca                                                            70

<210> SEQ ID NO 392
<211> LENGTH: 70
<212> TYPE: DNA
<213> ORGANISM: Artificial Sequence
<220> FEATURE:
<223> OTHER INFORMATION: Designed oligonucleotide primer for PCR

<400> SEQUENCE: 392
ctgggaagcc aggtctgtca cgatcagatg aaagccttgg atcagcgagt aatgccctag      60
ctgtggcatg                                                            70

<210> SEQ ID NO 393
<211> LENGTH: 1197
<212> TYPE: DNA
<213> ORGANISM: Artificial Sequence
<220> FEATURE:
<221> NAME/KEY: CDS
<222> LOCATION: (1)..(1197)
<223> OTHER INFORMATION: Designed polynucleotide encoding amino acid
      sequence of SEQ ID No.224

<400> SEQUENCE: 393 atg tct gat act aca gca cct gtt gct ttt cca caa tct cgt acc tgc       48
Met Ser Asp Thr Thr Ala Pro Val Ala Phe Pro Gln Ser Arg Thr Cys
 1               5                  10                  15 ccc tat cat cct cct gct gcc tat gaa ccg tta cgt gct gag aga ccc       96
Pro Tyr His Pro Pro Ala Ala Tyr Glu Pro Leu Arg Ala Glu Arg Pro
                 20                  25                  30 ttg act aga atc aca ctc ttt gat ggt aga gaa gcc tgg ttg gtc agt      144
Leu Thr Arg Ile Thr Leu Phe Asp Gly Arg Glu Ala Trp Leu Val Ser
             35                  40                  45 gga cat gcc aca gct agg gca tta ctc gct gat cca agg ctt tca tct      192
Gly His Ala Thr Ala Arg Ala Leu Leu Ala Asp Pro Arg Leu Ser Ser
         50                  55                  60 gat cgt gac aga cct ggc ttc cca gct ccc act gca agg ttt gct ggg      240
Asp Arg Asp Arg Pro Gly Phe Pro Ala Pro Thr Ala Arg Phe Ala Gly
 65                  70                  75                  80 ata agg aat agg aga act gca cta ctg ggt gtt gac gat cct gaa cat      288
Ile Arg Asn Arg Arg Thr Ala Leu Leu Gly Val Asp Asp Pro Glu His
                 85                  90                  95 cga gta caa cgt agg atg gtt gca ggg gac ttt aca ctc aaa aga gct      336
Arg Val Gln Arg Arg Met Val Ala Gly Asp Phe Thr Leu Lys Arg Ala
                100                 105                 110 gca gga ttg agg cca cgc att caa cgg att gtg gac agg cga ctc gat      384
Ala Gly Leu Arg Pro Arg Ile Gln Arg Ile Val Asp Arg Arg Leu Asp
            115                 120                 125 gcg atg ata gct cag ggt cca cct gca gac ctt gtg agc agc ttc gcg      432
Ala Met Ile Ala Gln Gly Pro Pro Ala Asp Leu Val Ser Ser Phe Ala
        130                 135                 140 tta cca gtt ccg tcc atg gtg atc tgt gcc ttg ctc gga gtt cca tac      480
Leu Pro Val Pro Ser Met Val Ile Cys Ala Leu Leu Gly Val Pro Tyr
145                 150                 155                 160
```

```
gcc gat cac gat ttc ttt gag acc cag tca agg aga cta ctt aga ggt      528
Ala Asp His Asp Phe Phe Glu Thr Gln Ser Arg Arg Leu Leu Arg Gly
                165                 170                 175 cct cag act gcc gat gtg atg gat gct aga gca cgg ttg gat gag tac      576
Pro Gln Thr Ala Asp Val Met Asp Ala Arg Ala Arg Leu Asp Glu Tyr
            180                 185                 190 ttt gga gaa ctg att gac agg aaa cgg aag gaa cca gga gct gga ctg      624
Phe Gly Glu Leu Ile Asp Arg Lys Arg Lys Glu Pro Gly Ala Gly Leu
        195                 200                 205 ctt gat gac ttg gtt caa cga cag ctt aga gat gga gca tta gac agg      672
Leu Asp Asp Leu Val Gln Arg Gln Leu Arg Asp Gly Ala Leu Asp Arg
    210                 215                 220 gaa ggt ctg att gcc ctt gca ctc atc ttg ctt gtt gct ggt cac gag      720
Glu Gly Leu Ile Ala Leu Ala Leu Ile Leu Leu Val Ala Gly His Glu
225                 230                 235                 240 acg aca gcc aac atg atc tct ctt ggc acc ttc acc cta ttg caa cat      768
Thr Thr Ala Asn Met Ile Ser Leu Gly Thr Phe Thr Leu Leu Gln His
                245                 250                 255 ccc gaa agg ctt gct gag ttg aga gca gat cct cgt cta ttg cct gct      816
Pro Glu Arg Leu Ala Glu Leu Arg Ala Asp Pro Arg Leu Leu Pro Ala
            260                 265                 270 gca gtc gag gaa ctg atg cgc atg ctg tcc ata gcg gat ggt ttg ctt      864
Ala Val Glu Glu Leu Met Arg Met Leu Ser Ile Ala Asp Gly Leu Leu
        275                 280                 285 aga ctc gcc gtt gag gac ata gaa gtt gct ggg acc aca att cgc aag      912
Arg Leu Ala Val Glu Asp Ile Glu Val Ala Gly Thr Thr Ile Arg Lys
    290                 295                 300 ggg gat gga gtg gtg ttt ctg act agt gtc atc aac cgc gat gag aca      960
Gly Asp Gly Val Val Phe Leu Thr Ser Val Ile Asn Arg Asp Glu Thr
305                 310                 315                 320 gtc tac cct gaa cca gac acc ctc gat tgg cac cgt tct gct aga cat     1008
Val Tyr Pro Glu Pro Asp Thr Leu Asp Trp His Arg Ser Ala Arg His
                325                 330                 335 cac gta gcg ttc ggc ttc ggc att cac cag tgc ctc ggc cag aat ctt     1056
His Val Ala Phe Gly Phe Gly Ile His Gln Cys Leu Gly Gln Asn Leu
            340                 345                 350 gca cgc gct gag ctt gag att gca ctt tgg acc ctc ttc gat cgt ttg     1104
Ala Arg Ala Glu Leu Glu Ile Ala Leu Trp Thr Leu Phe Asp Arg Leu
        355                 360                 365 ccc act cta cgc tta gca gct cca gcc gag gag att gcc ttc aag cca     1152
Pro Thr Leu Arg Leu Ala Ala Pro Ala Glu Glu Ile Ala Phe Lys Pro
    370                 375                 380 ggt gac acg att caa ggg atg ttg gaa ctt cct gtg act tgg taa         1197
Gly Asp Thr Ile Gln Gly Met Leu Glu Leu Pro Val Thr Trp
385                 390                 395

<210> SEQ ID NO 394
<211> LENGTH: 29
<212> TYPE: DNA
<213> ORGANISM: Artificial Sequence
<220> FEATURE:
<223> OTHER INFORMATION: Designed oligonucleotide primer for PCR

<400> SEQUENCE: 394
ggggatgcat gacagatatg acagatact                                       29

<210> SEQ ID NO 395
<211> LENGTH: 30
<212> TYPE: DNA
<213> ORGANISM: Artificial Sequence
<220> FEATURE:
<223> OTHER INFORMATION: Designed oligonucleotide primer for PCR
```

| | | |
|---|---|---|
| <400> SEQUENCE: 395 | | |
| ggggagctcc taccaggcca cgggaagatc | | 30 |

<210> SEQ ID NO 396
<211> LENGTH: 18
<212> TYPE: DNA
<213> ORGANISM: Artificial Sequence
<220> FEATURE:
<223> OTHER INFORMATION: Designed oligonucleotide primer for PCR

| | | |
|---|---|---|
| <400> SEQUENCE: 396 | | |
| acagatatga cagatact | | 18 |

<210> SEQ ID NO 397
<211> LENGTH: 27
<212> TYPE: DNA
<213> ORGANISM: Artificial Sequence
<220> FEATURE:
<223> OTHER INFORMATION: Designed oligonucleotide primer for PCR

| | | |
|---|---|---|
| <400> SEQUENCE: 397 | | |
| ggatgcatga cagatactac tgcacct | | 27 |

<210> SEQ ID NO 398
<211> LENGTH: 27
<212> TYPE: DNA
<213> ORGANISM: Artificial Sequence
<220> FEATURE:
<223> OTHER INFORMATION: Designed oligonucleotide primer for PCR

| | | |
|---|---|---|
| <400> SEQUENCE: 398 | | |
| gagctcttac caggtcacgg ggagttc | | 27 |

<210> SEQ ID NO 399
<211> LENGTH: 27
<212> TYPE: DNA
<213> ORGANISM: Artificial Sequence
<220> FEATURE:
<223> OTHER INFORMATION: Designed oligonucleotide primer for PCR

| | | |
|---|---|---|
| <400> SEQUENCE: 399 | | |
| ggggtcatga cagatactac tgcacct | | 27 |

<210> SEQ ID NO 400
<211> LENGTH: 27
<212> TYPE: DNA
<213> ORGANISM: Artificial Sequence
<220> FEATURE:
<223> OTHER INFORMATION: Designed oligonucleotide primer for PCR

| | | |
|---|---|---|
| <400> SEQUENCE: 400 | | |
| ggatgcatgt ctgatactac agcacct | | 27 |

<210> SEQ ID NO 401
<211> LENGTH: 27
<212> TYPE: DNA
<213> ORGANISM: Artificial Sequence
<220> FEATURE:
<223> OTHER INFORMATION: Designed oligonucleotide primer for PCR

| | | |
|---|---|---|
| <400> SEQUENCE: 401 | | |
| gagctcttac caagtcacag gaagttc | | 27 |

<210> SEQ ID NO 402
<211> LENGTH: 36
<212> TYPE: DNA

```
<213> ORGANISM: Artificial Sequence
<220> FEATURE:
<223> OTHER INFORMATION: Designed oligonucleotide linker for
      construction of expression vector

<400> SEQUENCE: 402
tgcaggtgtg gccaccaatt ggcaagaaga aatgca                               36

<210> SEQ ID NO 403
<211> LENGTH: 36
<212> TYPE: DNA
<213> ORGANISM: Artificial Sequence
<220> FEATURE:
<223> OTHER INFORMATION: Designed oligonucleotide linker for
      construction of expression vector

<400> SEQUENCE: 403
tttcttcttg ccaattggtg gccacacctg catgca                               36
```

WEED CONTROLLER METABOLISM PROTEINS, GENES, THEREOF AND USE OF THE SAME

CROSS-REFERENCE TO RELATED PATENT APPLICATIONS

This application is a Divisional of U.S. application Ser. No. 10/492,928, filed Apr. 19, 2004, which is a U.S. National Stage of PCT/JP02/10789, filed Oct. 17, 2002, which claims priority from Japanese Application 2001-321307, filed Oct. 19, 2001 and Japanese Application 2002-167239, filed Jun. 7, 2002, including the specification, drawings, claims and abstract are all incorporated herein by reference in its entirety.

TECHNICAL FIELD

The present invention relates to a protein having the ability to metabolize a herbicidal compound (Herbicide metabolizing protein), a gene thereof and use thereof.

BACKGROUND ART

Herbicides are utilized in a necessary amount of diluted solution when applied. There are situations in which extra amounts are left over. There are also situations in which the applied herbicide, after its application for awhile, remains in the soil or plant residue. Originally, given that the safety of such herbicides has been checked, such small amounts of left-over solutions or residues presented small effects to the environment or to the crops cultivated thereafter. However, if there is a method in which the contained herbicidal compound is converted to one of lower herbicidal activity, then for example there can be conducted treatments to inactivate the left-over solutions or residues described above as needed.

Further, in the case of using the herbicide, there were situations in which it was difficult to distinguish cultivated plants from weeds of allied species to selectively control only weeds. Then, there is a desire to develop a new method for conferring herbicidal resistance to a target plant.

DISCLOSURE OF THE INVENTION

Under such the circumstances, the present inventors intensively studied and, as a result, have found that a protoporphyrinogen oxidase (hereinafter, sometimes referred to as "PPO") inhibitory-type herbicidal compound may be converted by being reacted with a particular protein to a compound of lower herbicidal activity, which resulted in completion of the present invention.

That is, the present invention provides:
1. A DNA encoding a herbicide metabolizing protein, wherein said protein is selected from the group consisting of:
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;
(A4) a protein comprising the amino acid sequence shown in SEQ ID NO: 108;
(A5) a protein having an ability to convert in the presence of an electron transport system containing an electron donor, a compound of formula (II):

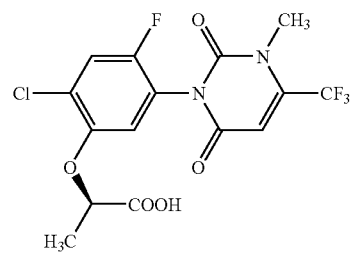

to a compound of formula (III):

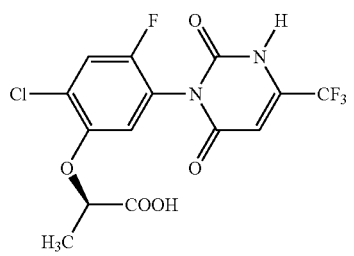

and comprising an amino acid sequence having at least 80% sequence identity with an amino acid sequence shown in any one of SEQ ID NO: 1, SEQ ID NO: 2, SEQ ID NO: 3 or SEQ ID NO: 108;
(A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
(A11) a protein comprising the amino acid sequence shown in SEQ ID NO: 159;
(A12) a protein comprising the amino acid sequence shown in SEQ ID NO: 160;
(A13) a protein comprising the amino acid sequence shown in SEQ ID NO: 136;
(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;
(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;

(A23) a protein comprising the amino acid sequence shown in SEQ ID NO: 222;
(A24) a protein comprising the amino acid sequence shown in SEQ ID NO: 223;
(A25) a protein comprising the amino acid sequence shown in SEQ ID NO: 224;
(A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224;
(A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224; and
(A28) a protein having an ability to convert in the presence of an electron transport system containing an electron donor, a compound of formula (II) to a compound of formula (III), and comprising an amino acid sequence encoded by a DNA amplifiable by a polymerase chain reaction with a primer comprising the nucleotide sequence shown in any one of SEQ ID NOs: 124 to 128, a primer comprising the nucleotide sequence shown in SEQ ID NO: 129 and as a template a chromosomal DNA of *Streptomyces phaeochromogenes, Streptomyces testaceus, Streptomyces achromogenes, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis, Streptomyces steffisburgensis* or *Saccharopolyspora taberi;*

2. A DNA comprising a nucleotide sequence selected from the group consisting of:
(a1) the nucleotide sequence shown in SEQ ID NO: 6;
(a2) the nucleotide sequence shown in SEQ ID NO: 7;
(a3) the nucleotide sequence shown in SEQ ID NO: 8;
(a4) the nucleotide sequence shown in SEQ ID NO: 109;
(a5) the nucleotide sequence shown in SEQ ID NO: 139;
(a6) the nucleotide sequence shown in SEQ ID NO: 140;
(a7) the nucleotide sequence shown in SEQ ID NO: 141;
(a8) the nucleotide sequence shown in SEQ ID NO: 142;
(a9) the nucleotide sequence shown in SEQ ID NO: 143;
(a10) the nucleotide sequence shown in SEQ ID NO: 225;
(a11) the nucleotide sequence shown in SEQ ID NO: 226;
(a12) the nucleotide sequence shown in SEQ ID NO: 227;
(a13) the nucleotide sequence shown in SEQ ID NO: 228;
(a14) the nucleotide sequence shown in SEQ ID NO: 229;
(a15) the nucleotide sequence shown in SEQ ID NO: 230;
(a16) the nucleotide sequence shown in SEQ ID NO: 231;
(a17) the nucleotide sequence shown in SEQ ID NO: 232;
(a18) the nucleotide sequence shown in SEQ ID NO: 233;
(a19) the nucleotide sequence shown in SEQ ID NO: 234;
(a20) a nucleotide sequence encoding an amino acid sequence of a protein having an ability to convert in the presence of an electron transport system containing an electron donor, a compound of formula (II) to a compound of formula (III), said nucleotide sequence having at least 80% sequence identity with a nucleotide sequence shown in any one of SEQ ID NO: 6, SEQ ID NO: 7, SEQ ID NO: 8 or SEQ ID NO: 109; and (a21) a nucleotide sequence encoding an amino acid sequence of a protein having an ability to convert in the presence of an electron transport system containing an electron donor, a compound of formula (II) to a compound of formula (III), said nucleotide sequence having at least 90% sequence identity with a nucleotide sequence shown in any one of SEQ ID NO: 139, SEQ ID NO: 140, SEQ ID NO: 141, SEQ ID NO: 142, SEQ ID NO: 143, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233 or SEQ ID NO: 234;

3. The DNA according to the above 1, comprising a nucleotide sequence encoding an amino acid sequence of said protein, wherein the codon usage in said nucleotide sequence is within the range of plus or minus 4% of the codon usage in genes from the species of a host cell to which the DNA is introduced and the GC content of said nucleotide sequence is at least 40% and at most 60%;

4. A DNA comprising the nucleotide sequence shown in SEQ ID NO: 214;

5. A DNA comprising the nucleotide sequence shown in SEQ ID NO: 368;

6. A DNA comprising the nucleotide sequence shown in SEQ ID NO: 393;

7. A DNA in which a DNA having a nucleotide sequence encoding an intracellular organelle transit signal sequence is linked upstream of the DNA according to the above 1 in frame;

8. A DNA in which the DNA according to the above 1 and a promoter functional in a host cell are operably linked;

9. A vector comprising the DNA according to the above 1;

10. A method of producing a vector comprising a step of inserting the DNA according to the above 1 into a vector replicable in a host cell;

11. A transformant in which the DNA according to the above 1 is introduced into a host cell;

12. The transformant according to the above 11, wherein the host cell is a microorganism cell or a plant cell;

13. A method of producing a transformant comprising a step of introducing into a host cell, the DNA according to the above 1;

14. A method of producing a protein having the ability to convert a compound of formula (II) to a compound of formula (III), said method comprising a steps of culturing the transformant according to the above 11 and recovering the produced said protein;

15. Use of the DNA according to the above 1 for producing a protein having the ability to convert a compound of formula (II) to a compound of formula (III);

16. A method of giving a plant resistance to a herbicide, said method comprising a step of introducing into and expressing in a plant cell, the DNA according to the above 1;

17. A polynucleotide having a partial nucleotide sequence of a DNA according to the above 1 or a nucleotide sequence complimentary to said partial nucleotide sequence;

18. A method of detecting a DNA encoding a protein having the ability to convert a compound of formula (II) to a compound of formula (III), said method comprising a step of detecting a DNA to which a probe is hybridized in a hybridization using as the probe the DNA according to the above 1 or the polynucleotide according to the above 17;

19. A method of detecting a DNA encoding a protein having the ability to convert a compound of formula (II) to a compound of formula (III), said method comprising a step of detecting a DNA amplified in a polymerase chain reaction with the polynucleotide according to the above 17 as a primer;

20. The method according to the above 19, wherein at least one of the primers is selected from the group consisting of a polynucleotide comprising the nucleotide sequence shown in any one of SEQ ID NOs:124 to 128 and a polynucleotide comprising the nucleotide sequence shown in SEQ ID NO: 129;

21. A method of obtaining a DNA encoding a protein having the ability to convert a compound of formula (II) to a compound of formula (III), said method comprising a step of recovering the DNA detected by the method according to the above 18 or 19.

22. A method of screening a cell having a DNA encoding a protein having the ability to convert a compound of formula (II) to a compound of formula (III), said method comprising a step of detecting said DNA from a test cell by the method according to the above 18 or 19;

23. A herbicide metabolizing protein selected from the group consisting of:
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;
(A4) a protein comprising the amino acid sequence shown in SEQ ID NO: 108;
(A5) a protein having an ability to convert in the presence of an electron transport system containing an electron donor, a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
(A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
(A11) a protein comprising the amino acid sequence shown in SEQ ID NO: 159;
(A12) a protein comprising the amino acid sequence shown in SEQ ID NO: 160;
(A13) a protein comprising the amino acid sequence shown in SEQ ID NO: 136;
(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;
(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;
(A23) a protein comprising the amino acid sequence shown in SEQ ID NO: 222;
(A24) a protein comprising the amino acid sequence shown in SEQ ID NO: 223;
(A25) a protein comprising the amino acid sequence shown in SEQ ID NO: 224;
(A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224;
(A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224; and
(A28) a protein having an ability to convert in the presence of an electron transport system containing an electron donor, a compound of formula (II) to a compound of formula (III), and comprising an amino acid sequence encoded by a DNA amplifiable by a polymerase chain reaction with a primer comprising the nucleotide sequence shown in any one of SEQ ID NOs: 124 to 128, a primer comprising the nucleotide sequence shown in SEQ ID NO: 129 and as a template a chromosomal DNA of *Streptomyces phaeochromogenes, Streptomyces testaceus, Streptomyces achromogenes, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis, Streptomyces steffisburgensis* or *Saccharopolyspora taberi;*

24. An antibody recognizing a herbicide metabolizing protein selected from the group consisting of:
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;

(A4) a protein comprising the amino acid sequence shown in SEQ ID NO: 108;
(A5) a protein having an ability to convert in the presence of an electron transport system containing an electron donor, a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
(A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
(A11) a protein comprising the amino acid sequence shown in SEQ ID NO: 159;
(A12) a protein comprising the amino acid sequence shown in SEQ ID NO: 160;
(A13) a protein comprising the amino acid sequence shown in SEQ ID NO: 136;
(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;
(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;
(A23) a protein comprising the amino acid sequence shown in SEQ ID NO: 222;
(A24) a protein comprising the amino acid sequence shown in SEQ ID NO: 223;
(A25) a protein comprising the amino acid sequence shown in SEQ ID NO: 224;
(A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224;
(A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224; and
(A28) a protein having an ability to convert in the presence of an electron transport system containing an electron donor, a compound of formula (II) to a compound of formula (III), and comprising an amino acid sequence encoded by a DNA amplifiable by a polymerase chain reaction with a primer comprising the nucleotide sequence shown in any one of SEQ ID NOs: 124 to 128, a primer comprising the nucleotide sequence shown in SEQ ID NO: 129 and as a template a chromosomal DNA of *Streptomyces phaeochromogenes, Streptomyces testaceus, Streptomyces achromogenes, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis, Streptomyces steffisburgensis* or *Saccharopolyspora taberi;*

25. A method of detecting a herbicide metabolizing protein, said method comprising: a step of contacting a test substance with an antibody recognizing said protein and a step of detecting a complex of said protein and said antibody, arising from said contact, wherein said protein is selected from the group consisting of:
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;
(A4) a protein comprising the amino acid sequence shown in SEQ ID NO: 108;
(A5) a protein having an ability to convert in the presence of an electron transport system containing an electron donor, a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
(A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
(A11) a protein comprising the amino acid sequence shown in SEQ ID NO: 159;
(A12) a protein comprising the amino acid sequence shown in SEQ ID NO: 160;
(A13) a protein comprising the amino acid sequence shown in SEQ ID NO: 136;
(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;

(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;
(A23) a protein comprising the amino acid sequence shown in SEQ ID NO: 222;
(A24) a protein comprising the amino acid sequence shown in SEQ ID NO: 223;
(A25) a protein comprising the amino acid sequence shown in SEQ ID NO: 224;
(A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224;
(A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224; and
(A28) a protein having an ability to convert in the presence of an electron transport system containing an electron donor, a compound of formula (II) to a compound of formula (III), and comprising an amino acid sequence encoded by a DNA amplifiable by a polymerase chain reaction with a primer comprising the nucleotide sequence shown in any one of SEQ ID NOs: 124 to 128, a primer comprising the nucleotide sequence shown in SEQ ID NO: 129 and as a template a chromosomal DNA of *Streptomyces phaeochromogenes, Streptomyces testaceus, Streptomyces achromogenes, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis, Streptomyces steffisburgensis* or *Saccharopolyspora taberi;*

26. An analysis or detection kit comprising the antibody according to the above 24;

27. A DNA encoding a ferredoxin selected from the group consisting of:
(B1) a protein comprising an amino acid sequence shown in SEQ ID NO: 12;
(B2) a protein comprising an amino acid sequence shown in SEQ ID NO: 13;
(B3) a protein comprising an amino acid sequence shown in SEQ ID NO: 14;
(B4) a protein comprising an amino acid sequence shown in SEQ ID NO: 111;
(B5) a ferredoxin comprising an amino acid sequence having at least 80% sequence identity with an amino acid sequence shown in any one of SEQ ID NO: 12, SEQ ID NO: 13, SEQ ID NO 14 or SEQ ID NO: 111;
(B6) a ferredoxin comprising an amino acid sequence encoded by a nucleotide sequence having at least 90% sequence identity with a nucleotide sequence encoding an amino acid sequence shown in any one of SEQ ID NO: 12, SEQ ID NO: 13, SEQ ID NO 14 or SEQ ID NO: 111;
(B7) a protein comprising an amino acid sequence shown in SEQ ID NO: 149;
(B8) a protein comprising an amino acid sequence shown in SEQ ID NO: 150;
(B9) a protein comprising an amino acid sequence shown in SEQ ID NO: 151;
(B10) a protein comprising an amino acid sequence shown in SEQ ID NO: 152;
(B11) a protein comprising an amino acid sequence shown in SEQ ID NO: 153;
(B12) a ferredoxin comprising an amino acid sequence having at least 80% sequence identity with an amino acid sequence shown in any one of SEQ ID NO: 149, SEQ ID NO: 151, SEQ ID NO: 152, SEQ ID NO: 153, SEQ ID NO: 245, SEQ ID NO: 247, SEQ ID NO: 248, SEQ ID NO: 249, SEQ ID NO: 250, SEQ ID NO: 251, or SEQ ID NO: 253 or an amino acid sequence having at least 90% sequence identity with an amino acid sequence shown in any one of SEQ ID NO: 150, SEQ ID NO: 252 or SEQ ID NO: 254;
(B13) a ferredoxin comprising an amino acid sequence encoded by a nucleotide sequence having at least 90% sequence identity with a nucleotide sequence encoding an amino acid sequence shown in any one of SEQ ID NO: 149, SEQ ID NO: 150, SEQ ID NO: 151, SEQ ID NO: 152, SEQ ID NO: 153, SEQ ID NO: 245, SEQ ID NO: 247, SEQ ID NO: 248, SEQ ID NO: 249, SEQ ID NO: 250, SEQ ID NO: 251, SEQ ID NO: 252, SEQ ID NO: 253 or SEQ ID NO: 254;
(B14) a protein comprising the amino acid sequence shown in SEQ ID NO: 245;
(B15) a protein comprising the amino acid sequence shown in SEQ ID NO: 247;
(B16) a protein comprising the amino acid sequence shown in SEQ ID NO: 248;
(B17) a protein comprising the amino acid sequence shown in SEQ ID NO: 249;
(B18) a protein comprising the amino acid sequence shown in SEQ ID NO: 250;
(B19) a protein comprising the amino acid sequence shown in SEQ ID NO: 251;
(B20) a protein comprising the amino acid sequence shown in SEQ ID NO: 252;
(B21) a protein comprising the amino acid sequence shown in SEQ ID NO: 253; and
(B22) a protein comprising the amino acid sequence shown in SEQ ID NO: 254;

28. A DNA comprising a nucleotide sequence selected from the group consisting of:
(b1) a nucleotide sequence shown in SEQ ID NO: 15;
(b2) a nucleotide sequence shown in SEQ ID NO: 16;
(b3) a nucleotide sequence shown in SEQ ID NO: 17;
(b4) a nucleotide sequence shown in SEQ ID NO: 112;
(b5) a nucleotide sequence shown in SEQ ID NO: 154;
(b6) a nucleotide sequence shown in SEQ ID NO: 155;

(b7) a nucleotide sequence shown in SEQ ID NO: 156;
(b8) a nucleotide sequence shown in SEQ ID NO: 157;
(b9) a nucleotide sequence shown in SEQ ID NO: 158;
(b10) a nucleotide sequence shown in SEQ ID NO: 255;
(b11) a nucleotide sequence shown in SEQ ID NO: 257;
(b12) a nucleotide sequence shown in SEQ ID NO: 258;
(b13) a nucleotide sequence shown in SEQ ID NO: 259;
(b14) a nucleotide sequence shown in SEQ ID NO: 260;
(b15) a nucleotide sequence shown in SEQ ID NO: 261;
(b16) a nucleotide sequence shown in SEQ ID NO: 262;
(b17) a nucleotide sequence shown in SEQ ID NO: 263;
(b18) a nucleotide sequence shown in SEQ ID NO: 264; and
(b19) a nucleotide sequence having at least 90% sequence identity with a nucleotide sequence shown in any one of SEQ ID NO: 15, SEQ ID NO: 16, SEQ ID NO: 17, SEQ ID NO: 112, SEQ ID NO: 154, SEQ ID NO: 155, SEQ ID NO: 156, SEQ ID NO: 157, SEQ ID NO: 158, SEQ ID NO: 255, SEQ ID NO: 257, SEQ ID NO: 258, SEQ ID NO: 259, SEQ ID NO: 260, SEQ ID NO: 261, SEQ ID NO: 262, SEQ ID NO: 263 or SEQ ID NO: 264;

29. A vector comprising a DNA according to the above 28;
30. A transformant in which the DNA according to the above 28 is introduced into a host cell;
31. A ferredoxin selected from the group consisting of:
(B1) a protein comprising an amino acid sequence shown in SEQ ID NO: 12;
(B2) a protein comprising an amino acid sequence shown in SEQ ID NO: 13;
(B3) a protein comprising an amino acid sequence shown in SEQ ID NO: 14;
(B4) a protein comprising an amino acid sequence shown in SEQ ID NO: 111;
(B5) a ferredoxin comprising an amino acid sequence having at least 80% sequence identity with an amino acid sequence shown in any one of SEQ ID NO: 12, SEQ ID NO: 13, SEQ ID NO 14 or SEQ ID NO: 111;
(B6) a ferredoxin comprising an amino acid sequence encoded by a nucleotide sequence having at least 90% sequence identity with a nucleotide sequence encoding an amino acid sequence shown in any one of SEQ ID NO: 12, SEQ ID NO: 13, SEQ ID NO 14 or SEQ ID NO: 111;
(B7) a protein comprising an amino acid sequence shown in SEQ ID NO: 149;
(B8) a protein comprising an amino acid sequence shown in SEQ ID NO: 150;
(B9) a protein comprising an amino acid sequence shown in SEQ ID NO: 151;
(B10) a protein comprising an amino acid sequence shown in SEQ ID NO: 152;
(B11) a protein comprising an amino acid sequence shown in SEQ ID NO: 153;
(B12) a ferredoxin comprising an amino acid sequence having at least 80% sequence identity with an amino acid sequence shown in any one of SEQ ID NO: 149, SEQ ID NO: 151, SEQ ID NO: 152, SEQ ID NO: 153, SEQ ID NO: 245, SEQ ID NO: 247, SEQ ID NO: 248, SEQ ID NO: 249, SEQ ID NO: 250, SEQ ID NO: 251, or SEQ ID NO: 253 or an amino acid sequence having at least 90% sequence identity with an amino acid sequence shown in any one of SEQ ID NO: 150, SEQ ID NO: 252 or SEQ ID NO: 254;
(B13) a ferredoxin comprising an amino acid sequence encoded by a nucleotide sequence having at least 90% sequence identity with a nucleotide sequence encoding an amino acid sequence shown in any one of SEQ ID NO: 149, SEQ ID NO: 150, SEQ ID NO: 151, SEQ ID NO: 152, SEQ ID NO: 153, SEQ ID NO: 245, SEQ ID NO: 247, SEQ ID NO: 248, SEQ ID NO: 249, SEQ ID NO: 250, SEQ ID NO: 251, SEQ ID NO: 252, SEQ ID NO: 253 or SEQ ID NO: 254;
(B14) a protein comprising the amino acid sequence shown in SEQ ID NO: 245;
(B15) a protein comprising the amino acid sequence shown in SEQ ID NO: 247;
(B16) a protein comprising the amino acid sequence shown in SEQ ID NO: 248;
(B17) a protein comprising the amino acid sequence shown in SEQ ID NO: 249;
(B18) a protein comprising the amino acid sequence shown in SEQ ID NO: 250;
(B19) a protein comprising the amino acid sequence shown in SEQ ID NO: 251;
(B20) a protein comprising the amino acid sequence shown in SEQ ID NO: 252;
(B21) a protein comprising the amino acid sequence shown in SEQ ID NO: 253; and
(B22) a protein comprising the amino acid sequence shown in SEQ ID NO: 254;

32. A DNA comprising a nucleotide sequence selected from the group consisting of:
(ab1) a nucleotide sequence shown in SEQ ID NO: 9;
(ab2) a nucleotide sequence shown in SEQ ID NO: 10;
(ab3) a nucleotide sequence shown in SEQ ID NO: 11;
(ab4) a nucleotide sequence shown in SEQ ID NO: 110;
(ab5) a nucleotide sequence shown in SEQ ID NO: 144;
(ab6) a nucleotide sequence shown in SEQ ID NO: 145;
(ab7) a nucleotide sequence shown in SEQ ID NO: 146;
(ab8) a nucleotide sequence shown in SEQ ID NO: 147;
(ab9) a nucleotide sequence shown in SEQ ID NO: 148;
(ab10) a nucleotide sequence shown in SEQ ID NO: 235;
(ab11) a nucleotide sequence shown in SEQ ID NO: 236;
(ab12) a nucleotide sequence shown in SEQ ID NO: 237;
(ab13) a nucleotide sequence shown in SEQ ID NO: 238;
(ab14) a nucleotide sequence shown in SEQ ID NO: 239;
(ab15) a nucleotide sequence shown in SEQ ID NO: 240;
(ab16) a nucleotide sequence shown in SEQ ID NO: 241;
(ab17) a nucleotide sequence shown in SEQ ID NO: 242;
(ab18) a nucleotide sequence shown in SEQ ID NO: 243; and
(ab19) a nucleotide sequence shown in SEQ ID NO: 244;

33. A vector comprising the DNA according to the above 32;
34. A transformant in which the DNA according to the above 32 is introduced into a host cell;
35. The transformant according to the above 34, wherein the host cell is a microorganism cell or a plant cell;
36. A method of producing a transformant comprising a step of introducing into a host cell the DNA according to the above 32;
37. A method of producing a protein having the ability to convert a compound of formula (II) to a compound of formula (III), said method comprising a step of culturing the transformant according to the above 34 and recovering the produced said protein;
38. A method of controlling weeds comprising a step of applying a compound to a cultivation area of a plant expressing at least one herbicide metabolizing protein selected from the group consisting of:
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;
(A4) a protein comprising the amino acid sequence shown in SEQ ID NO: 108;

(A5) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 1, SEQ ID NO: 2, SEQ ID NO: 3 or SEQ ID NO: 108;

(A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;

(A7) a protein having the ability to convert in the presence of an electron transport system containing an electron donor, a compound of formula (II) to a compound of formula (III), and comprising an amino acid sequence encoded by a DNA that hybridizes, under stringent conditions, to a DNA comprising a nucleotide sequence encoding an amino acid sequence shown in any one of SEQ ID NO: 1, SEQ ID NO: 2, SEQ ID NO: 3 or SEQ ID NO: 108;

(A8) a protein having the ability to convert in the presence of an electron transport system containing an electron donor, a compound of formula (II) to a compound of formula (III), and comprising an amino acid sequence encoded by a DNA amplifiable by a polymerase chain reaction with a primer comprising a nucleotide sequence shown in SEQ ID NO: 129, a primer comprising a nucleotide sequence shown in any one of SEQ ID NOs: 124 to 128, and as a template a chromosome of a microorganism belonging to *Streptomyces* or *Saccharopolyspora*;

(A9) a protein comprising an amino acid sequence shown in SEQ ID NO: 4;

(A11) a protein comprising the amino acid sequence shown in SEQ ID NO: 159;

(A12) a protein comprising the amino acid sequence shown in SEQ ID NO: 160;

(A13) a protein comprising the amino acid sequence shown in SEQ ID NO: 136;

(A14) a protein comprising the amino acid sequence shown in SEQ ID NO: 137;

(A15) a protein comprising the amino acid sequence shown in SEQ ID NO: 138;

(A16) a protein comprising the amino acid sequence shown in SEQ ID NO: 215;

(A17) a protein comprising the amino acid sequence shown in SEQ ID NO: 216;

(A18) a protein comprising the amino acid sequence shown in SEQ ID NO: 217;

(A19) a protein comprising the amino acid sequence shown in SEQ ID NO: 218;

(A20) a protein comprising the amino acid sequence shown in SEQ ID NO: 219;

(A21) a protein comprising the amino acid sequence shown in SEQ ID NO: 220;

(A22) a protein comprising the amino acid sequence shown in SEQ ID NO: 221;

(A23) a protein comprising the amino acid sequence shown in SEQ ID NO: 222;

(A24) a protein comprising the amino acid sequence shown in SEQ ID NO: 223;

(A25) a protein comprising the amino acid sequence shown in SEQ ID NO: 224;

(A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224; and (A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224, wherein said compound is a compound of formula (I):

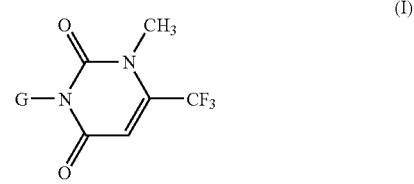

wherein in formula (I) G represents a group shown in any one of the following G-1 to G-9:

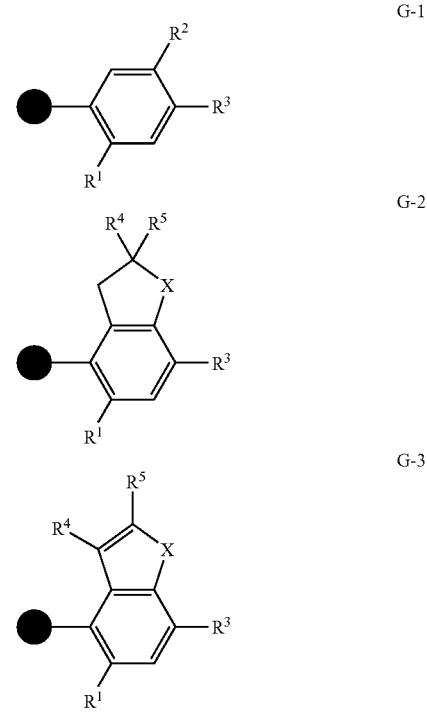

-continued

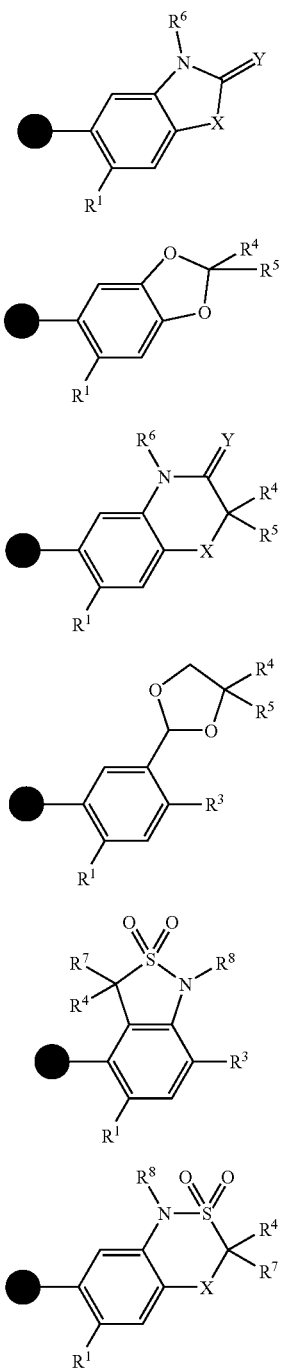

wherein in G-1 to G-9,
X represents an oxygen atom or sulfur atom;
Y represents an oxygen atom or sulfur atom;
$R^1$ represents a hydrogen atom or halogen atom;
$R^2$ represents a hydrogen atom, $C_1$-$C_8$ alkyl group, $C_1$-$C_8$ haloalkyl group, halogen atom, hydroxyl group, —$OR^9$ group, —SH group, —$S(O)pR^9$ group, —$COR^9$ group, —$CO_2R^9$ group, —$C(O)SR^9$ group, —$C(O)NR^{11}R^{12}$ group, —$CONH_2$ group, —CHO group, —$CR^9$=$NOR^{18}$ group, —CH=$CR^{19}CO_2R^9$ group, —$CH_2CHR^{19}CO_2R^9$ group, —$CO_2N$=$CR^{13}R^{14}$ group, nitro group, cyano group, —$NHSO_2R^{15}$ group, —$NHSO_2NHR^{15}$ group, —$NR^9R^{20}$ group, —$NH_2$ group or phenyl group that may be substituted with one or more $C_1$-$C_4$ alkyl groups which may be the same or different;
p represents 0, 1 or 2;
$R^3$ represents $C_1$-$C_2$ alkyl group, $C_1$-$C_2$ haloalkyl group, —$OCH_3$ group, —$SCH_3$ group, —$OCHF_2$ group, halogen atom, cyano group, nitro group or $C_1$-$C_3$ alkoxy group substituted with a phenyl group which may be substituted on the ring with at least one substituent selected from a halogen atom, $C_1$-$C_3$ alkyl group, $C_1$-$C_3$ haloalkyl group, $OR^{28}$ group, $NR^{11}R^{28}$ group, $SR^{28}$ group, cyano group, $CO_2R^{28}$ group and nitro group;
$R^4$ represents a hydrogen atom, $C_1$-$C_3$ alkyl group or $C_1$-$C_3$ haloalkyl group;
$R^5$ represents a hydrogen atom, $C_1$-$C_3$ alkyl group, $C_1$-$C_3$ haloalkyl group, cyclopropyl group, vinyl group, $C_2$ alkynyl group, cyano group, —$C(O)R^{20}$ group, —$CO_2R^{20}$ group, —$C(O)NR^{20}R^{21}$ group, —$CHR^{16}R^{17}CN$ group, —$CR^{16}R^{17}C(O)R^{20}$ group, —$C^{16}R^{17}C(O)R^{20}$ group, —$CR^{16}R^{17}C(O)NR^{20}R^{21}$ group, —$CHR^{16}OH$ group, —$CHR^{16}OC(O)R^{20}$ group or —$OCHR^{16}OC(O)NR^{20}R^{21}$ group, or, when G represents G-2 or G-6, $R^4$ and $R^5$ may represent C=O group together with the carbon atom to which they are attached;
$R^6$ represents $C_1$-$C_6$ alkyl group, $C_1$-$C_6$ haloalkyl group, $C_2$-$C_6$ alkoxyalkyl group, $C_3$-$C_6$ alkenyl group or $C_3$-$C_6$ alkynyl group;
$R^7$ represents a hydrogen atom, $C_1$-$C_6$ alkyl group, $C_1$-$C_6$ haloalkyl group, halogen atom, —$S(O)_2(C_1$-$C_6$ alkyl) group or —$C(=O)R^{22}$ group;
$R^8$ represents a hydrogen atom, $C_1$-$C_8$ alkyl group, $C_3$-$C_8$ cycloalkyl group, $C_3$-$C_8$ alkenyl group, $C_3$-$C_8$ alkynyl group, $C_1$-$C_8$ haloalkyl group, $C_2$-$C_8$ alkoxyalkyl group, $C_3$-$C_8$ alkoxyalkoxyalkyl group, $C_3$-$C_8$ haloalkynyl group, $C_3$-$C_8$ haloalkenyl group, $C_1$-$C_8$ alkylsulfonyl group, $C_1$-$C_8$ haloalkylsulfonyl group, $C_3$-$C_8$ alkoxycarbonylalkyl group, —$S(O)_2NH(C_1$-$C_8$ alkyl) group, —$C(O)R^{23}$ group or benzyl group which may be substituted with $R^{24}$ on the phenyl ring;
$R^9$ represents $C_1$-$C_8$ alkyl group, $C_3$-$C_8$ cycloalkyl group, $C_3$-$C_8$ alkenyl group, $C_3$-$C_8$ alkynyl group, $C_1$-$C_8$ haloalkyl group, $C_2$-$C_8$ alkoxyalkyl group, $C_2$-$C_8$ alkylthioalkyl group, $C_2$-$C_8$ alkylsulfinylalkyl group, $C_2$-$C_8$ alkylsulfonylalkyl group, $C_4$-$C_8$ alkoxyalkoxyalkyl group, $C_4$-$C_8$ cycloalkylalkyl group, $C_4$-$C_8$ cycloalkoxyalkyl group, $C_4$-$C_8$ alkenyloxyalkyl group, $C_4$-$C_8$ alkynyloxyalkyl group, $C_3$-$C_8$ haloalkoxyalkyl group, $C_4$-$C_8$ haloalkenyloxyalkyl group, $C_4$-$C_8$ haloalkynyloxyalkyl group, $C_4$-$C_8$ cycloalkylthioalkyl group, $C_4$-$C_8$ alkenylthioalkyl group, $C_4$-$C_8$ alkynylthioalkyl group, $C_1$-$C_4$ alkyl group substituted with a phenoxy group which may be substituted on the ring with at least one substituent selected from a halogen atom, $C_1$-$C_3$ alkyl group and $C_1$-$C_3$ haloalkyl group, $C_1$-$C_4$ alkyl group substituted with a benzyloxy group which may be substituted on the ring with at least one substituent selected from a halogen atom, $C_1$-$C_3$ alkyl group and $C_1$-$C_3$ haloalkyl group, $C_4$-$C_8$ trialkylsyrylalkyl group, $C_2$-$C_8$ cyanoalkyl group, $C_3$-$C_8$ halocycloalkyl group, $C_3$-$C_8$ haloalkenyl group, $C_5$-$C_8$ alkoxyalkenyl group, $C_5$-$C_8$ haloalkoxyalkenyl group, $C_5$-$C_8$ alkylthioalkenyl group, $C_3$-$C_8$ haloalkynyl group, $C_5$-$C_8$ alkoxyalkynyl group, $C_5$-$C_8$ haloalkoxyalkynyl group, $C_5$-$C_8$ alkylthioalkynyl group, $C_2$-$C_8$ alkylcarbonyl group, benzyl group which may be substituted on the ring with at least one substituent selected from a halogen atom, $C_1$-$C_3$ alkyl group, $C_1$-$C_3$ haloalkyl group, —$OR^{28}$ group, —$NR^{11}R^{28}$ group, —$SR^{28}$ group, cyano group, —$CO_2R^{28}$ group and nitro group, —$CR^{16}R^{17}COR^{10}$ group, —$CR^{16}R^{17}CO_2R^{20}$ group, —$CR^{16}R^{17}P(O)(OR^{10})_2$ group, —$CR^{16}R^{17}P(S)(OR^{10})_2$ group, —CR$^{16}$R$^{17}$C(O)NR$^{11}$R$^{12}$ group, —CR$^{16}$R$^{17}$C(O)NH$_2$ group, —C(=CR$^{26}$R$^{27}$)COR$^{10}$ group, —C(=CR$^{26}$R$^{27}$)CO$_2$R$^{20}$ group, —C(=CR$^{26}$R$^{27}$)P(O)(OR$^{10}$)$_2$ group, —C(=CR$^{26}$R$^{27}$)P(S)(OR$^{10}$)$_2$ group, —C(=CR$^{26}$R$^{27}$)C(O)NR$^{11}$R$^{12}$ group, —C(=CR$^{26}$R$^{27}$)C(O)NH$_2$ group, or any one of rings shown in Q-1 to Q-7:

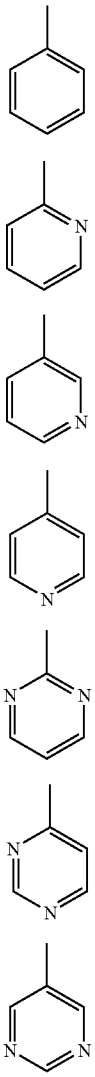

Q-1
Q-2
Q-3
Q-4
Q-5
Q-6
Q-7 which may be substituted on the ring with at least one substituent selected from a halogen atom, C$_1$-C$_6$ alkyl group, C$_1$-C$_6$ haloalkyl group, C$_2$-C$_6$ alkenyl group, C$_2$-C$_6$ haloalkenyl group, C$_2$-C$_6$ alkynyl group, C$_3$-C$_6$ haloalkynyl group, C$_2$-C$_8$ alkoxyalkyl group, —OR$^{28}$ group, —SR$^{28}$ group, —NR$^{11}$R$^{28}$ group, C$_3$-C$_8$ alkoxycarbonylalkyl group, C$_2$-C$_4$ carboxyalkyl group, —CO$_2$R$^{28}$ group and cyano group;

R$^{10}$ represents a C$_1$-C$_6$ alkyl group, C$_2$-C$_6$ alkenyl group, C$_3$-C$_6$ alkynyl group or tetrahydrofuranyl group;

R$^{11}$ and R$^{13}$ independently represent a hydrogen atom or C$_1$-C$_4$ alkyl group;

R$^{12}$ represents C$_1$-C$_6$ alkyl group, C$_3$-C$_6$ cycloalkyl group, C$_3$-C$_6$ alkenyl group, C$_3$-C$_6$ alkynyl group, C$_2$-C$_6$ alkoxyalkyl group, C$_1$-C$_6$ haloalkyl group, C$_3$-C$_6$ haloalkenyl group, C$_3$-C$_6$ haloalkynyl group, phenyl group which may be substituted on the ring with at least one substituent selected from a halogen atom, C$_1$-C$_4$ alkyl group and C$_1$-C$_4$ alkoxy group or —CR$^{16}$R$^{17}$CO$_2$R$^{25}$ group; or, R$^{11}$ and R$^{12}$ together may represent —(CH$_2$)$_5$—, —(CH$_2$)$_4$— or —CH$_2$CH$_2$OCH$_2$CH$_2$—, or in that case the resulting ring may be substituted with a substituent selected from a C$_1$-C$_3$ alkyl group, a phenyl group and benzyl group;

R$^{14}$ represents a C$_1$-C$_4$ alkyl group or phenyl group which may be substituted on the ring with a substituent selected from a halogen atom, C$_1$-C$_3$ alkyl group and C$_1$-C$_3$ haloalkyl group; or, R$^{13}$ and R$^{14}$ may represent C$_3$-C$_8$ cycloalkyl group together with the carbon atom to which they are attached;

R$^{15}$ represents C$_1$-C$_4$ alkyl group, C$_1$-C$_4$ haloalkyl group or C$_3$-C$_6$ alkenyl group;

R$^{16}$ and R$^{17}$ independently represent a hydrogen atom or C$_1$-C$_4$ alkyl group, C$_1$-C$_4$ haloalkyl group, C$_2$-C$_4$ alkenyl group, C$_2$-C$_4$ haloalkenyl group, C$_2$-C$_4$ alkynyl group, C$_3$-C$_4$ haloalkynyl group; or, R$^{16}$ and R$^{17}$ may represent C$_3$-C$_6$ cycloalkyl group with the carbon atom to which they are attached, or the ring thus formed may be substituted with at least one substituent selected from a halogen atom, a C$_1$-C$_3$ alkyl group and C$_1$-C$_3$ haloalkyl group;

R$^{18}$ represents a hydrogen atom, C$_1$-C$_6$ alkyl group, C$_3$-C$_6$ alkenyl group or C$_3$-C$_6$ alkynyl group;

R$^{19}$ represents a hydrogen atom, C$_1$-C$_4$ alkyl group or halogen atom,

R$^{20}$ represents a hydrogen atom, C$_1$-C$_6$ alkyl group, C$_3$-C$_6$ cycloalkyl group, C$_3$-C$_6$ alkenyl group, C$_3$-C$_6$ alkynyl group, C$_2$-C$_6$ alkoxyalkyl group, C$_1$-C$_6$ haloalkyl group, C$_3$-C$_6$ haloalkenyl group, C$_3$-C$_6$ haloalkynyl group, phenyl group which may be substituted on the ring with at least one substituent selected from a halogen atom, C$_1$-C$_4$ alkyl group and —OR$^{28}$ group, or —CR$^{16}$R$^{17}$CO$_2$R$^{25}$ group;

R$^{21}$ represents a hydrogen atom, C$_1$-C$_2$ alkyl group or —CO$_2$(C$_1$-C$_4$ alkyl) group;

R$^{22}$ represents a hydrogen atom, C$_1$-C$_6$ alkyl group, C$_1$-C$_6$ alkoxy group or NH(C$_1$-C$_6$ alkyl) group;

R$^{23}$ represents C$_1$-C$_6$ alkyl group, C$_1$-C$_6$ haloalkyl group, C$_1$-C$_6$ alkoxy group, NH(C$_1$-C$_6$ alkyl) group, benzyl group, C$_2$-C$_8$ dialkylamino group or phenyl group which may be substituted with R$^{24}$;

R$^{24}$ represents C$_1$-C$_6$ alkyl group, 1 to 2 halogen atoms, C$_1$-C$_6$ alkoxy group or CF$_3$ group;

R$^{25}$ represents C$_1$-C$_6$ alkyl group, C$_1$-C$_6$ haloalkyl group, C$_3$-C$_6$ alkenyl group, C$_3$-C$_6$ haloalkenyl group, C$_3$-C$_6$ alkynyl group or C$_3$-C$_6$ haloalkynyl group;

R$^{26}$ and R$^{27}$ each represent independently a hydrogen atom, C$_1$-C$_4$ alkyl group, C$^1$—C$^4$ haloalkyl group, C$^2$—C$^4$ alkenyl group, C$^2$—C$^4$ haloalkenyl group, C$^2$—C$^4$ alkynyl group, C$^3$—C$^4$ haloalkynyl group, —OR$^{28}$ group, —NHR$^{28}$ group, or —SR$^{28}$ group; or, R$^{26}$ and R$^{27}$ may represent C$_3$-C$_8$ cycloalkyl group with the carbon atom to which they are attached, or each of the ring thus formed may be substituted with at least one substituent selected from a halogen atom, C$_1$-C$_3$ alkyl group and C$_1$-C$_3$ haloalkyl group; and, R$^{28}$ represents a hydrogen atom, C$_1$-C$_6$ alkyl group, C$_1$-C$_6$ haloalkyl group, C$_3$-C$_6$ alkenyl group, C$_3$-C$_6$ haloalkenyl group, C$_3$-C$_6$ alkynyl group, C$_3$-C$_6$ haloalkynyl group, C$_2$-C$_4$ carboxyalkyl group, C$_3$-C$_8$ alkoxycarbonylalkyl group, C$_3$-C$_8$ haloalkoxycarbonylalkyl group, C$_5$-C$_9$ alkenyloxycabonylalkyl group, C$_5$-C$_9$ haloalkenyloxycabonylalkyl group, C$_5$-C$_9$ alkynyloxycabonylalkyl group, C$_5$-C$_9$ haloalkynyloxycabonylalkyl group, C$_5$-C$_9$ cycloalkoxycabonylalkyl group or C$_5$-C$_9$ halocycloalkoxycabonylalkyl group;

39. A method of controlling weeds comprising a step of applying a compound to a cultivation area of a plant expressing at least one protein selected from the group consisting of:
- (A1) a protein comprising the amino acid sequence shown in SEQ ID NO: 1;
- (A2) a protein comprising the amino acid sequence shown in SEQ ID NO: 2;
- (A3) a protein comprising the amino acid sequence shown in SEQ ID NO: 3;
- (A4) a protein comprising the amino acid sequence shown in SEQ ID NO: 108;
- (A5) a protein having an ability to convert in the presence of an electron transport system containing an electron donor, a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
- (A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
- (A11) a protein comprising the amino acid sequence shown in SEQ ID NO: 159;
- (A12) a protein comprising the amino acid sequence shown in SEQ ID NO: 160;
- (A13) a protein comprising the amino acid sequence shown in SEQ ID NO: 136;
- (A14) a protein comprising the amino acid sequence shown in SEQ ID NO: 137;
- (A15) a protein comprising the amino acid sequence shown in SEQ ID NO: 138;
- (A16) a protein comprising the amino acid sequence shown in SEQ ID NO: 215;
- (A17) a protein comprising the amino acid sequence shown in SEQ ID NO: 216;
- (A18) a protein comprising the amino acid sequence shown in SEQ ID NO: 217;
- (A19) a protein comprising the amino acid sequence shown in SEQ ID NO: 218;
- (A20) a protein comprising the amino acid sequence shown in SEQ ID NO: 219;
- (A21) a protein comprising the amino acid sequence shown in SEQ ID NO: 220;
- (A22) a protein comprising the amino acid sequence shown in SEQ ID NO: 221;
- (A23) a protein comprising the amino acid sequence shown in SEQ ID NO: 222;
- (A24) a protein comprising the amino acid sequence shown in SEQ ID NO: 223;
- (A25) a protein comprising the amino acid sequence shown in SEQ ID NO: 224;
- (A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224;
- (A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224; and
- (A28) a protein having an ability to convert in the presence of an electron transport system containing an electron donor, a compound of formula (II) to a compound of formula (III), and comprising an amino acid sequence encoded by a DNA amplifiable by a polymerase chain reaction with a primer comprising the nucleotide sequence shown in any one of SEQ ID NOs: 124 to 128, a primer comprising the nucleotide sequence shown in SEQ ID NO: 129 and as a template a chromosomal DNA of *Streptomyces phaeochromogenes, Streptomyces testaceus, Streptomyces achromogenes, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis, Streptomyces steffisburgensis* or *Saccharopolyspora taberi;*

40. A method of evaluating the resistance of a cell to a compound of formula (I), said method comprising:
    (1) a step of contacting said compound with a cell expressing at least one herbicide metabolizing protein selected from the group consisting of:
- (A1) a protein comprising the amino acid sequence shown in SEQ ID NO: 1;
- (A2) a protein comprising the amino acid sequence shown in SEQ ID NO: 2;
- (A3) a protein comprising the amino acid sequence shown in SEQ ID NO: 3;
- (A4) a protein comprising the amino acid sequence shown in SEQ ID NO: 108;
- (A5) a protein having an ability to convert in the presence of an electron transport system containing an electron donor, a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
- (A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
- (A7) a protein having the ability to convert in the presence of an electron transport system containing an electron donor, a compound of formula (II) to a compound of formula (III), and comprising an amino acid sequence encoded by a DNA that hybridizes, under stringent conditions, to a DNA comprising a nucleotide sequence encoding an amino acid sequence shown in any one of SEQ ID NO: 1, SEQ ID NO: 2, SEQ ID NO: 3 or SEQ ID NO: 108;

(A8) a protein having the ability to convert in the presence of an electron transport system containing an electron donor, a compound of formula (II) to a compound of formula (III), and comprising an amino acid sequence encoded by a DNA amplifiable by a polymerase chain reaction with a primer comprising a nucleotide sequence shown in SEQ ID NO: 129, a primer comprising a nucleotide sequence shown in any one of SEQ ID NOs: 124 to 128, and as a template a chromosome of a microorganism belonging to *Streptomyces* or *Saccharopolyspora*;

(A9) a protein comprising an amino acid sequence shown in SEQ ID NO: 4;

(A11) a protein comprising the amino acid sequence shown in SEQ ID NO: 159;

(A12) a protein comprising the amino acid sequence shown in SEQ ID NO: 160;

(A13) a protein comprising the amino acid sequence shown in SEQ ID NO: 136;

(A14) a protein comprising the amino acid sequence shown in SEQ ID NO: 137;

(A15) a protein comprising the amino acid sequence shown in SEQ ID NO: 138;

(A16) a protein comprising the amino acid sequence shown in SEQ ID NO: 215;

(A17) a protein comprising the amino acid sequence shown in SEQ ID NO: 216;

(A18) a protein comprising the amino acid sequence shown in SEQ ID NO: 217;

(A19) a protein comprising the amino acid sequence shown in SEQ ID NO: 218;

(A20) a protein comprising the amino acid sequence shown in SEQ ID NO: 219;

(A21) a protein comprising the amino acid sequence shown in SEQ ID NO: 220;

(A22) a protein comprising the amino acid sequence shown in SEQ ID NO: 221;

(A23) a protein comprising the amino acid sequence shown in SEQ ID NO: 222;

(A24) a protein comprising the amino acid sequence shown in SEQ ID NO: 223;

(A25) a protein comprising the amino acid sequence shown in SEQ ID NO: 224;

(A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224; and (A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223 or SEQ ID NO: 224; and (2) a step of evaluating the degree of damage to the cell which contacted the compound in the above step (1);

41. The method according to the above 40, wherein the cell is a microorganism cell or plaint cell;

42. A method of selecting a cell resistant to a compound of formula (I), said method comprising a step of selecting a cell based on the resistance evaluated in the method according to the above 40;

43. The cell resistant to herbicide selected by the method according to the above 42, or the culture thereof;

44. A method of evaluating the resistance of a plant to a compound of formula (I), said method comprising:

(1) a step of contacting said compound with a plant expressing at least one herbicide metabolizing protein selected from the group consisting of:

(A1) a protein comprising the amino acid sequence shown in SEQ ID NO: 1;

(A2) a protein comprising the amino acid sequence shown in SEQ ID NO: 2;

(A3) a protein comprising the amino acid sequence shown in SEQ ID NO: 3;

(A4) a protein comprising the amino acid sequence shown in SEQ ID NO: 108;

(A5) a protein having an ability to convert in the presence of an electron transport system containing an electron donor, a compound of formula (II) to a compound of formula (III) and comprising an amino acid sequence having at least 80% sequence identity with an amino acid sequences shown in any one of SEQ ID NO: 1, SEQ ID NO: 2, SEQ ID NO: 3 or SEQ ID NO: 108;

(A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;

(A7) a protein having the ability to convert in the presence of an electron transport system containing an electron donor, a compound of formula (II) to a compound of formula (III), and comprising an amino acid sequence encoded by a DNA that hybridizes, under stringent conditions, to a DNA comprising a nucleotide sequence encoding an amino acid sequence shown in SEQ ID NO: 1, SEQ ID NO: 2, SEQ ID NO: 3 or SEQ ID NO: 108;

(A8) a protein having the ability to convert in the presence of an electron transport system containing an electron donor a compound of formula (II) to a compound of formula (III), and comprising an amino acid sequence encoded by a DNA amplifiable by a polymerase chain reaction with a primer comprising a nucleotide sequence shown in SEQ ID NO: 129, a primer comprising a nucleotide sequence shown in any one of SEQ ID NOs: 124 to 128, and as a template a chromosome of a microorganism belonging to *Streptomyces* or *Saccharopolyspora*;

(A9) a protein comprising an amino acid sequence shown in SEQ ID NO: 4;

(A11) a protein comprising the amino acid sequence shown in SEQ ID NO: 159;

(A12) a protein comprising the amino acid sequence shown in SEQ ID NO: 160;

(A13) a protein comprising the amino acid sequence shown in SEQ ID NO: 136;

(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;
(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;
(A23) a protein comprising the amino acid sequence shown in SEQ ID NO: 222;
(A24) a protein comprising the amino acid sequence shown in SEQ ID NO: 223;
(A25) a protein comprising the amino acid sequence shown in SEQ ID NO: 224;
(A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224; and
(A27) a protein having the ability to convert in the presence of an electron transport system containing an electron donor a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224; and
(2) a step of evaluating the degree of damage to the plant which contacted the compound described in step (1);
45. A method of selecting a plant resistant to a compound of formula (I), said method comprising a step of selecting a plant based on the resistance evaluated in the method according to the above 44;
46. A herbicidally resistant plant selected from the method according to the above 45, or the progeny thereof;
47. A method of treating a compound of formula (I), said method comprising reacting said compound in the presence of an electron transport system containing an electron donor, with at least one herbicide metabolizing protein selected from the group consisting of:
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;
(A4) a protein comprising the amino acid sequence shown in SEQ ID NO: 108;
(A5) a protein having an ability to convert in the presence of an electron transport system containing an electron donor, a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
(A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
(A7) a protein having the ability to convert in the presence of an electron transport system containing an electron donor, a compound of formula (II) to a compound of formula (III), and comprising an amino acid sequence encoded by a DNA that hybridizes, under stringent conditions, to a DNA comprising a nucleotide sequence encoding an amino acid sequence shown in any one of SEQ ID NO: 1, SEQ ID NO: 2, SEQ ID NO: 3 or SEQ ID NO: 108;
(A8) a protein having the ability to convert in the presence of an electron transport system containing an electron donor, a compound of formula (II) to a compound of formula (III), and comprising an amino acid sequence encoded by a DNA amplifiable by a polymerase chain reaction with a primer comprising a nucleotide sequence shown in SEQ ID NO: 129, a primer comprising a nucleotide sequence shown in any one of SEQ ID NOs: 124 to 128, and as a template a chromosome of a microorganism belonging to *Streptomyces* or *Saccharopolyspora*;
(A9) a protein comprising an amino acid sequence shown in SEQ ID NO: 4;
(A11) a protein comprising the amino acid sequence shown in SEQ ID NO: 159;
(A12) a protein comprising the amino acid sequence shown in SEQ ID NO: 160;
(A13) a protein comprising the amino acid sequence shown in SEQ ID NO: 136;
(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;
(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;
(A23) a protein comprising the amino acid sequence shown in SEQ ID NO: 222;
(A24) a protein comprising the amino acid sequence shown in SEQ ID NO: 223;

(A25) a protein comprising the amino acid sequence shown in SEQ ID NO: 224;
(A26) a protein having an ability to convert in the presence of an electron transport system containing an electron donor a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224; and
(A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224;
48. The method according to the above 47, wherein reacting the compound with the herbicide metabolizing protein by contacting the compound with a transformant in which a DNA encoding the herbicide metabolizing protein is introduced into a host cell in a position enabling its expression in said cell;
49. Use for treating the compound of formula (I) of a herbicide metabolizing protein selected from the group consisting of:
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;
(A4) a protein comprising the amino acid sequence shown in SEQ ID NO: 108;
(A5) a protein having an ability to convert in the presence of an electron transport system containing an electron donor, a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
(A6) a protein having an ability to convert in the presence of an electron transport system containing an electron donor, a compound of formula (II) to a compound of formula (III), and comprising an amino acid sequence encoded by a nucleotide sequence having at least 80% sequence identity with a nucleotide sequence encoding any one of the amino acid sequences shown in any one of SEQ ID NO: 1, SEQ ID NO: 2, SEQ ID NO: 3 or SEQ ID NO: 108;
(A7) a protein having the ability to convert in the presence of an electron transport system containing an electron donor, a compound of formula (II) to a compound of formula (III), and comprising an amino acid sequence encoded by a DNA that hybridizes, under stringent conditions, to a DNA comprising a nucleotide sequence encoding an amino acid sequence shown in SEQ ID NO: 1, SEQ ID NO: 2, SEQ ID NO: 3 or SEQ ID NO: 108;
(A8) a protein having the ability to convert in the presence of an electron transport system containing an electron donor, a compound of formula (II) to a compound of formula (III), and comprising an amino acid sequence encoded by a DNA amplifiable by a polymerase chain reaction with a primer comprising a nucleotide sequence shown in SEQ ID NO: 129, a primer comprising a nucleotide sequence shown in any one of SEQ ID NOs: 124 to 128, and as a template chromosome of a microorganism belonging to Streptomyces or Saccharopolyspora;
(A9) a protein comprising an amino acid sequence shown in SEQ ID NO: 4;
(A11) a protein comprising the amino acid sequence shown in SEQ ID NO: 159;
(A12) a protein comprising the amino acid sequence shown in SEQ ID NO: 160;
(A13) a protein comprising the amino acid sequence shown in SEQ ID NO: 136;
(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;
(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;
(A23) a protein comprising the amino acid sequence shown in SEQ ID NO: 222;
(A24) a protein comprising the amino acid sequence shown in SEQ ID NO: 223;
(A25) a protein comprising the amino acid sequence shown in SEQ ID NO: 224;
(A26) a protein having an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224; and
(A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding the amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224; and 50. Use for treating a compound of formula (I) of a polynucleotide encoding a herbicide metabolizing protein selected from the group consisting of
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;
(A4) a protein comprising the amino acid sequence shown in SEQ ID NO: 108;
(A5) a protein having an ability to convert in the presence of an electron transport system containing an electron donor, a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
(A6) a protein having an ability to convert in the presence of an electron transport system containing an electron donor a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
(A7) a protein having the ability to convert in the presence of an electron transport system containing an electron donor, a compound of formula (II) to a compound of formula (III), and comprising an amino acid sequence encoded by a DNA that hybridizes, under stringent conditions, to a DNA comprising a nucleotide sequence encoding an amino acid sequence shown in SEQ ID NO: 1, SEQ ID NO: 2, SEQ ID NO: 3 or SEQ ID NO: 108;
(A8) a protein having the ability to convert in the presence of an electron transport system containing an electron donor, a compound of formula (II) to a compound of formula (III), and comprising an amino acid sequence encoded by a DNA amplifiable by a polymerase chain reaction with a primer comprising a nucleotide sequence shown in SEQ ID NO: 129, a primer comprising a nucleotide sequence shown in any one of SEQ ID NOs: 124 to 128, and as a template a chromosome of a microorganism belonging to *Streptomyces* or *Saccharopolyspora*;
(A9) a protein comprising an amino acid sequence shown in SEQ ID NO: 4;
(A11) a protein comprising the amino acid sequence shown in SEQ ID NO: 159;
(A12) a protein comprising the amino acid sequence shown in SEQ ID NO: 160;
(A13) a protein comprising the amino acid sequence shown in SEQ ID NO: 136;
(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;
(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;
(A23) a protein comprising the amino acid sequence shown in SEQ ID NO: 222;
(A24) a protein comprising the amino acid sequence shown in SEQ ID NO: 223;
(A25) a protein comprising the amino acid sequence shown in SEQ ID NO: 224;
(A26) a protein comprising an ability to convert in the presence of an electron transport system containing an electron donor, a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224; and
(A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224.

The arrows show the annealing sites of the oligonucleotide primers having the nucleotide sequence shown with the SEQ ID number thereof and the extention direction of the DNA polymerase reaction from the primers. The dotted lines represent the DNA amplified by the PCR utilizing the primers. The thick line represents the region adjacent to the DNA insertion site of the vector utilized to produce the chromosomal DNA library. However, the oligonucleotide primer represented by 57, is a primer which anneals to the region adjacent to the DNA insertion site of the vector utilized to produce the chromosomal DNA library, and fails to anneal with the present invention DNA (A4).

Figure 4:
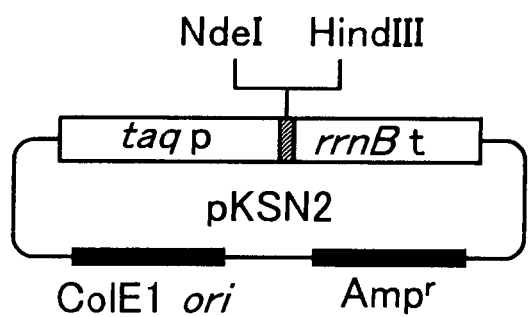

FIG. 4 shows the restriction map of the plasmid pKSN2.

Figure 5:
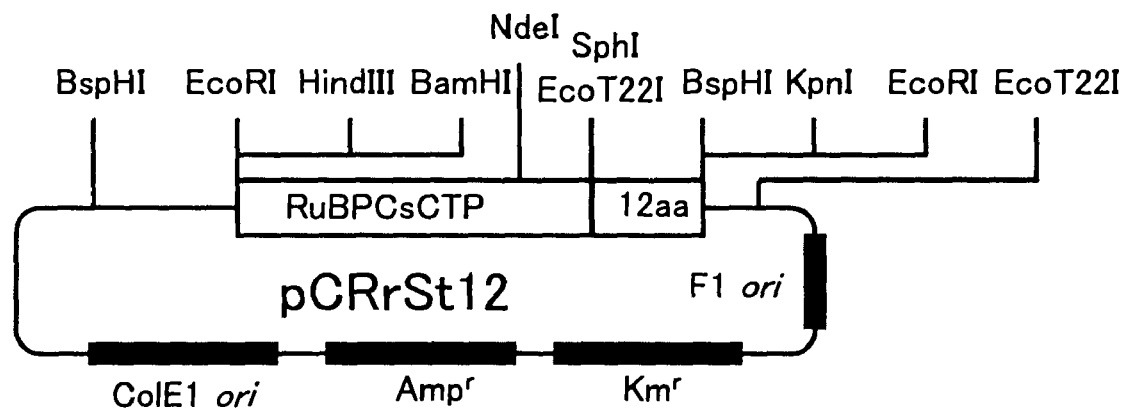

FIG. 5 shows the restriction map of the plasmid pCRrStl2.

Figure 6:
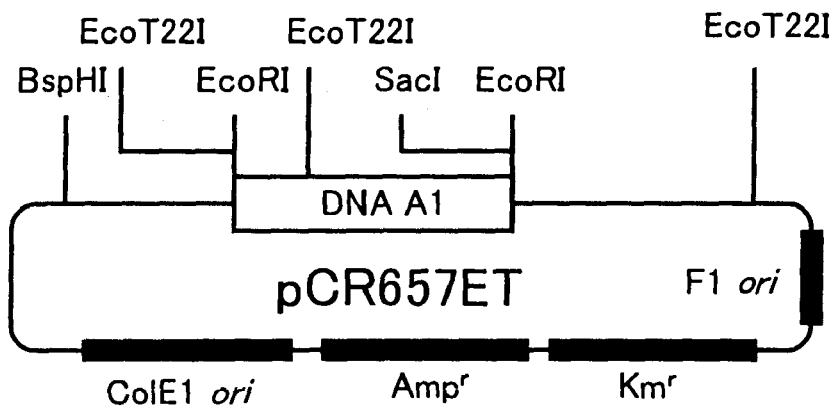

FIG. 6 shows the restriction map of the plasmid pCR657ET.

Figure 7:
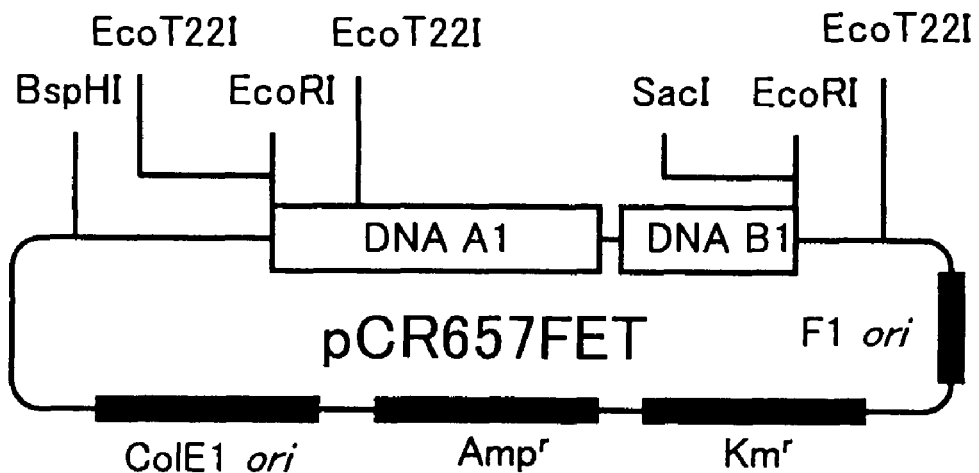

FIG. 7 shows the restriction map of the plasmid pCR657FET.

Figure 8:
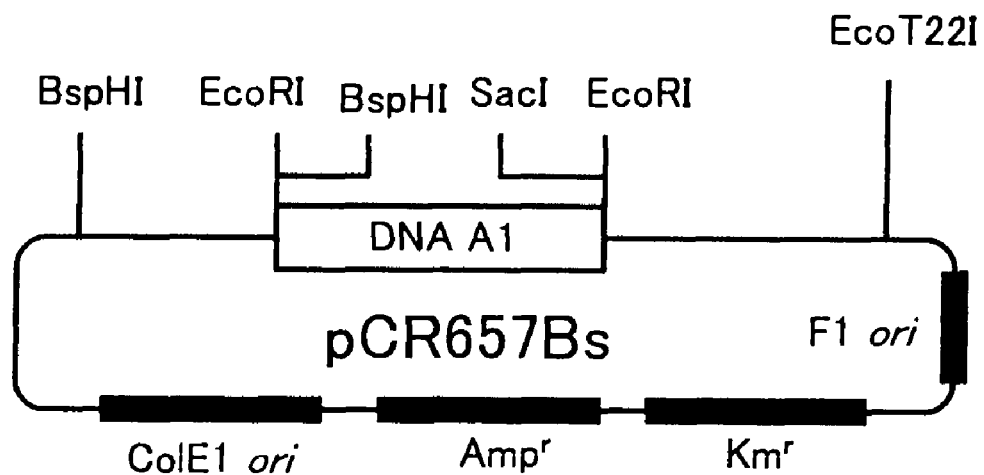

FIG. 8 shows the restriction map of the plasmid pCR657Bs.

Figure 9:
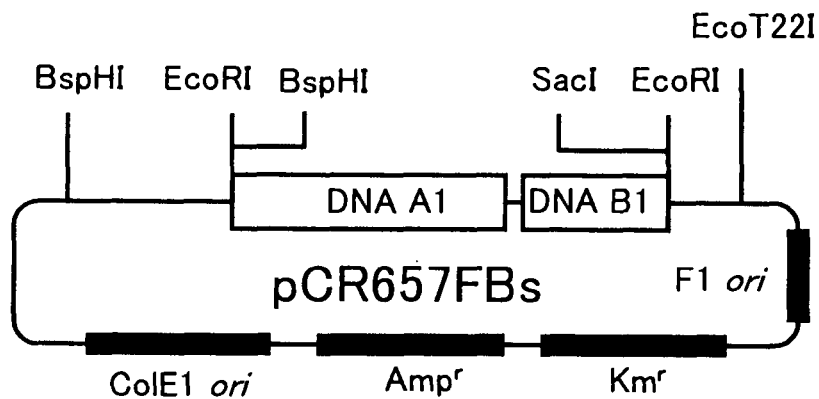

FIG. 9 shows the restriction map of the plasmid pCR657FBs.

Figure 10:
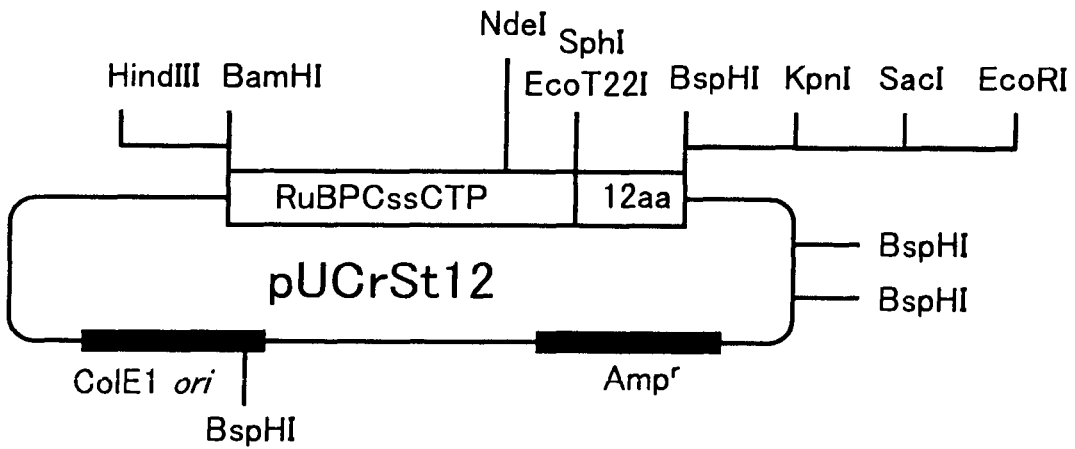
Figure 1:
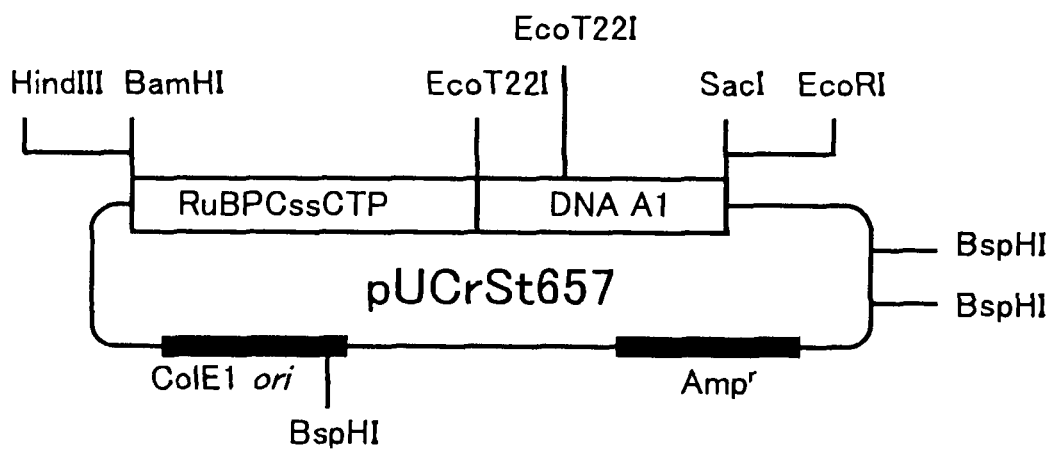
Figure 1:
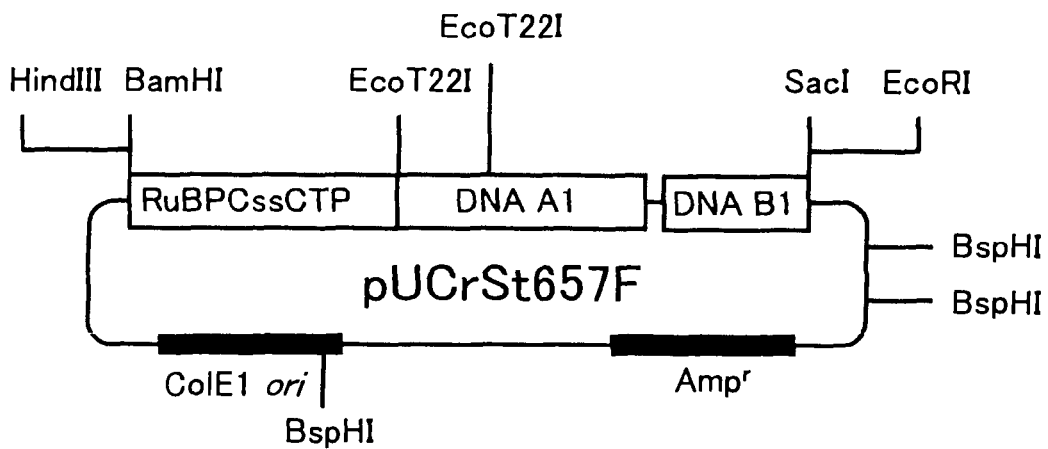
Figure 1:
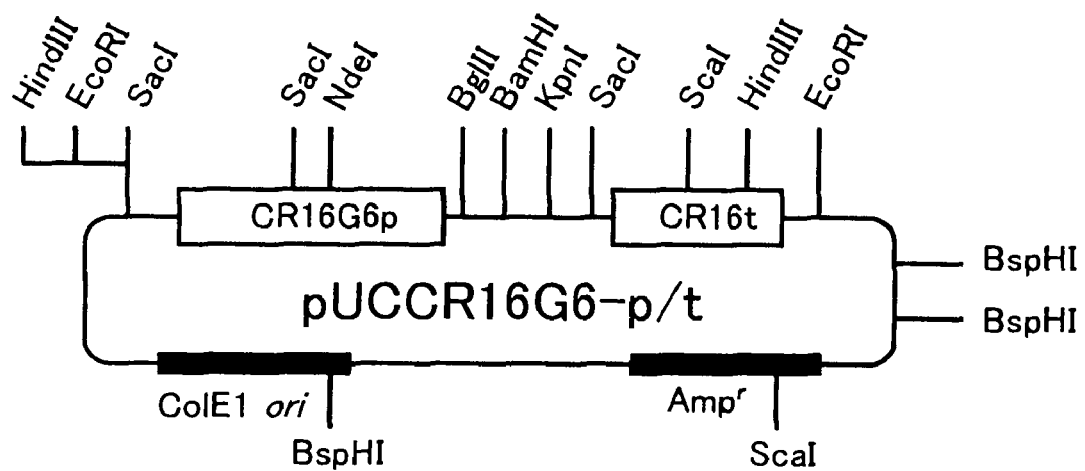

FIG. 10 shows the restriction map of the plasmid pUCrSt12.

FIG. 11 shows the restriction map of the plasmid pUCrSt657.

FIG. 12 shows the restriction map of the plasmid pUCrSt657F.

FIG. 13 shows the restriction map of the plasmid pUCCR16G6-p/t.

FIG. 14 shows the structure of the linker NotI-EcoRI produced by annealing the oligonucleotide consisting of the nucleotide sequence shown in SEQ ID NO: 89 and the oligonucleotide consisting of the nucleotide sequence shown in SEQ ID NO: 90.

FIG. 15 shows the restriction map of the plasmid pUCCR16G6-p/tΔ.

FIG. 16 shows the structure of the linker HindIII-NotI produced by annealing the oligonucleotide consisting of the nucleotide sequence shown in SEQ ID NO: 91 and the oligonucleotide consisting of the nucleotide sequence shown in SEQ ID NO: 92.

FIG. 17 shows the restriction map of the plasmid pNdG6-ΔT.

Figure 18:
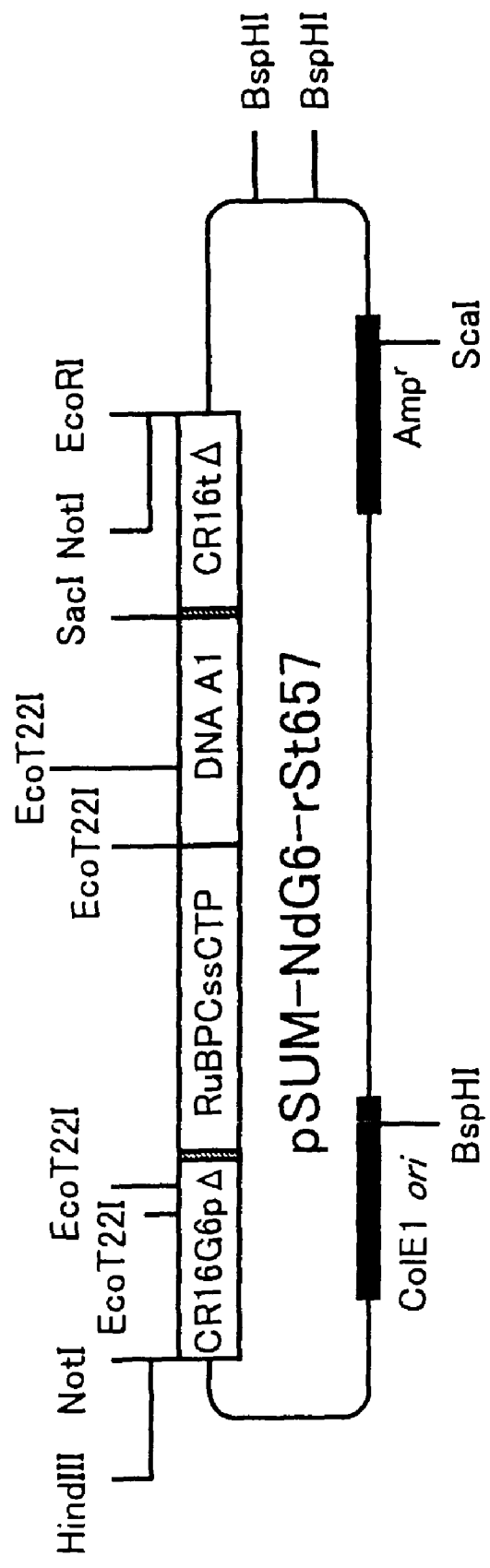

FIG. 18 shows the restriction map of the plasmid pSUM-NdG6-rSt657.

Figure 19:
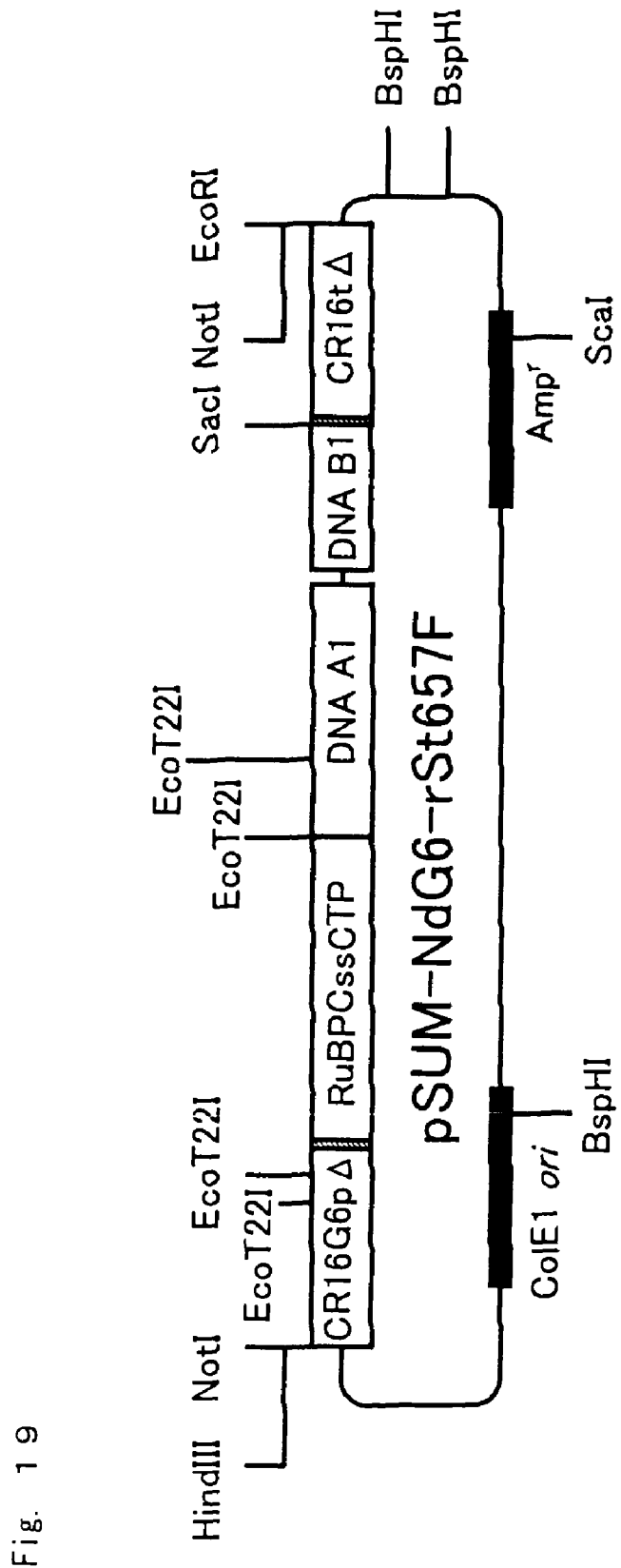

FIG. 19 shows the restriction map of the plasmid pSUM-NdG6-rSt657F.

Figure 20:
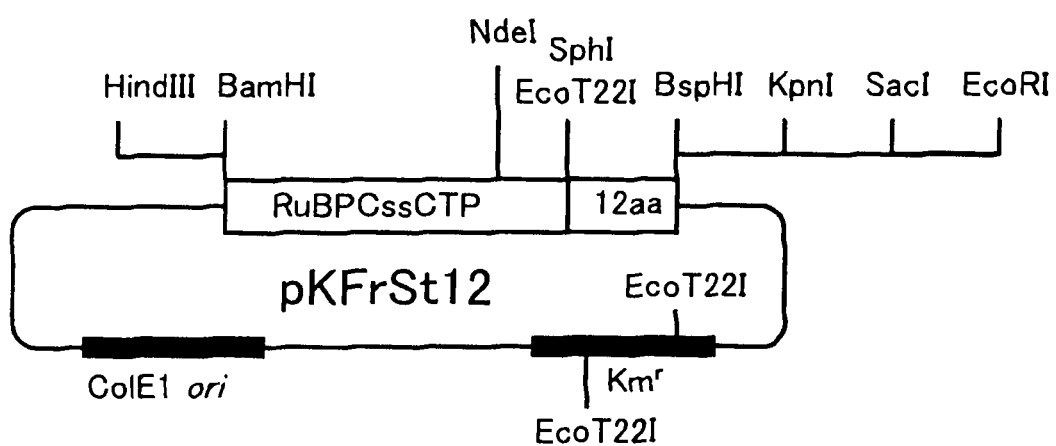

FIG. 20 shows the restriction map of the plasmid pKFrSt12.

Figure 21:
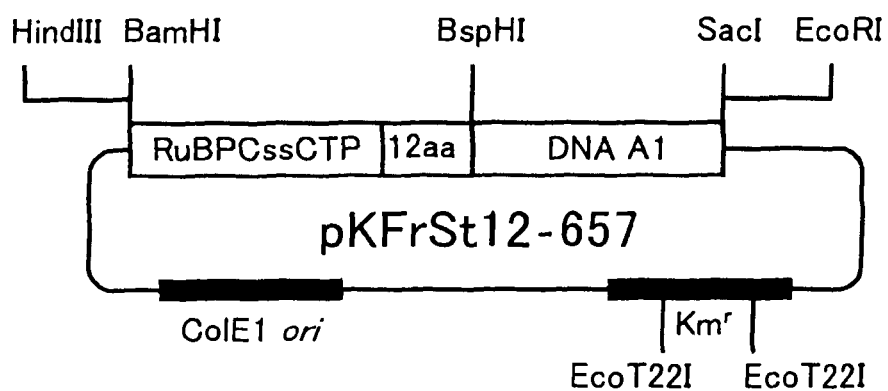

FIG. 21 shows the restriction map of the plasmid pKFrSt12-657.

Figure 22:
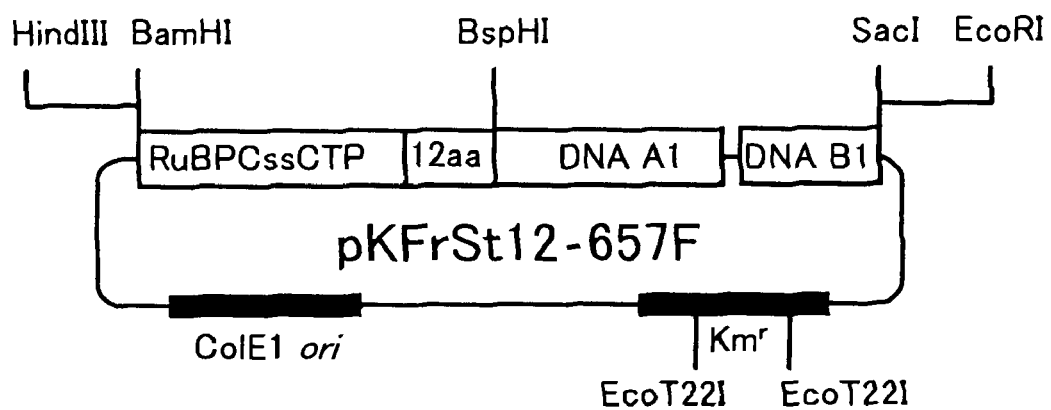

FIG. 22 shows the restriction map of the plasmid pKFrSt12-657F.

Figure 23:
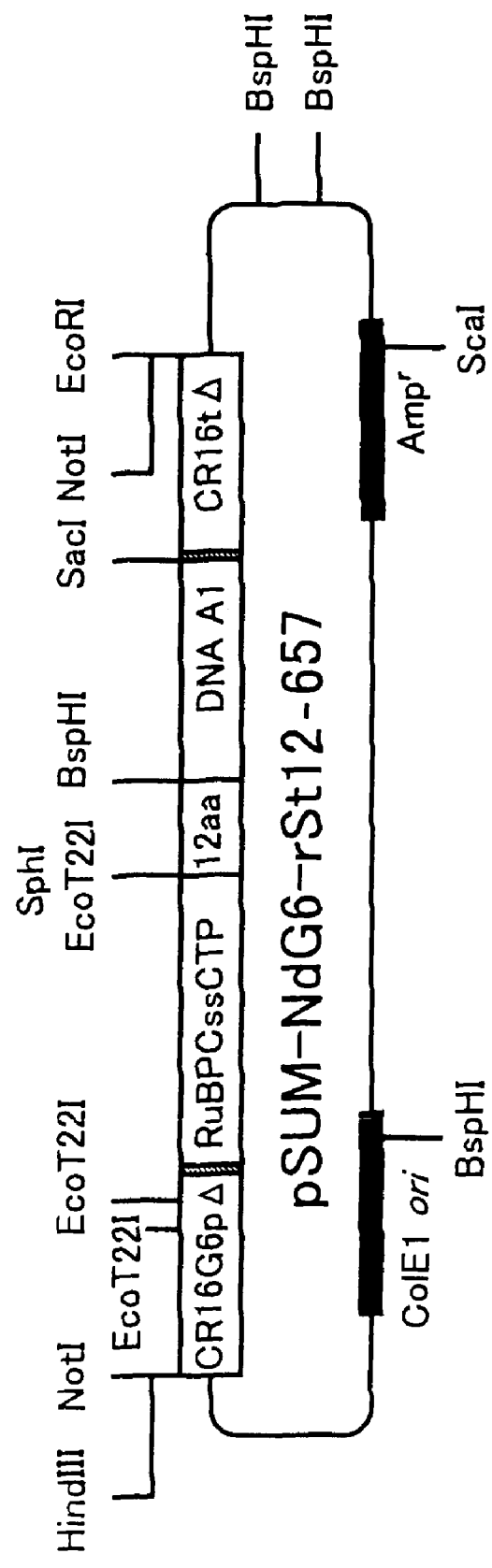

FIG. 23 shows the restriction map of the plasmid pSUM-NdG6-rSt12-657.

Figures 24, 25:
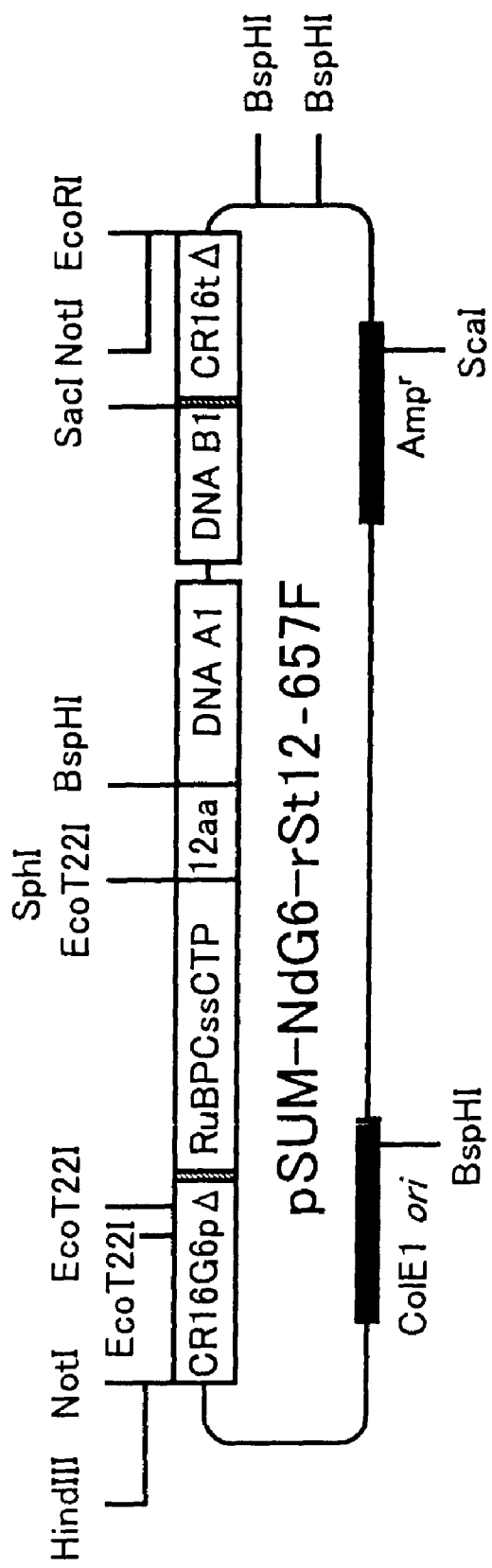

FIG. 24 shows the restriction map of the plasmid pSUM-NdG6-rSt12-657F.

FIG. 25 shows the structure of the linker HindIII-NotI-EcoRI produced by annealing the oligonucleotide consisting of the nucleotide sequence shown in SEQ ID NO: 98 and the oligonucleotide consisting of the nucleotide sequence shown in SEQ ID NO: 99.

Figure 26:
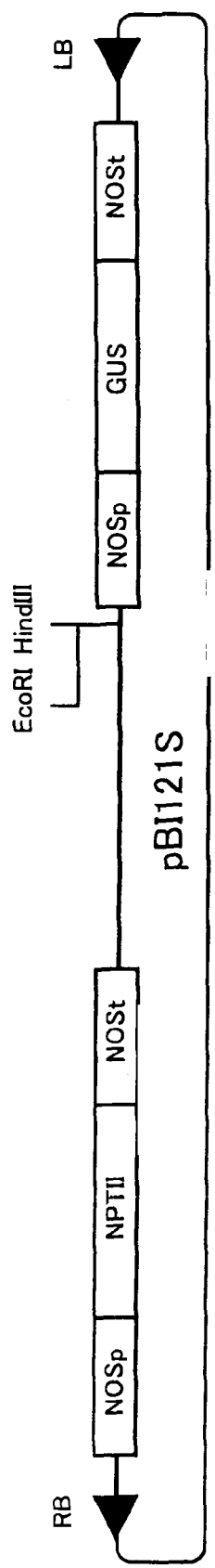

FIG. 26 shows the restriction map of the plasmid pBI121S.

Figure 27:
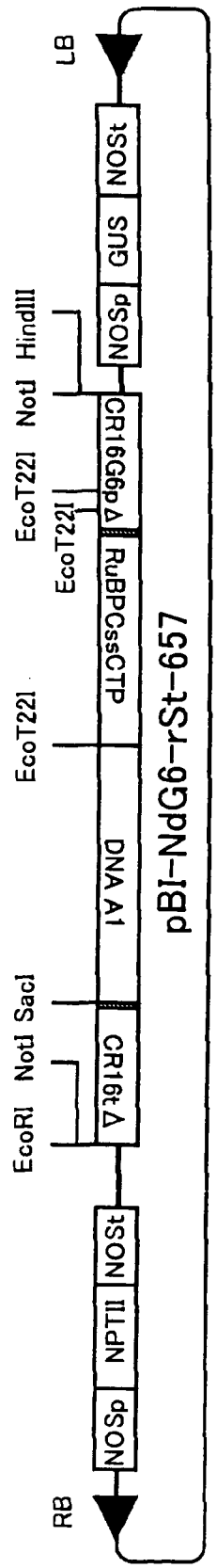

FIG. 27 shows the restriction map of the plasmid pBI-NdG6-rSt-657.

Figure 28:
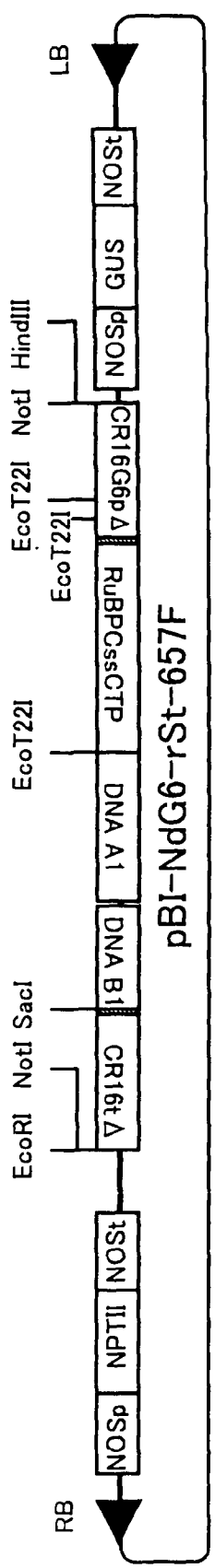

FIG. 28 shows the restriction map of the plasmid pBI-NdG6-rSt-657F.

Figure 29:
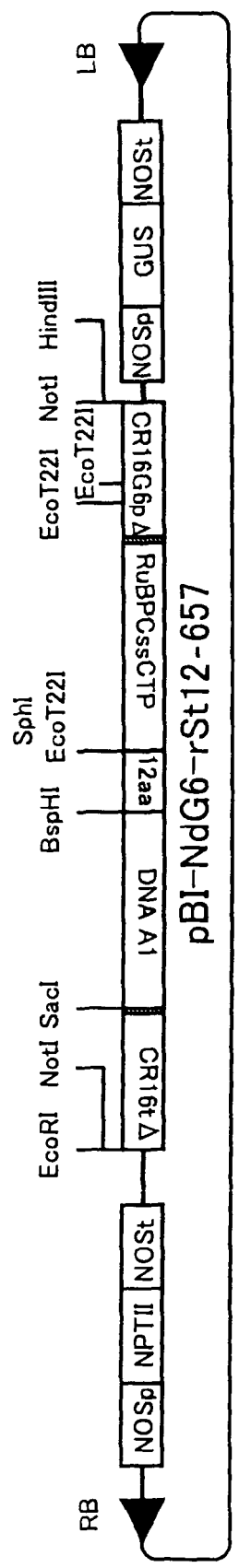

FIG. 29 shows the restriction map of the plasmid pBI-NdG6-rSt12-657.

Figure 30:
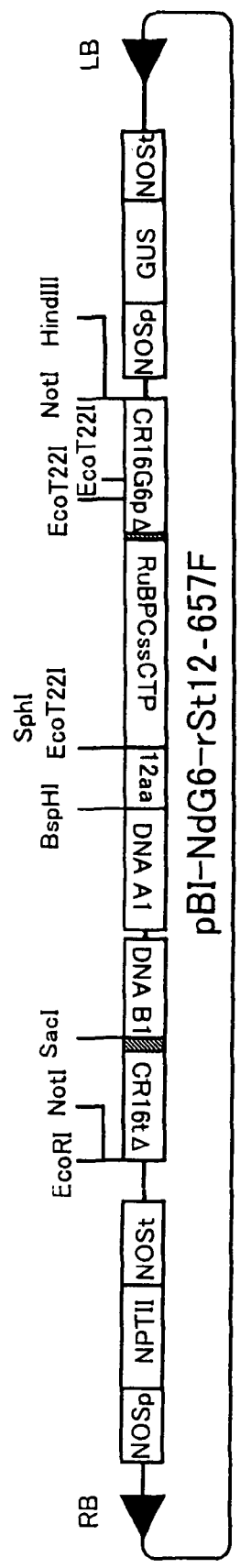

FIG. 30 shows the restriction map of the plasmid pBI-NdG6-rSt12-657F.

Figure 31:
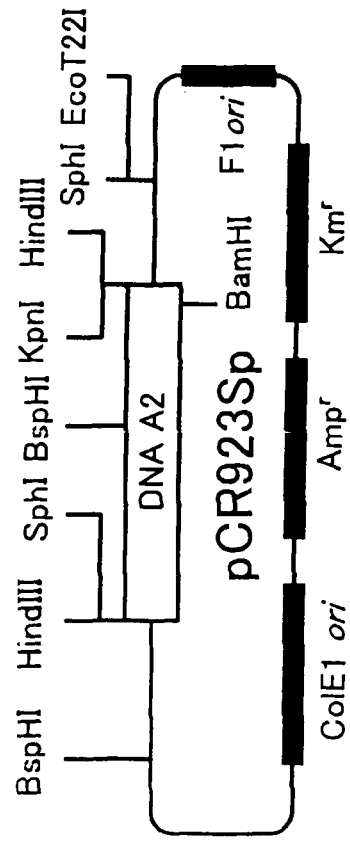

FIG. 31 shows the restriction map of the plasmid pCR923Sp.

Figure 32:
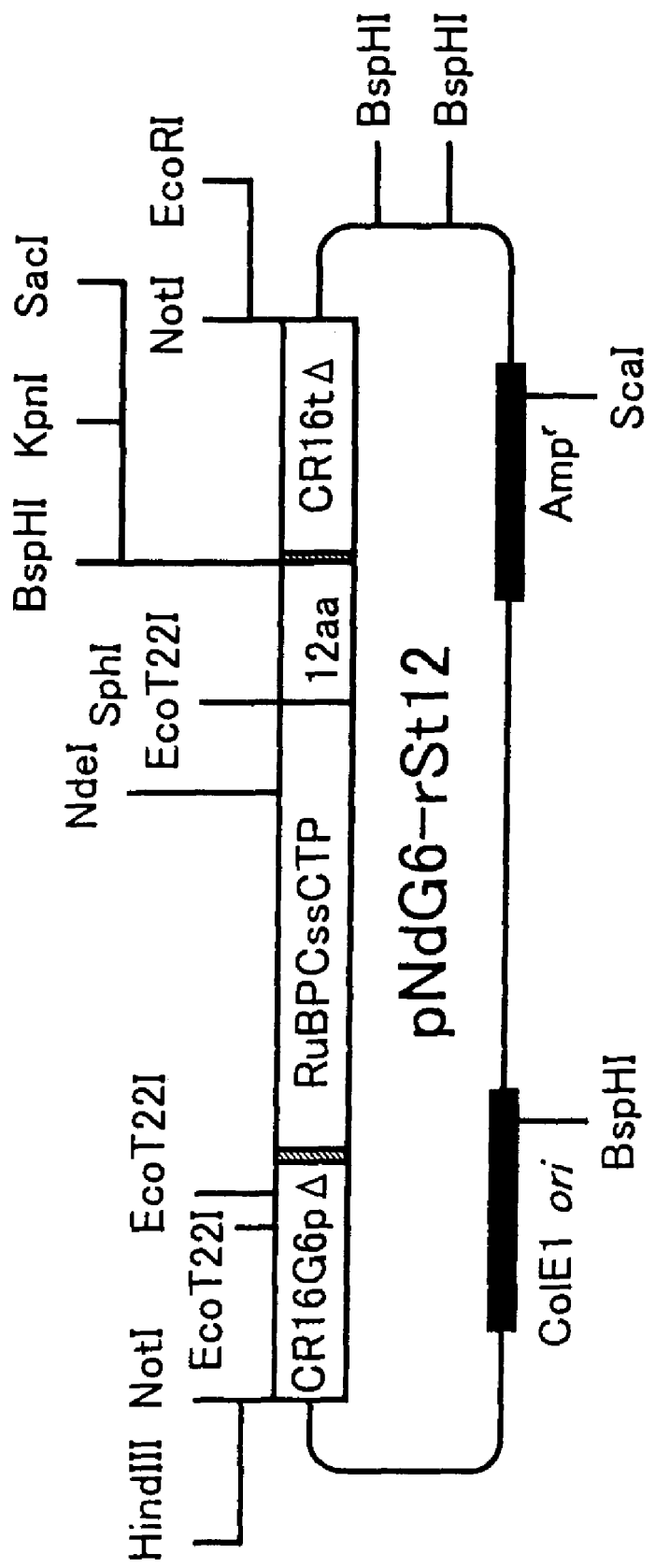

FIG. 32 shows the restriction map of the plasmid pNdG6-rSt12.

Figure 33:
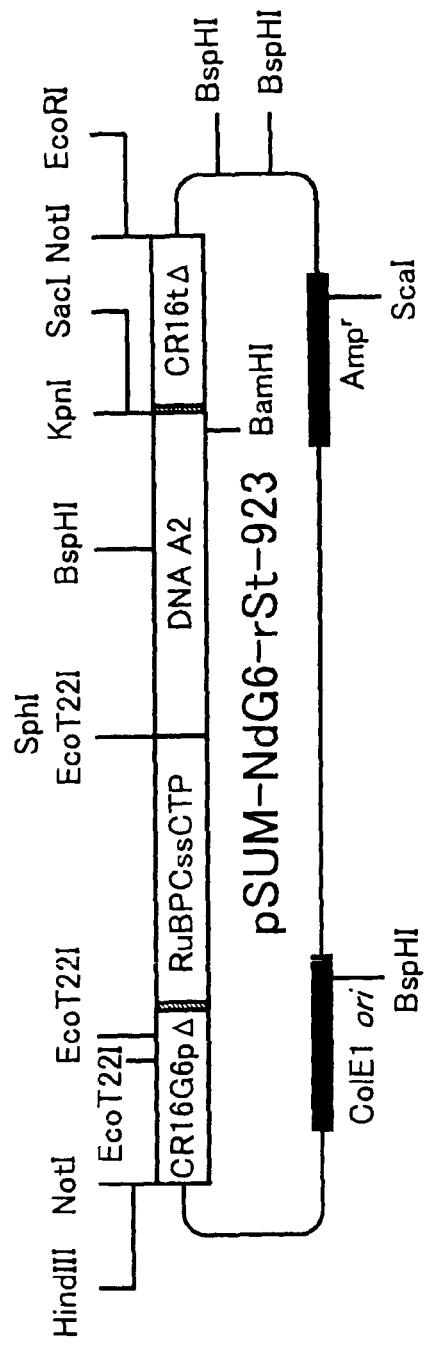

FIG. 33 shows the restriction map of the plasmid pSUM-NdG6-rSt-923.

Figure 34:
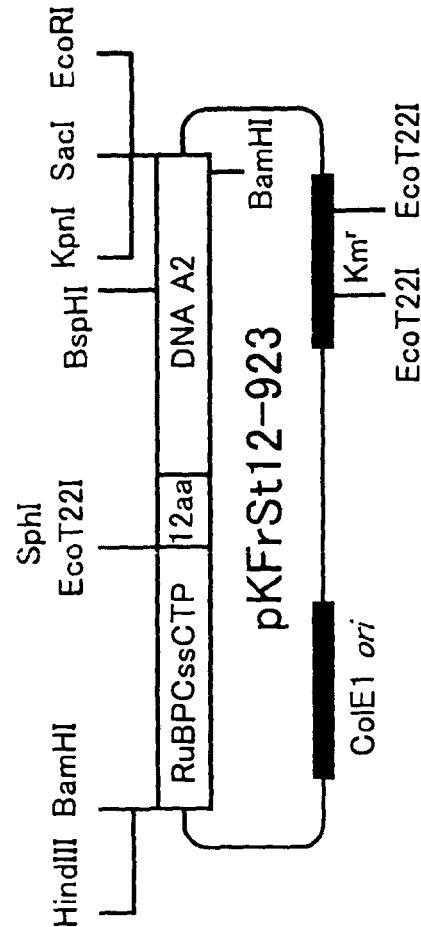

FIG. 34 shows the restriction map of the plasmid pKFrSt12-923.

Figure 35:
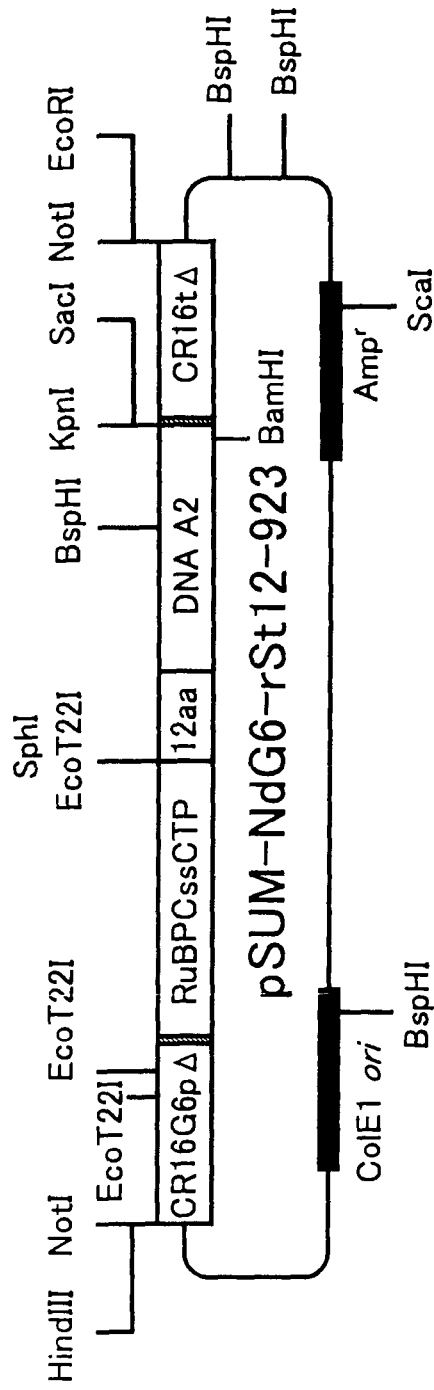

FIG. 35 shows the restriction map of the plasmid pSUM-NdG6-rSt12-923.

Figure 36:
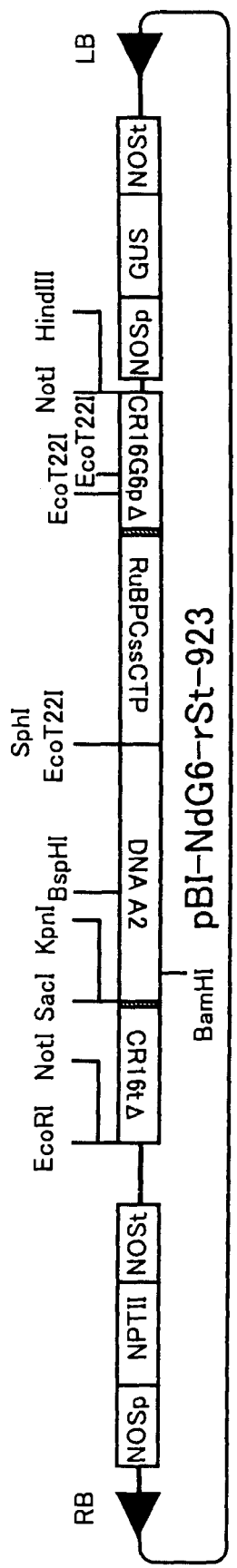

FIG. 36 shows the restriction map of the plasmid pBI-NdG6-rSt-923.

Figure 37:
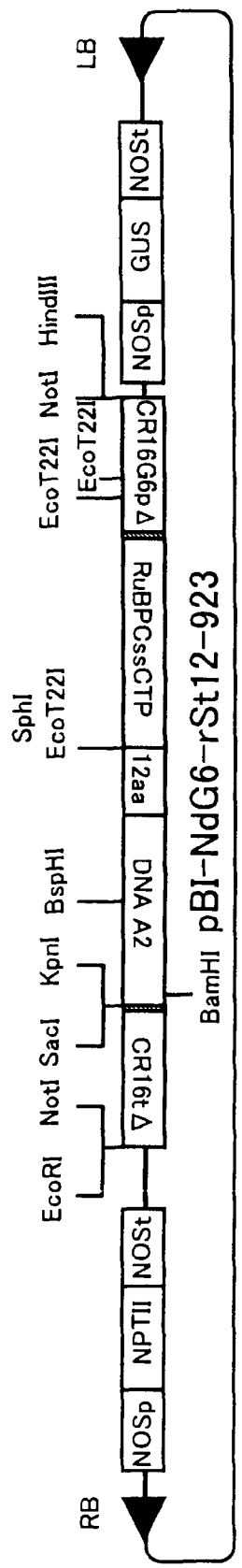

FIG. 37 shows the restriction map of the plasmid pBI-NdG6-rSt12-923.

Figure 38:
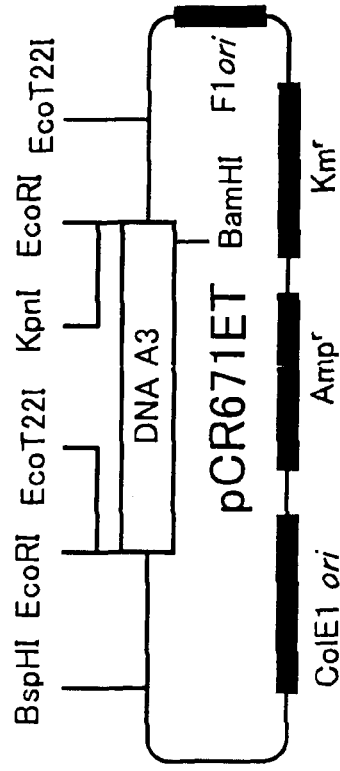

FIG. 38 shows the restriction map of the plasmid pCR671ET.

Figure 39:
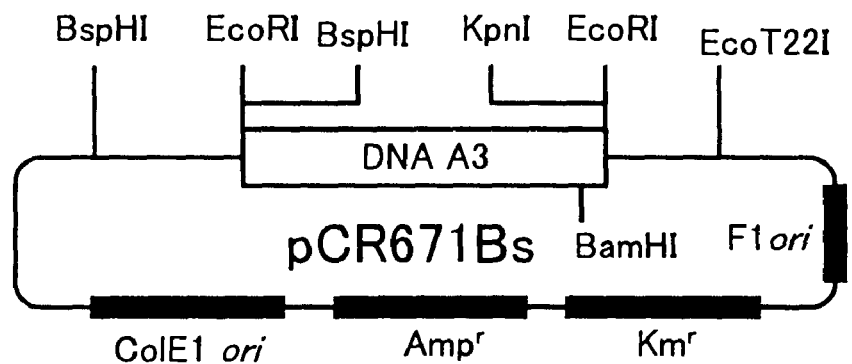

FIG. 39 shows the restriction map of the plasmid pCR671Bs.

Figure 40:
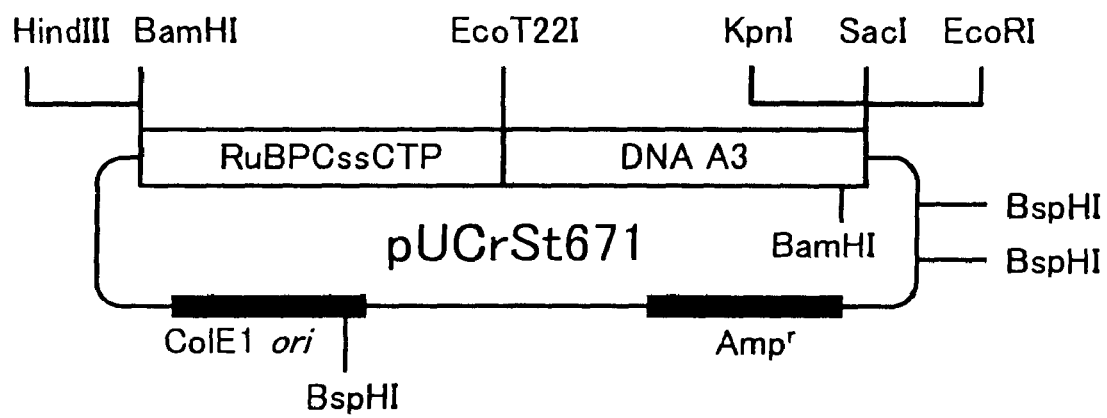

FIG. 40 shows the restriction map of the plasmid pUCrSt671.

Figure 41:
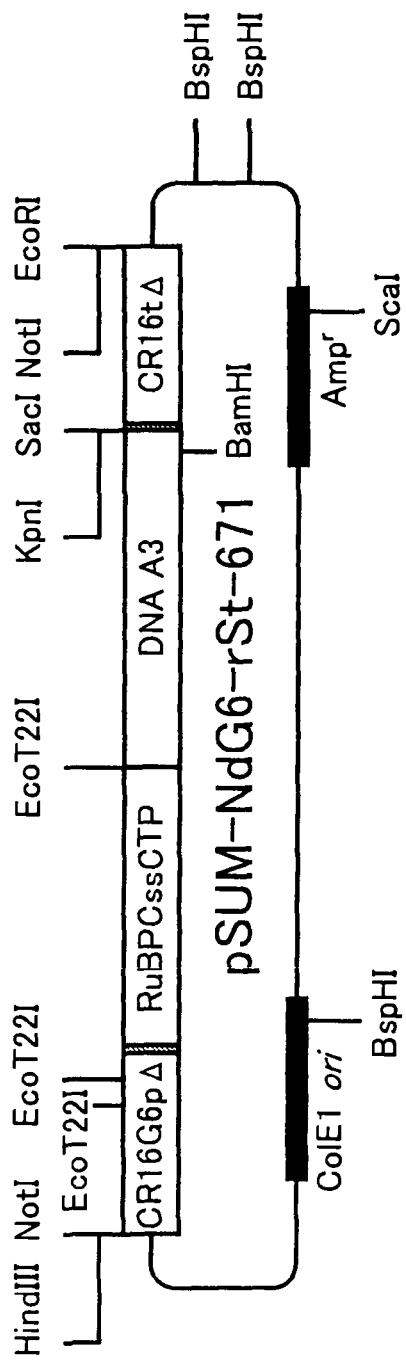

FIG. 41 shows the restriction map of the plasmid pSUM-NdG6-rSt-671.

Figure 42:
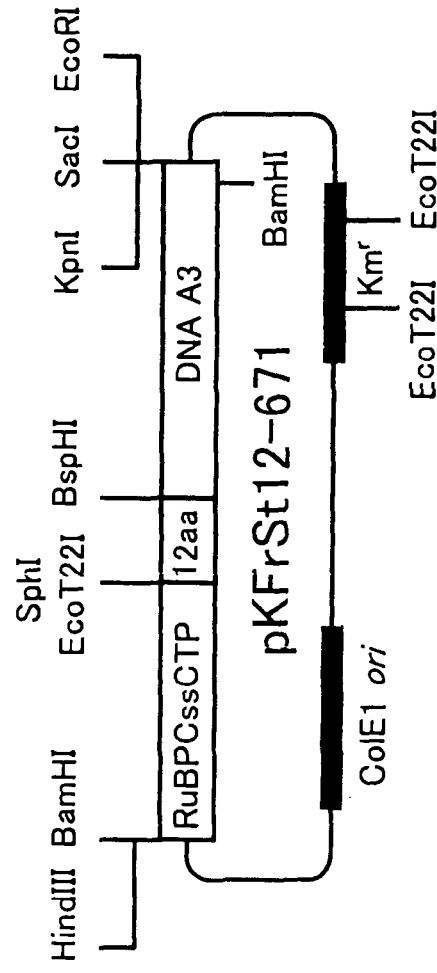

FIG. 42 shows the restriction map of the plasmid pKFrSt12-671.

Figure 43:
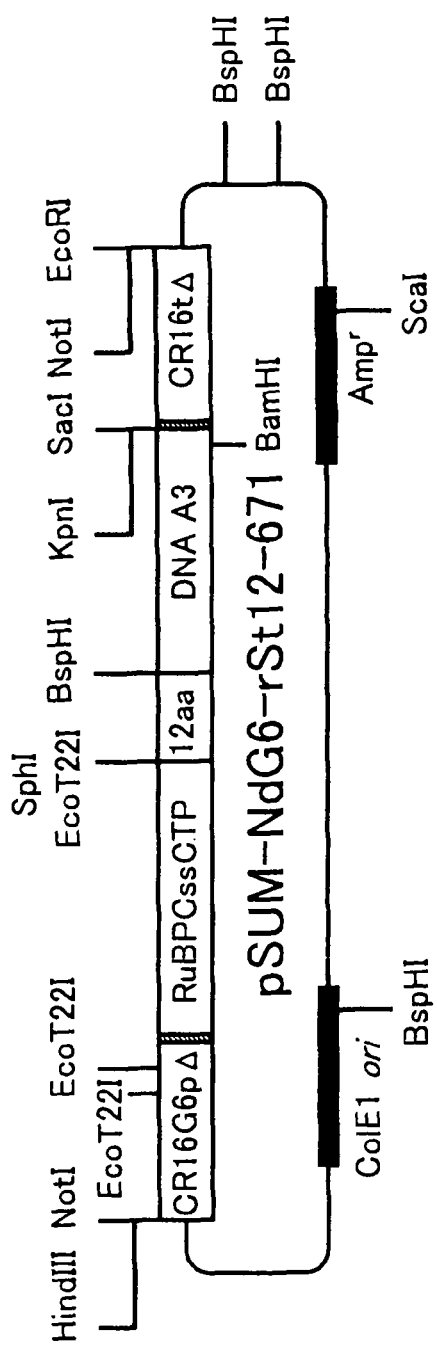

FIG. 43 shows the restriction map of the plasmid pSUM-NdG6-rSt12-671.

Figure 44:
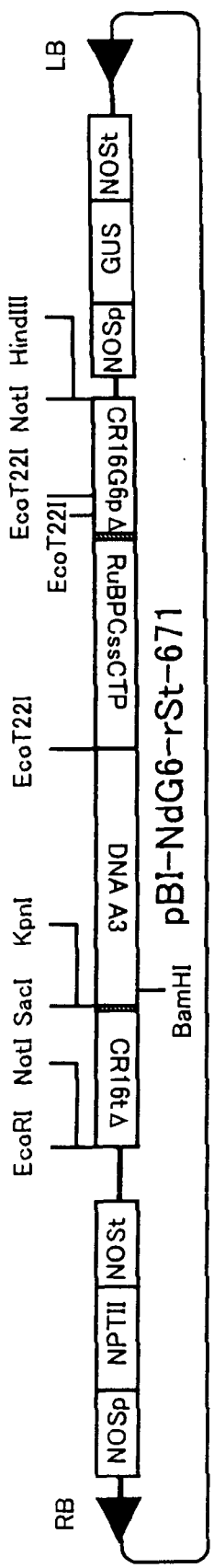

FIG. 44 shows the restriction map of the plasmid pBI-NdG6-rSt-671.

Figure 45:
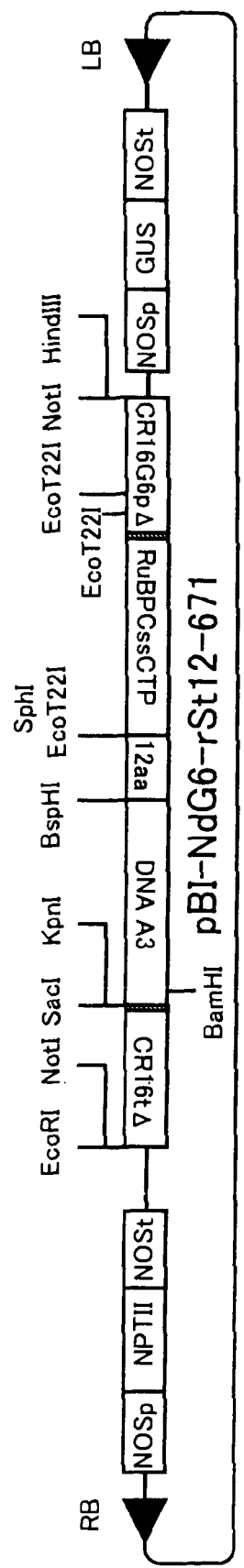

FIG. 45 shows the restriction map of the plasmid pBI-NdG6-rSt12-671.

Figure 46:
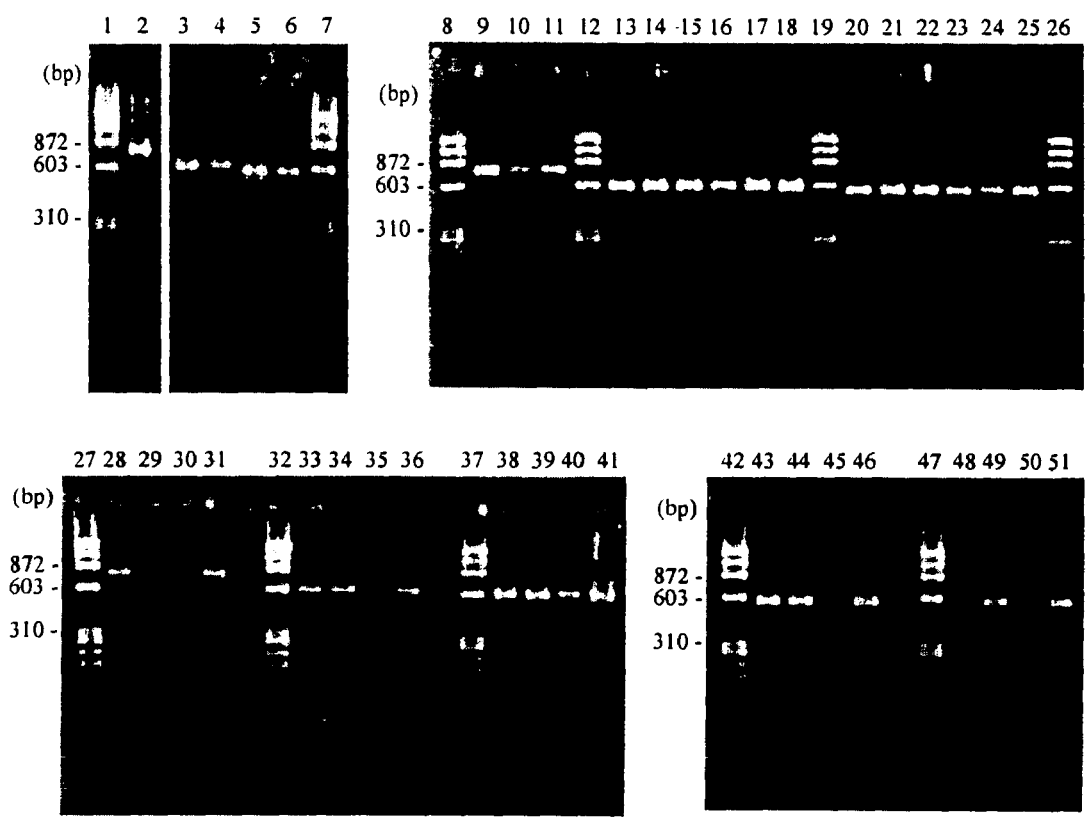
Figure 4:
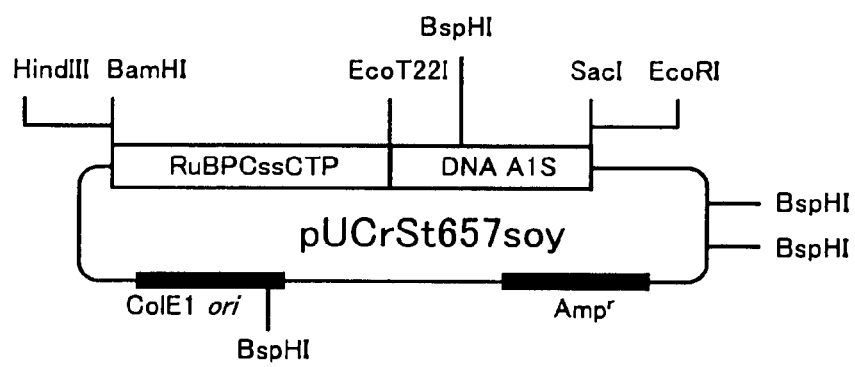

FIG. 46 shows the results obtained by detecting with agarose gel electrophoresis the DNA amplified by the PCR using as a primer the oligonucleotide having a partial nucleotide sequence of the present invention DNA(A). Lanes 1, 7, 8, 12, 19, 26, 27, 32, 37, 42 and 47 represent the electrophoresis of a DNA marker (φ174/HaeIII digest). The other lanes represent the electrophoresis of the samples shown in Tables 20 and 21.

FIG. 47 shows the structure of the linker produced by annealing the oligonucleotide consisting of the nucleotide sequence shown in SEQ ID NO: 134 and the oligonucleotide consisting of the nucleotide sequence shown in SEQ ID NO: 135.

FIG. 48 shows the restriction map of the plasmid pUCrSt657soy.

Figure 49:
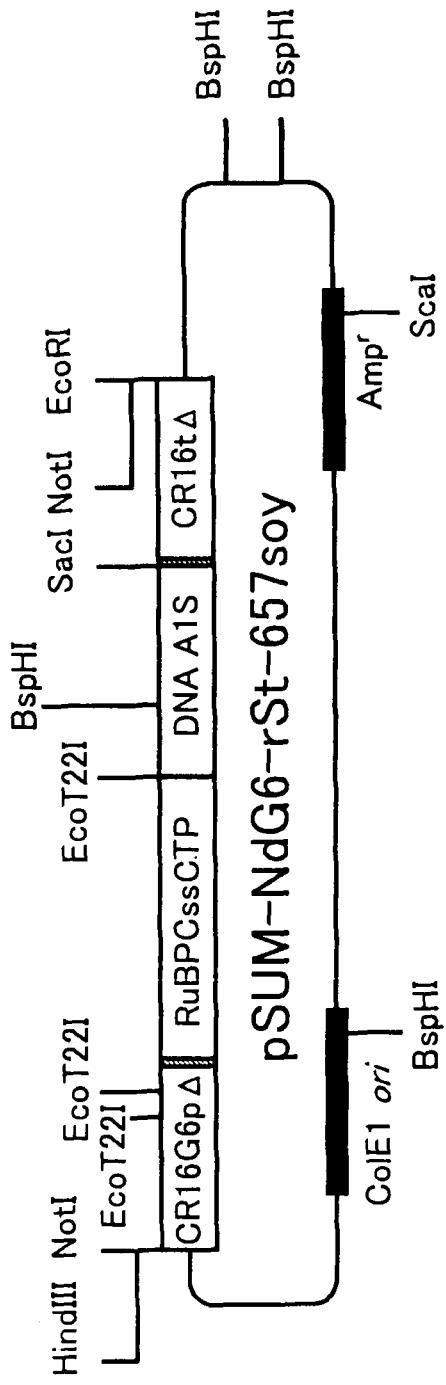

FIG. 49 shows the restriction map of the plasmid pSUM-NdG6-rSt-657soy.

Figure 50:
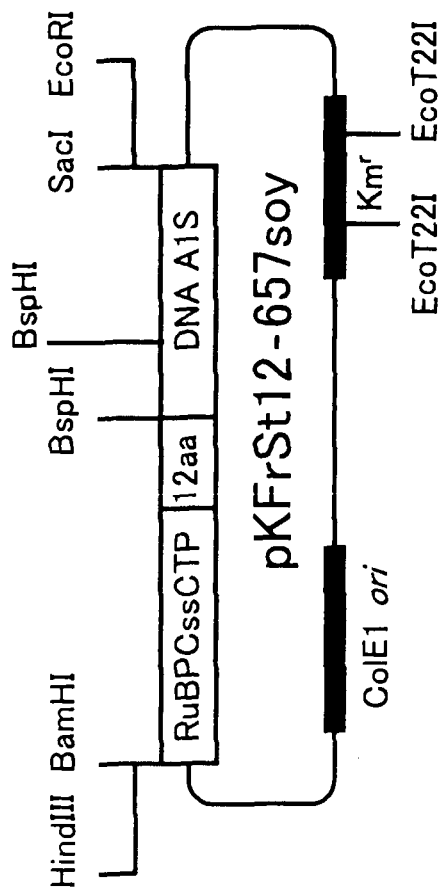

FIG. 50 shows the restriction map of the plasmid pKFrSt12-657soy.

FIG. 51 shows the restriction map of the plasmid pSUM-NdG6-rSt12-657soy.

FIG. 52 shows the restriction map of the plasmid pBI-NdG6-rSt-657soy.

Figure 53:
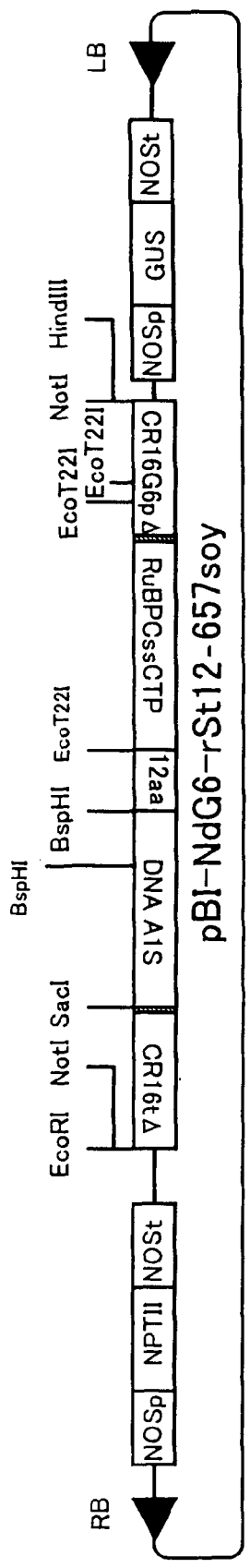

FIG. 53 shows the restriction map of the plasmid pBI-NdG6-rSt12-657soy.

Figure 54:
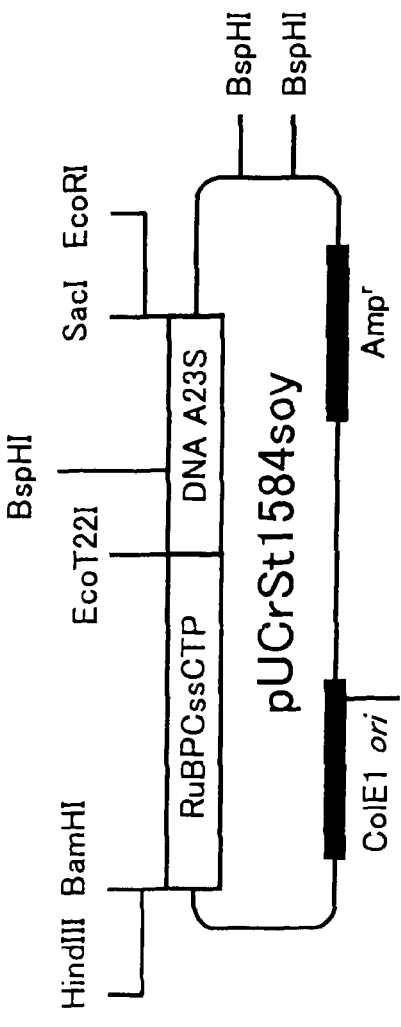

FIG. 54 shows the restriction map of the plasmid pUCrSt1584soy.

Figure 55:
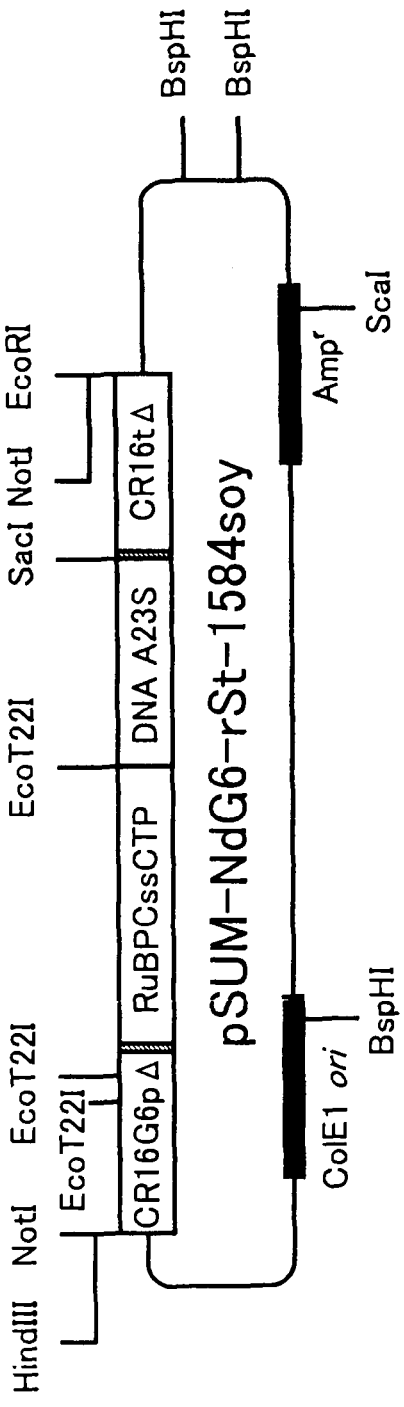

FIG. 55 shows the restriction map of the plasmid pSUM-NdG6-rSt-1584soy.

Figure 56:
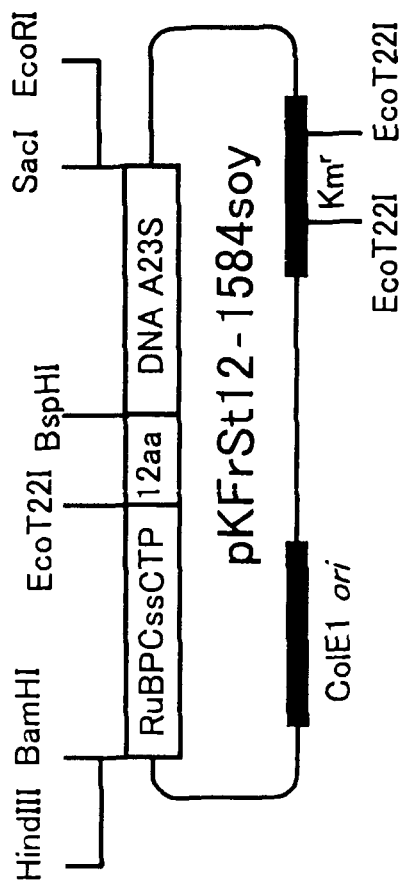

FIG. 56 shows the restriction map of the plasmid pKFrSt12-1584soy.

FIG. 57 shows the restriction map of the plasmid pSUM-NdG6-rSt12-1584soy.

FIG. 58 shows the restriction map of the plasmid pBI-NdG6-rSt-1584soy.

Figure 59:
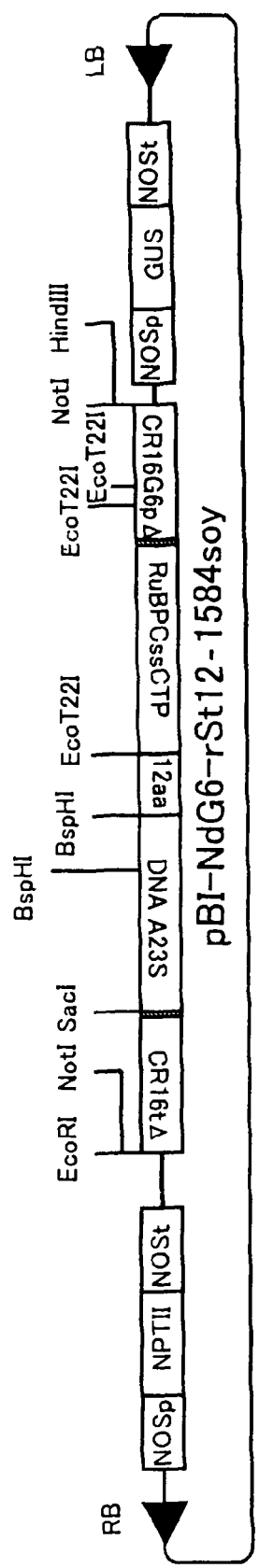

FIG. 59 shows the restriction map of the plasmid pBI-NdG6-rSt12-1584soy.

Figure 60:
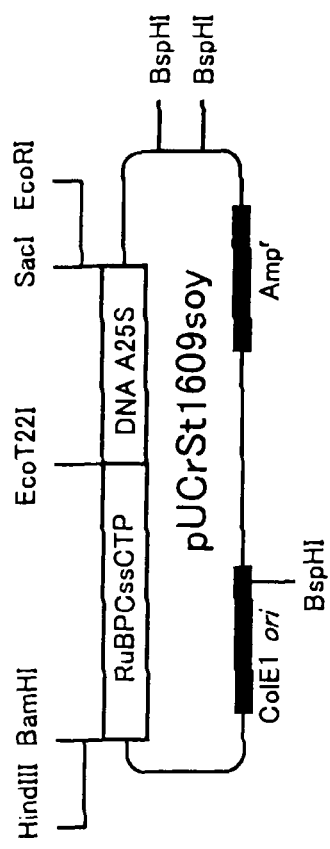

FIG. 60 shows the restriction map of the plasmid pUCrSt1609soy.

Figures 61, 62:
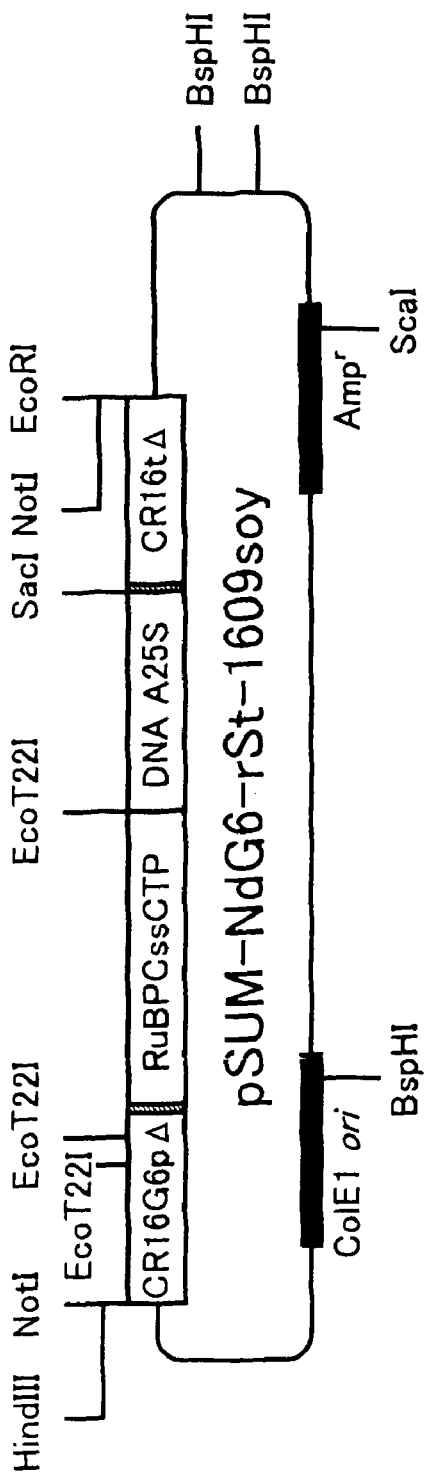

FIG. 61 shows the restriction map of the plasmid pSUM-NdG6-rSt-1609soy.

FIG. 62 shows the structure of the linker EcoT22I-12aa-EcoT22I produced by annealing the oligonucleotide consisting of the nucleotide sequence shown in SEQ ID NO: 402 and the oligonucleotide consisting of the nucleotide sequence shown in SEQ ID NO: 403.

Figure 63:
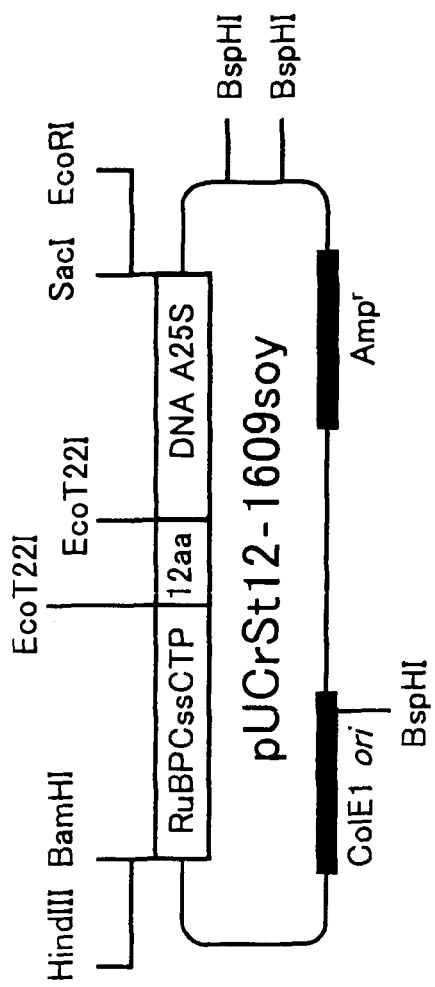

FIG. 63 shows the restriction map of the plasmid pUCrSt12-1609soy.

Figure 64:
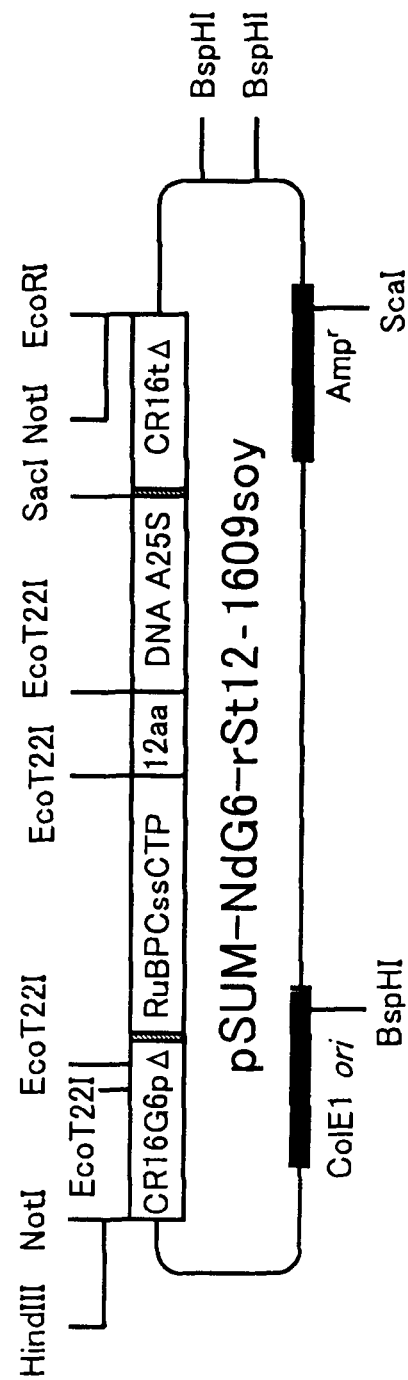

FIG. 64 shows the restriction map of the plasmid pSUM-NdG6-rSt12-1609soy.

Figure 65:
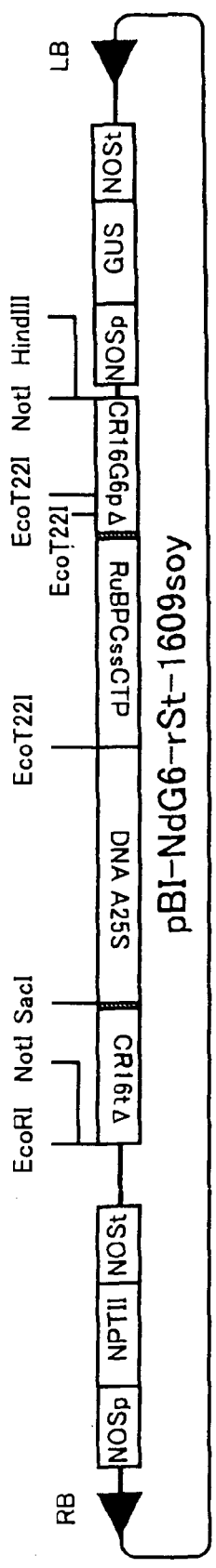

FIG. 65 shows the restriction map of the plasmid pBI-NdG6-rSt-1609soy.

Figure 66:
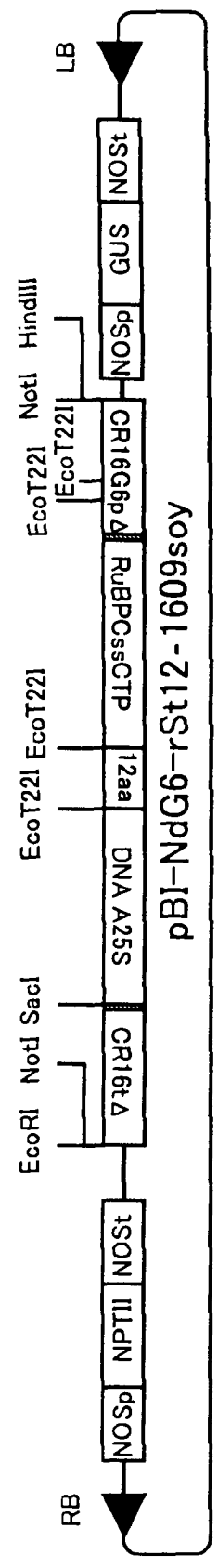

FIG. 66 shows the restriction map of the plasmid pBI-NdG6-rSt12-1609soy.

The abbreviations described in the above figures are explained below.

DNA A1: the present invention DNA (A1)
DNA A2: the present invention DNA (A2)
DNA A3: the present invention DNA (A3)
DNA A4: the present invention DNA (A4)
DNA B1: the present invention DNA (B1)
DNA B2: the present invention DNA (B2)
DNA B4: the present invention DNA (B4)
DNA A1S: the present invention DNA (A1)S
DNA A23S: the present invention DNA (A23)S
DNA A25S: the present invention DNA (A25)S
tac p: tac promoter
rrnB t: rrnB terminator
   ColE1 ori: the replication origin of plasmid ColE1
Amp$^r$: the ampicillin resistance gene
   RuBPCssCTP: the nucleotide sequence encoding the chloroplast transit peptide of the small subunit of ribulose-1,5-bisphosphate carboxylase of soybean (cv. Jack).
12aa: the nucleotide sequence encoding the 12 amino acids of a mature protein, following the chloroplast transit peptide of the small subunit of ribulose-1,5-bisphosphate carboxylase of soybean (cv. Jack).
Km$^r$: kanamycin resistance gene
F1 ori: replication origin of plasmid F1
CR16G6p: CR16G6 promoter
CR16t: CR16 terminator
CR16tΔ: DNA in which the nucleotide sequence downstream of restriction site of the restriction enzyme ScaI is removed from the CR16 terminator
CR16G6pΔ: DNA in which the nucleotide sequence upstream of restriction site of the restriction enzyme NdeI is removed from the CR16G6 terminator
NOSp: promoter of the nopaline synthase gene
NPTII: kanamycin resistance gene
NOSt: terminator of nopaline synthase gene
GUS: β-glucuronidase gene
RB: the right border sequence of T-DNA
LB: the left border sequence of T-DNA
NdeI, HindIII, BspHI, EcoRI, BamHI, EcoT22I, SphI, KpnI, SacI, BglII, NotI, ScaI: the restriction sites of the respective restriction enzyme

BEST MODE FOR CARRYING OUT THE INVENTION

The present invention is explained in detail below.

The herbicide metabolizing protein selected from the following protein group (hereinafter, sometimes referred to as "the present invention protein (A)") has the ability to convert the compound of formula (II) (hereinafter, sometimes referred to as "compound (II)") to the compound of formula (III) (hereinafter, sometimes referred to as "compound (III)").
<Protein Group>
(A1) a protein comprising the amino acid sequence shown in SEQ ID NO: 1;
(A2) a protein comprising the amino acid sequence shown in SEQ ID NO: 2;
(A3) a protein comprising the amino acid sequence shown in SEQ ID NO: 3;
(A4) a protein comprising the amino acid sequence shown in SEQ ID NO: 108;
(A5) a protein having an ability to convert in the presence of an electron transport system containing an electron donor a compound of formula (II) to a compound of formula (III) and comprising an amino acid sequence having at least 80% sequence identity with an amino acid sequence shown in any one of SEQ ID NO: 1, SEQ ID NO: 2, SEQ ID NO: 3 or SEQ ID NO: 108;
(A6) a protein having an ability to convert in the presence of an electron transport system containing an electron donor a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;
(A11) a protein comprising the amino acid sequence shown in SEQ ID NO: 159;
(A12) a protein comprising the amino acid sequence shown in SEQ ID NO: 160;
(A13) a protein comprising the amino acid sequence shown in SEQ ID NO: 136;
(A14) a protein comprising the amino acid sequence shown in SEQ ID NO: 137;
(A15) a protein comprising the amino acid sequence shown in SEQ ID NO: 138;
(A16) a protein comprising the amino acid sequence shown in SEQ ID NO: 215;
(A17) a protein comprising the amino acid sequence shown in SEQ ID NO: 216;
(A18) a protein comprising the amino acid sequence shown in SEQ ID NO: 217;
(A19) a protein comprising the amino acid sequence shown in SEQ ID NO: 218;
(A20) a protein comprising the amino acid sequence shown in SEQ ID NO: 219;
(A21) a protein comprising the amino acid sequence shown in SEQ ID NO: 220;
(A22) a protein comprising the amino acid sequence shown in SEQ ID NO: 221;
(A23) a protein comprising the amino acid sequence shown in SEQ ID NO: 222;
(A24) a protein comprising the amino acid sequence shown in SEQ ID NO: 223;
(A25) a protein comprising the amino acid sequence shown in SEQ ID NO: 224;
(A26) a protein having an ability to convert in the presence of an electron transport system containing an electron donor a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224;

(A27) a protein having the ability to convert in the presence of an electron transport system containing an electron donor a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224; and (A28) a protein having an ability to convert in the presence of an electron transport system containing an electron donor, a compound of formula (II) to a compound of formula (III), and comprising an amino acid sequence encoded by a DNA amplifiable by a polymerase chain reaction with a primer comprising the nucleotide sequence shown in any one of SEQ ID NOs: 124 to 128, a primer comprising the nucleotide sequence shown in SEQ ID NO: 129 and as a template a chromosomal DNA of *Streptomyces phaeochromogenes, Streptomyces testaceus, Streptomyces achromogenes, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis, Streptomyces steffisburgensis* or *Saccharopolyspora taberi.*

As specific examples of the present invention protein (A), there is mentioned:

a protein comprising the amino acid sequence shown in SEQ ID NO: 1 (hereinafter, sometimes referred to as "present invention protein (A1)");

a protein comprising the amino acid sequence shown in SEQ ID NO: 2 (hereinafter, sometimes referred to as "present invention protein (A2)");

a protein comprising the amino acid sequence shown in SEQ ID NO: 3 (hereinafter, sometimes referred to as "present invention protein (A3)");

a protein comprising the amino acid sequence shown in SEQ ID NO: 108 (hereinafter, sometimes referred to as "present invention protein (A4)");

a protein comprising the amino acid sequence shown in SEQ ID NO: 159 (hereinafter, sometimes referred to as "present invention protein (A 11)");

a protein comprising the amino acid sequence shown in SEQ ID NO: 160 (hereinafter, sometimes referred to as "present invention protein (A12)");

a protein comprising the amino acid sequence shown in SEQ ID NO: 136 (hereinafter, sometimes referred to as "present invention protein (A13)");

a protein comprising the amino acid sequence shown in SEQ ID NO: 137 (hereinafter, sometimes referred to as "present invention protein (A14)");

a protein comprising the amino acid sequence shown in SEQ ID NO: 138 (hereinafter, sometimes referred to as "present invention protein (A15)");

a protein comprising the amino acid sequence shown in SEQ ID NO: 215 (hereinafter, sometimes referred to as "present invention protein (A16)");

a protein comprising the amino acid sequence shown in SEQ ID NO: 216 (hereinafter, sometimes referred to as "present invention protein (A17)");

a protein comprising the amino acid sequence shown in SEQ ID NO: 217 (hereinafter, sometimes referred to as "present invention protein (A18)");

a protein comprising the amino acid sequence shown in SEQ ID NO: 218 (hereinafter, sometimes referred to as "present invention protein (A19)");

a protein comprising the amino acid sequence shown in SEQ ID NO: 219 (hereinafter, sometimes referred to as "present invention protein (A20)");

a protein comprising the amino acid sequence shown in SEQ ID NO: 220 (hereinafter, sometimes referred to as "present invention protein (A21)");

a protein comprising the amino acid sequence shown in SEQ ID NO: 221 (hereinafter, sometimes referred to as "present invention protein (A22)");

a protein comprising the amino acid sequence shown in SEQ ID NO: 222 (hereinafter, sometimes referred to as "present invention protein (A23)");

a protein comprising the amino acid sequence shown in SEQ ID NO: 223 (hereinafter, sometimes referred to as "present invention protein (A24)"); and a protein comprising the amino acid sequence shown in SEQ ID NO: 224 (hereinafter, sometimes referred to as "present invention protein (A25)").

For example, by reacting the PPO inhibitory-type herbicidal compound of formula (I) (hereinafter, sometimes referred to as "compound (I)") with the present invention protein (A), it is capable to convert the compound to a compound with lower herbicidal activity.

Further, in treatment to convert compound (I) to a compound of a lower herbicidal activity, there can also be utilized a herbicide metabolizing protein selected from the following group (hereinafter, sometimes referred to as "present protein (A)"):

<Protein Group>

(A1) a protein comprising the amino acid sequence shown in SEQ ID NO: 1;

(A2) a protein comprising the amino acid sequence shown in SEQ ID NO: 2;

(A3) a protein comprising the amino acid sequence shown in SEQ ID NO: 3;

(A4) a protein comprising the amino acid sequence shown in SEQ ID NO: 108;

(A5) a protein having an ability to convert in the presence of an electron transport system containing an electron donor a compound of formula (II) to a compound of formula (III), and comprising an amino acid sequence having at least 80% sequence identity with an amino acid sequence shown in any one of SEQ ID NO: 1, SEQ ID NO: 2, SEQ ID NO: 3 or SEQ ID NO: 108;

(A6) a protein having an ability to convert in the presence of an electron transport system containing an electron donor a compound of formula (II) to a compound of formula (III), and comprising an amino acid sequence encoded by a nucleotide sequence having at least 80% sequence identity with a nucleotide sequence encoding an amino acid sequence shown in any one of SEQ ID NO: 1, SEQ ID NO: 2, SEQ ID NO: 3 or SEQ ID NO: 108;

(A7) a protein having the ability to convert in the presence of an electron transport system containing an electron donor a compound of formula (II) to a compound of formula (III), and comprising an amino acid sequence encoded by a DNA that hybridizes, under stringent conditions, to a DNA comprising a nucleotide sequence encoding an amino acid sequence shown in any one of SEQ ID NO: 1, SEQ ID NO: 2, SEQ ID NO: 3 or SEQ ID NO: 108;

(A8) a protein having the ability to convert in the presence of an electron transport system containing an electron donor a compound of formula (II) to a compound of formula (III), and comprising an amino acid sequence encoded by a DNA amplifiable by a polymerase chain reaction with a primer comprising a nucleotide sequence shown in SEQ ID NO: 129, a primer comprising a nucleotide sequence shown in any one of SEQ ID NOs: 124 to 128, and as a template a chromosome of a microorganism belonging to *Streptomyces* or *Saccharopolyspora*;

(A9) a protein comprising an amino acid sequence shown in SEQ ID NO: 4;

(A11) a protein comprising the amino acid sequence shown in SEQ ID NO: 159;

(A12) a protein comprising the amino acid sequence shown in SEQ ID NO: 160;

(A13) a protein comprising the amino acid sequence shown in SEQ ID NO: 136;

(A14) a protein comprising the amino acid sequence shown in SEQ ID NO: 137;

(A15) a protein comprising the amino acid sequence shown in SEQ ID NO: 138;

(A16) a protein comprising the amino acid sequence shown in SEQ ID NO: 215;

(A17) a protein comprising the amino acid sequence shown in SEQ ID NO: 216;

(A18) a protein comprising the amino acid sequence shown in SEQ ID NO: 217;

(A19) a protein comprising the amino acid sequence shown in SEQ ID NO: 218;

(A20) a protein comprising the amino acid sequence shown in SEQ ID NO: 219;

(A21) a protein comprising the amino acid sequence shown in SEQ ID NO: 220;

(A22) a protein comprising the amino acid sequence shown in SEQ ID NO: 221;

(A23) a protein comprising the amino acid sequence shown in SEQ ID NO: 222;

(A24) a protein comprising the amino acid sequence shown in SEQ ID NO: 223;

(A25) a protein comprising the amino acid sequence shown in SEQ ID NO: 224;

(A26) a protein having an ability to convert in the presence of an electron transport system containing an electron donor a compound of formula (II) to a compound of formula (III), and comprising an amino acid sequence having at least 80% sequence identity with an amino acid sequence shown in any one of SEQ ID NO: 159, SEQ ID NO: 136, SEQ ID NO: 137, SEQ ID NO: 138, SEQ ID NO: 217, SEQ ID NO: 219, SEQ ID NO: 220, SEQ ID NO: 221 or SEQ ID NO: 223 or an amino acid sequence having at least 90% sequence identity with an amino acid sequence shown in any one of SEQ ID NO: 160, SEQ ID NO: 215, SEQ ID NO: 216, SEQ ID NO: 218, SEQ ID NO: 222 or SEQ ID NO: 224; and (A27) a protein having the ability to convert in the presence of an electron transport system containing an electron donor, a compound of formula (II) to a compound of formula (III), and comprising an amino acid sequence encoded by a nucleotide sequence having at least 90% sequence identity with a nucleotide sequence encoding an amino acid sequence shown in any one of SEQ ID NO: 159, SEQ ID NO: 160, SEQ ID NO: 136, SEQ ID NO: 137, SEQ ID NO: 138, SEQ ID NO: 215, SEQ ID NO: 216, SEQ ID NO: 217, SEQ ID NO:218, SEQ ID NO: 219, SEQ ID NO: 220, SEQ ID NO: 221, SEQ ID NO: 222, SEQ ID NO: 223 or SEQ ID NO: 224.

As examples of the present protein (A), there can be mentioned the present invention protein A, described above. Further, as other examples, there can be mentioned a protein comprising the amino acid sequence shown in SEQ ID NO: 4 (hereinafter, sometimes referred to as "present protein (A9)") and a protein comprising the amino acid sequence shown in SEQ ID NO: 5 (hereinafter, sometimes referred to as "present protein (A10)").

In the amino acid sequence of the protein shown in (A5), (A6), (A7), (A8), (A26), (A27) or (A28) in the above protein groups, the differences which may be observed from the amino acid sequences shown in SEQ ID NO: 1, 2, 3, 108, 159, 160, 136, 137, 138, 215, 216, 217, 218, 219, 220, 221, 222, 223 or 224, are such as deletion, substitution, and addition of certain amino acids. Such differences include, for example, the deletion from the processing which the above protein comprising the amino acid sequence shown in SEQ ID NO: 1, 2, 3, 108, 159, 160, 136, 137, 138, 215, 216, 217, 218, 219, 220, 221, 222, 223 or 224 receives within the cell. Further, there are included a polymorphic variation which occurs naturally resulting from the difference by such as the species, individual or the like of the organism from which the protein is derived; amino acid deletions, substitutions, and additions arising from genetic mutations artificially introduced by such as a site-directed mutagenesis method, a random mutagenesis method, a mutagenic treatment and the like.

The number of amino acids undergoing such deletions, substitutions and additions may be within the range in which the present protein (A) can develop the ability to convert compound (II) to compound (III). Further, as a substitution of the amino acid, there can be mentioned, for example, substitutions to an amino acid which is similar in hydrophobicity, charge, pK, stereo-structural feature, or the like. As such substitutions, specifically for example, there are mentioned substitutions within the groups of: (1.) glycine and alanine; (2.) valine, isoleucine and leucine; (3.) aspartic acid, glutamic acid, asparagine and glutamine; (4.) serine and threonine; (5.) lysine and arginine; (6.) phenylalanine and tyrosine; and the like.

Further, in the present protein (A), it is preferable that the cysteine present at the position aligning to the cysteine of amino acid number 357 in the amino acid sequence shown in SEQ ID NO: 1 is conserved (not undergo a deletion or substitution): examples of such cysteine include the cysteine shown at amino acid number 350 in the amino acid sequence shown in SEQ ID NO: 2, the cysteine shown at amino acid number 344 in the amino acid sequence shown in SEQ ID NO: 3, the cysteine shown at amino acid number 360 in the amino acid sequence shown in SEQ ID NO: 108; the cysteine shown at amino acid number 359 in the amino acid sequence shown in SEQ ID NO: 4, the cysteine shown at amino acid number 355 in the amino acid sequence shown in SEQ ID NO: 5, the cysteine shown at amino acid number 358 in the amino acid sequence shown in SEQ ID NO: 159, the cysteine shown at amino acid number 374 in the amino acid sequence shown in SEQ ID NO: 160, the cysteine shown at amino acid number 351 in the amino acid sequence shown in SEQ ID NO: 136, the cysteine shown at amino acid number 358 in the amino acid sequence shown in SEQ ID NO: 137, the cysteine shown at amino acid number 358 in the amino acid sequence shown in SEQ ID NO: 138, the cysteine shown at amino acid number 347 in the amino acid sequence shown in SEQ ID NO: 222, the cysteine shown at amino acid number 347 in the amino acid sequence shown in SEQ ID NO: 224 and the like.

As methods of artificially causing such amino acid deletions, additions or substitutions (hereinafter, sometimes, collectively referred to as "amino acid modification"), for example, there is mentioned a method comprising the steps of carrying out site-directed mutagenesis on the DNA encoding an amino acid sequence shown in any one of SEQ ID NO: 1, 2, 3, 108, 159, 160, 136, 137, 138, 215, 216, 217, 218, 219, 220, 221, 222, 223 or 224, and then allowing the expression of such DNA by a conventional method. As the site-directed mutagenesis method, for example, there is mentioned a method which utilizes amber mutations (Gapped Duplex method, Nucleic Acids Res., 12, 9441-9456 (1984)), a method by PCR utilizing primers for introducing a mutation and the like. Further, as methods of artificially modifying amino acids, for example, there is mentioned a method comprising the steps of carrying out random mutagenesis on the DNA encoding any one of the amino acid sequences shown in SEQ ID NO: 1, 2, 3, 108, 159, 160, 136, 137, 138, 215, 216, 217, 218, 219, 220, 221, 222, 223 or 224 and then allowing the expression of such DNA by a conventional method. As the random mutagenesis method, for example, there is mentioned method of conducting PCR by utilizing the DNA encoding any one of the above amino acid sequences as a template an by utilizing a primer pair which can amplify the full length of each of the DNA, under the condition in which the concentration of each of dATP, dTTP, dGTP and dCTP, utilized as a substrate, are different than usual or under the condition in which the concentration of Mg2+ that promotes the polymerase reaction is increased to more than usual. As such methods of PCR, for example, there is mentioned the method described in Method in Molecular Biology, (31), 1994, 97-112. Further, there may be mentioned the method described in PCT patent publication WO 00/09682.

In the present invention, "sequence identity" refers to the homology and identity between two nucleotide sequences or two amino acid sequences. Such "sequence identity" may be determined by comparing the two sequences, each aligned in an optimal state, over the whole region of the test sequences. As such, additions or deletions (for example, gaps) can be utilized in the optimal alignment of the test nucleic acid sequences or amino acid sequences. Such sequence identity can be calculated through the step of producing the alignment conducted by a homology analysis using a program such as FASTA (Pearson & Lipman, Proc. Natl. Acad. Sci. USA, 4, 2444-2448 (1988)), BLAST (Altschul et al., Journal of Molecular Biology, 215, 403-410 (1990)), CLUSTAL W (Thompson, Higgins & Gibson, Nucleic Acid Research, 22, 4673-4680 (1994a)) and the like. Such programs, for example, can be typically utilized on the webpage (http://www.ddbj.nig.ac.jp) of the DNA Data Bank of Japan (the international databank operated within the Center for Information Biology and DNA Data Bank of Japan). Further, the sequence identity may be determined by utilizing a commercially available sequence analysis software. Specifically for example, it can be calculated by producing an alignment conducted by a homology analysis by the Lipman-Pearson method (Lipman, D. J. and Pearson, W. R., Science, 227, 1435-1441, (1985)) utilizing GENETYX-WIN Ver. 5 (Software Development Company, Ltd.).

As the "stringent condition" described in (A7), there can be mentioned, for example, the conditions under which a hybrid is formed at 45° C. in a solution containing 6×SSC (let the solution containing 1.5 M NaCl and 0.15 M trisodium citrate be 10×SSC) and then the hybrid is washed at 50° C. with 2×SSC (Molecular Biology, John Wiley & Sons, N.Y. (1989), 6.3.1-6.3.6) in a hybridization conducted according to the conventional method described in such as Sambrook, J., Frisch, E. F., and Maniatis, T.; Molecular Cloning 2nd edition, Cold Spring Harbor Press. The salt concentration in the washing step can be selected, for example, from the conditions of 2×SSC (low stringency condition) to the conditions of 0.2×SSC (high stringency conditions). A temperature in the washing step can be selected, for example, from room temperature (low stringency condition) to 65° C. (high stringency condition). Alternatively, both of the salt concentration and temperature may be changed.

As a DNA which "hybridizes, under stringent conditions, to a DNA comprising a nucleotide sequence encoding an amino acid sequence shown in any one of SEQ ID NO: 1, SEQ ID NO: 2, SEQ ID NO: 3 or SEQ ID NO: 108," specifically for example, there can be mentioned a DNA comprising a nucleotide sequence encoding an amino acid sequence shown in any one of SEQ ID NO: 1, 2, 3, 4, 5, 108, 159, 160, 136, 137, 138, 215, 216, 217, 218, 219, 220, 221, 222, 223 or 224, a DNA comprising a nucleotide sequence shown in any one of SEQ ID NO: 6, 7, 8, 78, 84, 109, 139, 140, 141, 142, 143, 225, 226, 227, 228, 229, 230, 231, 232, 233 or 234, and the like. There can also be mentioned DNA comprising a nucleotide sequence having at least about 60% identity to a nucleotide sequence shown in any one of SEQ ID NO: 6, 7, 8, 78, 84, 109, 139, 140, 141, 142, 143, 225, 226, 227, 228, 229, 230, 231, 232, 233 or 234.

The molecular weight of the present protein (A) is about 30,000 to 60,000 and is typically about 40,000 to 50,000 (comparable to, for example, a protein consisting of the amino acid sequence shown in any one of SEQ ID NO: 1, 2, 3, 108, 159, 160, 136, 137, 138, 215, 216, 217, 218, 219, 220, 221, 222, 223 or 224), as the molecular weight identified by a sodium dodecyl sulfate-polyacrylamide gel electrophoresis (hereinafter, referred to as "SDS-PAGE"). Further, the present protein (A), as long as the ability to convert compound (II) to compound (II) is not eliminated, can be utilized as a protein to which amino acid sequence is added upstream to its amino terminus or downstream to its carboxy terminus.

As the marker of the ability of the present protein (A) to metabolize the PPO inhibitory-type herbicidal compound of formula (I), there can be mentioned the ability to convert compound (II) to compound (III). Such ability, for example, can be confirmed by reacting compound (II) with the present protein (A) in the presence of an electron transport system containing an electron donor such as coenzyme NADPH and by detecting the produced compound (III).

The "electron transport system containing an electron donor" refers to a system in which a redox chain reaction occurs and an electron is transferred from the electron donor to the present protein (A). As the electron donor, for example, there is mentioned coenzymes NADPH, NADH and the like. For example, as proteins which may constitute the electron transport system from NADPH to the present protein (A), there is mentioned ferredoxin and ferredoxin-NADP+ reductase, NADPH-cytochrome P-450 reductase, and the like.

To confirm the ability of converting compound (II) to compound (III), for example, a reaction solution of about pH 7, comprising the present protein (A), 13-NADPH, ferredoxin, ferredoxin-NADP+ reductase and compound (II) labeled with a radioisotope, is incubated at about 30° C. for about 10 minutes to 1 hour. Subsequently, after making the reaction solution acidic by adding hydrochloric acid, it is extracted with ethyl acetate. After subjecting the recovered ethyl acetate layer to thin layered chromatography (hereinafter referred to as "TLC"), autoradiography is conducted and the ability to convert compound (II) to compound (III) can be confirmed by detecting the labeled compound (III).

To prepare the present protein (A), for example, first, the DNA encoding the present protein (A) (hereinafter, sometimes collectively referred to as "present DNA (A)") is obtained according to the conventional genetic engineering methods (for example, the methods described in Sambrook, J., Frisch, E. F., Maniatis, T.; Molecular Cloning 2nd Edition, Cold Spring Harbor Laboratory press).

As examples of the present DNA (A), there can be mentioned a DNA encoding the present invention protein (A) (hereinafter, sometimes referred to as "present invention DNA (A)"). As specific examples of the present invention DNA (A), there can be mentioned:

a DNA encoding a protein comprising the amino acid sequence shown in SEQ ID NO: 1 (hereinafter, sometimes referred to as "present invention DNA (A1)");

a DNA encoding a protein comprising the amino acid sequence shown in SEQ ID NO: 2 (hereinafter, sometimes referred to as "present invention DNA (A2)");

a DNA encoding a protein comprising the amino acid sequence shown in SEQ ID NO: 3 (hereinafter, sometimes referred to as "present invention DNA (A3)");

a DNA encoding a protein comprising the amino acid sequence shown in SEQ ID NO: 108 (hereinafter, sometimes referred to as "present invention DNA (A4)");

a DNA encoding a protein comprising the amino acid sequence shown in SEQ ID NO: 159 (hereinafter, sometimes referred to as "present invention DNA (A11)");

a DNA encoding a protein comprising the amino acid sequence shown in SEQ ID NO: 160 (hereinafter, sometimes referred to as "present invention DNA (A12)");

a DNA encoding a protein comprising the amino acid sequence shown in SEQ ID NO: 136 (hereinafter, sometimes referred to as "present invention DNA (A13)");

a DNA encoding a protein comprising the amino acid sequence shown in SEQ ID NO: 137 (hereinafter, sometimes referred to as "present invention DNA (A14)");

a DNA encoding a protein comprising the amino acid sequence shown in SEQ ID NO: 138 (hereinafter, sometimes referred to as "present invention DNA (A15)");

a DNA encoding a protein comprising the amino acid sequence shown in SEQ ID NO: 215 (hereinafter, sometimes referred to as "present invention DNA (A16)");

a DNA encoding a protein comprising the amino acid sequence shown in SEQ ID NO: 216 (hereinafter, sometimes referred to as "present invention DNA (A17)");

a DNA encoding a protein comprising the amino acid sequence shown in SEQ ID NO: 217 (hereinafter, sometimes referred to as "present invention DNA (A18)");

a DNA encoding a protein comprising the amino acid sequence shown in SEQ ID NO: 218 (hereinafter, sometimes referred to as "present invention DNA (A19)");

a DNA encoding a protein comprising the amino acid sequence shown in SEQ ID NO: 219 (hereinafter, sometimes referred to as "present invention DNA (A20)");

a DNA encoding a protein comprising the amino acid sequence shown in SEQ ID NO: 220 (hereinafter, sometimes referred to as "present invention DNA (A21)");

a DNA encoding a protein comprising the amino acid sequence shown in SEQ ID NO: 221 (hereinafter, sometimes referred to as "present invention DNA (A22)");

a DNA encoding a protein comprising the amino acid sequence shown in SEQ ID NO: 222 (hereinafter, sometimes referred to as "present invention DNA (A23)");

a DNA encoding a protein comprising the amino acid sequence shown in SEQ ID NO: 223 (hereinafter, sometimes referred to as "present invention DNA (A24)");

a DNA encoding a protein comprising the amino acid sequence shown in SEQ ID NO: 224 (hereinafter, sometimes referred to as "present invention DNA (A25)"); and the like.

Further as more specific examples of the present invention DNA (A), there can be mentioned:

a DNA comprising the nucleotide sequence shown in SEQ ID NO: 6;

a DNA comprising the nucleotide sequence shown in SEQ ID NO: 9;

a DNA comprising the nucleotide sequence shown in SEQ ID NO: 7;

a DNA comprising the nucleotide sequence shown in SEQ ID NO: 10;

a DNA comprising the nucleotide sequence shown in SEQ ID NO: 8;

a DNA comprising the nucleotide sequence shown in SEQ ID NO: 11;

a DNA comprising the nucleotide sequence shown in SEQ ID NO: 109;

a DNA comprising the nucleotide sequence shown in SEQ ID NO: 110;

a DNA comprising the nucleotide sequence shown in SEQ ID NO: 139;

a DNA comprising the nucleotide sequence shown in SEQ ID NO: 144;

a DNA comprising the nucleotide sequence shown in SEQ ID NO: 140;

a DNA comprising the nucleotide sequence shown in SEQ ID NO: 145;

a DNA comprising the nucleotide sequence shown in SEQ ID NO: 141;

a DNA comprising the nucleotide sequence shown in SEQ ID NO: 146;

a DNA comprising the nucleotide sequence shown in SEQ ID NO: 142;

a DNA comprising the nucleotide sequence shown in SEQ ID NO: 147;

a DNA comprising the nucleotide sequence shown in SEQ ID NO: 143;

a DNA comprising the nucleotide sequence shown in SEQ ID NO: 148;

a DNA comprising the nucleotide sequence shown in SEQ ID NO: 225;

a DNA comprising the nucleotide sequence shown in SEQ ID NO: 235;

a DNA comprising the nucleotide sequence shown in SEQ ID NO: 226;

a DNA comprising the nucleotide sequence shown in SEQ ID NO: 236;

a DNA comprising the nucleotide sequence shown in SEQ ID NO: 227;

a DNA comprising the nucleotide sequence shown in SEQ ID NO: 237;

a DNA comprising the nucleotide sequence shown in SEQ ID NO: 228;

a DNA comprising the nucleotide sequence shown in SEQ ID NO: 238;

a DNA comprising the nucleotide sequence shown in SEQ ID NO: 229;

a DNA comprising the nucleotide sequence shown in SEQ ID NO: 239;

a DNA comprising the nucleotide sequence shown in SEQ ID NO: 230;

a DNA comprising the nucleotide sequence shown in SEQ ID NO: 240;

a DNA comprising the nucleotide sequence shown in SEQ ID NO: 231;

a DNA comprising the nucleotide sequence shown in SEQ ID NO: 241;

a DNA comprising the nucleotide sequence shown in SEQ ID NO: 232;

a DNA comprising the nucleotide sequence shown in SEQ ID NO: 242;

a DNA comprising the nucleotide sequence shown in SEQ ID NO: 233;

a DNA comprising the nucleotide sequence shown in SEQ ID NO: 243;

a DNA comprising the nucleotide sequence shown in SEQ ID NO: 234;

a DNA comprising the nucleotide sequence shown in SEQ ID NO: 244;

a DNA comprising the nucleotide sequence shown in SEQ ID NO: 214;

a DNA comprising the nucleotide sequence shown in SEQ ID NO: 368;

a DNA comprising the nucleotide sequence shown in SEQ ID NO: 393;

a DNA encoding a protein having an ability to convert in the presence of an electron transport system containing an electron donor a compound of formula (II) to a compound of formula (III), and having at least 80% sequence identity with a nucleotide sequence shown in any one of SEQ ID NO: 6, 7, 8 or 109;

a DNA encoding a protein having an ability to convert in the presence of an electron transport system containing an electron donor a compound of formula (II) to a compound of formula (III), and having at least 90% sequence identity with a nucleotide sequences shown in any one of SEQ ID NO: 139, 140, 141, 142, 143, 225, 226, 227, 228, 229, 230, 231, 232, 233 or 234; and the like.

Further, as examples of the present DNA (A), other than the present invention DNA (A) above, there is mentioned:

a DNA comprising the nucleotide sequence encoding a protein comprising the amino acid sequence shown in SEQ ID NO: 4 (hereinafter, sometimes referred to as "present DNA (A9)");

a DNA comprising the nucleotide sequence shown in SEQ ID NO: 78;

a DNA comprising the nucleotide sequence encoding a protein comprising the amino acid sequence shown in SEQ ID NO: 5 (hereinafter, sometimes referred to as "present DNA (A10)");

a DNA comprising the nucleotide sequence shown in SEQ ID NO: 84;

a DNA comprising the nucleotide sequence shown in SEQ ID NO: 85; and the like.

The present DNA(A), for example, may be a DNA cloned from nature and may be a DNA in which a deletion, substitution or addition of nucleotide(s) has been introduced to the DNA cloned from nature by such as a site-directed mutagenesis method, a random mutagenesis method, and may be an artificially synthesized DNA. Subsequently, the present protein (A) can be produced or obtained by expressing the obtained present DNA (A) according to the conventional genetic engineering methods. In such ways, the present protein (A) can be prepared.

The present DNA (A) can be prepared, for example, by the following methods. First, chromosomal DNA is prepared by conventional genetic engineering methods, such as those described in Molecular Cloning: A Laboratory Manual 2nd edition (1989), Cold Spring Harbor Laboratory Press; and Current Protocols in Molecular Biology (1987), John Wiley & Sons, Incorporated, from microorganisms belonging to *Streptomyces*, such as *Streptomyces phaeochromogenes*, *Streptomyces testaceus*, *Strepotomyces achromogenes*, *Streptomyces griseolus*, *Streptomyces carbophilus*, *Streptomyces griseofuscus*, *Streptomyces thermocoerulescens*, *Streptomyces nogalater*, *Streptomyces tsusimaensis*, *Streptomyces glomerochromogenes*, *Streptomyces olivochromogenes*, *Streptomyces ornatus*, *Streptomyces griseus*, *Streptomyces lanatus*, *Streptomyces misawanensis*, *Streptomyces pallidus*, *Streptomyces roseorubens*, *Streptomyces rutgersensis* and *Streptomyces steffisburgensis*, and more specifically, *Streptomyces phaeochromogenes* IFO12898, *Streptomyces testaceus* ATCC21469, *Streptomyces achromogenes* IFO 12735, *Streptomyces griseolus* ATCC11796, *Streptomyces carbophilus* SANK62585, *Streptomyces griseofuscus* IFO 12870t, *Streptomyces thermocoerulescens* IFO 14273t, *Streptomyces nogalater* IFO 13445, *Streptomyces tsusimaensis* IFO 13782, *Streptomyces glomerochromogenes* IFO 13673t, *Streptomyces olivochromogenes* IFO 12444, *Streptomyces ornatus* IFO 13069t, *Streptomyces griseus* ATCC 10137, *Streptomyces griseus* IFO 13849T, *Streptomyces lanatus* IFO 12787T, *Streptomyces misawanensis* IFO 13855T, *Streptomyces pallidus* IFO 13434T, *Streptomyces roseorubens* IFO 13682T, *Streptomyces rutgersensis* IFO 15875T and *Streptomyces steffisburgensis* IFO 13446T, and the like; or microorganisms belonging to *Saccharopolyspora*, such as *Saccharopolyspora taberi*, more specifically, *Saccharopolyspora taberi* JCM 9383t and the like. Next, after partial digestion of the chromosomal DNA with a restriction enzyme such as Sau3AI, a DNA of about 2 kb is recovered. The recovered DNA is cloned into a vector according to the conventional genetic engineering methods described in "Molecular Cloning: A Laboratory Manual 2nd edition" (1989), Cold Spring Harbor Laboratory Press; and "Current Protocols in Molecular Biology" (1987), John Wiley & Sons, Incorporated. As the vector, specifically for example, there can be utilized pUC 119 (TaKaRa Shuzo Company), pTVA 118N (Takara Shuzo Company), pBluescript II (Toyobo Company), pCR2.1-TOPO (Invitrogen), pTrc99A (Amersham Pharmacia Biotech Company), pKK331-1A (Amersham Pharmacia Biotech Company), and the like. A chromosomal DNA library can be obtained by extracting the plasmid from the obtained clone.

The present DNA (A) can be obtained by hybridizing a probe with the obtained chromosomal DNA library under the conditions described below, and by detecting and recovering the DNA which bound specifically with the probe. The probe can be a DNA consisting of about at least 20 nucleotides comprising the nucleotides sequence encoding an amino acid sequence shown in any one of SEQ ID NO: 1, 2, 3 or 108. As specific examples of the DNA which can be utilized as probes, there is mentioned a DNA comprising a nucleic acid shown in any one of SEQ ID NO: 6, 7, 8 or 109; a DNA comprising a partial nucleotide sequence of the nucleic acid sequence shown in any one of SEQ ID NO: 6, 7, 8 or 109; a DNA comprising a nucleotide sequence complimentary to said partial nucleotide sequence; and the like.

The DNA utilized as the probe is labeled with a radioisotope, fluorescent coloring or the like. To label the DNA with a radioisotope, for example, there can be utilized the Random Labeling Kit of Boehringer or Takara Shuzo Company. Further, a DNA labeled with $^{32}$P can be prepared by conducting PCR. The DNA to be utilized for the probe is utilized as the template. The dCTP typically utilized in the PCR reaction solution is exchanged with (α-$^{32}$P)dCTP. Further, when labeling the DNA with fluorescent coloring, for example, there can be utilized DIG-High Prime DNA labeling and Detection Starter Kit II (Roche Company).

A specific example of preparing the probe is explained next. For example, a DNA labeled with digoxigenin, comprising the full length of the nucleotide sequence shown in SEQ ID NO: 6 can be obtained by utilizing the chromosomal DNA prepared from *Streptomyces phaeochromogenes* IFO12898 as described above or a chromosomal DNA library as a template, by utilizing as primers an oligonucleotide consisting of the nucleotide sequence shown in SEQ ID NO: 93 and an oligonucleotide consisting of the nucleotide sequence shown in SEQ ID NO: 94, and by conducting PCR as described in the examples described below with, for example, PCR DIG Probe Synthesis Kit (Roche Diagnostics GmbH) according to the attached manual. Similarly, a DNA labeled with digoxigenin, comprising the nucleotide sequence of from nucleotide 57 to nucleotide 730 shown in SEQ ID NO: 6 can be obtained by utilizing the chromosomal DNA prepared from *Streptomyces* phaeochromogenes IFO12898 as described above or a chromosomal DNA library as the template. As primers, the PCR is conducted with an oligonucleotide consisting of the nucleotide sequence shown in SEQ ID NO: 130 and an oligonucleotide consisting of the nucleotide sequence shown in SEQ ID NO: 131. Further, a DNA labeled with digoxigenin, comprising the full length of the nucleotide sequence shown in SEQ ID NO: 7 can be obtained by utilizing the chromosomal DNA prepared from *Saccharopolyspora taberi* JCM 9383t as described above or a chromosomal DNA library as the template. As primers, the PCR is conducted with an oligonucleotide consisting of the nucleotide sequence shown in SEQ ID NO: 61 and an oligonucleotide consisting of the nucleotide sequence shown in SEQ ID NO: 62. Further, a DNA labeled with digoxigenin, comprising the full length of the nucleotide sequence shown in SEQ ID NO: 8 can be obtained by utilizing the chromosomal DNA prepared from *Streptomyces testaceus* ATCC21469 as described above or a chromosomal DNA library as the template. As primers, the PCR is conducted with an oligonucleotide consisting of the nucleotide sequence shown in SEQ ID NO: 70 and an oligonucleotide consisting of the nucleotide sequence shown in SEQ ID NO: 71. Further, a DNA labeled with digoxigenin, comprising the nucleotide sequence of from nucleotide 21 to nucleotide 691 shown in SEQ ID NO: 8 can be obtained by utilizing the chromosomal DNA prepared from *Streptomyces testaceus* ATCC21469 as described above or a chromosomal DNA library as the template. As primers, the PCR is conducted with an oligonucleotide consisting of the nucleotide sequence shown in SEQ ID NO: 132 and an oligonucleotide consisting of the nucleotide sequence shown in SEQ ID NO: 133.

The methods by which a probe is allowed to hybridize with the chromosomal DNA library may include colony hybridization and plaque hybridization, and an appropriate method may be selected, which is compatible with the type of vector used in the library preparation. When the utilized library is constructed with the use of plasmid vectors, colony hybridization is conducted. Specifically first, transformants are obtained by introducing the DNA of the library into microorganism in which the plasmid vector utilized to construct the library is replicable. The obtained transformants are diluted and spread onto an agar plate and cultured until colonies appear. When a phage vector is utilized to construct the library, plaque hybridization is conducted. Specifically, first, the microorganism in which the phage vector utilized to produce the library is replicable is mixed with the phage of the library, under the conditions in which infection is possible. The mixture is then further mixed with soft agar. This mixture is then spread onto an agar plate. Subsequently, the mixture is cultured until plaques appear.

Next, in the case of any one of the above hybridizations, a membrane is placed on the surface of the agar plate in which the above culturing was conducted and the colonies of the transformants or the phage particles in the plaques are transferred to the membrane. After alkali treatment of the membrane, there is a neutralization treatment. The DNA eluted from the transformants or the phage particles is then fixed onto the membrane. More specifically for example, in the event of plaque hybridization, the phage particles are absorbed onto the membrane by placing a nitrocellulose membrane or a nylon membrane, specifically for example, Hybond-N+ (Amersham Pharmacia Biotech Company) on the agar plate and waiting for 1 minute. The membrane is soaked in an alkali solution (1.5M NaCl and 0.5N NaOH) for about 3 minutes to dissolve the phage particles and elute the phage DNA onto the membrane. The membrane is then soaked in neutralization solution (1.5M NaCl and 0.5M tris-HCl buffer pH7.5) for about 5 minutes. After washing the membrane in washing solution (0.3M NaCl, 30 mM sodium citrate, 0.2M tris-HCl buffer pH7.5) for about 5 minutes, for example, the phage DNA is fixed onto the membrane by incubating about 80° C. for about 90 minutes in vacuo.

By utilizing the membrane prepared as such, hybridization is conducted with the above DNA as a probe. Hybridization can be conducted, for example, according to the description in "Molecular Cloning: A Laboratory Manual 2nd edition (1989)" Cold Spring Harbor Laboratory Press, and the like.

While various temperature conditions and reagents are available for conducting hybridization, the membrane prepared as described above is soaked with and maintained for 1 hour to 4 hours at 42° C. to 65° C. in a prehybridization solution, which is prepared at a ratio of from 50 μl to 200 μl per 1 cm$^2$ of the membrane. The prehybridization solution, for example, may contain 450 mM to 900 mM NaCl and 45 mM to 90 mM sodium citrate, contain sodium dodecyl sulfate (hereinafter, referred to as "SDS") at a concentration of 0.1% to 1.0%, and contain denatured unspecific DNA at a concentration of from 0 μg/ml to 200 μg/ml, and may sometimes contain albumin, phycol, and polyvinyl pyrrolidone, each at a concentration of 0% to 0.2%. Subsequently, for example, the membrane is soaked with and maintained for 12 hours to 20 hours at 42° C. to 65° C. in a hybridization solution, which is prepared at a ratio of from 50 μl to 200 μl per 1 cm$^2$ of the membrane. The hybridization solution is, for example, a mixture of the prehybridization solution, which may contain 450 mM to 900 mM NaCl and 45 mM to 90 mM sodium citrate, contain SDS at a concentration of 0.1% to 1.0%, and contain denatured unspecific DNA at a concentration of from 0 μg/ml to 200 μg/ml, and may sometimes contain albumin, phycol, and polyvinyl pyrrolidone, each at a concentration of 0% to 0.2%, with the probe obtained with the preparation method described above (in a relative amount of 1.0×104 cpm to 2.0×106 cpm per 1 cm2 of the membrane). Subsequently, the membrane is removed and a wash of 5 minutes to 15 minutes is conducted about 2 to 4 times, utilizing a washing solution of 42° C. to 65° C. that contains 15 mM to 300 mM of NaCl, 1.5 mM to 30 mM of sodium citrate and 0.1% to 1.0% of SDS. Further, after lightly rinsing with 2×SSC solution (300 mM NaCl and 30 mM sodium citrate), the membrane is dried. By detecting the position of the probe on the membrane by subjecting the membrane to autoradiography, the position of the DNA hybridizing to the utilized probe on the membrane is identified. Alternatively, prehybridization and hybridization can be conducted with the use of a commercially available hybridization kit, such as with the use of hybridization solution contained in the DIG-High Prime DNA Labeling and Detection Starter Kit II (Roche). After hybridization, for example, the membrane is washed twice for 5 minutes at room temperature in 2×SSC containing 0.1% SDS, followed by washing twice for 15 minutes at 65° C. in 0.5×SSC containing 0.1% SDS. The positions of DNAs on the membrane hybridizing with the utilized probe are detected, by treating in turn the washed membrane with the detection solution contained in the kit and by detecting the position of the probe on the membrane.

The clones corresponding to the positions of the detected DNAs on the membrane are identified on the original agar medium, and can be picked up to isolate clones carrying those DNAs.

The present DNA (A) obtained according to the above can be cloned into a vector according to conventional genetic engineering methods described in "Molecular Cloning: A Laboratory Manual 2nd edition" (1989), Cold Spring Harbor Laboratory Press, "Current Protocols in Molecular Biology" (1987), John Wiley & Sons Incorporated, and the like. As the vector, specifically for example, there can be utilized pUCA119 (Takara Shuzo Company), pTVA118N (Takara Shuzo Company), pBluescriptII (Toyobo Company), pCR2.1-TOPO (Invitrogen Company), pTrc99A (Pharmacia Company), pKK331-1A (Pharmacia Company) and the like.

Further, the nucleotide sequence of the present DNA (A) obtained according to the above description can be analyzed by the dideoxy terminator method described in F. Sanger, S. Nicklen, A. R. Coulson, Proceeding of National Academy of Science U.S.A. (1977) 74:5463-5467. In the sample preparation for the nucleotide sequence analysis, a commercially available reagent may be utilized, such as the ABI PRISM Dye Terminator Cycle Sequencing Ready Reaction Kit of Perkin Elmer Company.

The present DNA (A) can also be prepared as follows. The present DNA (A) can be amplified by conducting PCR. The PCR may utilize as a template the chromosomal DNA or chromosomal DNA library prepared as described above from microorganisms belonging to Streptomyces, such as Streptomyces phaeochromogenes, Streptomyces testaceus, Streptomyces achromogenes, Streptomyces griseolus, Streptomyces carbophilus, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis and Streptomyces steffisburgensis, and more specifically, Streptomyces phaeochromogenes IFO12898, Streptomyces testaceus ATCC21469, Streptomyces achromogenes IFO 12735, Streptomyces griseolus ATCC11796, Streptomyces carbophilus SANK62585, Streptomyces griseofuscus IFO 12870t, Streptomyces thermocoerulescens IFO 14273t, Streptomyces nogalater IFO 13445, Streptomyces tsusimaensis IFO 13782, Streptomyces glomerochromogenes IFO 13673t, Streptomyces olivochromogenes IFO 12444, Streptomyces ornatus IFO 13069t, Streptomyces griseus ATCC 10137, Streptomyces griseus IFO 13849T, Streptomyces lanatus IFO 12787T, Streptomyces misawanensis IFO 13855T, Streptomyces pallidus IFO 13434T, Streptomyces roseorubens IFO 13682T, Streptomyces rutgersensis IFO 15875T and Streptomyces steffisburgensis IFO 13446T, and the like; or microorganisms belonging to Saccharopolyspora, such as Saccharopolyspora taberi, more specifically, Saccharopolyspora taberi JCM 9383t and the like. The PCR may also utilize an oligonucleotide comprising at least about 20 nucleotides of the 5' terminus of the nucleotide sequence encoding an amino acid sequence shown in any one of SEQ ID NO: 1, 2, 3, 4, 5, 108, 159, 160, 136, 137, 138, 215, 216, 217, 218, 219, 220, 221, 222, 223 or 224, with an oligonucleotide comprising a nucleotide sequence complimentary to at least about 20 nucleotides adjacent to 3' terminus or downstream of the 3' terminus of the nucleotide sequence encoding any one of the amino acid sequences above. The PCR may be conducted under the conditions described below. On the 5' terminus side of the primer utilized for the PCR as described above, a restriction enzyme recognition sequence may be added.

More specifically for example, a DNA comprising a nucleotide sequence encoding the amino acid sequence shown in SEQ ID NO: 1, a DNA comprising the nucleotide sequence shown in SEQ ID NO: 6, or the like can be prepared by conducting PCR by utilizing as the template the chromosomal DNA or chromosomal DNA library prepared from Streptomyces phaeochromogenes IFO12898 and by utilizing as primers an oligonucleotide comprising the nucleotide sequence shown in SEQ ID NO: 51 and an oligonucleotide comprising the nucleotide sequence shown in SEQ ID NO: 52. Alternatively, a DNA comprising the nucleotide sequence shown in SEQ ID NO: 9 (containing a nucleotide sequence encoding the amino acid sequence shown in SEQ ID NO: 1) can be amplified by conducting PCR by utilizing as primers the oligonucleotide comprising the nucleotide sequence shown in SEQ ID NO: 51 and an oligonucleotide comprising the nucleotide sequence shown in SEQ ID NO: 53.

For example, a DNA comprising a nucleotide sequence encoding the amino acid sequence shown in SEQ ID NO: 2, a DNA comprising the nucleotide sequence shown in SEQ ID NO: 7, or the like can be prepared by conducting PCR by utilizing as the template the chromosomal DNA or chromosomal DNA library prepared from Saccharopolyspora taberi JCM 9383t and by utilizing as primers an oligonucleotide comprising the nucleotide sequence shown in SEQ ID NO: 61 and an oligonucleotide comprising the nucleotide sequence shown in SEQ ID NO: 62. Alternatively, a DNA comprising the nucleotide sequence shown in SEQ ID NO: 10 (containing a nucleotide sequence encoding the amino acid sequence shown in SEQ ID NO: 2) can be amplified by conducting PCR by utilizing as primers the oligonucleotide comprising the nucleotide sequence shown in SEQ ID NO: 61 and an oligonucleotide comprising the nucleotide sequence shown in SEQ ID NO: 63.

For example, a DNA comprising a nucleotide sequence encoding the amino acid sequence shown in SEQ ID NO: 108, a DNA comprising the nucleotide sequence shown in SEQ ID NO: 109, or the like can be prepared by conducting PCR by utilizing as the template the chromosomal DNA or chromosomal DNA library prepared from Streptomyces achromogenes IFO 12735 and by utilizing as primers an oligonucleotide comprising the nucleotide sequence shown in SEQ ID NO: 119 and an oligonucleotide comprising the nucleotide sequence shown in SEQ ID NO: 120. Alternatively, a DNA comprising the nucleotide sequence shown in SEQ ID NO: 110 (containing a nucleotide sequence encoding the amino acid sequence shown in SEQ ID NO: 108) can be amplified by conducting PCR by utilizing as primers the oligonucleotide comprising the nucleotide sequence shown in SEQ ID NO: 119 and an oligonucleotide comprising the nucleotide sequence shown in SEQ ID NO: 121.

For example, a DNA comprising the nucleotide sequence shown in SEQ ID NO: 144 (containing a nucleotide sequence encoding the amino acid sequence shown in SEQ ID NO: 159) can be prepared by conducting PCR by utilizing as the template the chromosomal DNA or chromosomal DNA library prepared from *Streptomyces nogalater* IFO 13445 and by utilizing as primers an oligonucleotide comprising the nucleotide sequence shown in SEQ ID NO: 165 and an oligonucleotide comprising the nucleotide sequence shown in SEQ ID NO: 166.

For example, a DNA comprising the nucleotide sequence shown in SEQ ID NO: 145 (containing a nucleotide sequence encoding the amino acid sequence shown in SEQ ID NO: 160) can be prepared by conducting PCR by utilizing as the template the chromosomal DNA or chromosomal DNA library prepared from *Streptomyces tsusimaensis* IFO 13782 and by utilizing as primers an oligonucleotide comprising the nucleotide sequence shown in SEQ ID NO: 171 and an oligonucleotide comprising the nucleotide sequence shown in SEQ ID NO: 172.

For example, a DNA comprising the nucleotide sequence shown in SEQ ID NO: 146 (containing a nucleotide sequence encoding the amino acid sequence shown in SEQ ID NO: 136) can be prepared by conducting PCR by utilizing as the template the chromosomal DNA or chromosomal DNA library prepared from *Streptomyces thermocoerulescens* IFO14273t and by utilizing as primers an oligonucleotide comprising the nucleotide sequence shown in SEQ ID NO: 177 and an oligonucleotide comprising the nucleotide sequence shown in SEQ ID NO: 178.

For example, a DNA comprising the nucleotide sequence shown in SEQ ID NO: 147 (containing a nucleotide sequence encoding the amino acid sequence shown in SEQ ID NO: 137) can be prepared by conducting PCR by utilizing as the template the chromosomal DNA or chromosomal DNA library prepared from *Streptomyces glomerochromogenes* IFO13673t and by utilizing as primers an oligonucleotide comprising the nucleotide sequence shown in SEQ ID NO: 183 and an oligonucleotide comprising the nucleotide sequence shown in SEQ ID NO: 184.

For example, a DNA comprising the nucleotide sequence shown in SEQ ID NO: 148 (containing a nucleotide sequence encoding the amino acid sequence shown in SEQ ID NO: 138) can be prepared by conducting PCR by utilizing as the template the chromosomal DNA or chromosomal DNA library prepared from *Streptomyces olivochromogenes* IFO 12444 and by utilizing as primers an oligonucleotide comprising the nucleotide sequence shown in SEQ ID NO: 184 and an oligonucleotide comprising the nucleotide sequence shown in SEQ ID NO: 185.

When utilizing as the template the DNA library in which the chromosomal DNA is introduced into the vector, for example, the present DNA (A) can also be amplified by conducting PCR by utilizing as primers an oligonucleotide comprising a nucleotide sequence selected from a nucleotide sequence encoding any one of the amino acid sequences shown in SEQ ID NO: 1, 2, 3, 4, 5, 108, 159, 160, 136, 137 or 138 (for example, an oligonucleotide comprising a nucleotide sequence of at least about 20 nucleotides of the 5' terminus side of the nucleotide sequence encoding the amino acid sequence shown in SEQ ID NO: 1) and an oligonucleotide of at least about 20 nucleotides comprising a nucleotide sequence complimentary to the nucleotide sequence adjacent to the DNA insertion site of the vector utilized to construct the library. On side of the 5' terminus of the primer utilized for the PCR as described above, a restriction enzyme recognition sequence may be added.

As the conditions for the such PCR described above, specifically for example, there can be mentioned the condition of maintaining 97° C. for 2 minutes, then repeating for 10 cycles a cycle that includes maintaining 97° C. for 15 seconds, followed by 65° C. for 30 seconds, and then 72° C. for 2 minutes; then conducting for 15 cycles a cycle that includes maintaining 97° C. for 15 seconds, followed by 68° C. for 30 seconds, and followed by 72° C. for 2 minutes (adding 20 seconds to every cycle in turn); and then maintaining 72° C. for 7 minutes. The PCR can utilize a reaction solution of 50 µl, containing 50 ng of chromosomal DNA, containing 300 nM of each of the 2 primers in such pairings described above, containing 5.0 µl of dNTP mixture (a mixture of 2.0 mM each of the 4 types of dNTPs), containing 5.0 µl of 10× Expand HF buffer (containing MgCl$_2$, Roche Molecular Biochemicals Company) and containing 0.75 µl of Expand HiFi enzyme mix (Roche Molecular Biochemicals Company).

Alternatively, there can be mentioned the condition of maintaining 97° C. for 2 minutes, then repeating for 30 cycles a cycle that includes 97° C. for 15 seconds, followed by 60° C. for 30 seconds, and followed by 72° C. for 90 seconds, and then maintaining the reaction solution at 72° C. for 4 minutes. The PCR can utilize a reaction solution of 50 µl containing 250 ng of chromosomal DNA, containing 200 nM of each of the 2 primers in such pairings described above, containing 5.0 µl of dNTP mixture (a mixture of 2.5 mM each of the 4 types of dNTPs), 5.0 µl of 10× ExTaq buffer (containing MgCl2, Takara Shuzo Company) and containing 0.5 µl of ExTaq Polymerase (Takara Shuzo Company).

Alternatively, for example, oligonucleotides can be designed and prepared for use as primers, based on the nucleotide sequence of a region to which the sequence identity is particularly high in the nucleotide sequence shown in SEQ ID NO: 6, 7, 8 or 109. The present DNA (A) can also be obtained by conducting PCR by utilizing the obtained oligonucleotides as primers and a chromosomal DNA or chromosomal DNA library. The chromosomal DNA or chromosomal DNA library can be prepared as described above from microorganisms belonging to *Streptomyces*, such as *Streptomyces phaeochromogenes*, *Streptomyces testaceus*, *Streptomyces achromogenes*, *Streptomyces griseolus*, *Streptomyces carbophilus*, *Streptomyces griseofuscus*, *Streptomyces thermocoerulescens*, *Streptomyces nogalater*, *Streptomyces tsusimaensis*, *Streptomyces glomerochromogenes*, *Streptomyces olivochromogenes*, *Streptomyces ornatus*, *Streptomyces griseus*, *Streptomyces lanatus*, *Streptomyces misawanensis*, *Streptomyces pallidus*, *Streptomyces roseorubens*, *Streptomyces rutgersensis* and *Streptomyces steffisburgensis*, and more specifically, *Streptomyces phaeochromogenes* IFO12898, *Streptomyces testaceus* ATCC21469, *Streptomyces achromogenes* IFO 12735, *Streptomyces griseolus* ATCC11796, *Streptomyces carbophilus* SANK62585, *Streptomyces griseofuscus* IFO 12870t, *Streptomyces thermocoerulescens* IFO 14273t, *Streptomyces nogalater* IFO 13445, *Streptomyces tsusimaensis* IFO 13782, *Streptomyces glomerochromogenes* IFO 13673t, *Streptomyces olivochromogenes* IFO 12444, *Streptomyces ornatus* IFO 13069t, *Streptomyces griseus* ATCC 10137, *Streptomyces griseus* IFO 13849T, *Streptomyces lanatus* IFO 12787T, *Streptomyces misawanensis* IFO 13855T, *Streptomyces pallidus* IFO 13434T, *Streptomyces roseorubens* IFO 13682T, *Streptomyces rutgersensis* IFO 15875T and *Streptomyces steffisburgensis* IFO 13446T, and the like; or microorganisms belonging to *Saccharopolyspora*, such as *Saccharopolyspora taberi*, more specifically, *Saccharopolyspora taberi* JCM 9383t and the like. As the "region to which the sequence identity is particularly high in the nucleotide sequence shown in SEQ ID NO: 6, 7, 8 or 109," for example, there is mentioned the region corresponding to the region shown with each of nucleotides 290 to 315, 458 to 485, 496 to 525 or 1046 to 1073 in the nucleotide sequence shown in SEQ ID NO: 6. As the primers designed on the basis of such regions of the nucleotide sequence, for example, there can be mentioned a primer comprising the nucleotide sequence shown in any one of SEQ ID NO: 124 to 129.

SEQ ID NO: 124; based on the nucleotide sequence of the region corresponding to the region shown with the above nucleotides 290 to 315;

SEQ ID NO: 125; based on the nucleotide sequence of the region corresponding to the region shown with the above nucleotides 458 to 485;

SEQ ID NO: 126; based on the nucleotide sequence of the region corresponding to the region shown with the above nucleotides 458 to 485;

SEQ ID NO: 127; based on the nucleotide sequence of the region corresponding to the region shown with the above nucleotides 496 to 525;

SEQ ID NO: 128; based on the nucleotide sequence of the region corresponding to the region shown with the above nucleotides 496 to 525; and SEQ ID NO: 129; based on the nucleotide sequence of the region corresponding to the region shown with the above nucleotides 1046 to 1073.

For example, a DNA of approximately 800 bp is amplified by utilizing as primers the pairing of the oligonucleotide comprising the nucleotide sequence shown in SEQ ID NO: 124 and the oligonucleotide comprising the nucleotide sequence shown in SEQ ID NO: 129. A DNA of approximately 600 bp is amplified by utilizing as primers the pairing of the oligonucleotide comprising the nucleotide sequence shown in SEQ ID NO: 125 and the oligonucleotide comprising the nucleotide sequence shown in SEQ ID NO: 129. A DNA of approximately 600 bp is amplified by utilizing as primers the pairing of the oligonucleotide comprising the nucleotide sequence shown in SEQ ID NO: 126 and the oligonucleotide comprising the nucleotide sequence shown in SEQ ID NO: 129. A DNA of approximately 580 bp is amplified by utilizing as primers the pairing of the oligonucleotide comprising the nucleotide sequence shown in SEQ ID NO: 127 and the oligonucleotide comprising the nucleotide sequence shown in SEQ ID NO: 129. Further, a DNA of approximately 580 bp is amplified by utilizing as primers the pairing of the oligonucleotide comprising the nucleotide sequence shown in SEQ ID NO: 128 and the oligonucleotide comprising the nucleotide sequence shown in SEQ ID NO: 129.

As the conditions for PCR, specifically for example, there is mentioned the condition of maintaining 95° C. for 1 minute; repeating for 30 cycles a cycle that includes maintaining 94° C. for 15 seconds, followed by 60° C. for 30 seconds, and followed by 72° C. for 1 minute; and then maintaining 72° C. for 5 minutes. There can be utilized the reaction solution of 25 µl containing 10 ng of chromosomal DNA, containing 200 nM of each of the 2 primers, containing 0.5 µl of dNTP mix (a mixture of 10 mM each of the 4 types of dNTPs), containing 5 µl of 5×GC genomic PCR reaction buffer, containing 5 µl of 5M GC-Melt and containing 0.5 µl of Advantage-GC genomic polymerase mix (Clontech Company).

By recovering the DNA amplified as described above, a DNA comprising a partial nucleotide sequence of the present DNA (A) can be obtained. Next, based on the nucleotide sequence possessed by the obtained "DNA comprising a partial nucleotide sequence of the present DNA (A)," there is designed and prepared an oligonucleotide comprising a partial nucleotide sequence of at least about 20 nucleotides of said nucleotide sequence or an oligonucleotide comprising a nucleotide sequence complimentary to the partial nucleotide sequence of at least about 20 nucleotides of said nucleotide sequence. A DNA comprising a partial nucleotide sequence of the present DNA (A) extended downstream of the 3' terminus or upstream of the 5' terminus of the "DNA comprising a partial nucleotide sequence of the present DNA (A)" obtained as described above can be obtained by conducting PCR. The PCR may utilize as primers a pairing of an oligonucleotide prepared as described above based on the nucleotide sequence of the "DNA comprising a partial nucleotide sequence of the present DNA (A)" and an oligonucleotide of at least about 20 nucleotides comprising a nucleotide sequence of the region adjacent to the DNA insertion site of the vector utilized to construct the above library or an oligonucleotide of at least about 20 bp comprising a nucleotide sequence complimentary to such nucleotide sequence thereof. The PCR may, for example, utilize as the template the chromosomal DNA library prepared from the microorganisms which have the ability to convert compound (II) to compound (III), as described above. By connecting such DNA comprising the partial nucleotide sequence of the present DNA (A), there can be obtained the present DNA (A). In such a production method, there can be utilized a commercially available kit, such as the Universal Genome Walker (Clontech Company). Alternatively, the present DNA (A) can be obtained by conducting PCR by preparing primers based on the full length nucleotide sequence of the present DNA (A) obtained by connecting the partial nucleotide sequences of the present DNA (A) as described above, by utilizing such primers and by utilizing as the template the chromosomal DNA library as described above.

For example, a DNA comprising the nucleotide sequence shown in nucleotides 316 to 1048 of SEQ ID NO: 139 (a partial nucleotide sequence of nucleotide sequence encoding the amino acid sequence shown in SEQ ID NO: 159), can be prepared by conducting PCR by utilizing as the template the chromosomal DNA or chromosomal DNA library prepared from *Streptomyces nogalater* IFO 13445 and by utilizing as primers an oligonucleotide comprising the nucleotide sequence shown in SEQ ID NO: 124 and an oligonucleotide comprising the nucleotide sequence shown in SEQ ID NO: 129. A DNA comprising a nucleotide sequence extended downstream of the 3' terminus or upstream of the 5' terminus thereof is obtained according to the above description based on the nucleotide sequence of the obtained DNA. A DNA comprising the nucleotide sequence shown in SEQ ID NO: 144 (containing a nucleotide sequence encoding the amino acid sequence shown in SEQ ID NO: 159 and the nucleotide sequence encoding the amino acid sequence shown in SEQ ID NO: 149) can be obtained by connecting the resulting DNA.

For example, a DNA comprising the nucleotide sequence shown in nucleotides 364 to 1096 of SEQ ID NO: 140 (a partial nucleotide sequence of nucleotide sequence encoding the amino acid sequence shown in SEQ ID NO: 160), can be prepared by conducting PCR by utilizing as the template the chromosomal DNA or chromosomal DNA library prepared from *Streptomyces tsusimaensis* IFO 13782 and by utilizing as primers an oligonucleotide comprising the nucleotide sequence shown in SEQ ID NO: 124 and an oligonucleotide comprising the nucleotide sequence shown in SEQ ID NO: 129. A DNA comprising a nucleotide sequence extended downstream of the 3' terminus or upstream of the 5' terminus thereof is obtained according to the above description based on the nucleotide sequence of the obtained DNA. A DNA comprising the nucleotide sequence shown in SEQ ID NO: 145 (containing a nucleotide sequence encoding the amino acid sequence shown in SEQ ID NO: 150 and the nucleotide sequence encoding the amino acid sequence shown in SEQ ID NO: 160) can be obtained by connecting the resulting DNA.

For example, a DNA comprising the nucleotide sequence shown in nucleotides 295 to 1027 of SEQ ID NO: 141 (a partial nucleotide sequence of nucleotide sequence encoding the amino acid sequence shown in SEQ ID NO: 136), can be prepared by conducting PCR by utilizing as the template the chromosomal DNA or chromosomal DNA library prepared from *Streptomyces thermocoerulescens* IFO 14273t and by utilizing as primers an oligonucleotide comprising the nucleotide sequence shown in SEQ ID NO: 124 and an oligonucleotide comprising the nucleotide sequence shown in SEQ ID NO: 129. A DNA comprising a nucleotide sequence extended downstream of the 3' terminus or upstream of the 5' terminus thereof is obtained according to the above description based on the nucleotide sequence of the obtained DNA. A DNA comprising the nucleotide sequence shown in SEQ ID NO: 146 (containing a nucleotide sequence encoding the amino acid sequence shown in SEQ ID NO: 136 and the nucleotide sequence encoding the amino acid sequence shown in SEQ ID NO: 151) can be obtained by connecting the resulting DNA.

For example, a DNA comprising the nucleotide sequence shown in nucleotides 316 to 1048 of SEQ ID NO: 142 (a partial nucleotide sequence of nucleotide sequence encoding the amino acid sequence shown in SEQ ID NO: 137), can be prepared by conducting PCR by utilizing as the template the chromosomal DNA or chromosomal DNA library prepared from *Streptomyces glomerochromogenes* IFO 13673t and by utilizing as primers an oligonucleotide comprising the nucleotide sequence shown in SEQ ID NO: 124 and an oligonucleotide comprising the nucleotide sequence shown in SEQ ID NO: 129. A DNA comprising a nucleotide sequence extended downstream of the 3' terminus or upstream of the 5' terminus thereof is obtained according to the above description based on the nucleotide sequence of the obtained DNA. A DNA comprising the nucleotide sequence shown in SEQ ID NO: 147 (containing a nucleotide sequence encoding the amino acid sequence shown in SEQ ID NO: 137 and the nucleotide sequence encoding the amino acid sequence shown in SEQ ID NO: 152) can be obtained by connecting the resulting DNA.

For example, a DNA comprising the nucleotide sequence shown in nucleotides 316 to 1048 of SEQ ID NO: 143 (a partial nucleotide sequence of nucleotide sequence encoding the amino acid sequence shown in SEQ ID NO: 138), can be prepared by conducting PCR by utilizing as the template the chromosomal DNA or chromosomal DNA library prepared from *Streptomyces olivochromogenes* IFO 12444 and by utilizing as primers an oligonucleotide comprising the nucleotide sequence shown in SEQ ID NO: 124 and an oligonucleotide comprising the nucleotide sequence shown in SEQ ID NO: 129. A DNA comprising a nucleotide sequence extended downstream of the 3' terminus or upstream of the 5' terminus thereof is obtained according to the above description based on the nucleotide sequence of the obtained DNA. A DNA comprising the nucleotide sequence shown in SEQ ID NO: 148 (containing a nucleotide sequence encoding the amino acid sequence shown in SEQ ID NO: 138 and the nucleotide sequence encoding the amino acid sequence shown in SEQ ID NO: 153) can be obtained by connecting the resulting DNA.

For example, a DNA comprising the nucleotide sequence shown in nucleotides 289 to 1015 of SEQ ID NO: 232 (a partial nucleotide sequence of nucleotide sequence encoding the amino acid sequence shown in SEQ ID NO: 222), can be prepared by conducting PCR by utilizing as the template the chromosomal DNA or chromosomal DNA library prepared from *Streptomyces roseorubens* IFO 13682T and by utilizing as primers an oligonucleotide comprising the nucleotide sequence shown in SEQ ID NO: 124 and an oligonucleotide comprising the nucleotide sequence shown in SEQ ID NO: 129. A DNA comprising a nucleotide sequence extended downstream of the 3' terminus or upstream of the 5' terminus thereof is obtained according to the above description based on the nucleotide sequence of the obtained DNA. A DNA comprising the nucleotide sequence shown in SEQ ID NO: 242 (containing a nucleotide sequence encoding the amino acid sequence shown in SEQ ID NO: 232 and the nucleotide sequence encoding the amino acid sequence shown in SEQ ID NO: 252) can be obtained by connecting the resulting DNA.

For example, a DNA comprising the nucleotide sequence shown in nucleotides 289 to 1015 of SEQ ID NO: 234 (a partial nucleotide sequence of nucleotide sequence encoding the amino acid sequence shown in SEQ ID NO: 224), can be prepared by conducting PCR by utilizing as the template the chromosomal DNA or chromosomal DNA library prepared from *Streptomyces steffisburgensis* IFO 13446T and by utilizing as primers an oligonucleotide comprising the nucleotide sequence shown in SEQ ID NO: 124 and an oligonucleotide comprising the nucleotide sequence shown in SEQ ID NO: 129. A DNA comprising a nucleotide sequence extended downstream of the 3' terminus or upstream of the 5' terminus thereof is obtained according to the above description based on the nucleotide sequence of the obtained DNA. A DNA comprising the nucleotide sequence shown in SEQ ID NO: 244 (containing a nucleotide sequence encoding the amino acid sequence shown in SEQ ID NO: 234 and the nucleotide sequence encoding the amino acid sequence shown in SEQ ID NO: 254) can be obtained by connecting the resulting DNA.

The present DNA (A) obtained by utilizing the PCR described above can be cloned into a vector by a method according to conventional genetic engineering methods described in "Molecular Cloning: A Laboratory Manual 2nd edition" (1989), Cold Spring Harbor Laboratory Press, "Current Protocols in Molecular Biology" (1987), John Wiley & Sons, Incorporated and the like. Specifically for example, cloning can be conducted by utilizing plasmid vectors such as pBluescriptII of Strategene Company or a plasmid vector contained in the TA Cloning Kit of Invitrogen Company.

Further, the present DNA (A) can be prepared, for example, as described below. First, a nucleotide sequence is designed. The nucleotide sequence encodes an amino acid sequence of a protein encoded by the present DNA (A). The nucleotide sequence has a GC content of at most 60% and at least 40%, preferably at most 55% and at least 45%. The codon usage in the nucleotide sequence encoding the amino acid sequence of the above protein is within the range of plus or minus 4% of the codon usage in genes from the species of a host cell to which the present DNA (A) is introduced. By preparing a DNA having the designed nucleotide sequence according to conventional genetic engineering methods, the present DNA (A) can be obtained.

For example, there can be designed in the way described below, a nucleotide sequence encoding an amino acid sequence (SEQ ID NO: 1) of the present invention protein (A1) and having a GC content of at most 55% and at least 45%, where the codon usage in the nucleotide sequence encoding the amino acid sequence of the above protein is within the range of plus or minus 4% of the codon usage in genes from soybean. First, for example, the codon usage (Table 22 and Table 23) in the nucleotide sequence (SEQ ID NO: 6) encoding the amino acid sequence of the present invention protein (A1) which can be obtained from *Streptomyces phaeochromogenes* IFO12898 and soybean codon usage (Table 24 and Table 25) are compared. Based on the result of the comparison, nucleotide substitutions are added to the nucleotide sequence shown in SEQ ID NO: 6, so that the GC content is at most 55% and at least 45% and the codon usage is within the range of plus or minus 4% of the soybean codon usage. As such a nucleotide substitution, there is selected a nucleotide substitution which does not result in an amino acid substitution. For example, the usage of the CTG codon encoding leucine is 1.22% in soybean genes and 7.09% in the nucleotide sequence shown in SEQ ID NO: 6. As such, for example, each of the CTG codons starting from nucleotides 106, 163, 181, 226, 289, 292, 544, 1111, and 1210 of the nucleotide sequence shown in SEQ ID NO: 6 is substituted to CTT codons; each of the CTG codons starting from nucleotides 211, 547 and 1084 is substituted to CTA codons; the CTG codon starting from nucleotide 334 is substituted to a TTA codon; each of the CTG codons starting from nucleotides 664, 718, 733, 772, 835, 1120 and 1141 is substituted to a TTG codon; and the CTG codon starting from nucleotide 787 is substituted to a TTA codon. One sequence of a nucleotide sequence designed in such a way is shown in SEQ ID NO: 214, the codon usage in which is shown in Table 26 and Table 27. In the nucleotide sequence shown in SEQ ID NO: 214, for example, the usage of the CTG codon encoding leucine is 1.71% and is within the range of plus or minus 4% of the codon usage (1.22%) for soybean. The DNA comprising the nucleotide sequence shown in SEQ ID NO: 214 can be prepared by introducing nucleotide substitutions to the DNA having the nucleotide sequence shown in SEQ ID NO: 6, according to site-directed mutagenesis methods described in such as Sambrook, J., Frisch, E. F., and Maniatis, T.; Molecular Cloning 2nd Edition, Cold Spring Harbor Press. Alternatively, the DNA having the nucleotide sequence shown in SEQ ID NO: 214 can be prepared by a DNA synthesis method employing the PCR described in Example 46 below.

Similarly, the nucleotide sequence shown in SEQ ID NO: 368 is an example of designing a nucleotide sequence encoding the amino acid sequence (SEQ ID NO: 222) of the present invention protein (A23) and having a GC content of at most 55% and at least 45%, where the codon usage in the nucleotide sequence encoding the amino acid sequence of the above protein is within the rage of plus or minus 4% with the codon usage for genes from soybean. Further, the nucleotide sequence shown in SEQ ID NO: 393 is an example of designing a nucleotide sequence encoding the amino acid sequence (SEQ ID NO: 224) of the present invention protein (A25) and having a GC content of at most 55% and at least 45%, where the codon usage in the nucleotide sequence encoding the amino acid sequence of the above protein is within the rage of plus or minus 4% with the codon usage for genes from soybean.

The present DNA (A) obtained in such a way can be cloned into a vector according to conventional genetic engineering methods described in such as Sambrook, J., Frisch, E. F., and Maniatis, T.; "Molecular Cloning 2nd Edition" (1989), Cold Spring Harbor Press; "Current Protocols in Molecular Biology" (1987), John Wiley & Sons, Incorporated, and the like. As the vector, specifically for example, there can be utilized pUC 119 (TaKaRa Shuzo Company), pTVA 118N (Takara Shuzo Company), pBluescript II (Toyobo Company), pCR2.1-TOPO (Invitrogen), pTrc99A (Pharmacia Company), pKK331-1A (Pharmacia Company), and the like.

Further, the nucleotide sequence of the present DNA (A) obtained in such a way can be analyzed by the dideoxy terminator method described in F. Sanger, S. Nicklen, A. R. Coulson, Proceeding of National Academy of Science U.S.A. (1977) 74:5463-5467.

The ability to metabolize the PPO inhibitory-type herbicidal compound of formula (I) of the present protein (A), which is encoded by the present DNA (A) obtained in such a way described above, can be confirmed with the ability of converting compound (II) to compound (III) as a marker in the way described below. First, as described below, said DNA is inserted into a vector so that it is connected downstream of a promoter which can function in the host cell and that is introduced into a host cell to obtain a transformant. Next, the culture of the transformant or the extract obtained from disrupting the culture is reacted with compound (II) in the presence of an electron transport system containing an electron donor, such as coenzyme NADPH. The reaction products resulting therefrom are analyzed to detect compound (III). In such a way, there can be detected a transformant having the ability of metabolizing compound (II) and producing compound (III), and be determined that such a transformant bears the present DNA (A) encoding the protein having such ability. More specifically for example, there is prepared 30 μl of a reaction solution consisting of a 0.1M potassium phosphate buffer (pH 7.0) comprising the culture or extract of the above transformant, an electron donor such as β-NADPH at a final concentration of about 2 mM, ferredoxin derived from spinach at a final concentration of about 2 mg/ml, ferredoxin reductase at a final concentration of about 0.1 U/ml and 3 ppm of compound (II) labeled with a radioisotope. The reaction solution is incubated at about 30° C. to 40° C. for 10 minutes to 1 hour. After such incubation, 3 μl of 2N HCl and 90 μl of ethyl acetate are added, stirred and centrifuged at 8,000 g to recover the supernatant. After drying the supernatant in vacuo, the residue is dissolved in ethyl acetate and the obtained solution is developed on a silica gel TLC plate. The TLC plate is analyzed by radio autography. By identifying the spots corresponding to compound (III) labeled with a radioisotope, there can be confirmed the ability to convert compound (II) to compound (III).

A DNA encoding a protein having the ability to convert compound (II) to compound (III) or a microorganism having such a DNA may be further searched by conducting the hybridizations or PCR as described above, utilizing the present invention DNA (A) or the polynucleotide comprising a partial nucleotide sequence of said DNA or a nucleotide sequence complimentary to the partial nucleotide sequence.

Specifically for example, hybridization as described above is conducted and the DNA to which a probe is hybridized is identified. The hybridization is conducted with the use of the present invention DNA (A) or a polynucleotide comprising a partial nucleotide sequence of the present invention DNA (A) of a nucleotide sequence complimentary to the partial nucleotide sequence as a probe, and genomic DNA derived from a natural microorganism, for example, microorganisms belonging to *streptomyces* such as *Streptomyces phaeochromogenes, Streptomyces testaceus, Streptomyces achromogenes, Streptomyces griseolus, Streptomyces carbophilus, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis* and *Streptomyces steffisburgensis*; microorganisms belonging to *Saccharopolyspora* such as *Saccharopolyspora*

*taberi*; and the like. As specific examples of DNA which can be utilized as the probe, there can be mentioned a DNA comprising the full length of the nucleotide sequence shown in any one of SEQ ID NO: 6, 7, 8, 109, 139, 140, 141, 142, 143, 225, 226, 227, 228, 229, 230, 231, 232, 233 or 234; a DNA comprising a nucleotide sequence shown in nucleotides 57 to 730 of the nucleotide sequence shown in SEQ ID NO: 6; a DNA comprising a nucleotide sequence show in nucleotides 21 to 691 of the nucleotide sequence shown in SEQ ID NO: 8; and the like.

Alternatively, PCR can be conducted as described above and the amplified DNA can be detected. The PCR utilizes a polynucleotide comprising a partial nucleotide sequence of the present invention DNA (A) or a nucleotide sequence complimentary to the partial nucleotide sequence. The PCR utilizes as the template genomic DNA derived from a natural microorganism, for example, microorganisms belonging to *streptomyces* such as *Streptomyces phaeochromogenes, Streptomyces testaceus, Streptomyces achromogenes, Streptomyces griseolus, Streptomyces carbophilus, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis* and *Streptomyces steffisburgensis*; microorganisms belonging to *Saccharopolyspora* such as *Saccharopolyspora taberi*; and the like. As the primers, there can be mentioned primers which were designed, based on the nucleotide sequence of the "region to which the sequence identity is particularly high in the nucleotide sequence shown in SEQ ID NO: 6, 7, 8 or 109" as described above. As more specific examples of the primers, there is mentioned pairings of a primer comprising a nucleotide sequence shown in any one of SEQ ID NO: 124 to 128 and a primer comprising a nucleotide sequence shown in SEQ ID NO: 129.

The DNA detected in such a way is recovered. When the recovered DNA does not contain the full length nucleotide sequence of the present DNA (A), such DNA is utilized and made into a DNA corresponding to the full length nucleotide sequence in a way described above. The obtained DNA is introduced into a host cell to produce a transformant. The ability to convert compound (II) to compound (III) of the protein encoded by the DNA introduced into the transformant can be evaluated by utilizing the culture of the obtained transformant and measuring the ability to convert compound (II) to compound (III) in a way described above.

To express the present DNA (A) in a host cell, the present DNA (A) is introduced into the host cell in a position enabling its expression in said cell. By introducing the present DNA (A) into a "position enabling its expression," it means that the present DNA (A) is introduced into a host cell so that it is placed in a position adjacent to a nucleotide sequence directed to transcription and translation from the nucleotide sequence thereof (that is, for example, a nucleotide sequence promoting the production of the present protein (A) and an RNA encoding the present protein (A)).

To introduce the present DNA (A) into the host cell so that it is placed in a position enabling its expression, for example, a DNA in which the present DNA (A) and a promoter functional in the host cell are operably linked is introduced into the host cell. The term "operably linked" here means that a condition in which the present DNA (A) is linked to a promoter so that it is expressed under the control of the promoter, when the DNA is introduced into a host cell.

When the host cell is a microorganism cell, as a functional promoter, for example, there can be mentioned the lactose operon promoter of *E. coli*, tryptophan operon promoter of *E. coli*, T7 phage promoter or artificial promoters functional in *E. coli* such as tac promoter or trc promoter and the like. Further, there may be utilized the promoter originally present upstream of the present DNA (A) in the chromosome of the microorganism belonging to *Streptomyces* or *Saccharopolyspora*.

When the host cell is a plant cell, as a functional promoter, for example, there is mentioned T-DNA derived constitutive promoters such as nopaline synthase gene promoter and octopine synthase gene promoter; plant virus-derived promoters such as cauliflower mosaic virus derived 19S and 35S promoters; inducible promoters such as phenylalanine ammonia-lyase gene promoter, chalcone synthase gene promoter and pathogenesis-related protein gene promoter; the plant promoter described in Japanese Unexamined Patent Publication No. 2000-166577. Further, a terminator functional in a plant cell may be connected to the DNA in which the promoter functional in a plant cell and the present DNA (A) are operably linked. In this case, it is generally preferred that the terminator is connected downstream from the present DNA (A). As the functional terminator, for example, there is mentioned T-DNA derived constitutive terminators such as nopaline synthase gene (NOS) terminator; plant virus derived terminators such as terminators of *allium* virus GV1 or GV2; the plant terminator described in Japanese Unexamined Patent Publication No. 2000-166577; and the like.

When introducing the present DNA (A) so that the DNA is placed in a position enabling its expression, for example, there can be utilized a DNA having a nucleotide sequence encoding a transit signal to an intracellular organelle, linked upstream of the present DNA (A), so that the reading frames are in frame. By being linked "so that the reading frames are in frame" it means that reading frame of the sequence of the transit signal to an intracellular organelle and the reading frame of the present DNA (A) are connected to form one continuous reading frame. As a transit signal sequence providing the transition and localization of a protein in an intracellular organelle in a plant cell, for example, there can be mentioned a transit signal derived from a cytoplasmic precursor of a protein localizing in the chloroplast of a plant as described in U.S. Pat. No. 5,717,084, the chimeric sequences formed from the variety of the transit signal sequences described in U.S. Pat. No. RE36,449. More specifically, there is mentioned the chloroplast transit peptide derived from the small subunit of ribulose-1,5-bisphosphate carboxylase of soybean, which is obtainable according to the method described in Example 15 below.

Typically, the present DNA (A), the present DNA (A) to which a DNA having a nucleotide sequence encoding a transit signal to an intracellular organelle is connected as described above, or a DNA in which such DNA is operably linked to a promoter functional in the host cell, can each be inserted into a vector usable in a host cell and this is introduced into the host cell. When utilizing a vector already possessing a promoter functional in the host cell, the present DNA (A) may be inserted downstream of a promoter present in the vector so that said promoter and the present DNA (A) can be operably linked.

As the vector, specifically when utilizing *E. coli* as the host cell, for example, there can be mentioned pUC 119 (TaKaRa Shuzo Company), pTVA 118N (Takara Shuzo Company), pBluescript II (Strategene Company), pCR2.1-TOPO (Invitrogen), pTrc99A (Amersham Pharmacia Biotech Company), pKK331-1A (Amercham Pharmacia Biotech Company), pET11d (Novagen) and the like. By utilizing a vector containing a selective marker (for example, genes conferring resistance to an antibiotic such as a kanamycin resistance gene, neomycin resistance gene, and the like), it is convenient in that the transformant to which the present DNA is introduced can be selected with the phenotype of the selective marker as an indicator.

As the method of introducing the present DNA (A) or a vector containing the present DNA (A) into a host cell, there can be mentioned the method described in Shin Seikagaku Zikken Kouza (Nippon-Seikagaku-Kai eds., Tokyo Kagaku Dozin), Vol. 17, Biseibutu-Zikken-Hou when the host cell is a microorganism, for example, *E. coli, Bacillus subtilis, Bacillus brevis, Pseudomonas* sp., *Zymomonas* sp., lactic acid bacteria, acetic acid bacteria, *Staphylococcus* sp., *Streptomyces* sp., *Saccharopolyspora* sp., or yeast such as *Saccharomyces cerevisiae, Schizosaccharomyces ponmbe*, fungus such as *Aspergillus*, and the like. Alternatively, for example, there may be utilized the calcium chloride method described in Sambrook, J., Frisch, E. F., and Maniatis, T.; "Molecular Cloning 2nd edition," Cold Spring Harbor Press (Molecular Biology, John Wiley & Sons, N.Y. (1989) or in "Current Protocols in Molecular Biology" (1987), John Wiley & Sons, Incorporated or the electroporation method described in "Methods in Electroporation: Gene Pulser/*E. coli* Pulser System," Bio-Rad Laboratories (1993).

The transformant to which the present DNA (A) or the vector containing the present DNA (A) has been introduced, for example, can be selected by selecting for the phenotype of the selective marker contained in the vector to which the present DNA (A) has been inserted as described above as an indicator. Further, whether the transformant contains the present DNA (A) or a vector containing the present DNA (A) can be confirmed by preparing the DNA from the transformant and then conducting with the prepared DNA genetic engineering analysis methods described in, for example, "Molecular Cloning 2nd edition," Cold Spring Harbor Press (Molecular Biology, John Wiley & Sons, N.Y. (1989) (such as confirming restriction enzyme sites, DNA sequencing, southern hybridizations, PCR and the like).

When the host cell is a plant cell, plant types can be mentioned, for example, dicotyledones such as tobacco, cotton, rapeseed, sugar beet, *Arabidopsis*, canola, flax, sunflower, potato, alfalfa, lettuce, banana, soybean, pea, legume, pine, poplar, apple, grape, orange, lemon, other citrus fruits, almond, walnut other nuts; monocotyledones such as corn, rice, wheat, barley, rye, oat, sorghum, sugar cane and lawn; and the like. As the cell to which the present DNA (A) is introduced there can be utilized plant tissue, plant body, cultured cells, seeds and the like.

As methods of introducing the present DNA (A) or the vector containing the present DNA (A) into a host cell, there is mentioned methods such as infection with *Agrobacterium* (Japanese Examined Patent Publication No. 2-58917 and Japanese Unexamined Patent Publication No. 60-70080), electroporation into protoplasts (Japanese Unexamined Patent Publication No. 60-251887 and Japanese Unexamined Patent Publication No. 5-68575) or particle gun method (Japanese Unexamined Patent Publication No. 5-508316 and Japanese Unexamined Patent Publication No. 63-258525).

In such cases, for example, the transformant to which the present DNA has been introduced can be selected with the phenotype of a selective marker as an indicator, by introducing into the plant cell at the same time with the vector containing the present DNA (A), a selective maker selected from the hygromycin phosphotransferase gene, neomycin phosphotransferase gene and chloramphenicol acetyltransferase gene. The selective marker gene and the present DNA (A) may be inserted into the same vector and introduced. A vector comprising the selective marker gene and a vector comprising the present DNA (A) may also be introduced at the same time. A transformant to which the present DNA (A) has been introduced may also be selected by culturing with a medium containing the PPO inhibitory-type herbicidal compound of formula (I) and by isolating a clone multipliable therein. Whether the transformant contains the present DNA (A) can be confirmed by preparing the DNA from the transformant and then conducting with the prepared DNA genetic engineering analysis methods described in, for example, "Molecular Cloning 2nd edition," Cold Spring Harbor Press (Molecular Biology, John Wiley & Sons, N.Y. (1989) (such as confirming restriction enzyme sites, DNA sequencing, southern hybridizations, PCR and the like). The present DNA (A) introduced in the plant cell may be maintained at locations in the cell other than the DNA contained in the nucleus, by being inserted into the DNA contained in intracellular organelles such as the chloroplast.

From the transformed plant cell obtained in such a way, a transgenic plant to which the present DNA (A) has been introduced can be obtained, by regenerating a plant body by the plant cell culturing method described in Shokubutu-Iden-shi-Sosa-Manual: Transgenic-Shokubutu-No-Tukurikata (Uchimiya, Kodansha-Scientific, 1990), pp. 27-55. Further, a targeted plant type to which the present DNA (A) has been introduced can be produced by mating the targeted type of plant with the transgenic plant to which the present DNA (A) has been introduced, so that the present DNA (A) is introduced into a chromosome of the targeted type of plant.

Specifically, for example, rice or *Arabidopsis* having introduced therein the present DNA (A) and expressing the present protein (A) can be obtained by the method described in Model-Shokubutu-No-Jikken-Protocol: Ine, Shiroi-nunazuna-Hen (Supervisors: Koh SHIMAMOTO and Kiyotaka OKADA, Shujun-sha, 1996), Fourth chapter. Further, there can be obtained a soybean having introduced therein the present DNA (A) and expressing the present protein (A) by an introduction into a soybean somatic embryo with a particle gun according to the method described in Japanese Unexamined Patent Publication No. 3-291501. Likewise, a maize having introduced therein the present DNA (A) and expressing the present protein (A) can be obtained by an introduction into maize somatic embryo with a particle gun according to the method described by Fromm, M. E., et al., Bio/Technology, 8; p 838 (1990). Wheat having introduced therein the present DNA (A) and expressing the present protein (A) can be obtained by introducing the gene into sterile-cultured wheat immature scutellum with a particle gun according to a conventional method described by TAKUMI et al., Journal of Breeding Society (1995), 44: Extra Vol. 1, p 57. Likewise, barley having introduced therein the present DNA (A) and expressing the present protein (A) can be obtained by an introduction into sterile-cultured barley immature scutellum with a particle gun according to a conventional method described by HAGIO, et al., Journal of Breeding Society (1995), 44; Extra Vol. 1, p 67.

The transformant having introduced therein the present DNA (A) and expressing the present protein (A) can reduce the plant damage by compound (I), by converting said herbicidal compound into a compound of lower herbicidal activity within its cells. Specifically, for example, by spreading the microorganism expressing the present protein (A) to the cultivation area of the desired cultivated plant before sowing seeds of the desired plant, the herbicidal compound remaining in the soil can be metabolized and the damage to the desired plant can be reduced. Further, by getting the desired variety of plant to express the present protein (A), the ability to metabolize the PPO inhibitory-type herbicidal compound of formula (I) to a compound of lower activity is conferred to said plant. As a result, the plant damage from the herbicidal compound in the plant is reduced and resistance to said compound is conferred.

The present protein (A) can be prepared, for example, by culturing a cell comprising the present DNA (A). As such a cell, there is mentioned a microorganism expressing the present DNA (A) and having the ability to produce the present protein (A), such as a microorganism strain isolated from nature comprising the present DNA (A), mutant strains derived from the natural strain by treatment with agents or ultraviolet rays or the like. More specifically for example, there is mentioned microorganisms belonging to *Streptomyces*, such as *Streptomyces phaeochromogenes* IFO12898, *Streptomyces testaceus* ATCC21469, *Streptomyces achromogenes* IFO 12735, *Streptomyces griseolus* ATCC11796, *Streptomyces carbophilus* SANK62585, *Streptomyces griseofuscus* IFO 12870t, *Streptomyces thermocoerulescens* IFO 14273t, *Streptomyces nogalater* IFO 13445, *Streptomyces tsusimaensis* IFO 13782, *Streptomyces glomerochromogenes* IFO 13673t, *Streptomyces olivochromogenes* IFO 12444, *Streptomyces ornatus* IFO 13069t, *Streptomyces griseus* ATCC 10137, *Streptomyces griseus* IFO 13849T, *Streptomyces lanatus* IFO 12787T, *Streptomyces misawanensis* IFO 13855T, *Streptomyces pallidus* IFO 13434T, *Streptomyces roseorubens* IFO 13682T, *Streptomyces rutgersensis* IFO 15875T and *Streptomyces steffisburgensis* IFO 13446T, and the like; or microorganisms belonging to *Saccharopolyspora*, such as *Saccharopolyspora taberi* JCM 9383t and the like. Further, there can be mentioned a transformant in which the present DNA (A) or a vector containing the present DNA (A) has been introduced. Specifically for example, there is mentioned a transformant in which the present DNA (A) operably linked to a tac promoter, trc promoter, lac promoter or t7 phage promoter is introduced into *E. coli*. As more specific examples, there is mentioned *E. coli* JM109/pKSN657, *E. coli* JM109/pKSN657F, *E. coli* JM109/pKSN923, *E. coli* JM109/pKSN923F, *E. coli* JM109/pKSN11796, *E. coli* JM109/pKSN11796F, *E. coli* JM109/pKSN671, *E. coli* JM109/pKSN671F, *E. coli* JM109/pKSNSCA, *E. coli* JM109/pKSN646, *E. coli* JM109/pKSN646F, *E. coli* JM109/pKSN849AF, *E. coli* JM109/pKSN1618F, *E. coli* JM109/pKSN474F, *E. coli* JM109/pKSN1491AF, *E. coli* JM109/pKSN1555AF, *E. coli* JM109/pKSN1584F, *E. coli* JM109/pKSN1609F and the like, described in the examples described below.

As a medium for culturing the above microorganisms comprising the present DNA (A), there can be utilized any of those employed usually for culturing a microorganism which contains carbon sources and nitrogen sources, organic and inorganic salts as appropriate. A compound which is a precursor to heme, such as aminolevulinic acid, may be added.

As the carbon source, for example, there is mentioned saccharides such as glucose, fructose, sucrose and dextrin; sugar alcohols such as glycerol and sorbitol; and organic acids such as fumaric acid, citric acid and pyruvic acid; and the like. The amount of carbon sources listed above to be added to a medium is usually about 0.1% (w/v) to about 10% (w/v) based on a total amount of the medium.

As the nitrogen source, for example, there is mentioned ammonium salts of inorganic acids such as ammonium chloride, ammonium sulfate and ammonium phosphate; ammonium salts of organic acids such as ammonium fumarate and ammonium citrate; organic nitrogen sources, such as meat extract, yeast extract, malt extract, soybean powder, corn steep liquor, cotton seed powder, dried yeast, casein hydrolysate; as well as amino acids. Among those listed above, ammonium salts of organic acids, organic nitrogen sources and amino acids may mostly be employed also as carbon sources. The amount of nitrogen sources to be added is usually about 0.1% (w/v) to about 10% (w/v) based on the total amount of the medium.

As the inorganic salt, for example, there is mentioned phosphates such as potassium phosphate, dipotassium phosphate, sodium phosphate, disodium phosphate; chlorides such as potassium chloride, sodium chloride, cobalt chloride hexahydrate; sulfates such as magnesium sulfate, ferrous sulfate heptahydrate, zinc sulfate heptahydrate, manganese sulfate trihydrate; and the like. The amount to be added is usually about 0.0001% (w/v) to about 1% (w/v) based on a total amount of the medium.

In case of culturing a transformant retaining the present DNA (A) connected downstream of a T7 phage promoter and a DNA in which the nucleotide sequence encoding T7 RNA polymerase ($\lambda$DE3 lysogen) is connected downstream of a lac UV5 promoter, typically, a small amount of, for example, isopropyl-$\beta$-D-thiogalactoside (hereinafter referred to as "IPTG") may be added as an inducer for inducing the production of the present protein (A). IPTG can also be added to the medium in case of culturing a transformant having introduced therein a DNA in which the present DNA (A) is operably linked to a type of promoter which is induced by lactose, such as tac promoter, trc promoter and lac promoter.

A microorganism comprising the present DNA (A) can be cultivated in accordance with a method employed usually to culture a microorganism, including a liquid phase cultivation such as a rotatory shaking cultivation, a reciprocal shaking cultivation, a jar fermentation (Jar Fermenter cultivation) and a tank cultivation; or a solid phase cultivation. When a jar fermenter is employed, aseptic air should be introduced into the Jar Fermenter usually at an aeration rate of about 0.1 to about 2 times culture fluid volume per minute. The temperature at which the cultivation is performed may vary within a range allowing a microorganism to be grown, and usually ranges from about 15° C. to about 40° C., and the pH of the medium ranges from about 6 to about 8. The cultivation time may vary depending on the cultivation conditions, and is usually about 1 day to about 10 days.

The present protein (A) produced by a microorganism comprising the present DNA (A), for example, can be utilized in various forms in the treatment of the PPO inhibitory-type herbicidal compound of formula (I), such as a culture of a microorganism producing the present protein (A), a cell of a microorganism producing the present protein (A), a material obtained by treating such a cell, a cell-free extract of a microorganism, a crudely purified protein, a purified protein and the like. A material obtained by treating a cell described above includes for example a lyophilized cell, an acetone-dried cell, a ground cell, an autolysate of a cell, an ultrasonically treated cell, an alkali-treated cell, an organic solvent-treated cell and the like. Alternatively, the present protein (A) in any of the various forms described above may be immobilized in accordance with known methods such as a support binding method employing an adsorption onto an inorganic carrier such as a silica gel or a ceramic material, a polysaccharide derivative such as a DEAE-cellulose, a synthesized polymer such as Amberite IRA-935 (Trade Name, manufactured by Rohm and Haas) and the like, and an inclusion method employing an inclusion into a network matrix of a polymer such as a polyacrylamide, a sulfur-containing polysaccharide gel (e.g. carrageenan gel), an alginic acid gel, an agar gel and the like, and then used in the treatment of the herbicidal compound described above.

As methods of purifying the present protein (A) from a culture of a microorganism comprising the present DNA (A), there can be employed conventional methods utilized in a purification of protein. For example, there can be mentioned the following method.

First, cells are harvested from a culture of a microorganism by centrifugation or the like, and then disrupted physically by an ultrasonic treatment, a DYNOMILL treatment, a FRENCH PRESS treatment and the like, or disrupted chemically by utilizing a surfactant or a cell-lyzing enzyme such as lysozyme. From the resultant lysate thus obtained, insoluble materials are removed by centrifugation, membrane filtration or the like to prepare a cell-free extract, which is then fractionated by any appropriate means for separation and purification, such as a cation exchange chromatography, an anion exchange chromatography, a hydrophobic chromatography, a gel filtration chromatography and the like, whereby purifying the present protein (A). Supporting materials employed in such chromatography include for example a resin support such as cellulose, dextran and agarose connected with a carboxymethyl (CM) group, a diethylaminoethyl (DEAE) group, a phenyl group or a butyl group. A commercially available column already packed with any support such as Q-Sepharose FF, Phenyl-Sepharose HP, PD-10 and HiLoad 26/10 Q Sepharose HP (Trade Name, from Amersham Pharmacia Biotech), TSK-gel G3000SW (Trade Name, TOSOH CORPORATION) may also be employed.

One example of purifying the present protein (A) is given.

Cells of a microorganism producing the present protein (A) are harvested by centrifugation, and then suspended in a buffer such as 0.1M potassium phosphate (pH7.0). The suspension is treated ultrasonically to disrupt the cells, and the resultant lysate thus obtained is centrifuged at about 40,000 g for about 30 minutes to obtain a supernatant, which is then centrifuged at 150,000 g for about 1 hour to recover the supernatant (the cell-free extract). The obtained cell-free extract is subjected to ammonium sulfate fractionation to obtain the fraction that is soluble in the presence of 45%-saturated ammonium sulfate and precipitates at 55%-saturated ammonium sulfate. After the solvent of the fraction is exchanged with a buffer containing no ammonium sulfate, such as 1M potassium phosphate, utilizing a PD 10 column (Amersham Pharmacia Biotech Company), the resulting fraction is loaded, for example, onto a HiLoad 26/10 Q Sepharose HP column (Amersham Pharmacia Biotech Company). The column is eluted with 20 mM bistrispropane with a linear gradient of NaCl to obtain a series of fractions of eluate. The fractions showing activity in converting compound (II) to compound (III) in the presence of an electron transport system containing an electron donor, such as coenzyme NADPH, are recovered. Next, after exchanging the buffer in the fractions by utilizing for example the PD10 column (Amersham Pharmacia Biotech Company), the recovered fractions are loaded onto a Bio-Scale Ceramic, for example, Hydroxyapatite, Type I column CHT10-I (BioRad Company). After washing the column with Buffer A (2 mM potassium phosphate buffer containing 1.5 mM of $CaCl_2$; pH7.0), the column is eluted with Buffer A with a linear gradient of Buffer B (100 mM potassium phosphate buffer containing 0.03 mM $CaCl_2$) to obtain a series of fractions of eluate. The fractions showing activity in converting compound (II) to compound (III) in the presence of an electron transport system containing an electron donor, such as coenzyme NADPH, are recovered. After exchanging the buffer in the fractions by utilizing for example the PD10 column (Amersham Pharmacia Biotech Company), the recovered fractions are concentrated by for example ultrafiltration (microcon filter unit microcon-30; Millipore Company). The resulting fraction is injected for example into a HiLoad 16/60 Superdex column 75 pg column (Amersham Pharmacia Biotech Company) and eluted with a 0.05M potassium phosphate buffer containing 0.15M NaCl (pH7.0) to obtain a series of fractions of eluate. The fractions showing activity in converting compound (II) to compound (III) in the presence of an electron transport system containing an electron donor, such as coenzyme NADPH, are recovered. The present protein (A) can be purified by a separation with an SDS-PAGE as needed.

By purifying the present invention protein (A) in the way described above, followed by utilizing the obtained present invention protein (A) as an immune antigen, there can be produced an antibody recognizing the present invention protein (A) (hereinafter sometimes referred to as the "present invention antibody (A)").

Specifically, for example, an animal is immunized with the present protein (A) purified in the way described above, as an antigen. For example, to immunize an animal such as a mouse, hamster, guinea pig, chicken, rat, rabbit, dog and the like, the antigen is administered at least once, utilizing a conventional method of immunization described in, for example, W. H. Newsome, J. Assoc. Off. Anal. Chem. 70(6) 1025-1027 (1987). As the schedule of administration, for example, there is mentioned an administration of 2 or 3 times at 7- to 30-day intervals, preferably, 12- to 16-day intervals. The dose thereof is, for example, from about 0.05 mg to 2 mg of the antigen for each administration. The administration route may be selected from subcutaneous administration, intracutaneous administration, intraperitoneal administration, intravenous administration, and intramuscular administration and an injection given intravenously, intraabdominally or subcutaneously is a typical administration form. The antigen is typically used after being dissolved in a suitable buffer, for example, sodium phosphate buffer or physiological saline containing at least one type of ordinarily used adjuvant such as complete Freund's adjuvant (a mixture of Aracel A, Bayol F and dead tubercule *bacillus*), RAS [MPL (monophosphoryl lipid A)+TDM (synthetic trehalose dicorynomycolate)+CWS (cell wall skeleton) adjuvant system] or aluminum hydroxide. However, depending on the administration route or conditions, the adjuvants described above may not be used. The "adjuvant" is a substance which upon administration with the antigen, enhances a immune reaction unspecifically against the antigen. After nurturing the animal administered with the antigen for 0.5 to 4 months, a small amount of blood is sampled from e.g. an ear vein of the animal and measured for antibody titer. When the antibody titer is increasing, then the antigen is further administered for an appropriate number of times, depending on cases. For example, the antigen may be administered for one more time at a dose of about 100 µg to 1000 µg. One or two months after the last administration, blood is collected in a usual manner from the immunized animal. By having the blood fractionated by conventional techniques such as precipitation by centrifugation or with ammonium sulfate or with polyethylene glycol, chromatography such as gel filtration chromatography, ion-exchange chromatography and affinity chromatography, and the like, the present invention antibody (A) may be obtained as a polyclonal antiserum. Further, the antiserum may be incubated e.g. at 56° C. for 30 minutes to inactivate the complement system.

Alternatively, a polypeptide comprising a partial amino acid sequence of the present invention protein (A) is synthesized chemically and administered as an immune antigen to an animal, whereby producing the present invention antibody (A). As the amino acid sequence of a polypeptide employed as an immune antigen, an amino acid sequence which has as a low homology as possible with the amino acid sequences of other proteins is selected from amino acid sequences of the present invention protein (A). A polypeptide having a length of 10 amino acids to 15 amino acids consisting of the selected amino acid sequence is synthesized chemically by a conventional method and crosslinked for example with a carrier protein such as *Limulus plyhemus* hemocyanin using MBS and the like and then used to immunize an animal such as a rabbit as described above.

The resultant present invention antibody (A) is then brought into contact with a test sample, and then a complex of the protein in the test sample with the antibody described above is detected by a conventional immunological method, whereby detecting the present invention protein (A) or a polypeptide comprising a partial amino acid thereof in the test sample. Specifically, for example, it is possible to evaluate the presence of the present invention protein (A) or to quantify the present invention protein (A) in the examined test sample by a western blot analysis utilizing the present invention antibody (A) as shown in Examples 45 or 73 described below.

Further, for example, a cell expressing the present protein (A) can be detected, by contacting the present invention antibody (A) with a test cell or a test sample prepared from the test cell followed by detecting a complex of the above antibody and the protein in the test cell or a test sample prepared from the test cell, according to conventional immunology methods. By detecting the cell expressing the present invention protein (A) in such a way, it is also possible to select from a variety of cells, a cell expressing the present invention protein (A). It is also possible to clone or select a clone containing the present invention protein (A) with the use of the present invention antibody (A). For example, a genomic library can be produced by extracting genomic DNA from a cell that expresses the present invention protein (A) followed by inserting the genomic DNA into an expression vector. The genomic library is introduced into a cell. From the obtained cell group, a cell expressing the present invention protein (A) is selected with the use of the present invention antibody (A) in the way described above.

A kit comprising the present invention antibody (A) can be utilized to detect the present invention protein (A) as described above or to analyze, detect or search for a cell expressing the present invention protein (A). The kit of the present invention may contain the reagents necessary for the above analysis methods, other than the present invention antibody (A), and may have such a reagent used together with the present invention antibody (A).

By reacting a PPO inhibitory-type herbicidal compound of formula (I) in the presence of an electron transport system containing an electron donor, such as coenzyme NADPH, with the present protein (A), the above compound is metabolized and is converted into a compound of lower herbicidal activity. Specifically for example, by reacting compound (II) in the presence of an electron transport system containing an electron donor, such as coenzyme NADPH, with the present protein (A), compound (II) is converted to compound (III), which shows substantially no herbicidal activity. An example of protein (A) in such cases is the present invention protein (A). One variation of the present protein (A) may be utilized and multiple variations may be utilized together.

The compound of formula (I) is a compound having a uracil structure. As specific examples, there can be mentioned compound (II) or a compound of any one of formulas (IV) to (IX) (hereinafter, referred respectively to as compound (IV) to compound (IX)). It is possible to synthesize compound (II) and compound (IX) according to the method described in Japanese Unexamined Patent Publication No. 2000-319264, compound (IV) and compound (V) according to the method described in U.S. Pat. No. 5,183,492, compound (VI) according to the method described in U.S. Pat. No. 5,674,810, compound (VII) according to the method described in Japanese Unexamined Patent Publication No. 3-204865, and compound (VIII) according to the method described in Japanese Unexamined Patent Publication No. 6-321941.

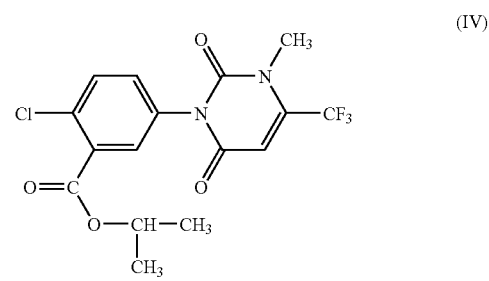

(IV)

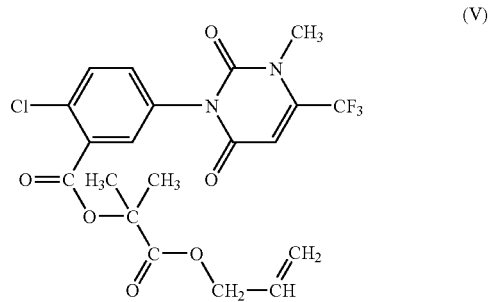

(V)

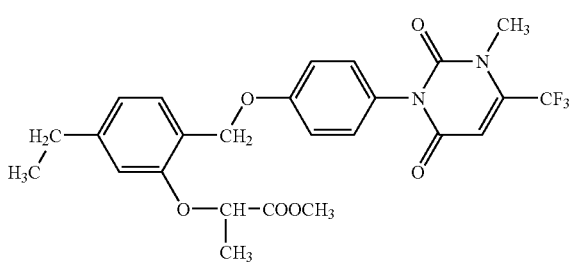

(VI)

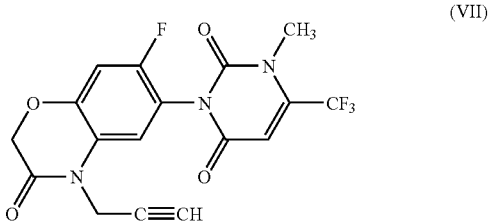

(VII)

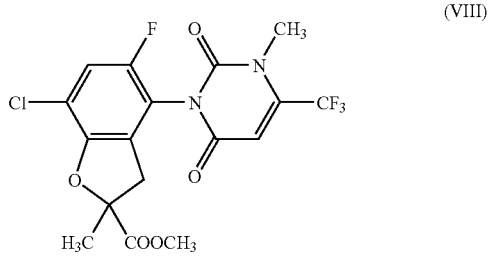

(VIII)

-continued

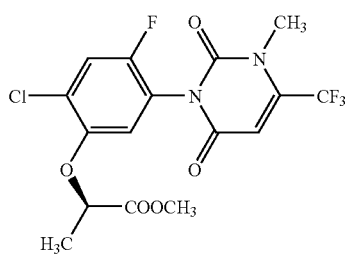
(IX)

Further, as specific examples of the compound of formula (I), there can be mentioned a compound of any one of formulas (X) to (XVII) (hereinafter, respectively referred to as compound (X) to compound (XVII)).

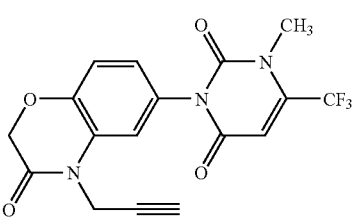
(X)

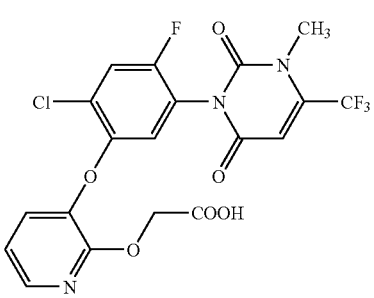
(XI)

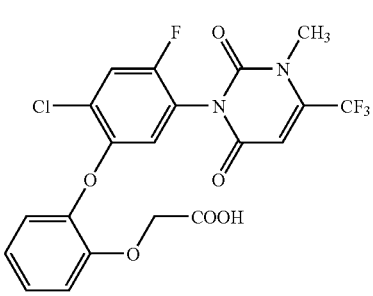
(XII)

(XIII)

-continued

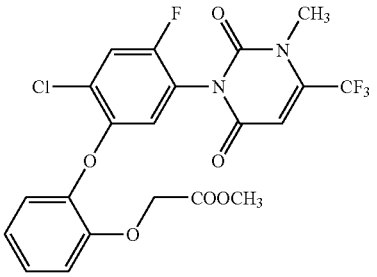
(XIV)

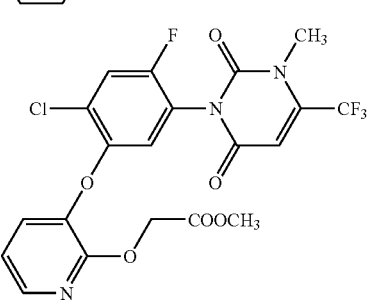
(XV)

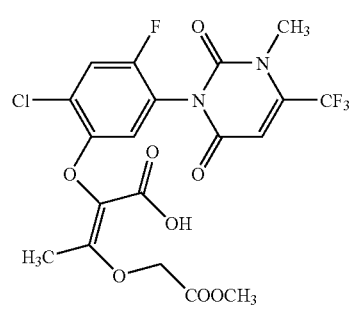
(XVI)

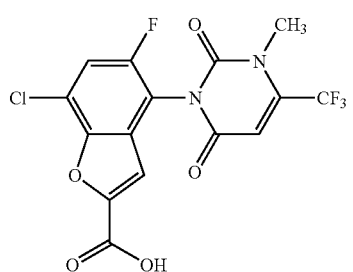
(XVII)

Compounds which can be a substrate of the metabolizing reaction by the present protein (A) can be selected by having the compound present in a reaction in which compound (II) labeled with a radioisotope is reacted with the present protein (A), in the presence of an electron transport system containing an electron donor, such as coenzyme NADPH, and detecting as a marker the competitive inhibition of the conversion reaction by the present protein (A) of the labeled compound (II) to the labeled compound (III). When assaying for the presence of the competitive inhibition from a test compound, the test compound is typically added to amount to a molar concentration of from 1 to 100 times of the labeled compound (II).

The reaction in which compound (I) is reacted with the present protein (A) can be conducted, for example, in an aqueous buffer containing salts of inorganic acids such as an alkaline metal phosphate such as sodium phosphate and potassium phosphate; or salts of organic acids such as an alkaline metal acetate such as sodium acetate and potassium acetate; or the like. The concentration of the compound of formula (I) in a metabolizing reaction solution is typically at most about 30% (w/v) and preferably about 0.001% (w/v) to 20% (w/v). The amount of the electron transport system containing the electron donor, such as NADPH, or of the present protein (A) may vary, for example, depending on reaction time period. The reaction temperature is chosen from the range of typically from about 10° C. to 70° C., and is preferably about 20° C. to 50° C. The pH of the reaction solution is chosen from the range of typically from about 4 to 12 and is preferably about 5 to 10. The reaction time period may vary as desired, and is typically from about 1 hour to 10 days.

Further, the reaction in which compound (I) is reacted with the present protein (A) can be conducted in a cell comprising the present DNA (A). As the cells comprising the present DNA (A), for example, there is mentioned a microorganism having the ability to express the present DNA (A) and produce the present protein (A), such as, a strain of those microorganisms isolated from nature comprising the present DNA (A), a mutant strain derived from the microorganism strain by treatment with chemicals or ultraviolet rays, a transformed microorganism cell in which the present DNA (A) or a vector containing the present DNA (A) is introduced into a host cell. Further, there is mentioned a transformed plant cell to which the present DNA (A) is introduced or a cell of a transformed plant to which the present DNA (A) is introduced. In such cases, the compound of formula (I) may be directly applied to a cell comprising the present DNA (A) or may be added to the culturing medium of the cell or the soil coming into contact with the cell, so as to enter the cell. The electron transport system containing the electron donor, such as NADPH, can be the system originally present in the cell and can be added from outside of the cell.

The metabolism of compound (I) by the present protein (A) can be confirmed, for example, by detecting the compound produced by the metabolism of compound (I). Specifically for example, compound (III) produced from metabolizing compound (II) can be detected with the HPLC analysis or TLC analysis, described above.

Further, the metabolism of compound (I) by the present protein (A) can be confirmed on the basis that the herbicidal activity in the reaction solution after compound (I) is reacted with the present protein (A) is comparatively lower than the case in which compound (I) is not reacted with the present protein (A). As a method of testing the herbicidal activity, for example, there is mentioned a method in which the above reaction solutions are applied onto weeds such as barnyardgrass (*Echinochloa crus-galli*), Blackgrass (*Alopercurus myosuroides*), Ivyleaf morningglory (*Ipomoea hederacea*) and Velvetleaf (*Abutilon theoprasti*), and the herbicidal effects are examined; or a method in which the weeds are cultivated on soil samples to which the above reaction solutions are applied and the herbicidal effects are examined; and the like. Further, there is mentioned a method in which the above reaction solutions may be spotted onto a leaf disk taken from a plant and the presence of plant damage (whitening) caused by the reaction solution is examined.

Further, the metabolism of compound (I) by the present protein (A) can be confirmed by detecting as a marker, the PPO inhibitory activity in the reaction solution after compound (I) is reacted with the present protein (A), which is comparatively lower than the activity in the reaction solution in which compound (I) is not reacted with the present protein (A). PPO is an enzyme catalyzing the conversion of protoporphyrinogen IX to protoporphyrin IX (hereinafter referred to as "PPIX"). For example, after adding the above reaction solutions to a reaction system of PPO, protoporphyrinogen IX, which is a substrate of PPO, is added and incubated for about 1 to 2 hours at 30° C. in the dark. Subsequently, the amount of PPIX in each of the incubated solutions is measured, utilizing an HPLC or the like. When the amount of PPIX in system to which the reaction solution after compound (I) is reacted with the present protein (A) is added is more than the amount of PPIX in system to which the reaction solution in which compound (I) is not reacted with the present protein (A) is added, it is determined that compound (I) had been metabolized by the present protein (A). As PPO, there may be utilized a protein purified from plants and the like or chloroplast fraction extracted from a plant. When utilizing the chloroplast fractions, aminolevulinic acid may be utilized in the reaction system of PPO, instead of protoporphyrinogen IX. Aminolevulinic acid is the precursor of protoporphyrinogen IX in the chlorophyll-heme biosynthesis pathway. A more specific example is given in Example 42 below.

By reacting with the present protein (A) in such a way, there can be conducted a treatment of the PPO inhibitory-type herbicidal compound of formula (I), which results in metabolization and conversion of the compound to a compound of lower herbicidal activity. The plant damage from said compound can be reduced by the treatment in which said compound which was sprayed onto the cultivation area of a plant, specifically for example, the compound which was sprayed onto the cultivation area of a plant and remains in plant residue or the soil or the like, is reacted with the present protein (A).

As the "electron transport system containing the electron donor" which can be utilized to react compound (I) with the present protein (A), for example, there can be mentioned a system containing NADPH, ferredoxin and ferredoxin-NADP+ reductase.

As a method of presenting the "electron transport system containing an electron donor" in a system for reacting compound (I) with the present protein (A), for example, there is mentioned a method of adding to the above reaction system, NADPH, ferredoxin derived from a plant such as spinach and ferredoxin-NADP+ reductase derived from a plant such as spinach. Further, there may be added to said reaction system, a fraction containing a component functional for the electron transport system in the reaction system of the present protein (A), which may be prepared from a microorganism such as *E. coli*. In order to prepare such a fraction, for example, after cells are harvested from a culture of a microorganism by centrifugation or the like, the cells are disrupted physically by an ultrasonic treatment, a DYNOMILL treatment, a FRENCH PRESS treatment and the like, or disrupted chemically by utilizing a surfactant or a cell-lyzing enzyme such as lysozyme. From the resultant lysate thus obtained, insoluble materials are removed by centrifugation, membrane filtration or the like to prepare a cell-free extract The cell-free extract as is can be utilized in exchange of the above ferredoxin as the fraction containing a component functional for the electron transport system in the reaction system of the present protein (A). Further, when a system which can transport an electron from an electron donor to the present protein (A) is present in such a cell, as with the case in which the reaction of the present protein (A) with compound (I) is conducted in a cell such as a microorganism or a plant cell, no electron transport system may be newly added.

As the ferredoxin, for example, there can be utilized a ferredoxin derived from microorganisms belonging to *Streptomyces*, such as *Streptomyces phaeochromogenes*, *Streptomyces testaceus*, *Streptomyces achromogenes*, *Streptomyces griseolus*, *Streptomyces thermocoerulescens*, *Streptomyces nogalater*, *Streptomyces tsusimaensis*, *Streptomyces glom-* erochromogenes, *Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis* and *Streptomyces steffisburgensis*, and more specifically, *Streptomyces phaeochromogenes* IFO 12898, *Streptomyces testaceus* ATCC21469, *Streptomyces achromogenes* IFO 12735, *Streptomyces griseolus* ATCC11796, *Streptomyces thermocoerulescens* IFO 14273t, *Streptomyces nogalater* IFO 13445, *Streptomyces tsusimaensis* IFO 13782, *Streptomyces glomerochromogenes* IFO 13673t, *Streptomyces olivochromogenes* IFO 12444, *Streptomyces ornatus* IFO 13069t, *Streptomyces griseus* ATCC 10137, *Streptomyces griseus* IFO 13849T, *Streptomyces lanatus* IFO 12787T, *Streptomyces misawanensis* IFO 13855T, *Streptomyces pallidus* IFO 13434T, *Streptomyces roseorubens* IFO 13682T, *Streptomyces rutgersensis* IFO 15875T and *Streptomyces steffisburgensis* IFO 13446T, and the like; or microorganisms belonging to *Saccharopolyspora*, such as *Saccharopolyspora taberi*, more specifically, *Saccharopolyspora taberi* JCM 9383t and the like (hereinafter, sometimes collectively referred to as the "present protein (B)"). Specifically for example, there can be mentioned a ferredoxin selected from the protein group below (hereinafter, sometimes referred to as the "present invention protein (B)").

<Protein Group>

(B1) a protein comprising an amino acid sequence shown in SEQ ID NO: 12 (hereinafter, sometimes referred to as the "present invention protein (B1)");

(B2) a protein comprising an amino acid sequence shown in SEQ ID NO: 13 (hereinafter, sometimes referred to as the "present invention protein (B2)");

(B3) a protein comprising an amino acid sequence shown in SEQ ID NO: 14 (hereinafter, sometimes referred to as the "present invention protein (B3)");

(B4) a protein comprising an amino acid sequence shown in SEQ ID NO: 111 (hereinafter, sometimes referred to as the "present invention protein (B4)");

(B5) a ferredoxin comprising an amino acid sequence having at least 80% sequence identity with an amino acid sequence shown in any one of SEQ ID NO: 12, SEQ ID NO: 13, SEQ ID NO 14 or SEQ ID NO: 111;

(B6) a ferredoxin comprising an amino acid sequence encoded by a nucleotide sequence having at least 90% sequence identity with a nucleotide sequence encoding an amino acid sequence shown in any one of SEQ ID NO: 12, SEQ ID NO: 13, SEQ ID NO 14 or SEQ ID NO: 111;

(B7) a protein comprising an amino acid sequence shown in SEQ ID NO: 149 (hereinafter, sometimes referred to as the "present invention protein (B7)");

(B8) a protein comprising an amino acid sequence shown in SEQ ID NO: 150 (hereinafter, sometimes referred to as the "present invention protein (B8)");

(B9) a protein comprising an amino acid sequence shown in SEQ ID NO: 151 (hereinafter, sometimes referred to as the "present invention protein (B9)");

(B10) a protein comprising an amino acid sequence shown in SEQ ID NO: 152 (hereinafter, sometimes referred to as the "present invention protein (B10)");

(B11) a protein comprising an amino acid sequence shown in SEQ ID NO: 153 (hereinafter, sometimes referred to as the "present invention protein (B11)");

(B12) a ferredoxin comprising an amino acid sequence having at least 80% sequence identity with any one of the amino acid sequence shown in SEQ ID NO: 149, SEQ ID NO: 151, SEQ ID NO: 152, SEQ ID NO: 153, SEQ ID NO: 245, SEQ ID NO: 247, SEQ ID NO: 248, SEQ ID NO: 249, SEQ ID NO: 250, SEQ ID NO: 251, or SEQ ID NO: 253 or an amino acid sequence having at least 90% sequence identity with any one of the amino acid sequence shown in SEQ ID NO: 150, SEQ ID NO: 252 or SEQ ID NO: 254;

(B13) a ferredoxin comprising an amino acid sequence encoded by a nucleotide sequence having at least 90% sequence identity with any of the nucleotide sequence encoding an amino acid sequence shown in SEQ ID NO: 149, SEQ ID NO: 150, SEQ ID NO: 151, SEQ ID NO: 152, SEQ ID NO: 153, SEQ ID NO: 245, SEQ ID NO: 247, SEQ ID NO: 248, SEQ ID NO: 249, SEQ ID NO: 250, SEQ ID NO: 251, SEQ ID NO: 252, SEQ ID NO: 253 or SEQ ID NO: 254;

(B14) a protein comprising the amino acid sequence shown in SEQ ID NO: 245;

(B15) a protein comprising the amino acid sequence shown in SEQ ID NO: 247;

(B16) a protein comprising the amino acid sequence shown in SEQ ID NO: 248;

(B17) a protein comprising the amino acid sequence shown in SEQ ID NO: 249;

(B18) a protein comprising the amino acid sequence shown in SEQ ID NO: 250;

(B19) a protein comprising the amino acid sequence shown in SEQ ID NO: 251;

(B20) a protein comprising the amino acid sequence shown in SEQ ID NO: 252;

(B21) a protein comprising the amino acid sequence shown in SEQ ID NO: 253; and (B22) a protein comprising the amino acid sequence shown in SEQ ID NO: 254.

A DNA encoding the present protein (B) (hereinafter, sometimes referred to as the "present DNA (B)") can be obtained according to conventional genetic engineering methods described in Molecular Cloning: A Laboratory Manual 2nd edition (1989), Cold Spring Harbor Laboratory Press; Current Protocols in Molecular Biology (1987), John Wiley & Sons, Incorporated and the like, based on the nucleotide sequences encoding the amino acid sequences of the present invention protein (B) shown in SEQ ID NO: 12, 13, 14, 111, 149, 150, 151, 152, 153, 245, 247, 248, 249, 250, 251, 252, 253 or 254.

As the DNA encoding the present invention protein (B) (hereinafter, sometimes collectively referred to as the "present invention DNA (B)"), there is mentioned a DNA encoding a protein comprising an amino acid sequence shown in SEQ ID NO: 12 (hereinafter, sometimes referred to as the "present invention DNA (B1)");

a DNA encoding a protein comprising an amino acid sequence shown in SEQ ID NO: 13 (hereinafter, sometimes referred to as the "present invention DNA (B2)");

a DNA encoding a protein comprising an amino acid sequence shown in SEQ ID NO: 14 (hereinafter, sometimes referred to as the "present invention DNA (B3)");

a DNA encoding a protein comprising an amino acid sequence shown in SEQ ID NO: 111 (hereinafter, sometimes referred to as the "present invention DNA (B4)");

a DNA encoding a ferredoxin comprising an amino acid sequence having at least 80% sequence identity with an amino acid sequence shown in any one of SEQ ID NO: 12, SEQ ID NO: 13, SEQ ID NO 14 or SEQ ID NO: 111;

a DNA encoding a ferredoxin comprising an amino acid sequence encoded by a nucleotide sequence having at least 90% sequence identity with a nucleotide sequence encoding an amino acid sequence shown in any one of SEQ ID NO: 12, SEQ ID NO: 13, SEQ ID NO 14 or SEQ ID NO: 111;

a DNA encoding a protein comprising an amino acid sequence shown in SEQ ID NO: 149 (hereinafter, sometimes referred to as the "present invention DNA (B7)");

a DNA encoding a protein comprising an amino acid sequence shown in SEQ ID NO: 150 (hereinafter, sometimes referred to as the "present invention DNA (B8)");

a DNA encoding a protein comprising an amino acid sequence shown in SEQ ID NO: 151 (hereinafter, sometimes referred to as the "present invention DNA (B9)");

a DNA encoding a protein comprising an amino acid sequence shown in SEQ ID NO: 152 (hereinafter, sometimes referred to as the "present invention DNA (B10)");

a DNA encoding a protein comprising an amino acid sequence shown in SEQ ID NO: 153 (hereinafter, sometimes referred to as the "present invention DNA (B11)");

a DNA encoding a ferredoxin comprising an amino acid sequence having at least 80% sequence identity with an amino acid sequence shown in any one of SEQ ID NO: 149, SEQ ID NO: 151, SEQ ID NO: 152, SEQ ID NO: 153, SEQ ID NO: 245, SEQ ID NO: 247, SEQ ID NO: 248, SEQ ID NO: 249, SEQ ID NO: 250, SEQ ID NO: 251, or SEQ ID NO: 253 or an amino acid sequence having at least 90% sequence identity with an amino acid sequence shown in any one of SEQ ID NO: 150, SEQ ID NO: 252 or SEQ ID NO: 254;

a DNA encoding a ferredoxin comprising an amino acid sequence encoded by a nucleotide sequence having at least 90% sequence identity with a nucleotide sequence encoding an amino acid sequence shown in any one of SEQ ID NO: 149, SEQ ID NO: 150, SEQ ID NO: 151, SEQ ID NO: 152, SEQ ID NO: 153, SEQ ID NO: 245, SEQ ID NO: 247, SEQ ID NO: 248, SEQ ID NO: 249, SEQ ID NO: 250, SEQ ID NO: 251, SEQ ID NO: 252, SEQ ID NO: 253 or SEQ ID NO: 254;

a DNA encoding a protein comprising the amino acid sequence shown in SEQ ID NO: 245;

a DNA encoding a protein comprising the amino acid sequence shown in SEQ ID NO: 247;

a DNA encoding a protein comprising the amino acid sequence shown in SEQ ID NO: 248;

a DNA encoding a protein comprising the amino acid sequence shown in SEQ ID NO: 249;

a DNA encoding a protein comprising the amino acid sequence shown in SEQ ID NO: 250;

a DNA encoding a protein comprising the amino acid sequence shown in SEQ ID NO: 251;

a DNA encoding a protein comprising the amino acid sequence shown in SEQ ID NO: 252;

a DNA encoding a protein comprising the amino acid sequence shown in SEQ ID NO: 253; and a DNA encoding a protein comprising the amino acid sequence shown in SEQ ID NO: 254.

As more specific examples of the present invention DNA (B), there can be mentioned a DNA comprising a nucleotide sequence shown in any one of SEQ ID NO: 15, 16, 17, 112, 154, 155, 156, 157, 158, 255, 257, 258, 259, 260, 261, 262, 263 or 264, or a DNA comprising a nucleotide sequence having at least 90% sequence identity with a nucleotide sequence shown in any one of SEQ ID NO: 15, 16, 17, 112, 154, 155, 156, 157, 158, 255, 257, 258, 259, 260, 261, 262, 263 or 264.

Such DNA can be prepared by conducting methods in which PCR is conducted with DNA comprising a partial nucleotide sequence of the nucleotide sequences thereof as primers or hybridization methods in which such DNA is used as probes, according to the conditions described above in the methods of preparing the present DNA (A).

Specifically for example, a DNA comprising a nucleotide sequence encoding the amino acid sequence shown in SEQ ID NO: 12 or a DNA comprising the nucleotide sequence shown in SEQ ID NO: 15, can be prepared by conducting PCR by utilizing as the template the chromosomal DNA or chromosomal DNA library prepared from *Streptomyces phaeochromogenes* IFO12898 and by utilizing as primers an oligonucleotide comprising the nucleotide sequence shown in SEQ ID NO: 105 and an oligonucleotide comprising the nucleotide sequence shown in SEQ ID NO: 53.

Further, a DNA comprising a nucleotide sequence encoding the amino acid sequence shown in SEQ ID NO: 13 or a DNA comprising the nucleotide sequence shown in SEQ ID NO: 16, can be prepared by conducting PCR by utilizing as the template the chromosomal DNA or chromosomal DNA library prepared from *Saccharopolyspora taberi* JCM 9383t and by utilizing as primers an oligonucleotide comprising the nucleotide sequence shown in SEQ ID NO: 106 and an oligonucleotide comprising the nucleotide sequence shown in SEQ ID NO: 63.

Further, a DNA comprising a nucleotide sequence encoding the amino acid sequence shown in SEQ ID NO: 14 or a DNA comprising the nucleotide sequence shown in SEQ ID NO: 17, can be prepared by conducting PCR by utilizing as the template the chromosomal DNA or chromosomal DNA library prepared from *Streptomyces testaceus* ATCC21469 and by utilizing as primers an oligonucleotide comprising the nucleotide sequence shown in SEQ ID NO: 107 and an oligonucleotide comprising the nucleotide sequence shown in SEQ ID NO: 72.

Further, for example, the present invention DNA (B) can be obtained by hybridizing with a chromosomal DNA library, a DNA consisting of about at least 20 nucleotides comprising the nucleotides sequence encoding an amino acid sequences shown in any one of SEQ ID NO: 12, 13, 14, 111, 149, 150, 151, 152 or 153, as a probe under the conditions described above, followed by detecting and recovering the DNA which bound specifically with said probe. The chromosomal DNA library can be prepared as described above from microorganisms belonging to *Streptomyces*, such as *Streptomyces phaeochromogenes, Streptomyces testaceus, Streptomyces achromogenes, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis* and *Streptomyces steffisburgensis*, and more specifically, *Streptomyces phaeochromogenes* IFO12898, *Streptomyces testaceus* ATCC21469, *Streptomyces achromogenes* IFO 12735, *Streptomyces thermocoerulescens* IFO 14273t, *Streptomyces nogalater* IFO 13445, *Streptomyces tsusimaensis* IFO 13782, *Streptomyces glomerochromogenes* IFO 13673t, *Streptomyces olivochromogenes* IFO 12444, *Streptomyces ornatus* IFO 13069t, *Streptomyces griseus* ATCC 10137, *Streptomyces griseus* IFO 13849T, *Streptomyces lanatus* IFO 12787T, *Streptomyces misawanensis* IFO 13855T, *Streptomyces pallidus* IFO 13434T, *Streptomyces roseorubens* IFO 13682T, *Streptomyces rutgersensis* IFO 15875T and *Streptomyces steffisburgensis* IFO 13446T, and the like; or microorganisms belonging to *Saccharopolyspora*, such as *Saccharopolyspora taberi*, more specifically, *Saccharopolyspora taberi* JCM 9383t and the like. As specific examples of the DNA which can be utilized as such probes, there is mentioned a DNA comprising a nucleotide sequence shown in any one of SEQ ID NO: 15, 16, 17, 112, 154, 155, 156, 157, 158, 255, 257, 258, 259, 260, 261, 262, 263 or 264; DNA comprising a partial nucleotide sequence of such nucleotide sequences; or a DNA comprising a nucleotide sequence complimentary to said partial nucleotides sequences.

To express the present DNA (B) with a host cell, for example, a DNA in which the present DNA (B) and a promoter functional in a host cell are operably linked is prepared according to conventional genetic engineering methods described in "Molecular Cloning: A Laboratory Manual 2nd edition (1989)," Cold Spring Harbor Laboratory Press; "Current Protocols in Molecular Biology (1987)," John Wiley & Sons, Incorporated and the like, and is introduced into a host cell. Whether the obtained transformant contains the present DNA (B) can be confirmed by preparing the DNA from the transformant and then conducting with the prepared DNA genetic engineering analysis methods described in, for example, "Molecular Cloning 2nd edition," Cold Spring Harbor Press (Molecular Biology, John Wiley & Sons, N.Y. (1989) (such as confirming restriction enzyme sites, DNA sequencing, southern hybridizations, PCR and the like).

The present DNA (B) and the present DNA (A) can be expressed in the same cell, by introducing into a cell comprising the present DNA (A), the DNA in which the present DNA (B) and a promoter functional in a host cell are operably linked.

The present protein (B) can be prepared, for example, by culturing a cell comprising the present DNA (B). As such a cell, there is mentioned a microorganism expressing the present DNA (B) and having the ability to produce the present protein (B), such as microorganism strain isolated from nature comprising the present DNA (B), mutant strains derived from said natural strain by treatment with agents or ultraviolet rays or the like. For example, there is mentioned microorganisms belonging to *Streptomyces*, such as *Streptomyces phaeochromogenes*, *Streptomyces testaceus*, *Streptomyces achromogenes*, *Streptomyces griseolus*, *Streptomyces thermocoerulescens*, *Streptomyces nogalater*, *Streptomyces tsusimaensis*, *Streptomyces glomerochromogenes*, *Streptomyces olivochromogenes*, *Streptomyces ornatus*, *Streptomyces griseus*, *Streptomyces lanatus*, *Streptomyces misawanensis*, *Streptomyces pallidus*, *Streptomyces roseorubens*, *Streptomyces rutgersensis* and *Streptomyces steffisburgensis*, and more specifically, *Streptomyces phaeochromogenes* IFO12898, *Streptomyces testaceus* ATCC21469, *Streptomyces achromogenes* IFO 12735, *Streptomyces griseolus* ATCC11796, *Streptomyces thermocoerulescens* IFO 14273t, *Streptomyces nogalater* IFO 13445, *Streptomyces tsusimaensis* IFO 13782, *Streptomyces glomerochromogenes* IFO 13673t, *Streptomyces olivochromogenes* IFO 12444, *Streptomyces ornatus* IFO 13069t, *Streptomyces griseus* ATCC 10137, *Streptomyces griseus* IFO 13849T, *Streptomyces lanatus* IFO 12787T, *Streptomyces misawanensis* IFO 13855T, *Streptomyces pallidus* IFO 13434T, *Streptomyces roseorubens* IFO 13682T, *Streptomyces rutgersensis* IFO 15875T and *Streptomyces steffisburgensis* IFO 13446T, and the like; or microorganisms belonging to *Saccharopolyspora*, such as *Saccharopolyspora taberi*, more specifically, *Saccharopolyspora taberi* JCM 9383t and the like. Further, there can be mentioned a transformant in which the present DNA (B) has been introduced. Specifically for example, there is mentioned a transformant in which the present DNA (B) operably linked to a tac promoter, trc promoter, lac promoter or T7 phage promoter has been introduced into *E. coli*. As more specific examples, there is mentioned *E. coli* JM109/pKSN657FD, *E. coli* JM109/pKSN923FD, *E. coli* JM109/pKSN671FD and the like described in the examples described below.

The microorganism comprising the present DNA (B) can be cultivated in accordance with a method employed usually to culture a microorganism, and more specifically, conducted according to the conditions described above in the methods of culturing the microorganism comprising the present DNA (A).

The present protein (B) produced by the microorganism comprising the present DNA (B), for example, can be utilized in various forms in reaction system of the present protein (A), such as a culture of a microorganism producing the present protein (B), a cell of a microorganism producing the present protein (B), a material obtained by treating such a cell, a cell-free extract of a microorganism, a crudely purified protein, a purified protein and the like. A material obtained by treating a cell described above includes for example a lyophilized cell, an acetone-dried cell, a ground cell, an autolysate of a cell, an ultrasonically treated cell, an alkali-treated cell, an organic solvent-treated cell and the like. Alternatively, the present protein (B) in any of the various forms described above may be immobilized in accordance with known methods such as a support binding method employing an adsorption onto a synthesized polymer and the like, and an inclusion method employing an inclusion into a network matrix of a polymer, and then used in the reaction system of the present protein (A).

As methods of purifying the present protein (B) from a culture of a microorganism comprising the present DNA (B), there can be employed conventional methods utilized in a purification of protein. For example, there can be mentioned the following method.

First, cells are harvested from a culture of a microorganism by centrifugation or the like, and then disrupted physically by an ultrasonic treatment and the like, or disrupted chemically by utilizing a surfactant or a cell-lyzing enzyme such as lysozyme. From the resultant lysate thus obtained, insoluble materials are removed by centrifugation, membrane filtration or the like to prepare a cell-free extract, which is then fractionated by any appropriate means for separation and purification, such as a cation exchange chromatography, an anion exchange chromatography, a hydrophobic chromatography, a gel filtration chromatography and the like, whereby purifying the present protein (B). By separation of the fraction thus obtained with an SDS-PAGE, the present protein (B) can be further purified.

The function of the present protein (B) as ferredoxin can be confirmed as a function of electron transporter from ferredoxin-NADP+ reductase to the present protein (A) in the reaction system in which compound (I) is reacted with the present protein (A). Specifically for example, there can be a confirmation by adding the present protein (B) with NADPH, ferredoxin-NADP+ reductase and the present protein (A) to the reaction system in which compound (I) is reacted with the present protein (A), followed by detecting the conversion of compound (II) to compound (III).

In the method of controlling weeds of the present invention, compound (I) is applied to the cultivation area of a plant expressing the present protein (A). Such a plant may express one variation of the present protein (A) or may express multiple variations of the present protein (A). As the present protein (A), for example, there may be mentioned the present invention protein (A). Plants expressing the present protein (A) can be obtained as a transgenic plant to which the present DNA (A) has been introduced. Such introduction involves introducing the present DNA (A) into a plant cell in the way described above so that the DNA is placed in a position enabling its expression, followed by regenerating a plant from the obtained transformed cell. The present DNA (A) introduced into the plant cell may have linked upstream therefrom, a nucleotide sequence encoding a transit signal to an intracellular organelle, so that the reading frames are in frame.

The plant having introduced therein the present DNA (A) and expressing the present protein (A) metabolizes compound (I), within its cells, into a compound of lower herbicidal activity. As a result, the plant damage from the herbicidal compound in the plant is reduced and resistance to said compound is conferred. As such, the plant having introduced therein the present DNA (A) and expressing the present protein (A) can grow well even in a case in which compound (I) is applied to a cultivation area thereof. Weeds other than the plant having introduced therein the present DNA (A) and expressing the present protein (A) can be removed effectively by cultivating said plant and applying the above herbicidal composition to the cultivation area. It is possible to improve the yield of the above plant, improve the quality, reduce the amount of utilized herbicide and save labor.

The evaluation of resistance of the cell expressing the present protein (A) to the compound of formula (I) or a herbicidal composition comprising said compound can be carried out by contacting the cell expressing the gene encoding the present protein (A) with said compound or said herbicidal composition and evaluating the degree of damage to the cell.

Specifically, to evaluate the resistance of a microorganism cell expressing the present protein (A) to compound (I) or the herbicidal composition comprising compound (I), a transformed E. coli expressing plant PPO and the present protein (A) may be prepared. Such preparation involves additionally introducing the present DNA (A) into, for example, a transformed E. coli which can be utilized to evaluate PPO activity inhibition and has been described in Japanese patent application No. 11-102534, more specifically, a transformed E. coli in which a plant PPO gene described in U.S. Pat. No. 5,939,602 or the like is operably introduced into the E. coli BT3 strain and expressing the PPO gene. The E. coli BT3 strain has a defect in PPO gene and has no proliferation ability, as described in F. Yamamoto, H. Inokuti, H. Ozaki, (1988) Japanese Journal of Genetics, Vol. 63, pg. 237-249. The resistance to the compound or the herbicidal composition can be evaluated by cultivating the resulting transformed E. coli with shaking for about 18 to 24 hours at 37° C. in a liquid culture medium containing compound (I) or the herbicidal composition comprising said compound in an amount of from 0 to 1.0 ppm and measuring the proliferation of said transformed E. coli with an optical density at 600 nm. As the present protein (A), for example, there can be mentioned the present invention protein (A).

As a method of evaluating the degree of resistance of a plant expressing the present protein (A) to the compound of formula (I) or a herbicidal composition comprising said compound, there is mentioned a method of applying the herbicidal composition to the plant and measuring the degree of growth of the plant. For more quantitative confirmation, for example, first, pieces of leaves of the plant are dipped in aqueous solutions containing compound (I) at various concentrations, or the aqueous solutions of compound (I) are sprayed on pieces of leaves of the plant, followed by allowing to stand on an agar medium in the light at room temperature. After several days, chlorophyll is extracted from the plant leaves according to the method described by Mackenney, G., J. Biol. Chem., 140; p 315 (1941) to determine the content of chlorophyll. Specifically for example, leaves of the plant are taken and are split equally into 2 pieces along the main vein. The herbicidal composition is spread onto the full surface of one of the leaf pieces. The other leaf piece is left untreated. These leaf pieces are placed on MS medium containing 0.8% agar and allowed to stand in the light at room temperature for 7 days. Then, each leaf piece is ground with pestle and mortar in 5 ml of 80% aqueous acetone solution to extract chlorophyll. The extract liquid is diluted 10 fold with 80% aqueous acetone solution and the absorbance is measured at 750 nm, 663 nm and 645 nm to calculate total chlorophyll content according to the method described by Mackenney G., J. Biol. Chem. (1941) 140, p 315. The degree of resistance to compound (I) can be comparatively evaluated by showing in percentiles the total chlorophyll content of the treated leaf piece with the total chlorophyll content of the untreated leaf piece. As the present protein (A), for example, the present invention protein (A) can be mentioned.

Based on the above method of evaluating the degree of resistance to compound (I) or a herbicidal composition comprising compound (I), there can be selected a plant or a plant cell showing a resistance to compound (I) or a herbicidal composition comprising compound (I). For example, there is selected a plant where no damage can be seen from spraying compound (I) or a herbicidal composition comprising the compound to the cultivation area of the plant, or plant cell that continuously grows through culturing in the presence of compound (I). Specifically, for example, soil is packed into a plastic pot having, for example, a diameter of 10 cm and a depth of 10 cm. Seeds of the plant are sowed and cultivated in a greenhouse. An emulsion is prepared by mixing 5 parts of a herbicidal composition comprising compound (I), 6 parts of sorpol3005X (Toho chemicals) and 89 parts of xylene. A certain amount thereof was diluted with water containing 0.1% (v/v) of a sticking agent at a proportion of 1000 L for 1 hectare and is spread uniformly with a spray-gun onto the all sides of the foliage from above the plant cultivated in the above pot. After cultivating the plants for 16 days in a greenhouse, the damage to the plants is investigated. The plants in which the damage is not observed or the plants in which the damage is reduced may be selected. Further, progeny plants can be obtained by mating such selected plants.

EXAMPLES

The present invention is explained in more detail with the Examples below, but the present invention is not limited to such examples.

The HPLC for content analysis in Examples 1, 41 and 42 and fraction purification of the compound was conducted under the conditions shown below.

(HPLC Analysis Condition 1)

column: SUMIPAX ODS211 (Sumika Chemical Analysis Service)

column temperature: 35° C.

flow rate: 1 ml/minute detection wave length: UV254 nm eluent A: 0.01% TFA aqueous solution eluent B: acetonitrile elution conditions: The sample is injected to the column equilibrated with a solvent mixture of 90% of eluent A and 10% eluent B. The solvent mixture of 90% of eluent A and 10% eluent B is then flowed for 5 minutes. This is followed by flowing a solvent mixture of eluent A and eluent B for 20 minutes, while increasing the proportion of eluent B from 10% to 90%. A solvent mixture of 10% of eluent A and 90% of eluent B is then flowed for 8 minutes.

Example

The Metabolism of Compound (II) by a Microorganism (1) Metabolism of Compound (II)

The various microorganisms shown in Tables 1 and 2 were grown in ISP2 agar medium (1.0% (w/v) malt extract, 0.4% (w/v) yeast extract, 0.4% (w/v) glucose, 2.0% (w/v) agar, pH 7.3). A "loopful" of the each microorganism was added to TGY medium (0.5% (w/v) tryptone, 0.5% (w/v) yeast extract, 0.1% (w/v) glucose, 0.01% (w/v) $KH_2PO_4$, pH 7.0) and incubated with shaking at 30° C. for 2 to 4 days. One-tenth milliliter (0.1 ml) of the obtained culture was incubated with shaking in 3 ml of sporulation medium (0.1% (w/v) of meat extract, 0.2% (w/v) tryptose, 1% glucose, pH 7.1) containing compound (II) at 100 ppm for 7 to 8 days at 30° C. Fifty microliters (50 µl) of 2N HCl was added to the resulting culture and this was extracted with 3 ml of ethyl acetate. The obtained ethyl acetate layer was analyzed on the HPLC. The concentration of compound (II) was reduced (column retention time of 23.9 minutes) and new peaks were detected for compounds at retention times of 21.6 minutes and 22.2 minutes (each referred to as metabolite (I) and metabolite (II)). The results are shown in Tables 1 and 2.

TABLE 1

| strain of the microorganism | concentration of compound (II) (ppm) | peak area of metabolite (I) (×104) | peak area of metabolite (II) (×104) |
|---|---|---|---|
| Streptomyces cacaoiasoensis IFO13813 | 77.8 | 3.43 | 3.57 |
| Streptomyces griseofuscus IFO12870t | 49.5 | 7.96 | 9.86 |
| Streptomyces ornatus IFO13069t | 65.3 | 4.30 | 5.00 |
| Streptomyces thermocoerulescens IFO14273t | 51.7 | 7.47 | 9.16 |
| Streptomyces roseochromogenes ATCC13400 | 81.9 | 0.71 | 0.82 |
| Streptomyces lavendulae ATCC11924 | 89.6 | 1.02 | 1.50 |
| Streptomyces griseus ATCC10137 | 65.6 | 6.19 | 1.30 |
| Streptomyces griseus ATCC11429 | 30.3 | 12.8 | 15 6 |
| Streptomyces griseus ATCC12475 | 51.1 | 0.52 | 2.27 |
| Streptomyces griseus ATCC15395 | 75.2 | 1.91 | 2.26 |
| Streptomyces erythreus ATCC11635 | 54.6 | 4.94 | 6.05 |
| Streptomyces scabies IFO3111 | 88.3 | 3.28 | 4.40 |
| Streptomyces griseus IFO3102 | 22.6 | 14.4 | 18.5 |
| Streptomyces catenulae IFO12848 | 85.3 | 3.81 | 1.59 |
| Streptomyces kasugaensis ATCC15714 | 92.4 | 1.08 | 0.91 |
| Streptomyces rimosus ATCC10970 | 70.9 | 2.30 | 2.87 |
| Streptomyces achromogenes IFO12735 | 0.0 | 15.9 | 21.8 |
| Streptomyces lydicus IFO13058 | 62.0 | 5.48 | 6.69 |

TABLE 2

| strain of the microorganism | concentration of compound (II) (ppm) | peak area of metabolite (I) (×104) | peak area of metabolite (II) (×104) |
|---|---|---|---|
| Streptomyces phaeochromogenes IFO12898 | 46.4 | 8.28 | 10.5 |
| Streptomyces afghaniensis IFO12831 | 80.6 | 2.54 | 3.59 |
| Streptomyces hachijoensis IFO12782 | 83.9 | 4.99 | 2.91 |
| Streptomyces argenteolus var. toyonakensis ATCC21468 | 13.0 | 14.9 | 19.2 |
| Streptomyces testaceus ATCC21469 | 18.4 | 11.6 | 14.4 |
| Streptomyces purpurascens ATCC25489 | 70.9 | 5.37 | 6.11 |
| Streptomyces griseochromogenes ATCC14511 | 53.9 | 3.00 | 3.97 |
| Streptomyces kasugaensis IFO13851 | 66.3 | 12.1 | 12.6 |
| Streptomyces argenteolus var. toyon ATCC21468t | 90.1 | 2.75 | 3.01 |
| Streptomyces roseochromogenes ATCC13400t | 71.8 | 4.66 | 4.00 |
| Streptomyces nogalater IFO13445 | 12.8 | 21.9 | 24.9 |
| Streptomyces roseochromogenus ATCC21895 | 74.2 | 4.14 | 5.87 |
| Streptomyces fimicarius ATCC21900 | 46.5 | 8.33 | 11.3 |
| Streptomyces chartreusis ATCC21901 | 61.1 | 3.70 | 3.94 |
| Streptomyces globisporus subsp. globisporus ATCC21903 | 79.9 | 2.86 | 2.52 |
| Streptomyces griseolus ATCC11796 | 0 | 14.4 | 19.9 |
| Saccharopolyspora taberi JCM9383T | 82.9 | 5.83 | 7.71 |
| Streptomyces sp. SANK62585 | 54.6 | 2.30 | 3.44 |

(2) Structure Determination of the Metabolite (I) and Metabolite (II)

A frozen stock of *Streptomyces griseus* ATCC11429 was added to 3 ml of a microorganism culture medium (0.7% (w/v) polypeptone, 0.5% (w/v) yeast extract, 1.0% (w/v) of glucose, 0.5% (w/v) of $K_2HPO_4$, pH7.2) and incubated with shaking in a test tube overnight to obtain a pre-culture. Such pre-culture was added to 300 ml of the microorganism medium containing compound (II) at a concentration of 100 ppm. This was divided into 100 small test tubes at 3 ml each and incubated with shaking at 30° C. for 6 days. After 250 ml of such culture was adjusted to a pH2 by adding HCl, this was extracted with 250 ml of ethyl acetate. The solvents were removed from the ethyl acetate layer. The residue was dissolved in 3 ml of acetone and spotted to a silica gel TLC plate (TLC plate silica gel $60F_{254}$, 20 cm×20×m, 0.25 mm thickness, Merck Company). The TLC plate was developed with 5:7:1 (v/v/v) mixture of toluene, formic acid and ethyl formate. The Rf value around 0.58 of the silica gel was taken. Such contents of the TLC plate were extracted with acetone. The acetone was removed from the extraction layer. The residue was dissolved in 10 ml of acetonitrile and fractionated with a HPLC. The fractions containing only metabolite (I) and metabolite (II) were recovered to obtain 3.7 mg of metabolites (hereinafter referred to as "metabolite A").

Mass spectrometry analysis of metabolite A was conducted. Metabolite A had a mass that was 14 smaller than compound (II). Further, from H-NMR analysis, it was determined that metabolite (A) was a compound having the structure shown in formula (III).

(3) Herbicidal Activity Test of Compound (III)

Soil was packed into a round plastic pot having a diameter of 10 cm and depth of 10 cm. Barnyardgrass, Blackgrass, Ivyleaf morningglory were seeded and cultivated in a greenhouse for 10 days. Five (5) parts of the test compound, 6 parts of sorpol3005X (Toho Chemical Company) and 89 parts of xylene were well mixed to produce an emulsion. A certain amount thereof was diluted with water containing 0.1% (v/v) of a sticking agent at a proportion of 1000 L for 1 hectare and was spread uniformly with a spray-gun onto the all sides of the foliage from above the plant cultivated in the above pot. After cultivating the plants for 16 days in a greenhouse, the herbicidal activity of the test compound was investigated. The results are shown in Table 3.

TABLE 3

| test compounds | concentration (g/ha) | Herbicidal Activity | | |
|---|---|---|---|---|
| | | Barnyard-grass | Black-grass | Ivyleaf Morning-glory |
| compound (II) | 500 | 10 | 10 | 10 |
| | 125 | 10 | 10 | 10 |
| compound (III) | 500 | 0 | 0 | 0 |
| | 125 | 0 | 0 | 0 |

Soil was packed into a round plastic pot having a diameter of 10 cm and depth of 10 cm. Barnyardgrass, Blackgrass, Ivyleaf morningglory were seeded. Five (5) parts of the test compound, 6 parts of sorpol3005X (Toho Chemical Company) and 89 parts of xylene were well mixed to produce an emulsion. A certain amount thereof was diluted with water containing 0.1% (v/v) of a sticking agent at a proportion of 1000 L for 1 hectare and was spread uniformly with a spray-gun onto the surface of the soil. After cultivating the plants for 19 days in a greenhouse, the herbicidal activity was investigated. The results are shown in Table 4.

TABLE 4

| test compounds | concentration (g/ha) | Herbicidal Activity | | |
|---|---|---|---|---|
| | | Barnyard-grass | Black-grass | Ivyleaf Morning-glory |
| compound (II) | 500 | 10 | 10 | 10 |
| compound (III) | 500 | 0 | 0 | 0 |

In the above Tables 3 and 4, the strength of the herbicidal activity is shown stepwise as 0, 1, 2, 3, 4, 5, 6, 7, 8, 9, and 10. The number "0" represents situations in which the condition of sprouting or vegetation at the time of examination of the plant utilized for the test was compared with and showed totally or substantially no difference with that of the untreated application. The number "10" represents situations in which the plant completely withered or the sprouting or vegetation was completely suppressed.

Example 2

Preparation of the Present Invention Protein (A1)

(1) Preparation of the Crude Cell Extract

A frozen stock of *Streptomyces phaeochromogenes* IFO12898 was added to 100 ml of A medium (0.1% (w/v) glucose, 0.5% (w/v) tryptone, 0.5% (w/v) yeast extract, 0.1% (w/v) of dipotassium hydrogenphosphate, pH7.0) in a 500 ml triangular flask and incubated with rotary shaking at 30° C. for 1 day to obtain a pre-culture. Eight milliliters (8 ml) of the pre-culture was added to 200 ml of A medium and was incubated with rotary shaking in 500 ml a baffled flask at 30° C. for 2 days. Cell pellets were recovered by centrifuging (3,000 g, 5 min.) the resulting culture. These cell pellets were suspended in 100 ml of B medium (1% (w/v) glucose, 0.1% beef extract, 0.2% (w/v) tryptose) containing compound (II) at 100 ppm and were incubated with reciprocal shaking in a 500 ml Sakaguchi flask for 16 hours at 30° C. Cell pellets were recovered by centrifuging (3,000 g, 5 min.) 10 L of the resulting culture. The resulting cell pellets were washed twice with 1 L of 0.1M potassium phosphate buffer (pH7.0) to provide 162 g of the cell pellets.

These cell pellets were suspended in 0.1M potassium phosphate buffer (pH7.0) at 2 ml for 1 g of the cell pellets, and 1 mM PMSF, 5 mM benzamidine HCl, 1 mM EDTA and 1 mM of dithiotritol were added thereto. A cell lysate solution was obtained by disrupting twice repetitively the suspension with a French press (1000 kg/cm$^2$) (Ohtake Seisakusho). After centrifuging the cell lysate solution (40,000×g, 30 minutes), the supernatant was recovered and centrifuged for 1 hour at 150,000×g to recover the supernatant (hereinafter referred to as the "crude cell extract").

(2) Determination of the Ability of Converting Compound (II) to Compound (III)

There was prepared 30 µl of a reaction solution of 0.1M potassium phosphate buffer (pH7.0) containing 3 ppm of compound (II) labeled with $^{14}$C, 2.4 mM of β-NADPH (hereinafter, referred to as "component A") (Oriental Yeast Company), 0.5 mg/ml of a ferredoxin derived from spinach (hereinafter referred to as "component B") (Sigma Company), 1 U/ml of ferredoxin reductase (hereinafter, referred to as "component C") (Sigma Company) and 18 µl of the crude cell extract recovered in Example 2(1). The reaction solution was maintained at 30° C. for a hour. Further, there was prepared and maintained similarly a reaction solution having no addition of at least one component utilized in the composition of the above reaction solution, selected from component A, component B and component C. Three microliters (3 μl) of 2N HCl and 90 μl of ethyl acetate were added and mixed into each of the reaction solutions after the maintenance. The resulting reaction solutions were centrifuged at 8,000×g to recover 75 μl of the ethyl acetate layer. After drying the ethyl acetate layers under reduced pressure, the residue was dissolved in 6.0 μl of ethyl acetate. Five microliters (5.0 μl) thereof was spotted to a TLC plate (TLC plate silica gel 60$F_{254}$ 20 cm×20 cm, 0.25 thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}C$ were examined (Rf value 0.24 and 0.29). The results are shown in Table 5.

TABLE 5

| | Reaction components | | | compound (II) labeled with 14C | spot of compound (III) |
|---|---|---|---|---|---|
| component A | component B | component C | crude cell extract | | |

(3) Fractionation of the Crude Cell Extract

Ammonium sulfate was added to the crude cell extract obtained in Example 2(1) to amount to 45% saturation. After stirring in ice-cooled conditions, the supernatant was recovered by centrifugation for 10 minutes at 12,000×g. After adding ammonium sulfate to the obtained supernatant to amount to 55% saturation and stirring in ice-cooled conditions, a pellet was recovered by centrifuging for 10 minutes at 12,000×g. The pellet was dissolved with 27.5 ml of 20 mM bistrispropane buffer (pH7.0). This solution was subjected to a PD10 column (Amersham Pharmacia Company) and eluted with 20 mM of bistrispropane buffer (pH7.0) to recover 38.5 ml of fractions containing proteins (hereinafter referred to as the "45-55% ammonium sulfate fraction").

(4) Isolation of the Present Invention Protein (A1)

The 45-55% ammonium sulfate fraction prepared in Example 2(3) was injected into a HiLoad26/10 Q Sepharose HP column (Amersham Pharmacia Company). Next, after flowing 106 ml of 20 mM bistrispropane buffer (pH7.0) into the column, 20 mM bistrispropane buffer was flown with a linear gradient of NaCl (gradient of NaCl was 0.001415M/minute, range of NaCl concentration was from 0M to 0.375M, flow rate was 3 ml/minute) to fraction recover 25 ml of fractions eluting at the NaCl concentration of from 0.21M to 0.22M. Further, the recovered fractions were subjected to a PD10 column (Amersham Pharmacia Biotech Company) and eluted with 20 mM bistrispropane buffer (pH7.0) to recover the fractions containing protein.

The recovered fractions were subjected to a PD10 column (Amersham Pharmacia Biotech Company) with the elution with Buffer A (2 mM potassium phosphate buffer containing 1.5 mM of NaCl, pH 7.0), in order to recover the fractions containing protein. Next, the fractions were injected into a Bio-Scale Ceramic Hydroxyapatite Type I column CHT10-I (BioRad Company). Thirty milliliters (30 ml) of Buffer A was flown into the column. Subsequently, Buffer A was flown with a linear gradient of Buffer B (100 mM potassium phosphate buffer containing 0.03 mM of NaCl; the linear gradient started at 100% Buffer A to increase to 50% Buffer B over a 100 minute period, flow rate was 2 ml/minute) to fraction recover the fractions eluting at a Buffer B concentration of from 17% to 20%. Further, the recovered fractions were subjected to a PD10 column (Amersham Pharmacia Biotech Company) and eluted with 0.05M potassium phosphate buffer (pH7.0) to recover the fractions containing protein.

The recovered fractions were concentrated 20 fold using an ultrafilter membrane (Microcon YM-30, Millipore Company) and injected into a HiLoad 16/60 Superdex 75 pg column (Amersham Pharmacia Biotech Company). Fifty millimolar (50 mM) potassium phosphate buffer containing 0.15M of NaCl (pH7.0) was flown (flow rate 1 ml/minute) into the column. The elution was fractioned at 2 ml each. The fractions eluting at the elution volumes of from 56 ml to 66 ml were each fraction recovered. The protein contained in each of the fractions was analyzed with a 10%-20% SDS-PAGE.

Instead of the crude cell extract in the reaction solution described in Example 2(2), the recovered fractions were added and maintained in the presence of component A, component B, component C and compound (II) labeled with $^{14}C$, similarly to Example 2(2). The reaction solutions after the maintenance were TLC analyzed to examine the intensity of the spots corresponding to compound (III) labeled with $^{14}C$. The protein moving to the position to 47 kDa in the above SDS-PAGE was observed to have its fluctuations in the concentrations of the bands of the fractions added in turn to be parallel with the fluctuations of the intensity of the spots corresponding to compound (III). Said protein was recovered from the SDS-PAGE gel and was subjected to an amino acid sequence analysis with a protein sequencer (Applied Biosystems Company, Procise 494HT, pulsed liquid method). As a result, the amino acid sequence shown in SEQ ID NO: 18 was provided. Further, after digesting the above protein with trypsin, the obtained digestion material was analyzed on a mass spectrometer (ThermoQuest Company, Ion Trap Mass Spectrometer LCQ, column: LC Packings Company PepMap C18 75 μm×150 mm, solvent A: 0.1% HOAc—H2O, solvent B: 0.1% HOAc-methanol, gradient: a linear gradient starting at an elution with a mixture of 95% of solvent A and 5% of solvent B and increasing to a concentration of 100% of solvent B over 30 minutes, flow rate: 0.2 μl/minute). As a result, the sequence shown in SEQ ID NO: 19 was provided.

Example 3

Obtaining the Present Invention DNA (A1)

(1) Preparation of the chromosomal DNA of *Streptomyces phaeochromogenes* IFO12898

*Streptomyces phaeochromogenes* IFO12898 was incubated with shaking at 30° C. for 1 day to 3 days in 50 ml of YEME medium (0.3% (w/v) yeast extract, 0.5% (w/v) bactopeptone, 0.3% (w/v) malt extract, 1.0% (w/v) glucose, 34%

(w/v) sucrose and 0.2% (v/v) 2.5M MgCl$_2$ 6H$_2$O). The cells were recovered. The obtained cells were suspended in YEME medium containing 1.4% (w/v) glycine and 60 mM EDTA and further incubated with shaking for a day. The cells were recovered from the culture medium. After washing once with distilled water, it was resuspended in buffer (100 mM Tris-HCl (pH8.0), 100 mM EDTA, 10 mM NaCl) at 1 ml per 200 mg of the cells. Two hundred micrograms per milliliter (200 µg/ml) of egg-white lysozyme were added. The cell suspension was incubated with shaking at 30° C. for a hour. Further, 0.5% of SDS and 1 mg/ml of Proteinase K was added. The cell suspension was incubated at 55° C. for 3 hours. The cell suspension was extracted twice with mixture of phenol, chloroform and isoamyl alcohol to recover each of the aqueous layers. Next, there was one extraction with mixture of chloroform and isoamyl alcohol to recover the aqueous layer. The chromosomal DNA was obtained by ethanol precipitation from the aqueous layer.

(2) Preparation of the Chromosomal DNA Library of *Streptomyces Phaeochromogenes* IFO12898

Nine hundred forty-three nanograms (943 ng) of the chromosomal DNA prepared in Example 3(1) were digested with 1 unit of restriction enzyme Sau3AI at 37° C. for 60 minutes. The obtained digestion solution was separated with 0.7% agarose gel electrophoresis. The DNA of about 2.0 kbp was recovered from the gel. The DNA was purified with a Prep-A-Gene® DNA purification kit (Bio-Rad company) according to the instructions attached to said kit to obtain 10 µl of the solution containing the target DNA. A microliter (1 µl) of the DNA solution, 98 ng of plasmid vector pUC118 digested with restriction enzyme BamHI and treated with dephosphorylation and 11 µl of the I solution from Ligation Kit Ver. 2 (Takara Shuzo Company) were mixed and incubated overnight at 16° C. *E. coli* DH5α was transformed utilizing 5 µl of the ligation solution. The *E. coli* was cultured with shaking overnight at 30° C. From the obtained culture medium, the *E. coli* was recovered. The plasmid was extracted to provide the chromosomal DNA library.

(3) Isolation of the Present Invention DNA (A1)

Figure 1:
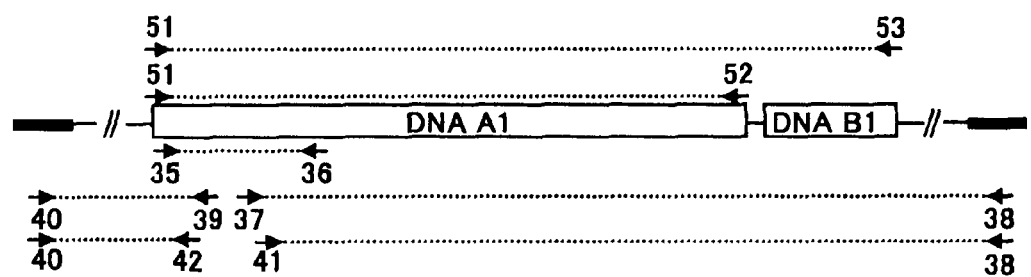
FIG. 1 shows the annealing site of the PCR primers utilized to obtain the present invention DNA (A1) and the present invention DNA (B1). Each of the numbers refers to the SEQ ID number showing the nucleotide sequence of the primers. The arrows show the annealing sites of the oligonucleotide primers having the nucleotide sequence shown with the SEQ ID number thereof and the extention direction of the DNA polymerase reaction from the primers. The dotted lines represent the DNA amplified by the PCR utilizing the primers. The thick line represents the region adjacent to the DNA insertion site of the vector utilized to produce the chromosomal DNA library.

PCR was conducted by utilizing as the template the chromosomal DNA prepared in Example 3(1) (FIG. 1). As the primers, there was utilized the pairing of an oligonucleotide having the nucleotide sequence shown in SEQ ID NO: 35 and an olignonucleotide having the nucleotide sequence shown in SEQ ID NO: 36 (hereinafter referred to as "primer paring 1"). The nucleotide sequence shown in SEQ ID NO: 35 was designed based on a nucleotide sequence encoding the amino acid sequence shown in SEQ ID NO: 18. Further, the nucleotide sequence shown in SEQ ID NO: 36 was designed based on a nucleotide sequence complimentary to the nucleotide sequence encoding the amino acid sequence shown in SEQ ID NO: 19. The PCR reaction solution amounted to 25 µl by adding the 2 primers each amounting to 200 nM, 250 ng of the above chromosomal DNA, 0.5 µl of dNTP mix (a mixture of 10 mM of each of the 4 types of dNTP; Clontech Company), 5 µl of 5×GC genomic PCR reaction buffer (Clontech Company), 1.1 µl of 25 mM Mg(OAc)$_2$, 5 µl of 5M GC-Melt (Clontech Company) and 0.5 µl of Advantage-GC genomic polymerase mix (Clontech Company) and distilled water. The reaction conditions of the PCR were after maintaining 95° C. for 1 minute, repeating 30 cycles of a cycle that included maintaining 94° C. for 15 seconds, followed by 60° C. for 30 seconds, followed by 72° C. for 1 minute, and then maintaining 72° C. for 5 minutes. After the maintenance, the reaction solution was subjected to 4% agarose gel electrophoresis. The gel area containing the DNA of about 150 bp was recovered. The DNA was purified from the recovered gel by utilizing QIAquick gel extraction kit (Qiagen Company) according to the attached instructions. The obtained DNA was ligated to the TA cloning vector pCR2.1 (Invitrogen Company) according to the instructions attached to said vector and was introduced into *E. Coli* TOP10F'. The plasmid DNA was prepared from the obtained *E. coli* transformant, utilizing QIAprep Spin Miniprep Kit (Qiagen Company). A sequencing reaction was conducted with Dye terminator cycle sequencing FS ready reaction kit (Applied Biosystems Japan Company) according to the instructions attached to said kit, utilizing as primers the −21M13 primer (Applied Biosystems Japan Company) and M13Rev primer (Applied Biosystems Japan Company). The sequencing reaction utilized the obtained plasmid DNA as the template. The reaction products were analyzed with a DNA sequencer 373A (Applied Biosystems Japan Company). As a result, the nucleotide sequence shown in nucleotides 36 to 132 of the nucleotide sequence shown in SEQ ID NO: 9 was provided. Said nucleotide sequence encoded the amino acid sequence shown in amino acids 12 to 23 of the amino acid sequence shown in SEQ ID NO: 18. In this regard, it was expected that said DNA encoded a part of the present invention protein (A1).

Next, PCR was conducted similar to the above with Advantage-GC genomic polymerase mix (Clontech Company) and by utilizing the chromosomal DNA prepared in Example 3(2) as the template. There was utilized as primers, a pairing of an oligonucleotide having the nucleotide sequence shown in SEQ ID NO: 37 with an oligonucleotide having the nucleotide sequence shown in SEQ ID NO: 38 (hereinafter referred to as the "primer pairing 2") or a pairing of an oligonucleotide having the nucleotide sequence shown in SEQ ID NO: 39 with an oligonucleotide having the nucleotide sequence shown in SEQ ID NO: 40 (hereinafter referred to as the "primer pairing 3").

Next, there was amplified by PCR a DNA having a nucleotide sequence in which the 3' terminus extends past the nucleotide shown as nucleotide 132 of the nucleotide sequence shown in SEQ ID NO: 9. The PCR was conducted by utilizing as the template solution the reaction solution obtained with the use of primer pairing 2 and by utilizing as primers a pairing of the oligonucleotide having the nucleotide sequence shown in SEQ ID NO: 41 and the oligonucleotide having the nucleotide sequence shown in SEQ ID NO: 38 (hereinafter referred to as "primer pairing 4"). Similarly, there was amplified by PCR a DNA having a nucleotide sequence in which the 5' terminus extends past the nucleotide shown as nucleotide 36 of the nucleotide sequence shown in SEQ ID NO: 9. The PCR was conducted by utilizing as the template solution the reaction solution obtained with the use of primer pairing 3 and by utilizing as primers a pairing of the oligonucleotide having the nucleotide sequence shown in SEQ ID NO: 42 and the oligonucleotide having the nucleotide sequence shown in SEQ ID NO: 40 (hereinafter referred to as "primer pairing 5"). The 2 kbp DNA amplified with the use of primer pairing 4 and the 150 bp DNA amplified with the use of primer pairing 5 are cloned into TA cloning vector pCR2.1, similar to the above. Plasmid DNA was prepared from the obtained E. coli transformant, utilizing QIAprep Spin Miniprep Kit (Qiagen Company). A sequencing reaction was conducted with Dye terminator cycle sequencing FS ready reaction kit (Applied Biosystems Japan Company) according to the instructions attached to said kit, utilizing as primers the −21M13 primer (Applied Biosystems Japan Company), M13Rev primer (Applied Biosystems Japan Company) and the oligonucleotides shown in SEQ ID NO: 43-50. The sequencing reaction utilized the obtained plasmid DNA as the template. The reaction products were analyzed with a DNA sequencer 373A (Applied Biosystems Japan Company). As a result of sequencing the nucleotide sequence of the 2 kbp DNA amplified by utilizing primer pairing 4, the nucleotide sequence shown in nucleotides 133 to 1439 of the nucleotide sequence shown in SEQ ID NO: 9 was provided. Further, as a result of sequencing the nucleotide sequence of the 150 bp DNA amplified by utilizing primer pairing 5, the nucleotide sequence shown in nucleotides 1 to 35 of the nucleotide sequence shown in SEQ ID NO: 9 was provided. As a result of connecting the obtained nucleotide sequences, the nucleotide sequence shown in SEQ ID NO: 9 was obtained. Two open reading frames (ORF) were present in said nucleotide sequence. As such, there was contained a nucleotide sequence (SEQ ID NO: 6) consisting of 1227 nucleotides (inclusive of the stop codon) and encoding a 408 amino acid residue as well as a nucleotide sequence (SEQ ID NO: 15) consisting of 201 nucleotides (inclusive of the stop codon) and encoding a 66 amino acid residue. The molecular weight of the protein consisting of the amino acid sequence (SEQ ID NO: 1) encoded by the nucleotide sequence shown in SEQ ID NO: 6 was calculated to be 45213 Da. Further, the amino acid sequence encoded by said nucleotide sequence contained the amino acid sequence (SEQ ID NO: 18) determined from the amino acid sequencing of from the N terminus of the present invention protein (A1) and the amino acid sequence (SEQ ID NO: 19) determined from the amino acid sequencing of the trypsin digestion fragments with the mass spectrometer analysis. The molecular weight of the protein consisting of the amino acid sequence (SEQ ID NO: 12) encoded by the nucleotide sequence shown in SEQ ID NO: 15 was calculated to be 6818 Da.

Example 4

Expression of the Present Invention Protein (A1) in E. coli (1) Production of a transformed E. coli having the present invention protein (A1)

PCR was conducted by utilizing as a template the chromosomal DNA prepared from Streptomyces phaeochromogenes IFO12898 in Example 3(1) and by utilizing Expand High Fidelity PCR System (Roche Molecular Biochemicals Company). As the primers, there was utilized the pairing of an oligonucleotide having the nucleotide sequence shown in SEQ ID NO: 51 and an oligonucleotide having the nucleotide sequence shown in SEQ ID NO: 52 (hereinafter referred to as "primer pairing 19") or a pairing of an oligonucleotide having the nucleotide sequence shown in SEQ ID NO: 51 and an oligonucleotide having the nucleotide sequence shown in SEQ ID NO: 53 (hereinafter referred to as "primer pairing 20"). The PCR reaction solution amounted to 50 µl by adding the 2 primers each amounting to 300 nM, 50 ng of the above chromosomal DNA, 5.0 µl of dNTP mix (a mixture of 2.0 mM of each of the 4 types of dNTP), 5.0 µl of 10× Expand HF buffer (containing MgCl2) and 0.75 µl of Expand HiFi enzyme mix and distilled water. The reaction conditions of the PCR were after maintaining 97° C. for 2 minutes; repeating 10 cycles of a cycle that included maintaining 97° C. for 15 seconds, followed by 65° C. for 30 seconds and followed by 72° C. for 2 minutes; then conducting 15 cycles of a cycle that included maintaining 97° C. for 15 seconds, followed by 68° C. for 30 seconds and followed by 72° C. for 2 minutes (wherein 20 seconds was added to the maintenance at 72° C. for each cycle); and then maintaining 72° C. for 7 minutes. After the maintenance, the reaction solution was subjected to 1% agarose gel electrophoresis. The gel area containing the DNA of about 1.2 kbp was recovered from the gel which was subjected the reaction solution utilizing primer pairing 19. The gel area containing the DNA of about 1.5 kbp was recovered from the gel which was subjected the reaction solution utilizing primer pairing 20. The DNA were purified from each of the recovered gels by utilizing QIAquick gel extraction kit (Qiagen Company) according to the attached instructions. The obtained DNA were ligated to the TA cloning vector pCR2.1 (Invitrogen Company) according to the instructions attached to said vector and were introduced into E. Coli TOP10F'. The plasmid DNA were prepared from the obtained E. coli transformants, utilizing QIAprep Spin Miniprep Kit (Qiagen Company). Sequencing reactions were conducted with Dye terminator cycle sequencing FS ready reaction kit (Applied Biosystems Japan Company) according to the instructions attached to said kit, utilizing as primers the −21M13 primer (Applied Biosystems Japan Company), M13Rev primer (Applied Biosystems Japan Company), the oligonucleotide having the nucleotide sequence shown in SEQ ID NO: 43 and the oligonucleotide having the nucleotide sequence shown in SEQ ID NO: 46. The sequencing reactions utilized the obtained plasmid DNA as the template. The reaction products were analyzed with a DNA sequencer 373A (Applied Biosystems Japan Company). Based on the results, the plasmid having the nucleotide sequence shown in SEQ ID NO: 6 was designated as pCR657 and the plasmid having the nucleotide sequence shown in SEQ ID NO: 9 was designated as pCR657F.

Furthermore, the oligonucleotide having the nucleotide sequence shown in SEQ ID NO: 134 and the oligonucleotide having the nucleotide sequence shown in SEQ ID NO: 135 were annealed together to provide a linker (FIG. 47). Plasmid pKSN24R2 (Akiyoshi-ShibaTa M. et al., Eur. J. Biochem. 224: P335 (1994)) was digested with HindIII and XmnI. The linker was inserted into the obtained DNA of about 3 kb. The obtained plasmid was designated as pKSN2 (FIG. 4).

Next, each of plasmids pCR657 and pCR657F was digested with restriction enzymes NdeI and HindIII. The digestion products were subjected to agarose gel electrophoresis. The gel area containing a DNA of about 1.2 kbp was cut from the gel subjected to the digestion products of pCR657. The gel area containing a DNA of about 1.5 kbp was cut from the gel subjected to the digestion products of pCR657F. The DNA were purified from each of the recovered gels by utilizing QIAquick gel extraction kit (Qiagen Company) according to the attached instructions. Each of the obtained DNA and the plasmid pKSN2 digested with NdeI and HindIII were ligated with ligation kit Ver. 1 (Takara Shuzo Company) according to the instructions attached to said kit and introduced into E. Coli JM109. The plasmid DNA were prepared from the obtained E. coli transformants. The structures thereof were analyzed. The plasmid containing the nucleotide sequence shown in SEQ ID NO: 6, in which the DNA of about 1.2 kbp encoding the present invention protein (A1) is inserted between the NdeI site and the HindIII site of pKSN2 was designated as pKSN657. Further, the plasmid containing the nucleotide sequence shown in SEQ ID NO: 9, in which the DNA of about 1.5 kbp encoding the present invention protein (A1) is inserted between the NdeI site and the HindIII site of pKSN2 was designated as pKSN657F. Each of the above plasmids of pKSN657 and pKSN657F were introduced into E. coli JM109. The obtained E. coli transformants were designated, respectively, JM109/pKSN657 and JM109/pKSN657F. Further, plasmid pKSN2 was introduced into E. coli JM109. The obtained E. coli transformant was designated as JM109/pKSN2.

(2) Expression of the Present Invention Protein (A1) in *E. Coli* and Recovery of Said Protein

*E. coli* JM109/pKSN657, JM109/pKSN657F and JM109/pKSN2 were each cultured overnight at 37° C. in 10 ml of TB medium (1.2% (w/v) tryptone, 2.4% (w/v) of yeast extract, 0.4% (w/v) of glycerol, 17 mM potassium dihydrogenphosphate, 72 mM dipotassium hydrogenphosphate) containing 50 µg/ml of ampicillin. A milliliter (1 ml) of the obtained culture medium was transferred to 100 ml of TB medium containing 50 µg/ml of ampicillin and cultured at 26° C. When OD660 reached about 0.5, 5-aminolevulinic acid was added to the final concentration of 500 µM, and the culturing was continued. Thirty (30) minutes thereafter, IPTG was added to a final concentration of 1 mM, and there was further culturing for 17 hours.

The cells were recovered from each of the culture mediums, washed with 0.1M tris-HCl buffer (pH7.5) and suspended in 10 ml of the above buffer containing 1 mM PMSF. The obtained cell suspensions were subjected 6 times to a sonicator (Sonifier (Branson Sonic Power Company)) at 3 minutes each under the conditions of output 3, duty cycle 30%, in order to obtain cell lysate solutions. After centrifuging the cell lysate solutions (1,200×g, 5 minutes) the supernatants were recovered and centrifuged (150,000×g, 70 minutes) to recover supernatant fractions (hereinafter, the supernatant fraction obtained from *E. coli* JM109/pKSN657 is referred to as "*E. coli* pKSN657 extract," the supernatant fraction obtained from *E. coli* JM109/pKSN657F is referred to as "*E. coli* pKSN657F extract," and the supernatant fraction obtained from *E. coli* JM109/pKSN2 is referred to as "*E. coli* pKSN2 extract"). A microliter (1 µl) of the above supernatant fractions was analyzed on a 15% to 25% SDS-PAGE and stained with Coomasie Blue (hereinafter referred to as "CBB"). As a result, notably more intense bands were detected in both *E. coli* pKSN657 extract and *E. coli* pKSN657F extract than the *E. coli* pKSN2 extract, at the electrophoresis locations corresponding to the molecular weight of 47 kDa. A more intense band was detected in *E. coli* pKSN657F extract than *E. coli* pKSN657 extract. It was shown that *E. coli* JM109/pKSN657F expressed the present invention protein (A1) to a higher degree than *E. coli* JM109/pKSN657.

(3) Detection of the Ability to Convert Compound (II) to Compound (III)

Reaction solutions of 30 µl were prepared and maintained for 1 hour at 30° C. The reaction solutions consisted of a 0.1M potassium phosphate buffer (pH7.0) containing 3 ppm of compound (II) labeled with $^{14}C$, 2 mM of β-NADPH (hereinafter, referred to as "component A") (Oriental Yeast Company), 0.2 mg/ml of a ferredoxin derived from spinach (hereinafter referred to as "component B") (Sigma Company), 1 U/ml of ferredoxin reductase (hereinafter, referred to as "component C") (Sigma Company) and 18 µl of the supernatant fraction recovered in Example 4(2). Further, there were prepared and maintained similarly reaction solutions having no addition of at least one component utilized in the composition of the above reaction solution, selected from component A, component B and component C. Three microliters (3 µl) of 2N HCl and 90 µl of ethyl acetate were added and stirred into each of the reaction solutions after the maintenance. The resulting reaction solutions were centrifuged at 8,000×g to recover 75 µl of the ethyl acetate layer. After drying the ethyl acetate layers under reduced pressure, the residue was dissolved in 6.0 µl of ethyl acetate. Five microliters (5.0 µl) thereof was spotted to a TLC plate (TLC plate silica gel $60F_{254}$ 20 cm×20 cm, 0.25 thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with 14C were examined (Rf value 0.24 and 0.29). The results are shown in Table 6.

TABLE 6

| | Reaction components | | | | |
|---|---|---|---|---|---|
| component A | component B | component C | *E. coli* extract | compound (II) labeled with 14C | spot of compound (III) |
| | | | pKSN2 | | |
| | | | pKSN657 | | |
| | | | pKSN657 | | |
| | | | pKSN657 | | |
| | | | pKSN657 | | |
| | | | pKSN657F | | |
| | | | pKSN657F | | |
| | | | pKSN657F | | |
| | | | pKSN657F | | |

Example 5

Preparation of the Present Invention Protein (A2)

(1) Preparation of the Crude Cell Extract

A frozen stock of *Saccharopolyspora taberi* JCM 9383t was added to 10 ml of A medium (0.1% (w/v) glucose, 0.5% (w/v) tryptone, 0.5% (w/v) yeast extract, 0.1% (w/v) of dipotassium hydrogenphosphate, pH7.0) in a 10 ml test tube and incubated with shaking at 30° C. for 1 day to obtain a pre-culture. Eight milliliters (8 ml) of the pre-culture was added to 200 ml of A medium and was revolve cultured in 500 ml a baffled flask at 30° C. for 2 days. Cell pellets were recovered by centrifuging (3,000×g, 10 min.) 10 L of the resulting culture. These cell pellets were suspended in 100 ml of B medium (1% (w/v) glucose, 0.1% beef extract, 0.2% (w/v) tryptose) containing compound (II) at 100 ppm and were incubated with reciprocal shaking in a 500 ml Sakaguchi flask for 20 hours at 30° C. Cell pellets were recovered by centrifuging (3,000×g, 10 min.) 10 L of the resulting culture. The resulting cell pellets were washed twice with 1 L of 0.1M potassium phosphate buffer (pH7.0) to provide 119 g of the cell pellets.

These cell pellets were suspended in 0.1M potassium phosphate buffer (pH7.0) at 2 ml for 1 g of the cell pellets. A millimolar of (1 mM) PMSF, 5 mM of benzamidine HCl, 1 mM of EDTA, 3 µg/ml of leupeptin, 3 µg/ml of pepstatin and 1 mM of dithiotritol were added. A cell lysate solution was obtained by disrupting twice repetitively the suspension with a French press (1000 kg/cm$^2$) (Ohtake Seisakusho). After centrifuging the cell lysate solution (40,000×g, 30 minutes), the supernatant was recovered and centrifuged for 1 hour at 150,000×g to recover the supernatant (hereinafter referred to as the "crude cell extract").

(2) Determination of the Ability of Converting Compound (II) to Compound (III)

There was prepared 30 µl of a reaction solution of 0.1M potassium phosphate buffer (pH7.0) containing 3 ppm of compound (II) labeled with $^{14}$C, 2.4 mM of β-NADPH (hereinafter, referred to as "component A") (Oriental Yeast Company), 0.5 mg/ml of a ferredoxin derived from spinach (hereinafter referred to as "component B") (Sigma Company), 1 U/ml of ferredoxin reductase (hereinafter, referred to as "component C") (Sigma Company) and 18 µl of the crude cell extract recovered in Example 5(1). The reaction solution was maintained at 30° C. for a hour. Further, there was prepared and maintained similarly a reaction solution having no addition of at least one component utilized in the composition of the above reaction solution, selected from component A, component B and component C. Three microliters (3 µl) of 2N HCl and 90 µl of ethyl acetate were added and mixed into each of the reaction solutions after the maintenance. The resulting reaction solutions were centrifuged at 8,000×g to recover 75 µl of the ethyl acetate layer. After drying the ethyl acetate layers under reduced pressure, the residue was dissolved in 6.0 µl of ethyl acetate. Five microliters (5.0 µl) thereof was spotted to a TLC plate (TLC plate silica gel 60F$_{254}$ 20 cm×20 cm, 0.25 thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}$C were examined (Rf value 0.24 and 0.29). The results are shown in Table 7.

HP column (Amersham Pharmacia Company). Next, after flowing 100 ml of 20 mM bistrispropane buffer (pH7.0) into the column, 20 mM bistrispropane buffer was flown with a linear gradient of NaCl (gradient of NaCl was 0.004M/minute, range of NaCl concentration was from 0M to 0.5M, flow rate was 8 ml/minute) to fraction recover 30 ml of fractions eluting at the NaCl concentration of from 0.25M to 0.26M. Further, the recovered fractions were subjected to a PD10 column (Amersham Pharmacia Biotech Company) and eluted with 20 mM bistrispropane buffer (pH7.0) to recover the fractions containing protein.

The recovered fractions were subjected to a PD10 column (Amersham Pharmacia Biotech Company) with the elution with Buffer A (2 mM potassium phosphate buffer containing 1.5 mM of NaCl, pH 7.0), in order to recover the fractions containing protein. Next, the fractions were injected into a Bio-Scale Ceramic Hydroxyapatite Type I column CHT10-I (BioRad Company). Twenty milliliters (20 ml) of Buffer A was flown into the column. Subsequently, Buffer A was flown with a linear gradient of Buffer B (100 mM potassium phosphate buffer containing 0.03 mM of NaCl; the linear gradient started at 100% Buffer A to increase to 50% Buffer B over a 100 minute period, flow rate was 2 ml/minute) to fraction recover 10 ml of fractions eluting at a Buffer B concentration of from 23% to 25%. Further, the recovered fractions were subjected to a PD10 column (Amersham Pharmacia Biotech Company) and eluted with 0.05M potassium phosphate buffer (pH7.0) to recover the fractions containing protein.

The recovered fractions were concentrated to about 770 µl using an ultrafilter membrane (Microcon YM-30, Millipore Company) and injected into a HiLoad 16/60 Superdex 75 pg column (Amersham Pharmacia Biotech Company). Fifty millimolar (50 mM) potassium phosphate buffer containing 0.15M of NaCl (pH7.0) was flown (flow rate 1 ml/minute) into the column. The elution was fractioned at 2 ml each. The fractions eluting at the elution volumes of more or less 61 ml were each fraction recovered. The protein contained in each of the fractions was analyzed with a 10%-20% SDS-PAGE.

TABLE 7

| | | Reaction components | | | |
|---|---|---|---|---|---|
| component A | component B | component C | crude cell extract | compound (II) labeled with 14C | spot of compound (III) |

(3) Fractionation of the Crude Cell Extract

Ammonium sulfate was added to the crude cell extract obtained in Example 5(1) to amount to 45% saturation. After stirring in ice-cooled conditions, the supernatant was recovered by centrifuging for 10 minutes at 12,000×g. After adding ammonium sulfate to the obtained supernatant to amount to 55% saturation and stirring in ice-cooled conditions, a pellet was recovered by centrifuging for 10 minutes at 12,000×g. The pellet was dissolved with 32.5 ml of 20 mM bistrispropane buffer (pH7.0). This solution was subjected to a PD 10 column (Amersham Pharmacia Company) and eluted with 20 mM of bistrispropane buffer (pH7.0) to recover 45.5 ml of fractions containing proteins (hereinafter referred to as the "45-55% ammonium sulfate fraction").

(4) Isolation of the Present Invention Protein (A2)

The 45-55% ammonium sulfate fraction prepared in Example 5(3) was injected into a HiLoad26/10 Q Sepharose Instead of the crude cell extract in the reaction solution described in Example 5(2), the recovered fractions were added and maintained in the presence of component A, component B, component C and compound (II) labeled with $^{14}$C, similarly to Example 5(2). The reaction solutions after the maintenance were TLC analyzed to examine the intensity of the spots corresponding to compound (III) labeled with $^{14}$C. The protein moving to the position to 47 kDa in the above SDS-PAGE was observed to have its fluctuations in the concentrations of the bands of the fractions added in turn to be parallel with the fluctuations of the intensity of the spots corresponding to compound (III). Said protein was recovered from the SDS-PAGE gel and was subjected to an amino acid sequence analysis with a protein sequencer (Applied Biosystems Company, Procise 494HT, pulsed liquid method) to sequence the N terminus amino acid sequence. As a result, the amino acid sequence shown in SEQ ID NO: 20 was provided.

Further, after digesting the above protein with trypsin, the obtained digestion material was analyzed on a mass spectrometer (ThermoQuest Company, Ion Trap Mass Spectrometer LCQ, column: LC Packings Company PepMap C18 75 μm×150 mm, solvent A: 0.1% HOAc—H$_2$O, solvent B: 0.1% HOAc-methanol, gradient: a linear gradient starting at an elution with a mixture of 95% of solvent A and 5% of solvent B and increasing to a concentration of 100% of solvent B over 30 minutes, flow rate: 0.2 μl/minute). As a result, the sequence shown in SEQ ID NO: 21 was provided.

Example 6

Obtaining the Present Invention DNA (A2)

(1) Preparation of the Chromosomal DNA of *Saccharopolyspora Taberi* JCM 9383t

*Saccharopolyspora taberi* JCM 9383t was shake cultured at 30° C. for 1 day to 3 days in 50 ml of YEME medium (0.3% (w/v) yeast extract, 0.5% (w/v) bacto-peptone, 0.3% (w/v) malt extract, 1.0% (w/v) glucose, 34% (w/v) sucrose and 0.2% (v/v) 2.5M MgCl$_2$ 6H$_2$O). The cells were recovered. The obtained cells were suspended in YEME medium containing 1.4% (w/v) glycine and 60 mM EDTA and further incubated with shaking for a day. The cells were recovered from the culture medium. After washing once with distilled water, it was resuspended in buffer (100 mM Tris-HCl (pH8.0), 100 mM EDTA, 10 mM NaCl) at 1 ml per 200 mg of the cell pellets. Two hundred micrograms per milliliter (200 μg/ml) of egg-white lysozyme were added. The cell suspension was shaken at 30° C. for a hour. Further, 0.5% of SDS and 1 mg/ml of Proteinase K was added. The cell suspension was incubated at 55° C. for 3 hours. The cell suspension was extracted twice with phenol chloroform isoamyl alcohol to recover each of the aqueous layers. Next, there was one extraction with chloroform isoamyl alcohol to recover the aqueous layer. The chromosomal DNA was obtained by ethanol precipitating the aqueous layer.

(2) Preparation of the Chromosomal DNA Library of *Saccharopolyspora Taberi* JCM 9383t Nineteen micrograms (19 μg) of the chromosomal DNA prepared in Example 5(1) were digested with 0.78 U of restriction enzyme Sau3AI at 37° C. for 60 minutes. The obtained digestion solution was separated with 1% agarose gel electrophoresis. The DNA of about 2.0 kbp was recovered from the gel. The DNA was purified with QIAquick Gel Extraction Kit (Qiagen Company) according to the instructions attached to said kit and was concentrated with an ethanol precipitation to obtain 10 μl of the solution containing the target DNA. Eight microliters (8 μl) of the DNA solution, 100 ng of plasmid vector pUC118 digested with restriction enzyme BamHI and treated with dephosphorylation and 12 μl of the I solution from Ligation Kit Ver. 2 (Takara Shuzo Company) were mixed and maintained for 3 hours at 16° C. *E. coli* DH5α was transformed with the ligation solution. The *E. coli* transformants were cultured overnight at 37° C. in LB agar medium containing 50 mg/l of ampicillin. The obtained colonies were recovered from an agar medium. The plasmids were extracted and were designated as the chromosomal DNA library.

(3) Isolation of the Present Invention DNA (A2)

Figure 2:
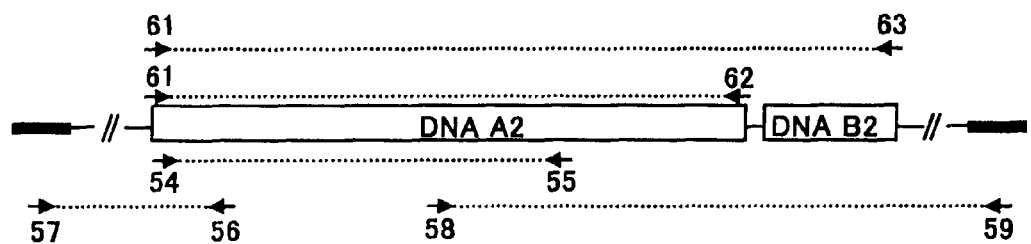
FIG. 2 shows the annealing site of the PCR primers utilized to obtain the present invention DNA (A2) and the present invention DNA (B2). Each of the numbers refers to the SEQ ID number showing the nucleotide sequence of the primers. The arrows show the annealing sites of the oligonucleotide primers having the nucleotide sequence shown with the SEQ ID number thereof and the extention direction of the DNA polymerase reaction from the primers. The dotted lines represent the DNA amplified by the PCR utilizing the primers. The thick line represents the region adjacent to the DNA insertion site of the vector utilized to produce the chromosomal DNA library.
Figure 3:
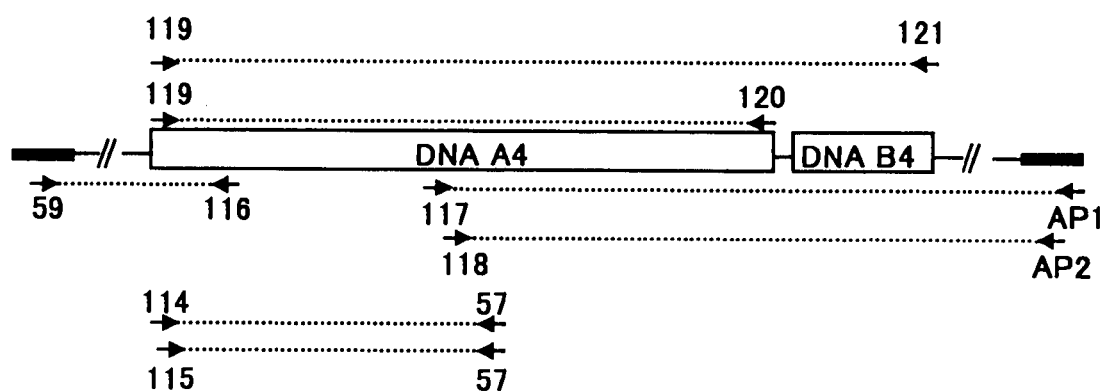
FIG. 3 shows the annealing site of the PCR primers utilized to obtain the present invention DNA (A4) and the present invention DNA (B4). Each of the numbers refers to the SEQ ID number showing the nucleotide sequence of the primers.

PCR was conducted by utilizing the chromosomal DNA prepared in Example 6(1) as the template with Expand HiFi PCR System (Boehringer Manheim Company) (FIG. 2). As the primers, there was utilized the pairing of an oligonucleotide having the nucleotide sequence shown in SEQ ID NO: 54 and an oligonucleotide having the nucleotide sequence shown in SEQ ID NO: 55 (hereinafter referred to as "primer paring 6"). The nucleotide sequence shown in SEQ ID NO: 54 was designed based on a nucleotide sequence encoding the N terminus amino acid sequence shown in SEQ ID NO: 20. Further, the nucleotide sequence shown in SEQ ID NO: 55 was designed based on a nucleotide sequence complimentary to the nucleotide sequence encoding the inner amino acid sequence shown in SEQ ID NO: 21. The PCR reaction solution amounted to 25 μl by adding 300 ng of the above chromosomal DNA, the 2 primers each amounting to 7.5 pmol, 0.2 μl of dNTP mix (a mixture of 2 mM of each of the 4 types of dNTP), 2.5 μl of 10× buffer (containing MgCl$_2$), 0.19 μl of Expand HiFi enzyme mix and distilled water. The reaction conditions of the PCR were after maintaining 97° C. for 2 minutes, repeating 10 cycles of a cycle that included maintaining 97° C. for 15 seconds, followed by 65° C. for 30 seconds and followed by 72° C. for 1 minute; then conducting 15 cycles of a cycle that included maintaining 97° C. for 15 seconds, followed by 65° C. for 30 seconds and followed by 72° C. for 1 minute (wherein 20 seconds was added to the maintenance at 72° C. for each cycle); and then maintaining 72° C. for 7 minutes. After the maintenance, the reaction solution was subjected to 2% agarose gel electrophoresis. The gel area containing the DNA of about 800 bp was recovered. The DNA was purified from the recovered gel by utilizing Qiagen quick gel extraction kit (Qiagen Company) according to the attached instructions. The obtained DNA was ligated to the TA cloning vector pCRII-TOPO (Invitrogen Company) according to the instructions attached to said vector and was introduced into *E. Coli* TOP10F'. The plasmid DNA was prepared from the obtained *E. coli* transformant, utilizing Qiagen Tip20 (Qiagen Company). A sequencing reaction was conducted with Dye terminator cycle sequencing FS ready reaction kit (Applied Biosystems Japan Company) according to the instructions attached to said kit, utilizing as primers the −21M13 primer (Applied Biosystems Japan Company) and M13Rev primer (Applied Biosystems Japan Company). The reaction products were analyzed with a DNA sequencer 373A (Applied Biosystems Japan Company). As a result, the nucleotide sequence shown in nucleotides 36 to 819 of the nucleotide sequence shown in SEQ ID NO: 10 was provided. Nucleotides 37-60 of the nucleotide sequence shown in SEQ ID NO: 10 encoded a part of the amino acid sequence shown in SEQ ID NO: 20. In this regard, it was expected that that said DNA encoded a part of the present invention protein (A2).

Next, PCR was conducted by utilizing the chromosomal DNA prepared in Example 6(2) as the template and similar to the above with Expand HiFi PCR system. There was utilized as primers, a pairing of an oligonucleotide having the nucleotide sequence shown in SEQ ID NO: 56 with an oligonucleotide having the nucleotide sequence shown in SEQ ID NO: 57 (hereinafter referred to as the "primer pairing 7"). By conducting the PCR with such primers, there was amplified a DNA having a nucleotide sequence in which the 5' terminus elongates past the nucleotide shown as nucleotide 36 of the nucleotide sequence shown in SEQ ID NO: 10. Further, there was utilized as primers, a pairing of an oligonucleotide having the nucleotide sequence shown in SEQ ID NO: 58 with an oligonucleotide having the nucleotide sequence shown in SEQ ID NO: 59 (hereinafter referred to as the "primer pairing 8"). By conducting the PCR with such primers, there was amplified a DNA having a nucleotide sequence in which the 3' terminus elongates past the nucleotide shown as nucleotide 819 of the nucleotide sequence shown in SEQ ID NO: 10. Each of the 1.3 kb DNA amplified with the use of primer pairing 7 and the 0.4 kb DNA amplified with the use of primer pairing 8 was cloned into TA cloning vector pCRII-TOPO.

Plasmid DNA was prepared from the obtained E. coli transformant, utilizing Qiagen Tip 20 (Qiagen Company). A sequencing reaction was conducted with Dye terminator cycle sequencing FS ready reaction kit (Applied Biosystems Japan Company) according to the instructions attached to said kit, utilizing as primers the −21M13 primer (Applied Biosystems Japan Company), M13Rev primer (Applied Biosystems Japan Company) and the oligonucleotide shown in SEQ ID NO: 60. The reaction products were analyzed with a DNA sequencer 373A (Applied Biosystems Japan Company). As a result of sequencing the nucleotide sequence of the 1.3 kb DNA amplified by utilizing primer pairing 7, the nucleotide sequence shown in nucleotides 1 to 35 of the nucleotide sequence shown in SEQ ID NO: 10 was provided. Further, as a result of sequencing the nucleotide sequence of the 0.4 kb DNA amplified by utilizing primer pairing 8, the nucleotide sequence shown in nucleotides 819 to 1415 of the nucleotide sequence shown in SEQ ID NO: 10 was provided. As a result of connecting the obtained nucleotide sequences, the nucleotide sequence shown in SEQ ID NO: 10 was obtained. Two open reading frames (ORF) were present in said nucleotide sequence. As such, there was contained a nucleotide sequence (SEQ ID NO: 7) consisting of 1206 nucleotides (inclusive of the stop codon) and encoding a 401 amino acid residue as well as a nucleotide sequence (SEQ ID NO: 16) consisting of 198 nucleotides (inclusive of the stop codon) and encoding a 65 amino acid residue. The molecular weight of the protein consisting of the amino acid sequence (SEQ ID NO: 2) encoded by the nucleotide sequence shown in SEQ ID NO: 7 was calculated to be 43983 Da. Further, the amino acid sequence encoded by said nucleotide sequence contained the amino acid sequence (SEQ ID NO: 20) determined from the amino acid sequencing of from the N terminus of the present invention protein (A2) and the amino acid sequence (SEQ ID NO: 21) determined from the amino acid sequencing of the mass spectrometer analysis with the trypsin digestion fragments. The molecular weight of the protein consisting of the amino acid sequence (SEQ ID NO: 13) encoded by the nucleotide sequence shown in SEQ ID NO: 16 was calculated be 6707 Da.

Example 7

Expression of the Present Invention Protein (A2) in E. coli (1) Production of a Transformed E. Coli Having the Present Invention Protein (A2)

PCR was conducted by utilizing as a template the chromosomal DNA prepared from Saccharopolyspora taberi JCM 9383t in Example 6(1) and by utilizing Expand HiFi PCR System (Boehringer Manheim Company). As the primers, there was utilized the pairing of an oligonucleotide having the nucleotide sequence shown in SEQ ID NO: 61 and an oligonucleotide having the nucleotide sequence shown in SEQ ID NO: 62 (hereinafter referred to as "primer pairing 21") or a pairing of an oligonucleotide having the nucleotide sequence shown in SEQ ID NO: 61 and an oligonucleotide having the nucleotide sequence shown in SEQ ID NO: 63 (hereinafter referred to as "primer pairing 22"). The PCR reaction solution amounted to 50 µl by adding the 2 primers each amounting to 300 nM, 50 ng of the above chromosomal DNA, 5.0 µl of dNTP mix (a mixture of 2.0 mM of each of the 4 types of dNTP), 5.0 µl of 10× Expand HF buffer (containing MgCl2) and 0.75 µl of Expand HiFi enzyme mix and distilled water. The reaction conditions of the PCR were after maintaining 97° C. for 2 minutes; repeating 10 cycles of a cycle that included maintaining 97° C. for 15 seconds, followed by 60° C. for 30 seconds and followed by 72° C. for 1 minute; then conducting 15 cycles of a cycle that included maintaining 97° C. for 15 seconds, followed by 60° C. for 30 seconds and followed by 72° C. for 1 minute (wherein 20 seconds was added to the maintenance at 72° C. for each cycle); and then maintaining 72° C. for 7 minutes. After the maintenance, the reaction solution was subjected to 1% agarose gel electrophoresis. The gel area containing the DNA of about 1.2 kbp was recovered from the gel which was subjected the reaction solution utilizing primer pairing 21. The gel area containing the DNA of about 1.4 kbp was recovered from the gel which was subjected the reaction solution utilizing primer pairing 22. The DNA were purified from each of the recovered gels by utilizing Qiagen quick gel extraction kit (Qiagen Company) according to the attached instructions. The obtained DNA were ligated to the cloning vector pCRII-TOPO (Invitrogen Company) according to the instructions attached to said vector and were introduced into E. Coli TOP10F'. The plasmid DNA were prepared from the obtained E. coli transformants, utilizing Qiagen Tip20 (Qiagen Company). Next, sequencing reactions were conducted with Dye terminator cycle sequencing FS ready reaction kit (Applied Biosystems Japan Company) according to the instructions attached to said kit, utilizing as primers the −21M13 primer (Applied Biosystems Japan Company), M13Rev primer (Applied Biosystems Japan Company), the oligonucleotide having the nucleotide sequence shown in SEQ ID NO: 56 and the oligonucleotide having the nucleotide sequence shown in SEQ ID NO: 64. The reaction products were analyzed with a DNA sequencer 373A (Applied Biosystems Japan Company). Based on the results, the plasmid having the nucleotide sequence shown in SEQ ID NO: 7 was designated as pCR923 and the plasmid having the nucleotide sequence shown in SEQ ID NO: 10 was designated as pCR923F.

Next, each of plasmids pCR923 and pCR923F was digested with restriction enzymes NdeI and HindIII. The digestion products were subjected to agarose gel electrophoresis. The gel area containing a DNA of about 1.2 kbp was cut from the gel subjected to the digestion products of pCR923. The gel area containing a DNA of about 1.4 kbp was cut from the gel subjected to the digestion products of pCR923F. The DNA were purified from each of the recovered gels by utilizing Qiagen quick gel extraction kit (Qiagen Company) according to the attached instructions. Each of the obtained DNA and the plasmid pKSN2 digested with NdeI and HindIII were ligated with ligation kit Ver. 1 (Takara Shuzo Company) according to the instructions attached to said kit and introduced into E. Coli JM109. The plasmid DNA were prepared from the obtained E. coli transformants. The structures thereof were analyzed. The plasmid containing the nucleotide sequence shown in SEQ ID NO: 7, in which the DNA of about 1.2 kbp encoding the present invention protein (A2) is inserted between the NdeI site and the HindIII site of pKSN2 was designated as pKSN923. Further, the plasmid containing the nucleotide sequence shown in SEQ ID NO: 10, in which the DNA of about 1.4 kbp encoding the present invention protein (A2) is inserted between the NdeI site and the HindIII site of pKSN2 was designated as pKSN923F. Each of the above plasmids of pKSN923 and pKSN923F was introduced into E. coli JM109. The obtained E. coli transformants were designated, respectively, JM109/pKSN923 and JM109/pKSN923F. Further, plasmid pKSN2 was introduced into E. coli JM109. The obtained E. coli transformant was designated as JM109/pKSN2.

(2) Expression of the Present Invention Protein (A2) in *E. Coli* and Recovery of Said Protein

*E. coli* JM109/pKSN657, JM109/pKSN657F and JM109/pKSN2 were each cultured overnight at 37° C. in 10 ml of TB medium (1.2% (w/v) tryptone, 2.4% (w/v) yeast extract, 0.4% (w/v) glycerol, 17 mM potassium dihydrogenphosphate, 72 mM dipotassium hydrogenphosphate) containing 50 μg/ml of ampicillin. A milliliter (1 ml) of the obtained culture medium was transferred to 100 ml of TB medium containing 50 μg/ml of ampicillin and cultured at 26° C. When OD660 reached about 0.5, 5-aminolevulinic acid was added to the final concentration of 500 μM, and the culturing was continued. Thirty (30) minutes thereafter, IPTG was added to a final concentration of 1 mM, and there was further culturing for 17 hours.

The cells were recovered from each of the culture mediums, washed with 0.1M tris-HCl buffer (pH7.5) and suspended in 10 ml of said buffer containing 1 mM PMSF. The obtained cell suspensions were subjected 6 times to a sonicator (Sonifier (Branson Sonic Power Company)) at 3 minutes each under the conditions of output 3, duty cycle 30%, in order to obtain cell lysate solutions. After centrifuging the cell lysate solutions (1,200×g, 5 minutes) the supernatants were recovered and centrifuged (150,000×g, 70 minutes) to recover supernatant fractions (hereinafter, the supernatant fraction obtained from *E. coli* JM109/pKSN923 is referred to as "*E. coli* pKSN923 extract," the supernatant fraction obtained from *E. coli* JM109/pKSN923F is referred to as "*E. coli* pKSN923F extract," and the supernatant fraction obtained from *E. coli* JM109/pKSN2 is referred to as "*E. coli* pKSN2 extract"). A microliter (1 μl) of the above supernatant fractions was analyzed on a 15% to 25% SDS-PAGE and stained with CBB. As a result, notably more intense bands were detected in both *E. coli* pKSN923 extract and *E. coli* pKSN923F extract than the *E. coli* pKSN2 extract, at the electrophoresis locations corresponding to the molecular weight of 47 kDa. It was confirmed that *E. coli* JM109/pKSN923 and *E. coli* JM109/pKSN923F expressed the present invention protein (A2).

(3) Detection of the Ability to Convert Compound (II) to Compound (III)

Reaction solutions of 30 μl were prepared and maintained for 10 minutes at 30° C. The reaction solutions consisted of a 0.1M potassium phosphate buffer (pH7.0) containing 3 ppm of compound (II) labeled with $^{14}C$, 2 mM of β-NADPH (hereinafter, referred to as "component A") (Oriental Yeast Company), 0.2 mg/ml of a ferredoxin derived from spinach (hereinafter referred to as "component B") (Sigma Company), 1 U/ml of ferredoxin reductase (hereinafter, referred to as "component C") (Sigma Company) and 18 μl of the supernatant fraction recovered in Example 7(2). Further, there were prepared and maintained similarly reaction solutions having no addition of at least one component utilized in the composition of the above reaction solution, selected from component A, component B and component C. Three microliters (3 μl) of 2N HCl and 90 μl of ethyl acetate were added and mixed into each of the reaction solutions after the maintenance. The resulting reaction solutions were centrifuged at 8,000×g to recover 75 μl of the ethyl acetate layer. After drying the ethyl acetate layers under reduced pressure, the residue was dissolved in 6.0 μl of ethyl acetate. Five microliters (5.0 μl) thereof was spotted to a silica gel TLC plate (TLC plate silica gel 60F$_{254}$, 20 cm×20 cm, 0.25 mm thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}C$ were examined (Rf value 0.24 and 0.29). The results are shown in Table 8.

TABLE 8

| | Reaction components | | | compound (II) labeled with 14C | spot of compound (III) |
|---|---|---|---|---|---|
| component A | component B | component C | *E. coli* extract | | |
| | | | pKSN2 | | |
| | | | pKSN923 | | |
| | | | pKSN923 | | |
| | | | pKSN923 | | |
| | | | pKSN923 | | |
| | | | pKSN923F | | |
| | | | pKSN923F | | |
| | | | pKSN923F | | |
| | | | pKSN923F | | |

Example 8

Preparation of the Present Protein (A10)

(1) Preparation of the Crude Cell Extract

A frozen stock of *Streptomyces griseolus* ATCC 11796 was added to 250 ml of B medium (1% (w/v) glucose, 0.1% (w/v) meat extract, 0.2% (w/v) tryptose) in a 500 ml baffled flask and incubated with rotary shaking at 30° C. for 3 days to obtain a pre-culture. Forty milliliters (40 ml) of the pre-culture was added to 400 ml of B medium and was incubated with rotary shaking in a 1 L triangular flask at 30° C. for 24 hours. After stopping the culturing, the culture was allowed to settle. Two hundred and twenty milliliters (220 ml) of only the supernatant was removed. Two hundred and twenty milliliters (220 ml) of fresh medium similarly prepared was added to the remaining 220 ml of the culture medium to amount to 440 ml. Compound (II) was added thereto to amount to 100 ppm. The cells were incubated with rotary shaking in the 1 L triangular flask at 30° C. for 40 hours. Cell pellets were recovered by centrifuging (3,000 g, 5 min.) 2.6 L of the resulting culture. The resulting cell pellets were washed with 1 L of 0.1M PIPES-NaOH buffer (pH6.8) to provide 26 g of the cell pellets.

These cell pellets were suspended of 0.1M PIPES-NaOH buffer (pH6.8) at 3 ml for 1 g of the cell pellets, and 1 mM of PMSF, 5 mM of benzamidine HCl, 1 mM of EDTA, 3 μg/ml of leupeptin, 3 μg/ml of pepstatin A and 1 mM of dithiotritol were added. A cell lysate solution was obtained by disrupting twice repetitively the suspension with a French press (1000 kg/cm$_2$) (Ohtake Seisakusho). After centrifuging the cell lysate solution (40,000×g, 30 minutes), the supernatant was recovered and centrifuged for 1 hour at 150,000×g to recover the supernatant (hereinafter referred to as the "crude cell extract").

(2) Determination of the Ability of Converting Compound (II) to Compound (III)

There was prepared 30 μl of a reaction solution of 0.1M potassium phosphate buffer (pH7.0) containing 3 ppm of compound (II) labeled with $^{14}$C, 2.4 mM of β-NADPH (hereinafter, referred to as "component A") (Oriental Yeast Company), 0.5 mg/ml of a ferredoxin derived from spinach (hereinafter referred to as "component B") (Sigma Company), 1 U/ml of ferredoxin reductase (hereinafter, referred to as "component C") (Sigma Company) and 18 μl of the crude cell extract recovered in Example 8(1). The reaction solution was maintained at 30° C. for a hour. Further, there was prepared and maintained similarly a reaction solution having no addition of at least one component utilized in the composition of the above reaction solution, selected from component A, component B and component C. Three microliters (3 μl) of 2N HCl and 90 μl of ethyl acetate were added and stirred into each of the reaction solutions after the maintenance. The resulting reaction solutions were centrifuged at 8,000×g to recover 75 μl of the ethyl acetate layer. After drying the ethyl acetate layers under reduced pressure, the residue was dissolved in 6.0 μl of ethyl acetate. Five microliters (5.0 μl) thereof was spotted to a silica gel TLC plate (TLC plate silica gel 60F$_{254}$, 20 cm×20 cm, 0.25 thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}$C were examined (Rf value 0.24 and 0.29). The results are shown in Table 9.

(Amersham Pharmacia Company). Next, after flowing 16 ml of 20 mM bistrispropane buffer (pH7.0) into the column, 20 mM bistrispropane buffer was flown with a linear gradient of NaCl (gradient of NaCl was 0.00625M/minute, range of NaCl concentration was from 0M to 0.5M, flow rate was 4 ml/minute) to fraction recover 15 ml of fractions eluting at the NaCl concentration of from 0.28M to 0.31M. Further, the recovered fractions were subjected to a PD10 column (Amersham Pharmacia Biotech Company) and eluted with 20 mM bistrispropane buffer (pH7.0) to recover the fractions containing protein.

The recovered fractions were subjected to a PD10 column (Amersham Pharmacia Biotech Company) with the elution with Buffer A (2 mM potassium phosphate buffer containing 1.5 mM of NaCl, pH 7.0), in order to recover the fractions containing protein. Next, the fractions were injected into a Bio-Scale Ceramic Hydroxyapatite Type I column CHT10-I (BioRad Company). Fifty milliliters (50 ml) of Buffer A was flown into the column. Subsequently, Buffer A was flown with a linear gradient of Buffer B (100 mM potassium phosphate buffer containing 0.03 mM of NaCl; the linear gradient started at 100% Buffer A to increase to 50% Buffer B over a 40 minute period, flow rate was 5 ml/minute) to fraction recover the fractions eluting at a Buffer B concentration of from 16% to 31%. Further, the recovered fractions were subjected to a PD10 column (Amersham Pharmacia Biotech Company) and eluted with 0.05M potassium phosphate buffer (pH7.0) to recover the fractions containing protein. The protein contained in each of the fractions were analyzed on a 10%-20% SDS-PAGE.

Instead of the crude cell extract in the reaction solution described in Example 8(2), the recovered fractions were added and maintained in the presence of component A, component B, component C and compound (II) labeled with $^{14}$C, similarly to Example 8(2). The reaction solutions after the maintenance were TLC analyzed to examine the intensity of the spots corresponding to compound (III) labeled with $^{14}$C.

TABLE 9

| Reaction components | | | | | |
|---|---|---|---|---|---|
| component A | component B | component C | crude cell extract | compound (II) labeled with 14C | spot of compound (III) |

(3) Fractionation of the Crude Cell Extract

Ammonium sulfate was added to the crude cell extract obtained in Example 8(1) to amount to 45% saturation. After stirring in ice-cooled conditions, the supernatant was recovered by centrifuging for 10 minutes at 12,000×g. After adding ammonium sulfate to the obtained supernatant to amount to 55% saturation and stirring in ice-cooled conditions, a pellet was recovered by centrifuging for 10 minutes at 12,000×g. The pellet was dissolved with 20 mM bistrispropane buffer (pH7.0) to amount to 10 ml. This solution was subjected to a PD10 column (Amersham Pharmacia Company) and eluted with 20 mM of bistrispropane buffer (pH7.0) to recover 14 ml of fractions containing proteins (hereinafter referred to as the "45-55% ammonium sulfate fraction").

(4) Isolation of the Present Protein (A10)

The 45-55% ammonium sulfate fraction prepared in Example 8(3) was injected into a MonoQ HR 10/10 column The protein moving to the position to 47 kDa in the above SDS-PAGE was observed to have its fluctuations in the concentrations of the bands of the fractions added in turn to be parallel with the fluctuations of the intensity of the spots corresponding to compound (III). Said protein was recovered from the SDS-PAGE gel and digested with trypsin. The obtained digestion material was analyzed on a mass spectrometer (ThermoQuest Company, Ion Trap Mass Spectrometer LCQ, column: LC Packings Company PepMap C18 75 μm×150 mm, solvent A: 0.1% HOAc—H2O, solvent B: 0.1% HOAc-methanol, gradient: a linear gradient starting at an elution with a mixture of 95% of solvent A and 5% of solvent B and increasing to a concentration of 100% of solvent B over 30 minutes, flow rate: 0.2 μl/minute). As a result, the amino acid sequences shown in each and any one of SEQ ID NO: 22-34 were provided.

Example 9

Preparation of the Chromosomal DNA of *Streptomyces* Griseolus ATCC 11796

*Streptomyces griseolus* ATCC 11796 was incubated with shaking at 30° C. for 1 day to 3 days in 50 ml of YEME medium (0.3% (w/v) yeast extract, 0.5% (w/v) bacto-peptone, 0.3% (w/v) malt extract, 1.0% (w/v) glucose, 34% (w/v) sucrose and 0.2% (v/v) 2.5M $MgCl_2$ $6H_2O$). The cells were recovered. The obtained cells were suspended in YEME medium containing 1.4% (w/v) glycine and 60 mM EDTA and further incubated with shaking for a day. The cells were recovered from the culture medium. After washing once with distilled water, it was resuspended in buffer (100 mM Tris-HCl (pH8.0), 100 mM EDTA, 10 mM NaCl) at 1 ml per 200 mg of the cells. Two hundred micrograms per milliliter (200 µg/ml) of egg-white lysozyme were added. The cell suspension was shaken at 30° C. for a hour. Further, 0.5% of SDS and 1 mg/ml of Proteinase K was added. The cell suspension was incubated at 55° C. for 3 hours. The cell suspension was extracted twice with phenol chloroform isoamyl alcohol to recover each of the aqueous layers. Next, there was one extraction with chloroform isoamyl alcohol to recover the aqueous layer. The chromosomal DNA was obtained by ethanol precipitating the aqueous layer.

Example 10

Obtaining a DNA Encoding the Present DNA (A10) and Expression in *E. coli*

(1) Production of a Transformed *E. Coli* Having the Present DNA

PCR was conducted by utilizing as a template the chromosomal DNA prepared from *Streptomyces griseolus* ATCC 11796 in Example 9 and by utilizing Expand High Fidelity PCR System (Roche Molecular Biochemicals Company). As the primers, there was utilized the pairing of an oligonucleotide having the nucleotide sequence shown in SEQ ID NO: 79 and an oligonucleotide having the nucleotide sequence shown in SEQ ID NO: 80 (hereinafter referred to as "primer pairing 23") or a pairing of an oligonucleotide having the nucleotide sequence shown in SEQ ID NO: 79 and an oligonucleotide having the nucleotide sequence shown in SEQ ID NO: 81 (hereinafter referred to as "primer pairing 24"). The PCR reaction solutions amounted to 50 µl by adding the 2 primers each amounting to 300 nM, 50 ng of the above chromosomal DNA, 5.0 µl of dNTP mix (a mixture of 2.0 mM of each of the 4 types of dNTP), 5.0 µl of 10× Expand HF buffer (containing $MgCl_2$) and 0.75 µl of Expand HiFi enzyme mix and distilled water. The reaction conditions of the PCR were after maintaining 97° C. for 2 minutes; repeating 10 cycles of a cycle that included maintaining 97° C. for 15 seconds, followed by 65° C. for 30 seconds and followed by 72° C. for 2 minutes; then conducting 15 cycles of a cycle that included maintaining 97° C. for 15 seconds, followed by 68° C. for 30 seconds and followed by 72° C. for 2 minutes (wherein 20 seconds was added to the maintenance at 72° C. for each cycle); and then maintaining 72° C. for 7 minutes. After the maintenance, each of the reaction solutions was subjected to 1% agarose gel electrophoresis. The gel area containing the DNA of about 1.2 kbp was recovered from the gel which was subjected to the reaction solution utilizing primer pairing 23. The gel area containing the DNA of about 1.5 kbp was recovered from the gel which was subjected to the reaction solution utilizing primer pairing 24. The DNA were purified from each of the recovered gels by utilizing Qiagen quick gel extraction kit (Qiagen Company) according to the attached instructions. The obtained DNA were ligated to the cloning vector pCR2.1-TOPO (Invitrogen Company) according to the instructions attached to said vector and were introduced into *E. Coli* TOP10F'. The plasmid DNA were prepared from the obtained *E. coli* transformants, utilizing Qiaprep Spin Miniprep Kit (Qiagen Company). Next, sequencing reactions were conducted with Dye terminator cycle sequencing FS ready reaction kit (Applied Biosystems Japan Company) according to the instructions attached to said kit, utilizing as primers the −21M13 primer (Applied Biosystems Japan Company), M13Rev primer (Applied Biosystems Japan Company), the oligonucleotide having the nucleotide sequence shown in SEQ ID NO: 82 and the oligonucleotide having the nucleotide sequence shown in SEQ ID NO: 83. The sequencing reactions utilized the obtained plasmid DNA as the template. The reaction products were analyzed with a DNA sequencer 373A (Applied Biosystems Japan Company). Based on the results, the plasmid having the nucleotide sequence shown in SEQ ID NO: 84 was designated as pCR11796 and the plasmid having the nucleotide sequence shown in SEQ ID NO: 85 was designated as pCR11796F. Two open reading frames (ORF) were present in said nucleotide sequence shown in SEQ ID NO: 85. As such, there was contained a nucleotide sequence (SEQ ID NO: 84) consisting of 1221 nucleotides (inclusive of the stop codon) and encoding a 406 amino acid residue (the amino acid sequence shown in SEQ ID NO: 5) and a nucleotide sequence consisting of 210 nucleotides (inclusive of the stop codon) and encoding a 69 amino acid residue.

Next, each of pCR11796 and pCR11796F was digested with restriction enzymes NdeI and HindIII. The digestion products were subjected to agarose gel electrophoresis. The gel area containing a DNA of about 1.2 kbp was cut from the gel subjected to the digestion products of pCR11796. The gel area containing a DNA of about 1.5 kbp was cut from the gel subjected to the digestion products of pCR11796F. The DNA were purified from each of the recovered gels by utilizing Qiagen quick gel extraction kit (Qiagen Company) according to the attached instructions. Each of the obtained DNA and the plasmid pKSN2 digested with NdeI and HindIII were ligated with ligation kit Ver. 1 (Takara Shuzo Company) according to the instructions attached to said kit and introduced into *E. Coli* JM109. The plasmid DNA were prepared from the obtained *E. coli* transformants. The structures thereof were analyzed. The plasmid containing the nucleotide sequence shown in SEQ ID NO: 84, in which the DNA of about 1.2 kbp encoding the present protein (A10) is inserted between the NdeI site and the HindIII site of pKSN2 was designated as pKSN11796. Further, the plasmid containing the nucleotide sequence shown in SEQ ID NO: 85, in which the DNA of about 1.5 kbp encoding the present protein (A10) is inserted between the NdeI site and the HindIII site of pKSN2 was designated as pKSN11796F. Each of the above plasmids of pKSN11796 and pKSN11796F was introduced into *E. coli* JM109. The obtained *E. coli* transformants were designated, respectively, JM109/pKSN11796 and JM109/pKSN11796F. Further, plasmid pKSN2 was introduced into *E. coli* JM109. The obtained *E. coli* transformant was designated as JM109/pKSN2.

(2) Expression of the Present Protein (A10) in *E. Coli* and Recovery of Said Protein

*E. coli* JM109/pKSN11796, JM109/pKSN11796F and JM109/pKSN2 were each cultured overnight at 37° C. in 10 ml of TB medium (1.2% (w/v) tryptone, 2.4% (w/v) yeast extract, 0.4% (w/v) glycerol, 17 mM potassium dihydrogenphosphate, 72 mM dipotassium hydrogenphosphate) containing 50 µg/ml of ampicillin. A milliliter (1 ml) of the obtained culture medium was transferred to 100 ml of TB medium containing 50 µg/ml of ampicillin and cultured at 26° C. When OD660 reached about 0.5, 5-aminolevulinic acid was added to the final concentration of 500 µM, and the culturing was continued. Thirty (30) minutes thereafter, IPTG was added to a final concentration of 1 mM, and there was further culturing for 17 hours.

The cells were recovered from each of the culture mediums, washed with 0.1M tris-HCl buffer (pH7.5) and suspended in 10 ml of the above buffer containing 1 mM PMSF. The obtained cell suspensions were subjected 6 times to a sonicator (Sonifier (Branson Sonic Power Company)) at 3 minutes each under the conditions of output 3, duty cycle 30%, in order to obtain cell lysate solutions. After centrifuging the cell lysate solutions (1,200×g, 5 minutes) the supernatants were recovered and centrifuged (150,000×g, 70 minutes) to recover supernatant fractions (hereinafter, the supernatant fraction obtained from E. coli JM109/pKSN11796 is referred to as "E. coli pKSN11796 extract," the supernatant fraction obtained from E. coli JM109/pKSN11796F is referred to as "E. coli pKSN11796F extract," and the supernatant fraction obtained from E. coli JM109/pKSN2 is referred to as "E. coli pKSN2 extract"). A microliter (1 µl) of the above supernatant fractions was analyzed on a 15% to 25% SDS-PAGE and stained with Coomasie Blue (hereinafter referred to as "CBB"). As a result, notably more intense bands were identified in both E. coli pKSN11796 extract and E. coli pKSN11796F extract than the E. coli pKSN2 extract, at the electrophoresis locations corresponding to the molecular weight of 45 kDa. A more intense band was identified in E. coli pKSN11796F extract than E. coli pKSN11796 extract. It was shown that E. coli JM109/pKSN11796F expressed the present protein (A10) to a higher degree than E. coli JM109/pKSN11796.

(3) Detection of the Ability to Convert Compound (II) to Compound (III)

Reaction solutions of 30 µl were prepared and maintained for 1 hour at 30° C. The reaction solutions consisted of a 0.1M potassium phosphate buffer (pH7.0) containing 3 ppm of compound (II) labeled with $^{14}$C, 2 mM of β-NADPH (hereinafter, referred to as "component A") (Oriental Yeast Company), 2 mg/ml of a ferredoxin derived from spinach (hereinafter referred to as "component B") (Sigma Company), 0.1 U/ml of ferredoxin reductase (hereinafter, referred to as "component C") (Sigma Company) and 18 µl of the supernatant fraction recovered in Example 10(2). Further, there were prepared and maintained similarly reaction solutions having no addition of at least one component utilized in the composition of the above reaction solution, selected from component A, component B and component C. Three microliters (3 µl) of 2N HCl and 90 µl of ethyl acetate were added and mixed into each of the reaction solutions after the maintenance. The resulting reaction solutions were centrifuged at 8,000×g to recover 75 µl of the ethyl acetate layer. After drying the ethyl acetate layers under reduced pressure, the residue was dissolved in 6.0 µl of ethyl acetate. Five microliters (5.0 µl) thereof was spotted to a silica gel TLC plate (TLC plate silica gel 60F$_{254}$ 20 cm×20 cm, 0.25 mm thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}$C were examined (Rf value 0.24 and 0.29). The results are shown in Table 10.

TABLE 10

| Reaction components | | | | compound (II) labeled with 14C | spot of compound (III) |
|---|---|---|---|---|---|
| component A | component B | component C | E. coli extract | | |
| | | | pKSN2 | | |
| | | | pKSN11796 | | |
| | | | pKSN11796 | | |
| | | | pKSN11796 | | |
| | | | pKSN11796 | | |
| | | | pKSN11796F | | |
| | | | pKSN11796F | | |
| | | | pKSN11796F | | |
| | | | pKSN11796F | | |

Example 11

Obtaining the Present Invention DNA (A3)

(1) Preparation of the Chromosomal DNA of *Streptomyces testaceus* ATCC21469

*Streptomyces testaceus* ATCC21469 was incubated with shaking at 30° C. for 1 day to 3 days in 50 ml of YEME medium (0.3% (w/v) yeast extract, 0.5% (w/v) bacto-peptone, 0.3% (w/v) malt extract, 1.0% (w/v) glucose, 34% (w/v) sucrose and 0.2% (v/v) 2.5M MgCl$_2$ 6H$_2$O). The cells were recovered. The obtained cells were suspended in YEME medium containing 1.4% (w/v) glycine and 60 mM EDTA and further incubated with shaking for a day. The cells were recovered from the culture medium. After washing once with distilled water, it was resuspended in buffer (100 mM Tris-HCl (pH8.0), 100 mM EDTA, 10 mM NaCl) at 1 ml per 200 mg of the cells. Two hundred micrograms per milliliter (200 µg/ml) of egg-white lysozyme were added. The cell suspension was shaken at 30° C. for a hour. Further, 0.5% of SDS and 1 mg/ml of Proteinase K was added. The cell suspension was incubated at 55° C. for 3 hours. The cell suspension was extracted twice with phenol chloroform isoamyl alcohol to recover each of the aqueous layers. Next, there was one extraction with chloroform isoamyl alcohol to recover the aqueous layer. The chromosomal DNA was obtained by ethanol precipitating the aqueous layer.

(2) Isolation of the Present Invention DNA (A3)

PCR was conducted by utilizing the chromosomal DNA prepared in Example 11(1) as the template. As the primers, there was utilized the pairing of an oligonucleotide having the nucleotide sequence shown in SEQ ID NO: 65 and an oligonucleotide having the nucleotide sequence shown in SEQ ID NO: 66 (hereinafter referred to as "primer pairing 9"). The PCR reaction solution amounted to 50 µl by adding 250 ng of the above chromosomal DNA, the 2 primers each amounting to 200 nM, 4 µl of dNTP mix (a mixture of 2.5 mM of each of the 4 types of dNTP), 5 µl of 10× ExTaq buffer, 0.5 µl of ExTaq polymerase (Takara Shuzo Company) and distilled water. The reaction conditions of the PCR were maintaining 97° C. for 2 minutes; repeating 30 cycles of a cycle that included maintaining 97° C. for 15 seconds, followed by 60° C. for 30 seconds and followed by 72° C. for 90 seconds; and then maintaining 72° C. for 4 minutes. After the maintenance, the reaction solution was subjected to 0.8% agarose gel electrophoresis. The gel area containing the DNA of about 1.4 kbp was recovered. The DNA was purified from the recovered gel by utilizing QIAquick gel extraction kit (Qiagen Company) according to the attached instructions. The obtained DNA was ligated to the TA cloning vector pCR2.1 (Invitrogen Company) according to the instructions attached to said vector and was introduced into E. Coli TOP10F'. The plasmid DNA was prepared from the obtained E. coli transformant, utilizing QIAprep Spin Miniprep Kit (Qiagen Company). A sequencing reaction was conducted with Dye terminator cycle sequencing FS ready reaction kit (Applied Biosystems Japan Company) according to the instructions attached to said kit, utilizing as primers the oligonucleotide having the nucleotide sequence shown in SEQ ID NO: 67 and the oligonucleotide having the nucleotide sequence shown in SEQ ID NO: 68. The sequencing reactions utilized the obtained plasmid as the template. The reaction products were analyzed with a DNA sequencer 373A (Applied Biosystems Japan Company). As a result, the nucleotide sequence shown in SEQ ID NO: 69 was provided. Two open reading frames (ORF) were present in said nucleotide sequence. As such, there was contained a nucleotide sequence consisting of 1188 nucleotides (inclusive of the stop codon) and encoding a 395 amino acid residue and a nucleotide sequence (SEQ ID NO: 17) consisting of 195 nucleotides (inclusive of the stop codon) and encoding a 64 amino acid residue. The molecular weight of the amino acid sequence encoded by the nucleotide sequence shown in SEQ ID NO: 17 was calculated to be 6666 Da.

Example 12

Expression of the Present Invention Protein (A3) in E. Coli (1) Production of a Transformed E. Coli Having the Present Invention DNA (A3)

PCR was conducted by utilizing as a template the chromosomal DNA prepared in Example 11(1) and by utilizing ExTaq polymerase (Takara Shuzo Company) under similar conditions as above. As the primers, there was utilized the pairing of an oligonucleotide having the nucleotide sequence shown in SEQ ID NO: 70 and an oligonucleotide having the nucleotide sequence shown in SEQ ID NO: 71 (hereinafter referred to as "primer pairing 10") or a pairing of an oligonucleotide having the nucleotide sequence shown in SEQ ID NO: 70 and an oligonucleotide having the nucleotide sequence shown in SEQ ID NO: 72 (hereinafter referred to as "primer pairing 11"). The DNA of 1.2 kb amplified by utilizing the primer pairing 10 and the DNA of 1.5 kbp amplified by utilizing the primer pairing 11 were cloned into TA cloning vector pCR2.1 according to the above methods. The plasmid DNA were prepared from the obtained E. coli transformants, utilizing QIAprep Spin Miniprep Kit (Qiagen Company). Sequencing reactions were conducted with Dye terminator cycle sequencing FS ready reaction kit (Applied Biosystems Japan Company) according to the instructions attached to said kit, utilizing as primers the oligonucleotide having the nucleotide sequence shown in SEQ ID NO: 67 and the oligonucleotide having the nucleotide sequence shown in SEQ ID NO: 68. The sequencing reactions utilized the obtained plasmid DNA as the template. The reaction products were analyzed with a DNA sequencer 373A (Applied Biosystems Japan Company). As a result, the plasmid cloned with the DNA amplified by the primer pairing 10 was confirmed to have the nucleotide sequence shown in SEQ ID NO: 8. The plasmid cloned with the DNA amplified by primer pairing 11 was confirmed to have the nucleotide sequence shown in SEQ ID NO: 11. Two open reading frames (ORF) were present in said nucleotide sequence shown in SEQ ID NO: 11. As such, there was contained a nucleotide sequence (SEQ ID NO: 8) consisting of 1188 nucleotides (inclusive of the stop codon) and encoding a 395 amino acid residue and a nucleotide sequence consisting of 195 nucleotides (inclusive of the stop codon) and encoding a 64 amino acid residue. The molecular weight of the protein consisting of the amino acid sequence encoded by the nucleotide sequence shown in SEQ ID NO: 8 was calculated to be 43752 Da. With the obtained plasmids, the plasmid having the nucleotide sequence shown in SEQ ID NO: 8 was designated as pCR671 and the plasmid having the nucleotide sequence shown in SEQ ID NO: 11 was designated as pCR671F.

Next, each of pCR671 and pCR671F was digested with restriction enzymes NdeI and HindIII. The digestion products were subjected to agarose gel electrophoresis. The gel area containing a DNA of about 1.2 kbp was cut from the gel subjected to the digestion products of pCR671. The gel area containing a DNA of about 1.5 kbp was cut from the gel subjected to the digestion products of pCR671F. The DNA were purified from each of the recovered gels by utilizing Qiagen quick gel extraction kit (Qiagen Company) according to the attached instructions. Each of the obtained DNA and the plasmid pKSN2 digested with NdeI and HindIII were ligated with ligation kit Ver. 1 (Takara Shuzo Company) according to the instructions attached to said kit and introduced into E. Coli JM109. The plasmid DNA were prepared from the obtained E. coli transformants. The structures thereof were analyzed. The plasmid containing the nucleotide sequence shown in SEQ ID NO: 8, in which the DNA of about 1200 bp encoding the present invention protein (A3) is inserted between the NdeI site and the HindIII site of pKSN2 was designated as pKSN671. Further, the plasmid containing the nucleotide sequence shown in SEQ ID NO: 11, in which the DNA of about 1400 bp encoding the present invention protein (A3) is inserted between the NdeI site and the HindIII site of pKSN2 was designated as pKSN671F. Each of the above plasmids of pKSN671 and pKSN671F was introduced into E. coli JM109. The obtained E. coli transformants were designated, respectively, JM109/pKSN671 and JM109/pKSN671F. Further, plasmid pKSN2 was introduced into E. coli JM109. The obtained E. coli transformant was designated as JM109/pKSN2.

(2) Expression of the Present Invention Protein (A3) in E. Coli and Recovery of Said Protein E. coli JM109/pKSN671, JM109/pKSN671F and JM109/pKSN2 were each cultured overnight at 37° C. in 10 ml of TB medium (1.2% (w/v) tryptone, 2.4% (w/v) yeast extract, 0.4%

(w/v) glycerol, 17 mM potassium dihydrogenphosphate, 72 mM dipotassium hydrogenphosphate) containing 50 µg/ml of ampicillin. A milliliter (1 ml) of the obtained culture medium was transferred to 100 ml of TB medium containing 50 µg/ml of ampicillin and cultured at 26° C. When OD660 reached about 0.5, 5-aminolevulinic acid was added to the final concentration of 500 µM, and the culturing was continued. Thirty (30) minutes thereafter, IPTG was added to a final concentration of 1 mM, and there was further culturing for 17 hours.

The cells were recovered from each of the culture mediums, washed with 0.1M tris-HCl buffer (pH7.5) and suspended in 10 ml of said buffer containing 1 mM PMSF. The obtained cell suspensions were subjected 6 times to a sonicator (Sonifier (Branson Sonic Power Company)) at 3 minutes each under the conditions of output 3, duty cycle 30%, in order to obtain cell lysate solutions. After centrifuging the cell lysate solutions (1,200×g, 5 minutes) the supernatants were recovered and centrifuged (150,000×g, 70 minutes) to recover supernatant fractions (hereinafter, the supernatant fraction obtained from E. coli JM109/pKSN671 is referred to as "E. coli pKSN671 extract," the supernatant fraction obtained from E. coli JM109/pKSN671F is referred to as "E. coli pKSN671F extract," and the supernatant fraction obtained from E. coli JM109/pKSN2 is referred to as "E. coli pKSN2 extract").

(3) Detection of the Ability to Convert Compound (II) to Compound (III)

Reaction solutions of 30 µl were prepared and maintained for 1 hour at 30° C. The reaction solutions consisted of a 0.1M potassium phosphate buffer (pH7.0) containing 3 ppm of compound (II) labeled with $^{14}$C, 2 mM of β-NADPH (hereinafter, referred to as "component A") (Oriental Yeast Company), 2 mg/ml of a ferredoxin derived from spinach (hereinafter referred to as "component B") (Sigma Company), 0.1 U/ml of ferredoxin reductase (hereinafter, referred to as "component C") (Sigma Company) and 18 µl of the supernatant fraction recovered in Example 12(2). Further, there were prepared and maintained similarly reaction solutions having no addition of at least one component utilized in the composition of the above reaction solution, selected from component A, component B and component C. Three microliters (3 µl) of 2N HCl and 90 µl of ethyl acetate were added and stirred into each of the reaction solutions after the maintenance. The resulting reaction solutions were centrifuged at 8,000×g to recover 75 µl of the ethyl acetate layer. After drying the ethyl acetate layers under reduced pressure, the residue was dissolved in 6.0 µl of ethyl acetate. Five microliters (5.0 µl) thereof was spotted to a silica gel TLC plate (TLC plate silica gel 60F$_{254}$, 20 cm×20 cm, 0.25 mm thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}$C were examined (Rf value 0.24 and 0.29). The results are shown in Table 11.

TABLE 11

| | Reaction components | | | | |
|---|---|---|---|---|---|
| component A | component B | component C | E. coli extract | compound (II) labeled with 14C | spot of compound (III) |
| | | | pKSN2 | | |
| | | | pKSN671 | | |
| | | | pKSN671 | | |
| | | | pKSN671 | | |
| | | | pKSN671 | | |
| | | | pKSN671F | | |
| | | | pKSN671F | | |
| | | | pKSN671F | | |
| | | | pKSN671F | | |

Example 13

Obtaining the Present DNA (A9)

(1) Preparation of the Chromosomal DNA of Streptomyces carbophilus SANK62585

Streptomyces carbophilus SANK62585 (FERM BP-1145) was incubated with shaking at 30° C. for 1 day in 50 ml of YEME medium (0.3% (w/v) yeast extract, 0.5% (w/v) bactopeptone, 0.3% (w/v) malt extract, 1.0% (w/v) glucose, 34% (w/v) sucrose and 0.2% (v/v) 2.5M MgCl$_2$ 6H$_2$O). The cells were then recovered. The obtained cells were suspended in YEME medium containing 1.4% (w/v) glycine and 60 mM EDTA and further incubated with shaking for a day. The cells were recovered from the culture medium. After washing once with distilled water, it was resuspended in buffer (100 mM Tris-HCl (pH8.0), 100 mM EDTA, 10 mM NaCl) at 1 ml per 200 mg of the cells. Two hundred micrograms per milliliter (200 µg/ml) of egg-white lysozyme were added. The cell suspension was shaken at 30° C. for a hour. Further, 0.5% of SDS and 1 mg/ml of Proteinase K was added. The cell suspension was incubated at 55° C. for 3 hours. The cell suspension was extracted twice with phenol chloroform isoamyl alcohol to recover each of the aqueous layers. Next, there was one extraction with chloroform isoamyl alcohol to recover the aqueous layer. The chromosomal DNA was obtained by ethanol precipitating the aqueous layer.

(2) Isolation of the Present DNA (A9)

PCR was conducted by utilizing as the template the chromosomal DNA prepared in Example 13(1). As the primers, there was utilized the pairing of an oligonucleotide having the nucleotide sequence shown in SEQ ID NO: 74 and an oligonucleotide having the nucleotide sequence shown in SEQ ID NO: 75 (hereinafter referred to as "primer paring 12") or the pairing of an oligonucleotide having the nucleotide sequence shown in SEQ ID NO: 76 and an oligonucleotide having the nucleotide sequence shown in SEQ ID NO: 77 (hereinafter referred to as "primer paring 13"). The PCR reaction solution amounted to 50 µl by adding the 2 primers each amounting to 200 nM, 250 ng of the above chromosomal DNA, 4 µl of dNTP mix (a mixture of 2.5 mM of each of the 4 types of dNTP), 5 µl of 10× ExTaq buffer, 0.5 µl of ExTaq polymerase (Takara Shuzo Company) and distilled water. The reaction conditions of the PCR were maintaining 95° C. for 2 minutes;

repeating 30 cycles of a cycle that included maintaining 97° C. for 15 seconds, followed by 60° C. for 30 seconds, followed by 72° C. for 90 seconds, and then maintaining 72° C. for 4 minutes. After the maintenance, the reaction solution was subjected to 0.8% agarose gel electrophoresis. The gel area containing the DNA of about 500 bp was recovered from the gel subjected to the PCR reaction solution utilizing primer pairing 12. The gel area containing the DNA of about 800 bp was recovered from the gel subjected to the PCR reaction solution utilizing primer pairing 13. The DNA were purified from each of the recovered gels by utilizing QIAquick gel extraction kit (Qiagen Company) according to the attached instructions. The obtained DNA were ligated to the TA cloning vector pCR2.1 (Invitrogen Company) according to the instructions attached to said vector and was introduced into E. Coli TOP10F'. The plasmid DNA were prepared from the obtained E. coli transformants, utilizing QIAprep Spin Miniprep Kit (Qiagen Company). A sequencing reaction was conducted with Dye terminator cycle sequencing FS ready reaction kit (Applied Biosystems Japan Company) according to the instructions attached to said kit, utilizing as primers the oligonucleotide having the nucleotide sequence shown in SEQ ID NO:67 and the oligonucleotide having the nucleotide sequence shown in SEQ ID NO: 68. The sequencing reaction utilized the obtained plasmid DNA as the templates. The reaction products were analyzed with a DNA sequencer 373A (Applied Biosystems Japan Company). As a result, the nucleotide sequence shown in nucleotides 1 to 498 of the nucleotide sequence shown in SEQ ID NO: 78 was provided by the DNA obtained by the PCR utilizing primer pairing 12. The nucleotide sequence shown in nucleotides 469 to 1233 of the nucleotide sequence shown in SEQ ID NO: 78 was provided by the DNA obtained by the PCR utilizing primer pairing 13. The plasmid having the nucleotide sequence of nucleotides 1 to 498 shown in SEQ ID NO: 78 was designated as pCRSCA1. The plasmid having the nucleotide sequence of nucleotides 469 to 1233 shown in SEQ ID NO: 78 was designated as pCRSCA2.

Example 14

Expression of the Present Protein (A9) in E. Coli (1) Production of a Transformed E. Coli Having the Present DNA (A9)

With the plasmids obtained in Example 13(2), the above plasmid pCRSCA1 was digested with NdeI and NcoI and pCRSCA2 was digested with NdeI and NcoI. The digestion products were subjected to agarose gel electrophoresis. The gel area containing a DNA of about 500 bp was cut from the gel subjected to the digestion products of pCRSCA2. The gel area containing a DNA of about 800 bp was cut from the gel subjected to the digestion products of pCRSCA2. The DNA were purified from each of the recovered gels by utilizing QIAquick gel extraction kit (Qiagen Company) according to the attached instructions. The 2 types of the obtained DNA were ligated together with the plasmid pKSN2 digested with NdeI and HindIII, utilizing ligation kit Ver. 1 (Takara Shuzo Company) in accordance with the instructions attached to said kit and introduced into E. Coli JM109. The plasmid DNA was prepared from the obtained E. coli transformants. The structure thereof was analyzed. The plasmid containing the nucleotide sequence shown in SEQ ID NO: 78, in which the DNA encoding the present protein (A9) is inserted between the NdeI site and the HindIII site of pKSN2 was designated as pKSNSCA.

(2) Expression of the Present Protein (A9) in E. Coli and Recovery of Said Protein E. coli JM109/pKSNSCA was cultured overnight at 37° C. in 10 ml of TB medium (1.2% (w/v) tryptone, 2.4% (w/v) yeast extract, 0.4% (w/v) glycerol, 17 mM potassium dihydrogenphosphate, 72 mM dipotassium hydrogenphosphate) containing 50 µg/ml of ampicillin. The obtained culture medium was transferred to 100 ml of TB medium containing 50 µg/ml of ampicillin and cultured at 26° C., so that the OD660 was 0.2. When OD660 reached about 2.0, 5-aminolevulinic acid was added to the final concentration of 500 µM, and the culturing was continued. Thirty (30) minutes thereafter, IPTG was added to a final concentration of 200 µM, and there was further culturing for 5 hours.

The cells were recovered from each of the culture mediums, washed with 0.1M tris-HCl buffer (pH7.5) and suspended in 10 ml of said buffer containing 1 mM PMSF. The obtained cell suspensions were subjected 6 times to a sonicator (Sonifier (Branson Sonic Power Company)) at 3 minutes each under the conditions of output 3, duty cycle 30%, in order to obtain cell lysate solutions. After centrifuging the cell lysate solutions (1,200×g, 5 minutes) the supernatants were recovered and centrifuged (150,000×g, 70 minutes) to recover supernatant fractions (hereinafter, the supernatant fraction obtained from E. coli JM109/pKSNSCA is referred to as "E. coli pKSNSCA extract").

(3) Detection of the Ability to Convert Compound (II) to Compound (III)

Reaction solutions of 30 µl were prepared and maintained for 10 minutes at 30° C. The reaction solutions consisted of a 0.1M potassium phosphate buffer (pH7.0) containing 3 ppm of compound (II) labeled with $^{14}C$, 2 mM of β-NADPH (hereinafter, referred to as "component A") (Oriental Yeast Company), 2 mg/ml of a ferredoxin derived from spinach (hereinafter referred to as "component B") (Sigma Company), 0.1 U/ml of ferredoxin reductase (hereinafter, referred to as "component C") (Sigma Company) and 18 µl of the supernatant fraction recovered in Example 14(2). Further, there were prepared and maintained similarly reaction solutions having no addition of at least one component utilized in the composition of the above reaction solution, selected from component A, component B and component C. Three microliters (3 µl) of 2N HCl and 90 µl of ethyl acetate were added and stirred into each of the reaction solutions after the maintenance. The resulting reaction solutions were centrifuged at 8,000×g to recover 75 µl of the ethyl acetate layer. After drying the ethyl acetate layers under reduced pressure, the residue was dissolved in 6.0 µl of ethyl acetate. Five microliters (5.0 µl) thereof was spotted to a silica gel TLC plate (TLC plate silica gel 60$F_{254}$, 20 cm×20 cm, 0.25 mm thick, Merck Company). The TLC plate was developed with 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}C$ were examined (Rf value 0.24 and 0.29). The results are shown in Table 12.

TABLE 12

| | | Reaction components | | | |
|---|---|---|---|---|---|
| component A | component B | component C | E. coli extract | compound (II) labeled with 14C | spot of compound (III) |
| | | | pKSNSCA | | |

Example 15

Isolation of Soybean RuBPC Gene

After seeding soybean (cv. Jack), the soybean was cultivated at 27° C. for 30 days and the leaves were gathered. Two-tenths grams (0.2 g) to 0.3 g of the gathered leaves were frozen with liquid nitrogen and were milled with a mortar and pestle. Subsequently, the total RNA was extracted from the milled product according to the manual attached with RNA extraction solvent ISOGEN (Nippon Gene Company). Further, cDNA was synthesized with the use of Superscript First-strand Synthesis System for RT-PCR (Invitrogen Company), by conducting the procedures in accordance with the attached manual. Specifically, a 1st strand cDNA was synthesized by utilizing the Oligo(dT)12-18 primer provided by the kit as a primer and the total soybean RNA as the template and by adding thereto the reverse transcriptase provided by the kit. Next, there is amplified by PCR a DNA encoding the chloroplast transit peptide of the small subunit of ribulose-1,5-bisphosphate carboxylase (hereinafter, the ribulose-1,5-bisphosphate carboxylase is referred to as "RuBPC") of soybean (cv. Jack) followed by the 12 amino acids of a mature protein (hereinafter, the chloroplast transit peptide of the small subunit of RuBPC of soybean (cv. Jack) is sometimes referred to as "rSt;" and the DNA encoding the chloroplast transit peptide of the small subunit of RuBPC of soybean (cv. Jack) followed by the 12 amino acids of a mature protein is referred to as "the present rSt12 DNA"). The PCR utilized the obtained cDNA as a template and as primers the oligonucleotide having the nucleotide sequence shown in SEQ ID NO: 86 and the oligonucleotide having the nucleotide sequence shown in SEQ ID NO: 87. The PCR utilized LA Taq polymerase (Takara Shuzo Company). The PCR was conducted by maintaining once 94° C. for 3 minutes; conducting 30 cycles of a cycle that included maintaining 98° C. for 25 seconds and then 68° C. for 1 minute; and maintaining once 72° C. for 10 minutes. Plasmid pCRrSt12 (FIG. 5) was obtained by inserting the amplified DNA into the PCR-product cloning site of plasmid pCR2.1 (Invitrogen Company). Next, plasmid was introduced into the competent cells of E. coli JM109 strain and the ampicillin resistant strains were selected. Further, the nucleotide sequence of the plasmid contained in the selected ampicillin resistant strains was determined by utilizing the Dye Terminator Cycle Sequencing FS Ready Reaction kit (PE Applied Biosystems Company) and the DNA sequencer 373S PE Applied Biosystems Company). As a result, the nucleotide sequence shown in SEQ ID NO: 88 was provided. It was confirmed that plasmid pCRrSt12 contained the present rSt12 DNA.

Example 16

Construction of a Chloroplast Expression Plasmid Containing the Present Invention DNA (A1) for Direct Introduction (1) Isolation of the Present Invention DNA (A1)

A DNA comprising the nucleotide sequence shown in SEQ ID NO: 6 was amplified by PCR. The PCR was conducted by utilizing as the template the genomic DNA of *Actinomyces Streptomyces* phaeochromogenes IFO12898 and by utilizing as primers the oligonucleotide consisting of the nucleotide sequence shown in SEQ ID NO: 93 and the oligonucleotide consisting of the nucleotide sequence shown in SEQ ID NO: 94. Further, a DNA comprising the nucleotide sequence shown in SEQ ID NO: 9 was amplified by PCR. The PCR was conducted by utilizing as primers the oligonucleotide consisting of the nucleotide sequence shown in SEQ ID NO: 93 and the oligonucleotide sequence shown in SEQ ID NO: 95. Said PCR utilized the Expand High Fidelity PCR System (Boehringer Company). There was conducted after maintaining once 97° C. for 2 minutes; conducting 10 cycles of a cycle that included maintaining 97° C. for 15 seconds, followed by 60° C. for 30 seconds and followed by 72° C. for 1 minute; then conducting 15 cycles of a cycle that included maintaining 97° C. for 15 seconds, followed by 60° C. for 30 seconds and followed by 72° C. for 1 minute (wherein 20 seconds were added to the maintenance at 72° C. for each cycle); and then maintaining 72° C. for 7 minutes. Plasmids pCR657ET (FIG. 6) and pCR657FET (FIG. 7) were produced by inserting the amplified DNA into the PCR product cloning region of pCR2.1 (Invitrogen Company). Furthermore, other than utilizing the oligonucleotide consisting of the nucleotide sequence shown in SEQ ID NO: 96 and the oligonucleotide consisting of the nucleotide sequence shown in SEQ ID NO: 94, plasmid pCR657Bs (FIG. 8) was obtained with procedures similar to the method described above. Even further, other than utilizing the oligonucleotide consisting of the nucleotide sequence shown in SEQ ID NO: 96 and the oligonucleotide consisting of the nucleotide sequence shown in SEQ ID NO: 97, plasmid pCR657FBs (FIG. 9) was obtained with procedures similar to the method described above. Next, the plasmids were introduced into *E. Coli* DH5α competent cells (Takara Shuzo Company) and the ampicillin resistant cells were selected. Further, the nucleotide sequences of the plasmids contained in the ampicillin resistant strains were determined by utilizing BigDye Terminator Cycle Sequencing Ready Reaction kit v2.0 (PE Applied Biosystems Company) and DNA sequencer 3100 (PE Applied Biosystems Company). As a result, it was confirmed that plasmids pCR657ET and pCR657Bs have the nucleotide sequence shown in SEQ ID NO: 6. It was confirmed that plasmids pCR657FET and pCR657FBs have the nucleotide sequence shown in SEQ ID NO: 9.

(2) Construction of a Chloroplast Expression Plasmid Having the Present Invention DNA (A1) for Direct Introduction—Part (1)

A plasmid containing a chimeric DNA in which the present invention DNA (A1) was connected immediately after the nucleotide sequence encoding the chloroplast transit peptide of soybean (cv. Jack) RuBPC small subunit (hereinafter sometimes referred to as the "sequence encoding the chloroplast transit peptide") without a change of frames in the codons was constructed as a plasmid for introducing the present invention DNA (A1) into a plant with the particle gun method.

First, pCRrSt12 was digested with restriction enzyme HindIII and KpnI. The DNA comprising the present rSt12DNA was isolated. Further, a DNA of about 2640 bp was obtained by removing about a 40 bp DNA from plasmid vector pUC19 (Takara Shuzo Company) with a digestion with restriction enzymes HindIII and KpnI. Next, the 5' terminus of the DNA was dephosphorylated with calf intestine alkaline phosphatase (Takara Shuzo Company). The DNA containing the present rSt12DNA, obtained from pCRrSt12, was inserted thereto to obtain pUCrSt12 (FIG. 10). Next, DNA comprising the present invention DNA (A1) were isolated by digesting each of plasmids pCR657ET and pCR657FET with restriction enzymes EcoT22I and SacI. Each of the obtained DNA was inserted between the EcoT22I restriction site and the SacI restriction site of pUCrSt12 to obtain plasmids pUCrSt657 (FIG. 11) and pUCrSt657F (FIG. 12) containing a chimeric DNA in which the present invention DNA (A1) was connected immediately after the nucleotide sequence encoding the chloroplast transit peptide of soybean (cv. Jack) RuBPC small subunit without a change of frames in the codons.

pBICR16G6PT (described in Japanese unexamined patent 2000-166577) was digested with restriction enzyme EcoRI to isolate a DNA of about 3 kb. (Hereinafter, the promoter contained in the DNA described in the above Japanese unexamined patent is referred to as the "CR16G6 promoter." Further, the terminator contained in the DNA described in the above Japanese unexamined patent is referred to as the "CR16 terminator.") After digesting the plasmid vector pUC19 (Takara Shuzo Company) with restriction enzyme EcoRI, the 5' terminus of said DNA was dephosphorylated with calf intestine alkaline phosphatase (Takara Shuzo Company). The 3 kb DNA derived from pBICR16G6PT was inserted thereto to obtain plasmid pUCCR16G6-p/t (FIG. 13). pUCCR16G6-p/t was digested with restriction enzymes HindIII and ScaI to isolate a DNA comprising the CR16G6 promoter. Further, by digesting plasmid vector pUC19 (Takara Shuzo Company) with restriction enzymes HindIII and EcoRI, a DNA of 51 bp was removed and the remaining DNA consisting of 2635 bp was obtained. Next, the 5' terminus of said DNA was dephosphorylated with calf intestine alkaline phosphatase (Takara Shuzo Company). The above DNA comprising the CR16G6 promoter obtained from pUCCR16G6-p/t and a NotI-EcoRI linker (FIG. 14) obtained from annealing the oligonucleotide consisting of the nucleotide sequence shown in SEQ ID No: 89 with the oligonucleotide consisting of the nucleotide sequence shown in SEQ ID No: 90 were inserted thereto to obtain pUCCR12G6-p/tΔ (FIG. 15). pUCCR12G6-p/tΔ was digested with restriction enzymes NdeI and EcoRI to isolate a DNA having a partial nucleotide sequence of the CR16t terminator. Further, plasmid vector pUC19 (Takara Shuzo Company) was digested with restriction enzymes HindIII and EcoRI to obtain a DNA of 2635 bp. The 5' terminus of said DNA was dephosphorylated with calf intestine alkaline phosphatase (Takara Shuzo Company). The above DNA having a partial nucleotide sequence of the CR16t terminator obtained from pUCCR12G6-p/tΔ and a HindIII-NotI linker (FIG. 16) obtained by annealing the oligonucleotide consisting of the nucleotide sequence shown in SEQ ID NO: 91 with the oligonucleotide consisting of the nucleotide sequence shown in SEQ ID NO: 92 were inserted thereto to obtain pNdG6-ΔT (FIG. 17).

Next, by digesting each of plasmids pUCrSt657 and pUCr657F with restriction enzymes BamHI and SacI, there was isolated the DNA comprising a chimeric DNA in which the present invention DNA (A1) was connected immediately after the nucleotide sequence encoding the chloroplast transit peptide of soybean (cv. Jack) RuBPC small subunit without a change of frames in the codons. The DNA were inserted between the restriction enzyme site of BglII and the restriction enzyme site of SacI of plasmid pNdG6-ΔT to obtain each of plasmid pSUM-NdG6-rSt-657 (FIG. 18) and plasmid pSUM-NdG6-rSt-657F (FIG. 19).

(3) Construction of a Chloroplast Expression Plasmid Having the Present Invention DNA (A1) for Direct Introduction—Part (2)

A plasmid containing a chimeric DNA in which the present invention DNA (A1) was connected immediately after the nucleotide sequence encoding the chloroplast transit peptide of soybean (cv. Jack) RuBPC small subunit and encoding thereafter 12 amino acids of the mature protein, without a change of frames in the codons was constructed as a plasmid for introducing the present invention DNA (A1) into a plant with the particle gun method. First, after digesting plasmid vector pKF19 (Takara Shuzo Company) with restriction enzyme BspHI, the DNA termini were blunt ended by adding nucleotides to the double stranded gap, utilizing KOD DNA polymerase (Toyobo Corporation). Plasmid pKF19ΔBs was obtained by a self-cyclizing the resulting DNA with T4 DNA ligase. The pCRrSt12 obtained in Example 1 was digested with restriction enzyme HindIII and KpnI. The DNA comprising the present rSt12DNA was isolated. Plasmid pKF19ΔBs was digested with restriction enzymes HindIII and KpnI to obtain a DNA of about 2160 bp. The 5' termini of said DNA were dephosphorylated with calf intestine alkaline phosphatase (Takara Shuzo Company). The DNA comprising the present rSt12DNA obtained from pCRrSt12 was inserted thereto to obtain pKFrSt12 (FIG. 20). Next, the plasmids pCR657Bs and pCR657FBs obtained in Example 16(1) were each digested with restriction enzymes BspHI and SacI to isolate DNA comprising the present invention DNA (A1). Each of these DNA were inserted between the restriction site of BspHI and restriction site of SacI of plasmid pKFrSt12 to obtain plasmid pKFrSt12-657 (FIG. 21) and plasmid pKFrSt12-657F (FIG. 22), which contained a chimeric DNA in which the present invention DNA (A1) was connected immediately after the nucleotide sequence encoding the chloroplast transit peptide of soybean (cv. Jack) RuBPC small subunit and encoding thereafter 12 amino acids of the mature protein, without a change of frames in the codons.

Next, each of plasmids pKFrSt12-657 and pKFrSt12-657F was digested with BamHI and SacI to obtain DNA comprising the present invention DNA (A1). Each of these DNA were inserted between the BglII restriction site and SacI restriction site of plasmid pNdG6-ΔT obtained in Example 16(2) to obtain plasmids pSUM-NdG6-rSt12-657 (FIG. 23) and pSUM-NdG6-rSt12-657F (FIG. 24) wherein the chimeric DNA, in which the present invention DNA (A1) was connected immediately after the nucleotide sequence encoding the chloroplast transit peptide of soybean (cv. Jack) RuBPC small subunit and encoding thereafter 12 amino acids of the mature protein, without a change of frames in the codons, was connected downstream of promoter CR16G6.

Example 17

Introduction of the Present Invention DNA (A1) into Soybean (1) Preparation of Proliferative Somatic Embryos After dipping pods of soybeans (cultivar: Fayette and Jack) in 1% sodium hypochlorite solution to sterilize, the immature seeds were taken out. The seed coat was exfoliated from the seed to remove the immature embryo having a diameter of 2 to 5 mm. The embryonic axis of the obtained immature embryo was excised with a scalpel to prepare the immature cotyledon. The immature cotyledon was divided into 2 cotyledon parts. Each cotyledon part was placed in the somatic embryo development medium, respectively. The somatic embryo development medium was a solidified medium where 0.2% (w/v) Gelrite was added to Murashige-Skoog medium (described in Murashige T. and Skoog F., Physiol. Plant (1962) 15, p 473; hereinafter referred to as "MS medium") that was set to a pH of 7.0 and that had 180 µM of 2,4-D and 30 g/L of sucrose added thereto. About 1 month after the placement, the formed globular embryo was transplanted to the somatic embryo growth medium. The somatic embryo growth medium was a solidified medium where 0.2% (w/v) Gelrite was added to MS medium that was set to pH5.8 and that had 90 µM of 2,4-D and 30 g/L of sucrose added thereto. The globular embryo was thereafter transplanted to fresh somatic embryo growth medium 5 to 8 times at intervals of 2 to 3 weeks. Each of the culturing conditions utilizing the above somatic embryo development medium and somatic embryo growth medium was 23 hours of light with 1 hour of darkness and 23 to 25° C. for the whole day.

(2) Introduction of the Gene to Proliferative Somatic Embryos

After the globular embryo obtained in Example 17(1) is transplanted to fresh somatic embryo growth medium and cultured for 2 to 3 days, the globular embryo was utilized to introduce the gene. Plasmids pSUM-NdG6-rSt657, pSUM-NdG6-rSt657F, pSUM-NdG6-rSt12657 and pSUM-NdG6-rSt12657F were coated onto gold particles of a diameter of 1.0 µm to conduct the gene introduction employing the particle gun method. The amount of the plasmids was 1.66 µg for 1 mg of the gold particles. After introducing the gene, the embryo was cultured further for 2 to 3 days. Each of the culturing conditions was 23 hours of light with 1 hour of darkness and 23 to 25° C. for the whole day.

(3) Selection of an Somatic Embryo with Hygromycin

The globular embryo after introducing the gene obtained in Example 17(2) was transplanted to an somatic embryo selection medium. The somatic embryo selection medium was a solidified medium where 0.2% (w/v) Gelrite and 15 mg/L of hygromycin were added to MS medium that was set to pH5.8 and that had 90 µM of 2,4-D and 30 g/L of sucrose added thereto. The surviving globular embryo was thereafter transplanted to fresh somatic embryo selection medium 5 to 8 times at intervals of 2 to 3 weeks. In that time, the somatic embryo selection medium was a solidified medium where 0.2% (w/v) Gelrite and 30 mg/L of hygromycin were added to MS medium that was set to pH5.8 and that had 90 µM of 2,4-D and 30 g/L of sucrose added thereto. Each of the culturing conditions utilizing the above somatic embryo selection medium was 23 hours of light with 1 hour of darkness and 23 to 25° C. for the whole day.

(4) Selection of Somatic Embryo with Compound (II)

The globular embryo after introducing the gene obtained in Example 17(2) was transplanted to an somatic embryo selection medium. The somatic embryo selection medium was a solidified medium where 0.2% (w/v) Gelrite and 0.1 mg/L of compound (II) were added to MS medium that was set to pH5.8 and that had 90 µM of 2,4-D and 30 g/L of sucrose added thereto. The surviving globular embryo was thereafter transplanted to fresh somatic embryo selection medium 5 to 8 times at intervals of 2 to 3 weeks. In that time, the somatic embryo selection medium was a solidified medium where 0.2% (w/v) Gelrite and 0.3 to 1 mg/L of compound (II) were added to MS medium that was set to pH5.8 and that had 90 µM of 2,4-D and 30 g/L of sucrose added thereto. Each of the culturing conditions utilizing the above somatic embryo selection medium was 23 hours of light with 1 hour of darkness and 23 to 25° C. for the whole day.

(5) Plant Regeneration from the Somatic Embryo

The globular embryos selected in Example 17(3) or 17(4) are transplanted to development medium and are cultured for 4 weeks in 23 hours of light with 1 hour of darkness and at 23 to 25° C. for the whole day. The development medium is a solidified medium where 0.8% (w/v) of agar (Wako Pure Chemical Industries, Ltd., use for plant tissue cultures) is added to MS medium that is set to pH5.8 and that has 60 g/L of maltose added thereto. White to yellow colored cotyledon-type embryos are obtained 6 to 8 weeks thereafter. These cotyledon-type embryos are transplanted to germination medium and cultured for 2 weeks. The germination medium is a solidified medium where 0.2% (w/v) of Gelrite was added to MS medium that is set to pH5.8 and has 30 g/L of sucrose added thereto. As a result, there can be obtained a soybean that has developed leaves and has roots.

(6) Acclimation and Cultivation of the Regenerated Plant

The soybean obtained in Example 17(5) is transplanted to gardening soil and acclimated in an incubation chamber of 23 hours of light with 1 hour of darkness and 23 to 25° C. for the whole day. Two (2) weeks thereafter, the rooted plant is transferred to a pot having a diameter of 9 cm and cultivated at room temperature. The cultivation conditions at room temperature are natural light conditions at 23° C. to 25° C. for the whole day. Two to four (2 to 4) months thereafter, the soybean seeds are gathered.

(7) Evaluation of the Resistance to Herbicidal Compound (II)

Leaves of the regenerated plant are gathered and are split equally into 2 pieces along the main vein. Compound (II) is spread onto the full surface of one of the leaf pieces. The other leaf piece is left untreated. These leaf pieces are placed on MS medium containing 0.8% agar and allowed to stand at room temperature for 7 days in light place. Then, each leaf piece is grounded with pestle and mortar in 5 ml of 80% aqueous acetone solution to extract chlorophyll. The extract liquid is diluted 10 fold with 80% aqueous acetone solution and the absorbance is measured at 750 nm, 663 nm and 645 nm to calculate total chlorophyll content according to the method described by Mackenney G., J. Biol. Chem. (1941) 140, p 315. The degree of resistance to compound (II) can be comparatively evaluated by showing in percentiles the total chlorophyll content of the treated leaf piece with the total chlorophyll content of the untreated leaf piece.

Further, soil is packed into a plastic pot having a diameter of 10 cm and a depth of 10 cm. Seeds of the above-described plant are seeded and cultivated in a greenhouse. An emulsion is prepared by mixing 5 parts of compound (II), 6 parts of sorpol3005X (Toho chemicals) and 89 parts of xylene. A certain amount thereof was diluted with water containing 0.1% (v/v) of a sticking agent at a proportion of 1000 L for 1 hectare and is spread uniformly with a spray-gun onto the all sides of the foliage from above the plant cultivated in the above pot. After cultivating the plants for 16 days in a greenhouse, the damage to the plants is investigated, and the resistance to compound (II) is evaluated.

Example 18

Construction of a Chloroplast Expression Plasmid Having the Present Invention DNA (A1) for Agrobacterium Introduction A plasmid for introducing the present invention DNA (A1) into a plant with the *agrobacterium* method was constructed. First, after binary plasmid vector pBI121 (Clontech Company) was digested with restriction enzyme NotI, the DNA termini were blunt ended by adding nucleotides to the double stranded gap, utilizing DNA polymerase I (Takara Shuzo Corporation). T4 DNA ligase was utilized for self-cyclization. After the obtained plasmid was digested with restriction enzyme EcoRI, the DNA termini were blunt ended by adding nucleotides to the double stranded gap, utilizing DNA polymerase I (Takara Shuzo Corporation). T4 DNA ligase was utilized for self-cyclization to obtain plasmid pBI121ΔNotIEcoRI. After digesting the plasmid with HindIII, the 5' DNA terminus of the obtained DNA was dephosphorylated with calf intestine alkaline phosphatase (Takara Shuzo Company). A HindIII-NotI-EcoRI linker (FIG. 25) obtained by annealing the oligonucleotide consisting of the nucleotide sequence shown in SEQ ID NO: 98 with the oligonucleotide consisting of the nucleotide sequence shown in SEQ ID NO: 99 was inserted thereto. Binary plasmid vector pBI121S (FIG. 26) was obtained by self-cyclization. Said plasmid has a structure in which the HindIII-NotI-EcoRI linker was inserted in a direction in which the HindIII restriction site, the NotI restriction site, and the EcoRI restriction site line up in turn from a location close to the O-glucuronidase gene.

Next, each of plasmids pSUM-NdG6-rSt-657 and pSUM-NdG6-rSt-657F was digested with restriction enzymes HindIII and EcoRI, to obtain from each thereof a chimeric DNA in which the present invention DNA (A1) was connected immediately after the nucleotide sequence encoding the chloroplast transit peptide of soybean (cv. Jack) RuBPC small subunit without a change of frames in the codons. These DNA were inserted between the HindIII restriction site and EcoRI restriction site of the above binary plasmid vector pBI121S to obtain plasmids pBI-NdG6-rSt-657 (FIG. 27) and pBI-NdG6-rSt-657F (FIG. 28). Further, each of the above plasmids pSUM-NdG6-rSt12-657 and pSUM-NdG6-rSt12-657F was digested with restriction enzymes HindIII and EcoRI, to obtain from each a chimeric DNA in which the present invention DNA (A1) was connected immediately after the nucleotide sequence encoding the chloroplast transit peptide of soybean (cv. Jack) RuBPC small subunit and encoding thereafter 12 amino acids of the mature protein, without a change of frames in the codons. These DNA were inserted between the HindIII restriction site and EcoRI restriction site of the above binary plasmid vector pBI121S to obtain plasmids pBI-NdG6-rSt12-657 (FIG. 29) and pBI-NdG6-rSt12-657F (FIG. 30).

Example 19

Introduction of the Present Invention DNA (A1) to Tobacco

The present invention DNA (A1) was introduced into tobacco with the *agrobacterium* method, utilizing plasmid pBI-NdG6-rSt-657, plasmid pBI-NdG6-rSt-657F, plasmid pBI-NdG6-rSt12-657 and plasmid pBI-NdG6-rSt12-657F, obtained in Example 18.

First, the plasmids pBI-NdG6-rSt-657, pBI-NdG6-rSt-657F, pBI-NdG6rSt12-657 and pBI-NdG6-rSt12-657F were introduced into *Agrobacterium tumefaciens* LBA4404 (Clontech Company), respectively. Transformed *agrobacterium* strains bearing pBI-NdG6-rSt-657, pBI-NdG6-rSt-657F, pBI-NdG6-rSt12-657 or pBI-NdG6-rSt12-657F were isolated by culturing the resultant transformants in LB agar medium (0.5% yeast extract, 1.0% Bacto tryptone, 0.5% NaCl) containing 300 mg/L streptomycin, 100 mg/L rifampicin and 25 mg/L kanamycin and by selecting the resistant colonies.

Then, according to the method described in Manual for Gene Manipulation of Plant (by Hirofumi UCHIMIYA, Kodan-sha Scientific, 1992), the gene was introduced into tobacco. *Agrobacterium* strains bearing the above plasmids were each cultured at 28° C. overnight in LB medium containing 300 mg/L streptomycin, 100 mg/L rifampicin and 25 mg/L kanamycin, and then leaf pieces of tobacco (*Nicotiana tabacum* strain SR1) cultured sterilely were dipped in the liquid culture medium. The leaf pieces were planted and cultured at room temperature for 2 days in the light in MS agar medium (MS inorganic salts, MS vitamins, 3% sucrose and 0.8% agar; described in Murashige T. and Skoog F., Physiol. Plant. (1962) 15, p 473) containing 0.1 mg/L of naphthalene acetic acid and 1.0 mg/L of benzyl aminopurine. Then, the leaf pieces were washed with sterilized water and cultured for 7 days on MS agar medium containing 0.1 mg/L of naphthalene acetic acid, 1.0 mg/L of benzyl aminopurine and 500 mg/L of cefotaxime. Next, the leaf pieces were transplanted and cultured in MS agar medium containing 0.1 mg/L of naphthalene acetic acid, 1.0 mg/L of benzyl aminopurine, 500 mg/L of cefotaxime and 100 mg/L of kanamycin. The culture was conducted continuously for 4 months while transplanting the leaf pieces to fresh medium of the same composition at intervals of 4 weeks. At that time, the unfixed buds developing from the leave pieces were transplanted and rooted in MS agar medium containing 300 mg/L of cefotaxime and 50 mg/L of kanamycin to obtain regenerated bodies. The regenerated bodies were transplanted to and cultured in MS agar medium containing 50 mg/L of kanamycin to obtain, respectively, a transgenic tobacco to which the T-DNA region of pBI-NdG6-rSt-657, pBI-NdG6-rSt-657F, pBI-NdG6-rSt12-657 or pBI-NdG6-rSt12-657F has been introduced.

Further, the plasmid pBI121S obtained in Example 18 was introduced into tobacco with the *agrobacterium* method. A transformed *agrobacterium* strain bearing pBI121S was isolated similarly to the above, other than utilizing plasmid pBI121S instead of pBI-NdG6-rSt-657, pBI-NdG6-rSt-657F, pBI-NdG6-rSt12-657 and pBI-NdG6-rSt12-657F. Next, a transgenic tobacco to which the T-DNA region of plasmid pBI121S has been introduced was obtained similarly to the above, utilizing said transformed *agrobacterium*.

Three (3) leaves were taken from the transgenic tobacco. Each leaf was divided into 4 pieces in which each piece was 5 to 7 mm wide. Each of the leaf pieces were planted onto MS agar medium containing 0.1 mg/L of compound (II) and cultured in the light at room temperature. On the 7th day of culturing, the herbicidal damage of each of the leaf pieces was observed. The leaf pieces derived from the tobacco to which the control DNA (T-DNA region of plasmid pBI121S) was introduced turned white and withered. In contrast, the leaf pieces derived from the tobacco to which the present invention DNA (A1) (the T-DNA region of plasmid p pBI-NdG6-rSt-657, plasmid pBI-NdG6-rSt12-657, pBI-NdG6-rSt-657F or pBI-NdG6-rSt12-657F) was introduced grew continuously.

Example 20

Introduction of the Present Invention DNA into a Plant

Plasmids were constructed for introducing the present invention DNA (A2) with the particle gun method and the agrobacterium method. First, the present invention DNA (A2) having the nucleotide sequence shown in SEQ ID NO: 7 was amplified by PCR. The PCR was conducted by utilizing as the template the genomic DNA of Actinomyces Saccharopolyspora taberi JCM9383t and by utilizing as primers the oligonucleotide consisting of the nucleotide sequence shown in SEQ ID NO: 100 and the oligonucleotide consisting of the nucleotide sequence shown in SEQ ID NO: 101. Said PCR utilized the Expand High Fidelity PCR System (Boehringer Company). There were conducted after maintaining once 97° C. for 2 minutes; repeating 10 cycles of a cycle that included maintaining 97° C. for 15 seconds, followed by 60° C. for 30 seconds and followed by 72° C. for 60 seconds; then conducting 15 cycles of a cycle that included maintaining 97° C. for 15 seconds, followed by 60° C. for 30 seconds and followed by 72° C. for 1 minute (wherein 20 seconds were added to the maintenance at 72° C. for each cycle); and then maintaining 72° C. for 7 minutes. Plasmids pCR923Sp (FIG. 31) was produced by inserting the amplified DNA into the PCR product cloning region of pCR2.1-TOPO (Invitrogen Company). Next, the plasmid was introduced into E. Coli JM109 competent cells (Takara Shuzo Company) and the ampicillin resistant cells were selected. Further, the nucleotide sequences of the plasmids contained in the ampicillin resistant strains were determined by utilizing BigDye Terminator Cycle Sequencing Ready Reaction kit v2.0 (PE Applied Biosystems Company) and DNA sequencer 373S (PE Applied Biosystems Company). As a result, it was confirmed that plasmid pCR923Sp has the nucleotide sequence shown in SEQ ID NO: 7.

Plasmid pKFrSt12, designed in Example 16(3), was digested with restriction enzymes BamHI and SacI to isolate a DNA comprising the present rSt12DNA. Said DNA was inserted between the BglII restriction site and SacI restriction site of pNdG6-ΔT obtained in Example 16(2) to obtain plasmid pNdG6-rSt12 (FIG. 32). Plasmid pCR923Sp was digested with restriction enzymes SphI and KpnI to obtain the DNA comprising the present invention DNA (A2). Plasmid pNdG6-rSt12 was digested with restriction enzymes SphI and KpnI to remove the DNA encoding the 12 amino acids of the mature protein of soybean (cv. Jack) RuBPC small subunit. In its place, the above DNA containing the present invention DNA (A2) obtained from plasmid pCR923Sp was inserted to obtain pSUM-NdG6-rSt-923 (FIG. 33) wherein the CR16G6 promoter has connected downstream therefrom the chimeric DNA in which said DNA was connected immediately after the sequence encoding the chloroplast transit peptide of soybean (cv. Jack) RuBPC small subunit, without a change of frame in the codons.

Next, plasmid pCR923Sp was digested with restriction enzyme SphI. After blunting the ends of the obtained DNA with KOD DNA polymerase, said DNA is further digested with restriction enzyme KpnI to isolate a DNA containing the present invention DNA (A2). Plasmid pKFrSt12 produced in Example 16(3) was digested with restriction enzyme BspHI. After blunting the ends of the obtained DNA with KOD DNA polymerase, said DNA is further digested with restriction enzyme KpnI to remove DNA of about 20 bp. In its place, the above DNA containing the present invention DNA (A2) obtained from plasmid pCR923Sp was inserted to obtain plasmid pKFrSt12-923 (FIG. 34) comprising the chimeric DNA in which the present invention DNA (A2) was connected immediately after the nucleotide sequence encoding the chloroplast transit peptide of soybean (cv. Jack) RuBPC small subunit and encoding thereafter 12 amino acids of the mature protein, without a change of frames in the codons. pKFrSt12-923 was digested with restriction enzymes SphI and KpnI to obtain the chimeric DNA in which the present invention DNA (A2) and the DNA encoding the first 12 amino acids of the mature protein of soybean (cv. Jack) RuBPC small subunit are connected. Plasmid pNdG6-rSt12 was digested with restriction enzymes SphI and KpnI to remove the DNA encoding the 12 amino acids of the mature protein of soybean (cv. Jack) RuBPC small subunit. In its place, the above chimeric DNA obtained from plasmid pKFrSt12-923 was inserted to obtain plasmid pSUM-NdG6-rSt12-923 (FIG. 35) in which the CR16G6 promoter has connected downstream therefrom the chimeric DNA in which said DNA containing the present invention DNA (A2) was connected immediately after the sequence encoding the chloroplast transit peptide of soybean (cv. Jack) RuBPC small subunit and encoding thereafter 12 amino acids of the mature protein, without a change of frame in the codons.

The present invention DNA (A2) was introduced into soybean with the particle gun method with the identical procedures of the method described in Example 17, utilizing the obtained plasmids pSUM-NdG6-rSt-923 and pSUM-NdG6-rSt12-923.

The above plasmid pSUM-NdG6-rSt-923 was digested with restriction enzymes HindIII and EcoRI to isolate the DNA comprising the chimeric DNA in which said DNA containing the present invention DNA (A2) was connected immediately after the sequence encoding the chloroplast transit peptide of soybean (cv. Jack) RuBPC small subunit, without a change of frame in the codons. As in producing pBI-NdG6-rSt657 in Example 18, the above DNA containing the chimeric DNA obtained from plasmid pSUM-NdG6-rSt-923 was inserted between the HindIII restriction site and the EcoRI restriction site of binary vector pBI121S to obtain pBI-NdG6-rSt-923 (FIG. 36). Further, the above plasmid pSUM-NdG6-rSt12-923 was digested with HindIII and EcoRI, to isolate the DNA containing chimeric DNA in which said DNA containing the present invention DNA (A2) was connected immediately after the sequence encoding the chloroplast transit peptide of soybean (cv. Jack) RuBPC small subunit and encoding thereafter 12 amino acids of the mature protein, without a change of frame in the codons. The chimeric DNA obtained from pSUM-NdG6-rSt12-923 was inserted between the HindIII restriction site and EcoRI restriction sites of binary vector pBI121S to obtain pBI-NdG6-rSt12-923 (FIG. 37).

Each of the plasmids pBI-NdG6-rSt-923 and pBI-NdG6-rSt12-923 was introduced into Agrobacterium tumefaciens LBA4404. The resultant transformants were cultured in LB medium containing 300 μg/ml of streptomycin, 100 μg/ml of rifampicin and 25 μg/ml of kanamycin. The transformants were selected to isolate agrobacterium strains bearing pBI-NdG6-rSt-923 or pBI-NdG6-rSt12-923.

Leaf pieces of sterily cultured tobacco were infected with each of the agrobacterium strain bearing pBI-NdG6-rSt-923 and the agrobacterium strain bearing pBI-NdG6-rSt12-923. Tobaccos in which the present invention DNA (A2) has been introduced were obtained under the procedures similar to the methods described in Example 19.

Three (3) leaves were taken from the obtained transgenic tobacco. Each leaf was divided into 4 pieces in which each piece was 5 to 7 mm wide. Each of the leaf pieces were planted onto MS agar medium containing 0.1 mg/L of compound (II) and cultured in the light at room temperature. On the 7th day of culturing, the herbicidal damage of each of the leaf pieces was observed. The leaf pieces derived from the tobacco to which the control DNA (T-DNA region of plasmid pBI121S) was introduced turned white and withered. In contrast, the leaf pieces derived from the tobacco to which the present invention DNA (A2) (the T-DNA region of plasmid pBI-NdG6-rSt923 or plasmid pBI-NdG6-rSt12-923) was introduced grew continuously.

Example 21

Introduction of the Present Invention DNA (A3) into Tobacco

Plasmids were constructed for introducing the present invention DNA (A3) into a plant with the particle gun method and with the *agrobacterium* method.

First, the present invention DNA (A3) having the nucleotide sequence shown in SEQ ID NO: 8 was amplified by PCR. The PCR was conducted by utilizing as the template the genomic DNA of *Actinomyces Streptomyces* testaceus ATCC21469 and by utilizing as primers the oligonucleotide consisting of the nucleotide sequence shown in SEQ ID NO: 102 and the oligonucleotide consisting of the nucleotide sequence shown in SEQ ID NO: 103. Said PCR utilized the Expand High Fidelity PCR System (Boehringer Company). There were conducted after maintaining once 97° C. for 2 minutes; repeating 10 cycles of a cycle that included maintaining 97° C. for 15 seconds, followed by 60° C. for 30 seconds and followed by 72° C. for 1 minute; then conducting 15 cycles of a cycle that included maintaining 97° C. for 15 seconds, followed by 60° C. for 30 seconds and followed by 72° C. for 1 minute (wherein 20 seconds were added to the maintenance at 72° C. for each cycle); and then maintaining once 72° C. for 7 minutes. Plasmid pCR671ET (FIG. 38) was produced by inserting the amplified DNA into the PCR product cloning region of pCR2.1 (Invitrogen Company). Further, plasmid pCR671Bs (FIG. 39) was obtained with the procedures similar to the method described above, other than utilizing as the PCR primers, the oligonucleotide consisting of the nucleotide sequence shown in SEQ ID NO: 104 and the oligonucleotide consisting of the nucleotide sequence shown in SEQ ID NO: 103. Next, the plasmids were introduced into *E. Coli* JM109 competent cells (Takara Shuzo Company) and the ampicillin resistant cells were selected. Further, the nucleotide sequences of the plasmids contained in the ampicillin resistant strains were determined by utilizing BigDye Terminator Cycle Sequencing Ready Reaction kit v2.0 (PE Applied Biosystems Company) and DNA sequencer 3100 (PE Applied Biosytems Company). As a result, it was confirmed that plasmids pCR671ET and pCR671Bs have the nucleotide sequence shown in SEQ ID NO: 8.

Plasmid pCR671ET was digested with restriction enzymes EcoT22I and KpnI to isolate DNA comprising the present invention DNA (A3). Said DNA was inserted between the EcoT22I restriction site and the KpnI restriction site to obtain plasmid pUCrSt671 (FIG. 40) comprising the chimeric DNA in which the present invention DNA (A3) was connected immediately after the sequence encoding the chloroplast transit peptide of soybean (cv. Jack) RuBPC small subunit, without a change of frame in the codons. Plasmid pUCrSt671 was digested with restriction enzymes NheI and KpnI to isolate DNA comprising the present invention DNA (A3). Plasmid pNdG6-rSt12, obtained in Example 16(2), was digested with restriction enzymes NheI and KpnI to remove DNA of about 80 bp. In its place, the above DNA containing the present invention DNA (A3) obtained from plasmid pUCrSt671 was inserted to obtain pSUM-NdG6-rSt-671 (FIG. 41) wherein the CR16G6 promoter has connected downstream therefrom the chimeric DNA in which the present invention DNA (A3) was connected immediately after the sequence encoding the chloroplast transit peptide of soybean (cv. Jack) RuBPC small subunit, without a change of frame in the codons.

Plasmid pCR671Bs was digested with restriction enzymes BspHI and KpnI to isolate a DNA comprising the present invention DNA (A3). Said DNA was inserted between the BspHI restriction site and KpnI restriction site of pKFrSt12 obtained in Example 16(3) to obtain plasmid pKFrSt12-671 (FIG. 42) containing the chimeric DNA in which the present invention DNA (A3) was connected immediately after the sequence encoding the chloroplast transit peptide of soybean (cv. Jack) RuBPC small subunit and encoding thereafter 12 amino acids of the mature protein, without a change of frame in the codons. Plasmid pNdG6-rSt12 obtained in Example 20 was digested with restriction enzymes NheI and KpnI to remove DNA of about 80 bp. In its place, the above DNA containing the present invention DNA (A3) obtained from plasmid pKFrSt12-671 was inserted to obtain pSUM-NdG6-rSt12-671 (FIG. 43) wherein the CR16G6 promoter has connected downstream therefrom the chimeric DNA in which the present invention DNA (A3) was connected immediately after the sequence encoding the chloroplast transit peptide of soybean (cv. Jack) RuBPC small subunit and encoding thereafter 12 amino acids of the mature protein, without a change of frame in the codons.

The present invention DNA (A3) was introduced into soybean with the particle gun method with procedures similar to the method described in Example 17, utilizing the obtained plasmids pSUM-NdG6-rSt-671 and pSUM-NdG6-rSt12-671.

The above plasmid pSUM-NdG6-rSt-671 was digested with restriction enzymes HindIII and EcoRI to isolate the chimeric DNA in which the present invention DNA (A3) was connected immediately after the sequence encoding the chloroplast transit peptide of soybean (cv. Jack) RuBPC small subunit, without a change of frame in the codons. The above DNA containing the chimeric DNA obtained from plasmid pSUM-NdG6-rSt-671 was inserted between the HindIII restriction site and the EcoRI restriction site of binary vector plasmid pBI121S obtained in Example 18, to obtain pBI-NdG6-rSt-671 (FIG. 44). Further, the above plasmid pSUM-NdG6-rSt12-671 was digested with restriction enzymes HindIII and EcoRI, to isolate the DNA containing chimeric DNA in which said DNA containing the present invention DNA (A3) was connected immediately after the sequence encoding the chloroplast transit peptide of soybean (cv. Jack) RuBPC small subunit and encoding thereafter 12 amino acids of the mature protein, without a change of frame in the codons. The chimeric DNA obtained from pSUM-NdG6-rSt12-671 was inserted between the HindIII restriction site and EcoRI restriction sites of binary plasmid vector pBI121S to obtain pBI-NdG6-rSt12-671 (FIG. 45).

Each of the plasmids pBI-NdG6-rSt-671 and pBI-NdG6-rSt12-671 were introduced into *Agrobacterium tumefaciens* LBA4404. The resultant transformants were cultured in LB medium containing 300 μg/ml of streptomycin, 100 μg/ml of rifampicin and 25 μg/ml of kanamycin. The transformants were selected to isolate *agrobacterium* strains bearing pBI-NdG6-rSt-671 or pBI-NdG6-rSt12-671.

Leaf pieces of sterily cultured tobacco were infected with each of the *agrobacterium* strain bearing pBI-NdG6-rSt-671 and the *agrobacterium* strain bearing pBI-NdG6-rSt12-671. Tobaccos in which the present invention DNA (A3) has been introduced were obtained under the procedures similar to the methods described in Example 19.

Three (3) leaves are taken from the transgenic tobaccos. Each leaf is divided into 4 pieces in which each piece was 5 to 7 mm wide. Each of the leaf pieces are planted onto MS agar medium containing 0.1 mg/L of compound (II) and cultured in the light at room temperature. On the 7th day of culturing, the herbicidal damage of each of the leaf pieces is observed.

Example 22

Expression of the Present Invention Protein (B1) in *E. Coli*

(1) Production of a Transformed *E. Coli* of the Present Invention DNA (B1)

PCR was conducted by utilizing as a template the chromosomal DNA prepared from *Streptomyces* phaeochromogenes IFO12898 in Example 3(1). The PCR reaction solution amounted to 50 μl by adding 300 ng of the above chromosomal DNA, 4 μl of dNTP mix (a mixture of 2.5 mM of each of the 4 types of dNTP), 5 μl of 10× ExTaq buffer, 0.5 μl of ExTaq polymerase (Takara Shuzo Company), distilled water and 200 nM of each of the oligonucleotide having the nucleotide sequence shown in SEQ ID NO: 105 and the oligonucleotide having the nucleotide sequence shown in SEQ ID NO: 53. The reaction conditions of the PCR were after maintaining 97° C. for 2 minutes; repeating 25 cycles of a cycle that included maintaining 97° C. for 15 seconds, followed by 60° C. for 30 seconds and followed by 72° C. for 90 seconds; and then maintaining 72° C. for 4 minutes. The reaction solution after the maintenance and the vector pCR2.1-TOPO (Invitrogen Company) were ligated according to the instructions attached to said vector and were introduced into *E. Coli* TOP10F'. The plasmid DNA were prepared from the obtained *E. coli* transformants, utilizing QIAprep Spin Miniprep Kit (Qiagen Company). Sequencing reactions were conducted with Dye terminator cycle sequencing FS ready reaction kit (Applied Biosystems Japan Company) according to the instructions attached to said kit, utilizing as primers the oligonucleotide consisting of the nucleotide sequence shown in SEQ ID NO: 67 and the oligonucleotide consisting of the nucleotide sequence shown in SEQ ID NO: 68. The sequencing reactions utilized the obtained plasmid DNA as the template. The reaction products were analyzed with a DNA sequencer 373A (Applied Biosystems Japan Company). Based on the results, the plasmid having the nucleotide sequence shown in SEQ ID NO: 15 was designated as pCR657FD.

Next, pCR657FD was digested with restriction enzymes NdeI and HindIII. The digestion products were subjected to agarose gel electrophoresis. The gel area containing a DNA of about 200 bp was cut from the gel. The DNA was purified from the recovered gels by utilizing QIA quick gel extraction kit (Qiagen Company) according to the attached instructions. The obtained DNA and the plasmid pKSN2 digested with NdeI and HindIII were ligated with ligation kit Ver. 1 (Takara Shuzo Company) according to the instructions attached to said kit and introduced into *E. Coli* JM109. The plasmid DNA were prepared from the obtained *E. coli* transformants. The structures thereof were analyzed. The plasmid containing the nucleotide sequence shown in SEQ ID NO: 15, in which the DNA of about 200 bp encoding the present invention protein (B1) is inserted between the NdeI site and the HindIII site of pKSN2 was designated as pKSN657FD. The plasmid pKSN657FD was introduced into *E. coli* JM109. The obtained *E. coli* transformant was designated JM109/pKSN657FD. Further, plasmid pKSN2 was introduced into *E. coli* JM109. The obtained *E. coli* transformant was designated as JM109/pKSN2.

(2) Expression of the Present Invention Protein (B1) in *E. Coli* and Recovery of Said Protein

*E. coli* JM109/pKSN657FD and *E. Coli* JM109/pKSN2 were each cultured overnight at 37° C. in 10 ml of TB medium (1.2% (w/v) tryptone, 2.4% (w/v) yeast extract, 0.4% (w/v) glycerol, 17 mM potassium dihydrogenphosphate, 72 mM dipotassium hydrogenphosphate) containing 50 μg/ml of ampicillin. A milliliter (1 ml) of the obtained culture medium was transferred to 100 ml of TB medium containing 50 μg/ml of ampicillin and cultured at 26° C. Thirty (30) minutes after the OD660 reached about 0.5, IPTG was added to a final concentration of 1 mM, and there was further culturing for 20 hours.

The cells were recovered from each of the culture mediums, washed with 0.1M tris-HCl buffer (pH7.5) and suspended in 10 ml of said buffer containing 1 mM PMSF. The obtained cell suspensions were subjected 6 times to a sonicator (Sonifier (Branson Sonic Power Company)) at 3 minutes each under the conditions of output 3, duty cycle 30%, in order to obtain cell lysate solutions. After centrifuging the cell lysate solutions (1,200×g, 5 minutes) the supernatants were recovered and centrifuged (150,000×g, 70 minutes) to recover supernatant fractions (hereinafter, the supernatant fraction obtained from *E. coli* JM109/pKSN657FD is referred to as "*E. coli* pKSN657FD extract" and the supernatant fraction obtained from *E. coli* JM109/pKSN2 is referred to as "*E. coli* pKSN2 extract"). A microliter (1 μl) of the above supernatant fractions was analyzed on a 15% to 25% SDS-PAGE and stained with CBB. As a result, notably more intense bands were identified in the *E. coli* pKSN657FD extract than the *E. coli* pKSN2 extract, at the electrophoresis locations corresponding to the molecular weight of 7 kDa. It was shown that *E. coli* JM109/pKSN657FD expressed the present invention protein (B1).

(3) Use of the Present Invention Protein (B1) for a Reaction System of Converting Compound (II) to Compound (III)

Reaction solutions of 30 μl were prepared and maintained for 10 minutes at 30° C. The reaction solutions consisted of a 0.1M potassium phosphate buffer (pH7.0) containing 3 ppm of compound (II) labeled with $^{14}C$, 2 mM of β-NADPH (hereinafter, referred to as "component A") (Oriental Yeast Company), 9 μl of the *E. coli* pKSN657FD extract recovered in Example 22(2), 0.1 U/ml of ferredoxin reductase (hereinafter, referred to as "component C") (Sigma Company) and 15 μl of the *E. coli* pKSN657F extract recovered in Example 4(2) (hereinafter referred to as "component D"). Further, there were prepared reaction solutions in which 2 mg/ml of ferredoxin derived from spinach (hereinafter referred to as "component B") (Sigma Company) was added in the place of the *E. coli* pKSN657FD extract and a reaction solution in which nothing was added in the place of the *E. coli* pKSN657FD extract. Such reaction solutions were maintained similarly. Three microliters (3 μl) of 2N HCl and 90 μl of ethyl acetate were added and mixed into each of the reaction solutions after the maintenance. The resulting reaction solutions were centrifuged at 8,000×g to recover 75 μl of the ethyl acetate layer. After drying the ethyl acetate layers under reduced pressure, the residue was dissolved in 6.0 μl of ethyl acetate. Five microliters (5.0 μl) thereof was spotted to a silica gel TLC plate (TLC plate silica gel 60F$_{254}$, 20 cm×20 cm, 0.25 mm thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}C$ were examined (Rf value 0.24 and 0.29). The results are shown in Table 13.

TABLE 13

| Reaction components | | | | | | | |
|---|---|---|---|---|---|---|---|
| component A | E. coli extract | component B | component C | component D | compound (II) labeled with 14C | spot of compound (III) |
| | pKSN657FD | | | | | | |

Example 23

Expression of the Present Invention Protein (B2) in E. Coli (1) Production of a Transformed E. Coli Having the Present Invention DNA (B2)

PCR is conducted by utilizing as a template the chromosomal DNA prepared from *Saccharopolyspora taberi* JCM9383t in Example 6(1). The PCR reaction solution amounts to 50 µl by adding 300 ng of the above chromosomal DNA, 4 µl of dNTP mix (a mixture of 2.5 mM of each of the 4 types of dNTP), 5 µl of 10× ExTaq buffer, 0.5 µl of ExTaq polymerase (Takara Shuzo Company), distilled water and 200 nM of each of the oligonucleotide having the nucleotide sequence shown in SEQ ID NO: 106 and the oligonucleotide having the nucleotide sequence shown in SEQ ID NO: 63. The reaction conditions of the PCR are after maintaining 97° C. for 2 minutes; repeating 25 cycles of a cycle that included maintaining 97° C. for 15 seconds, followed by 60° C. for 30 seconds and followed by 72° C. for 90 seconds; and then maintaining 72° C. for 4 minutes. The reaction solution after the maintenance and the vector pCR2.1-TOPO (Invitrogen Company) are ligated according to the instructions attached to said vector and introduced into E. Coli TOP10F'. The plasmid DNA are prepared from the obtained E. coli transformants, utilizing QIAprep Spin Miniprep Kit (Qiagen Company). Sequencing reactions are conducted with Dye terminator cycle sequencing FS ready reaction kit (Applied Biosystems Japan Company) according to the instructions attached to said kit, utilizing as primers the oligonucleotide consisting of the nucleotide sequence shown in SEQ ID NO: 67 and the oligonucleotide consisting of the nucleotide sequence shown in SEQ ID NO: 68. The sequencing reactions utilize the obtained plasmid DNA as the template. The reaction products are analyzed with a DNA sequencer 373A (Applied Biosystems Japan Company). Based on the results, the plasmid having the nucleotide sequence shown in SEQ ID NO: 16 is designated as pCR923FD.

Next, plasmid pCR923FD is digested with restriction enzymes NdeI and HindIII. The digestion products are subjected to agarose gel electrophoresis. The gel area containing a DNA of about 200 bp is cut from the gel. The DNA is purified from the recovered gels by utilizing QIA quick gel extraction kit (Qiagen Company) according to the attached instructions. The obtained DNA and the plasmid pKSN2 digested with NdeI and HindIII are ligated with ligation kit Ver. 1 (Takara Shuzo Company) according to the instructions attached to said kit and introduced into E. Coli JM109. The plasmid DNA are prepared from the obtained E. coli transformants. The structures thereof are analyzed. The plasmid containing the nucleotide sequence shown in SEQ ID NO: 16, in which the DNA of about 200 bp encoding the present invention protein (B2) is inserted between the NdeI site and the HindIII site of pKSN2 is designated as pKSN923FD. The plasmid pKSN923FD is introduced into E. coli JM109. The obtained E. coli transformant is designated as JM109/pKSN923FD. Further, plasmid pKSN2 is introduced into E. coli JM109. The obtained E. coli transformant is designated as JM109/pKSN2.

(2) Expression of the Present Invention Protein (B2) in E. Coli and Recovery of Said Protein E. coli JM109/pKSN923FD and E. Coli JM109/pKSN2 are each cultured overnight at 37° C. in 10 ml of TB medium (1.2% (w/v) tryptone, 2.4% (w/v) yeast extract, 0.4% (w/v) glycerol, 17 mM potassium dihydrogenphosphate, 72 mM of dipotassium hydrogenphosphate) containing 50 µg/ml of ampicillin. A milliliter (1 ml) of the obtained culture medium is transferred to 100 ml of TB medium containing 50 µg/ml of ampicillin and cultured at 26° C. Thirty (30) minutes after the OD660 reached about 0.5, IPTG is added to a final concentration of 1 mM, and there is further culturing for 20 hours.

The cells are recovered from each of the culture mediums, washed with 0.1M tris-HCl buffer (pH7.5) and suspended in 10 ml of said buffer containing 1 mM PMSF. The obtained cell suspensions are subjected 6 times to a sonicator (Sonifier (Branson Sonic Power Company)) at 3 minutes each under the conditions of output 3, duty cycle 30%, in order to obtain cell lysate solutions. After centrifuging the cell lysate solutions (1,200×g, 5 minutes) the supernatants are recovered and centrifuged (150,000×g, 70 minutes) to recover supernatant fractions (hereinafter, the supernatant fraction obtained from E. coli JM109/pKSN923FD is referred to as "E. coli pKSN923FD extract" and the supernatant fraction obtained from E. coli JM109/pKSN2 is referred to as "E. coli pKSN2 extract"). A microliter (1 µl) of the above supernatant fractions is analyzed on a 15% to 25% SDS-PAGE and stained with CBB. By detecting notably more intense bands in the E. coli pKSN923FD extract than the E. coli pKSN2 extract, at the electrophoresis locations corresponding to the molecular weight of 7 kDa, it is possible to confirm to E. coli expression of the present invention protein (B2).

(3) Use of the Present Invention Protein (B2) for a Reaction System of Converting Compound (II) to Compound (III)

Reaction solutions of 30 µl are prepared and maintained for 10 minutes at 30° C. The reaction solutions consist of a 0.1M potassium phosphate buffer (pH7.0) containing 3 ppm of compound (II) labeled with $^{14}C$, 2 mM of β-NADPH (hereinafter, referred to as "component A") (Oriental Yeast Company), 9 µl of the E. coli pKSN923FD extract recovered in Example 23(3), 0.1 U/ml of ferredoxin reductase (hereinafter, referred to as "component C") (Sigma Company) and 15 µl of the E. coli pKSN657F extract recovered in Example 4(2)

(hereinafter referred to as "component D"). Further, there are prepared reaction solutions in which 2 mg/ml of ferredoxin derived from spinach (hereinafter referred to as "component B") (Sigma Company) is added in the place of the *E. coli* pKSN923FD extract and a reaction solution in which nothing is added in the place of the *E. coli* pKSN923FD extract. Such reaction solutions are maintained similarly. Three microliters (3 μl) of 2N HCl and 90 μl of ethyl acetate are added and mixed into each of the reaction solutions after the maintenance. The resulting reaction solutions are centrifuged at 8,000×g to recover 75 μl of the ethyl acetate layer. After drying the ethyl acetate layers under reduced pressure, the residue is dissolved in 6.0 μl of ethyl acetate. Five microliters (5.0 μl) thereof is spotted to a silica gel TLC plate (TLC plate silica gel $60F_{254}$, 20 cm×20 cm, 0.25 mm thick, Merck Company). The TLC plate is developed with a 6:1:2 mixture of chloroform, acetic acid and ethyl acetate for about 1 hour. The solvents are then allowed to evaporate. The TLC plate is exposed overnight to an imaging plate (Fuji Film Company). Next, the imaging plate is analyzed on Image Analyzer BAS2000 (Fuji Film Company). The presence of a spot corresponding to compound (III) labeled with $^{14}C$ are examined (Rf value 0.24 and 0.29). By confirming that compound (III) is produced in the reaction including component A, *E. coli* pKSN923FD extract, component C and component D, it can be confirmed that the present invention protein (B2) can be used instead of the ferredoxin derived from spinach in a reaction system of converting compound (II) to compound (III).

Example 24

Expression of the Present Invention Protein (B3) in *E. Coli*

(1) Production of a Transformed *E. Coli* Having the Present Invention DNA (B3)

PCR is conducted similarly to the methods described in Example 23(1), other than utilizing as a template the chromosomal DNA prepared from *Streptomyces testaceus* ATCC 21469 in Example 11(1) and utilizing as the primers the oligonucleotide having the nucleotide sequence shown in SEQ ID NO: 107 and the oligonucleotide having the nucleotide sequence shown in SEQ ID NO: 72. Plasmid pCR671FD having the nucleotide sequence shown in SEQ ID NO: 17 is obtained similarly to the method described in Example 23(1) utilizing the obtained reaction solution.

Next, utilizing said plasmid, plasmid pKSN671FD in which the present invention DNA (B3) is inserted between the NdeI site and HindIII site of pKSN2 is obtained similarly to the method described in Example 23(1). By introducing the plasmid into *E. coli* JM109, *E. coli* JM109/pKSN671FD having the present invention DNA (B3) can be obtained.

(2) Expression of the Present Invention Protein (B3) in *E. Coli* and Recovery of Said Protein Utilizing *E. coli* JM109/pKSN671FD, supernatant fractions (hereinafter referred to as "*E. coli* pKSN671FD extract") are recovered similarly to the method described in Example 23(2). A microliter (1 μl) of the above supernatant fractions is analyzed on a 15% to 25% SDS-PAGE and stained with CBB. As a result, by detecting notably more intense bands in the *E. coli* pKSN671FD extract than the *E. coli* pKSN2 extract, at the electrophoresis location corresponding to the molecular weight of 7 kDa, it is possible to confirm the expression of the present invention protein (B3) in *E. coli*.

(3) Use of the Present Invention Protein (B3) for a Reaction System of Converting Compound (II) to Compound (III)

Other than utilizing *E. coli* pKSN671FD extract recovered in Example 24(2), the spot corresponding to compound (III) labeled with $^{14}C$ (Rf values 0.24 and 0.29) is confirmed similarly to the method described in Example 23(3). By confirming that compound (III) is produced in the reaction including component A, *E. coli* pKSN671FD extract, component C and component D, it can be confirmed that the present invention protein (B3) can be used instead of the ferredoxin derived from spinach in a reaction system of converting compound (II) to compound (III).

Example 25

Preparation of the Present Invention Protein (A4)

(1) Preparation of the Crude Cell Extract

A frozen stock of *Streptomyces achromogenes* IFO12735 was added to 10 ml of A medium (0.1% (w/v) of glucose, 0.5% (w/v) tryptone, 0.5% (w/v) yeast extract, 0.1% (w/v) of dipotassium hydrogenphosphate, pH7.0) in a large test tube and incubated with shaking at 30° C. for 1 day to obtain a pre-culture. Eight milliliters (8 ml) of the pre-culture was added to 200 ml of A medium and was incubated with rotary shaking in a 500 ml baffled flask at 30° C. for 2 days. Cell pellets were recovered by centrifuging (3,000×g, 10 min.) the resulting culture. These cell pellets were suspended in 100 ml of B medium (1% (w/v) glucose, 0.1% beef extract, 0.2% (w/v) tryptose) containing compound (II) at 100 ppm and were incubated with reciprocal shaking in a 500 ml Sakaguchi flask for 20 hours at 30° C. Cell pellets were recovered by centrifuging (3,000×g, 10 min.) 2 L of the resulting culture. The resulting cell pellets were washed twice with 1 L of 0.1M potassium phosphate buffer (pH7.0) to provide 136 g of the cell pellets.

These cell pellets were suspended in 0.1M potassium phosphate buffer (pH7.0) at 1 ml to 2 ml for 1 g of the cell pellets. A millimolar of (1 mM) PMSF, 5 mM of benzamidine HCl, 1 mM of EDTA, 3 μg/ml of leupeptin, 3 μg/ml of pepstatin and 1 mM of dithiotritol were added to the cell suspension. A cell lysate solution was obtained by disrupting twice repetitively the suspension with a French press (1000 kg/cm2) (Ohtake Seisakusho). After centrifuging the cell lysate solution (40,000×g, 30 minutes), the supernatant was recovered and centrifuged for 1 hour at 150,000×g to recover the supernatant (hereinafter referred to as the "crude cell extract")

(2) Determination of the Ability of Converting Compound (II) to Compound (III)

There was prepared 30 μl of a reaction solution consisting of 0.1M potassium phosphate buffer (pH7.0) containing 3 ppm of compound (II) labeled with $^{14}C$, 2.4 mM of β-NADPH (hereinafter, referred to as "component A") (Oriental Yeast Company), 0.5 mg/ml of a ferredoxin derived from spinach (hereinafter referred to as "component B") (Sigma Company), 1 U/ml of ferredoxin reductase (hereinafter, referred to as "component C") (Sigma Company) and 15 μl of the crude cell extract recovered in Example 25(1). The reaction solution was maintained at 30° C. for a hour. Further, there was prepared and maintained similarly a reaction solution having no addition of at least one component utilized in the composition of the above reaction solution, selected from component A, component B and component C. Three microliters (3 μl) of 2N HCl and 90 μl of ethyl acetate were added and mixed into each of the reaction solutions after the maintenance. The resulting reaction solutions were centrifuged at 8,000×g to recover 75 μl of the ethyl acetate layer. After drying the ethyl acetate layers under reduced pressure, the residue was dissolved in 6.0 μl of ethyl acetate. Five microliters (5.0 μl) thereof was spotted to a silica gel TLC plate (TLC plate silica gel 60F$_{254}$, 20 cm×20 cm, 0.25 mm thick, Merck Company). The TLC plate was developed with a 6:1:2 mixture of chloroform, acetic acid and ethyl acetate for about 1 hour. The solvents were then allowed to evaporate. The TLC plate was exposed overnight to an imaging plate (Fuji Film Company). Next, the imaging plate was analyzed on Image Analyzer BAS2000 (Fuji Film Company). The presence of a spot corresponding to compound (III) labeled with $^{14}$C were examined (Rf value 0.24 and 0.29). The results are shown in Table 14.

TABLE 14

| | | Reaction components | | | |
|---|---|---|---|---|---|
| component A | component B | component C | crude cell extract | compound (II) labeled with 14C | spot of compound (III) |
| | | | | | |
| | | | | | |

(3) Fractionation of the Crude Cell Extract

Ammonium sulfate was added to the crude cell extract obtained in Example 25(1) to amount to 45% saturation. After stirring in ice-cooled conditions, the supernatant was recovered by centrifuging for 30 minutes at 12,000×g. After adding ammonium sulfate to the obtained supernatant to amount to 55% saturation and stirring in ice-cooled conditions, a pellet was recovered by centrifuging for 10 minutes at 12,000×g. The pellet was dissolved with 12.5 ml of 20 mM bistrispropane buffer (pH7.0). This solution was subjected to a PD10 column (Amersham Pharmacia Company) and eluted with 20 mM of bistrispropane buffer (pH7.0) to recover 17.5 ml of fractions containing proteins (hereinafter referred to as the "45-55% ammonium sulfate fraction").

(4) Isolation of the Present Invention Protein (A4)

The 45-55% ammonium sulfate fraction prepared in Example 25(3) was injected into a HiLoad26/10 Q Sepharose HP column (Amersham Pharmacia Company). Next, after flowing 100 ml of 20 mM bistrispropane buffer (pH7.0) into the column, 20 mM bistrispropane buffer was flown with a linear gradient of NaCl (gradient of NaCl was 0.004M/minute, range of NaCl concentration was from 0M to 1M, flow rate was 4 ml/minute) to fraction recover 30 ml of fractions eluting at the NaCl concentration of from 0.12M to 0.165M. Further, the recovered fractions were subjected to a PD10 column (Amersham Pharmacia Biotech Company) and eluted with 20 mM bistrispropane buffer (pH7.0) to recover the fractions containing protein.

The recovered fractions were subjected to a PD10 column (Amersham Pharmacia Biotech Company) with the elution with Buffer A (2 mM potassium phosphate buffer containing 1.5 mM of NaCl, pH 7.0), in order to recover the fractions containing protein. Next, the fractions were injected into a Bio-Scale Ceramic Hydroxyapatite Type I column CHT10-I (BioRad Company). Twenty milliliters (20 ml) of Buffer A was flown into the column. Subsequently, Buffer A was flown with a linear gradient of Buffer B (100 mM potassium phosphate buffer containing 0.03 mM of NaCl; the linear gradient started at 100% Buffer A to increase to 50% Buffer B over a 100 minute period, flow rate was 2 ml/minute) to fraction recover the fractions eluting at a Buffer B concentration of from 4% to 6%. Further, the recovered fractions were subjected to a PD10 column (Amersham Pharmacia Biotech Company) and eluted with 0.05M potassium phosphate buffer (pH7.0) to recover the fractions containing protein.

A similar amount of 0.05M potassium phosphate buffer (pH7.0) containing 2.0M ammonium sulfate was added and mixed into the recovered fractions. The recovered fractions were then injected into a 1 ml RESOURSE PHE column (Amersham Pharmacia Biotech Company). After flowing 5 ml of 0.05M potassium phosphate buffer (pH7.0) containing 1M ammonium sulfate, the 0.05M potassium phosphate buffer (pH7.0) was flown with a linear gradient of ammonium sulfate (gradient of the ammonium sulfate concentration was 0.1M/minute, range of NaCl concentration was 1M to 0M, flow rate was 2 ml/minute) to fraction recover the fractions eluting at an ammonium sulfate concentration of from about 0.4M to 0.5M. The protein contained in each of the fractions were analyzed on a 10%-20% SDS-PAGE.

Instead of the crude cell extract in the reaction solutions described in Example 25(2), the recovered fractions were added and maintained in the presence of component A, component B, component C and compound (II) labeled with $^{14}$C, similarly to Example 25(2). The reaction solutions after the maintenance were TLC analyzed to examine the intensity of the spots corresponding to compound (III) labeled with $^{14}$C. Said protein moving to a location of about 45 kDa in the above SDS-PAGE was recovered from the gel and was subjected to an amino acid sequence analysis with a protein sequencer (Applied Biosystems Company, Procise 494HT, pulsed liquid method) to sequence the N terminus amino acid sequence. As a result, the amino acid sequence shown in SEQ ID NO: 113 was provided.

Example 26

Obtaining the Present Invention DNA (A4)

(1) Preparation of the Chromosomal DNA of *Streptomyces Achromogenes* IFO 12735

*Streptomyces achromogenes* IFO 12735 cultured with shaking at 30° C. for 1 day to 3 days in 50 ml of YEME medium (0.3% (w/v) yeast extract, 0.5% (w/v) bacto-peptone, 0.3% (w/v) malt extract, 1.0% (w/v) glucose, 34% (w/v) sucrose and 0.2% (v/v) 2.5M MgCl$_2$ 6H$_2$O). The cells were recovered. The obtained cells were suspended in YEME medium containing 1.4% (w/v) glycine and 60 mM EDTA and further incubated with shaking for a day. The cells were recovered from the culture medium. After washing once with distilled water, it was resuspended in buffer (100 mM Tris-HCl (pH8.0), 100 mM EDTA, 10 mM NaCl) at 1 ml per 200 mg of the cells. Two hundred micrograms per milliliter (200 μg/ml) of egg-white lysozyme were added. The cell suspension was shaken at 30° C. for a hour. Further, 0.5% of SDS and 1 mg/ml of Proteinase K was added. The cell suspension was incubated at 55° C. for 3 hours. The cell suspension was extracted twice with phenol chloroform isoamyl alcohol to recover each of the aqueous layers. Next, there was one extraction with chloroform isoamyl alcohol to recover the aqueous layer. The chromosomal DNA was obtained by ethanol precipitating the aqueous layer.

(2) Preparation of the Chromosomal DNA Library of *Streptomyces Achromogenes* IFO 12735

Thirty-eight micrograms (38 μg) of the chromosomal DNA prepared in Example 26(1) were digested with 3.2 U of restriction enzyme Sau3A1 at 37° C. for 60 minutes. The obtained digestion solution was separated with 1% agarose gel electrophoresis. The DNA of about 2.0 kbp was recovered from the gel. The DNA was purified with QIAquick Gel Extraction Kit (Qiagen Company) according to the instructions attached to said kit and was concentrated with an ethanol precipitation to obtain 20 μl of the solution containing the target DNA. Eight microliters (8 μl) of the DNA solution, 100 ng of plasmid vector pUC118 digested with restriction enzyme BamHI and treated with dephosphorylation and 16 μl of the I solution from Ligation Kit Ver. 2 (Takara Shuzo Company) were mixed and maintained for 3 hours at 16° C. *E. coli* DH5α were transformed utilizing the ligation solution and were spread onto LB agar medium containing 50 mg/l of ampicillin to culture overnight at 37° C. The obtained colonies were recovered from an agar medium. The plasmid was extracted. The obtained plasmids were designated as the chromosomal DNA library.

(3) Isolation of the Present Invention DNA (A4)

PCR was conducted by utilizing the chromosomal DNA prepared in Example 26(2) as the template. As the primers, there was utilized the pairing of an oligonucleotide having the nucleotide sequence shown in SEQ ID NO: 114 and an oligonucleotide having the nucleotide sequence shown in SEQ ID NO: 57. The nucleotide sequence shown in SEQ ID NO: 114 was designed based on the amino acid sequence shown in SEQ ID NO: 113. The Expand HiFi PCR System (Boehringer Manheim Company) was utilized to prepare the reaction solution. The PCR reaction solution amounted to 25 μl by adding 2.5 μl of the above chromosomal DNA library, the 2 primers each amounting to 7.5 pmol, 0.2 μl of dNTP mix (a mixture of 2 mM of each of the 4 types of dNTP), 0.2 μl of 10× buffer (containing MgCl2), 0.38 μl of Expand HiFi enzyme mix and distilled water. The reaction conditions of the PCR were after maintaining 97° C. for 2 minute, repeating 10 cycles of a cycle that included maintaining 97° C. for 15 seconds, followed by 65° C. for 30 seconds and followed by 72° C. for 1 minute; then conducting 15 cycles of a cycle that included maintaining 97° C. for 15 seconds, followed by 65° C. for 30 seconds and followed by 72° C. for 1 minute (wherein 20 seconds was added to the maintenance at 72° C. for each cycle); and then maintaining 72° C. for 7 minutes. After the maintenance, 2.5 μl of the reaction solution was utilized as a template solution for conducting PCR for a second time. As the primers, there was utilized the pairing of an oligonucleotide having the nucleotide sequence shown in SEQ ID NO: 115 and an oligonucleotide having the nucleotide sequence shown in SEQ ID NO: 57. The nucleotide sequence shown in SEQ ID NO: 115 was designed based on the amino acid sequence shown in SEQ ID NO: 113. Similar to the above method, the Expand HiFi PCR System (Boehringer Manheim Company) was utilized to conduct PCR. The reaction solution after the maintenance was subjected to 2% agarose gel electrophoresis. The gel area containing the DNA of about 800 bp was recovered. The DNA was purified from the recovered gel by utilizing QIA quick gel extraction kit (Qiagen Company) according to the attached instructions. The obtained DNA was ligated to the TA cloning vector pCRII-TOPO (Invitrogen Company) according to the instructions attached to said vector and was introduced into *E. Coli* TOP10F'. The plasmid DNA was prepared from the obtained *E. coli* transformant, utilizing Qiagen Tip20 (Qiagen Company). A sequencing reaction was conducted with Big Dye terminator cycle sequencing FS ready reaction kit (Applied Biosystems Japan Company) according to the instructions attached to said kit, utilizing a primers having the nucleotide sequence shown in SEQ ID NO: 67 and a primer having the nucleotide sequence shown in SEQ ID NO: 68. The obtained plasmid was utilized as a template in the sequencing reaction. The reaction products were analyzed with a DNA sequencer 3100 (Applied Biosystems Japan Company). As a result, the nucleotide sequence shown in nucleotides 57 to 832 of the nucleotide sequence shown in SEQ ID NO: 110 was provided. In the provided nucleotide sequence, nucleotides 58-60 of the nucleotide sequence shown in SEQ ID NO: 110 encoded amino acid 20 in the amino acid sequence shown in SEQ ID NO: 113.

Next, PCR was conducted with the Expand HiFi PCR System (Boehringer Manheim Company) under the above-described conditions, utilizing as a template the chromosomal DNA library prepared in Example 26(2). As the primers, there was utilized a primer pairing of the oligonucleotide having the nucleotide sequence shown in SEQ ID NO: 116 and the oligonucleotide having the nucleotide sequence shown in SEQ ID NO: 59. The amplified DNA of about 1.4 kbp was cloned into the cloning vector pCRII-TOPO. The plasmid DNA was prepared from the obtained *E. coli* transformants, utilizing Qiagen Tip20 (Qiagen Company). A sequencing reaction was conducted with Big Dye terminator cycle sequencing FS ready reaction kit (Applied Biosystems Japan Company) according to the instructions attached to said kit, utilizing a primer having the nucleotide sequence shown in SEQ ID NO: 67 and a primer having the nucleotide sequence shown in SEQ ID NO: 68. The obtained plasmid was utilized as a template in the sequencing reaction. The reaction products were analyzed with a DNA sequencer 3100 (Applied Biosystems Japan Company). As a result, the nucleotide sequence shown in nucleotides 1 to 58 in the nucleotide sequence shown in SEQ ID NO: 110 was provided.

The cloning of the DNA elongating downstream from the 3' terminus of the nucleotide shown as nucleotide 832 of the nucleotide sequence shown in SEQ ID NO: 110 was conducted. Specifically, 13 μg of the chromosomal DNA of *Streptomyces achromogenes* IFO 12735 prepared in Example 26(1) was digested overnight with 200 U of restriction enzyme HincII at 37° C. After a phenol extraction, the DNA was purified by an ethanol precipitation. The obtained DNA was used to produce 20 μl of an aqueous solution. Four microliters (4 μl) thereof, 1.9 μl of 15 μM Genome Walker Adaptor, 1.6 μl of 10× ligation buffer and 0.5 μl of 6 U/μl T4 ligase were mixed and maintained overnight at 16° C. After that, there was a maintenance at 70° C. for 5 minutes and an addition of 72 μl of distilled water to provide a Genome Walker library. PCR was conducted by utilizing said library as a template. A PCR reaction solution amounting to 50 μl was provided by adding 1 μl of Genome Walker library and primer AP1 (provided with Universal Genome Walker Kit) and the oligonucleotide having the nucleotide sequence shown in SEQ ID NO: 117 to each amount to 200 nM, adding 1 μl of dNTP mix (a mixture of 10 mM each of the 4 types of dNTPs), 10 μl of 5×GC genomic PCR buffer, 2.2 μl of 25 mM Mg(OAc)$_2$, 10 μl of 5M GC-Melt and 1 μl of Advantage-GC genomic polymerase mix and adding distilled water. The reaction conditions of the PCR were after maintaining 95° C. for 1 minute; conducting 7 cycles of a cycle that included maintaining 94° C. for 10 seconds and then 72° C. for 3 minutes; 36 cycles of a cycle that included maintaining 94° C. for 10 seconds and then 68° C. for 3 minutes; and maintaining 68° C. for 7 minutes. The reaction solution after the maintenance was diluted 50 fold with distilled water. The PCR products were designated as the first PCR products and were utilized as a template to conduct another PCR. The PCR amounting 50 µl was provided by adding 1 µl of the first PCR products and primer AP2 (provided with Universal Genome Walker Kit) and the oligonucleotide shown in SEQ ID NO: 118 to each amount to 200 nM, adding 1 µl of dNTP mix (a mixture of 10 mM each of the 4 types of dNTPs), 10 µl of 5×GC genomic PCR buffer, 2.2 µl of 25 mM Mg(OAc)$_2$, 10 µl of 5M GC-Melt and 1 µl of Advantage-GC genomic polymerase mix and adding distilled water. The reaction conditions of the PCR were after maintaining 95° C. for 1 minute; conducting 5 cycles of a cycle that included maintaining 94° C. for 10 seconds and then 72° C. for 3 minutes; 20 cycles of a cycle that included maintaining 94° C. for 10 seconds and then 68° C. for 3 minutes; and maintaining 68° C. for 7 minutes. The reaction solution after the maintenance was subjected to 1% agarose gel electrophoresis. The gel area containing the DNA of about 1300 bp was recovered. The DNA was purified from the recovered gel by utilizing QIA quick gel extraction kit (Qiagen Company) according to the attached instructions. The obtained DNA was ligated to cloning vector pCR11-TOPO (Invitrogen Company) according to the instructions attached to said vector and was introduced into *E. Coli* TOP10F'. The plasmid DNA was prepared from the *E. coli* transformant by utilizing Qiagen Tip20 (Qiagen Company). A sequencing reaction was conducted with Big Dye terminator cycle sequencing FS ready reaction kit (Applied Biosystems Japan Company) according to the instructions attached to said kit, utilizing as primers the oligonucleotide shown in SEQ ID NO: 67 and the oligonucleotide shown in SEQ ID NO: 68. The obtained plasmid was utilized as a template in the sequencing reaction. The reaction products were analyzed with a DNA sequencer 3100 (Applied Biosystems Japan Company). As a result, the nucleotide sequence shown in nucleotides 644 to 1454 in the nucleotide sequence shown in SEQ ID NO: 110 was provided. As a result of connecting all of the analyzed nucleotide sequences, the nucleotide sequence shown in SEQ ID No: 110 was provided. Two open reading frames (ORF) were present in said nucleotide sequence. As such, there was contained a nucleotide sequence (SEQ ID NO: 109) consisting of 1236 nucleotides (inclusive of the stop codon) and encoding a 411 amino acid residue (SEQ ID NO: 108) and a nucleotide sequence (SEQ ID NO: 112) consisting of 192 nucleotides (inclusive of the stop codon) and encoding a 63 amino acid residue (SEQ ID NO: 111). The molecular weight of the protein consisting of the amino acid sequence (SEQ ID NO: 108) encoded by the nucleotide sequence shown in SEQ ID NO: 109 was calculated to be 45465 Da. Further, the amino acid sequence encoded by said nucleotide sequence contained the amino acid sequence (SEQ ID NO: 113) determined from the amino acid sequencing of from the N terminus of the present invention protein (A4). The molecular weight of the protein consisting of the amino acid sequence (SEQ ID NO: 111) encoded by the nucleotide sequence shown in SEQ ID NO: 112 was calculated to be 6871 Da.

Example 27

The Expression of the Present Invention Protein (A4) in *E. Coli*

(1) Production of a Transformed *E. Coli* Having the Present Invention DNA (A4)

PCR was conducted by utilizing as a template the chromosomal DNA prepared from *Streptomyces achromogenes* IFO 12735 in Example 26(1) and by utilizing Expand HiFi PCR System (Boehringer Manheim Company). As the primers, there was utilized the pairing of an oligonucleotide having the nucleotide sequence shown in SEQ ID NO: 119 and an oligonucleotide having the nucleotide sequence shown in SEQ ID NO: 120 (hereinafter referred to as "primer pairing 25") or a pairing of an oligonucleotide having the nucleotide sequence shown in SEQ ID NO: 119 and an oligonucleotide having the nucleotide sequence shown in SEQ ID NO: 121 (hereinafter referred to as "primer pairing 26"). The PCR reaction solution amounted to 50 µl by adding the 2 primers each amounting to 300 nM, 50 ng of the above chromosomal DNA, 5.0 µl of dNTP mix (a mixture of 2.0 mM of each of the 4 types of dNTP), 5.0 µl of 10× Expand HF buffer (containing MgCl2) and 0.75 µl of Expand HiFi enzyme mix and distilled water. The reaction conditions of the PCR were after maintaining 97° C. for 2 minutes; repeating 10 cycles of a cycle that included maintaining 97° C. for 15 seconds, followed by 60° C. for 30 seconds and followed by 72° C. for 1 minute; then conducting 15 cycles of a cycle that included maintaining 97° C. for 15 seconds, followed by 60° C. for 30 seconds and followed by 72° C. for 1 minute (wherein 20 seconds was added to the maintenance at 72° C. for each cycle); and then maintaining 72° C. for 7 minutes. After the maintenance, the reaction solution was subjected to 1% agarose gel electrophoresis. The gel area containing the DNA of about 1.3 kbp was recovered from the gel which was subjected the reaction solution utilizing primer pairing 25. The gel area containing the DNA of about 1.6 kbp was recovered from the gel which was subjected the reaction solution utilizing primer pairing 26. The DNA were purified from each of the recovered gels by utilizing QIA quick gel extraction kit (Qiagen Company) according to the attached instructions. The obtained DNA were ligated to the cloning vector pCRII-TOPO (Invitrogen Company) according to the instructions attached to said vector and were introduced into *E. Coli* TOP10F'. The plasmid DNA were prepared from the obtained *E. coli* transformants, utilizing Qiagen Tip20 (Qiagen Company). Next, sequencing reactions were conducted with Big Dye terminator cycle sequencing FS ready reaction kit (Applied Biosystems Japan Company) according to the instructions attached to said kit, utilizing as primers the oligonucleotides shown in SEQ ID NO: 67, SEQ ID NO: 68, SEQ ID NO: 122 and SEQ ID NO: 123. The sequencing reactions utilized the obtained plasmid DNA as the template. The reaction products were analyzed with a DNA sequencer 3100 (Applied Biosystems Japan Company). Based on the results, the plasmid having the nucleotide sequence shown in SEQ ID NO: 109 was designated as pCR646 and the plasmid having the nucleotide sequence shown in SEQ ID NO: 110 was designated as pCR646F.

Next, each of plasmids pCR646 and pCR646F was digested with restriction enzymes NdeI and HindIII. The digestion products were subjected to agarose gel electrophoresis. The gel area containing a DNA of about 1.3 kbp was cut from the gel subjected to the digestion products of pCR646. The gel area containing a DNA of about 1.6 kbp was cut from the gel subjected to the digestion products of pCR646F. The DNA were purified from each of the recovered gels by utilizing QIA quick gel extraction kit (Qiagen Company) according to the attached instructions. Each of the obtained DNA and the plasmid pKSN2 digested with NdeI and HindIII were ligated with ligation kit Ver. 1 (Takara Shuzo Company) according to the instructions attached to said kit and introduced into *E. Coli* JM109. The plasmid DNA were prepared from the obtained *E. coli* transformants. The structures thereof were analyzed. The plasmid containing the nucleotide sequence shown in SEQ ID NO: 109, in which the DNA of about 1.3 kbp encoding the present invention protein (A4) is inserted between the NdeI site and the HindIII site of pKSN2 was designated as pKSN646. Further, the plasmid containing the nucleotide sequence shown in SEQ ID NO: 110, in which the DNA of about 1.6 kbp encoding the present invention protein (A4) is inserted between the NdeI site and the HindIII site of pKSN2 was designated as pKSN646F. Each of the above plasmids of pKSN646 and pKSN646F was introduced into *E. coli* JM109. The obtained *E. coli* transformants were designated, respectively, JM109/pKSN646 and JM109/pKSN646F. Further, plasmid pKSN2 was introduced into *E. coli* JM109. The obtained *E. coli* transformant was designated as JM109/pKSN2.

(2) Expression of the Present Invention Protein (A4) in *E. Coli* and Recovery of Said Protein

*E. coli* JM109/pKSN646, JM109/pKSN646F and JM109/pKSN2 are each cultured overnight at 37° C. in 10 ml of TB medium (1.2% (w/v) tryptone, 2.4% (w/v) yeast extract, 0.4% (w/v) glycerol, 17 mM potassium dihydrogenphosphate, 72 mM dipotassium hydrogenphosphate) containing 50 μg/ml of ampicillin. A milliliter (1 ml) of the obtained culture medium is transferred to 100 ml of TB medium containing 50 μg/ml of ampicillin and cultured at 26° C. When OD660 reaches about 0.5, 5-aminolevulinic acid is added to the final concentration of 500 μM, and the culturing is continued. Thirty (30) minutes thereafter, IPTG is added to a final concentration of 1 mM, and there is further culturing for 17 hours.

The cells are recovered from each of the culture mediums, washed with 0.1M tris-HCl buffer (pH7.5) and suspended in 10 ml of the above buffer containing 1 mM PMSF. The obtained cell suspensions are subjected 6 times to a sonicator (Sonifier (Branson Sonic Power Company)) at 3 minutes each under the conditions of output 3, duty cycle 30%, in order to obtain cell lysate solutions. After centrifuging the cell lysate solutions (1,200×g, 5 minutes) the supernatants are recovered and centrifuged (150,000×g, 70 minutes) to recover supernatant fractions (hereinafter, the supernatant fraction obtained from *E. coli* JM109/pKSN646 is referred to as "*E. coli* pKSN646 extract," the supernatant fraction obtained from *E. coli* JM109/pKSN646F is referred to as "*E. coli* pKSN646F extract," and the supernatant fraction obtained from *E. coli* JM109/pKSN2 is referred to as "*E. coli* pKSN2 extract"). A microliter (1 μl) of the above supernatant fractions is analyzed on a 15% to 25% SDS-PAGE and stained with CBB. As a result, by detecting notably more intense bands in both *E. coli* pKSN646 extract and *E. coli* pKSN646F extract than the *E. coli* pKSN2 extract, at the electrophoresis locations corresponding to the molecular weight of 45 kDa, it can be confirmed that the present invention protein (A4) is expressed in *E. coli*.

(3) Detection of the Ability to Convert Compound (II) to Compound (III)

Reaction solutions of 30 μl are prepared and maintained for 10 minutes at 30° C. The reaction solutions consist of a 0.1M potassium phosphate buffer (pH7.0) containing 3 ppm of compound (II) labeled with $^{14}$C, 2 mM of β-NADPH (hereinafter, referred to as "component A") (Oriental Yeast Company), 2 mg/ml of a ferredoxin derived from spinach (hereinafter referred to as "component B") (Sigma Company), 0.1 U/ml of ferredoxin reductase (hereinafter, referred to as "component C") (Sigma Company) and 18 μl of the supernatant fraction recovered in Example 27(2). Further, there are prepared and maintained similarly reaction solutions having no addition of at least one component utilized in the composition of the above reaction solution, selected from component A, component B and component C. Three microliters (3 μl) of 2N HCl and 90 μl of ethyl acetate are added and mixed into each of the reaction solutions after the maintenance. The resulting reaction solutions are centrifuged at 8,000×g to recover 75 μl of the ethyl acetate layer. After drying the ethyl acetate layers under reduced pressure, the residue is dissolved in 6.0 μl of ethyl acetate. Five microliters (5.0 μl) thereof is spotted to a silica gel TLC plate (TLC plate silica gel 60F$_{254}$, 20 cm×20 cm, 0.25 mm thick, Merck Company). The TLC plate is developed with a 6:1:2 mixture of chloroform, acetic acid and ethyl acetate for about 1 hour. The solvents are then allowed to evaporate. The TLC plate is exposed overnight to an imaging plate (Fuji Film Company). Next, the imaging plate was analyzed on Image Analyzer BAS2000 (Fuji Film Company). The presence of a spot corresponding to compound (III) labeled with $^{14}$C is examined (Rf value 0.24 and 0.29). The production of compound (III) in reaction solutions containing component A, component B, component C and *E. coli* pKSN646 extract, or in reaction solutions containing component A, component B, component C and *E. coli* pKSN646F extract can be confirmed.

Example 28

Sequence Identity Relating to the Present Invention Protein

The sequence identity relating to the proteins of the present invention and the DNA of the present invention was analyzed by utilizing GENETYX-WIN Ver. 5 (Software Development Company). The alignments were produced by conducting the homology analysis with the Lipman-Pearson method (Lipman, D. J. and Pearson, W. R., Science, 227, 1435-1441, (1985)).

In regards to amino acid sequences of the present invention proteins (A1) to (A4), there were determined the sequence identities to each other and to known proteins of the highest homology. The results are shown in Table 15.

TABLE 15

|  | present invention protein (A1) | present invention protein (A2) | present invention protein (A3) | present invention protein (A4) | known proteins of the highest homology* |
|---|---|---|---|---|---|
| present invention protein (A1) | 100% | 47% | 64% | 48% | 73% AAC25766 |

TABLE 15-continued

| | present invention protein (A1) | present invention protein (A2) | present invention protein (A3) | present invention protein (A4) | known proteins of the highest homology* |
|---|---|---|---|---|---|
| present invention protein (A2) | 47% | 100% | 48% | 51% | 52% CAB46536 |
| present invention protein (A3) | 64% | 48% | 100% | 46% | 67% AAC25766 |
| present invention protein (A4) | 48% | 51% | 46% | 100% | 50% CAB46536 |

*the sequence identity is shown on top and the accession number of the provided protein in the Entrez database (provided by Center for Biotechnology Information, http://www3.ncbi.nlm.nih.gov/Entrez/) is shown on the bottom.

In regards to the nucleotide sequences of the present invention DNA (A1) having the nucleotide sequence shown in SEQ ID NO: 6, the present invention DNA (A2) having the nucleotide sequence shown in SEQ ID NO: 7, the present invention DNA (A3) having the nucleotide sequence shown in SEQ ID NO: 8 and the present invention DNA (A4) having the nucleotide sequence shown in SEQ ID NO: 109, there were determined the sequence identities to each other and to known genes of the highest homology. The results are shown in Table 16.

TABLE 16

| | SEQ ID NO: 6 [present invention DNA (A1)] | SEQ ID NO: 7 [present invention DNA (A2)] | SEQ ID NO: 8 [present invention DNA (A3)] | SEQ ID NO: 109 [present invention DNA (A4)] | known genes of the highest homology* |
|---|---|---|---|---|---|
| SEQ ID NO: 6 [present invention DNA (A1)] | 100% | 61% | 74% | 62% | 77% AF072709 |
| SEQ ID NO: 7 [present invention DNA (A2)] | 61% | 100% | 64% | 65% | 66% Y18574 |
| SEQ ID NO: 8 [present invention DNA (A3)] | 74% | 64% | 100% | 63% | 75% AF072709 |
| SEQ ID NO: 109 [present invention DNA (A4)] | 62% | 65% | 63% | 100% | 64% Y18574 |

*the sequence identity is shown on top and the accession number of the provided gene in the Entrez database (provided by Center for Biotechnology Information, http://www3.ncbi.nlm.nih.gov/Entrez/) is shown on the bottom.

In regards to the amino acid sequences of the present invention proteins (B1) to (B4), there were determined the sequence identities to each other and to known proteins of the highest homology. The results are shown in Table 17.

TABLE 17

| | present invention protein (B1) | present invention protein (B2) | present invention protein (B3) | present invention protein (B4) | known proteins of the highest homology* |
|---|---|---|---|---|---|
| present invention protein (B1) | 100% | 45% | 78% | 41% | 76% AAC25765 |
| present invention protein (B2) | 45% | 100% | 40% | 41% | 60% AAF71770 |
| present invention protein (B3) | 78% | 40% | 100% | 40% | 73% AAC25765 |
| present invention protein (B4) | 41% | 41% | 40% | 100% | 55% AAA26824 |

*the sequence identity is shown on top and the accession number of the provided protein in the Entrez database (provided by Center for Biotechnology Information, http://www3.ncbi.nlm.nih.gov/Entrez/) is shown on the bottom.

In regards to the nucleotide sequences of the present invention DNA (B1) having the nucleotide sequence shown in SEQ ID NO: 15, the present invention DNA (B2) having the nucleotide sequence shown in SEQ ID NO: 16, the present invention DNA (B3) having the nucleotide sequence shown in SEQ ID NO: 17 and the present invention DNA (B4) having the nucleotide sequence shown in SEQ ID NO: 112, there were determined the sequence identities to each other and to known genes of the highest homology. The results are shown in Table 18.

TABLE 18

| | SEQ ID NO: 15 [present invention DNA (B1)] | SEQ ID NO: 16 [present invention DNA (B2)] | SEQ ID NO: 17 [present invention DNA (B3)] | SEQ ID NO: 112 [present invention DNA (B4)] | known genes of the highest homology* |
|---|---|---|---|---|---|
| SEQ ID NO: 15 [present invention DNA (B1)] | 100% | 60% | 80% | 59% | 84% AF072709 |
| SEQ ID NO: 16 [present invention DNA (B2)] | 60% | 100% | 60% | 59% | 66% M32238 |
| SEQ ID NO: 17 [present invention DNA (B3)] | 80% | 60% | 100% | 65% | 79% AF072709 |
| SEQ ID NO: 112 [present invention DNA (B4)] | 59% | 59% | 65% | 100% | 66% M32239 |

*the sequence identity is shown on top and the accession number of the provided gene in the Entrez database (provided by Center for Biotechnology Information, http://www3.ncbi.nlm.nih.gov/Entrez/) is shown on the bottom.

Example 29

PCR Utilizing an Oligonucleotide Having a Partial Nucleotide Sequence of the Present Invention DNA (A) as a Primer PCR was conducted by utilizing as a template each of: the chromosomal DNA of *Streptomyces* phaeochromogenes IFO 12898 prepared in Example 2; the chromosomal DNA of *Saccharopolyspora taberi* JCM 9383t prepared in Example 5; the chromosomal DNA of *Streptomyces griseolus* ATCC 11796 prepared in Example 9; the chromosomal DNA of *Streptomyces testaceus* ATCC 21469 prepared in Example 11; the chromosomal DNA of *Streptomyces achromogenes* IFO 12735 prepared in Example 26; and each of the chromosomal DNA of *Streptomyces griseofuscus* IFO 12870t, *Streptomyces thermocoerulescens* IFO 14273t and *Streptomyces nogalater* IFO 13445 prepared similarly to the method described in Example 2. As the primers, the 5 pairings of primers shown in Table 19 were utilized. The predicted size of the DNA amplified by the PCR utilizing each of the primer pairings based on the nucleotide sequence shown in SEQ ID NO: 6 is shown in Table 19.

TABLE 19

| primer pairing | primer | primer | amplified DNA |
|---|---|---|---|
| 14 | SEQ ID NO: 124 | SEQ ID NO: 129 | about 800 bp |
| 15 | SEQ ID NO: 125 | SEQ ID NO: 129 | about 600 bp |
| 16 | SEQ ID NO: 126 | SEQ ID NO: 129 | about 600 bp |

TABLE 19-continued

| primer pairing | primer | primer | amplified DNA |
|---|---|---|---|
| 17 | SEQ ID NO: 127 | SEQ ID NO: 129 | about 580 bp |
| 18 | SEQ ID NO: 128 | SEQ ID NO: 129 | about 580 bp |

The PCR reaction solution amounted to 25 μl by adding 200 nM of each of the 2 primers of the pairing shown in Table 19, adding 10 ng of the chromosomal DNA, 0.5 μl of dNTP mix (a mixture of 10 mM of each of the 4 types of dNTP), 5 μl of 5×GC genomic PCR buffer, 1.1 μl of 25 mM Mg(OAc)$_2$, 5 μl of 5M GC-Melt and 0.5 μl of Advantage-GC genomic polymerase mix and adding water. The reaction conditions were maintaining 95° C. for 1 minute; repeating 30 cycles of a cycle that included maintaining 94° C. for 15 seconds, followed by 60° C. for 30 seconds, and followed by 72° C. for 1 minute; and maintaining 72° C. for 5 minutes. Each of the reaction solutions after the maintenance was analyzed with 3% agarose gel electrophoresis. The results are shown in FIG. 46 and in Table 20 and Table 21. The amplification of the predicted size of the DNA was observed in each or all of the cases with primer pairings 14, 15, 16, 17 and 18 as well as in the cases of utilizing the chromosomal DNA prepared from any of the strains as a template.

TABLE 20

| | Reagents | | amplification |
|---|---|---|---|
| Lane | origin of the template chromosomal DNA | primer pairing | of DNA* |
| 2 | *Streptomyces phaeochromogenes* IFO 12898 | 14 | |
| 3 | *Streptomyces phaeochromogenes* IFO 12898 | 15 | |
| 4 | *Streptomyces phaeochromogenes* IFO 12898 | 16 | |
| 5 | *Streptomyces phaeochromogenes* IFO 12898 | 17 | |
| 6 | *Streptomyces phaeochromogenes* IFO 12898 | 18 | |
| 9 | *Streptomyces testaceus* ATCC 21469 | 14 | |
| 10 | *Saccharopolyspora taberi* JCM 9393t | 14 | |
| 11 | *Streptomyces griseolus* ATCC 11796 | 14 | |
| 13 | *Streptomyces testaceus* ATCC 21469 | 15 | |
| 14 | *Saccharopolyspora taberi* JCM 9393t | 15 | |
| 15 | *Streptomyces griseolus* ATCC 11796 | 15 | |

TABLE 20-continued

| Lane | origin of the template chromosomal DNA | primer pairing | amplification of DNA* |
|---|---|---|---|
| 16 | Streptomyces testaceus ATCC 21469 | 16 | |
| 17 | Saccharopolyspora taberi JCM 9393t | 16 | |
| 18 | Streptomyces griseolus ATCC 11796 | 16 | |
| 20 | Streptomyces testaceus ATCC 21469 | 17 | |
| 21 | Saccharopolyspora taberi JCM 9393t | 17 | |
| 22 | Streptomyces griseolus ATCC 11796 | 17 | |
| 23 | Streptomyces testaceus ATCC 21469 | 18 | |
| 24 | Saccharopolyspora taberi JCM 9393t | 18 | |
| 25 | Streptomyces griseolus ATCC 11796 | 18 | |

*"+" represents that the predicted size of the DNA was detected and "−" represents that there was no detection.

TABLE 21

| Lane | Origin of template chromosomal DNA | primer pairing | amplification of DNA* |
|---|---|---|---|
| 28 | Streptomyces griseofuscus IFO 12870t | 14 | |
| 29 | Streptomyces thermocoerulescens IFO 14273t | 14 | |
| 30 | Streptomyces achromogenes IFO 12735 | 14 | |
| 31 | Streptomyces nogalater IFO 13445 | 14 | |
| 33 | Streptomyces griseofuscus IFO 12870t | 15 | |
| 34 | Streptomyces thermocoerulescens IFO 14273t | 15 | |
| 35 | Streptomyces achromogenes IFO 12735 | 15 | |
| 36 | Streptomyces nogalater IFO 13445 | 15 | |
| 38 | Streptomyces griseofuscus IFO 12870t | 16 | |
| 39 | Streptomyces thermocoerulescens IFO 14273t | 16 | |
| 40 | Streptomyces achromogenes IFO 12735 | 16 | |
| 41 | Streptomyces nogalater IFO 13445 | 16 | |
| 43 | Streptomyces griseofuscus IFO 12870t | 17 | |
| 44 | Streptomyces thermocoerulescens IFO 14273t | 17 | |
| 45 | Streptomyces achromogenes IFO 12735 | 17 | |
| 46 | Streptomyces nogalater IFO 13445 | 17 | |
| 48 | Streptomyces griseofuscus IFO 12870t | 18 | |
| 49 | Streptomyces thermocoerulescens IFO 14273t | 18 | |
| 50 | Streptomyces achromogenes IFO 12735 | 18 | |
| 51 | Streptomyces nogalater IFO 13445 | 18 | |

*"+" represents that the predicted size of the DNA was detection and "−" represents that there was no detection.

Example 30

Hybridization Utilizing as a Probe a DNA Consisting of a Partial Nucleotide Sequence of the Present DNA (A) and the Present Invention DNA (A)

(1) Preparation of a Probe

DNA consisting of a partial nucleotide sequence of the present invention DNA (A1) or a partial nucleotide sequence of the present invention DNA (A1) was produced as a probe labeled with digoxigenin (DIG labeled probe). PCR was conducted with PCR DIG Probe synthesis kit (Roche Diagnostics GmbH Company) according to the attached manual by utilizing as a template the chromosomal DNA of *Streptomyces phaeochromogenes* IFO 12898 prepared in Example 3 and by utilizing as primers the oligonucleotide consisting of the nucleotide sequence shown in SEQ ID NO: 93 and the oligonucleotide consisting of the nucleotide sequence shown in SEQ ID NO: 94. The PCR reaction solution amounted to 50 µl by adding the 2 primers each amounting to 200 nM, adding 50 ng of the chromosomal DNA, 2.5 µl of dNTP mix (a mixture of 2.0 mM of each of the 4 types of dNTP), 2.5 µl of PCR DIG mix (a mixture of 2.0 mM of each of the 4 types of dNTP labeled with DIG), 5 µl of 10×PCR buffer and 0.75 µl of Expand HiFi enzyme mix and adding distilled water. The reaction conditions were after maintaining 95° C. for 2 minutes; repeating 10 cycles of a cycle that included maintaining 95° C. for 10 seconds, followed by 60° C. for 30 seconds and followed by 72° C. for 2 minutes; then conducting 15 cycles of a cycle that included maintaining 95° C. for 10 seconds, followed by 60° C. for 30 seconds and followed by 72° C. for 2 minutes (wherein 20 seconds was added to the maintenance at 72° C. for each cycle); and then maintaining 72° C. for 7 minutes. The reaction solution after the maintenance was subjected to 1% agarose gel electrophoresis. As a result, amplification of a DNA of about 1.3 kb was confirmed. The amplified DNA was recovered to obtain a DNA labeled with digoxigenin and having the nucleotide sequence shown in SEQ ID NO: 6. Under a similar method, PCR was conducted by utilizing as a template the chromosomal DNA of *Streptomyces* phaeochromogenes IFO 12898 and by utilizing as the primers the oligonucleotide consisting of the nucleotide sequence shown in SEQ ID NO: 130 and the oligonucleotide consisting of the nucleotide sequence show in SEQ ID NO: 131. The DNA amplified by said PCR was recovered to obtain a DNA labeled with digoxigenin and having the nucleotide sequence shown in nucleotides 57 to 730 of the nucleotide sequence shown in SEQ ID NO: 6.

Under a similar method, PCR was conducted by utilizing as a template the chromosomal DNA of *Saccharopolyspora taberi* JCM 9393t prepared in Example 6 and by utilizing as primers the oligonucleotide consisting of the nucleotide sequence shown in SEQ ID NO: 61 and the oligonucleotide sequence consisting of the nucleotide sequence shown in SEQ ID NO: 62. The DNA amplified by said PCR was recovered to obtain a DNA labeled with digoxigenin and having the nucleotide sequence shown in SEQ ID NO: 7.

Further, under a similar method, PCR was conducted by utilizing as the template the chromosomal DNA of *Streptomyces testaceus* ATCC 21469 prepared in Example 11 and by utilizing as primers the oligonucleotide consisting of the nucleotide sequence shown in SEQ ID NO: 70 and the oligonucleotide sequence consisting of the nucleotide sequence shown in SEQ ID NO: 71. The DNA amplified by said PCR was recovered to obtain a DNA labeled with digoxigenin and having the nucleotide sequence shown in SEQ ID NO: 8. Further, PCR was conducted by utilizing the above-mentioned chromosomal DNA as the template and by utilizing as the primers the oligonucleotide consisting of the nucleotide sequence shown in SEQ ID NO: 132 and the oligonucleotide consisting of the nucleotide sequence shown in SEQ ID NO: 133. The DNA amplified by said PCR was recovered to obtain a DNA labeled with digoxigenin and having the nucleotide sequence shown in nucleotides 21 to 691 of the nucleotide sequence shown in SEQ ID NO: 8.

(2) Dot-Blot Hybridization

Each of the DNA of pKSN657 prepared in Example 4 (the DNA comprising the present invention DNA (A1)), the DNA of pKSN923 prepared in Example 7 (the DNA comprising the present invention DNA (A2)), the DNA of pKSN671 prepared in Example 12 (the DNA comprising the present invention DNA (A3)), the DNA of pKSNSCA prepared in Example 14 (the DNA comprising the present DNA (A9)) and the DNA of pKSN11796 prepared in Example 10 (the DNA comprising the present DNA (A10)) was blotted onto a nylon membrane Hybond N+(Amersham Pharmacia Company) to amount to 100 ng and 10 ng. Ultraviolet light was directed at the obtained membranes with a transilluminator for 5 minutes.

DIG-High Prime DNA Labeling and Detection Starter Kit II (Roche Diagnostics GmbH Company) was utilized for the hybridization and detection according to the attached manual. As the probes, each of the DNA labeled with digoxigenin and produced in Example 30(1) which were maintained at 100° C. for 5 minutes and then quickly cooled in ice (hereinafter, referred to as "DIG labeled probe") was utilized. The dotted above membrane was shaken at 42° C. for 30 minutes in 2.0 ml of DIGEasyHyb that was provided with said kit. Next, 2.0 ml of Dig Easy Hyb, 5.0 μl of the DIG labeled probes and the membrane were enclosed in a plastic bag for hybridization and maintained at 42° C. for 18 hours. The membrane was recovered, was shaken twice in 2×SSC containing 0.1% SDS for 5 minutes at room temperature and was then shaken twice in 0.5×SSC containing 0.1% SDS at 65° C. for 15 minutes. Subsequently, the membrane was shaken in 50 ml of washing buffer for 2 minutes, then shaken in 50 ml of blocking solution at room temperature for 30 minutes, then shaken in 2.0 ml of antibody solution for 30 minutes, and then shaken twice in 50 ml of washing buffer for 15 minutes. Further, after shaking in 50 ml of detection buffer for 5 minutes, the membrane was enclosed in a hybridization bag with 2.0 ml of Color Substrate solution and maintained at room temperature for 18 hours. A signal was detected in each of the cases of conducting hybridization with each of the reagents of 10 ng and 100 ng of each of pKSN657, pKSN923, pKSN671, pKSNSCA and pKSN11796.

Example 31

Obtaining the Present Invention DNA (A11)

(1) Preparation of the chromosomal DNA of *Streptomyces nogalator*

IFO13445*Streptomyces* nogalator IFO13445 was cultivated with shaking at 30° C. for 3 days in 50 ml of YGY medium (0.5% (w/v) yeast extract, 0.5% (w/v) tryptone, 0.1% (w/v) glucose and 0.1% (w/v) K2HPO4, pH7.0). The cells were recovered. The obtained cells were suspended in YGY medium containing 1.4% (w/v) glycine and 60 mM EDTA and further incubated with shaking for a day. The cells were recovered from the culture medium. After washing once with distilled water, it was suspended in 3.5 ml of Buffer B1 (50 mM Tris-HCl (pH8.0), 50 mM EDTA, 0.5% of Tween-20 and 0.5% Triton X-100). Eighty microliters (80 μl) of a 100 μg/ml lysozyme solution and 100 μl of Qiagen Protease (600 mAU/ml, Qiagen Company) were added to the suspension and maintained at 37° C. for a hour. Next, 1.2 ml of Buffer B2 (3M guanidine HCl and 20% tween-20) was added, mixed and maintained at 50° C. for 30 minutes. The obtained cell lysate solution added to a Qiagen genomic chip 100G (Qiagen Company) equalized in Buffer QBT (750 mM NaCl, 50 mM MOPS (pH7.0), 15% isopropanol and 0.15% Triton X-100). Next, after the chip was washed twice with 7.5 ml of Buffer QC (50 mM MOPS (pH7.0) and 15% isopropanol), the DNA was eluted by flowing 5 ml of Buffer QF (1.25M NaCl, 50 mM Tris HCl (pH8.5), 15% isopropanol). Three and five-tenths milliliters (3.5 ml) of isopropanol was mixed into the obtained DNA solution to precipitate and recover the chromosomal DNA. After washing with 70% ethanol, the recovered chromosomal DNA was dissolved in 1 ml of TB buffer.

(2) Isolation of DNA Having a Partial Nucleotide Sequence of the Present Invention DNA (A11)

PCR was conducted by utilizing as the template the chromosomal DNA prepared in Example 31(1) and by utilizing primer pairing 14, in accordance with the method described in Example 29. The amplified DNA was ligated to cloning vector pCRII-TOPO (Invitrogen Company) according to the instructions attached to said vector and was then introduced into *E. Coli* TOP10F'. The plasmid DNA was prepared from the obtained *E. coli* transformant, utilizing Qiagen Tip20 (Qiagen Company). A sequencing reaction was conducted with Dye terminator cycle sequencing FS ready reaction kit (Applied Biosystems Japan Company) according to the instructions attached to said kit, utilizing a primer having the nucleotide sequence shown in SEQ ID NO: 57 and a primer having the nucleotide sequence shown in SEQ ID NO: 59. The sequence reaction utilized the obtained plasmid as a template. The reaction products were analyzed with a DNA sequencer 3100 (Applied Biosystems Japan Company). As a result, the nucleotide sequence shown in nucleotides 316 to 1048 of the nucleotide sequence shown in SEQ ID NO: 139 was provided.

Further, the chromosomal DNA prepared in Example 31(1) was digested with restriction enzyme PvuII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 161 and primer AP1 (Universal Genome Walker Kit (Clontech Company)). Next, PCR was conducted under the conditions described in Example 26(3), by utilizing the first PCR products as the template and by utilizing the oligonucleotide having the nucleotide sequence shown in SEQ ID NO: 162 and primer AP2 (Universal Genome Walker Kit (Clontech Company)). The nucleotide sequence of the obtained DNA was analyzed. The nucleotide sequence shown in nucleotides 1 to 330 of the nucleotide sequence shown in SEQ ID NO: 144 was provided.

Further, the chromosomal DNA prepared in Example 31(1) was digested with restriction enzyme HincII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 163 and primer AP1 (Universal Genome Walker Kit (Clontech Company)). Next, PCR was conducted under the conditions described in Example 26(3), by utilizing the first PCR products as the template and by utilizing the oligonucleotide having the nucleotide sequence shown in SEQ ID NO: 164 and primer AP2 (Universal Genome Walker Kit (Clontech Company)). The nucleotide sequence of the obtained DNA was analyzed. The nucleotide sequence shown in nucleotides 983 to 1449 of the nucleotide sequence shown in SEQ ID NO: 144 was provided.

(3) Sequence Analysis of the Present Invention DNA (A11)

The nucleotide sequence shown in SEQ ID NO: 144 was obtained by connecting the nucleotide sequences provided by the DNA obtained in Example 31(2). Two open reading frames (ORF) were present. As such, there was contained a nucleotide sequence (SEQ ID NO: 139) consisting of 1230 nucleotides (inclusive of the stop codon) and encoding a 409 amino acid residue (SEQ ID NO: 159) and a nucleotide sequence (SEQ ID NO: 154) consisting of 207 nucleotides (inclusive of the stop codon) and encoding a 68 amino acid residue (SEQ ID NO: 149). The molecular weight of the protein consisting of the amino acid sequence (SEQ ID NO: 159) encoded by the nucleotide sequence shown in SEQ ID NO: 139 was calculated to be 45177 Da. Further, the molecular weight of the protein consisting of the amino acid sequence (SEQ ID NO: 149) encoded by the nucleotide sequence shown in SEQ ID NO: 154 was calculated to be 7147 Da.

Example 32

Expression of the Present Invention Protein (A11) in E. Coli (1) Production of a Transformed E. Coli Having the Present Invention DNA(A11)

PCR was conducted by utilizing as a template the chromosomal DNA prepared from Streptomyces nogalator IFO13445 in Example 31(1) and by utilizing Expand HiFi PCR System (Boehringer Manheim Company). As the primers, there was utilized the pairing of an oligonucleotide having the nucleotide sequence shown in SEQ ID NO: 165 and an oligonucleotide having the nucleotide sequence shown in SEQ ID NO: 166. The reaction solution composition and the maintenance were similar to the conditions described in Example 27(1). The reaction solution after the maintenance was subjected to 1% agarose gel electrophoresis. The gel area containing the DNA of about 1.5 kbp was recovered. The DNA was purified from the recovered gel by utilizing QIA quick gel extraction kit (Qiagen Company) according to the attached instructions. The obtained DNA was ligated to the cloning vector pCRII-TOPO (Invitrogen Company) according to the instructions attached to said vector and was introduced into E. Coli TOP10F'. The plasmid DNA was prepared from the obtained E. coli transformants, utilizing Qiagen Tip20 (Qiagen Company). Sequencing reactions were conducted with Dye terminator cycle sequencing FS ready reaction kit (Applied Biosystems Japan Company) according to the instructions attached to said kit, utilizing as primers the oligonucleotides having the nucleotide sequences shown in, respectively, SEQ ID NOs: 57, 59, and 186. The sequencing reactions utilized the obtained plasmid DNA as the template. The reaction products were analyzed with a DNA sequencer 3100 (Applied Biosystems Japan Company). Based on the results, the plasmid having the nucleotide sequence shown in SEQ ID NO: 144 was designated as pCR849AF.

Next, pCR849AF was digested with restriction enzymes NdeI and HindIII. The digestion products were subjected to agarose gel electrophoresis. The gel area containing a DNA of about 1.5 kbp was cut from the gel. The DNA was purified from the recovered gels by utilizing QIA quick gel extraction kit (Qiagen Company) according to the attached instructions. The obtained DNA and the plasmid pKSN2 digested with NdeI and HindIII were ligated with ligation kit Ver. 2 (Takara Shuzo Company) according to the instructions attached to said kit and introduced into E. Coli JM109. The plasmid DNA were prepared from the obtained E. coli transformants. The structures thereof were analyzed. The plasmid containing the nucleotide sequence shown in SEQ ID NO: 144, in which the DNA of about 1.5 kbp encoding the present invention protein (A11) is inserted between the NdeI site and the HindIII site of pKSN2 was designated as pKSN849AF. Plasmid pKSN849AF was introduced into E. coli JM109. The obtained E. coli transformant was designated JM109/pKSN849AF. Further, plasmid pKSN2 was introduced into E. coli JM109. The obtained E. coli transformant was designated as JM109/pKSN2.

(2) Expression of the Present Invention Protein (A11) in E. Coli and Recovery of Said Protein Similarly to Example 4(2), each of E. coli JM109/pKSN849AF and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN849AF is referred to as "E. coli pKSN849AF extract" and the supernatant fraction obtained from JM109/pKSN2 is referred to as "E. coli pKSN2 extract").

(3) Detection of the Ability to Convert Compound (II) to Compound (III)

Reaction solutions of 30 µl were prepared and maintained for 10 minutes at 30° C. The reaction solutions consisted of a 0.1M potassium phosphate buffer (pH7.0) containing 3 ppm of compound (II) labeled with $^{14}C$, 2 mM of β-NADPH (hereinafter, referred to as "component A") (Oriental Yeast Company), 2 mg/ml of a ferredoxin derived from spinach (hereinafter referred to as "component B") (Sigma Company), 0.1 U/ml of ferredoxin reductase (hereinafter, referred to as "component C") (Sigma Company) and 23 µl of the supernatant fraction recovered in Example 32(2). Similarly to Example 4(3), the reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN849AF extract. In contrast, such a spot was not detected from the reaction solution containing E. coli pKSN2 extract.

Example 33

Obtaining the Present Invention DNA (A12)

(1) Preparation of the Chromosomal DNA of Streptomyces tsusimaensis IFO 13782

Under the method described in Example 31(1), the chromosomal DNA of Streptomyces tsusimaensis IFO 13782 was prepared.

(2) Isolation of DNA Having a Partial Nucleotide Sequence of the Present Invention DNA (A12)

PCR was conducted by utilizing as the template the chromosomal DNA of Streptomyces tsusimaensis IFO 13782 prepared in Example 33(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 364 to 1096 of the nucleotide sequence shown in SEQ ID NO: 140 was provided.

Further, the chromosomal DNA prepared in Example 33(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 167 and primer AP1. Next, PCR was conducted under the conditions described in Example 26(3), by utilizing the first PCR products as the template and by utilizing the oligonucleotide having the nucleotide sequence shown in SEQ ID NO: 168 and primer AP2. The nucleotide sequence of the obtained DNA was analyzed. The nucleotide sequence shown in nucleotides 1 to 392 of the nucleotide sequence shown in SEQ ID NO: 145 was provided.

Further, the chromosomal DNA prepared in Example 33(1) was digested with restriction enzyme PvuII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 169 and primer AP1. Next, PCR was conducted under the conditions described in Example 26(3), by utilizing the first PCR products as the template and by utilizing the oligonucleotide having the nucleotide sequence shown in SEQ ID NO: 170 and primer AP2. The nucleotide sequence of the obtained DNA was analyzed. The nucleotide sequence shown in nucleotides 1048 to 1480 of the nucleotide sequence shown in SEQ ID NO: 145 was provided.

(3) Sequence Analysis of the Present Invention DNA (A12)

The nucleotide sequence shown in SEQ ID NO: 145 was obtained by connecting the nucleotide sequences provided by the DNA obtained in Example 33(2). Two open reading frames (ORF) were present in said nucleotide sequence. As such, there was contained a nucleotide sequence (SEQ ID NO: 140) consisting of 1278 nucleotides (inclusive of the stop codon) and encoding a 425 amino acid residue (SEQ ID NO: 160) and a nucleotide sequence (SEQ ID NO: 155) consisting of 198 nucleotides (inclusive of the stop codon) and encoding a 65 amino acid residue (SEQ ID NO: 150). The molecular weight of the protein consisting of the amino acid sequence (SEQ ID NO: 160) encoded by the nucleotide sequence shown in SEQ ID NO: 140 was calculated to be 46549 Da. Further, the molecular weight of the protein consisting of the amino acid sequence (SEQ ID NO: 150) encoded by the nucleotide sequence shown in SEQ ID NO: 155 was calculated to be 6510 Da.

Example 34

Expression of the Present Invention DNA (A12) in E. Coli (1) Production of a Transformed E. Coli Having the Present Invention DNA (A12)

PCR was conducted similarly to Example 32(1), other than utilizing as a template the chromosomal DNA prepared from Streptomyces tsusimaensis IFO 13782 in Example 33(1) and utilizing as the primers the oligonucleotide having the nucleotide sequence shown in SEQ ID NO: 171 and an oligonucleotide having the nucleotide sequence shown in SEQ ID NO: 172. Similarly to Example 32(1), the DNA was purified from the reaction solution of PCR and cloned into the cloning vector pCRII-TOPO (Invitrogen Company). The nucleotide sequence of the obtained plasmid DNA was analyzed with oligonucleotides having the nucleotide sequences shown, respectively, in SEQ ID NOs: 57, 59, 171, 172 and 187. Based on the obtained results, the plasmid having the nucleotide sequence shown in SEQ ID NO: 145 was designated as pCR1618F. Similarly to Example 32(1), pCR1618F was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 145, in which the DNA encoding the present invention protein (A12) is inserted between the NdeI site and the HindIII site of pKSN2 (hereinafter referred to as "pKSN1618F"). Said plasmid was introduced into E. Coli JM109. The obtained E. coli transformant was designated JM109/pKSN1618F.

(2) Expression of the Present Invention Protein (A12) in E. Coli and Recovery of Said Protein Similarly to Example 4(2), each of E. coli JM109/pKSN1618F and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1618F is referred to as "E. coli pKSN1618F extract" and the supernatant fraction obtained from E. coli JM109/pKSN2 is referred to as "E. coli pKSN2 extract").

(3) Detection of the Ability to Convert Compound (II) to Compound (III)

Reaction solutions of 30 µl were prepared and maintained for 10 minutes at 30° C. Other than utilizing the supernatant fractions recovered in Example 34(2) (E. coli pKSN1618F extract or E. coli pKSN2 extract), the reaction solutions were prepared similarly to Example 32(3). The reaction solutions after the maintenance were extracted with ethyl acetate and the extracted layers were TLC analyzed. After developing the TLC plate, the presence of a spot thereon corresponding to compound (III) labeled with $^{14}$C were examined (Rf value 0.24 and 0.29). A spot corresponding to compound (III) was detected from the reaction solution containing E. coli pKSN1618F extract. In contrast, such a spot was not detected from the reaction solution containing E. coli pKSN2 extract.

Example 35

Obtaining the Present Invention DNA (A13)

(1) Preparation of the Chromosomal DNA of Streptomyces Thermocoerulesces IFO 14273t Under the method described in Example 31(1), the chromosomal DNA of Streptomyces thermocoerulesces IFO 14273t was prepared.

(2) Isolation of DNA Having a Partial Nucleotide Sequence of the Present Invention DNA (A13)

PCR was conducted by utilizing as the template the chromosomal DNA of Streptomyces thermocoerulesces IFO 14273t prepared in Example 35(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 295 to 1027 of the nucleotide sequence shown in SEQ ID NO: 141 was provided.

Further, the chromosomal DNA prepared in Example 35(1) was digested with restriction enzyme HincII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 173 and primer AP1. Next, PCR was conducted under the conditions described in Example 26(3), by utilizing the first PCR products as the template and by utilizing the oligonucleotide having the nucleotide sequence shown in SEQ ID NO: 174 and primer AP2. The nucleotide sequence of the obtained DNA was analyzed. The nucleotide sequence shown in nucleotides 1 to 370 of the nucleotide sequence shown in SEQ ID NO: 146 was provided.

Further, the chromosomal DNA prepared in Example 35(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 175 and primer AP1. Next, PCR was conducted under the conditions described in Example 26(3), by utilizing the first PCR products as the template and by utilizing the oligonucleotide having the nucleotide sequence shown in SEQ ID NO: 176 and primer AP2. The nucleotide sequence of the obtained DNA was analyzed. The nucleotide sequence shown in nucleotides 960 to 1473 of the nucleotide sequence shown in SEQ ID NO: 146 was provided.

(3) Sequence Analysis of the Present Invention DNA (A13)

The nucleotide sequence shown in SEQ ID NO: 146 was obtained by connecting the nucleotide sequences provided by the DNA obtained in Example 35(2). Two open reading frames (ORF) were present in said nucleotide sequence. As such, there was contained a nucleotide sequence (SEQ ID NO: 141) consisting of 1209 nucleotides (inclusive of the stop codon) and encoding a 402 amino acid residue (SEQ ID NO: 136) and a nucleotide sequence (SEQ ID NO: 156) consisting of 252 nucleotides (inclusive of the stop codon) and encoding a 83 amino acid residue (SEQ ID NO: 151). The molecular weight of the protein consisting of the amino acid sequence (SEQ ID NO: 136) encoded by the nucleotide sequence shown in SEQ ID NO: 141 was calculated to be 44629 Da. Further, the molecular weight of the protein consisting of the amino acid sequence (SEQ ID NO: 151) encoded by the nucleotide sequence shown in SEQ ID NO: 156 was calculated to be 8635 Da.

Example 36

Expression of the Present Invention DNA (A13) in E. Coli (1) Production of a Transformed E. Coli Having the Present Invention DNA (A13)

PCR was conducted similarly to Example 32(1), other than utilizing as a template the chromosomal DNA prepared from Streptomyces thermocoerulesces IFO 14273t in Example 35(1) and utilizing as the primers the oligonucleotide having the nucleotide sequence shown in SEQ ID NO: 177 and an oligonucleotide having the nucleotide sequence shown in SEQ ID NO: 178. Similarly to Example 32(1), the DNA was purified from the reaction solution of PCR and cloned into the cloning vector pCRII-TOPO (Invitrogen Company). The nucleotide sequence of the obtained plasmid DNA was analyzed with oligonucleotides having nucleotide sequences shown, respectively, in SEQ ID NOs: 57, 59, 173, 175 and 188. Based on the obtained results, the plasmid having the nucleotide sequence shown in SEQ ID NO: 146 was designated as pCR474F. Similarly to Example 32(1), pCR474F was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 146, in which the DNA encoding the present invention protein (A13) is inserted between the NdeI site and the HindIII site of pKSN2 (hereinafter referred to as "pKSN474F"). Said plasmid was introduced into E. Coli JM109. The obtained E. coli transformant was designated JM109/pKSN474F.

(2) Expression of the Present Invention Protein (A13) in E. Coli and Recovery of Said Protein Similarly to Example 4(2), each of E. coli JM109/pKSN474F and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN474F is referred to as "E. coli pKSN474F extract" and the supernatant fraction obtained from JM109/pKSN2 is referred to as "E. coli pKSN2 extract").

(3) Detection of the Ability to Convert Compound (II) to Compound (III)

Reaction solutions of 30 µl were prepared and maintained for 10 minutes at 30° C. Other than utilizing the supernatant fractions recovered in Example 36(2) (E. coli pKSN474F extract or E. coli pKSN2 extract), the reaction solutions were prepared similarly to Example 32(3). The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN474F extract. In contrast, such a spot was not detected from the reaction solution containing E. coli pKSN2 extract.

Example 37

Obtaining the Present Invention DNA (A14)

(1) Preparation of the Chromosomal DNA of Streptomyces thermocoerulesces IFO 14273t Under the method described in Example 31(1), the chromosomal DNA of Streptomyces glomerochromogenes IFO 13673t was prepared.

(2) Isolation of DNA Having a Partial Nucleotide Sequence of the Present Invention DNA (A13)

PCR was conducted by utilizing as the template the chromosomal DNA of Streptomyces glomerochromogenes IFO 13673t prepared in Example 37(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 316 to 1048 of the nucleotide sequence shown in SEQ ID NO: 142 was provided.

Further, the chromosomal DNA prepared in Example 37(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 179 and primer AP1. Next, PCR was conducted under the conditions described in Example 26(3), by utilizing the first PCR products as the template and by utilizing the oligonucleotide having the nucleotide sequence shown in SEQ ID NO: 180 and primer AP2. The nucleotide sequence of the obtained DNA was analyzed. The nucleotide sequence shown in nucleotides 1 to 330 of the nucleotide sequence shown in SEQ ID NO: 147 was provided.

Further, the chromosomal DNA prepared in Example 37(1) was digested with restriction enzyme HincII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 181 and primer AP1. Next, PCR was conducted under the conditions described in Example 26(3), by utilizing the first PCR products as the template and by utilizing the oligonucleotide having the nucleotide sequence shown in SEQ ID NO: 182 and primer AP2. The nucleotide sequence of the obtained DNA was analyzed. The nucleotide sequence shown in nucleotides 982 to 1449 of the nucleotide sequence shown in SEQ ID NO: 147 was provided.

(3) Sequence Analysis of the Present Invention DNA (A14)

The nucleotide sequence shown in SEQ ID NO: 147 was obtained by connecting the nucleotide sequences provided by the DNA obtained in Example 37(2). Two open reading frames (ORF) were present in said nucleotide sequence. As such, there was contained a nucleotide sequence (SEQ ID NO: 142) consisting of 1230 nucleotides (inclusive of the stop codon) and encoding a 409 amino acid residue (SEQ ID NO: 137) and a nucleotide sequence (SEQ ID NO: 157) consisting of 207 nucleotides (inclusive of the stop codon) and encoding a 68 amino acid residue (SEQ ID NO: 152). The molecular weight of the protein consisting of the amino acid sequence (SEQ ID NO: 137) encoded by the nucleotide sequence shown in SEQ ID NO: 142 was calculated to be 45089 Da. Further, the molecular weight of the protein consisting of the amino acid sequence (SEQ ID NO: 152) encoded by the nucleotide sequence shown in SEQ ID NO: 157 was calculated to be 7174 Da.

Example 38

Expression of the Present Invention DNA (A14) in E. Coli (1) Production of a Transformed E. Coli Having the Present Invention DNA (A14)

PCR was conducted similarly to Example 32(1), other than utilizing as a template the chromosomal DNA of Streptomyces glomerochromogenes IFO 13673t prepared in Example 37(1) and utilizing as the primers the oligonucleotide having the nucleotide sequence shown in SEQ ID NO: 183 and an oligonucleotide having the nucleotide sequence shown in SEQ ID NO: 184. Similarly to Example 32(1), the DNA was purified from the PCR reaction solution and cloned into cloning vector pCRII-TOPO (Invitrogen Company). The nucleotide sequence of the obtained plasmid DNA was analyzed with oligonucleotides having nucleotide sequences shown, respectively, in SEQ ID NOs: 57, 59 and 189. Based on the obtained results, the plasmid having the nucleotide sequence shown in SEQ ID NO: 147 was designated as pCR1491AF. Similarly to Example 32(1), pCR1491AF was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 147, in which the DNA encoding the present invention protein (A14) is inserted between the NdeI site and the HindIII site of pKSN2 (hereinafter referred to as "pKSN1491AF"). Said plasmid was introduced into E. Coli JM109. The obtained E. coli transformant was designated JM109/pKSN1491AF.

(2) Expression of the Present Invention Protein (A14) in E. Coli and Recovery of Said Protein Similarly to Example 4(2), each of E. coli JM109/pKSN1491AF and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1491AF is referred to as "E. coli pKSN1491AF extract" and the supernatant fraction obtained from JM109/pKSN2 is referred to as "E. coli pKSN2 extract").

(3) Detection of the Ability to Convert Compound (II) to Compound (III)

Reaction solutions of 30 µl were prepared and maintained for 10 minutes at 30° C. Other than utilizing the supernatant fractions recovered in Example 38(2) (E. coli pKSN1491AF extract or E. coli pKSN2 extract), the reaction solutions were prepared similarly to Example 32(3). The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN1491AF extract. In contrast, such a spot was not detected from the reaction solution containing E. coli pKSN2 extract.

Example 39

Obtaining the Present Invention DNA (A15)

(1) Preparation of the Chromosomal DNA of Streptomyces olivochromogenes IFO 12444

Under the method described in Example 31(1), the chromosomal DNA of Streptomyces olivochromogenes IFO 12444 was prepared.

(2) Isolation of DNA Having a Partial Nucleotide Sequence of the Present Invention DNA (A15)

PCR was conducted by utilizing as the template the chromosomal DNA of Streptomyces olivochromogenes IFO 12444 prepared in Example 39(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 316 to 1048 of the nucleotide sequence shown in SEQ ID NO: 143 was provided.

Further, the chromosomal DNA prepared in Example 37(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained DNA as the template and by utilizing the oligonucleotide having the nucleotide sequence shown in SEQ ID NO: 179 and primer AP1. Next, PCR was conducted under the conditions described in Example 26(3), by utilizing the first PCR products as the template and by utilizing the oligonucleotide having the nucleotide sequence shown in SEQ ID NO: 180 and primer AP2. The nucleotide sequence of the obtained DNA was analyzed. The nucleotide sequence shown in nucleotides 1 to 330 of the nucleotide sequence shown in SEQ ID NO: 148 was provided.

Further, the chromosomal DNA prepared in Example 39(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 181 and primer AP1. Next, PCR was conducted under the conditions described in Example 26(3), by utilizing the first PCR products as the template and by utilizing the oligonucleotide having the nucleotide sequence shown in SEQ ID NO: 182 and primer AP2. The nucleotide sequence of the obtained DNA was analyzed. The nucleotide sequence shown in nucleotides 982 to 1449 of the nucleotide sequence shown in SEQ ID NO: 148 was provided.

(3) Sequence Analysis of the Present Invention DNA (A15)

The nucleotide sequence shown in SEQ ID NO: 148 was obtained by connecting the nucleotide sequences provided by the DNA obtained in Example 39(2). Two open reading frames (ORF) were present in said nucleotide sequence. As such, there was contained a nucleotide sequence (SEQ ID NO: 143) consisting of 1230 nucleotides (inclusive of the stop codon) and encoding a 409 amino acid residue (SEQ ID NO: 138) and a nucleotide sequence (SEQ ID NO: 158) consisting of 207 nucleotides (inclusive of the stop codon) and encoding a 68 amino acid residue (SEQ ID NO: 153). The molecular weight of the protein consisting of the amino acid sequence (SEQ ID NO: 138) encoded by the nucleotide sequence shown in SEQ ID NO: 143 was calculated to be 45116 Da. Further, the molecular weight of the protein consisting of the amino acid sequence (SEQ ID NO: 153) encoded by the nucleotide sequence shown in SEQ ID NO: 158 was calculated to be 7179 Da.

Example 40

Expression of the Present Invention DNA (A15) in E. Coli (1) Production of a Transformed E. Coli Having the Present Invention DNA (A15)

PCR was conducted similarly to Example 32(1), other than utilizing as a template the chromosomal DNA of Streptomyces olivochromogenes IFO 12444 prepared in Example 39(1) and utilizing as the primers the oligonucleotide having the nucleotide sequence shown in SEQ ID NO: 184 and an oligonucleotide having the nucleotide sequence shown in SEQ ID NO: 185. Similarly to Example 32(1), the DNA was purified from the PCR reaction solution and cloned into cloning vector pCRII-TOPO (Invitrogen Company). The nucleotide sequence of the obtained plasmid DNA was analyzed with oligonucleotides having nucleotide sequences shown, respectively, in SEQ ID NOs: 57, 59 and 189. Based on the obtained results, the plasmid having the nucleotide sequence shown in SEQ ID NO: 148 was designated as pCR1555AF. Similarly to Example 32(1), pCR1555AF was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 148, in which the DNA encoding the present invention protein (A15) is inserted between the NdeI site and the HindIII site of pKSN2 (hereinafter referred to as "pKSN1555AF"). Said plasmid was introduced into E. Coli JM109. The obtained E. coli transformant was designated JM109/pKSN1555AF.

(2) Expression of the Present Invention Protein (A15) in E. Coli and Recovery of Said Protein Similarly to Example 4(2), each of E. coli JM109/pKSN1555AF and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1555AF is referred to as "E. coli pKSN1555AF extract" and the supernatant fraction obtained from JM109/pKSN2 is referred to as "E. coli pKSN2 extract").

(3) Detection of the Ability to Convert Compound (II) to Compound (III)

Reaction solutions of 30 µl were prepared and maintained for 10 minutes at 30° C. Other than utilizing the supernatant fractions recovered in Example 40(2) (E. coli pKSN1555AF extract or E. coli pKSN2 extract), the reaction solutions were prepared similarly to Example 32(3). The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN1555AF extract. In contrast, such a spot was not detected from the reaction solution containing E. coli pKSN2 extract.

Example 41

Metabolism of Compounds by the Present Invention Protein (A1)

(1) Preparation of Plastid Fractions

A hundred grams (100 g) of Radish greens seeds (Takii Seed) were sawed into a dampened paper laboratory wipe in a tray, cultivated at 25° C. for 6 days in the dark and then cultivated for 4 hours under a fluorescent lamp. Thirty grams (30 g) of the newly greened cotyledons were ground with a Nissei AM-8 homoginizer (Nihonseiki Seisakusho; 18,000 to 20,000 rpm, 4° C., 5 seconds) in disruption buffer (1 mM magnesium chloride, 20 mM N-tris (hydroxymethyl)methyl-2-aminoethanesulfonate, 10 mM N-2-hydroxyethylpiperidine-N'-2-ethanesulfonate, 0.5 mM EDTA, 5 mM cysteine, 0.5M sucrose; pH7.7). The obtained cell lysate solution was passed through 4 layers of nylon gause. The obtained solution was centrifuged (13,170×g, 4° C., 1 minute). The obtained residue fractions were suspended with 60 ml of disruption buffer and centrifuged (2,640×g, 4° C., 2 minutes). The residue fractions were resuspended in 10 ml of disruption buffer, were layered with the high density buffer (1 mM magnesium chloride, 20 mM N-tris(hydroxymethyl)methyl-2-aminoethanesulfonate, 30 mM N-2-hydroxyethylpiperidine-N'-2-ethanesulfonate, 0.5 mM EDTA, 5 mM cysteine, 0.6M sucrose; pH7.7) in a centrifuge tube, and were centrifuged (675×g, 4° C., 15 minutes). The residues were suspended in 3 ml of suspension buffer (1 mM magnesium chloride, 20 mM N-tris (hydroxymethyl)methyl-2-aminoethanesulfonate, 30 mM N-2-hydroxyethylpiperidine-N'-2-ethanesulfonate, 0.5 mM EDTA; pH7.7) and were designated as a plastid fraction.

(2) Metabolism of Compound (XII) by the Present Invention Protein (A1)

There was prepared 100 µl of a reaction solution of 50 mM potassium phosphate buffer (pH7.0) containing 5 ppm of compound (XII), 3 mM of 13-NADPH (hereinafter, referred to as "component A") (Oriental Yeast Company), 1 mg/ml of a ferredoxin derived from spinach (hereinafter referred to as "component B") (Sigma Company), 0.15 U/ml of ferredoxin reductase (hereinafter, referred to as "component C") (Sigma Company) and 20 µl of the supernatant fraction recovered in Example 4(2). The reaction solution was maintained at 30° C. for 10 minutes. Further, there was prepared and maintained similarly 100 µl of a reaction solution of a 50 mM potassium phosphate buffer (pH 7.0) having no addition of at least one component utilized in the composition of the above reaction solution, selected from component A, component B, component C and the supernatant fraction prepared in Example 4(2). Ten microliters (10 µl) of 2N HCl and 500 µl of ethyl acetate were added and mixed into each of the reaction solutions after the maintenance. The resulting reaction solutions were centrifuged at 8,000×g to recover 490 µl of the ethyl acetate layer. After drying the ethyl acetate layers under reduced pressure, the residue was dissolved in 100 µl of 50 mM of potassium phosphate buffer (pH7.0). Forty microliters (40 µl) of the fraction solutions (hereinafter, the fraction solution derived from the reaction solution containing component A, component B, component C and 20 µl of supernatant fraction recovered in Example 4(2) is referred to as "(XII) metabolism solution (A1);" further, the fraction solution derived from the reaction solution containing no component A, no component B, no component C and no supernatant fraction recovered in Example 4(2) is referred to as "(XII) control solution (A1)") were analyzed on a HPLC. Compared to the concentration of compound (XII) detected from (XII) control solution (A1), the concentration of compound (XII) detected from (XII) metabolism solution (A1) was lower. Further a peak, which was not detected from the (XII) control solution (A1), was detected from the (XII) metabolism solution (A1). Mass spectrometry was conducted for the compound contained in such a peak. The mass of the compound contained in such a peak was 14 smaller than the mass of compound (XII).

Twenty microliters (20 µl) of a 32-fold dilution of the above (XII) metabolism solution (A1) and 60 µl of the plastid fraction prepared in Example 41(1) were mixed. In darkened conditions, 20 µl of substrate solution (10 mM adenosine triphosphate, 5 mM aminolevulinic acid, 4 mM glutathion reductase and 0.6 mM NAD+; pH6.5; hereinafter, such a substrate solution is referred to as "PPO substrate solution") were added and maintained at 30° C. for 1.5 hours. Further, instead of said 20 µl of the 32-fold dilution of (XII) metabolism solution (A1), a reaction solution to which 20 µl of the 32-fold dilution of (XII) control solution (A1) was added was prepared, and the PPO substrate solution was added and maintained similarly. Three hundred (300 µl) of a dimethylsulfoxide-methanol mixture (dimethylsulfoxide: methanol=7:3) was added to each of the reaction solutions after the maintenance and centrifuged (8000×g, 4° C., 10 minutes). The supernatants were recovered and were subjected to reverse phase HPC analysis under the analysis conditions below to measure the amount of PPIX. The PPIX amount in the reaction solution to which (XII) metabolism solution (A1) was added was more than the PPIX amount in the reaction solution to which (XII) control solution (A1) was added.
(HPLC Analysis Condition 2)
column: SUMIPAX ODS212 (Sumika Chemical Analysis Service)
flow rate: 2 ml/minute
detection wave length: fluorescent Ex:410 nm Em:630 nm
eluent:95:5 mixture of methanol and 1M ammonium acetate (pH5.7)
(3) Metabolism of Compound (XIII) by the Present Invention Protein (A1)

Other than utilizing 5 ppm of compound (XIII) instead of 5 ppm of compound (XII), reaction solutions were prepared and maintained similarly to the method described in Example 41(2). Similarly to Example 41(2), each of the reaction solutions after the maintenance was extracted with ethyl acetate and the obtained residues were dissolved in 100 µl of dimethylsulfoxide. The obtained solutions (hereinafter, the solution derived from the reaction solution containing component A, component B, component C and 20 µl of supernatant fraction recovered in Example 4(2) is referred to as "(XIII) metabolism solution (A1);" further, the solution derived from the reaction solution containing no component A, no component B, no component C and no supernatant fraction recovered in Example 4(2) is referred to as "(XIII) control solution (A1)") were analyzed on a HPLC under the above analysis condition 1. Compared to the concentration of compound (XIII) detected from (XIII) control solution (A1), the concentration of compound (XIII) detected from (XIII) metabolism solution (A1) was lower. Further a peak, which was not detected from the (XIII) control solution (A1), was detected from the (XIII) metabolism solution (A1). Mass spectrometry was conducted for the compound contained in such a peak. The mass of the compound contained in such a peak was 14 smaller than the mass of compound (XIII).

Twenty microliters (20 µl) of a 128-fold dilution of the above (XIII) metabolism solution (A1) and 60 µl of the plastid fraction were mixed. In darkened conditions, 20 µl of PPO substrate solution were added and maintained at 30° C. for 1.5 hours. Further, instead of said 20 µl of the 128-fold dilution of (XIII) metabolism solution (A1), a reaction solution to which 20 µl of the 128-fold dilution of (XIII) control solution (A1) was added was prepared, and the PPO substrate solution was added and maintained similarly. Similar to Example 41(2), each of the reaction solutions after the maintenance were prepared and subjected to reverse phase HPLC analysis under the above analysis condition 2 to measure the amount of PPIX. The PPIX amount in the reaction solution to which (XIII) metabolism solution (A1) was added was more than the PPIX amount in the reaction solution to which (XIII) control solution (A1) was added.
(4) Metabolism of Compound (XVI) by the Present Invention Protein (A1)

Other than utilizing 12.5 ppm of compound (XVI) instead of 5 ppm of compound (XII), reaction solutions were prepared and maintained similarly to the method described in Example 41(2). Similarly to Example 41(2), each of the reaction solutions after the maintenance was extracted with ethyl acetate and the obtained residues were dissolved in 200 µl of 50 mM potassium phosphate buffer (pH7.0). The obtained solutions (hereinafter, the solution derived from the reaction solution containing component A, component B, component C and 20 µl of supernatant fraction recovered in Example 4(2) is referred to as "(XVI) metabolism solution (A1);" further, the solution derived from the reaction solution containing no component A, no component B, no component C and no supernatant fraction recovered in Example 4(2) is referred to as "(XVI) control solution (A1)") were analyzed on a HPLC under the above analysis condition 1. Compared to the concentration of compound (XVI) detected from (XVI) control solution (A1), the concentration of compound (XVI) detected from (XVI) metabolism solution (A1) was lower. Further a peak, which was not detected from the (XVI) control solution (A1), was detected from the (XVI) metabolism solution (A1).

Twenty microliters (20 µl) of a 8-fold dilution of the above (XVI) metabolism solution (A1) and 60 µl of the plastid fraction were mixed. In darkened conditions, 20 µl of PPO substrate solution were added and maintained at 30° C. for 1.5 hours. Further, instead of said 20 µl of the 8-fold dilution of (XVI) metabolism solution (A1), a reaction solution to which 20 μl of the 8-fold dilution of (XVI) control solution (A1) was added was prepared, and the PPO substrate solution was added and maintained similarly. Similar to Example 41(2), each of the reaction solutions after the maintenance were prepared and subjected to reverse phase HPLC analysis under the above analysis condition 2 to measure the amount of PPIX. The PPIX amount in the reaction solution to which (XVI) metabolism solution (A1) was added was more than the PPIX amount in the reaction solution to which (XVI) control solution (A1) was added.

(5) Metabolism of Compound (XVII) by the Present Invention Protein (A1)

Other than utilizing 12.5 ppm of compound (XVII) instead of 5 ppm of compound (XII), reaction solutions were prepared and maintained similarly to the method described in Example 41(2). Similarly to Example 41(2), each of the reaction solutions after the maintenance was extracted with ethyl acetate and the obtained residues were dissolved in 200 μl of 50 mM potassium phosphate buffer (pH7.0). The obtained solutions (hereinafter, the solution derived from the reaction solution containing component A, component B, component C and 20 μl of supernatant fraction recovered in Example 4(2) is referred to as "(XVII) metabolism solution (A1);" further, the solution derived from the reaction solution containing no component A, no component B, no component C and no supernatant fraction recovered in Example 4(2) is referred to as "(XVII) control solution (A1)") were analyzed on a HPLC under the above analysis condition 1. Compared to the concentration of compound (XVII) detected from (XVII) control solution (A1), the concentration of compound (XVII) detected from (XVII) metabolism solution (A1) was lower. Further a peak, which was not detected from the (XVII) control solution (A1), was detected from the (XVII) metabolism solution (A1).

Twenty microliters (20 μl) of a 32-fold dilution of the above (XVII) metabolism solution (A1) and 60 μl of the plastid fraction were mixed. In darkened conditions, 20 μl of PPO substrate solution were added and maintained at 30° C. for 1.5 hours. Further, instead of said 20 μl of the 32-fold dilution of (XVII) metabolism solution (A1), a reaction solution to which 20 μl of the 32-fold dilution of (XVII) control solution (A1) was added was prepared, and the PPO substrate solution was added and maintained similarly. Similar to Example 41(2), each of the reaction solutions after the maintenance were prepared and subjected to reverse phase HPLC analysis under the above analysis condition 2 to measure the amount of PPIX. The PPIX amount in the reaction solution to which (XVII) metabolism solution (A1) was added was more than the PPIX amount in the reaction solution to which (XVII) control solution (A1) was added.

(6) Metabolism of Compound (VI) by the Present Invention Protein (A1)

E. coli JM109/pKSN657F was cultured overnight at 37° C. in 3 ml of TB medium containing 50 μg/ml of ampicillin. A milliliter (1 ml) of the obtained culture medium was transferred to 100 ml of TB medium containing 50 μg/ml of ampicillin and cultured at 26° C. When OD660 reached about 0.5, 5-aminolevulinic acid was added to the final concentration of 500 μM, and the culturing was continued. Thirty (30) minutes thereafter, IPTG was added to a final concentration of 1 mM, and there was further culturing for 20 hours.

The cells were recovered from the culture medium, washed with 0.1M tris-HCl buffer (pH7.5) and suspended in 10 ml of 0.1M Tris-HCl buffer containing 1% glucose. Compound (VI) was added to the obtained cell suspension to a final concentration of 100 ppm and that was incubated with shaking at 30° C. At each of 0 hours after and 1 day after the start of shaking, 2 ml of the cell suspension were fractioned. Fifty microliters (50 μl) of 2N HCl were added to each and those were extracted with 2 ml of ethyl acetate. The obtained ethyl acetate layers were analyzed on a HPLC under reaction condition 1. Compared to the concentration of compound (VI) detected from the ethyl acetate layer prepared from the cell suspension at 0 hours after the start of shaking, the concentration of compound (VI) detected from the ethyl acetate later prepared from the cell suspension at 1 day after the start of shaking was lower. Further a peak, which was not detected from the ethyl acetate layer prepared from the cell suspension at 0 hours after the start of shaking, was detected from the ethyl acetate layer prepared from the cell suspension at 1 day after the start of shaking Mass spectrometry of the compound contained in said peak was conducted. The mass of the compound contained in said peak was 14 less than the mass of compound (VI).

(7) Metabolism of Compound (VIII) by the Present Protein (A1)

Other than utilizing compound (VIII) instead of compound (VI), there was conducted in accordance with the method described in Example 41(6), a culturing of E. coli JM109/pKSN657F, preparation of the cell suspension solution, incubation with shaking of the cell suspension solution to which compound (VIII) was added, reagent preparation from the cell suspension solution and HPLC analysis of the reagents. Compared to the concentration of compound (VIII) detected from the ethyl acetate layer prepared from the cell suspension at 0 hours after the start of shaking, the concentration of compound (VIII) detected from the ethyl acetate layer prepared from the cell suspension at 1 day after the start of shaking was lower. Further two peaks, which were not detected from the ethyl acetate layer prepared from the cell suspension at 0 hours after the start of shaking, were detected from the ethyl acetate layer prepared from the cell suspension at 1 day after the start of shaking Mass spectrometry of the compounds contained in said peaks were conducted. The mass of the compound contained in one of said peaks was 14 less and the mass of the compound contained in the other peak was 28 less than the mass of compound (VIII).

(8) Metabolism of Compound (X) by the Present Invention Protein (A1)

Other than utilizing compound (X) instead of compound (VI), there was conducted in accordance with the method described in Example 41(6), a culturing of E. coli JM109/pKSN657F, preparation of the cell suspension solution, shake culturing of the cell suspension solution to which compound (X) was added, reagent preparation from the cell suspension solution and HPLC analysis of the reagents. Compared to the concentration of compound (X) detected from the ethyl acetate layer prepared from the cell suspension at 0 hours after the start of shaking, the concentration of compound (X) detected from the ethyl acetate later prepared from the cell suspension at 1 day after the start of shaking was lower. Further two peaks, which were not detected from the ethyl acetate layer prepared from the cell suspension at 0 hours after the start of shaking, were detected from the ethyl acetate layer prepared from the cell suspension at 1 day after the start of shaking Mass spectrometry of the compounds contained in said peaks was conducted. The mass of the compound contained in one of said peaks was 40 less and the mass of the compound contained in the other peak was 54 less than the mass of compound (X).

(9) Metabolism of Compound (XI) by the Present Invention Protein (A1)

Other than utilizing compound (XI) instead of compound (VI), there was conducted in accordance with the method described in Example 41(6), a culturing of *E. coli* JM109/pKSN657F, preparation of the cell suspension solution, shake culturing of the cell suspension solution to which compound (XI) was added, reagent preparation from the cell suspension solution and HPLC analysis of the reagents. Compared to the concentration of compound (XI) detected from the ethyl acetate layer prepared from the cell suspension at 0 hours after the start of shaking, the concentration of compound (XI) detected from the ethyl acetate layer prepared from the cell suspension at 1 day after the start of shaking was lower. Further two peaks, which were not detected from the ethyl acetate layer prepared from the cell suspension at 0 hours after the start of shaking, were detected from the ethyl acetate layer prepared from the cell suspension at 1 day after the start of shaking Mass spectrometry of the compounds contained in said peaks was conducted. The mass of the compound contained in one of said peaks was 14 less and the mass of the compound contained in the other peak was 16 less than the mass of compound (XI).

Example 42

Metabolism of Compounds by the Present Invention Protein (A11)

(1) Metabolism of Compound (X) by the Present Invention Compound (A11)

Each of *E. coli* JM109/pKSN849AF and *E. coli* JM109/pKSN2 was cultured overnight at 37° C. in 3 ml of TB culture containing 50 µg/ml of ampicillin. A milliliter (1 ml) of the obtained culture mediums was transferred to 100 ml of TB medium containing 50 µg/ml of ampicillin and cultured at 26° C. When OD660 reached about 0.5, 5-aminolevulinic acid was added to the final concentration of 500 µM, and the culturing was continued. Thirty (30) minutes thereafter, IPTG was added to a final concentration of 1 mM, and there was further culturing for 18 hours.

The cells were recovered from the culture medium, washed with 0.1M tris-HCl buffer (pH7.5) and suspended in 10 ml of 0.1M Tris-HCl buffer containing 1% glucose. Compound (X) was added to the obtained cell suspension to a final concentration of 25 ppm and that was incubated with shaking at 30° C. At each of 0 hours after and 4 days after the start of shaking, 2 ml of the cell suspension were fractioned. Fifty microliters (50 µl) of 2N HCl were added to each and those were extracted with 2 ml of ethyl acetate. The obtained ethyl acetate layers were analyzed on a HPLC under reaction condition 1. Compared to the concentration of compound (X) detected from the ethyl acetate layer prepared from the JM109/pKSN2 cell suspension, the concentration of compound (X) detected from the ethyl acetate layer prepared from the JM109/pKSN849AF cell suspension was lower. Further 3 peaks, which were not detected from the ethyl acetate layer prepared from the JM109/pKSN2 cell suspension, were detected from the ethyl acetate layer prepared from the JM109/pKSN849AF cell suspension. Of the 3 peaks, the elution time in the HPLC of 1 of the peaks matched with the elution time of a peak of a compound that has a mass of 40 less than compound (X) detected in Example 41(8). Further, the elution time in the HPLC of another peak matched with the elution time of a peak of a compound that has a mass of 54 less than compound (X) detected in Example 41(8).

After drying, respectively, 1 ml of the ethyl acetate layer prepared from the above JM109/pKSN2 cell suspension and 1 ml of the ethyl acetate layer prepared from the above JM109/pKSN849AF cell suspension, the residues were dissolved in 1 ml of dimethylsulfoxide (hereinafter, the solution derived from the ethyl acetate layer prepared from JM109/pKSN849AF is referred to as "(X) metabolism solution (A11);" further, the solution derived from the ethyl acetate layer prepared from JM109/pKSN2 cell suspension is referred to as "(X) control solution (A11)").

Twenty microliters (20 µl) of a 128-fold dilution of the above (X) metabolism solution (A11) and 60 µl of the plastid fraction were mixed. In darkened conditions, 20 µl of PPO substrate solution were added and maintained at 30° C. for 1.5 hours. Further, instead of said 20 µl of the 128-fold dilution of (X) metabolism solution (A11), a reaction solution to which 20 µl of the 128-fold dilution of (X) control solution (A11) was added was prepared, and the PPO substrate solution was added and maintained similarly. Similar to Example 41(2), each of the reaction solutions after the maintenance were prepared and subjected to reverse phase HPLC analysis under the above analysis condition 2 to measure the amount of PPIX. The PPIX amount in the reaction solution to which (X) metabolism solution (A11) was added was more than the PPIX amount in the reaction solution to which (X) control solution (A11) was added.

(2) Metabolism of Compound (XII) by the Present Invention Protein (A11)

Other than utilizing 20 µl of the supernatant fraction recovered in Example 32(2) instead of 20 µl of the supernatant fraction recovered in Example 4(2), the reaction solutions were prepared and maintained in accordance with the method described in Example 41(2). Similar to Example 41(2), each of the reaction solutions after the maintenance was extracted with ethyl acetate and the obtained residue was dissolved in 100 µl of 50 mM potassium phosphate buffer (pH7.0). The obtained solutions (hereinafter, the solution derived from the reaction solution containing component A, component B, component C and 20 µl of supernatant fraction recovered in Example 32(2) is referred to as "(XII) metabolism solution (A11);" further, the solution derived from the reaction solution containing no component A, no component B, no component C and no supernatant fraction recovered in Example 32(2) is referred to as "(XII) control solution (A11)") were analyzed on a HPLC under the above analysis condition 1. Compared to the concentration of compound (XII) detected from (XII) control solution (A11), the concentration of compound (XII) detected from (XII) metabolism solution (A11) was lower. Further a peak, which was not detected from the (XII) control solution (A11), was detected from the (XII) metabolism solution (A11). The elution time of said peak on the HPLC matched an elution time of a peak of a compound in which the mass is 14 less than said compound (XII) detected from (XII) metabolism solution (A1) in Example 41(2).

(3) Metabolism of Compound (XIII) by the Present Invention Protein (A11)

Other than utilizing 20 µl of the supernatant fraction recovered in Example 32(2) instead of 20 µl of the supernatant fraction recovered in Example 4(2), the reaction solutions were prepared and maintained in accordance with the method described in Example 41(3). Similar to Example 41(2), each of the reaction solutions after the maintenance was extracted with ethyl acetate and the obtained residue was dissolved in 100 µl of dimethylsulfoxide. The obtained solutions (hereinafter, the solution derived from the reaction solution containing component A, component B, component C and 20 µl of supernatant fraction recovered in Example 32(2) is referred to as "(XIII) metabolism solution (A11);" further, the solution derived from the reaction solution containing no component A, no component B, no component C and no supernatant fraction recovered in Example 32(2) is referred to as "(XIII)

control solution (A11)") were analyzed on a HPLC under the above analysis condition 1. Compared to the concentration of compound (XIII) detected from (XIII) control solution (A11), the concentration of compound (XIII) detected from (XIII) metabolism solution (A11) was lower. Further a peak, which was not detected from the (XIII) control solution (A11), was detected from the (XIII) metabolism solution (A11). The elution time of said peak on the HPLC matched an elution time of a peak of a compound in which the mass is 14 less than said compound (XIII) detected from (XIII) metabolism solution (A11) in Example 41(3).

(4) Metabolism of Compound (XVI) by the Present Invention Protein (A11)

Other than utilizing 20 µl of the supernatant fraction recovered in Example 32(2) instead of 20 µl of the supernatant fraction recovered in Example 4(2), the reaction solutions were prepared and maintained in accordance with the method described in Example 41(4). Similar to Example 41(2), each of the reaction solutions after the maintenance was extracted with ethyl acetate and the obtained residue was dissolved in 200 µl of 50 mM potassium phosphate buffer (pH7.0). The obtained solutions (hereinafter, the solution derived from the reaction solution containing component A, component B, component C and 20 µl of supernatant fraction recovered in Example 32(2) is referred to as "(XVI) metabolism solution (A11);" further, the solution derived from the reaction solution containing no component A, no component B, no component C and no supernatant fraction recovered in Example 32(2) is referred to as "(XVI) control solution (A11)") were analyzed on a HPLC under the above analysis condition 1. Compared to the concentration of compound (XVI) detected from (XVI) control solution (A11), the concentration of compound (XVI) detected from (XVI) metabolism solution (A11) was lower. Further a peak, which was not detected from the (XVI) control solution (A11), was detected from the (XVI) metabolism solution (A11). The elution time of said peak on the HPLC matched an elution time of a peak in Example 41(4) which was detected from (XVI) metabolism solution (A11) and not detected in (XVI) control solution (A11).

(5) Metabolism of Compound (XVII) by the Present Invention Protein (A11)

Other than utilizing 20 µl of the supernatant fraction recovered in Example 32(2) instead of 20 µl of the supernatant fraction recovered in Example 4(2), the reaction solutions were prepared and maintained in accordance with the method described in Example 41(5). Similar to Example 41(2), each of the reaction solutions after the maintenance was extracted with ethyl acetate and the obtained residue was dissolved in 200 µl of 50 mM potassium phosphate buffer (pH7.0). The obtained solutions (hereinafter, the solution derived from the reaction solution containing component A, component B, component C and 20 µl of supernatant fraction recovered in Example 32(2) is referred to as "(XVII) metabolism solution (A11);" further, the solution derived from the reaction solution containing no component A, no component B, no component C and no supernatant fraction recovered in Example 32(2) is referred to as "(XVII) control solution (A11)") were analyzed on a HPLC under the above analysis condition 1. Compared to the concentration of compound (XVII) detected from (XVII) control solution (A11), the concentration of compound (XVII) detected from (XVII) metabolism solution (A11) was lower. Further a peak, which was not detected from the (XVII) control solution (A11), was detected from the (XVII) metabolism solution (A11). The elution time of said peak on the HPLC matched an elution time of a peak in Example 41(5) which was detected from (XVII) metabolism solution (A1) and not detected in (XVII) control solution (A1).

Example 43

Metabolism of Compounds by the Present Invention Protein (A2), (A3), (A12), (A13), (A14) or (A15) or the Present Protein (A10)

(1) Metabolism of Compound (XII) by the Present Invention Protein (A2)

Other than utilizing 20 µl of the supernatant fraction recovered in Example 7(2) instead of 20 µl of the supernatant fraction recovered in Example 4(2), the reaction solutions were prepared and maintained in accordance with the method described in Example 41(2). Similar to Example 41(2), each of the reaction solutions after the maintenance was extracted with ethyl acetate and the obtained residue was dissolved in 100 µl of 50 mM potassium phosphate buffer (pH7.0). The obtained solutions (hereinafter, the solution derived from the reaction solution containing component A, component B, component C and 20 µl of supernatant fraction recovered in Example 7(2) is referred to as "(XII) metabolism solution (A2);" further, the solution derived from the reaction solution containing no component A, no component B, no component C and no supernatant fraction recovered in Example 7(2) is referred to as "(XII) control solution (A2)") were analyzed on a HPLC under the above analysis condition 1. Compared to the concentration of compound (XII) detected from (XII) control solution (A2), the concentration of compound (XII) detected from (XII) metabolism solution (A2) was lower. Further a peak, which was not detected from the (XII) control solution (A2), was detected from the (XII) metabolism solution (A2). The elution time of said peak on the HPLC matched an elution time of a peak of a compound in which the mass is 14 less than said compound (XII) detected from (XII) metabolism solution (A1) in Example 41(2).

(2) Metabolism of Compound (XII) by the Present Invention Protein (A3)

Other than utilizing 20 µl of the supernatant fraction recovered in Example 12(2) instead of 20 µl of the supernatant fraction recovered in Example 4(2), the reaction solutions were prepared and maintained in accordance with the method described in Example 41(2). Similar to Example 41(2), each of the reaction solutions after the maintenance was extracted with ethyl acetate and the obtained residue was dissolved in 100 µl of 50 mM potassium phosphate buffer (pH7.0). The obtained solutions (hereinafter, the solution derived from the reaction solution containing component A, component B, component C and 20 µl of supernatant fraction recovered in Example 12(2) is referred to as "(XII) metabolism solution (A3);" further, the solution derived from the reaction solution containing no component A, no component B, no component C and no supernatant fraction recovered in Example 7(2) is referred to as "(XII) control solution (A3)") were analyzed on a HPLC under the above analysis condition 1. Compared to the concentration of compound (XII) detected from (XII) control solution (A3), the concentration of compound (XII) detected from (XII) metabolism solution (A3) was lower. Further a peak, which was not detected from the (XII) control solution (A3), was detected from the (XII) metabolism solution (A3). The elution time of said peak on the HPLC matched an elution time of a peak of a compound in which the mass is 14 less than said compound (XII) detected from (XII) metabolism solution (A1) in Example 41(2).

(3) Metabolism of Compound (XII) by the Present Protein (A10)

Other than utilizing 20 μl of the supernatant fraction recovered in Example 10(2) instead of 20 μl of the supernatant fraction recovered in Example 4(2), the reaction solutions were prepared and maintained in accordance with the method described in Example 41(2). Similar to Example 41(2), each of the reaction solutions after the maintenance was extracted with ethyl acetate and the obtained residue was dissolved in 100 μl of 50 mM potassium phosphate buffer (pH7.0). The obtained solutions (hereinafter, the solution derived from the reaction solution containing component A, component B, component C and 20 μl of supernatant fraction recovered in Example 10(2) is referred to as "(XII) metabolism solution (A10);" further, the solution derived from the reaction solution containing no component A, no component B, no component C and no supernatant fraction recovered in Example 12(3) is referred to as "(XII) control solution (A10)") were analyzed on a HPLC under the above analysis condition 1. Compared to the concentration of compound (XII) detected from (XII) control solution (A10), the concentration of compound (XII) detected from (XII) metabolism solution (A10) was lower. Further a peak, which was not detected from the (XII) control solution (A10), was detected from the (XII) metabolism solution (A10). The elution time of said peak on the HPLC matched an elution time of a peak of a compound in which the mass is 14 less than said compound (XII) detected from (XII) metabolism solution (A1) in Example 41(2).

(4) Metabolism of Compound (XII) by the Present Invention Protein (A12)

Other than utilizing 20 μl of the supernatant fraction recovered in Example 34(2) instead of 20 μl of the supernatant fraction recovered in Example 4(2), the reaction solutions were prepared and maintained in accordance with the method described in Example 41(2). Similar to Example 41(2), each of the reaction solutions after the maintenance was extracted with ethyl acetate and the obtained residue was dissolved in 100 μl of 50 mM potassium phosphate buffer (pH7.0). The obtained solutions (hereinafter, the solution derived from the reaction solution containing component A, component B, component C and 20 μl of supernatant fraction recovered in Example 34(2) is referred to as "(XII) metabolism solution (A12);" further, the solution derived from the reaction solution containing no component A, no component B, no component C and no supernatant fraction recovered in Example 34(2) is referred to as "(XII) control solution (A12)") were analyzed on a HPLC under the above analysis condition 1. Compared to the concentration of compound (XII) detected from (XII) control solution (A12), the concentration of compound (XII) detected from (XII) metabolism solution (A12) was lower. Further a peak, which was not detected from the (XII) control solution (A12), was detected from the (XII) metabolism solution (A12). The elution time of said peak on the HPLC matched an elution time of a peak of a compound in which the mass is 14 less than said compound (XII) detected from (XII) metabolism solution (A1) in Example 41(2).

(5) Metabolism of Compound (XII) by the Present Invention Protein (A13)

Other than utilizing 20 μl of the supernatant fraction recovered in Example 36(2) instead of 20 μl of the supernatant fraction recovered in Example 4(2), the reaction solutions were prepared and maintained in accordance with the method described in Example 41(2). Similar to Example 41(2), each of the reaction solutions after the maintenance was extracted with ethyl acetate and the obtained residue was dissolved in 100 μl of 50 mM potassium phosphate buffer (pH7.0). The obtained solutions (hereinafter, the solution derived from the reaction solution containing component A, component B, component C and 20 μl of supernatant fraction recovered in Example 36(2) is referred to as "(XII) metabolism solution (A13);" further, the solution derived from the reaction solution containing no component A, no component B, no component C and no supernatant fraction recovered in Example 36(2) is referred to as "(XII) control solution (A13)") were analyzed on a HPLC under the above analysis condition 1. Compared to the concentration of compound (XII) detected from (XII) control solution (A13), the concentration of compound (XII) detected from (XII) metabolism solution (A13) was lower. Further a peak, which was not detected from the (XII) control solution (A13), was detected from the (XII) metabolism solution (A13). The elution time of the said peak on the HPLC matched an elution time of a peak of a compound in which the mass is 14 less than said compound (XII) detected from (XII) metabolism solution (A1) in Example 41(2).

(6) Metabolism of Compound (XII) by the Present Invention Protein (A14)

Other than utilizing 20 μl of the supernatant fraction recovered in Example 38(2) instead of 20 μl of the supernatant fraction recovered in Example 4(2), the reaction solutions were prepared and maintained in accordance with the method described in Example 41(2). Similar to Example 41(2), each of the reaction solutions after the maintenance was extracted with ethyl acetate and the obtained residue was dissolved in 100 μl of 50 mM potassium phosphate buffer (pH7.0). The obtained solutions (hereinafter, the solution derived from the reaction solution containing component A, component B, component C and 20 μl of supernatant fraction recovered in Example 38(2) is referred to as "(XII) metabolism solution (A14);" further, the solution derived from the reaction solution containing no component A, no component B, no component C and no supernatant fraction recovered in Example 38(2) is referred to as "(XII) control solution (A14)") were analyzed on a HPLC under the above analysis condition 1. Compared to the concentration of compound (XII) detected from (XII) control solution (A14), the concentration of compound (XII) detected from (XII) metabolism solution (A14) was lower. Further a peak, which was not detected from the (XII) control solution (A14), was detected from the (XII) metabolism solution (A14). The elution time of said peak on the HPLC matched an elution time of a peak of a compound in which the mass is 14 less than said compound (XII) detected from (XII) metabolism solution (A1) in Example 41(2).

(7) Metabolism of compound (XII) by the present invention protein (A15)

Other than utilizing 20 μl of the supernatant fraction recovered in Example 40(2) instead of 20 μl of the supernatant fraction recovered in Example 4(2), the reaction solutions were prepared and maintained in accordance with the method described in Example 41(2). Similar to Example 41(2), each of the reaction solutions after the maintenance was extracted with ethyl acetate and the obtained residue was dissolved in 100 μl of 50 mM potassium phosphate buffer (pH7.0). The obtained solutions (hereinafter, the solution derived from the reaction solution containing component A, component B, component C and 20 μl of supernatant fraction recovered in Example 40(2) is referred to as "(XII) metabolism solution (A15);" further, the solution derived from the reaction solution containing no component A, no component B, no component C and no supernatant fraction recovered in Example 40(2) is referred to as "(XII) control solution (A15)") were analyzed on a HPLC under the above analysis condition 1.

Compared to the concentration of compound (XII) detected from (XII) control solution (A15), the concentration of compound (XII) detected from (XII) metabolism solution (A15) was lower. Further a peak, which was not detected from the (XII) control solution (A15), was detected from the (XII) metabolism solution (A15). The elution time of said peak on the HPLC matched an elution time of a peak of a compound in which the mass is 14 less than said compound (XII) detected from (XII) metabolism solution (A1) in Example 41(2).

(8) Metabolism of Compound (XIII) by the Present Invention Protein (A2)

Other than utilizing 20 µl of the supernatant fraction recovered in Example 7(2) instead of 20 µl of the supernatant fraction recovered in Example 4(2), the reaction solutions were prepared and maintained in accordance with the method described in Example 41(3). Similar to Example 41(2), each of the reaction solutions after the maintenance was extracted with ethyl acetate and the obtained residue was dissolved in 100 µl of dimethylsulfoxide. The obtained solutions (hereinafter, the solution derived from the reaction solution containing component A, component B, component C and 20 µl of supernatant fraction recovered in Example 7(2) is referred to as "(XIII) metabolism solution (A2);" further, the solution derived from the reaction solution containing no component A, no component B, no component C and no supernatant fraction recovered in Example 7(2) is referred to as "(XIII) control solution (A2)") were analyzed on a HPLC under the above analysis condition 1. Compared to the concentration of compound (XIII) detected from (XIII) control solution (A2), the concentration of compound (XIII) detected from (XIII) metabolism solution (A2) was lower. Further a peak, which was not detected from the (XIII) control solution (A2), was detected from the (XIII) metabolism solution (A2). The elution time of said peak on the HPLC matched an elution time of a peak of a compound in which the mass is 14 less than said compound (XIII) detected from (XIII) metabolism solution (A1) in Example 41(3).

(9) Metabolism of Compound (XIII) by the Present Invention Protein (A3)

Other than utilizing 20 µl of the supernatant fraction recovered in Example 12(2) instead of 20 µl of the supernatant fraction recovered in Example 4(2), the reaction solutions were prepared and maintained in accordance with the method described in Example 41(3). Similar to Example 41(2), each of the reaction solutions after the maintenance was extracted with ethyl acetate and the obtained residue was dissolved in 100 µl of dimethylsulfoxide. The obtained solutions (hereinafter, the solution derived from the reaction solution containing component A, component B, component C and 20 µl of supernatant fraction recovered in Example 12(2) is referred to as "(XIII) metabolism solution (A3);" further, the solution derived from the reaction solution containing no component A, no component B, no component C and no supernatant fraction recovered in Example 12(2) is referred to as "(XIII) control solution (A3)") were analyzed on a HPLC under the above analysis condition 1. Compared to the concentration of compound (XIII) detected from (XIII) control solution (A3), the concentration of compound (XIII) detected from (XIII) metabolism solution (A3) was lower. Further a peak, which was not detected from the (XIII) control solution (A3), was detected from the (XIII) metabolism solution (A3). The elution time of said peak on the HPLC matched an elution time of a peak of a compound in which the mass is 14 less than said compound (XIII) detected from (XIII) metabolism solution (A1) in Example 41(3).

(10) Metabolism of Compound (XIII) by the Present Protein (A10)

Other than utilizing 20 µl of the supernatant fraction recovered in Example 10(2) instead of 20 µl of the supernatant fraction recovered in Example 4(2), the reaction solutions were prepared and maintained in accordance with the method described in Example 41(3). Similar to Example 41(2), each of the reaction solutions after the maintenance was extracted with ethyl acetate and the obtained residue was dissolved in 100 µl of dimethylsulfoxide. The obtained solutions (hereinafter, the solution derived from the reaction solution containing component A, component B, component C and 20 µl of supernatant fraction recovered in Example 10(2) is referred to as "(XIII) metabolism solution (A10);" further, the solution derived from the reaction solution containing no component A, no component B, no component C and no supernatant fraction recovered in Example 10(2) is referred to as "(XIII) control solution (A10)") were analyzed on a HPLC under the above analysis condition 1. Compared to the concentration of compound (XIII) detected from (XIII) control solution (A10), the concentration of compound (XIII) detected from (XIII) metabolism solution (A10) was lower. Further a peak, which was not detected from the (XIII) control solution (A10), was detected from the (XIII) metabolism solution (A10). The elution time of the said peak on the HPLC matched an elution time of a peak of a compound in which the mass is 14 less than said compound (XIII) detected from (XIII) metabolism solution (A1) in Example 41(3).

(11) Metabolism of Compound (XIII) by the Present Invention Protein (A12)

Other than utilizing 20 µl of the supernatant fraction recovered in Example 34(2) instead of 20 µl of the supernatant fraction recovered in Example 4(2), the reaction solutions were prepared and maintained in accordance with the method described in Example 41(3). Similar to Example 41(2), each of the reaction solutions after the maintenance was extracted with ethyl acetate and the obtained residue was dissolved in 100 µl of dimethylsulfoxide. The obtained solutions (hereinafter, the solution derived from the reaction solution containing component A, component B, component C and 20 µl of supernatant fraction recovered in Example 34(2) is referred to as "(XIII) metabolism solution (A12);" further, the solution derived from the reaction solution containing no component A, no component B, no component C and no supernatant fraction recovered in Example 34(2) is referred to as "(XIII) control solution (A12)") were analyzed on a HPLC under the above analysis condition 1. Compared to the concentration of compound (XIII) detected from (XIII) control solution (A12), the concentration of compound (XIII) detected from (XIII) metabolism solution (A12) was lower. Further a peak, which was not detected from the (XIII) control solution (A12), was detected from the (XIII) metabolism solution (A12). The elution time of said peak on the HPLC matched an elution time of a peak of a compound in which the mass is 14 less than said compound (XIII) detected from (XIII) metabolism solution (A1) in Example 41(3).

(12) Metabolism of Compound (XIII) by the Present Invention Protein (A13)

Other than utilizing 20 µl of the supernatant fraction recovered in Example 36(2) instead of 20 µl of the supernatant fraction recovered in Example 4(2), the reaction solutions were prepared and maintained in accordance with the method described in Example 41(3). Similar to Example 41(2), each of the reaction solutions after the maintenance was extracted with ethyl acetate and the obtained residue was dissolved in 100 µl of dimethylsulfoxide. The obtained solutions (hereinafter, the solution derived from the reaction solution containing component A, component B, component C and 20 µl of supernatant fraction recovered in Example 36(2) is referred to as "(XIII) metabolism solution (A13);" further, the solution derived from the reaction solution containing no component A, no component B, no component C and no supernatant fraction recovered in Example 36(2) is referred to as "(XIII) control solution (A13)") were analyzed on a HPLC under the above analysis condition 1. Compared to the concentration of compound (XIII) detected from (XIII) control solution (A13), the concentration of compound (XIII) detected from (XIII) metabolism solution (A13) was lower. Further a peak, which was not detected from the (XIII) control solution (A13), was detected from the (XIII) metabolism solution (A13). The elution time of said peak on the HPLC matched an elution time of a peak of a compound in which the mass is 14 less than said compound (XIII) detected from (XIII) metabolism solution (A1) in Example 41(3).

(13) Metabolism of Compound (XIII) by the Present Invention Protein (A14)

Other than utilizing 20 µl of the supernatant fraction recovered in Example 38(2) instead of 20 µl of the supernatant fraction recovered in Example 4(2), the reaction solution were prepared and maintained in accordance with the method described in Example 41(3). Similar to Example 41(2), each of the reaction solutions after the maintenance was extracted with ethyl acetate and the obtained residue was dissolved in 100 µl of dimethylsulfoxide. The obtained solutions (hereinafter, the solution derived from the reaction solution containing component A, component B, component C and 20 µl of supernatant fraction recovered in Example 38(2) is referred to as "(XIII) metabolism solution (A14);" further, the solution derived from the reaction solution containing no component A, no component B, no component C and no supernatant fraction recovered in Example 38(2) is referred to as "(XIII) control solution (A14)") were analyzed on a HPLC under the above analysis condition 1. Compared to the concentration of compound (XIII) detected from (XIII) control solution (A14), the concentration of compound (XIII) detected from (XIII) metabolism solution (A14) was lower. Further a peak, which was not detected from the (XIII) control solution (A14), was detected from the (XIII) metabolism solution (A14). The elution time of said peak on the HPLC matched an elution time of a peak of a compound in which the mass is 14 less than said compound (XIII) detected from (XIII) metabolism solution (A1) in Example 41(3).

(14) Metabolism of Compound (XIII) by the Present Invention Protein (A15)

Other than utilizing 20 µl of the supernatant fraction recovered in Example 40(2) instead of 20 µl of the supernatant fraction recovered in Example 4(2), the reaction solutions were prepared and maintained in accordance with the method described in Example 41(3). Similar to Example 41(2), each of the reaction solutions after the maintenance was extracted with ethyl acetate and the obtained residue was dissolved in 100 µl of dimethylsulfoxide. The obtained solutions (hereinafter, the solution derived from the reaction solution containing component A, component B, component C and 20 µl of supernatant fraction recovered in Example 40(2) is referred to as "(XIII) metabolism solution (A15);" further, the solution derived from the reaction solution containing no component A, no component B, no component C and no supernatant fraction recovered in Example 40(2) is referred to as "(XIII) control solution (A15)") were analyzed on a HPLC under the above analysis condition 1. Compared to the concentration of compound (XIII) detected from (XIII) control solution (A15), the concentration of compound (XIII) detected from (XIII) metabolism solution (A15) was lower. Further a peak, which was not detected from the (XIII) control solution (A15), was detected from the (XIII) metabolism solution (A15). The elution time of said peak on the HPLC matched an elution time of a peak of a compound in which the mass is 14 less than said compound (XIII) detected from (XIII) metabolism solution (A1) in Example 41(3).

Example 44

Preparation of the Present Invention Antibody (A) Recognizing the Present Invention Protein (A1) (Hereinafter Referred to as "Present Invention Antibody (A1)")

(1) Preparation of the Extract of an $E.$ $Coli$ Expressing the Present Invention Protein (A1)

In accordance with the method described in Example 4(2), $E.$ $coli$ JM109/pKSN657F, which expresses the present invention protein (A1), was pre-cultured overnight and then cultured in 1L of TB medium containing 50 µg/ml of ampicillin. After recovering and disrupting the cells, supernatant fractions ($E.$ $coli$ pKSN657F extract) were prepared from the obtained cell lysate solution.

(2) Purification of the Present Invention Protein (A1)

The present invention protein (A1) was purified according to the method described in Example 2(4) by subjecting the supernatant fraction obtained in Example 44(1) ($E.$ $coli$ pKSN657F extract) in turn to a Hiload HiLoad26/10 Q Sepharose HP column and then a Bio-Scale Ceramic Hydroxyapatite, Type I column CHT10-1 column. The purified fractions were analyzed on a 10% to 20% SDS-PAGE, to confirm that those were fractions of only the present invention protein (A1).

(3) Preparation of the Present Invention Antibody (A1)

The present invention protein (A1) prepared in Example 44(2) was dissolved in 0.05M potassium phosphate buffer (pH7.0) so that the concentration was 1 mg/ml. Forty microliters (40 µl) of RAS (MPL (Monophosphoryl lipid A)+TDM (Synthetic Trehalose Dicorynomycolate)+CWS (Cell Wall Skeleton) Adjuvant System (Sigma Company)) already incubated at 42° C. to 43° C. was added and well mixed into 2 ml of the obtained solution. The obtained mixture was administered, respectively, to New Zealand White rabbits (female, 14 weeks old, average of 2.4 kg) at 1 ml per rabbit. As such, 100 µl was injected subcutaneously at 10 locations on the back. About ½ of the amount of the first administration was administered after each of 3 weeks and 5 weeks. During such time, the antibody titer was measured by sampling the blood from a ear vein of the rabbit. Since the antibody titer increased after the third administration, the immunized rabbit at 2 weeks after the third administration was exsanguinated from the neck. The obtained blood was added into a Separapit Tube (Sekisui Chemical Company), incubated at 37° C. for 2 hours and was then centrifuged (3000 rpm, 20 minutes, room temperature). The antiserum (containing the present invention antibody (A1)) was obtained by recovering the supernatant.

Example 45

Detection of the Present Protein by the Present Invention Antibody (A1) and Detection of a Cell Expressing the Present Protein An immunoblot was conducted by utilizing the present invention antibody (A1) obtained in Example 44 with each of the $E.$ $coli$ extracts. There was a SDS polyacrylamide electrophoresis (40 mA, 1 hour) of: the $E.$ $coli$ pKSN657F extract obtained in Example 4(2) (containing about 0.5 pmol of the present invention protein (A1), containing about 0.78 mg of protein); the *E. coli* pKSN2 extract obtained in Example 4(2) (containing about 0.78 mg of protein) the *E. coli* pKSN923F extract obtained in Example 7(2) (containing about 2 pmol of the present invention protein (A2)); the *E. coli* pKSN671F extract obtained in Example 12(2) (containing about 2 pmol of the present invention protein (A3)); the *E. coli* pKSN646F extract obtained in Example 27(2) (containing about 2 pmol of the present invention protein (A4)); the *E. coli* pKSN11796F extract obtained in Example 10(2) (containing about 2 pmol of the present protein (A10)); the *E. coli* pKSN-SCA extract obtained in Example 14(2) (containing about 2 pmol of the present protein (A9)); the *E. coli* pKSN849AF extract obtained in Example 32(2) (containing about 2 pmol of the present invention protein (A11)); the *E. coli* pKSN1618F extract obtained in Example 34(2) (containing about 2 pmol of the present invention protein (A12)); the *E. coli* pKSN474F extract obtained in Example 36(2) (containing about 2 pmol of the present invention protein (A13)); the *E. coli* pKSN1491AF extract obtained in Example 38(2) (containing about 2 pmol of the present invention protein (A14)); and the *E. coli* pKSN1555AF extract obtained in Example 40(2) (containing about 2 pmol of the present invention protein (A15)). A PVDF membrane was placed on the gel. The proteins in the gel were transferred onto the PVDF membrane by a treatment with a BioRad blotting device at 4° C., 30V for 2 hours, while in the condition of being soaked in transfer buffer (25 mM Tris, 192 mM glycine, 10% methanol). After washing with TBS+Tween 20 solution (50 mM Tris-HCl (pH7.5), 200 mM NaCl, 0.05% Tween 20), the obtained PVDF membrane was incubated for 30 minutes in TBS+Tween 20 solution containing 3% BSA and was then utilized for a reaction with the above antiserum diluted 30,000 fold for 30 minutes in TBS+Tween 20 solution containing 3% BSA. After the reaction, the PVDF membrane was washed twice with TBS+Tween 20 solution. The PVDF membrane was then utilized for a reaction in TBS+Tween 20 solution containing 3% BSA for 30 minutes with a 3000 fold dilution of anti-rabbit IgG goat anti-serum labeled with alkaline phosphatase (Santa Cruz Biotechnology Company). After the reaction, the PVDF membrane was washed twice with TBS+Tween 20 solution and was soaked in NBT-BCIP solution (Sigma Company). There was detected a stain for a band corresponding to each of the present invention proteins (A1), (A2), (A3), (A4), (A11), (A12), (A13), (A14) and (A15) as well as the present proteins (A9) and (A10). No stained band was detected with the reagent of *E. coli* pKSN2 extract (containing about 0.78 mg of protein) obtained in Example 4(2).

Example 46

Preparation and Expression of the Present Invention DNA (A1) in which the Codon Usage has been Adjusted for Expression in Soybean (Hereinafter Referred to as the "Present Invention DNA (A1)S")

(1) Preparation of the Present Invention DNA (A1)S

PCR was conducted with Pyrobest DNA polymerase (Takara Shuzo Company) according to the attached manual, by utilizing a primer having a nucleotide sequence shown in SEQ ID NO: 192 and a primer having a nucleotide sequence shown in SEQ ID NO: 213. An aliquot of the obtained PCR product was utilized as a template for a PCR conducted similarly utilizing a primer having the nucleotide sequence shown in SEQ ID NO: 191 and a primer having the nucleotide sequence shown in SEQ ID NO: 212. Further, an aliquot of that PCR product was utilized as a template for a PCR conducted similarly utilizing a primer having the nucleotide sequence shown in SEQ ID NO: 190 and a primer having the nucleotide sequence shown in SEQ ID NO: 211. The obtained reaction solution was designated as reaction solution 1.

PCR was conducted with Pyrobest DNA polymerase (Takara Shuzo Company) according to the attached manual, by utilizing a primer having a nucleotide sequence shown in SEQ ID NO: 195 and a primer having a nucleotide sequence shown in SEQ ID NO: 210. An aliquot of the obtained PCR product was utilized as a template for a PCR conducted similarly utilizing a primer having the nucleotide sequence shown in SEQ ID NO: 194 and a primer having the nucleotide sequence shown in SEQ ID NO: 209. Further, an aliquot of that PCR product was utilized as a template for a PCR conducted similarly utilizing a primer having the nucleotide sequence shown in SEQ ID NO: 193 and a primer having the nucleotide sequence shown in SEQ ID NO: 208. The obtained reaction solution was designated as reaction solution 2.

PCR was conducted with Pyrobest DNA polymerase (Takara Shuzo Company) according to the attached manual by utilizing a primer having a nucleotide sequence shown in SEQ ID NO: 198 and a primer having a nucleotide sequence shown in SEQ ID NO: 207. An aliquot of the obtained PCR product was utilized as a template for a PCR conducted similarly utilizing a primer having the nucleotide sequence shown in SEQ ID NO: 197 and a primer having the nucleotide sequence shown in SEQ ID NO: 206. Further, an aliquot of that PCR product was utilized as a template for a PCR conducted similarly utilizing a primer having the nucleotide sequence shown in SEQ ID NO: 196 and a primer having the nucleotide sequence shown in SEQ ID NO: 205. The obtained reaction solution was designated as reaction solution 3.

PCR was conducted with Pyrobest DNA polymerase (Takara Shuzo Company) according to the attached manual, by utilizing a primer having a nucleotide sequence shown in SEQ ID NO: 201 and a primer having a nucleotide sequence shown in SEQ ID NO: 204. An aliquot of the obtained PCR product was utilized as a template for a PCR conducted similarly utilizing a primer having the nucleotide sequence shown in SEQ ID NO: 200 and a primer having the nucleotide sequence shown in SEQ ID NO: 203. Further, an aliquot of that PCR product was utilized as a template for a PCR conducted similarly utilizing a primer having the nucleotide sequence shown in SEQ ID NO: 199 and a primer having the nucleotide sequence shown in SEQ ID NO: 202. The obtained reaction solution was designated as reaction solution 4.

The reaction solutions 1 to 4 obtained in such a way were mixed. PCR was conducted with Pyrobest DNA polymerase (Takara Shuzo Company) according to the attached manual, by utilizing as a template an aliquot of the mixture thereof and by utilizing a primer having a nucleotide sequence shown in SEQ ID NO: 190 and a primer having a nucleotide sequence shown in SEQ ID NO: 202. The nucleotide sequence of the amplified DNA was confirmed. There was obtained a DNA having a sequence in which the nucleotide sequence 5'-cat-3' is connected upstream of the 5' terminus and the nucleotide sequence 5'-aagctt-3' is connected downstream of the 3' terminus of the nucleotide sequence shown in SEQ ID NO: 214.

The codon usage of the present invention DNA (A1) having the nucleotide sequence shown in SEQ ID NO: 6 (GC content of 70.58%) is shown in Table 22 and Table 23. The codon usage of soybean (GC content of 46.12%, Codon Usage Database published by Kazusa DNA Research Institute (http//:www.kazusa.or.jp/codon)) is shown in Table 24 and Table 25. The codon usage of the present invention DNA (A1) having the nucleotide sequence shown in SEQ ID NO: 214 (GC content of 51.59%) is shown in Table 26 and Table 27.

TABLE 22

| codon | % | codon | % |
|---|---|---|---|
| TTT | 0.00 | TCT | 0.00 |
| TTC | 3.18 | TCC | 1.71 |
| TTA | 0.00 | TCA | 0.00 |
| TTG | 1.22 | TCG | 2.20 |
| CTT | 0.00 | CCT | 0.00 |
| CTC | 3.67 | CCC | 4.16 |
| CTA | 0.00 | CCA | 0.00 |
| CTG | 7.09 | CCG | 2.69 |
| ATT | 0.24 | ACT | 0.24 |
| ATC | 4.16 | ACC | 2.69 |
| ATA | 0.00 | ACA | 0.24 |
| ATG | 2.69 | ACG | 1.96 |
| GTT | 0.24 | GCT | 0.00 |
| GTC | 3.67 | GCC | 7.58 |
| GTA | 0.00 | GCA | 0.49 |
| GTG | 3.18 | GCG | 3.42 |

TABLE 23

| codon | % | codon | % |
|---|---|---|---|
| TAT | 0.00 | TGT | 0.24 |
| TAC | 1.47 | TGC | 0.98 |
| TAA | 0.00 | TGA | 0.00 |
| TAG | 0.24 | TGG | 0.98 |
| CAT | 0.24 | CGT | 1.22 |
| CAC | 2.20 | CGC | 4.40 |
| CAA | 0.24 | CGA | 0.24 |
| CAG | 2.93 | CGG | 4.16 |
| AAT | 0.00 | AGT | 0.00 |
| AAC | 1.22 | AGC | 0.49 |
| AAA | 0.24 | AGA | 0.00 |
| AAG | 0.98 | AGG | 0.00 |
| GAT | 0.98 | GGT | 0.98 |
| GAC | 7.82 | GGC | 3.42 |
| GAA | 0.73 | GGA | 0.24 |
| GAG | 5.38 | GGG | 1.22 |

TABLE 24

| codon | % | codon | % |
|---|---|---|---|
| TTT | 2.03 | TCT | 1.71 |
| TTC | 2.09 | TCC | 1.21 |
| TTA | 0.82 | TCA | 1.45 |
| TTG | 2.21 | TCG | 0.44 |
| CTT | 2.36 | CCT | 2.00 |
| CTC | 1.66 | CCC | 1.01 |
| CTA | 0.82 | CCA | 2.05 |
| CTG | 1.22 | CCG | 0.40 |
| ATT | 2.61 | ACT | 1.78 |
| ATC | 1.64 | ACC | 1.49 |
| ATA | 1.27 | ACA | 1.51 |
| ATG | 2.27 | ACG | 0.41 |
| GTT | 2.67 | GCT | 2.81 |
| GTC | 1.24 | GCC | 1.69 |
| GTA | 0.73 | GCA | 2.27 |
| GTG | 2.20 | GCG | 0.59 |

TABLE 25

| codon | % | codon | % |
|---|---|---|---|
| TAT | 1.61 | TGT | 0.72 |
| TAC | 1.53 | TGC | 0.75 |
| TAA | 0.11 | TGA | 0.09 |
| TAG | 0.06 | TGG | 1.21 |
| CAT | 1.33 | CGT | 0.72 |
| CAC | 1.09 | CGC | 0.63 |
| CAA | 2.04 | CGA | 0.38 |
| CAG | 1.71 | CGG | 0.27 |
| AAT | 2.10 | AGT | 1.21 |
| AAC | 2.27 | AGC | 1.08 |
| AAA | 2.63 | AGA | 1.42 |
| AAG | 3.83 | AGG | 1.35 |
| GAT | 3.29 | GGT | 2.17 |
| GAC | 2.06 | GGC | 1.38 |
| GAA | 3.35 | GGA | 2.23 |
| GAG | 3.46 | GGG | 1.29 |

TABLE 26

| codon | % | codon | % |
|---|---|---|---|
| TTT | 1.71 | TCT | 0.98 |
| TTC | 1.47 | TCC | 0.73 |
| TTA | 0.98 | TCA | 0.98 |
| TTG | 2.93 | TCG | 0.24 |
| CTT | 3.18 | CCT | 2.44 |
| CTC | 2.20 | CCC | 1.22 |
| CTA | 0.98 | CCA | 2.69 |
| CTG | 1.71 | CCG | 0.49 |
| ATT | 2.20 | ACT | 1.71 |
| ATC | 1.22 | ACC | 1.47 |
| ATA | 0.98 | ACA | 1.47 |
| ATG | 2.69 | ACG | 0.49 |
| GTT | 2.93 | GCT | 4.16 |
| GTC | 1.22 | GCC | 2.69 |
| GTA | 0.73 | GCA | 3.67 |
| GTG | 2.20 | GCG | 0.98 |

TABLE 27

| codon | % | codon | % |
|---|---|---|---|
| TAT | 0.73 | TGT | 0.73 |
| TAC | 0.73 | TGC | 0.49 |
| TAA | 0.00 | TGA | 0.00 |
| TAG | 0.24 | TGG | 0.98 |
| CAT | 1.47 | CGT | 1.47 |
| CAC | 0.98 | CGC | 1.47 |
| CAA | 1.71 | CGA | 0.73 |
| CAG | 1.47 | CGG | 0.49 |
| AAT | 0.73 | AGT | 0.73 |
| AAC | 0.49 | AGC | 0.73 |
| AAA | 0.49 | AGA | 2.93 |
| AAG | 0.73 | AGG | 2.93 |
| GAT | 5.38 | GGT | 1.71 |
| GAC | 3.42 | GGC | 1.22 |
| GAA | 2.69 | GGA | 1.96 |
| GAG | 3.42 | GGG | 0.98 |

(2) Production of a Transformed *E. Coli* Having the Present Invention Protein (A1)S The DNA having the nucleotide sequence shown in SEQ ID NO: 214 obtained in Example 46(1) was digested with restriction enzymes NdeI and HindIII. The obtained DNA and the plasmid pKSN2 digested with NdeI and HindIII were ligated to obtain a plasmid in which the DNA having the nucleotide sequence shown in SEQ ID NO: 214 is inserted between the NdeI site and the HindIII site of pKSN2 (hereinafter referred to as "pKSN657 soy"). Said plasmid was introduced into *E. coli* JM109. The obtained *E. coli* transformant was designated JM109/pKSN657soy.

(3) Expression of the Present Invention Protein (A1) in *E. Coli* and Recovery of Said Protein Similarly to Example 4(2), each of *E. coli* JM109/pKSN657soy obtained in Example 46(2) and *E. coli* JM109/pKSN657 obtained in Example 4(1) was cultured. The cells were recovered. Cell lysate solutions were prepared. Under the method described in Example 4(2), supernatant fractions were prepared from the cell lysate solutions (hereinafter, the supernatant fraction obtained from *E. coli* JM109/pKSN657soy is referred to as "*E. coli* pKSN849soy extract" and the supernatant fraction obtained from *E. coli* JM109/pKSN657 is referred to as "*E. coli* pKSN657 extract"). The amount of P450 per the protein amount contained in *E. coli* pKSN657soy extract was compared to and was higher than the amount of P450 per the protein amount contained in *E. coli* pKSN657 extract.

Example 47

Introduction of the Present Invention DNA (A1)S into a Plant (1) Construction of a Chloroplast Expression Plasmid Containing the Present Invention DNA (A1)S for Direct Introduction—Part 1

A plasmid containing a chimeric DNA in which the present invention DNA (A1)S was connected immediately after the nucleotide sequence encoding the chloroplast transit peptide of soybean (cv. Jack) RuBPC small subunit without a change of frames in the codons was constructed as a plasmid for introducing the present invention DNA (A1)S into a plant with the particle gun method.

First, DNA comprising the nucleotide sequence shown in SEQ ID NO: 214 was amplified by PCR. The PCR was conducted by utilizing as a template pKSN657soy obtained in Example 46(2) and by utilizing as primers an oligonucleotide consisting of the nucleotide sequence shown in SEQ ID NO: 394 and an oligonucleotide consisting of the nucleotide sequence shown in SEQ ID NO: 395. The PCR utilized KOD-plus (Toyobo Company). The PCR carried out after conducting a maintenance at 94° C. for 2 minutes; 30 cycles of a cycle that included maintaining 94° C. for 30 seconds, followed by 50° C. for 30 seconds, and followed by 68° C. for 60 seconds; and a final maintenance at 68° C. for 30 seconds. The amplified DNA was recovered and purified with MagExtractor-PCR & Gel-Clean up (Toyobo Company) by conducting the procedures according to the attached manual. After digesting the purified DNA with restriction enzymes EcoT22I and SacI, the DNA comprising the nucleotide sequence shown in SEQ ID NO: 214 was recovered. After digesting plasmid pUCrSt657 obtained in Example 16(2) with restriction enzymes EcoT22I and SacI, there was isolated a DNA of about 2.9 kbp having a nucleotide sequence derived from pUC19 and a sequence encoding a chloroplast transit peptide of soybean (cv. Jack) RuBPC small subunit. The obtained DNA and the above DNA comprising the nucleotide sequence shown in SEQ ID NO: 214 were ligated to obtain pUCrSt657soy (FIG. 48) containing a chimeric DNA in which the present invention DNA (A1)S was connected immediately after the nucleotide sequence encoding the chloroplast transit peptide of soybean (cv. Jack) RuBPC small subunit without a change of frames in the codons.

The obtained plasmid pUCrSt657soy was digested with restriction enzymes BamHI and SacI to isolate a DNA comprising a nucleotide sequence shown in SEQ ID NO: 214. Said DNA was inserted between the restriction enzyme site of BglII and the restriction enzyme site of SacI of plasmid pNdG6-ΔT obtained in Example 16(2) to obtain plasmid pSUM-NdG6-rSt-657soy (FIG. 49) wherein the CR16G6 promoter has connected downstream the chimeric DNA in which the present invention DNA (A1)S was connected immediately after the nucleotide sequence encoding the chloroplast transit peptide of soybean (cv. Jack) RuBPC small subunit without a change of frames in the codons.

Next, the plasmid was introduced into *E. coli* DH5α competent cells (Takara Shuzo Company) and the ampicillin resistant cells were selected. Further, the nucleotide sequences of the plasmids contained in the selected ampicillin resistant strains were determined by utilizing BigDye Terminator Cycle Sequencing Ready Reaction kit v3.0 (PE Applied Biosystems Company) and DNA sequencer 3100 (PE Applied Biosytems Company). As a result, it was confirmed that plasmid pSUM-NdG6-rSt-657soy had the nucleotide sequence shown in SEQ ID NO: 214.

(2) Construction of a Chloroplast Expression Plasmid Having the Present Invention DNA (A1)S for Direct Introduction—Part (2)

A plasmid was constructed for introducing the present invention DNA (A1)S into a plant with the particle gun method. The plasmid contained a chimeric DNA in which the present invention DNA (A1)S was connected immediately after the nucleotide sequences encoding the chloroplast transit peptide of soybean (cv. Jack) RuBPC small subunit and encoding thereafter 12 amino acids of the mature protein, without a change of frames in the codons. First, DNA comprising the nucleotide sequence shown in SEQ ID NO: 214 was amplified by PCR. The PCR was conducted by utilizing as a template pKSN657soy obtained in Example 46(2) and by utilizing as primers an oligonucleotide consisting of the nucleotide sequence shown in SEQ ID NO: 395 and an oligonucleotide consisting of the nucleotide sequence shown in SEQ ID NO: 396. The PCR utilized KOD-plus (Toyobo Company). The PCR carried out after conducting a maintenance at 94° C. for 2 minutes; 25 cycles of a cycle that included maintaining 94° C. for 30 seconds, followed by 46° C. for 30 seconds, and followed by 68° C. for 60 seconds; and a final maintenance at 68° C. for 3 minutes. The amplified DNA was recovered and purified with MagExtractor-PCR & Gel-Clean up (Toyobo Company) by conducting the procedures according to the attached manual. After digesting the purified DNA with restriction enzyme SacI, the DNA comprising the nucleotide sequence shown in SEQ ID NO: 214 was recovered.

Plasmid pKFrSt12-657 obtained in Example 16(3) was digested with restriction enzyme BspHI. The DNA was then blunt ended and the 5' terminus was dephosphorylated by utilizing TaKaRa BKL Kit (Takara Shuzo Company) in accordance with the attached manual. Next, after the DNA was digested with restriction enzyme SacI, the DNA derived from plasmid pKFrSt12 was isolated. Said DNA was ligated with the DNA which was digested with SacI and which comprises the nucleotide sequence shown in SEQ ID NO: 214, in order to obtain plasmid pKFrSt12-657soy (FIG. 50) containing the chimeric DNA in which the present invention DNA (A1)S was connected immediately after the nucleotide sequences encoding the chloroplast transit peptide of soybean (cv. Jack) RuBPC small subunit and encoding thereafter 12 amino acids of the mature protein, without a change of frames in the codons.

The obtained plasmid pKFrSt12-657soy was digested with restriction enzymes BamHI and SacI to isolate DNA comprising the nucleotide sequence shown in SEQ ID NO: 214. Said DNA was inserted between the restriction enzyme site of BglII and the restriction enzyme site of SacI of plasmid pNdG6-ΔT to obtain plasmid pSUM-NdG6-rSt12-657soy (FIG. 51) wherein the CR16G6 promoter has connected downstream the chimeric DNA in which said DNA was connected immediately after the nucleotide sequence encoding the chloroplast transit peptide of soybean (cv. Jack) RuBPC small subunit without a change of frames in the codons.

Next, the plasmid was introduced into *E. coli* DH5α competent cells (Takara Shuzo Company) and the ampicillin resistant cells were selected. Further, the nucleotide sequences of the plasmids contained in the ampicillin resistant strains were determined by utilizing BigDye Terminator Cycle Sequencing Ready Reaction kit v3.0 (PE Applied Biosystems Company) and DNA sequencer 3100 (PE Applied Biosytems Company). As a result, it was confirmed that plasmid pSUM-NdG6-rSt12-657soy had the nucleotide sequence shown in SEQ ID NO: 214.

(3) Introduction of the Present Invention DNA (A1)S into Soybean

The globular embryos of soybeans (cultivar: Fayette and Jack) were prepared according to the method described in Example 17(1), other than substituting the vitamin source of MS medium with the vitamin source of B5 medium (O. L. Gamborg et al., Exp. Cell Res. (1986) 50 p 151).

The obtained globular embryo was transplanted into fresh somatic embryo growth medium and cultured for 2 to 3 days. In accordance with the method described in Example 17(2), plasmid pSUM-NdG6-rSt-657soy constructed in Example 47(1) or plasmid pSUM-NdG6-rSt12-657soy constructed in Example 47(2) was introduced to said globular embryos.

(4) Selection of Somatic Embryo with Hygromycin

Selection by hygromycin of a globular embryo after the gene introduction obtained in Example 47(3) was conducted according to the method described in Example 17(3), other than substituting the vitamin source of MS medium with the vitamin source of B5 medium. However, after the second transplant, a medium to which 0.2 (w/v) % of Gelrite was added or a liquid medium to which no Gelrite was added was utilized as the somatic embryo selection medium. In the case of the liquid medium, the culturing had 90 gentle revolutions per minute.

(5) Selection of Somatic Embryo with Compound (II)

Selection by compound (II) of a globular embryo after the gene introduction obtained in Example 47(3) is conducted according to the method described in Example 17(4), other than substituting the vitamin source of MS medium with the vitamin source of B5 medium.

(6) Plant Regeneration from the Somatic Embryo, Acclimation and Cultivation

In accordance with the method described in Example 17(5), the plant regeneration is conducted from the globular embryos selected in Example 47(4) or 47(5). However, the agar concentration in the development medium is adjusted to 0.8 (w/v) % or 1.0 (w/v) %. Further, the vitamin source of the MS medium of the germination medium is substituted with the vitamin source of B5 medium.

The plant with roots and developed leaves undergo the acclimation and cultivation accordingly with the method described in Example 17(6) and are harvested.

(7) Evaluation of the Resistance to Herbicidal Compound (II)

The degree of resistance against compound (II) of the regenerated plant obtained in Example 47(6) is evaluated in accordance with the method described in Example 17(4).

(8) Construction of a Chloroplast Expression Plasmid Having the Present Invention DNA (A1)S for *Agrobacterium* Introduction A plasmid for introducing the present invention DNA (A1)S into a plant with the *agrobacterium* method is constructed. Plasmid pSUM-NdG6-rSt-657soy was digested with restriction enzyme NotI, to obtain a chimeric DNA in which the present invention DNA (A1)S was connected immediately after the nucleotide sequence encoding the chloroplast transit peptide of soybean (cv. Jack) RuBPC small subunit without a change of frames in the codons. Said DNA was inserted into the NotI restriction site of the above binary plasmid vector pBI121S obtained in Example 18 to obtain plasmid pBI-NdG6-rSt-657soy (FIG. 52). Further, plasmid pSUM-NdG6-rSt12-657soy was digested with restriction enzyme NotI, to isolate a chimeric DNA in which the present invention DNA (A1)S was connected immediately after the nucleotide sequences encoding the chloroplast transit peptide of soybean (cv. Jack) RuBPC small subunit and encoding thereafter 12 amino acids of the mature protein, without a change of frames in the codons. Such a DNA was inserted into the NotI restriction site of the above binary plasmid vector pBI121S to obtain plasmid pBI-NdG6-rSt12-657soy (FIG. 53).

(9) Introduction of the Present Invention DNA (A1)S to Tobacco

The present invention DNA (A1)S was introduced into tobacco with the *agrobacterium* method, utilizing plasmid pBI-NdG6-rSt-657soy and pBI-NdG6-rSt12-657soy obtained in Example 47(8).

First, in accordance with the method described in Example 19, each of the plasmids pBI-NdG6-rSt-657soy and pBI-NdG6-rSt12-657soy was introduced into *Agrobacterium tumefaciens* LBA4404 (Clontech Company). The transgenic *agrobacterium* bearing pBI-NdG6-rSt-657soy or pBI-NdG6-rSt12-657soy were isolated.

Next, other than culturing overnight the transgenic *agrobacterium* bearing the above plasmid at 30° C. in LB liquid medium containing 25 mg/L kanamycin, said *agrobacterium* were utilized to introduce genes into tobacco according to the method described in Example 19. There were obtained, respectively, transgenic tobaccos which have incorporated the T-DNA region of pBI-NdG6-rSt-657soy or pBI-NdG6-rSt12-657soy.

(10) Evaluation of the Resistance Utilizing a Leaf Piece of the Present Invention DNA (A1)S Transgenic Tobacco Leaves were taken from 35 transgenic tobaccos obtained in Example 47(9). Each leaf was divided into pieces in which each piece was 5 to 7 mm wide. Leaf pieces were planted onto MS agar medium containing 0, 0.05, 0.1 or 0.2 mg/L of compound (II) and cultured in the light at room temperature. On the 11th day of culturing, the herbicidal damage of each of the leaf pieces was observed. Further, leaf pieces were planted onto MS agar mediums containing 0, 0.01, 0.02, 0.05 or 0.1 mg/L of compound (XII) and cultured in the light at room temperature. On the 7th day of culturing, the herbicidal damage of each of the leaf pieces was observed. As a control, 20 leaf pieces of tobacco to which no genetic introduction has been conducted (hereinafter, referred to as "wild type tobacco") were utilized on each concentration. An average score for each group was determined by scoring 1 point to a leaf piece that continuously grew, 0.5 points to a halfly withered leaf piece in which chemical damage was observed, and 0 points to a leaf piece which turned white and had withered. The leaf pieces of the tobacco to which the present invention DNA (A1)S (the T-DNA region of plasmid pBI-NdG6-rSt-657soy or pBI-NdG6-rSt12-657soy) has been introduced provided a higher score than the wild type tobacco with each of compound (II) and compound (XII).

Example 48

Obtaining the Present Invention DNA (A16)

(1) Preparation of the Chromosomal DNA of *Streptomyces ornatus* IFO 13069t

Under the method described in Example 31(1), the chromosomal DNA of *Streptomyces* ornatus IFO 13069t was prepared.

(2) Isolation of DNA Having a Partial Nucleotide Sequence of the Present Invention DNA (A11)

PCR was conducted by utilizing as the template the chromosomal DNA prepared from *Streptomyces ornatus* IFO 13069t in Example 48(1) and by utilizing primer pairing 14, in accordance with the method described in Example 29. Similarly to Example 31(2), the amplified DNA was cloned into cloning vector pCRII-TOPO (Invitrogen Company). The sequence thereof was analyzed. As a result, the nucleotide sequence shown in nucleotides 343 to 1069 of the nucleotide sequence shown in SEQ ID NO: 225 was provided.

Further, the chromosomal DNA prepared in Example 48(1) was digested with restriction enzyme PvuII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 265 and primer AP1. Next, PCR was conducted under the conditions described in Example 26(3), by utilizing the first PCR products as the template and by utilizing the oligonucleotide having the nucleotide sequence shown in SEQ ID NO: 266 and primer AP2. The nucleotide sequence of the obtained DNA was analyzed. The nucleotide sequence shown in nucleotides 1 to 501 of the nucleotide sequence shown in SEQ ID NO: 235 was provided.

Further, the chromosomal DNA prepared in Example 48(1) was digested with restriction enzyme PvuII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 267 and primer AP1. Next, PCR was conducted under the conditions described in Example 26(3), by utilizing the first PCR products as the template and by utilizing the oligonucleotide having the nucleotide sequence shown in SEQ ID NO: 268 and primer AP2. The nucleotide sequence of the obtained DNA was analyzed. The nucleotide sequence shown in nucleotides 1044 to 1454 of the nucleotide sequence shown in SEQ ID NO: 235 was provided.

(3) Sequence Analysis of the Present Invention DNA (A16)

The nucleotide sequence shown in SEQ ID NO: 235 was obtained by connecting the nucleotide sequences provided by the DNA obtained in Example 48(2). Two open reading frames (ORF) were present in said nucleotide sequence. As such, there was contained a nucleotide sequence (SEQ ID NO: 225) consisting of 1251 nucleotides (inclusive of the stop codon) and encoding a 416 amino acid residue (SEQ ID NO: 215) and a nucleotide sequence (SEQ ID NO: 255) consisting of 198 nucleotides (inclusive of the stop codon) and encoding a 65 amino acid residue (SEQ ID NO: 245). The molecular weight of the protein consisting of the amino acid sequence (SEQ ID NO: 215) encoded by the nucleotide sequence shown in SEQ ID NO: 225 was calculated to be 46013 Da. Further, the molecular weight of the protein consisting of the amino acid sequence (SEQ ID NO: 245) encoded by the nucleotide sequence shown in SEQ ID NO: 255 was calculated to be 6768 Da.

Example 49

Expression of the Present Invention DNA (A16) in E. Coli (1) Production of a Transformed E. Coli Having the Present Invention DNA (A16)

PCR was conducted by utilizing the GeneAmp High Fidelity PCR System (Applied Biosystems Japan Company) and by utilizing as the template the chromosomal DNA prepared from Streptomyces ornatus IFO 13069t in Example 48(1). As the primers, there was utilized a pairing of the oligonucleotide having the nucleotide sequence shown in SEQ ID NO: 269 and the oligonucleotide having the nucleotide sequence shown in SEQ ID NO: 286. The PCR reaction solution amounted to 50 µl by adding the 2 primers each amounting to 200 nM, 50 ng of the above chromosomal DNA, 5.0 µl of dNTP mix (a mixture of 2.0 mM of each of the 4 types of dNTP; Clontech Company), 5.0 µl of 10× buffer (containing MgCl2) and 0.5 µl of GeneAmp HF enzyme mix and by adding distilled water. The reaction conditions of the PCR were after maintaining 97° C. for 1 minute; repeating 10 cycles of a cycle that included maintaining 97° C. for 15 seconds, followed by 60° C. for 30 seconds, and followed by 72° C. for 90 seconds; then conducting 15 cycles of a cycle that included maintaining 97° C. for 15 seconds, followed by 60° C. for 30 seconds and followed by 72° C. for 90 seconds (wherein 20 seconds was added to the maintenance at 72° C. for each cycle); and then maintaining 72° C. for 7 minutes. Similarly to Example 32(1), the DNA was purified from the reaction solution of PCR and cloned into the cloning vector pCRII-TOPO (Invitrogen Company). The nucleotide sequence of the obtained plasmid DNA was analyzed by utilizing as primers the oligonucleotides having the nucleotide sequences shown, respectively, in SEQ ID NOs: 57, 59, 267, 286 and 288. Based on the obtained results, the plasmid having the nucleotide sequence shown in SEQ ID NO: 235 was designated as pCR452F. Similarly to Example 32(1), pCR452F was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 235, in which the DNA encoding the present invention protein (A16) is inserted between the NdeI site and the HindIII site of pKSN2 (hereinafter referred to as "pKSN452F"). Said plasmid was introduced into E. Coli JM109. The obtained E. coli transformant was designated JM109/pKSN452F.

(2) Expression of the Present Invention Protein (A16) in E. Coli and Recovery of Said Protein Similarly to Example 4(2), each of E. coli JM109/pKSN452F and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN452F is referred to as "E. coli pKSN452F extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 µl were prepared and maintained for 10 minutes at 30° C. However, as the supernatant fraction, the supernatant fraction prepared in Example 49(2) (E. coli pKSN452F extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN452F extract. In contrast, such a spot was not detected from the reaction solution containing E. coli pKSN2 extract.

Example 50

Obtaining the Present Invention DNA (A17)

(1) Preparation of the Chromosomal DNA of Streptomyces griseus ATCC 10137

Under the method described in Example 31(1), the chromosomal DNA of Streptomyces griseus ATCC 10137 was prepared.

(2) Isolation of DNA Having a Partial Nucleotide Sequence of the Present Invention DNA (A17)

PCR was conducted by utilizing as the template the chromosomal DNA of Streptomyces griseus ATCC 10137 prepared in Example 50(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 343 to 1069 of the nucleotide sequence shown in SEQ ID NO: 226 was provided.

Further, the chromosomal DNA prepared in Example 50(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 270 and primer AP1. Next, PCR was conducted under the conditions described in Example 26(3), by utilizing the first PCR products as the template and by utilizing the oligonucleotide having the nucleotide sequence shown in SEQ ID NO: 271 and primer AP2. The nucleotide sequence of the obtained DNA was analyzed. The nucleotide sequence shown in nucleotides 1 to 361 of the nucleotide sequence shown in SEQ ID NO: 236 was provided.

Further, the chromosomal DNA prepared in Example 50(1) was digested with restriction enzyme PvuII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 272 and primer AP1. Next, PCR was conducted under the conditions described in Example 26(3), by utilizing the first PCR products as the template and by utilizing the oligonucleotide having the nucleotide sequence shown in SEQ ID NO: 273 and primer AP2. The nucleotide sequence of the obtained DNA was analyzed. The nucleotide sequence shown in nucleotides 1035 to 1454 of the nucleotide sequence shown in SEQ ID NO: 236 was provided.

(3) Sequence Analysis of the Present Invention DNA (A17)

The nucleotide sequence shown in SEQ ID NO: 236 was obtained by connecting the nucleotide sequences provided by the DNA obtained in Example 50(2). Two open reading frames (ORF) were present in said nucleotide sequence. As such, there was contained a nucleotide sequence (SEQ ID NO: 226) consisting of 1251 nucleotides (inclusive of the stop codon) and encoding a 416 amino acid residue (SEQ ID NO: 216) and a nucleotide sequence (SEQ ID NO: 256) consisting of 198 nucleotides (inclusive of the stop codon) and encoding a 65 amino acid residue (SEQ ID NO: 246). The molecular weight of the protein consisting of the amino acid sequence (SEQ ID NO: 216) encoded by the nucleotide sequence shown in SEQ ID NO: 226 was calculated to be 46082Da. The molecular weight of the protein consisting of the amino acid sequence (SEQ ID NO: 246) encoded by the nucleotide sequence shown in SEQ ID NO: 256 was calculated to be 6768 Da. The nucleotide sequence shown in SEQ ID NO: 256 is 100% identical to the nucleotide sequence shown in SEQ ID NO: 255. The amino acid sequence shown in SEQ ID NO: 246 is 100% identical to the amino acid sequence shown in SEQ ID NO: 245.

Example 51

Expression of the Present Invention DNA (A17) in E. Coli (1) Production of a Transformed E. Coli Having the Present Invention DNA (A17)

PCR was conducted similarly to Example 32(1), other than utilizing as a template the chromosomal DNA prepared from Streptomyces griseus ATCC 10137 in Example 50(1) and utilizing as the primers the oligonucleotide having the nucleotide sequence shown in SEQ ID NO: 274 and an oligonucleotide having the nucleotide sequence shown in SEQ ID NO: 275. Similarly to Example 32(1), the DNA was purified from the reaction solution of PCR and cloned into the cloning vector pCRII-TOPO (Invitrogen Company). The nucleotide sequence of the obtained plasmid DNA was sequenced by utilizing as primers the oligonucleotides having the nucleotide sequences shown, respectively, in SEQ ID NOs: 57, 59, 274, 276 and 277. Based on the obtained results, the plasmid having the nucleotide sequence shown in SEQ ID NO: 236 was designated as pCR608F. Similarly to Example 32(1), pCR608F was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 236, in which the DNA encoding the present invention protein (A17) is inserted between the NdeI site and the HindIII site of pKSN2 (hereinafter referred to as "pKSN608F"). Said plasmid was introduced into E. Coli JM109. The obtained E. coli transformant was designated JM109/pKSN608F.

(2) Expression of the Present Invention Protein (A17) in E. Coli and Recovery of Said Protein Similarly to Example 4(2), each of E. coli JM109/pKSN608F and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN608F is referred to as "E. coli pKSN608F extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 µl were prepared and maintained for 10 minutes at 30° C. However, as the supernatant fraction, the supernatant fraction prepared in Example 51(2) (E. coli pKSN608F extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN608F extract. In contrast, such a spot was not detected from the reaction solution containing E. coli pKSN2 extract.

Example 52

Obtaining the Present Invention DNA (A18)

(1) Preparation of the Chromosomal DNA of Streptomyces Achromogenes IFO 12735

Under the method described in Example 31(1), the chromosomal DNA of Streptomyces achromogenes IFO 12735 was prepared.

(2) Isolation of DNA Having a Partial Nucleotide Sequence of the Present Invention DNA (A18)

PCR was conducted by utilizing as the template the chromosomal DNA of Streptomyces achromogenes IFO 12735 prepared in Example 52(1) and by utilizing primer pairing 17, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 526 to 1048 of the nucleotide sequence shown in SEQ ID NO: 227 was provided.

Further, the chromosomal DNA prepared in Example 52(1) was digested with restriction enzyme HincII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 278 and primer AP1. Next, PCR was conducted under the conditions described in Example 26(3), by utilizing the first PCR products as the template and by utilizing the oligonucleotide having the nucleotide sequence shown in SEQ ID NO: 279 and primer AP2. The nucleotide sequence of the obtained DNA was analyzed. The nucleotide sequence shown in nucleotides 1 to 600 of the nucleotide sequence shown in SEQ ID NO: 237 was provided.

Further, the chromosomal DNA prepared in Example 52(1) was digested with restriction enzyme BalI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 163 and primer AP1. Next, PCR was conducted under the conditions described in Example 26(3), by utilizing the first PCR products as the template and by utilizing the oligonucleotide having the nucleotide sequence shown in SEQ ID NO: 164 and primer AP2. The nucleotide sequence of the obtained DNA was analyzed. The nucleotide sequence shown in nucleotides 983 to 1449 of the nucleotide sequence shown in SEQ ID NO: 237 was provided.

(3) Sequence Analysis of the Present Invention DNA (A18)

The nucleotide sequence shown in SEQ ID NO: 237 was obtained by connecting the nucleotide sequences provided by the DNA obtained in Example 52(2). Two open reading frames (ORF) were present in said nucleotide sequence. As such, there was contained a nucleotide sequence (SEQ ID NO: 227) consisting of 1230 nucleotides (inclusive of the stop codon) and encoding a 409 amino acid residue (SEQ ID NO: 217) and a nucleotide sequence (SEQ ID NO: 257) consisting of 207 nucleotides (inclusive of the stop codon) and encoding a 68 amino acid residue (SEQ ID NO: 247). The molecular weight of the protein consisting of the amino acid sequence (SEQ ID NO: 217) encoded by the nucleotide sequence shown in SEQ ID NO: 227 was calculated to be 45099 Da. The molecular weight of the protein consisting of the amino acid sequence (SEQ ID NO: 247) encoded by the nucleotide sequence shown in SEQ ID NO: 257 was calculated to be 7193 Da.

Example 53

Expression of the Present Invention DNA (A18) in *E. Coli*

(1) Production of a Transformed *E. Coli* Having the Present Invention DNA (A18)

PCR was conducted similarly to Example 49(1), other than utilizing as a template the chromosomal DNA prepared from *Streptomyces achromogenes* IFO 12735 in Example 52(1) and utilizing as the primers the oligonucleotide having the nucleotide sequence shown in SEQ ID NO: 183 and an oligonucleotide having the nucleotide sequence shown in SEQ ID NO: 280. Similarly to Example 32(1), the DNA was purified from the reaction solution of PCR and cloned into the cloning vector pCRII-TOPO (Invitrogen Company). The nucleotide sequence of the obtained plasmid DNA was analyzed by utilizing as primers the oligonucleotides having the nucleotide sequences shown, respectively, in SEQ ID NOs: 67, 68, 163, 279 and 281. Based on the obtained results, the plasmid having the nucleotide sequence shown in SEQ ID NO: 237 was designated as pCR646BF. Similarly to Example 32(1), pCR646BF was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 237, in which the DNA encoding the present invention protein (A18) is inserted between the NdeI site and the HindIII site of pKSN2 (hereinafter referred to as "pKSN646BF"). Said plasmid was introduced into *E. Coli* JM109. The obtained *E. coli* transformant was designated JM109/pKSN646BF.

(2) Expression of the Present Invention Protein (A18) in *E. Coli* and Recovery of Said Protein Similarly to Example 4(2), each of *E. coli* JM109/pKSN464BF and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from *E. coli* JM109/pKSN646BF is referred to as "*E. coli* pKSN646BF extract" and the supernatant fraction obtained from *E. coli* JM109/pKSN2 is referred to as "*E. coli* pKSN2 extract").

(3) Detection of the Ability to Convert Compound (II) to Compound (III)

Similarly to Example 32(3), reaction solutions of 30 μl were prepared and maintained for 10 minutes at 30° C. However, as the supernatant fraction, the supernatant fraction prepared in Example 53(2) (*E. coli* pKSN646BF extract or *E. coli* pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing *E. coli* pKSN646BF extract. In contrast, such a spot was not detected from the reaction solution containing *E. coli* pKSN2 extract.

Example 54

Obtaining the Present Invention DNA (A19)

(1) Preparation of the Chromosomal DNA of *Streptomyces griseus* IFO 13849t

Under the method described in Example 31(1), the chromosomal DNA of *Streptomyces griseus* IFO 13849T was prepared.

(2) Isolation of DNA Having a Partial Nucleotide Sequence of the Present Invention DNA (A19)

PCR was conducted by utilizing as the template the chromosomal DNA of *Streptomyces griseus* IFO 13849T prepared in Example 54(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 343 to 1069 of the nucleotide sequence shown in SEQ ID NO: 228 was provided.

Further, the chromosomal DNA prepared in Example 54(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 282 and primer AP1. Next, PCR was conducted under the conditions described in Example 26(3), by utilizing the first PCR products as the template and by utilizing the oligonucleotide having the nucleotide sequence shown in SEQ ID NO: 283 and primer AP2. The nucleotide sequence of the obtained DNA was analyzed. The nucleotide sequence shown in nucleotides 1 to 358 of the nucleotide sequence shown in SEQ ID NO: 238 was provided.

Further, the chromosomal DNA prepared in Example 54(1) was digested with restriction enzyme HincII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 284 and primer AP1. Next, PCR was conducted under the conditions described in Example 26(3), by utilizing the first PCR products as the template and by utilizing the oligonucleotide having the nucleotide sequence shown in SEQ ID NO: 285 and primer AP2. The nucleotide sequence of the obtained DNA was analyzed. The nucleotide sequence shown in nucleotides 1005 to 1454 of the nucleotide sequence shown in SEQ ID NO: 238 was provided.

(3) Sequence Analysis of the Present Invention DNA (A19)

The nucleotide sequence shown in SEQ ID NO: 238 was obtained by connecting the nucleotide sequences provided by the DNA obtained in Example 54(2). Two open reading frames (ORF) were present in said nucleotide sequence. As such, there was contained a nucleotide sequence (SEQ ID NO: 228) consisting of 1251 nucleotides (inclusive of the stop codon) and encoding a 416 amino acid residue (SEQ ID NO: 218) and a nucleotide sequence (SEQ ID NO: 258) consisting of 156 nucleotides (inclusive of the stop codon) and encoding a 51 amino acid residue (SEQ ID NO: 248). The molecular weight of the protein consisting of the amino acid sequence (SEQ ID NO: 218) encoded by the nucleotide sequence shown in SEQ ID NO: 228 was calculated to be 45903 Da. The molecular weight of the protein consisting of the amino acid sequence (SEQ ID NO: 248) encoded by the nucleotide sequence shown in SEQ ID NO: 258 was calculated to be 5175 Da.

Example 55

Expression of the Present Invention DNA (A19) in E. Coli (1) Production of a Transformed E. Coli Having the Present Invention DNA (A19)

PCR was conducted similarly to Example 49(1), other than utilizing as a template the chromosomal DNA prepared from Streptomyces griseus IFO 13849T in Example 54(1) and utilizing as the primers the oligonucleotide having the nucleotide sequence shown in SEQ ID NO: 286 and an oligonucleotide having the nucleotide sequence shown in SEQ ID NO: 287. Similarly to Example 32(1), the DNA was purified from the reaction solution of PCR and cloned into the cloning vector pCRII-TOPO (Invitrogen Company). The nucleotide sequence of the obtained plasmid DNA was analyzed by utilizing as primers the oligonucleotides having the nucleotide sequences shown, respectively, in SEQ ID NOs: 57, 59, 284, 286 and 288. Based on the obtained results, the plasmid having the nucleotide sequence shown in SEQ ID NO: 238 was designated as pCR1502F. Similarly to Example 32(1), pCR1502F was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 238, in which the DNA encoding the present invention protein (A19) is inserted between the NdeI site and the HindIII site of pKSN2 (hereinafter referred to as "pKSN1502F"). Said plasmid was introduced into E. Coli JM109. The obtained E. coli transformant was designated JM109/pKSN1502F.

(2) Expression of the Present Invention Protein (A18) in E. Coli and Recovery of Said Protein Similarly to Example 4(2), each of E. coli JM109/pKSN1502F and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1502F is referred to as "E. coli pKSN1502F extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 µl were prepared and maintained for 10 minutes at 30° C. However, as the supernatant fraction, the supernatant fraction prepared in Example 55(2) (E. coli pKSN1502F extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN1502F extract. In contrast, such a spot was not detected from the reaction solution containing E. coli pKSN2 extract.

Example 56

Obtaining the Present Invention DNA (A20)

(1) Preparation of the Chromosomal DNA of Streptomyces lanatus IFO 12787t

Under the method described in Example 31(1), the chromosomal DNA of Streptomyces lanatus IFO 12787T was prepared.

(2) Isolation of DNA Having a Partial Nucleotide Sequence of the Present Invention DNA (A20)

PCR was conducted by utilizing as the template the chromosomal DNA of Streptomyces lanatus IFO 12787T prepared in Example 56(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 304 to 1036 of the nucleotide sequence shown in SEQ ID NO: 229 was provided.

Further, the chromosomal DNA prepared in Example 56(1) was digested with restriction enzyme PmacI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 278 and primer AP1. Next, PCR was conducted under the conditions described in Example 26(3), by utilizing the first PCR products as the template and by utilizing the oligonucleotide having the nucleotide sequence shown in SEQ ID NO: 289 and primer AP2. The nucleotide sequence of the obtained DNA was analyzed. The nucleotide sequence shown in nucleotides 1 to 318 of the nucleotide sequence shown in SEQ ID NO: 239 was provided.

Further, the chromosomal DNA prepared in Example 56(1) was digested with restriction enzyme StuI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 290 and primer AP1. Next, PCR was conducted under the conditions described in Example 26(3), by utilizing the first PCR products as the template and by utilizing the oligonucleotide having the nucleotide sequence shown in SEQ ID NO: 291 and primer AP2. The nucleotide sequence of the obtained DNA was analyzed. The nucleotide sequence shown in nucleotides 969 to 1461 of the nucleotide sequence shown in SEQ ID NO: 239 was provided.

(3) Sequence Analysis of the Present Invention DNA (A20)

The nucleotide sequence shown in SEQ ID NO: 239 was obtained by connecting the nucleotide sequences provided by the DNA obtained in Example 56(2). Two open reading frames (ORF) were present in said nucleotide sequence. As such, there was contained a nucleotide sequence (SEQ ID NO: 229) consisting of 1218 nucleotides (inclusive of the stop codon) and encoding a 405 amino acid residue (SEQ ID NO: 219) and a nucleotide sequence (SEQ ID NO: 259) consisting of 231 nucleotides (inclusive of the stop codon) and encoding a 76 amino acid residue (SEQ ID NO: 249). The molecular weight of the protein consisting of the amino acid sequence (SEQ ID NO: 219) encoded by the nucleotide sequence shown in SEQ ID NO: 229 was calculated to be 45071 Da. The molecular weight of the protein consisting of the amino acid sequence (SEQ ID NO: 249) encoded by the nucleotide sequence shown in SEQ ID NO: 259 was calculated to be 7816 Da.

Example 57

Expression of the Present Invention DNA (A20) in E. Coli (1) Production of a Transformed E. Coli Having the Present Invention DNA (A20)

PCR was conducted similarly to Example 49(1), other than utilizing as a template the chromosomal DNA prepared from Streptomyces lanatus IFO 12787T in Example 56(1) and utilizing as the primers the oligonucleotide having the nucleotide sequence shown in SEQ ID NO: 292 and an oligonucleotide having the nucleotide sequence shown in SEQ ID NO: 293. Similarly to Example 32(1), the DNA was purified from the reaction solution of PCR and cloned into the cloning vector pCRII-TOPO (Invitrogen Company). The nucleotide sequence of the obtained plasmid DNA was analyzed by utilizing as primers the oligonucleotides having the nucleotide sequences shown, respectively, in SEQ ID NOs: 67, 68, 188, 278 and 290. Based on the obtained results, the plasmid having the nucleotide sequence shown in SEQ ID NO: 239 was designated as pCR1525F. Similarly to Example 32(1), pCR1525F was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 239, in which the DNA encoding the present invention protein (A20) is inserted between the NdeI site and the HindIII site of pKSN2 (hereinafter referred to as "pKSN1525F"). Said plasmid was introduced into E. Coli JM109. The obtained E. coli transformant was designated JM109/pKSN1525F.

(2) Expression of the Present Invention Protein (A20) in E. Coli and Recovery of Said Protein Similarly to Example 4(2), each of E. coli JM109/pKSN1525F and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1525F is referred to as "E. coli pKSN1525F extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 µl were prepared and maintained for 10 minutes at 30° C. However, as the supernatant fraction, the supernatant fraction prepared in Example 57(2) (E. coli pKSN1525F extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN1525F extract. In contrast, such a spot was not detected from the reaction solution containing E. coli pKSN2 extract.

Example 58

Obtaining the Present Invention DNA (A21)

(1) Preparation of the Chromosomal DNA of Streptomyces misawanensis IFO 13855t

Under the method described in Example 31(1), the chromosomal DNA of Streptomyces misawanensis IFO 13855T was prepared.

(2) Isolation of DNA Having a Partial Nucleotide Sequence of the Present Invention DNA (A21)

PCR was conducted by utilizing as the template the chromosomal DNA of Streptomyces misawanensis IFO 13855T prepared in Example 58(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 328 to 1063 of the nucleotide sequence shown in SEQ ID NO: 230 was provided.

Further, the chromosomal DNA prepared in Example 58(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 294 and primer AP1. Next, PCR was conducted under the conditions described in Example 26(3), by utilizing the first PCR products as the template and by utilizing the oligonucleotide having the nucleotide sequence shown in SEQ ID NO: 295 and primer AP2. The nucleotide sequence of the obtained DNA was analyzed. The nucleotide sequence shown in nucleotides 1 to 341 of the nucleotide sequence shown in SEQ ID NO: 240 was provided.

Further, the chromosomal DNA prepared in Example 58(1) was digested with restriction enzyme HincII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 296 and primer AP1. Next, PCR was conducted under the conditions described in Example 26(3), by utilizing the first PCR products as the template and by utilizing the oligonucleotide having the nucleotide sequence shown in SEQ ID NO: 297 and primer AP2. The nucleotide sequence of the obtained DNA was analyzed. The nucleotide sequence shown in nucleotides 1017 to 1458 of the nucleotide sequence shown in SEQ ID NO: 240 was provided.

(3) Sequence Analysis of the Present Invention DNA (A21)

The nucleotide sequence shown in SEQ ID NO: 240 was obtained by connecting the nucleotide sequences provided by the DNA obtained in Example 58(2). Two open reading frames (ORF) were present in said nucleotide sequence. As such, there was contained a nucleotide sequence (SEQ ID NO: 230) consisting of 1245 nucleotides (inclusive of the stop codon) and encoding a 414 amino acid residue (SEQ ID NO: 220) and a nucleotide sequence (SEQ ID NO: 260) consisting of 201 nucleotides (inclusive of the stop codon) and encoding a 66 amino acid residue (SEQ ID NO: 250). The molecular weight of the protein consisting of the amino acid sequence (SEQ ID NO: 220) encoded by the nucleotide sequence shown in SEQ ID NO: 230 was calculated to be 45806 Da. The molecular weight of the protein consisting of the amino acid sequence (SEQ ID NO: 250) encoded by the nucleotide sequence shown in SEQ ID NO: 260 was calculated to be 6712Da.

Example 59

Expression of the Present Invention DNA (A21) in E. Coli (1) Production of a Transformed E. Coli Having the Present Invention DNA (A21)

PCR was conducted similarly to Example 32(1), other than utilizing as a template the chromosomal DNA prepared from Streptomyces misawanensis IFO 13855T in Example 58(1) and utilizing as the primers the oligonucleotide having the nucleotide sequence shown in SEQ ID NO: 298 and an oligonucleotide having the nucleotide sequence shown in SEQ ID NO: 299. Similarly to Example 32(1), the DNA was purified from the reaction solution of PCR and cloned into the cloning vector pCRII-TOPO (Invitrogen Company). The nucleotide sequence of the obtained plasmid DNA was analyzed by utilizing as primers the oligonucleotides having the nucleotide sequences shown, respectively, in SEQ ID NOs: 57, 59, 296, 298 and 300. Based on the obtained results, the plasmid having the nucleotide sequence shown in SEQ ID NO: 240 was designated as pCR1543BF. Similarly to Example 32(1), pCR1543BF was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 240, in which the DNA encoding the present invention protein (A21) is inserted between the NdeI site and the HindIII site of pKSN2 (hereinafter referred to as "pKSN1543BF"). Said plasmid was introduced into E. Coli JM109. The obtained E. coli transformant was designated JM109/pKSN1543BF.

(2) Expression of the Present Invention Protein (A21) in E. Coli and Recovery of Said Protein Similarly to Example 4(2), each of E. coli JM109/pKSN1543BF and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1543BF is referred to as "E. coli pKSN1543BF extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 μl were prepared and maintained for 10 minutes at 30° C. However, as the supernatant fraction, the supernatant fraction prepared in Example 59(2) (E. coli pKSN1543BF extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN1543BF extract. In contrast, such a spot was not detected from the reaction solution containing E. coli pKSN2 extract.

Example 60

Obtaining the Present Invention DNA (A22)

(1) Preparation of the Chromosomal DNA of Streptomyces pallidus IFO 13434t

Under the method described in Example 31(1), the chromosomal DNA of Streptomyces pallidus IFO 13434T was prepared.

(2) Isolation of DNA Having a Partial Nucleotide Sequence of the Present Invention DNA (A22)

PCR was conducted by utilizing as the template the chromosomal DNA of Streptomyces pallidus IFO 13434T prepared in Example 60(1) and by utilizing primer pairing 15, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 483 to 1048 of the nucleotide sequence shown in SEQ ID NO: 231 was provided.

Further, the chromosomal DNA prepared in Example 60(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 301 and primer AP1. Next, PCR was conducted under the conditions described in Example 26(3), by utilizing the first PCR products as the template and by utilizing the oligonucleotide having the nucleotide sequence shown in SEQ ID NO: 302 and primer AP2. The nucleotide sequence of the obtained DNA was analyzed. The nucleotide sequence shown in nucleotides 68 to 516 of the nucleotide sequence shown in SEQ ID NO: 241 was provided.

Further, the chromosomal DNA prepared in Example 60(1) was digested with restriction enzyme HincII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 302 and primer AP1. Next, PCR was conducted under the conditions described in Example 26(3), by utilizing the first PCR products as the template and by utilizing the oligonucleotide having the nucleotide sequence shown in SEQ ID NO: 303 and primer AP2. The nucleotide sequence of the obtained DNA was analyzed. The nucleotide sequence shown in nucleotides 1 to 270 of the nucleotide sequence shown in SEQ ID NO: 241 was provided.

Further, the chromosomal DNA prepared in Example 60(1) was digested with restriction enzyme HincII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 304 and primer AP1. Next, PCR was conducted under the conditions described in Example 26(3), by utilizing the first PCR products as the template and by utilizing the oligonucleotide having the nucleotide sequence shown in SEQ ID NO: 305 and primer AP2. The nucleotide sequence of the obtained DNA was analyzed. The nucleotide sequence shown in nucleotides 982 to 1448 of the nucleotide sequence shown in SEQ ID NO: 241 was provided.

(3) Sequence Analysis of the Present Invention DNA (A22)

The nucleotide sequence shown in SEQ ID NO: 241 was obtained by connecting the nucleotide sequences provided by the DNA obtained in Example 60(2). Two open reading frames (ORF) were present in said nucleotide sequence. As such, there was contained a nucleotide sequence (SEQ ID NO: 231) consisting of 1230 nucleotides (inclusive of the stop codon) and encoding a 409 amino acid residue (SEQ ID NO: 221) and a nucleotide sequence (SEQ ID NO: 261) consisting of 195 nucleotides (inclusive of the stop codon) and encoding a 64 amino acid residue (SEQ ID NO: 251). The molecular weight of the protein consisting of the amino acid sequence (SEQ ID NO: 221) encoded by the nucleotide sequence shown in SEQ ID NO: 231 was calculated to be 45050 Da. The molecular weight of the protein consisting of the amino acid sequence (SEQ ID NO: 251) encoded by the nucleotide sequence shown in SEQ ID NO: 261 was calculated to be 6914 Da.

Example 61

Expression of the Present Invention DNA (A22) in E. Coli (1) Production of a Transformed E. Coli Having the Present Invention DNA (A22)

PCR was conducted similarly to Example 32(1), other than utilizing as a template the chromosomal DNA prepared from Streptomyces pallidus IFO 13434T in Example 60(1) and utilizing as the primers the oligonucleotide having the nucleotide sequence shown in SEQ ID NO: 306 and an oligonucleotide having the nucleotide sequence shown in SEQ ID NO: 307. Similarly to Example 32(1), the DNA was purified from the reaction solution of PCR and cloned into the cloning vector pCRII-TOPO (Invitrogen Company). The nucleotide sequence of the obtained plasmid DNA was analyzed by utilizing as primers the oligonucleotides having the nucleotide sequences shown, respectively, in SEQ ID NOs: 67, 68 and 308. Based on the obtained results, the plasmid having the nucleotide sequence shown in SEQ ID NO: 241 was designated as pCR1558BF. Similarly to Example 32(1), pCR1558BF was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 241, in which the DNA encoding the present invention protein (A22) is inserted between the NdeI site and the HindIII site of pKSN2 (hereinafter referred to as "pKSN1558BF"). Said plasmid was introduced into E. Coli JM109. The obtained E. coli transformant was designated JM109/pKSN1558BF.

(2) Expression of the Present Invention Protein (A22) in E. Coli and Recovery of Said Protein Similarly to Example 4(2), each of E. coli JM109/pKSN1558BF and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1558BF is referred to as "E. coli pKSN1558BF extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 μl were prepared and maintained for 10 minutes at 30° C. However, as the supernatant fraction, the supernatant fraction prepared in Example 61(2) (E. coli pKSN1558BF extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN1558BF extract. In contrast, such a spot was not detected from the reaction solution containing E. coli pKSN2 extract.

Example 62

Obtaining the Present Invention DNA (A23)

(1) Preparation of the Chromosomal DNA of Streptomyces roseorubens IFO 13682t

Under the method described in Example 31(1), the chromosomal DNA of Streptomyces roseorubens IFO 13682T was prepared.

(2) Isolation of DNA Having a Partial Nucleotide Sequence of the Present Invention DNA (A23)

PCR was conducted by utilizing as the template the chromosomal DNA of Streptomyces roseorubens IFO 13682T prepared in Example 62(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 289 to 1015 of the nucleotide sequence shown in SEQ ID NO: 232 was provided.

Further, the chromosomal DNA prepared in Example 62(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 309 and primer AP1. Next, PCR was conducted under the conditions described in Example 26(3), by utilizing the first PCR products as the template and by utilizing the oligonucleotide having the nucleotide sequence shown in SEQ ID NO: 310 and primer AP2. The nucleotide sequence of the obtained DNA was analyzed. The nucleotide sequence shown in nucleotides 1 to 354 of the nucleotide sequence shown in SEQ ID NO: 242 was provided.

Further, the chromosomal DNA prepared in Example 62(1) was digested with restriction enzyme PvuII. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 311 and primer AP1. Next, PCR was conducted under the conditions described in Example 26(3), by utilizing the first PCR products as the template and by utilizing the oligonucleotide having the nucleotide sequence shown in SEQ ID NO: 312 and primer AP2. The nucleotide sequence of the obtained DNA was analyzed. The nucleotide sequence shown in nucleotides 966 to 1411 of the nucleotide sequence shown in SEQ ID NO: 242 was provided.

(3) Sequence Analysis of the Present Invention DNA (A23)

The nucleotide sequence shown in SEQ ID NO: 242 was obtained by connecting the nucleotide sequences provided by the DNA obtained in Example 62(2). Two open reading frames (ORF) were present in said nucleotide sequence. As such, there was contained a nucleotide sequence (SEQ ID NO: 232) consisting of 1197 nucleotides (inclusive of the stop codon) and encoding a 398 amino acid residue (SEQ ID NO: 222) and a nucleotide sequence (SEQ ID NO: 262) consisting of 201 nucleotides (inclusive of the stop codon) and encoding a 66 amino acid residue (SEQ ID NO: 252). The molecular weight of the protein consisting of the amino acid sequence (SEQ ID NO: 222) encoded by the nucleotide sequence shown in SEQ ID NO: 232 was calculated to be 43624 Da. The molecular weight of the protein consisting of the amino acid sequence (SEQ ID NO: 252) encoded by the nucleotide sequence shown in SEQ ID NO: 262 was calculated to be 6797 Da.

Example 63

Expression of the Present Invention DNA (A23) in E. Coli (1) Production of a Transformed E. Coli Having the Present Invention DNA (A23)

PCR was conducted similarly to Example 49(1), other than utilizing as a template the chromosomal DNA prepared from Streptomyces roseorubens IFO 13682T in Example 62(1) and utilizing as the primers the oligonucleotide having the nucleotide sequence shown in SEQ ID NO: 313 and an oligonucleotide having the nucleotide sequence shown in SEQ ID NO: 314. Similarly to Example 32(1), the DNA was purified from the reaction solution of PCR and cloned into the cloning vector pCRII-TOPO (Invitrogen Company). The nucleotide sequence of the obtained plasmid DNA was analyzed by utilizing as primers the oligonucleotides having the nucleotide sequences shown, respectively, in SEQ ID NOs: 67, 68, 309, 311 and 315. Based on the obtained results, the plasmid having the nucleotide sequence shown in SEQ ID NO: 242 was designated as pCR1584F. Similarly to Example 32(1), pCR1584F was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 242, in which the DNA encoding the present invention protein (A23) is inserted between the NdeI site and the HindIII site of pKSN2 (hereinafter referred to as "pKSN1584F"). Said plasmid was introduced into E. Coli JM109. The obtained E. coli transformant was designated JM109/pKSN1584F.

(2) Expression of the Present Invention Protein (A23) in E. Coli and Recovery of Said Protein Similarly to Example 4(2), each of E. coli JM109/pKSN1584F and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1584F is referred to as "E. coli pKSN1584F extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 μl were prepared and maintained for 10 minutes at 30° C. However, as the supernatant fraction, the supernatant fraction prepared in Example 63(2) (E. coli pKSN1584F extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN1584F extract. In contrast, such a spot was not detected from the reaction solution containing E. coli pKSN2 extract.

Example 64

Obtaining the Present Invention DNA (A24)

(1) Preparation of the Chromosomal DNA of Streptomyces Rutgersensis IFO 15875t

Under the method described in Example 31(1), the chromosomal DNA of Streptomyces rutgersensis IFO 15875T was prepared.

(2) Isolation of DNA Having a Partial Nucleotide Sequence of the Present Invention DNA (A24)

PCR was conducted by utilizing as the template the chromosomal DNA of Streptomyces rutgersensis IFO 15875T prepared in Example 64(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 322 to 1057 of the nucleotide sequence shown in SEQ ID NO: 233 was provided.

Further, the chromosomal DNA prepared in Example 64(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 316 and primer AP1. Next, PCR was conducted under the conditions described in Example 26(3), by utilizing the first PCR products as the template and by utilizing the oligonucleotide having the nucleotide sequence shown in SEQ ID NO: 317 and primer AP2. The nucleotide sequence of the obtained DNA was analyzed. The nucleotide sequence shown in nucleotides 1 to 384 of the nucleotide sequence shown in SEQ ID NO: 243 was provided.

Further, the chromosomal DNA prepared in Example 64(1) was digested with restriction enzyme NaeI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 318 and primer AP1. Next, PCR was conducted under the conditions described in Example 26(3), by utilizing the first PCR products as the template and by utilizing the oligonucleotide having the nucleotide sequence shown in SEQ ID NO: 319 and primer AP2. The nucleotide sequence of the obtained DNA was analyzed. The nucleotide sequence shown in nucleotides 992 to 1466 of the nucleotide sequence shown in SEQ ID NO: 243 was provided.

(3) Sequence Analysis of the Present Invention DNA (A24)

The nucleotide sequence shown in SEQ ID NO: 243 was obtained by connecting the nucleotide sequences provided by the DNA obtained in Example 64(2). Two open reading frames (ORF) were present in said nucleotide sequence. As such, there was contained a nucleotide sequence (SEQ ID NO: 233) consisting of 1245 nucleotides (inclusive of the stop codon) and encoding a 414 amino acid residue (SEQ ID NO: 223) and a nucleotide sequence (SEQ ID NO: 263) consisting of 198 nucleotides (inclusive of the stop codon) and encoding a 65 amino acid residue (SEQ ID NO: 253). The molecular weight of the protein consisting of the amino acid sequence (SEQ ID NO: 223) encoded by the nucleotide sequence shown in SEQ ID NO: 233 was calculated to be 45830 Da. The molecular weight of the protein consisting of the amino acid sequence (SEQ ID NO: 253) encoded by the nucleotide sequence shown in SEQ ID NO: 263 was calculated to be 7034 Da.

Example 65

Expression of the Present Invention DNA (A24) in E. Coli (1) Production of a Transformed E. Coli Having the Present Invention DNA (A24)

PCR was conducted similarly to Example 49(1), other than utilizing as a template the chromosomal DNA prepared from Streptomyces rutgersensis IFO 15875T in Example 64(1) and utilizing as the primers the oligonucleotide having the nucleotide sequence shown in SEQ ID NO: 320 and an oligonucleotide having the nucleotide sequence shown in SEQ ID NO: 321. Similarly to Example 32(1), the DNA was purified from the reaction solution of PCR and cloned into the cloning vector pCRII-TOPO (Invitrogen Company). The nucleotide sequence of the obtained plasmid DNA was sequenced by utilizing as primers the oligonucleotides having the nucleotide sequences shown, respectively, in SEQ ID NOs: 67, 68 and 322. Based on the obtained results, the plasmid having the nucleotide sequence shown in SEQ ID NO: 243 was designated as pCR1589BF. Similarly to Example 32(1), pCR1589BF was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 243, in which the DNA encoding the present invention protein (A24) is inserted between the NdeI site and the HindIII site of pKSN2 (hereinafter referred to as "pKSN1589BF"). Said plasmid was introduced into E. Coli JM109. The obtained E. coli transformant was designated JM109/pKSN1589BF.

(2) Expression of the Present Invention Protein (A24) in E. Coli and Recovery of Said Protein Similarly to Example 4(2), each of E. coli JM109/pKSN1589BF and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1589BF is referred to as "E. coli pKSN1589BF extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 µl were prepared and maintained for 10 minutes at 30° C. However, as the supernatant fraction, the supernatant fraction prepared in Example 65(2) (E. coli pKSN1589BF extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}C$ were examined (Rf value 0.24 and 0.29). A spot corresponding to compound (III) was detected from the reaction solution containing E. coli pKSN1589BF extract. In contrast, such a spot was not detected from the reaction solution containing E. coli pKSN2 extract.

Example 66

Obtaining the Present Invention DNA (A25)

(1) Preparation of the Chromosomal DNA of Streptomyces steffisburgensis IFO 13446t Under the method described in Example 31(1), the chromosomal DNA of Streptomyces steffisburgensis IFO 13446T was prepared.

(2) Isolation of DNA Having a Partial Nucleotide Sequence of the Present Invention DNA (A25)

PCR was conducted by utilizing as the template the chromosomal DNA of Streptomyces steffisburgensis IFO 13446T prepared in Example 66(1) and by utilizing primer pairing 14, in accordance with the method described in Example 29. Similarly to Example 31(2), the amplified DNA was cloned to cloning vector pCRII-TOPO (Invitrogen Company). The nucleotide sequence thereof was analyzed. As a result, the nucleotide sequence shown in nucleotides 289 to 1015 of the nucleotide sequence shown in SEQ ID NO: 234 was provided.

Further, the chromosomal DNA prepared in Example 66(1) was digested with restriction enzyme SmaI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 323 and primer AP1. Next, PCR was conducted under the conditions described in Example 26(3), by utilizing the first PCR products as the template and by utilizing the oligonucleotide having the nucleotide sequence shown in SEQ ID NO: 324 and primer AP2. The nucleotide sequence of the obtained DNA was analyzed. The nucleotide sequence shown in nucleotides 1 to 303 of the nucleotide sequence shown in SEQ ID NO: 244 was provided.

Further, the chromosomal DNA prepared in Example 66(1) was digested with restriction enzyme PmacI. A genome walker library was produced by utilizing the obtained DNA, according to the method described in Example 26(3). PCR was conducted under the conditions described in Example 26(3) to obtain the first PCR products, by utilizing the obtained library as the template and by utilizing the oligonucleotide having the nucleotide sequence shown in SEQ ID NO: 311 and primer AP1. Next, PCR was conducted under the conditions described in Example 26(3), by utilizing the first PCR products as the template and by utilizing the oligonucleotide having the nucleotide sequence shown in SEQ ID NO: 325 and primer AP2. The nucleotide sequence of the obtained DNA was analyzed. The nucleotide sequence shown in nucleotides 966 to 1411 of the nucleotide sequence shown in SEQ ID NO: 244 was provided.

(3) Sequence Analysis of the Present Invention DNA (A25)

The nucleotide sequence shown in SEQ ID NO: 244 was obtained by connecting the nucleotide sequences provided by the DNA obtained in Example 66(2). Two open reading frames (ORF) were present in said nucleotide sequence. As such, there was contained a nucleotide sequence (SEQ ID NO: 234) consisting of 1197 nucleotides (inclusive of the stop codon) and encoding a 398 amino acid residue (SEQ ID NO: 224) and a nucleotide sequence (SEQ ID NO: 264) consisting of 201 nucleotides (inclusive of the stop codon) and encoding a 66 amino acid residue (SEQ ID NO: 254). The molecular weight of the protein consisting of the amino acid sequence (SEQ ID NO: 224) encoded by the nucleotide sequence shown in SEQ ID NO: 234 was calculated to be 44175 Da. The molecular weight of the protein consisting of the amino acid sequence (SEQ ID NO: 254) encoded by the nucleotide sequence shown in SEQ ID NO: 264 was calculated to be 6685 Da.

Example 67

Expression of the Present Invention DNA (A25) in E. Coli (1) Production of a Transformed E. Coli Having the Present Invention DNA (A25)

PCR was conducted similarly to Example 49(1), other than utilizing as a template the chromosomal DNA prepared from Streptomyces steffisburgensis IFO 13446T in Example 66(1) and utilizing as the primers the oligonucleotide having the nucleotide sequence shown in SEQ ID NO: 326 and an oligonucleotide having the nucleotide sequence shown in SEQ ID NO: 327. Similarly to Example 32(1), the DNA was purified from the reaction solution of PCR and cloned into the cloning vector pCRII-TOPO (Invitrogen Company). The nucleotide sequence of the obtained plasmid DNA was sequenced by utilizing as primers the oligonucleotides having the nucleotide sequences shown, respectively, in SEQ ID NOs: 67, 68, 311, 315 and 323. Based on the obtained results, the plasmid having the nucleotide sequence shown in SEQ ID NO: 244 was designated as pCR1609F. Similarly to Example 32(1), pCR1609F was digested with restriction enzymes NdeI and HindIII. A DNA of about 1.5 kbp was purified from the digestion products. The obtained DNA and the plasmid pKSN2 digested with NdeI and HindIII were ligated to obtain a plasmid containing the nucleotide sequence shown in SEQ ID NO: 244, in which the DNA encoding the present invention protein (A25) is inserted between the NdeI site and the HindIII site of pKSN2 (hereinafter referred to as "pKSN1609F"). Said plasmid was introduced into E. Coli JM109. The obtained E. coli transformant was designated JM109/pKSN1609F.

(2) Expression of the Present Invention Protein (A25) in E. Coli and Recovery of Said Protein Similarly to Example 4(2), each of E. coli JM109/pKSN1609F and JM109/pKSN2 was cultured. The cells were recovered. Cell lysate solutions were prepared. Under the method described in Example 4(2), supernatant fractions were prepared from the cell lysate solutions (hereinafter, the supernatant fraction obtained from E. coli JM109/pKSN1609F is referred to as "E. coli pKSN1609F extract" and the supernatant fraction obtained from E. coli JM109/pKSN2 is referred to as "E. coli pKSN2 extract").

(3) Detection of the Ability to Convert Compound (II) to Compound (III)

Similarly to Example 32(3), reaction solutions of 30 µl were prepared and maintained for 10 minutes at 30° C. However, as the supernatant fraction, the supernatant fraction prepared in Example 67(2) (E. coli pKSN1609F extract or E. coli pKSN2 extract) was utilized. The reaction solutions after the maintenance were extracted with ethyl acetate and the extracted layers were TLC analyzed. After developing the TLC plate, the presence of a spot thereon corresponding to compound (III) labeled with $^{14}$C were examined (Rf value 0.24 and 0.29). A spot corresponding to compound (III) was detected from the reaction solution containing E. coli pKSN1609F extract. In contrast, such a spot was not detected from the reaction solution containing E. coli pKSN2 extract.

Example 68

Metabolism of Compounds by the Present Invention Protein (A16), (A17), (A18), (A19), (A20), (A21), (A22), (A23), (A24) or (A25)

(1) Metabolism of Compound (XII) by the Present Invention Protein (A16)

There was prepared 100 µl of a reaction solution of 50 mM potassium phosphate buffer (pH7.0) containing 12.5 ppm of compound (XII), 3 mM of β-NADPH (hereinafter, referred to as "component A") (Oriental Yeast Company), 1 mg/ml of a ferredoxin derived from spinach (hereinafter referred to as "component B") (Sigma Company), 0.15 U/ml of ferredoxin reductase (hereinafter, referred to as "component C") (Sigma Company) and 20 µl of the supernatant fraction recovered in Example 49(2). The reaction solution was maintained at 30° C. for 10 minutes. Further, there was prepared and maintained similarly 100 µl of a reaction solution of a 50 mM potassium phosphate buffer (pH 7.0) having no addition of at least one component utilized in the composition of the above reaction solution, selected from component A, component B, component C and the supernatant fraction prepared in Example 49(2). Five microliters (5 µl) of 2N HCl and 100 µl of ethyl acetate were added and mixed into each of the reaction solutions after the maintenance. The supernatant centrifuged at 8,000×g was filtered with UltraFree MC 0.22 µm filter unit (Millipore Company). Forty microliters (40 µl) of the liquid filtrate (hereinafter, the liquid filtrate derived from the reaction solution containing component A, component B, component C and 20 µl of supernatant fraction recovered in Example 49(2) is referred to as "(XII) metabolism solution (A16);" further, the liquid filtrate derived from the reaction solution containing no component A, no component B, no component C and no supernatant fraction recovered in Example 49(2) is referred to as "(XII) control solution (A16)

") were analyzed on a HPLC under the above analysis condition 1. Compared to the concentration of compound (XII) detected from (XII) control solution (A16), the concentration of compound (XII) detected from (XII) metabolism solution (A16) was lower. Further a peak, which was not detected from the (XII) control solution (A16), was detected from the (XII) metabolism solution (A16). The elution time of said peak on the HPLC matched an elution time of a peak of a compound in which the mass is 14 less than said compound (XII) detected from (XII) metabolism solution (A1) in Example 41(2).

(2) Metabolism of Compound (XII) by the Present Invention Protein (A17)

Other than utilizing 20 μl of the supernatant fraction recovered in Example 51(2) instead of 20 μl of the supernatant fraction recovered in Example 49(2), the reaction solution was prepared and maintained in accordance with the method described in Example 68(1). Similar to Example 68(1), the reaction solution after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 51(2) is referred to as "(XII) metabolism solution (A17);" further, the liquid filtrate derived from the reaction solution containing no component A, no component B, no component C and no supernatant fraction recovered in Example 51(2) is referred to as "(XII) control solution (A17)") were analyzed on a HPLC under the above analysis condition 1. Compared to the concentration of compound (XII) detected from (XII) control solution (A17), the concentration of compound (XII) detected from (XII) metabolism solution (A17) was lower. Further a peak, which was not detected from the (XII) control solution (A17), was detected from the (XII) metabolism solution (A17). The elution time of the said peak on the HPLC matched an elution time of a peak of a compound in which the mass is 14 less than said compound (XII) detected from (XII) metabolism solution (A1) in Example 41(2).

(3) Metabolism of Compound (XII) by the Present Invention Protein (A18)

Other than utilizing 20 μl of the supernatant fraction recovered in Example 53(2) instead of 20 μl of the supernatant fraction recovered in Example 49(2), the reaction solution was prepared and maintained in accordance with the method described in Example 68(1). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 53(2) is referred to as "(XII) metabolism solution (A18);" further, the liquid filtrate derived from the reaction solution containing no component A, no component B, no component C and no supernatant fraction recovered in Example 53(2) is referred to as "(XII) control solution (A18)") was analyzed on a HPLC under analysis condition 1. Compared to the concentration of compound (XII) detected from (XII) control solution (A18), the concentration of compound (XII) detected from (XII) metabolism solution (A18) was lower. Further a peak, which was not detected from the (XII) control solution (A18), was detected from the (XII) metabolism solution (A18). The elution time of said peak on the HPLC matched an elution time of a peak of a compound in which the mass is 14 less than said compound (XII) detected from (XII) metabolism solution (A1) in Example 41(2).

(4) Metabolism of Compound (XII) by the Present Invention Protein (A19)

Other than utilizing 20 μl of the supernatant fraction recovered in Example 55(2) instead of 20 μl of the supernatant fraction recovered in Example 49(2), the reaction solution was prepared and maintained in accordance with the method described in Example 68(1). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 55(2) is referred to as "(XII) metabolism solution (A19);" further, the liquid filtrate derived from the reaction solution containing no component A, no component B, no component C and no supernatant fraction recovered in Example 55(2) is referred to as "(XII) control solution (A19)") was analyzed on a HPLC under analysis condition 1. Compared to the concentration of compound (XII) detected from (XII) control solution (A19), the concentration of compound (XII) detected from (XII) metabolism solution (A19) was lower. Further a peak, which was not detected from the (XII) control solution (A19), was detected from the (XII) metabolism solution (A19). The elution time of said peak on the HPLC matched an elution time of a peak of a compound in which the mass is 14 less than said compound (XII) detected from (XII) metabolism solution (A1) in Example 41(2).

(5) Metabolism of Compound (XII) by the Present Invention Protein (A20)

Other than utilizing 20 μl of the supernatant fraction recovered in Example 57(2) instead of 20 μl of the supernatant fraction recovered in Example 49(2), the reaction solution was prepared and maintained in accordance with the method described in Example 68(1). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 57(2) is referred to as "(XII) metabolism solution (A20);" further, the liquid filtrate derived from the reaction solution containing no component A, no component B, no component C and no supernatant fraction recovered in Example 57(2) is referred to as "(XII) control solution (A20)") was analyzed on a HPLC under analysis condition 1. Compared to the concentration of compound (XII) detected from (XII) control solution (A20), the concentration of compound (XII) detected from (XII) metabolism solution (A20) was lower. Further a peak, which was not detected from the (XII) control solution (A20), was detected from the (XII) metabolism solution (A20). The elution time of said peak on the HPLC matched an elution time of a peak of a compound in which the mass is 14 less than said compound (XII) detected from (XII) metabolism solution (A1) in Example 41(2).

(6) Metabolism of Compound (XII) by the Present Invention Protein (A21)

Other than utilizing 20 μl of the supernatant fraction recovered in Example 59(2) instead of 20 μl of the supernatant fraction recovered in Example 49(2), the reaction solution was prepared and maintained in accordance with the method described in Example 68(1). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 59(2) is referred to as "(XII) metabolism solution (A21);" further, the liquid filtrate derived from the reaction solution containing no component A, no component B, no component C and no supernatant fraction recovered in Example 59(2) is referred to as "(XII) control solution (A21)") was analyzed on a HPLC under analysis condition 1. Compared to the concentration of compound (XII) detected from (XII) control solution (A21), the concentration of compound (XII) detected from (XII) metabolism solution (A21) was lower. Further a peak, which was not detected from the (XII) control solution (A21), was detected from the (XII) metabolism solution (A21). The elution time of said peak on the HPLC matched an elution time of a peak of a compound in which the mass is 14 less than said compound (XII) detected from (XII) metabolism solution (A1) in Example 41(2).

(7) Metabolism of Compound (XII) by the Present Invention Protein (A22)

Other than utilizing 20 μl of the supernatant fraction recovered in Example 61(2) instead of 20 μl of the supernatant fraction recovered in Example 49(2), the reaction solution was prepared and maintained in accordance with the method described in Example 68(1). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 61(2) is referred to as "(XII) metabolism solution (A22);" further, the liquid filtrate derived from the reaction solution containing no component A, no component B, no component C and no supernatant fraction recovered in Example 61(2) is referred to as "(XII) control solution (A22)") was analyzed on a HPLC under analysis condition 1. Compared to the concentration of compound (XII) detected from (XII) control solution (A22), the concentration of compound (XII) detected from (XII) metabolism solution (A22) was lower. Further a peak, which was not detected from the (XII) control solution (A22), was detected from the (XII) metabolism solution (A22). The elution time of said peak on the HPLC matched an elution time of a peak of a compound in which the mass is 14 less than said compound (XII) detected from (XII) metabolism solution (A1) in Example 41(2).

(8) Metabolism of Compound (XII) by the Present Invention Protein (A23)

Other than utilizing 20 μl of the supernatant fraction recovered in Example 63(2) instead of 20 μl of the supernatant fraction recovered in Example 49(2), the reaction solution was prepared and maintained in accordance with the method described in Example 68(1). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 63(2) is referred to as "(XII) metabolism solution (A23);" further, the liquid filtrate derived from the reaction solution containing no component A, no component B, no component C and no supernatant fraction recovered in Example 63(2) is referred to as "(XII) control solution (A23)") was analyzed on a HPLC under analysis condition 1. Compared to the concentration of compound (XII) detected from (XII) control solution (A23), the concentration of compound (XII) detected from (XII) metabolism solution (A23) was lower. Further a peak, which was not detected from the (XII) control solution (A23), was detected from the (XII) metabolism solution (A23). The elution time of said peak on the HPLC matched an elution time of a peak of a compound in which the mass is 14 less than said compound (XII) detected from (XII) metabolism solution (A1) in Example 41(2).

(9) Metabolism of Compound (XII) by the Present Invention Protein (A24)

Other than utilizing 20 μl of the supernatant fraction recovered in Example 65(2) instead of 20 μl of the supernatant fraction recovered in Example 49(2), the reaction solution was prepared and maintained in accordance with the method described in Example 68(1). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 65(2) is referred to as "(XII) metabolism solution (A24);" further, the liquid filtrate derived from the reaction solution containing no component A, no component B, no component C and no supernatant fraction recovered in Example 65(2) is referred to as "(XII) control solution (A24)") was analyzed on a HPLC under analysis condition 1. Compared to the concentration of compound (XII) detected from (XII) control solution (A24), the concentration of compound (XII) detected from (XII) metabolism solution (A24) was lower. Further a peak, which was not detected from the (XII) control solution (A24), was detected from the (XII) metabolism solution (A24). The elution time of said peak on the HPLC matched an elution time of a peak of a compound in which the mass is 14 less than said compound (XII) detected from (XII) metabolism solution (A1) in Example 41(2).

(10) Metabolism of Compound (XII) by the Present Invention Protein (A25)

Other than utilizing 20 μl of the supernatant fraction recovered in Example 67(2) instead of 20 μl of the supernatant fraction recovered in Example 49(2), the reaction solution was prepared and maintained in accordance with the method described in Example 68(1). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20 μl of supernatant fraction recovered in Example 67(2) is referred to as "(XII) metabolism solution (A25);" further, the liquid filtrate derived from the reaction solution containing no component A, no component B, no component C and no supernatant fraction recovered in Example 67(2) is referred to as "(XII) control solution (A25)") was analyzed on a HPLC under analysis condition 1. Compared to the concentration of compound (XII) detected from (XII) control solution (A25), the concentration of compound (XII) detected from (XII) metabolism solution (A25) was lower. Further a peak, which was not detected from the (XII) control solution (A25), was detected from the (XII) metabolism solution (A25). The elution time of said peak on the HPLC matched an elution time of a peak of a compound in which the mass is 14 less than said compound (XII) detected from (XII) metabolism solution (A1) in Example 41(2).

(11) Metabolism of Compound (XIII) by the Present Invention Protein (A17)

Other than utilizing 12.5 ppm of compound (XIII) instead of 12.5 ppm of compound (XII), the reaction solution was prepared and maintained in accordance with the method described in Example 68(2). Similar to Example 68(1), each of the reaction solutions after the maintenance was prepared. Forty microliters (40 μl) of the obtained liquid filtrate (hereinafter, the liquid filtrate derived from the reaction solution containing component A, component B, component C and 20

µl of supernatant fraction recovered in Example 51(2) is referred to as "(XIII) metabolism solution (A17);" further, the liquid filtrate derived from the reaction solution containing no component A, no component B, no component C and no supernatant fraction recovered in Example 51(2) is referred to as "(XIII) control solution (A17)") were analyzed on a HPLC under the above analysis condition 1. Compared to the concentration of compound (XIII) detected from (XIII) control solution (A17), the concentration of compound (XIII) detected from (XIII) metabolism solution (A17) was lower. Further a peak, which was not detected from the (XIII) control solution (A17), was detected from the (XIII) metabolism solution (A17). The elution time of the said peak on the HPLC matched an elution time of a peak of a compound in which the mass is 14 less than said compound (XIII) detected from (XIII) metabolism solution (A1) in Example 41(3).

(12) Metabolism of Compound (XIII) by the Present Invention Protein (A18)

Other than utilizing 20 µl of the supernatant fraction recovered in Example 53(2) instead of 20 µl of the supernatant fraction recovered in Example 51(2), the reaction solution was prepared and maintained in accordance with the method described in Example 68(11). Similar to Example 68(1), each of the reaction solutions after the maintenance was prepared. Forty microliters (40 µl) of the obtained liquid filtrate (hereinafter, the liquid filtrate derived from the reaction solution containing component A, component B, component C and 20 µl of supernatant fraction recovered in Example 53(2) is referred to as "(XIII) metabolism solution (A18);" further, the liquid filtrate derived from the reaction solution containing no component A, no component B, no component C and no supernatant fraction recovered in Example 53(2) is referred to as "(XIII) control solution (A18)") was analyzed on a HPLC under analysis condition 1. Compared to the concentration of compound (XIII) detected from (XIII) control solution (A18), the concentration of compound (XIII) detected from (XIII) metabolism solution (A18) was lower. Further a peak, which was not detected from the (XIII) control solution (A18), was detected from the (XIII) metabolism solution (A18). The elution time of said peak on the HPLC matched an elution time of a peak of a compound in which the mass is 14 less than said compound (XIII) detected from (XIII) metabolism solution (A1) in Example 41(3).

(13) Metabolism of Compound (XIII) by the Present Invention Protein (A19)

Other than utilizing 20 µl of the supernatant fraction recovered in Example 55(2) instead of 20 µl of the supernatant fraction recovered in Example 51(2), the reaction solution was prepared and maintained in accordance with the method described in Example 68(11). Similar to Example 68(1), each of the reaction solutions after the maintenance was prepared. Forty microliters (40 µl) of the obtained liquid filtrate (hereinafter, the liquid filtrate derived from the reaction solution containing component A, component B, component C and 20 µl of supernatant fraction recovered in Example 55(2) is referred to as "(XIII) metabolism solution (A19);" further, the liquid filtrate derived from the reaction solution containing no component A, no component B, no component C and no supernatant fraction recovered in Example 55(2) is referred to as "(XIII) control solution (A19)") was analyzed on a HPLC under analysis condition 1. Compared to the concentration of compound (XIII) detected from (XIII) control solution (A19), the concentration of compound (XIII) detected from (XIII) metabolism solution (A19) was lower. Further a peak, which was not detected from the (XIII) control solution (A19), was detected from the (XIII) metabolism solution (A19). The elution time of said peak on the HPLC matched an elution time of a peak of a compound in which the mass is 14 less than said compound (XIII) detected from (XIII) metabolism solution (A1) in Example 41(3).

(14) Metabolism of Compound (XIII) by the Present Invention Protein (A20)

Other than utilizing 20 µl of the supernatant fraction recovered in Example 57(2) instead of 20 µl of the supernatant fraction recovered in Example 51(2), the reaction solution was prepared and maintained in accordance with the method described in Example 68(11). Similar to Example 68(1), each of the reaction solutions after the maintenance was prepared. Forty microliters (40 µl) of the obtained liquid filtrate (hereinafter, the liquid filtrate derived from the reaction solution containing component A, component B, component C and 20 µl of supernatant fraction recovered in Example 57(2) is referred to as "(XIII) metabolism solution (A20);" further, the liquid filtrate derived from the reaction solution containing no component A, no component B, no component C and no supernatant fraction recovered in Example 57(2) is referred to as "(XIII) control solution (A20)") was analyzed on a HPLC under analysis condition 1. Compared to the concentration of compound (XIII) detected from (XIII) control solution (A20), the concentration of compound (XIII) detected from (XIII) metabolism solution (A20) was lower. Further a peak, which was not detected from the (XIII) control solution (A20), was detected from the (XIII) metabolism solution (A20). The elution time of said peak on the HPLC matched an elution time of a peak of a compound in which the mass is 14 less than said compound (XIII) detected from (XIII) metabolism solution (A1) in Example 41(3).

(15) Metabolism of Compound (XIII) by the Present Invention Protein (A21)

Other than utilizing 20 µl of the supernatant fraction recovered in Example 59(2) instead of 20 µl of the supernatant fraction recovered in Example 51(2), the reaction solution was prepared and maintained in accordance with the method described in Example 68(11). Similar to Example 68(1), each of the reaction solutions after the maintenance was prepared. Forty microliters (40 µl) of the obtained liquid filtrate (hereinafter, the liquid filtrate derived from the reaction solution containing component A, component B, component C and 20 µl of supernatant fraction recovered in Example 59(2) is referred to as "(XIII) metabolism solution (A21);" further, the liquid filtrate derived from the reaction solution containing no component A, no component B, no component C and no supernatant fraction recovered in Example 59(2) is referred to as "(XIII) control solution (A21)") was analyzed on a HPLC under analysis condition 1. Compared to the concentration of compound (XIII) detected from (XIII) control solution (A21), the concentration of compound (XIII) detected from (XIII) metabolism solution (A21) was lower. Further a peak, which was not detected from the (XIII) control solution (A21), was detected from the (XIII) metabolism solution (A21). The elution time of said peak on the HPLC matched an elution time of a peak of a compound in which the mass is 14 less than said compound (XIII) detected from (XIII) metabolism solution (A1) in Example 41(3).

(16) Metabolism of Compound (XIII) by the Present Invention Protein (A23)

Other than utilizing 20 µl of the supernatant fraction recovered in Example 63(2) instead of 20 µl of the supernatant fraction recovered in Example 51(2), the reaction solution was prepared and maintained in accordance with the method described in Example 68(11). Similar to Example 68(1), each of the reaction solutions after the maintenance was prepared. Forty microliters (40 µl) of the obtained liquid filtrate (hereinafter, the liquid filtrate derived from the reaction solution containing component A, component B, component C and 20 µl of supernatant fraction recovered in Example 63(2) is referred to as "(XIII) metabolism solution (A23);" further, the liquid filtrate derived from the reaction solution containing no component A, no component B, no component C and no supernatant fraction recovered in Example 63(2) is referred to as "(XIII) control solution (A23)") was analyzed on a HPLC under analysis condition 1. Compared to the concentration of compound (XIII) detected from (XIII) control solution (A23), the concentration of compound (XIII) detected from (XIII) metabolism solution (A23) was lower. Further a peak, which was not detected from the (XIII) control solution (A23), was detected from the (XIII) metabolism solution (A23). The elution time of said peak on the HPLC matched an elution time of a peak of a compound in which the mass is 14 less than said compound (XIII) detected from (XIII) metabolism solution (A1) in Example 41(3).

(17) Metabolism of Compound (XIII) by the Present Invention Protein (A25)

Other than utilizing 20 µl of the supernatant fraction recovered in Example 67(2) instead of 20 µl of the supernatant fraction recovered in Example 51(2), the reaction solution was prepared and maintained in accordance with the method described in Example 68(11). Similar to Example 68(1), each of the reaction solutions after the maintenance was prepared. Forty microliters (40 µl) of the obtained liquid filtrate (hereinafter, the liquid filtrate derived from the reaction solution containing component A, component B, component C and 20 µl of supernatant fraction recovered in Example 67(2) is referred to as "(XIII) metabolism solution (A25);" further, the liquid filtrate derived from the reaction solution containing no component A, no component B, no component C and no supernatant fraction recovered in Example 67(2) is referred to as "(XIII) control solution (A25)") was analyzed on a HPLC under analysis condition 1. Compared to the concentration of compound (XIII) detected from (XIII) control solution (A25), the concentration of compound (XIII) detected from (XIII) metabolism solution (A25) was lower. Further a peak, which was not detected from the (XIII) control solution (A25), was detected from the (XIII) metabolism solution (A25). The elution time of said peak on the HPLC matched an elution time of a peak of a compound in which the mass is 14 less than said compound (XIII) detected from (XIII) metabolism solution (A1) in Example 41(3).

Example 69

Hybridization in which the Present Invention DNA (A1), (A2), (A3) or (A4) was a Probe (1) Preparation of a Probe PCR was conducted in accordance with the method described in Example 30(1). However, as the template, 10 ng of the chromosomal DNA of *Streptomyces achromogenes* IFO 12735 prepared in Example 26(1) was utilized instead of said 50 ng of the chromosomal DNA of *Streptomyces phaeochromogenes* IFO12898 prepared in Example 3(1). As the primers, there was utilized an oligonucleotide having the nucleotide sequence shown in SEQ ID NO: 328 and the oligonucleotide having the nucleotide sequence shown in SEQ ID NO: 329. The DNA amplified by said PCR was recovered to produce a probe having the nucleotide sequence shown in SEQ ID NO: 109 labeled with digoxigenin (hereinafter referred to as "DIG labeled probe (A4)").

(2) Preparation of the Plasmid Solution

PCR was conducted by utilizing Advantage-GC genomic polymerase mix (Clontech Company) and by utilizing as the template the chromosomal DNA of *Streptomyces* nogalator IFO13445 prepared in Example 31(1). As the primers, there was utilized the oligonucleotide having the nucleotide sequence shown in SEQ ID NO: 330 and the oligonucleotide having the nucleotide sequence shown in SEQ ID NO: 331. The PCR reaction solution amounted to 50 µl by adding the 2 primers each amounting to 200 nM, 10 ng of the chromosomal DNA, 4.0 µl of dNTP mix (a mixture of 2.5 mM of each of the 4 types of dNTP; Clontech Company), 10.0 µl of 5×GC buffer, 2.2 µl of 25 mM Mg(OAc)$_2$, 10.0 µl of 5M GC-Melt and 1.0 µl of Advantage-GC genomic polymerase mix (Clontech Company) and distilled water. The reaction conditions of the PCR were after maintaining 94° C. for 1 minute; repeating 7 cycles of a cycle that included maintaining 94° C. for 10 seconds and then 72° C. for 3 minutes; repeating 36 cycles of a cycle that included 94° C. for 10 seconds and then 67° C. for 3 minutes; and then maintaining 67° C. for 7 minutes. The DNA was purified from the PCR reaction solution with QIAquick PCR Purification Kit (Qiagen Company) according to the instructions attached to said kit. The obtained DNA was ligated to TA cloning vector pCR2.1 (Invitrogen Company), according to the attached manual, and was introduced into *E. Coli* TOP10F' (Invitrogen Company). The plasmid DNA was prepared from the obtained *E. coli* transformant, utilizing QIAprep Spin Miniprep Kit (Qiagen Company) to obtain a plasmid solution containing the present invention DNA (A11).

Similarly, PCR was conducted by utilizing as the template the chromosomal DNA of *Streptomyces tsusimaensis* IFO 13782 prepared in Example 33(1) and by utilizing as primers the oligonucleotide having the nucleotide sequence shown in SEQ ID NO: 332 and the oligonucleotide having the nucleotide sequence shown in SEQ ID NO: 333. The DNA obtained by the PCR was ligated to the vector similar to the above. *E. coli* was then transformed. The plasmid was prepared from the obtained *E. coli* transformant to obtain a plasmid solution containing the present invention DNA (A12).

Similarly, PCR was conducted by utilizing as the template the chromosomal DNA of *Streptomyces thermocoerulesces* IFO 14273t prepared in Example 35(1) and by utilizing as primers the oligonucleotide having the nucleotide sequence shown in SEQ ID NO: 331 and the oligonucleotide having the nucleotide sequence shown in SEQ ID NO: 334. The DNA obtained by the PCR was ligated to the vector similar to the above. *E. coli* was then transformed. The plasmid was prepared from the obtained *E. coli* transformant to obtain a plasmid solution containing the present invention DNA (A13).

Similarly, PCR was conducted by utilizing as the template the chromosomal DNA of *Streptomyces glomerochromogenes* IFO 13673t prepared in Example 37(1) and by utilizing as primers the oligonucleotide having the nucleotide sequence shown in SEQ ID NO: 330 and the oligonucleotide having the nucleotide sequence shown in SEQ ID NO: 331. The DNA obtained by the PCR was ligated to the vector similar to the above. *E. coli* was then transformed. The plasmid was prepared from the obtained *E. coli* transformant to obtain a plasmid solution containing the present invention DNA (A14).

Similarly, PCR was conducted by utilizing as the template the chromosomal DNA of *Streptomyces olivochromogenes* IFO 12444 prepared in Example 39(1) and by utilizing as primers the oligonucleotide having the nucleotide sequence shown in SEQ ID NO: 330 and the oligonucleotide having the nucleotide sequence shown in SEQ ID NO: 331. The DNA obtained by the PCR was ligated to the vector similar to the above. *E. coli* was then transformed. The plasmid was prepared from the obtained *E. coli* transformant to obtain a plasmid solution containing the present invention DNA (A15).

Similarly, PCR was conducted by utilizing as the template the chromosomal DNA of *Streptomyces ornatus* IFO 13069t prepared in Example 48(1) and by utilizing as primers the oligonucleotide having the nucleotide sequence shown in SEQ ID NO: 335 and the oligonucleotide having the nucleotide sequence shown in SEQ ID NO: 336. The DNA obtained by the PCR was ligated to the vector similar to the above. *E. coli* was then transformed. The plasmid was prepared from the obtained *E. coli* transformant to obtain a plasmid solution containing the present invention DNA (A16).

Similarly, PCR was conducted by utilizing as the template the chromosomal DNA of *Streptomyces griseus* ATCC 10137 prepared in Example 50(1) and by utilizing as primers the oligonucleotide having the nucleotide sequence shown in SEQ ID NO: 335 and the oligonucleotide having the nucleotide sequence shown in SEQ ID NO: 336. The DNA obtained by the PCR was ligated to the vector similar to the above. *E. coli* was then transformed. The plasmid was prepared from the obtained *E. coli* transformant to obtain a plasmid solution containing the present invention DNA (A17).

Similarly, PCR was conducted by utilizing as the template the chromosomal DNA of *Streptomyces achromogenes* IFO 12735 prepared in Example 52(1) and by utilizing as primers the oligonucleotide having the nucleotide sequence shown in SEQ ID NO: 330 and the oligonucleotide having the nucleotide sequence shown in SEQ ID NO: 331. The DNA obtained by the PCR was ligated to the vector similar to the above. *E. coli* was then transformed. The plasmid was prepared from the obtained *E. coli* transformant to obtain a plasmid solution containing the present invention DNA (A18).

Similarly, PCR was conducted by utilizing as the template the chromosomal DNA of *Streptomyces griseus* IFO 13849T prepared in Example 54(1) and by utilizing as primers the oligonucleotide having the nucleotide sequence shown in SEQ ID NO: 333 and the oligonucleotide having the nucleotide sequence shown in SEQ ID NO: 335. The DNA obtained by the PCR was ligated to the vector similar to the above. *E. coli* was then transformed. The plasmid was prepared from the obtained *E. coli* transformant to obtain a plasmid solution containing the present invention DNA (A19).

Similarly, PCR was conducted by utilizing as the template the chromosomal DNA of *Streptomyces lanatus* IFO 12787T prepared in Example 56(1) and by utilizing as primers the oligonucleotide having the nucleotide sequence shown in SEQ ID NO: 331 and the oligonucleotide having the nucleotide sequence shown in SEQ ID NO: 337. The DNA obtained by the PCR was ligated to the vector similar to the above. *E. coli* was then transformed. The plasmid was prepared from the obtained *E. coli* transformant to obtain a plasmid solution containing the present invention DNA (A20).

Similarly, PCR was conducted by utilizing as the template the chromosomal DNA of *Streptomyces misawanensis* IFO 13855T prepared in Example 58(1) and by utilizing as primers the oligonucleotide having the nucleotide sequence shown in SEQ ID NO: 331 and the oligonucleotide having the nucleotide sequence shown in SEQ ID NO: 338. The DNA obtained by the PCR was ligated to the vector similar to the above. *E. coli* was then transformed. The plasmid was prepared from the obtained *E. coli* transformant to obtain a plasmid solution containing the present invention DNA (A21).

Similarly, PCR was conducted by utilizing as the template the chromosomal DNA of *Streptomyces roseorubens* IFO 13682T prepared in Example 62(1) and by utilizing as primers the oligonucleotide having the nucleotide sequence shown in SEQ ID NO: 331 and the oligonucleotide having the nucleotide sequence shown in SEQ ID NO: 339. The DNA obtained by the PCR was ligated to the vector similar to the above. *E. coli* was then transformed. The plasmid was prepared from the obtained *E. coli* transformant to obtain a plasmid solution containing the present invention DNA (A23).

Similarly, PCR was conducted by utilizing as the template the chromosomal DNA of *Streptomyces steffisburgensis* IFO 13446T prepared in Example 66(1) and by utilizing as primers the oligonucleotide having the nucleotide sequence shown in SEQ ID NO: 331 and the oligonucleotide having the nucleotide sequence shown in SEQ ID NO: 339. The DNA obtained by the PCR was ligated to the vector similar to the above. *E. coli* was then transformed. The plasmid was prepared from the obtained *E. coli* transformant to obtain a plasmid solution containing the present invention DNA (A25).

Further, similarly, PCR was conducted by utilizing as the template the chromosomal DNA of *Streptomyces pallidus* IFO 13434T prepared in Example 60(1) and by utilizing as primers the oligonucleotide having the nucleotide sequence shown in SEQ ID NO: 340 and the oligonucleotide having the nucleotide sequence shown in SEQ ID NO: 341. The DNA obtained by the PCR was ligated to the vector similar to the above. *E. coli* was then transformed. The plasmid was prepared from the obtained *E. coli* transformant to obtain a plasmid solution containing the present invention DNA (A22).

Similarly, PCR was conducted by utilizing as the template the chromosomal DNA of *Streptomyces rutgersensis* IFO 15875T prepared in Example 64(1) and by utilizing as primers the oligonucleotide having the nucleotide sequence shown in SEQ ID NO: 342 and the oligonucleotide having the nucleotide sequence shown in SEQ ID NO: 343. The DNA obtained by the PCR was ligated to the vector similar to the above. *E. coli* was then transformed. The plasmid was prepared from the obtained *E. coli* transformant to obtain a plasmid solution containing the present invention DNA (A24).

(3) Dot Blot Hybridization

About 100 ng and 10 ng of each of the plasmids prepared in Example 69(2) was blotted on a Hybond N+ Nylon Membrane (Amersham Biosciences Company). The plasmids were: the plasmid DNA containing the present invention DNA (A11), the plasmid DNA containing the present invention DNA (A12), the plasmid DNA containing the present invention DNA (A13), the plasmid DNA containing the present invention DNA (A14), the plasmid DNA containing the present invention DNA (A15), the plasmid DNA containing the present invention DNA (A16), the plasmid DNA containing the present invention DNA (A17), the plasmid DNA containing the present invention DNA (A18), the plasmid DNA containing the present invention DNA (A19), the plasmid DNA containing the present invention DNA (A20), the plasmid DNA containing the present invention DNA (A21), the plasmid DNA containing the present invention DNA (A23), and the plasmid DNA containing the present invention DNA (A25). Ultraviolet light was directed at the obtained membranes with a transilluminator for 5 minutes.

Hybridization and detection were conducted according to the method described in Example 30(2). The probes prepared in Example 30(1) were maintained at 100° C. for 5 minutes and then cooled on ice. As the probes, there was utilized the DNA having the nucleotide sequence shown in SEQ ID NO: 6 labeled with digoxigenin (hereinafter referred to as "DIG labeled probe (A1)"), the DNA having the nucleotide sequence shown in SEQ ID NO: 7 labeled with digoxigenin (hereinafter referred to as "DIG labeled probe (A2)"), the DNA having the nucleotide sequence shown in SEQ ID NO: 8 labeled with digoxigenin (hereinafter referred to as "DIG labeled probe (A3)") or the DIG labeled probe (A4) produced in Example 69(1). In the events of utilizing any one of the DIG labeled probe (A1), (A2), (A3) or (A4) for hybridization, a signal was detected for each of the reagents of the 10 ng and 100 ng of each of the above plasmid DNA.

Further, similarly, about 10 ng and 100 ng of each of the plasmid DNA containing the present invention DNA (A22) prepared in Example 69(2) and the plasmid DNA containing the present invention DNA (A24) are blotted onto a Hybond N+ nylon membrane (Amersham Biosciences Company). Hybridization and detection are conducted accordingly to Example 30(2).

Example 70

Preparation of the Present Invention DNA (A23) in which the Codon Usage has been Adjusted for Expression in Soybean (Hereinafter, Referred to as the "Present Invention DNA (A23)S")

(1) Preparation of the Present Invention DNA (A23)S

PCR was conducted with Pyrobest DNA polymerase (Takara Shuzo Company) according to the attached manual, by utilizing as primers the oligonucleotide having a nucleotide sequence shown in SEQ ID NO: 346 and the oligonucleotide having a nucleotide sequence shown in SEQ ID NO: 367. An aliquot of the obtained PCR product was utilized as a template for a PCR conducted similarly utilizing as primers the oligonucleotide having the nucleotide sequence shown in SEQ ID NO: 345 and oligonucleotide having the nucleotide sequence shown in SEQ ID NO: 366. Further, an aliquot of that PCR product was utilized as a template for a PCR conducted similarly utilizing as primers the oligonucleotide having the nucleotide sequence shown in SEQ ID NO: 344 and oligonucleotide having the nucleotide sequence shown in SEQ ID NO: 365. The obtained reaction solution was designated as reaction solution 1.

Further, PCR was conducted with Pyrobest DNA polymerase (Takara Shuzo Company) according to the attached manual, by utilizing as primers the oligonucleotide having a nucleotide sequence shown in SEQ ID NO: 349 and the oligonucleotide having a nucleotide sequence shown in SEQ ID NO: 364. An aliquot of the obtained PCR product was utilized as a template for a PCR conducted similarly utilizing as primers the oligonucleotide having the nucleotide sequence shown in SEQ ID NO: 348 and oligonucleotide having the nucleotide sequence shown in SEQ ID NO: 363. Further, an aliquot of that PCR product was utilized as a template for a PCR conducted similarly utilizing as primers the oligonucleotide having the nucleotide sequence shown in SEQ ID NO: 347 and oligonucleotide having the nucleotide sequence shown in SEQ ID NO: 362. The obtained reaction solution was designated as reaction solution 2.

Further, PCR was conducted with Pyrobest DNA polymerase (Takara Shuzo Company) according to the attached manual by utilizing as primers the oligonucleotide having a nucleotide sequence shown in SEQ ID NO: 352 and oligonucleotide having a nucleotide sequence shown in SEQ ID NO: 361. An aliquot of the obtained PCR product was utilized as a template for a PCR conducted similarly utilizing as primers having the nucleotide sequence shown in SEQ ID NO: 351 and oligonucleotide having the nucleotide sequence shown in SEQ ID NO: 360. Further, an aliquot of that PCR product was utilized as a template for a PCR conducted similarly utilizing as primers the oligonucleotide having the nucleotide sequence shown in SEQ ID NO: 350 and oligonucleotide having the nucleotide sequence shown in SEQ ID NO: 359. The obtained reaction solution was designated as reaction solution 3.

Further, PCR was conducted with Pyrobest DNA polymerase (Takara Shuzo Company) according to the attached manual, by utilizing as primers the oligonucleotide having a nucleotide sequence shown in SEQ ID NO: 355 and oligonucleotide having a nucleotide sequence shown in SEQ ID NO: 358. An aliquot of the obtained PCR product was utilized as a template for a PCR conducted similarly utilizing as primers the oligonucleotide having the nucleotide sequence shown in SEQ ID NO: 354 and oligonucleotide having the nucleotide sequence shown in SEQ ID NO: 357. Further, an aliquot of that PCR product was utilized as a template for a PCR conducted similarly utilizing as primers the oligonucleotide having the nucleotide sequence shown in SEQ ID NO: 353 and oligonucleotide having the nucleotide sequence shown in SEQ ID NO: 356. The obtained reaction solution was designated as reaction solution 4.

The reaction solutions 1 to 4 obtained in such a way were mixed. PCR was conducted with Pyrobest DNA polymerase (Takara Shuzo Company) according to the attached manual, by utilizing as a template an aliquot of the mixture thereof and by utilizing as primers the oligonucleotide having a nucleotide sequence shown in SEQ ID NO: 344 and oligonucleotide having a nucleotide sequence shown in SEQ ID NO: 356. The nucleotide sequence of the amplified DNA was confirmed. There was obtained a DNA having a sequence in which the nucleotide sequence 5'-cat-3' is connected upstream of the 5' terminus and the nucleotide sequence 5'-aagctt-3' is connected downstream of the 3' terminus of the nucleotide sequence shown in SEQ ID NO: 368.

The codon usage of the present invention DNA (A23) having the nucleotide sequence shown in SEQ ID NO: 232 (GC content of 73.10%) is shown in Table 28 and Table 29. The codon usage of soybean (GC content of 46.12%) is shown in Table 24 and Table 25. The codon usage of the present invention DNA (A23)S having the nucleotide sequence shown in SEQ ID NO: 368 (GC content of 52.38%) is shown in Table 30 and Table 31.

TABLE 28

| codon | % | codon | % |
|---|---|---|---|
| TTT | 0.00 | TCT | 0.00 |
| TTC | 4.01 | TCC | 1.50 |
| TTA | 0.00 | TCA | 0.00 |
| TTG | 0.00 | TCG | 0.50 |
| CTT | 0.00 | CCT | 0.00 |
| CTC | 4.26 | CCC | 5.76 |
| CTA | 0.00 | CCA | 0.00 |

TABLE 28-continued

| codon | % | codon | % |
|---|---|---|---|
| CTG | 7.77 | CCG | 2.26 |
| ATT | 0.00 | ACT | 0.00 |
| ATC | 4.51 | ACC | 3.76 |
| ATA | 0.00 | ACA | 0.00 |
| ATG | 2.26 | ACG | 2.76 |
| GTT | 0.00 | GCT | 0.25 |
| GTC | 3.51 | GCC | 9.27 |
| GTA | 0.00 | GCA | 0.75 |
| GTG | 2.51 | GCG | 1.75 |

TABLE 29

| codon | % | codon | % |
|---|---|---|---|
| TAT | 0.00 | TGT | 0.00 |
| TAC | 1.00 | TGC | 0.75 |
| TAA | 0.25 | TGA | 0.00 |
| TAG | 0.00 | TGG | 0.75 |
| CAT | 0.00 | CGT | 0.50 |
| CAC | 2.26 | CGC | 6.02 |
| CAA | 0.50 | CGA | 0.25 |
| CAG | 2.51 | CGG | 3.01 |
| AAT | 0.00 | AGT | 0.00 |
| AAC | 1.00 | AGC | 1.25 |
| AAA | 0.25 | AGA | 0.00 |
| AAG | 0.50 | AGG | 0.50 |
| GAT | 0.00 | GGT | 0.98 |
| GAC | 7.27 | GGC | 6.27 |
| GAA | 1.25 | GGA | 0.25 |
| GAG | 5.26 | GGG | 1.00 |

TABLE 30

| codon | % | codon | % |
|---|---|---|---|
| TTT | 2.01 | TCT | 0.75 |
| TTC | 2.01 | TCC | 0.50 |
| TTA | 1.00 | TCA | 0.75 |
| TTG | 3.01 | TCG | 0.25 |
| CTT | 3.26 | CCT | 3.01 |
| CTC | 2.26 | CCC | 1.50 |
| CTA | 1.00 | CCA | 3.01 |

TABLE 30-continued

| codon | % | codon | % |
|---|---|---|---|
| CTG | 1.50 | CCG | 0.50 |
| ATT | 2.26 | ACT | 2.26 |
| ATC | 1.25 | ACC | 1.75 |
| ATA | 1.00 | ACA | 2.01 |
| ATG | 2.26 | ACG | 0.50 |
| GTT | 2.26 | GCT | 4.51 |
| GTC | 1.00 | GCC | 2.76 |
| GTA | 0.75 | GCA | 3.76 |
| GTG | 2.01 | GCG | 1.00 |

TABLE 31

| codon | % | codon | % |
|---|---|---|---|
| TAT | 0.50 | TGT | 0.25 |
| TAC | 0.50 | TGC | 0.50 |
| TAA | 0.25 | TGA | 0.00 |
| TAG | 0.00 | TGG | 0.75 |
| CAT | 1.25 | CGT | 1.50 |
| CAC | 1.00 | CGC | 1.25 |
| CAA | 1.75 | CGA | 0.75 |
| CAG | 1.25 | CGG | 0.50 |
| AAT | 0.50 | AGT | 0.50 |
| AAC | 0.50 | AGC | 0.50 |
| AAA | 0.25 | AGA | 3.26 |
| AAG | 0.50 | AGG | 3.01 |
| GAT | 4.51 | GGT | 2.26 |
| GAC | 2.76 | GGC | 1.50 |
| GAA | 3.26 | GGA | 2.26 |
| GAG | 3.26 | GGG | 1.50 |

(2) Production of a Transformed *E. Coli* Having the Present Invention Protein (A23)S The DNA having the nucleotide sequence shown in SEQ ID NO: 368 obtained in Example 70(1) was digested with restriction enzymes NdeI and HindIII. The obtained DNA and the plasmid pKSN2 digested with NdeI and HindIII were ligated to obtain a plasmid in which the DNA having the nucleotide sequence shown in SEQ ID NO: 368 is inserted between the NdeI site and the HindIII site of pKSN2 (hereinafter referred to as "pKSN1584soy"). Said plasmid was introduced into *E. coli* JM109. The obtained *E. coli* transformant was designated JM109/pKSN1584soy.

(3) Expression of the Present Invention Protein (A23)S in *E. Coli* and Recovery of Said Protein Similarly to Example 4(2), each of *E. coli* JM109/pKSN1584soy obtained in Example 70(2) and *E. coli* JM109/pKSN1584F obtained in Example 63(1) was cultured. The cells were recovered. Cell lysate solutions were prepared.

Under the method described in Example 4(2), supernatant fractions were prepared from the cell lysate solutions (hereinafter, the supernatant fraction obtained from *E. coli* JM109/pKSN1584soy is referred to as "*E. coli* pKSN1584soy extract" and the supernatant fraction obtained from *E. coli* JM109/pKSN1584F is referred to as "*E. coli* pKSN1584F extract"). The amount of P450 per the protein amount contained in *E. coli* pKSN1584soy extract was compared to and was higher than the amount of P450 per the protein amount contained in *E. coli* pKSN1584F extract.

Example 71

Preparation and Expression of the Present Invention DNA (A25) in which the Codon Usage has been Adjusted for Expression in Soybean (Hereinafter, Referred to as the "Present Invention DNA (A25)S")

(1) Preparation of the Present Invention DNA (A25)S

PCR was conducted with Pyrobest DNA polymerase (Takara Shuzo Company) according to the attached manual, by utilizing as primers the oligonucleotide having a nucleotide sequence shown in SEQ ID NO: 371 and the oligonucleotide having a nucleotide sequence shown in SEQ ID NO: 392. An aliquot of the obtained PCR product was utilized as a template for a PCR conducted similarly utilizing as primers the oligonucleotide having the nucleotide sequence shown in SEQ ID NO: 370 and oligonucleotide having the nucleotide sequence shown in SEQ ID NO: 391. Further, an aliquot of that PCR product was utilized as a template for a PCR conducted similarly utilizing as primers the oligonucleotide having the nucleotide sequence shown in SEQ ID NO: 369 and oligonucleotide having the nucleotide sequence shown in SEQ ID NO: 390. The obtained reaction solution was designated as reaction solution 1.

Further, PCR was conducted with Pyrobest DNA polymerase (Takara Shuzo Company) according to the attached manual, by utilizing as primers the oligonucleotide having a nucleotide sequence shown in SEQ ID NO: 374 and the oligonucleotide having a nucleotide sequence shown in SEQ ID NO: 389. An aliquot of the obtained PCR product was utilized as a template for a PCR conducted similarly utilizing as primers the oligonucleotide having the nucleotide sequence shown in SEQ ID NO: 373 and oligonucleotide having the nucleotide sequence shown in SEQ ID NO: 388. Further, an aliquot of that PCR product was utilized as a template for a PCR conducted similarly utilizing as primers the oligonucleotide having the nucleotide sequence shown in SEQ ID NO: 372 and oligonucleotide having the nucleotide sequence shown in SEQ ID NO: 387. The obtained reaction solution was designated as reaction solution 2.

Further, PCR was conducted with Pyrobest DNA polymerase (Takara Shuzo Company) according to the attached manual by utilizing as primers the oligonucleotide having a nucleotide sequence shown in SEQ ID NO: 377 and oligonucleotide having a nucleotide sequence shown in SEQ ID NO: 386. An aliquot of the obtained PCR product was utilized as a template for a PCR conducted similarly utilizing as primers having the nucleotide sequence shown in SEQ ID NO: 376 and oligonucleotide having the nucleotide sequence shown in SEQ ID NO: 385. Further, an aliquot of that PCR product was utilized as a template for a PCR conducted similarly utilizing as primers the oligonucleotide having the nucleotide sequence shown in SEQ ID NO: 375 and oligonucleotide having the nucleotide sequence shown in SEQ ID NO: 384. The obtained reaction solution was designated as reaction solution 3.

Further, PCR was conducted with Pyrobest DNA polymerase (Takara Shuzo Company) according to the attached manual, by utilizing as primers the oligonucleotide having a nucleotide sequence shown in SEQ ID NO: 380 and oligonucleotide having a nucleotide sequence shown in SEQ ID NO: 383. An aliquot of the obtained PCR product was utilized as a template for a PCR conducted similarly utilizing as primers the oligonucleotide having the nucleotide sequence shown in SEQ ID NO: 379 and oligonucleotide having the nucleotide sequence shown in SEQ ID NO: 382. Further, an aliquot of that PCR product was utilized as a template for a PCR conducted similarly utilizing as primers the oligonucleotide having the nucleotide sequence shown in SEQ ID NO: 378 and oligonucleotide having the nucleotide sequence shown in SEQ ID NO: 381. The obtained reaction solution was designated as reaction solution 4.

The reaction solutions 1 to 4 obtained in such a way were mixed. PCR was conducted with Pyrobest DNA polymerase (Takara Shuzo Company) according to the attached manual, by utilizing as a template an aliquot of the mixture thereof and by utilizing as primers the oligonucleotide having a nucleotide sequence shown in SEQ ID NO: 369 and oligonucleotide having a nucleotide sequence shown in SEQ ID NO: 381. The nucleotide sequence of the amplified DNA was confirmed. There was obtained a DNA having a sequence in which the nucleotide sequence 5'-cat-3' is connected upstream of the 5' terminus and the nucleotide sequence 5'-aagctt-3' is connected downstream of the 3' terminus of the nucleotide sequence shown in SEQ ID NO: 393.

The codon usage of the present invention DNA (A25) having the nucleotide sequence shown in SEQ ID NO: 234 (GC content of 71.93%) is shown in Table 32 and Table 33. The codon usage of soybean (GC content of 46.12%) is shown in Table 24 and Table 25. The codon usage of the present invention DNA (A25)S having the nucleotide sequence shown in SEQ ID NO: 393 (GC content of 52.05%) is shown in Table 34 and Table 35.

TABLE 32

| codon | % | codon | % |
|-------|------|-------|------|
| TTT | 0.00 | TCT | 0.00 |
| TTC | 3.76 | TCC | 1.25 |
| TTA | 0.00 | TCA | 0.25 |
| TTG | 0.00 | TCG | 0.75 |
| CTT | 0.00 | CCT | 0.25 |
| CTC | 4.01 | CCC | 4.01 |
| CTA | 0.00 | CCA | 0.25 |
| CTG | 9.52 | CCG | 2.76 |
| ATT | 0.00 | ACT | 0.25 |
| ATC | 4.26 | ACC | 4.01 |
| ATA | 0.25 | ACA | 0.00 |
| ATG | 2.26 | ACG | 1.75 |
| GTT | 0.00 | GCT | 0.00 |
| GTC | 3.01 | GCC | 8.52 |

TABLE 32-continued

| codon | % | codon | % |
|---|---|---|---|
| GTA | 0.00 | GCA | 0.50 |
| GTG | 2.51 | GCG | 3.01 |

TABLE 33

| codon | % | codon | % |
|---|---|---|---|
| TAT | 0.00 | TGT | 0.25 |
| TAC | 1.25 | TGC | 0.50 |
| TAA | 0.25 | TGA | 0.00 |
| TAG | 0.00 | TGG | 1.00 |
| CAT | 0.25 | CGT | 0.75 |
| CAC | 2.26 | CGC | 5.51 |
| CAA | 0.00 | CGA | 1.25 |
| CAG | 3.01 | CGG | 3.26 |
| AAT | 0.00 | AGT | 0.00 |
| AAC | 1.00 | AGC | 1.00 |
| AAA | 0.25 | AGA | 0.25 |
| AAG | 1.00 | AGG | 0.00 |
| GAT | 0.00 | GGT | 0.25 |
| GAC | 7.52 | GGC | 4.76 |
| GAA | 1.00 | GGA | 0.25 |
| GAG | 4.76 | GGG | 1.25 |

TABLE 34

| codon | % | codon | % |
|---|---|---|---|
| TTT | 1.75 | TCT | 1.25 |
| TTC | 2.01 | TCC | 0.50 |
| TTA | 1.25 | TCA | 0.50 |
| TTG | 3.26 | TCG | 0.00 |
| CTT | 3.51 | CCT | 2.76 |
| CTC | 2.51 | CCC | 1.25 |
| CTA | 1.25 | CCA | 2.76 |
| CTG | 1.75 | CCG | 0.50 |
| ATT | 2.26 | ACT | 2.01 |
| ATC | 1.25 | ACC | 1.75 |
| ATA | 1.00 | ACA | 1.75 |
| ATG | 2.26 | ACG | 0.50 |
| GTT | 2.26 | GCT | 4.51 |
| GTC | 1.00 | GCC | 2.76 |
| GTA | 0.50 | GCA | 3.76 |
| GTG | 1.75 | GCG | 1.00 |

TABLE 35

| codon | % | codon | % |
|---|---|---|---|
| TAT | 0.50 | TGT | 0.25 |
| TAC | 0.75 | TGC | 0.50 |
| TAA | 0.25 | TGA | 0.00 |
| TAG | 0.00 | TGG | 1.00 |
| CAT | 1.25 | CGT | 1.75 |
| CAC | 1.25 | CGC | 1.50 |
| CAA | 1.50 | CGA | 0.75 |
| CAG | 1.50 | CGG | 0.75 |
| AAT | 0.50 | AGT | 0.50 |
| AAC | 0.50 | AGC | 0.50 |
| AAA | 0.50 | AGA | 3.26 |
| AAG | 0.75 | AGG | 3.01 |
| GAT | 4.76 | GGT | 2.01 |
| GAC | 2.76 | GGC | 1.25 |
| GAA | 2.76 | GGA | 2.01 |
| GAG | 3.01 | GGG | 1.25 |

(2) Production of a Transformed *E. Coli* Having the Present Invention Protein (A25)S The DNA having the nucleotide sequence shown in SEQ ID NO: 393 obtained in Example 71(1) was digested with restriction enzymes NdeI and HindIII. The obtained DNA and the plasmid pKSN2 digested with NdeI and HindIII were ligated to obtain a plasmid in which the DNA having the nucleotide sequence shown in SEQ ID NO: 393 is inserted between the NdeI site and the HindIII site of pKSN2 (hereinafter referred to as "pKSN1609soy"). Said plasmid was introduced into *E. coli* JM109. The obtained *E. coli* transformant was designated JM109/pKSN1609soy.

(3) Expression of the Present Invention Protein (A25)S in *E. Coli* and Recovery of Said Protein Similarly to Example 4(2), each of *E. coli* JM109/pKSN1609soy obtained in Example 71(2) and *E. coli* JM109/pKSN1609F obtained in Example 67(1) was cultured. The cells were recovered. Cell lysate solutions were prepared. Under the method described in Example 4(2), supernatant fractions were prepared from the cell lysate solutions (hereinafter, the supernatant fraction obtained from *E. coli* JM109/pKSN1609soy is referred to as "*E. coli* pKSN1609soy extract" and the supernatant fraction obtained from *E. coli* JM109/pKSN1609F is referred to as "*E. coli* pKSN1609F extract"). The amount of P450 per the protein amount contained in *E. coli* pKSN1609soy extract was compared to and was higher than the amount of P450 per the protein amount contained in *E. coli* pKSN1609F extract.

Example 72

Preparation of the Present Invention Antibody (A) Recognizing the Present Invention Protein (A25) (Hereinafter Referred to as "Present Invention Antibody (A25)")

(1) Preparation of the Extract of an *E. Coli* Expressing the Present Invention Protein (A25)

In accordance with the method described in Example 4(2), *E. coli* JM109/pKSN1609soy, produced in Example 71(2), was pre-cultured overnight. The obtained cultured medium was inoculated to 1 L of TB medium containing 50 µg/ml of ampicillin and cultured at 26° C. Then 5-aminolevulinic acid was added to the final concentration of 500 µM, and IPTG was added to a final concentration of 1 mM, and that was further cultured. The cells were recovered from the cultured medium, were washed with 0.05M Tris-HCl Buffer (pH7.5) and then suspended in 100 ml of said buffer containing 1 mM PMSF. The obtained cell culture medium was subjected 3 times to a sonicator (Sonifier (Branson Sonic Power Company)) at 10 minutes each under the conditions of output 5, duty cycle 30%, in order to obtain cell lysate solutions. After centrifuging the cell lysate solutions (9,000×g, 10 minutes) the supernatants were recovered and centrifuged (200,000×g, 70 minutes) to recover supernatant fractions (hereinafter, the supernatant fraction obtained from *E. coli* JM109/pKSN1609soy is referred to as "*E. coli* pKSN1609soy extract"

(2) Purification of the Present Invention Protein (A25)

The supernatant fraction obtained in Example 72(1) (*E. coli* pKSN1609soy extract) was injected into a Hiload HiLoad16/10 Q Sepharose HP column (Amersham Bioscience Company). Next, after flowing 40 ml of 20 mM bistrispropane buffer (pH7.0) into the column, 20 mM bistrispropane buffer was flown with a linear gradient of NaCl (gradient of NaCl was 0.00125M/minute, range of NaCl concentration was from 0M to 0.375M, flow rate was 3 ml/minute) to fraction recover 10 ml of fractions eluting at the NaCl concentration of from 0.088M to 0.100M.

The recovered fractions were subjected to a PD-10 column (Amersham Biosciences Company) and eluted with 20 mM bistrispropane buffer (pH7.0) to recover the fractions containing protein. Next, said fractions were injected into a MonoQ HR 10/10 (Amersham Biosciences Company). Sixteen milliliters (16 ml) of 20 mM bistrispropane buffer was flown into the column. Next, 20 mM bistrispropane buffer was flown with a linear gradient of NaCl (gradient of NaCl was 0.001042M/minute, range of NaCl concentration was from 0M to 0.25M, flow rate was 4 ml/minute) to fraction recover 8 ml of fractions eluting at the NaCl concentration of from 0.060M to 0.069M.

The recovered fractions were diluted 2.5 fold with 20 mM bistrispropane buffer (pH7.0) and injected into a MonoQ HR 5/5 column (Amersham Biosciences Company). Next, after flowing 2 ml of 20 mM bistrispropane buffer (pH7.0) into the column, 20 mM bistrispropane buffer was flown with a linear gradient of NaCl (gradient of NaCl was 0.008333M/minute, range of NaCl concentration was from 0M to 0.25M, flow rate was 1 ml/minute) to fraction recover 0.5 ml of fractions eluting at the NaCl concentration of from 0.073M to 0.077M.

The fractions purified in such a way were analyzed with SDS-PAGE by utilizing a "PAG mini Daiichi 10/20" (Daiichi Pure Chemicals Co., Ltd.) to confirm that those fractions were fractions which mainly contain the present invention protein (A25).

(3) Preparation of the Present Invention Antibody (A25)

Preparation of the Present Invention Antibody was Conducted Accordingly to the Method described in Example 44(3). However, instead of utilizing the present invention protein (A1), the present invention protein (A25) obtained in Example 72(2) was utilized to obtain antiserum containing the present invention antibody (A25).

Example 73

Detection of the Present Invention Protein by the Present Invention Antibody (A25)

An immunoblot was conducted by utilizing the present invention antibody (A25) obtained in Example 72(3) with each of the *E. coli* extracts. There was a SDS polyacrylamide electrophoresis (40 mA, 1 hour) of: the *E. coli* pKSN452F extract obtained in Example 49(2) (containing about 2 pmol of the present invention protein (A16)); the *E. coli* pKSN608F extract obtained in Example 51(2) (containing about 2 pmol of the present invention protein (A17)); the *E. coli* pKSN646BF extract obtained in Example 53(2) (containing about 2 pmol of the present invention protein (A18)); the *E. coli* pKSN1502F extract obtained in Example 55(2) (containing about 2 pmol of the present invention protein (A19)); the *E. coli* pKSN1525F extract obtained in Example 57(2) (containing about 2 pmol of the present invention protein (A20)); the *E. coli* pKSN1543BF extract obtained in Example 59(2) (containing about 2 pmol of the present invention protein (A21)); the *E. coli* pKSN1558BF extract obtained in Example 61(2) (containing about 2 pmol of the present invention protein (A22)); the *E. coli* pKSN1584F extract obtained in Example 63(2) (containing about 2 pmol of the present invention protein (A23)); the *E. coli* pKSN1589BF extract obtained in Example 65(2) (containing about 2 pmol of the present invention protein (A24)); the *E. coli* pKSN1609F extract obtained in Example 67(2) (containing about 0.5 pmol of the present invention protein (A25)); the *E. coli* pKSN1584soy extract obtained in Example 70(3) (containing about 2 pmol of the present invention protein (A23)); the *E. coli* pKSN1609soy extract obtained in Example 71(3) (containing about 0.5 pmol of the present invention protein (A25)); and the *E. coli* pKSN2 extract obtained in Example 67(2) (containing about 0.8 mg of protein). The proteins in said gel were transferred to a PVDF membrane according to the method described in Example 45. The PDVF membrane obtained in Example 45 (hereinafter referred to as "PDVF membrane (A)") and the PDVF membrane obtained from the above method (hereinafter referred to as "PDVF membrane (B)") were reacted with the antiserum obtained in Example 72(3), according to the method described Example 45. Subsequently, there was conducted a reaction with the secondary antibody, a washing and a staining in accordance with the method described in Example 45. Stains for bands corresponding to the present invention proteins (A1), (A2), (A3), (A4), (A11), (A12), (A13), (A14) and (A15) as well as the present proteins (A9) and (A10) were detected on the PDVF membrane (A). Stains for bands corresponding to the present invention proteins (A16), (A17), (A18), (A19), (A20), (A21), (A22), (A23), (A24) and (A25) were detected on the PDVF membrane (B). No stained band was detected with the reagent of *E. coli* pKSN2 extract obtained in Example 4(2) (containing 0.78 mg of protein) of PVDF membrane (A) and with the reagent of *E. coli* pKSN2 extract obtained in Example 67(2) (containing 0.8 mg of protein) of PVDF membrane (B).

Example 74

Introduction of the Present Invention DNA (A23)S into a Plant (1) Construction of a Chloroplast Expression Plasmid Containing the Present Invention DNA (A23)S for Direct Introduction—Part 1

A plasmid containing a chimeric DNA in which the present invention DNA (A23)S was connected immediately after the nucleotide sequence encoding the chloroplast transit peptide of soybean (cv. Jack) RuBPC small subunit without a change of frames in the codons was constructed as a plasmid for introducing the present invention DNA (A23)S into a plant with the particle gun method.

First, DNA comprising the nucleotide sequence shown in SEQ ID NO: 398 was amplified by PCR. The PCR was conducted by utilizing as a template pKSN1584soy obtained in Example 70(2) and by utilizing as primers an oligonucleotide consisting of the nucleotide sequence shown in SEQ ID NO: 397 and an oligonucleotide consisting of the nucleotide sequence shown in SEQ ID NO: 398. The PCR utilized KOD-plus (Toyobo Company). The PCR carried out after conducting once a maintenance at 94° C. for 2 minutes; 20 cycles of a cycle that included maintaining 94° C. for 30 seconds, followed by 53° C. for 30 seconds, and followed by 68° C. for 90 seconds; and a final maintenance at 68° C. for 3 minutes. The amplified DNA was recovered and purified with MagExtractor-PCR & Gel-Clean up (Toyobo Company) by conducting the procedures according to the attached manual. By treating the obtained DNA with TaKaRa BKLKit (Takara Shuzo Company) according to the attached manual, the DNA was blunt ended and had the 5' terminus phosphorylated. A DNA comprising a nucleotide sequence shown in SEQ ID NO: 368 was recovered. After digesting plasmid pUC19 (Takara Shuzo Company) with SmaI, the 5' terminus was dephosphorylated with calf intestine alkaline phosphatase (Takara Shuzo Company). A plasmid was produced by ligating the resulting dephosphorylated DNA and the DNA comprising the nucleotide sequence shown in SEQ ID NO: 368. After digesting the obtained plasmid with restriction enzymes EcoT22I and SacI, the DNA comprising the nucleotide sequence shown in SEQ ID NO: 368 was recovered. After digesting plasmid pUCrSt657 obtained in Example 16(2) with restriction enzymes EcoT22I and SacI, there was isolated a DNA of about 2.9 kbp having a nucleotide sequence derived from pUC19 and a sequence encoding a chloroplast transit peptide of soybean (cv. Jack) RuBPC small subunit. The obtained DNA and the above DNA comprising the nucleotide sequence shown in SEQ ID NO: 368 were ligated to obtain pUCrSt1584soy (FIG. 54) containing a chimeric DNA in which the present invention DNA (A23)S was connected immediately after the nucleotide sequence encoding the chloroplast transit peptide of soybean (cv. Jack) RuBPC small subunit without a change of frames in the codons.

The obtained plasmid pUCrSt1584soy was digested with restriction enzymes BamHI and SacI to isolate a DNA comprising a nucleotide sequence shown in SEQ ID NO: 368. Said DNA was inserted between the BglII restriction site and the SacI restriction site of plasmid pNdG6-ΔT obtained in Example 16(2) to obtain plasmid pSUM-NdG6-rSt-1584soy (FIG. 55) wherein the CR16G6 promoter has connected downstream the chimeric DNA in which said DNA was connected immediately after the nucleotide sequence encoding the chloroplast transit peptide of soybean (cv. Jack) RuBPC small subunit without a change of frames in the codons.

Next, the plasmid was introduced into *E. coli* DH5α competent cells (Takara Shuzo Company) and the ampicillin resistant cells were selected. Further, the nucleotide sequences of the plasmids contained in the ampicillin resistant strains were determined by utilizing BigDye Terminator Cycle Sequencing Ready Reaction kit v3.0 (PE Applied Biosystems Company) and DNA sequencer 3100 (PE Applied Biosytems Company). As a result, it was confirmed that plasmid pSUM-NdG6-rSt-1584soy has the nucleotide sequence shown in SEQ ID NO: 368.

(2) Construction of a Chloroplast Expression Plasmid Having the Present Invention DNA (A23)S for Direct Introduction—Part (2)

A plasmid was constructed for introducing the present invention DNA (A23)S into a plant with the particle gun method. The plasmid contained a chimeric DNA in which the present invention DNA (A23)S was connected immediately after the nucleotide sequences encoding the chloroplast transit peptide of soybean (cv. Jack) RuBPC small subunit and encoding thereafter 12 amino acids of the mature protein, without a change of frames in the codons. First, DNA comprising the nucleotide sequence shown in SEQ ID NO: 368 was amplified by PCR. The PCR was conducted by utilizing as a template pKSN1584soy obtained in Example 70 and by utilizing as primers an oligonucleotide consisting of the nucleotide sequence shown in SEQ ID NO: 399 and an oligonucleotide consisting of the nucleotide sequence shown in SEQ ID NO: 398. The PCR utilized KOD-plus (Toyobo Company). The PCR carried out after conducting once a maintenance at 94° C. for 2 minutes; 25 cycles of a cycle that included maintaining 94° C. for 30 seconds, followed by 46° C. for 30 seconds, and followed by 68° C. for 90 seconds; and a final maintenance at 68° C. for 3 minutes. The amplified DNA was recovered and purified with MagExtractor-PCR & Gel-Clean up (Toyobo Company) by conducting the procedures according to the attached manual. By treating the obtained DNA with TaKaRa BKLKit (Takara Shuzo Company) according to the attached manual, the DNA was blunt ended and had the 5' terminus phosphorylated. A DNA comprising a nucleotide sequence shown in SEQ ID NO: 368 was recovered. After digesting plasmid pKF19ΔBs obtained in Example 15(3) with SmaI, the 5' terminus was dephosphorylated with calf intestine alkaline phosphatase (Takara Shuzo Company). A plasmid was produced by ligating the resulting dephosphorylated DNA and the DNA comprising the nucleotide sequence shown in SEQ ID NO: 368. After digesting the obtained plasmid with restriction enzymes BspHI and SacI, the DNA comprising the nucleotide sequence shown in SEQ ID NO: 368 was recovered. Next, plasmid pKFrSt12-657 obtained in Example 16(3) was digested with restriction enzymes BspHI and SacI to isolate the DNA derived from plasmid pKFrSt12. Said DNA was ligated with the DNA which was digested with restriction enzymes SacI and BspHI and which comprises the nucleotide sequence shown in SEQ ID NO: 368, in order to obtain plasmid pKFrSt12-1584soy (FIG. 56) containing the chimeric DNA in which the present invention DNA (A23)S was connected immediately after the nucleotide sequences encoding the chloroplast transit peptide of soybean (cv. Jack) RuBPC small subunit and encoding thereafter 12 amino acids of the mature protein, without a change of frames in the codons.

The obtained plasmid pKFrSt12-1584soy was digested with restriction enzymes BamHI and SacI to isolate the DNA comprising the nucleotide sequence shown in SEQ ID NO: 368. Said DNA was inserted between the BglII restriction site and the SacI restriction site of plasmid pNdG6-ΔT to obtain plasmid pSUM-NdG6-rSt12-1584soy (FIG. 57) wherein the CR16G6 promoter has connected downstream the chimeric DNA in which said DNA was connected immediately after the nucleotide sequence encoding the chloroplast transit peptide of soybean (cv. Jack) RuBPC small subunit without a change of frames in the codons.

Next, the plasmid was introduced into *E. coli* DH5α competent cells (Takara Shuzo Company) and the ampicillin resistant cells were selected. Further, the nucleotide sequences of the plasmids contained in the ampicillin resistant strains were determined by utilizing BigDye Terminator Cycle Sequencing Ready Reaction kit v3.0 (PE Applied Biosystems Company) and DNA sequencer 3100 (PE Applied Biosytems Company). As a result, it was confirmed that plasmid pSUM-NdG6-rSt12-1584soy has the nucleotide sequence shown in SEQ ID NO: 368.
(3) Introduction of the Present Invention DNA (A23)S into Soybean The globular embryos of soybeans (cultivar: Fayette and Jack) were prepared according to the method described in Example 47(3).

The obtained globular embryo was transplanted into fresh somatic embryo growth medium and cultured for 2 to 3 days. The plasmid pSUM-NdG6-rSt-1584soy produced in Example 74(1) or the plasmid pSUM-NdG6-rSt12-1584soy produced in Example 74(2) were introduced into those globular embryos according to the method described in Example 17(2).
(4) Selection of Somatic Embryo with Hygromycin Selection by hygromycin of a spherica-type1 embryo after the introduction of the gene, obtained in Example 74(3), is conducted according to the method described in Example 47(4).
(5) Selection of Somatic Embryo with Compound (II)

Selection by compound (II) of a globular embryo after the introduction of the gene, obtained in Example 74(3), is conducted according to the method described in Example 47(5).
(6) Plant Regeneration from the Somatic Embryo, Acclimation and Cultivation In accordance with the method described in Example 47(6), the plant regeneration is conducted from the globular embryos selected in Examples 74(4) or 74(5).

The plant with roots and developed leaves undergo the acclimation and cultivation accordingly with the method described in Example 17(6) and are harvested.
(7) Evaluation of the Resistance to Herbicidal Compound (II)

The degree of resistance against compound (II) of the regenerated plant obtained in Example 74(6) is evaluated in accordance with the method described in Example 17(4).
(8) Construction of a Chloroplast Expression Plasmid Having the Present Invention DNA (A23)S for *Agrobacterium* Introduction A plasmid for introducing the present invention DNA (A23)S into a plant with the *agrobacterium* method is constructed. Plasmid pSUM-NdG6-rSt-1584soy was digested with restriction enzymes HindIII and EcoRI, to isolate the chimeric DNA in which the present invention DNA (A23)S was connected immediately after the nucleotide sequence encoding the chloroplast transit peptide of soybean (cv. Jack) RuBPC small subunit without a change of frames in the codons. Said DNA was inserted into between the HindIII restriction site and the EcoRI restriction site of the above binary plasmid vector pBI121S obtained in Example 18 to obtain plasmid pBI-NdG6-rSt-1584soy (FIG. 58). Further, plasmid pSUM-NdG6-rSt12-1584soy was digested with restriction enzyme NotI, to isolate a chimeric DNA in which the present invention DNA (A23)S was connected immediately after the nucleotide sequences encoding the chloroplast transit peptide of soybean (cv. Jack) RuBPC small subunit and encoding thereafter 12 amino acids of the mature protein, without a change of frames in the codons. Such a DNA was inserted between the HindIII restriction site and EcoRI restriction site of the above binary plasmid vector pBI121S to obtain plasmids pBI-NdG6-rSt12-1584soy (FIG. 59).
(9) Introduction of the Present Invention DNA (A23)S to Tobacco The present invention DNA (A23)S was introduced into tobacco with the *agrobacterium* method, utilizing plasmid pBI-NdG6-rSt-1584soy and pBI-NdG6-rSt12-1584soy obtained in Example 74(8).

First, in accordance with the method described in Example 19, each of the plasmids pBI-NdG6-rSt-1584soy and pBI-NdG6-rSt12-1584soy was introduced into *Agrobacterium tumefaciens* LBA4404 (Clontech Company). Each of the transgenic *agrobacterium* bearing pBI-NdG6-rSt-1584soy or pBI-NdG6-rSt12-1584soy were isolated.

Next, said *agrobacterium* bearing the plasmids are utilized to introduce genes into tobacco according to the method described in Example 47(9) to obtain, respectively, transgenic tobaccos which have incorporated the T-DNA region of pBI-NdG6-rSt-1584soy or pBI-NdG6-rSt12-1584soy.
(10) Evaluation of the Resistance Utilizing a Leaf Piece of the Present Invention DNA (A23)S Transgenic Tobacco Leaves are taken from 35 transgenic tobaccos obtained in Example 74(9). Each leaf is divided into pieces in which each piece is 5 to 7 mm wide. Leaf pieces are planted onto MS agar medium containing compound (II) or compound (XII) and cultured in the light at room temperature. After several days of culturing, the herbicidal damage of each of the leaf pieces is observed. As a control, leaf pieces of wild type tobacco are utilized. The resistance of the transgenic tobacco is evaluated by scoring the leaf pieces which continuously grow, leaf pieces which have chemical damage, and leaf pieces which turned white and have withered.

Example 75

Introduction of the Present Invention DNA (A25)S into a Plant (1) Construction of a Chloroplast Expression Plasmid Containing the Present Invention DNA (A25)S for Direct Introduction—Part 1

A plasmid containing a chimeric DNA in which the present invention DNA (A25)S was connected immediately after the nucleotide sequence encoding the chloroplast transit peptide of soybean (cv. Jack) RuBPC small subunit without a change of frames in the codons was constructed as a plasmid for introducing the present invention DNA (A25)S into a plant with the particle gun method.

First, DNA comprising the nucleotide sequence shown in SEQ ID NO: 393 was amplified by PCR. The PCR was conducted by utilizing as a template pKSN1609soy obtained in Example 71(2) and by utilizing as primers an oligonucleotide consisting of the nucleotide sequence shown in SEQ ID NO: 400 and an oligonucleotide consisting of the nucleotide sequence shown in SEQ ID NO: 401. The PCR utilized KOD-plus (Toyobo Company). The PCR carried out after conducting once a maintenance at 94° C. for 2 minutes; 20 cycles of a cycle that included maintaining 94° C. for 30 seconds, followed by 53° C. for 30 seconds, and followed by 68° C. for 90 seconds; and a final maintenance at 68° C. for 3 minutes. The amplified DNA was recovered and purified with MagExtractor-PCR & Gel-Clean up (Toyobo Company) by conducting the procedures according to the attached manual. By treating the obtained DNA with TaKaRa BKLKit (Takara Shuzo Company) according to the attached manual, the DNA was blunt ended and had the 5' terminus phosphorylated. A DNA comprising a nucleotide sequence shown in SEQ ID NO: 393 was recovered. After digesting plasmid pUC19 (Takara Shuzo Company) with SmaI, the 5' terminus was dephosphorylated with calf intestine alkaline phosphatase (Takara Shuzo Company). A plasmid was produced by ligating the resulting dephosphorylated DNA and the DNA comprising the nucleotide sequence shown in SEQ ID NO: 393. After digesting the obtained plasmid with restriction enzymes EcoT22I and SacI, the DNA comprising the nucleotide sequence shown in SEQ ID NO: 393 was recovered. After digesting plasmid pUCrSt657 obtained in Example 16(2) with restriction enzymes EcoT22I and SacI, there was isolated a DNA of about 2.9 kbp having a nucleotide sequence derived from pUC19 and a sequence encoding a chloroplast transit peptide of soybean (cv. Jack) RuBPC small subunit. The obtained DNA and the above DNA comprising the nucleotide sequence shown in SEQ ID NO: 393 were ligated to obtain pUCrSt1609soy (FIG. 60) containing a chimeric DNA in which the present invention DNA (A25)S was connected immediately after the nucleotide sequence encoding the chloroplast transit peptide of soybean (cv. Jack) RuBPC small subunit without a change of frames in the codons.

The obtained plasmid pUCrSt1609soy was digested with restriction enzymes BamHI and SacI to isolate a DNA comprising a nucleotide sequence shown in SEQ ID NO: 393. Said DNA was inserted between the BglII restriction site and the SacI restriction site of plasmid pNdG6-ΔT to obtain plasmid pSUM-NdG6-rSt-1609soy (FIG. 61) wherein the CR16G6 promoter has connected downstream the chimeric DNA in which said DNA was connected immediately after the nucleotide sequence encoding the chloroplast transit peptide of soybean (cv. Jack) RuBPC small subunit without a change of frames in the codons.

Next, the plasmid was introduced into *E. coli* DH5α competent cells (Takara Shuzo Company) and the ampicillin resistant cells were selected. Further, the nucleotide sequences of the plasmids contained in the ampicillin resistant strains were determined by utilizing BigDye Terminator Cycle Sequencing Ready Reaction kit v3.0 (PE Applied Biosystems Company) and DNA sequencer 3100 (PE Applied Biosytems Company). As a result, it was confirmed that plasmid pSUM-NdG6-rSt-1609soy has the nucleotide sequence shown in SEQ ID NO: 393.
(2) Construction of a Chloroplast Expression Plasmid Having the Present Invention DNA (A25)S for Direct Introduction—Part (2)

A plasmid was constructed for introducing the present invention DNA (A25)S into a plant with the particle gun method. The plasmid contained a chimeric DNA in which the present invention DNA (A25)S was connected immediately after the nucleotide sequences encoding the chloroplast transit peptide of soybean (cv. Jack) RuBPC small subunit and encoding thereafter 12 amino acids of the mature protein, without a change of frames in the codons. First, plasmid pUCrSt1609soy obtained in Example 75(1) has inserted into its EcoT22I restriction site, the linker EcoT22I-12aa-EcoT22I (FIG. 62) obtained by annealing the oligonucleotide consisting of the nucleotide sequence shown in SEQ ID NO: 402 and the oligonucleotide consisting of the nucleotide sequence shown in SEQ ID NO: 403. There was obtained plasmid pUCrSt12-1609soy (FIG. 63) containing the chimeric DNA in which the present invention DNA (A25)S was connected immediately after the nucleotide sequences encoding the chloroplast transit peptide of soybean (cv. Jack) RuBPC small subunit and encoding thereafter 12 amino acids of the mature protein, without a change of frames in the codons.

The obtained plasmid pUCrSt12-1609soy was digested with restriction enzymes BamHI and SacI to isolate the DNA comprising the nucleotide sequence shown in SEQ ID NO: 393. Said DNA was inserted between the BglII restriction site and the SacI restriction site of plasmid pNdG6-ΔT, obtained in Example 16(2), to obtain plasmid pSUM-NdG6-rSt12-1609soy (FIG. 64) wherein the CR16G6 promoter has connected downstream the chimeric DNA in which said DNA was connected immediately after the nucleotide sequence encoding the chloroplast transit peptide of soybean (cv. Jack) RuBPC small subunit without a change of frames in the codons.

Next, the plasmid was introduced into *E. coli* DH5α competent cells (Takara Shuzo Company) and the ampicillin resistant cells were selected. Further, the nucleotide sequences of the plasmids contained in the ampicillin resistant strains were determined by utilizing BigDye Terminator Cycle Sequencing Ready Reaction kit v3.0 (PE Applied Biosystems Company) and DNA sequencer 3100 (PE Applied Biosytems Company). As a result, it was confirmed that plasmid pSUM-NdG6-rSt12-1609soy has the nucleotide sequence shown in SEQ ID NO: 393.
(3) Introduction of the Present Invention DNA (A23)S into Soybean The globular embryos of soybeans (cultivar: Fayette and Jack) were prepared according to the method described in Example 47(3).

The obtained globular embryo was transplanted into fresh somatic embryo growth medium and cultured for 2 to 3 days. The plasmid pSUM-NdG6-rSt-1609soy produced in Example 75(1) or the plasmid pSUM-NdG6-rSt12-1609soy produced in Example 75(2) were introduced into those globular embryos according to the method described in Example 17(2).
(4) Selection of Somatic Embryo with Hygromycin Selection by hygromycin of a globular embryo after the introduction of the gene, obtained in Example 75(3), is conducted according to the method described in Example 47(4).
(5) Selection of Somatic Embryo with Compound (II)

Selection by compound (II) of a globular embryo after the introduction of the gene, obtained in Example 75(3), is conducted according to the method described in Example 47(5).
(6) Plant Regeneration from the Somatic Embryo, Acclimation and Cultivation In accordance with the method described in Example 47(6), the plant regeneration is conducted from the globular embryos selected in Examples 74(4) or 74(5).

The plant with roots and developed leaves undergo the acclimation and cultivation accordingly with the method described in Example 17(6) and are harvested.
(7) Evaluation of the Resistance to Herbicidal Compound (II)

The degree of resistance against compound (II) of the regenerated plant obtained in Example 75(6) is evaluated in accordance with the method described in Example 17(4).
(8) Construction of a Chloroplast Expression Plasmid Having the Present Invention DNA (A25)S for *agrobacterium* Introduction A plasmid for introducing the present invention DNA (A25)S into a plant with the *agrobacterium* method is constructed. Plasmid pSUM-NdG6-rSt-1609soy was digested with restriction enzymes HindIII and EcoRI, to isolate the chimeric DNA in which the present invention DNA (A25)S was connected immediately after the nucleotide sequence encoding the chloroplast transit peptide of soybean (cv. Jack)

RuBPC small subunit without a change of frames in the codons. Said DNA was inserted into between the HindIII restriction site and the EcoRI restriction site of the binary plasmid vector pBI121S obtained in Example 18 to obtain plasmid pBI-NdG6-rSt-1609soy (FIG. 65). Further, plasmid pSUM-NdG6-rSt12-1609soy was digested with restriction enzyme NotI, to isolate a chimeric DNA in which the present invention DNA (A25)S was connected immediately after the nucleotide sequences encoding the chloroplast transit peptide of soybean (cv. Jack) RuBPC small subunit and encoding thereafter 12 amino acids of the mature protein, without a change of frames in the codons. Such a DNA was inserted between the HindIII restriction site and EcoRI restriction site of the above binary plasmid vector pBI121S to obtain plasmids pBI-NdG6-rSt12-1609soy (FIG. 66).

(9) Introduction of the Present Invention DNA (A23)S to Tobacco

The present invention DNA (A25)S was introduced into tobacco with the *agrobacterium* method, utilizing plasmid pBI-NdG6-rSt-1609soy and pBI-NdG6-rSt12-1609soy obtained in Example 75(8).

First, in accordance with the method described in Example 19, each of the plasmids pBI-NdG6-rSt-1609soy and pBI-NdG6-rSt12-1609soy was introduced into *Agrobacterium tumefaciens* LBA4404 (Clontech Company). Each of the transgenic *agrobacterium* bearing pBI-NdG6-rSt-1609soy or pBI-NdG6-rSt12-1609soy were isolated.

Next, said *agrobacterium* bearing the plasmids are utilized to introduce genes into tobacco according to the method described in Example 47(9) to obtain, respectively, transgenic tobaccos which have incorporated the T-DNA region of pBI-NdG6-rSt-1609soy or pBI-NdG6-rSt12-1609soy.

(10) Evaluation of the Resistance Utilizing a Leaf Piece of the Present Invention DNA (A25)S transgenic tobacco Leaves are taken from the transgenic tobaccos obtained in Example 75(9). Such leaves are utilized to evaluate the resistance of the transgenic tobacco against compound (II) or compound (XII) according to the method of Example 74(10).

APPLICABILITY TO INDUSTRY

With the present invention, it is possible to provide a protein having the ability to metabolize a PPO inhibiting herbicidal compound and to convert such a compound to a compound of lower herbicidal activity; a DNA encoding such a protein; and a plant resistant to a herbicidal compound expressing such a protein.

Sequence Free Text

SEQ ID NO: 35
Designed oligonucleotide primer for PCR
SEQ ID NO: 36
Designed oligonucleotide primer for PCR
SEQ ID NO: 37
Designed oligonucleotide primer for PCR
SEQ ID NO: 38
Designed oligonucleotide primer for PCR
SEQ ID NO: 39
Designed oligonucleotide primer for PCR
SEQ ID NO: 40
Designed oligonucleotide primer for PCR
SEQ ID NO: 41
Designed oligonucleotide primer for PCR
SEQ ID NO: 42
Designed oligonucleotide primer for PCR
SEQ ID NO: 43
Designed oligonucleotide primer for PCR
SEQ ID NO: 44
Designed oligonucleotide primer for PCR
SEQ ID NO: 45
Designed oligonucleotide primer for PCR
SEQ ID NO: 46
Designed oligonucleotide primer for PCR
SEQ ID NO: 47
Designed oligonucleotide primer for PCR
SEQ ID NO: 48
Designed oligonucleotide primer for PCR
SEQ ID NO: 49
Designed oligonucleotide primer for PCR
SEQ ID NO: 50
Designed oligonucleotide primer for PCR
SEQ ID NO: 51
Designed oligonucleotide primer for PCR
SEQ ID NO: 52
Designed oligonucleotide primer for PCR
SEQ ID NO: 53
Designed oligonucleotide primer for PCR
SEQ ID NO: 54
Designed oligonucleotide primer for PCR
SEQ ID NO: 55
Designed oligonucleotide primer for PCR
SEQ ID NO: 56
Designed oligonucleotide primer for PCR
SEQ ID NO: 57
Designed oligonucleotide primer for PCR
SEQ ID NO: 58
Designed oligonucleotide primer for PCR
SEQ ID NO: 59
Designed oligonucleotide primer for PCR
SEQ ID NO: 60
Designed oligonucleotide primer for PCR
SEQ ID NO: 61
Designed oligonucleotide primer for PCR
SEQ ID NO: 62
Designed oligonucleotide primer for PCR
SEQ ID NO: 63
Designed oligonucleotide primer for PCR
SEQ ID NO: 64
Designed oligonucleotide primer for PCR
SEQ ID NO: 65
Designed oligonucleotide primer for PCR
SEQ ID NO: 66
Designed oligonucleotide primer for PCR
SEQ ID NO: 67
Designed oligonucleotide primer for PCR
SEQ ID NO: 68
Designed oligonucleotide primer for PCR
SEQ ID NO: 70
Designed oligonucleotide primer for PCR
SEQ ID NO: 71
Designed oligonucleotide primer for PCR
SEQ ID NO: 72
Designed oligonucleotide primer for PCR
SEQ ID NO: 73
Designed oligonucleotide primer for PCR
SEQ ID NO: 74
Designed oligonucleotide primer for PCR
SEQ ID NO: 75
Designed oligonucleotide primer for PCR
SEQ ID NO: 76
Designed oligonucleotide primer for PCR SEQ ID NO: 77
Designed oligonucleotide primer for PCR
SEQ ID NO: 79
Designed oligonucleotide primer for PCR
SEQ ID NO: 80
Designed oligonucleotide primer for PCR
SEQ ID NO: 81
Designed oligonucleotide primer for PCR
SEQ ID NO: 82
Designed oligonucleotide primer for PCR
SEQ ID NO: 83
Designed oligonucleotide primer for PCR
SEQ ID NO: 86
Designed oligonucleotide primer for PCR
SEQ ID NO: 87
Designed oligonucleotide primer for PCR
SEQ ID NO: 89
Designed oligonucleotide linker for construction of expression vector
SEQ ID NO: 90
Designed oligonucleotide linker for construction of expression vector
SEQ ID NO: 91
Designed oligonucleotide linker for construction of expression vector
SEQ ID NO: 92
Designed oligonucleotide linker for construction of expression vector
SEQ ID NO: 93
Designed oligonucleotide primer for PCR
SEQ ID NO: 94
Designed oligonucleotide primer for PCR
SEQ ID NO: 95
Designed oligonucleotide primer for PCR
SEQ ID NO: 96
Designed oligonucleotide primer for PCR
SEQ ID NO: 97
Designed oligonucleotide primer for PCR
SEQ ID NO: 98
Designed oligonucleotide linker for construction of expression vector
SEQ ID NO: 99
Designed oligonucleotide linker for construction of expression vector
SEQ ID NO: 100
Designed oligonucleotide primer for PCR
SEQ ID NO: 101
Designed oligonucleotide primer for PCR
SEQ ID NO: 102
Designed oligonucleotide primer for PCR
SEQ ID NO: 103
Designed oligonucleotide primer for PCR
SEQ ID NO: 104
Designed oligonucleotide primer for PCR
SEQ ID NO: 105
Designed oligonucleotide primer for PCR
SEQ ID NO: 106
Designed oligonucleotide primer for PCR
SEQ ID NO: 107
Designed oligonucleotide primer for PCR
SEQ ID NO: 114
Designed oligonucleotide primer for PCR
SEQ ID NO: 115
Designed oligonucleotide primer for PCR
SEQ ID NO: 116
Designed oligonucleotide primer for PCR
SEQ ID NO: 117
Designed oligonucleotide primer for PCR
SEQ ID NO: 118
Designed oligonucleotide primer for PCR
SEQ ID NO: 119
Designed oligonucleotide primer for PCR
SEQ ID NO: 120
Designed oligonucleotide primer for PCR
SEQ ID NO: 121
Designed oligonucleotide primer for PCR
SEQ ID NO: 122
Designed oligonucleotide primer for PCR
SEQ ID NO: 123
Designed oligonucleotide primer for PCR
SEQ ID NO: 124
Designed oligonucleotide primer for PCR
SEQ ID NO: 125
Designed oligonucleotide primer for PCR
SEQ ID NO: 126
Designed oligonucleotide primer for PCR
SEQ ID NO: 127
Designed oligonucleotide primer for PCR
SEQ ID NO: 128
Designed oligonucleotide primer for PCR
SEQ ID NO: 129
Designed oligonucleotide primer for PCR
SEQ ID NO: 130
Designed oligonucleotide primer for PCR
SEQ ID NO: 131
Designed oligonucleotide primer for PCR
SEQ ID NO: 132
Designed oligonucleotide primer for PCR
SEQ ID NO: 133
Designed oligonucleotide primer for PCR
SEQ ID NO: 134
Designed oligonucleotide linker for construction of expression vector
SEQ ID NO: 135
Designed oligonucleotide linker for construction of expression vector
SEQ ID NO: 161
Designed oligonucleotide primer for PCR
SEQ ID NO: 162
Designed oligonucleotide primer for PCR
SEQ ID NO: 163
Designed oligonucleotide primer for PCR
SEQ ID NO: 164
Designed oligonucleotide primer for PCR
SEQ ID NO: 165
Designed oligonucleotide primer for PCR
SEQ ID NO: 166
Designed oligonucleotide primer for PCR
SEQ ID NO: 167
Designed oligonucleotide primer for PCR
SEQ ID NO: 168
Designed oligonucleotide primer for PCR
SEQ ID NO: 169
Designed oligonucleotide primer for PCR
SEQ ID NO: 170
Designed oligonucleotide primer for PCR
SEQ ID NO: 171
Designed oligonucleotide primer for PCR
SEQ ID NO: 172
Designed oligonucleotide primer for PCR
SEQ ID NO: 173
Designed oligonucleotide primer for PCR SEQ ID NO: 174
Designed oligonucleotide primer for PCR
SEQ ID NO: 175
Designed oligonucleotide primer for PCR
SEQ ID NO: 176
Designed oligonucleotide primer for PCR
SEQ ID NO: 177
Designed oligonucleotide primer for PCR
SEQ ID NO: 178
Designed oligonucleotide primer for PCR
SEQ ID NO: 179
Designed oligonucleotide primer for PCR
SEQ ID NO: 180
Designed oligonucleotide primer for PCR
SEQ ID NO: 181
Designed oligonucleotide primer for PCR
SEQ ID NO: 182
Designed oligonucleotide primer for PCR
SEQ ID NO: 183
Designed oligonucleotide primer for PCR
SEQ ID NO: 184
Designed oligonucleotide primer for PCR
SEQ ID NO: 185
Designed oligonucleotide primer for PCR
SEQ ID NO: 186
Designed oligonucleotide primer for DNA sequencing
SEQ ID NO: 187
Designed oligonucleotide primer for DNA sequencing
SEQ ID NO: 188
Designed oligonucleotide primer for DNA sequencing
SEQ ID NO: 189
Designed oligonucleotide primer for DNA sequencing
SEQ ID NO: 190
Designed oligonucleotide primer for PCR
SEQ ID NO: 191
Designed oligonucleotide primer for PCR
SEQ ID NO: 192
Designed oligonucleotide primer for PCR
SEQ ID NO: 193
Designed oligonucleotide primer for PCR
SEQ ID NO: 194
Designed oligonucleotide primer for PCR
SEQ ID NO: 195
Designed oligonucleotide primer for PCR
SEQ ID NO: 196
Designed oligonucleotide primer for PCR
SEQ ID NO: 197
Designed oligonucleotide primer for PCR
SEQ ID NO: 198
Designed oligonucleotide primer for PCR
SEQ ID NO: 199
Designed oligonucleotide primer for PCR
SEQ ID NO: 200
Designed oligonucleotide primer for PCR
SEQ ID NO: 201
Designed oligonucleotide primer for PCR
SEQ ID NO: 202
Designed oligonucleotide primer for PCR
SEQ ID NO: 203
Designed oligonucleotide primer for PCR
SEQ ID NO: 204
Designed oligonucleotide primer for PCR
SEQ ID NO: 205
Designed oligonucleotide primer for PCR
SEQ ID NO: 206
Designed oligonucleotide primer for PCR
SEQ ID NO: 207
Designed oligonucleotide primer for PCR
SEQ ID NO: 208
Designed oligonucleotide primer for PCR
SEQ ID NO: 209
Designed oligonucleotide primer for PCR
SEQ ID NO: 210
Designed oligonucleotide primer for PCR
SEQ ID NO: 211
Designed oligonucleotide primer for PCR
SEQ ID NO: 212
Designed oligonucleotide primer for PCR
SEQ ID NO: 213
Designed oligonucleotide primer for PCR
SEQ ID NO: 214
Designed polynucleotide encoding amino acid sequence of SEQ ID No. 1
SEQ ID NO: 265
Designed oligonucleotide primer for PCR
SEQ ID NO: 266
Designed oligonucleotide primer for PCR
SEQ ID NO: 267
Designed oligonucleotide primer for PCR
SEQ ID NO: 268
Designed oligonucleotide primer for PCR
SEQ ID NO: 269
Designed oligonucleotide primer for PCR
SEQ ID NO: 270
Designed oligonucleotide primer for PCR
SEQ ID NO: 271
Designed oligonucleotide primer for PCR
SEQ ID NO: 272
Designed oligonucleotide primer for PCR
SEQ ID NO: 273
Designed oligonucleotide primer for PCR
SEQ ID NO: 274
Designed oligonucleotide primer for PCR
SEQ ID NO: 275
Designed oligonucleotide primer for PCR
SEQ ID NO: 276
Designed oligonucleotide primer for DNA sequencing
SEQ ID NO: 277
Designed oligonucleotide primer for DNA sequencing
SEQ ID NO: 278
Designed oligonucleotide primer for PCR
SEQ ID NO: 279
Designed oligonucleotide primer for PCR
SEQ ID NO: 280
Designed oligonucleotide primer for PCR
SEQ ID NO: 281
Designed oligonucleotide primer for DNA sequencing
SEQ ID NO: 282
Designed oligonucleotide primer for PCR
SEQ ID NO: 283
Designed oligonucleotide primer for PCR
SEQ ID NO: 284
Designed oligonucleotide primer for PCR
SEQ ID NO: 285
Designed oligonucleotide primer for PCR
SEQ ID NO: 286
Designed oligonucleotide primer for PCR
SEQ ID NO: 287
Designed oligonucleotide primer for PCR
SEQ ID NO: 288
Designed oligonucleotide primer for DNA sequencing
SEQ ID NO: 289
Designed oligonucleotide primer for PCR SEQ ID NO: 290
Designed oligonucleotide primer for PCR
SEQ ID NO: 291
Designed oligonucleotide primer for PCR
SEQ ID NO: 292
Designed oligonucleotide primer for PCR
SEQ ID NO: 293
Designed oligonucleotide primer for PCR
SEQ ID NO: 294
Designed oligonucleotide primer for PCR
SEQ ID NO: 295
Designed oligonucleotide primer for PCR
SEQ ID NO: 296
Designed oligonucleotide primer for PCR
SEQ ID NO: 297
Designed oligonucleotide primer for PCR
SEQ ID NO: 298
Designed oligonucleotide primer for PCR
SEQ ID NO: 299
Designed oligonucleotide primer for PCR
SEQ ID NO: 300
Designed oligonucleotide primer for DNA sequencing
SEQ ID NO: 301
Designed oligonucleotide primer for PCR
SEQ ID NO: 302
Designed oligonucleotide primer for PCR
SEQ ID NO: 303
Designed oligonucleotide primer for PCR
SEQ ID NO: 304
Designed oligonucleotide primer for PCR
SEQ ID NO: 305
Designed oligonucleotide primer for PCR
SEQ ID NO: 306
Designed oligonucleotide primer for PCR
SEQ ID NO: 307
Designed oligonucleotide primer for PCR
SEQ ID NO: 308
Designed oligonucleotide primer for DNA sequencing
SEQ ID NO: 309
Designed oligonucleotide primer for PCR
SEQ ID NO: 310
Designed oligonucleotide primer for PCR
SEQ ID NO: 311
Designed oligonucleotide primer for PCR
SEQ ID NO: 312
Designed oligonucleotide primer for PCR
SEQ ID NO: 313
Designed oligonucleotide primer for PCR
SEQ ID NO: 314
Designed oligonucleotide primer for PCR
SEQ ID NO: 315
Designed oligonucleotide primer for DNA sequencing
SEQ ID NO: 316
Designed oligonucleotide primer for PCR
SEQ ID NO: 317
Designed oligonucleotide primer for PCR
SEQ ID NO: 318
Designed oligonucleotide primer for PCR
SEQ ID NO: 319
Designed oligonucleotide primer for PCR
SEQ ID NO: 320
Designed oligonucleotide primer for PCR
SEQ ID NO: 321
Designed oligonucleotide primer for PCR
SEQ ID NO: 322
Designed oligonucleotide primer for DNA sequencing
SEQ ID NO: 323
Designed oligonucleotide primer for PCR
SEQ ID NO: 324
Designed oligonucleotide primer for PCR
SEQ ID NO: 325
Designed oligonucleotide primer for PCR
SEQ ID NO: 326
Designed oligonucleotide primer for PCR
SEQ ID NO: 327
Designed oligonucleotide primer for PCR
SEQ ID NO: 328
Designed oligonucleotide primer for PCR
SEQ ID NO: 329
Designed oligonucleotide primer for PCR
SEQ ID NO: 330
Designed oligonucleotide primer for PCR
SEQ ID NO: 331
Designed oligonucleotide primer for PCR
SEQ ID NO: 332
Designed oligonucleotide primer for PCR
SEQ ID NO: 333
Designed oligonucleotide primer for PCR
SEQ ID NO: 334
Designed oligonucleotide primer for PCR
SEQ ID NO: 335
Designed oligonucleotide primer for PCR
SEQ ID NO: 336
Designed oligonucleotide primer for PCR
SEQ ID NO: 337
Designed oligonucleotide primer for PCR
SEQ ID NO: 338
Designed oligonucleotide primer for PCR
SEQ ID NO: 339
Designed oligonucleotide primer for PCR
SEQ ID NO: 340
Designed oligonucleotide primer for PCR
SEQ ID NO: 341
Designed oligonucleotide primer for PCR
SEQ ID NO: 342
Designed oligonucleotide primer for PCR
SEQ ID NO: 343
Designed oligonucleotide primer for PCR
SEQ ID NO: 344
Designed oligonucleotide primer for PCR
SEQ ID NO: 345
Designed oligonucleotide primer for PCR
SEQ ID NO: 346
Designed oligonucleotide primer for PCR
SEQ ID NO: 347
Designed oligonucleotide primer for PCR
SEQ ID NO: 348
Designed oligonucleotide primer for PCR
SEQ ID NO: 349
Designed oligonucleotide primer for PCR
SEQ ID NO: 350
Designed oligonucleotide primer for PCR
SEQ ID NO: 351
Designed oligonucleotide primer for PCR
SEQ ID NO: 352
Designed oligonucleotide primer for PCR
SEQ ID NO: 353
Designed oligonucleotide primer for PCR
SEQ ID NO: 354
Designed oligonucleotide primer for PCR
SEQ ID NO: 355
Designed oligonucleotide primer for PCR SEQ ID NO: 356
Designed oligonucleotide primer for PCR
SEQ ID NO: 357
Designed oligonucleotide primer for PCR
SEQ ID NO: 358
Designed oligonucleotide primer for PCR
SEQ ID NO: 359
Designed oligonucleotide primer for PCR
SEQ ID NO: 360
Designed oligonucleotide primer for PCR
SEQ ID NO: 361
Designed oligonucleotide primer for PCR
SEQ ID NO: 362
Designed oligonucleotide primer for PCR
SEQ ID NO: 363
Designed oligonucleotide primer for PCR
SEQ ID NO: 364
Designed oligonucleotide primer for PCR
SEQ ID NO: 365
Designed oligonucleotide primer for PCR
SEQ ID NO: 366
Designed oligonucleotide primer for PCR
SEQ ID NO: 367
Designed oligonucleotide primer for PCR
SEQ ID NO: 368
Designed polynucleotide encoding amino acid sequence of SEQ ID No. 222
SEQ ID NO: 369
Designed oligonucleotide primer for PCR
SEQ ID NO: 370
Designed oligonucleotide primer for PCR
SEQ ID NO: 371
Designed oligonucleotide primer for PCR
SEQ ID NO: 372
Designed oligonucleotide primer for PCR
SEQ ID NO: 373
Designed oligonucleotide primer for PCR
SEQ ID NO: 374
Designed oligonucleotide primer for PCR
SEQ ID NO: 375
Designed oligonucleotide primer for PCR
SEQ ID NO: 376
Designed oligonucleotide primer for PCR
SEQ ID NO: 377
Designed oligonucleotide primer for PCR
SEQ ID NO: 378
Designed oligonucleotide primer for PCR
SEQ ID NO: 379
Designed oligonucleotide primer for PCR
SEQ ID NO: 380
Designed oligonucleotide primer for PCR
SEQ ID NO: 381
Designed oligonucleotide primer for PCR
SEQ ID NO: 382
Designed oligonucleotide primer for PCR
SEQ ID NO: 383
Designed oligonucleotide primer for PCR
SEQ ID NO: 384
Designed oligonucleotide primer for PCR
SEQ ID NO: 385
Designed oligonucleotide primer for PCR
SEQ ID NO: 386
Designed oligonucleotide primer for PCR
SEQ ID NO: 387
Designed oligonucleotide primer for PCR
SEQ ID NO: 388
Designed oligonucleotide primer for PCR
SEQ ID NO: 389
Designed oligonucleotide primer for PCR
SEQ ID NO: 390
Designed oligonucleotide primer for PCR
SEQ ID NO: 391
Designed oligonucleotide primer for PCR
SEQ ID NO: 392
Designed oligonucleotide primer for PCR
SEQ ID NO: 393
Designed polynucleotide encoding amino acid sequence of SEQ ID No. 224
SEQ ID NO: 394
Designed oligonucleotide primer for PCR
SEQ ID NO: 395
Designed oligonucleotide primer for PCR
SEQ ID NO: 396
Designed oligonucleotide primer for PCR
SEQ ID NO: 397
Designed oligonucleotide primer for PCR
SEQ ID NO: 398
Designed oligonucleotide primer for PCR
SEQ ID NO: 399
Designed oligonucleotide primer for PCR
SEQ ID NO:400
Designed oligonucleotide primer for PCR
SEQ ID NO:401
Designed oligonucleotide primer for PCR
SEQ ID NO:402
Designed oligonucleotide linker for construction of expression vector
SEQ ID NO:403
Designed oligonucleotide linker for construction of expression vector

The invention claimed is:

1. An isolated DNA encoding a herbicide metabolizing protein, wherein said protein is selected from the group consisting of:
   (a) a protein comprising the amino acid sequence of SEQ ID NO: 222;
   (b) a protein having an ability to convert in the presence of an electron transport system containing an electron donor, a compound of formula (II)

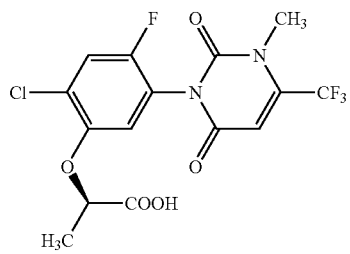

to a compound of formula (III),

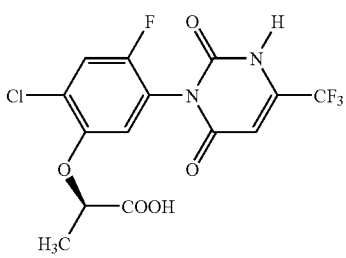

and comprising an amino acid sequence which has at least 90% sequence identity with the amino acid sequence of SEQ ID NO: 222, and which contains an amino acid sequence encoded by a DNA amplifiable by a polymerase chain reaction with a primer comprising the nucleotide sequence of SEQ ID NO: 124 and a primer comprising the nucleotide sequence of SEQ ID NO: 129, and which retains a cysteine at a position corresponding to amino acid number 347 in the amino acid sequence of SEQ ID NO: 222; and (c) a protein having an ability to convert in the presence of an electron transport system containing an electron donor, a compound of formula (II) to a compound of formula (III), and comprising an amino acid sequence encoded by a DNA amplifiable by a polymerase chain reaction with a primer comprising the nucleotide sequence of any one of SEQ ID NOs: 124 to 128, a primer comprising the nucleotide sequence of SEQ ID NO: 129 and as a template a chromosomal DNA of *Streptomyces roseorubens*.

2. An isolated DNA comprising the nucleotide sequence of SEQ ID NO: 232.

3. The DNA according to claim 1, comprising a nucleotide sequence encoding an amino acid sequence of said protein, wherein the codon usage in said nucleotide sequence is within the range of plus or minus 4% of the codon usage in genes from the species of a host cell to which the DNA is introduced and the GC content of said nucleotide sequence is at least 40% and at most 60%.

4. An isolated DNA comprising the nucleotide sequence shown in SEQ ID NO: 368.

5. An isolated DNA in which a DNA having a nucleotide sequence encoding an intracellular organelle transit signal sequence is linked upstream of the DNA according to claim 1 in frame.

6. An isolated DNA in which the DNA according to claim 1 and a promoter functional in a host cell are operably linked.

7. A vector comprising the DNA according to claim 1.

8. A method of producing a vector comprising a step of inserting the DNA according to claim 1 into a vector replicable in a host cell.

9. A transformant in which the DNA according to claim 1 is introduced into a host cell.

10. The transformant according to claim 9, wherein the host cell is a microorganism cell or a plant cell.

11. A method of producing a transformant comprising a step of introducing into a host cell, the DNA according to claim 1.

12. A method of producing a protein having the ability to convert a compound of formula (II) to a compound of formula (III), said method comprising a step(s) of culturing the transformant according to claim 9 and recovering the produced said protein.

13. A method of giving a plant resistance to a herbicide, said method comprising step of introducing into and expressing in a plant cell, the DNA according to claim 1.

14. A method of detecting a DNA encoding a protein having the ability to convert a compound of formula (II) to a compound of formula (III), said method comprising a step of detecting a DNA to which a probe is hybridized in a hybridization using as the probe the DNA according to claim 1.

15. A method of detecting a DNA encoding a protein having the ability to convert a compound of formula (II) to a compound of formula (III), said method comprising a step of detecting a DNA amplified in a polymerase chain reaction with a polynucleotide having a partial nucleotide sequence of a DNA according to claim 1 or a nucleotide sequence complimentary to said partial nucleotide sequence as a primer.

16. The method according to claim 15, wherein at least one of the primers is selected from the group consisting of a polynucleotide comprising the nucleotide sequence shown in any one of SEQ ID NOs: 124 to 128 and a polynucleotide comprising the nucleotide sequence shown in SEQ ID NO: 129.

17. A method of obtaining a DNA encoding a protein having the ability to convert a compound of formula (II) to a compound of formula (III), said method comprising a step of recovering the DNA detected by the method according to claim 14.

18. A method of screening a cell having a DNA encoding a protein having the ability to convert a compound of formula (II) to a compound of formula (III), said method comprising a step of detecting said DNA from a test cell by the method according to claim 14.

19. The DNA according to claim 3 comprising the nucleotide sequence of SEQ ID NO: 368.

20. A method of controlling weeds comprising a step of applying a herbical compound to a cultation area of a plant expressing the DNA according to claim 1.

* * * * *